(12) United States Patent
Bassil et al.

(10) Patent No.: US 9,242,962 B2
(45) Date of Patent: Jan. 26, 2016

(54) METHOD OF TREATMENT

(71) Applicant: GlaxoSmithKline Intellectual Property (No. 2) Limited, Brentford, Middlesex (GB)

(72) Inventors: Anna K. Bassil, Stevenage (GB); Soren Beinke, Stevenage (GB); Rabinder Kumar Prinjha, Stevenage (GB)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 14/355,964

(22) PCT Filed: Nov. 2, 2012

(86) PCT No.: PCT/US2012/063235
§ 371 (c)(1),
(2) Date: May 2, 2014

(87) PCT Pub. No.: WO2013/067296
PCT Pub. Date: May 10, 2013

(65) Prior Publication Data
US 2014/0256739 A1    Sep. 11, 2014

Related U.S. Application Data

(60) Provisional application No. 61/555,650, filed on Nov. 4, 2011.

(51) Int. Cl.
| | |
|---|---|
| A61K 31/497 | (2006.01) |
| C07D 401/14 | (2006.01) |
| C12N 9/10 | (2006.01) |
| A61K 31/4439 | (2006.01) |
| A61K 31/405 | (2006.01) |

(52) U.S. Cl.
CPC .......... C07D 401/14 (2013.01); A61K 31/4439 (2013.01); C12N 9/1007 (2013.01); *A61K 31/405* (2013.01)

(58) Field of Classification Search
CPC ...................................................... A61K 31/405
USPC ...................................................... 514/252.13
See application file for complete search history.

(56) References Cited

U.S. PATENT DOCUMENTS

| | | | |
|---|---|---|---|
| 7,087,637 | B2 | 8/2006 | Grandel et al. |
| 8,536,179 | B2 | 9/2013 | Miller et al. |
| 2009/0012031 | A1 | 1/2009 | Chinnaiyan et al. |
| 2011/0064664 | A1 | 3/2011 | Lopez-Berestein et al. |

FOREIGN PATENT DOCUMENTS

| | | |
|---|---|---|
| EP | 0 213 984 A1 | 3/1987 |
| WO | WO 2004/112719 A2 | 12/2004 |
| WO | WO 2005/034845 A2 | 4/2005 |
| WO | WO 2007/053114 A1 | 5/2007 |
| WO | WO 2009/103552 A1 | 8/2009 |
| WO | WO 2010/036213 A1 | 4/2010 |
| WO | WO 2010/090723 A2 | 8/2010 |
| WO | WO 2011/140325 A1 | 11/2011 |
| WO | WO 2012/005805 A1 | 1/2012 |
| WO | WO 2012/118812 A2 | 9/2012 |

OTHER PUBLICATIONS

McCabe, et al. Nature, 1, DOI: 10.1038/nature11606 (2012).

*Primary Examiner* — Kevin E Weddington
(74) *Attorney, Agent, or Firm* — Duke M. Fitch; Edward R. Gimmi; William R. Majarian

(57) ABSTRACT

The present invention relates to a method of treating T cell mediated inflammatory immune diseases or T cell mediated hypersensitivity diseases, which comprises administering to a human in need thereof an effective amount of a compound which inhibits EZH2 and/or EZH1, or a pharmaceutically acceptable salt thereof.

4 Claims, 5 Drawing Sheets

FIG. 4

|            | IL-10       | IL-13       | IL-17       | IFN         | TNF         |
|------------|-------------|-------------|-------------|-------------|-------------|
| Compound A | 5.65 ± 0.06 | 5.33 ± 0.06 | 5.59 ± 0.11 | 5.23 ± 0.03 | 5.38 ± 0.05 |
| Compound B | 5.18 ± 0.06 | 4.95 ± 0.07 | 5.21 ± 0.09 | 4.94 ± 0.03 | 5.04 ± 0.02 |

METHOD OF TREATMENT

This application is a §371 of International Application No. PCT/US2012/063235, filed 2 Nov. 2012, which claims the benefit of U.S. Provisional Application No. 61/555,650, filed 4 Nov. 2011, which are incorporated herein in their entireties.

FIELD OF THE INVENTION

This invention relates to compounds which inhibit EZH2/EZH1 and their uses for treating T cell mediated inflammatory immune diseases.

BACKGROUND OF THE INVENTION

Posttranslational modifications of proteins play a critical role in the regulation of signal transduction from receptors, chromatin remodelling and gene transcription. These modifications include acetylation, methylation, phosphorylation, ubiquitinylation, SUMOylation. EZH (enhancer of zeste homolog) 1 and 2 are the catalytic subunits of the Polycomb Repressor Complex 2 (PRC2) and exhibit methyltransferase activity that can catalyse the methylation of lysine amino acids (Margueron R, Reinberg D: The Polycomb complex PRC2 and its mark in life. Nature. 2011 Jan. 20; 469 (7330): 343-9)

EZH1 and EZH2 play a critical role in the epigenetic long term silencing of gene expression by di- or tri-methylating lysine 27 of histone H3 (H3K27me2/3). Histone H3 is one of the five main histone proteins involved in the structure of chromatin in eukaryotic cells. Chromatin is the complex combination of DNA and protein that makes up chromosomes. It is found inside the nuclei of eukaryotic cells and is divided between heterochromatin (condensed) and euchromatin (extended). The basic building blocks of chromatin are nucleosomes, each of which is composed of 146 base pairs of DNA wrapped around a histone octamer that consists of 2 copies of each H2A, H2B, H3 and H4. The functions of chromatin are to package DNA into a smaller volume to fit in the cell, to strengthen the DNA to allow mitosis and meiosis, and to serve as a mechanism to control gene expression and DNA replication. The chromatin structure is controlled by a series of post translational modifications to histone proteins, notably histones H3 and H4, and most commonly within the "histone tails" which extend beyond the core nucleosome structure. Binding of enzymes and adaptor proteins to posttranslational modification in histone tails regulates chromatin dynamics and gene expression. H3K27me3 is thought to silence gene expression by recruiting histone deacetylases to the modified nucleosomes and stall transcriptional elongation by polymerase II. Thus, inhibition of the enzymatic activity of EZH1 and EZH2 may result in a loss of H3K27me3 and up-regulation of target genes.

In addition to its nuclear function in histone H3 modification EZH2 has been implicated in the regulation of signal transduction that leads to actin polymerization in the cytoplasm of cells (Su I H, Dobenecker M W, Dickinson E, Oser M, Basavaraj A, Marqueron R, Viale A, Reinberg D, Wülfing C, Tarakhovsky A: Polycomb group protein ezh2 controls actin polymerization and cell signaling. Cell. 2005 May 6; 121(3):425-36). The reorganization of the actin cytoskeleton critically contributes to T cell responses by facilitating the interaction of T cells with antigen presenting cells or target cells. In addition, actin remodelling plays an important role in T cell migration and motility during their recruitment to the sites of inflammation. A fraction of EZH2 protein was found to localize to the cytoplasm of T cells and to interact with the small GTPase VAV1, which is involved in actin remodelling. Genetic elimination of EZH2 resulted in impaired polymerization of actin in TCR stimulated T cells or at the T cell-antigen presenting cell interphase. Furthermore, actin polymerization induced by EZH2 over-expression was dependent on the methylransferase activity of EZH2. Proliferation of T cells in response to TCR was also impaired in the absence of EZH2. Thus, inhibition of EZH1 and/or EZH2 may suppress the activation of T cells.

Mature T cell respond to foreign peptide antigens in the presence of appropriate co-stimulation by antigen presenting cells. They have the capability to discriminate between self and non self as a consequence of the selection of a TCR repertoire specific for foreign antigens in the thymus, tolerance induction of self reactive T cell clones in the periphery, and control of T cell activation by self antigen by regulatory T cells. T cells provide protection against different classes of pathogens by mediating distinct types of adaptive immune responses as a consequence of the expression of distinct sets of cytokines and other soluble and cell-bound products. In addition, they act as principle amplifiers and inducers of the appropriate inflammatory and effector responses in cells of the innate immune system and nonimmune cells. While such concerted immune responses can provide powerful protection against pathogens it can also result in inflammation associated with unwanted immune responses against self and environmental antigens and commensal microorganisms as well as collateral damage to the host as a side effect of immune responses against pathogens. CD8 T cells can lyse cells bearing intracellular pathogens but may also contribute to tissue damage and secrete pro-inflammatory cytokines, e.g. TNF and IFNg. CD4 T cells can have diverse functions in inflammation depending on their specific cytokine expression profiles. CD4$^+$ Th1 cells are important for the clearance of intracellular pathogens but also play a critical role in inflammation through the expression of TNF and IFNg. IL-17 expressing CD4$^+$ Th17 cells, which mediate neutrophilia and tissue remodelling and repair, have also been shown to be involved in many inflammatory conditions. CD4$^+$ Th2 cells are involved in allergic responses by expressing IL-13, IL-5 and IL-4 which mediate airway hyper reactivity, eosinophil recruitment and IgE production. Thus, T cell activation is considered central to many inflammatory immune diseases. Accordingly, compounds that inhibit EZH1 and/or EZH2 activity and suppress T cell activation would be useful for the treatment of T cell mediated inflammatory immune diseases. Inhibitors of EZH1/EZH2 that are useful in treating cancer have been reported in PCT applications PCT/US2011/035336, PCT/US2011/035340, and PCT/US2011/035344.

SUMMARY OF THE INVENTION

The present invention relates to a method of treating T cell mediated inflammatory immune diseases or T cell mediated hypersensitivity diseases, which comprises administering to a human in need thereof an effective amount of a compound which inhibits EZH2 and/or EZH1, or a pharmaceutically acceptable salt thereof.

In a further aspect the invention relates to a compound or a pharmaceutically acceptable salt thereof which inhibits EZH2 and/or EZH1 for use in treating T cell mediated inflammatory immune diseases or T cell mediated hypersensitivity diseases.

In a further aspect the invention relates to the use of a compound or a pharmaceutically acceptable salt thereof which inhibits EZH2 and/or EZH1 in the manufacture of a medicament for treating T cell mediated inflammatory immune diseases or T cell mediated hypersensitivity diseases.

BRIEF DESCRIPTION OF DRAWINGS

FIG. 4: $EZH_1/EZH_2$ inhibitors impair T cell receptor-induced effector cytokine production in CD4+ T cells. Cytokine production was measured 72 h post stimulation with 10 µg/mL αCD3+2 µg/mL αCD28. Data are presented as $pIC_{50}$±sem; n=4

DETAILED DESCRIPTION OF THE INVENTION

Figure 1:
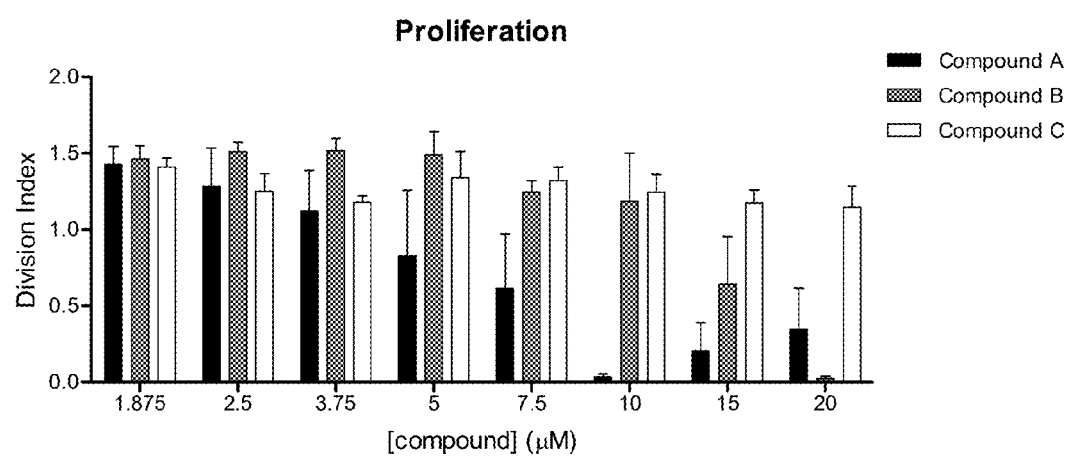
FIG. 1: $EZH_1/EZH_2$ inhibitors impair T cell receptor-induced CD4+ T cell proliferation. Division index was calculated by CFSE fluorescence 6 days post stimulation with 10 µg/mL αCD3+2 µg/mL αCD28. Data are presented as mean±standard error of the mean, n=4.

The present invention relates to a method of treating T cell mediated inflammatory immune diseases as described above.

The present invention relates to a method of treating T cell mediated hypersensitivity diseases as described above.

The present invention relates to a method of treating T cell mediated inflammatory immune disease or T cell mediated hypersensitivity diseases, which comprises administering to a human in need thereof an effective amount of a compound of Formula (I)

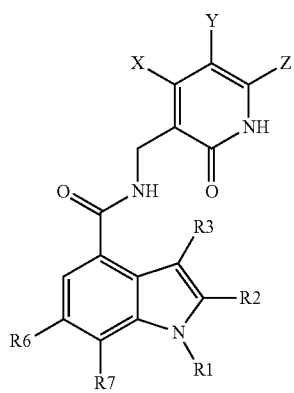

(I)

wherein

X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, —$CONR^aNR^aR^b$;

$R^2$ is hydrogen, $(C_1-C_8)$alkyl, trifluoromethyl, alkoxy, or halo, in which said $(C_1-C_8)$alkyl may be substituted with one to two groups selected from: amino, and $(C_1-C_3)$alkylamino;

$R^7$ is hydrogen, $(C_1-C_3)$alkyl, or alkoxy;

$R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, —$B(OH)_2$, substituted or unsubstituted $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, $(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2H$, —$CO_2$($C_1$-$C_4$)alkyl, —$CONH_2$, —$CONH$($C_1$-$C_4$)alkyl, —$CON$(($C_1$-$C_4$)alkyl)(($C_1$-$C_4$)alkyl), —$SO_2$($C_1$-$C_4$)alkyl, —$SO_2NH_2$, —$SO_2NH$($C_1$-$C_4$)alkyl, or —$SO_2N$(($C_1$-$C_4$)alkyl)(($C_1$-$C_4$)alkyl);

each $R^c$ is independently ($C_1$-$C_4$)alkylamino, —$NR^aSO_2R^b$, —$SOR^a$, —$SO_2R^a$, —$NR^aC(O)OR^a$, —$NR^aR^b$, or —$CO_2R^a$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring;

or a salt thereof.

The present invention also relates to the above method, wherein the compound of Formula (I) is further defined in one of the subgroups below:

Subgroup (I)(A)

X and Z are selected from the group consisting of ($C_1$-$C_8$)alkyl, ($C_3$-$C_8$)cycloalkyl, heterocycloalkyl, aryl, heteroaryl, —$NR^aR^b$, and —$OR^a$;

Y is H or F;

$R^1$ is selected from the group consisting of ($C_1$-$C_8$)alkyl, ($C_3$-$C_8$)cycloalkyl, heterocycloalkyl, aryl, and heteroaryl;

$R^2$ is hydrogen, ($C_1$-$C_8$)alkyl, trifluoromethyl, alkoxy, or halo, in which said ($C_1$-$C_8$)alkyl maybe substituted with one to two groups selected from: amino, and ($C_1$-$C_3$)alkylamino;

$R^7$ is hydrogen, ($C_1$-$C_3$)alkyl, or alkoxy;

$R^3$ is selected from the group consisting of hydrogen, ($C_1$-$C_8$)alkyl, cyano, trifluoromethyl, —$NR^aR^b$, and halo;

$R^6$ is selected from the group consisting of hydrogen, halo, cyano, trifluoromethyl, amino, ($C_1$-$C_8$)alkyl, ($C_3$-$C_8$)cycloalkyl, aryl, heteroaryl, acylamino, ($C_2$-$C_8$)alkynyl, arylalkynyl, heteroarylalkynyl, —$SO_2R^a$, —$SO_2NR^aR^b$, and —$NR^aSO_2R^b$;

wherein any ($C_1$-$C_8$)alkyl, ($C_3$-$C_8$)cycloalkyl, ($C_2$-$C_8$)alkynyl, arylalkynyl, heteroarylalkynyl group is optionally substituted by 1, 2 or 3 groups independently selected from —$O$($C_1$-$C_6$)alkyl($R^c$)$_{1-2}$, —$S$($C_1$-$C_6$)alkyl($R^c$)$_{1-2}$, —($C_1$-$C_6$)alkyl($R^c$)$_{1-2}$, ($C_1$-$C_8$)alkyl-heterocycloalkyl, ($C_3$-$C_8$)cycloalkyl-heterocycloalkyl, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1$-$C_4$)alkyl, and heteroaryl($C_1$-$C_4$)alkyl;

each $R^c$ is independently ($C_1$-$C_4$)alkylamino, —$NR^aSO_2R^b$, —$SOR^a$, —$SO_2R^a$, —$NR^aC(O)OR^a$, —$NR^aR^b$, or —$CO_2R^a$;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2H$, —$CO_2$($C_1$-$C_4$)alkyl, —$CONH_2$, —$CONH$($C_1$-$C_4$)alkyl, —$CON$(($C_1$-$C_4$)alkyl)(($C_1$-$C_4$)alkyl), —$SO_2$($C_1$-$C_4$)alkyl, —$SO_2NH_2$, —$SO_2NH$($C_1$-$C_4$)alkyl, and —$SO_2N$(($C_1$-$C_4$)alkyl)(($C_1$-$C_4$)alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

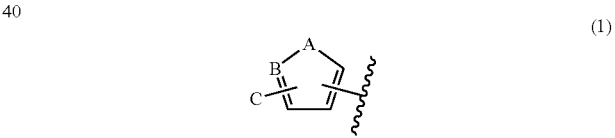

(1)

wherein in (1),

A is O, NH, or S; B is CH or N, and C is hydrogen or $C_1$-$C_8$ alkyl; or

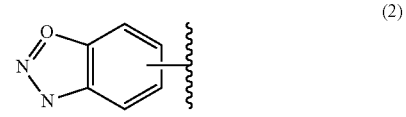

(2)

wherein in (2),

D is N or C optionally substituted by hydrogen or $C_1$-$C_8$ alkyl; or

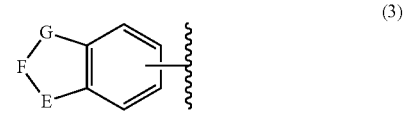

(3)

wherein in (3),
E is NH or CH$_2$; F is O or CO; and G is NH or CH$_2$; or

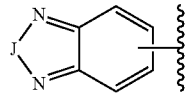
(4)

wherein in (4),
J is O, S or CO; or

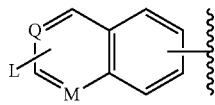
(5)

wherein in (5),
Q is CH or N;
M is CH or N; and
L/(5) is hydrogen, halo, amino, cyano, (C$_1$-C$_8$)alkyl, (C$_3$-C$_8$)cycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$;
wherein R$^a$ and R$^b$ are defined as above; or

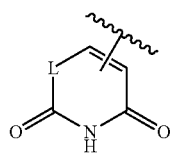
(6)

wherein in 6,
L/(6) is NH or CH$_2$; or

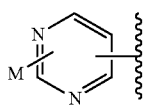
(7)

wherein in 7,
M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
wherein any (C$_1$-C$_8$)alkyl, (C$_3$-C$_8$)cycloalkyl, heterocycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above; or (8)

wherein in (8),
P is CH$_2$, NH, O, or S; Q/(8) is CH or N; and n is 0-2; or (9)

wherein in (9),
S/(9) and T(9) is C, or S/(9) is C and T(9) is N, or S/(9) is N and T/(9) is C;
R is hydrogen, amino, methyl, trifluoromethyl, halo;
U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazol-4-yl),
wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$;
wherein R$^a$ and R$^b$ are defined as above.
Subgroup (I)(B)
X and Z are selected independently from the group consisting of (C$_1$-C$_8$)alkyl, (C$_3$-C$_8$)cycloalkyl, heterocycloalkyl, aryl, heteroaryl, —NR$^a$R$^b$, and —OR$^a$;
Y is H;
R$^1$ is (C$_1$-C$_8$)alkyl, (C$_3$-C$_8$)cycloalkyl, or heterocycloalkyl;
R$_2$ is hydrogen, (C$_1$-C$_3$)alkyl, or halo, in which said (C$_1$-C$_3$)alkyl maybe substituted with one to two groups selected from: amino, and (C$_1$-C$_3$)alkylamino;
R$^7$ is hydrogen, (C$_1$-C$_3$)alkyl, or alkoxy;
R$^3$ is hydrogen, (C$_1$-C$_8$)alkyl or halo;
R$^6$ is hydrogen, halo, cyano, trifluoromethyl, amino, (C$_1$-C$_8$)alkyl, (C$_3$-C$_8$)cycloalkyl, aryl, heteroaryl, acylamino, (C$_2$-C$_8$)alkynyl, arylalkynyl, heteroarylalkynyl, —SO$_2$R$^a$, —SO$_2$NR$^a$R$^b$, or —NR$^a$SO$_2$R$^b$;
wherein any (C$_1$-C$_8$)alkyl, (C$_3$-C$_8$)cycloalkyl, (C$_2$-C$_8$)alkynyl, arylalkynyl, heteroarylalkynyl group is optionally substituted by 1, 2 or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1-C_4$)alkyl, and heteroaryl($C_1-C_4$)alkyl;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)$((C_1-C_4)$alkyl), —$SO_2(C_1-C_4)$alkyl, —$SO_2NH_2$, —$SO_2NH(C_1-C_4)$alkyl, and —$SO_2N((C_1-C_4)$alkyl)$((C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine as or a compound of or another aryl or heteroaryl group as follows:

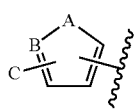

(1)

wherein in (1),
A is O, NH, or S; B is CH or N, and C is hydrogen or $C_1-C_8$ alkyl; or

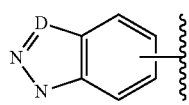

(2)

wherein in (2),
D is N or C optionally substituted by hydrogen or $C_1-C_8$ alkyl; or

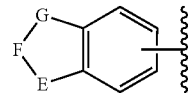

(3)

wherein in (3),
E is NH or $CH_2$; F is O or CO; and G is NH or $CH_2$; or

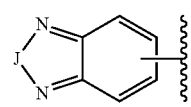

(4)

wherein in (4),
J is O, S or CO; or

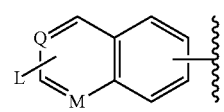

(5)

wherein in (5),
Q is CH or N;
M is CH or N; and
L/(5) is hydrogen, halo, amino, cyano, $(C_1-C_8)$alkyl, $(C_3-C_8)$cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
wherein any $(C_1-C_8)$alkyl, $(C_3-C_8)$cycloalkyl, group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$,
wherein $R^a$ and $R^b$ are defined as above; or

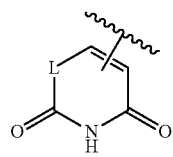

(6)

wherein in 6,
L/(6) is NH or $CH_2$; or

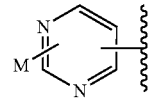

(7)

wherein in 7,
M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

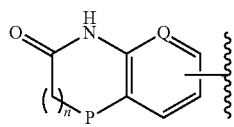

(8)

wherein in (8),
P is $CH_2$, NH, O, or S; Q/(8) is CH or N; and n is 0-2; or

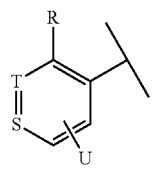

(9)

wherein in (9),
S/(9) and T(9) is C, or S/(9) is C and T(9) is N, or S/(9) is N and T/(9) is C;
R is hydrogen, amino, methyl, trifluoromethyl, halo;
U is hydrogen, halo, amino, cyano, nitro, trifluoromethyl, ($C_1$-$C_8$)alkyl, ($C_3$-$C_8$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, 4-(1H-pyrazol-4-yl),
wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$,
wherein $R^a$ and $R^b$ are defined as above.
Subgroup (I)(C)
X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;
Y is H;
Z is methyl, ethyl, n-propyl, isopropyl, trifluoromethyl, or benzyl;
$R^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;
$R_2$ is hydrogen, ($C_1$-$C_3$)alkyl, or halo, in which said ($C_1$-$C_3$)alkyl may be substituted with one to two groups selected from: amino, and ($C_1$-$C_3$)alkylamino;
$R^7$ is hydrogen, ($C_1$-$C_3$)alkyl, or alkoxy;
$R^3$ is H, methyl, or Br; and
$R^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl) phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

The present invention also relates to a method of treating T cell mediated inflammatory immune diseases or a T cell mediated hypersensitivity diseases, which comprises administering to a human in need thereof an effective amount of a compound, which is selected from the group comprising:
6-Bromo-N-[(4,6-dimethyl-2-oxo-1,2-dihydro-3-pyridinyl) methyl]-1-(1-methylethyl)-1H-indole-4-carboxamide;
N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide;
N-[(4,6-Dimethyl-2-oxo-1,2-dihydro-3-pyridinyl)methyl]-1-(1-methylethyl)-6-phenyl-1H-indole-4-carboxamide;
N-[(4,6-Dimethyl-2-oxo-1,2-dihydro-3-pyridinyl)methyl]-1-(1-methylethyl)-6-(2-oxo-2,3-dihydro-1H-benzimidazol-5-yl)-1H-indole-4-carboxamide;
1-(1-methylethyl)-N-[(6-methyl-2-oxo-4-propyl-1,2-dihydro-3-pyridinyl)methyl]-6-[2-(4-methyl-1-piperazinyl)-4-pyridinyl]-1H-indole-4-carboxamide;
1-(1-Methylethyl)-N-[(6-methyl-2-oxo-4-propyl-1,2-dihydro-3-pyridinyl)methyl]-6-(2-oxo-2,3-dihydro-1H-benzimidazol-5-yl)-1H-indole-4-carboxamide;
6-Bromo-1-cyclopentyl-N-[(4,6-dimethyl-2-oxo-1,2-dihydro-3-pyridinyl)methyl]-1H-indole-4-carboxamide;
1-(1-Methylethyl)-N-[(6-methyl-2-oxo-4-propyl-1,2-dihydro-3-pyridinyl)methyl]-6-(3-pyridinyl)-1H-indole-4-carboxamide;
6-Bromo-1-(1-methylethyl)-N-[(6-methyl-2-oxo-4-propyl-1,2-dihydro-3-pyridinyl)methyl]-1H-indole-4-carboxamide;

1-(1-Methylethyl)-N-[(6-methyl-2-oxo-4-propyl-1,2-dihydro-3-pyridinyl)methyl]-6-phenyl-1H-indole-4-carboxamide;

6-Bromo-N-[(4-cyclopropyl-6-methyl-2-oxo-1,2-dihydro-3-pyridinyl)methyl]-1-(1-methylethyl)-1H-indole-4-carboxamide;

6-Bromo-1-(1-methylethyl)-N-{[6-methyl-4-(1-methylethyl)-2-oxo-1,2-dihydro-3-pyridinyl]methyl}-1H-indole-4-carboxamide;

6-Bromo-N-[(4-cyclobutyl-6-methyl-2-oxo-1,2-dihydro-3-pyridinyl)methyl]-1-(1-methylethyl)-1H-indole-4-carboxamide;

6-Bromo-1-(1-methylethyl)-N-[(4-methyl-2-oxo-6-propyl-1,2-dihydro-3-pyridinyl)methyl]-1H-indole-4-carboxamide;

6-Bromo-1-(1-methylethyl)-N-[(6-methyl-2-oxo-4-phenyl-1,2-dihydro-3-pyridinyl)methyl]-1H-indole-4-carboxamide;

N-((4,6-dimethyl-2-oxo-1,2-dihydropyridin-3-yl)methyl)-1-isopropyl-6-(6-(2-oxopyrrolidin-1-yl)pyridin-3-yl)-1H-indole-4-carboxamide;

1-isopropyl-N-((6-methyl-2-oxo-4-propyl-1,2-dihydropyridin-3-yl)methyl)-6-(2-methylpyridin-3-yl)-1H-indole-4-carboxamide;

1-isopropyl-N-((6-methyl-2-oxo-4-propyl-1,2-dihydropyridin-3-yl)methyl)-6-(2-methylpyrimidin-5-yl)-1H-indole-4-carboxamide;

1-isopropyl-N-((6-methyl-2-oxo-4-propyl-1,2-dihydropyridin-3-yl)methyl)-6-(6-methylpyridin-3-yl)-1H-indole-4-carboxamide;

N-((4,6-dimethyl-2-oxo-1,2-dihydropyridin-3-yl)methyl)-6-(4-((dimethylamino)methyl)phenyl)-1-isopropyl-3-methyl-1H-indole-4-carboxamide;

N-((4,6-dimethyl-2-oxo-1,2-dihydropyridin-3-yl)methyl)-1-isopropyl-6-(6-methoxypyridin-3-yl)-3-methyl-1H-indole-4-carboxamide;

N-((4,6-dimethyl-2-oxo-1,2-dihydropyridin-3-yl)methyl)-1-isopropyl-3-methyl-6-(6-morpholinopyridin-3-yl)-1H-indole-4-carboxamide;

N-((4,6-dimethyl-2-oxo-1,2-dihydropyridin-3-yl)methyl)-1-isopropyl-3-methyl-6-(4-(4-methylpiperazin-1-yl)phenyl)-1H-indole-4-carboxamide;

N-((4,6-dimethyl-2-oxo-1,2-dihydropyridin-3-yl)methyl)-1-isopropyl-3-methyl-6-(3-((methylsulfonyl)methyl)phenyl)-1H-indole-4-carboxamide;

N-((4,6-dimethyl-2-oxo-1,2-dihydropyridin-3-yl)methyl)-1-isopropyl-3-methyl-6-(2-methylpyrimidin-5-yl)-1H-indole-4-carboxamide;

6-(2-aminopyrimidin-5-yl)-N-((4,6-dimethyl-2-oxo-1,2-dihydropyridin-3-yl)methyl)-1-isopropyl-3-methyl-1H-indole-4-carboxamide;

6-(6-aminopyridin-3-yl)-N-((4,6-dimethyl-2-oxo-1,2-dihydropyridin-3-yl)methyl)-1-isopropyl-3-methyl-1H-indole-4-carboxamide;

N-((4,6-dimethyl-2-oxo-1,2-dihydropyridin-3-yl)methyl)-6-(6-(dimethylamino)pyridin-3-yl)-1-isopropyl-3-methyl-1H-indole-4-carboxamide;

N-((4,6-dimethyl-2-oxo-1,2-dihydropyridin-3-yl)methyl)-1-isopropyl-3-methyl-6-(6-(pyrrolidin-1-yl)pyridin-3-yl)-1H-indole-4-carboxamide;

N-((4,6-dimethyl-2-oxo-1,2-dihydropyridin-3-yl)methyl)-6-(4-fluorophenyl)-1-isopropyl-3-methyl-1H-indole-4-carboxamide;

N-((4,6-dimethyl-2-oxo-1,2-dihydropyridin-3-yl)methyl)-1-isopropyl-6-(4-(4-isopropylpiperazin-1-yl)phenyl)-3-methyl-1H-indole-4-carboxamide;

N-((4,6-dimethyl-2-oxo-1,2-dihydropyridin-3-yl)methyl)-6-(1H-indazol-6-yl)-1-isopropyl-3-methyl-1H-indole-4-carboxamide;

6-bromo-N-[(4-ethyl-6-methyl-2-oxo-1,2-dihydro-3-pyridinyl)methyl]-3-methyl-1-(1-methylethyl)-1H-indole-4-carboxamide;

N-[(4-ethyl-6-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide;

6-{3-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide;

6-{4-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide;

N-[(4-ethyl-6-methyl-2-oxo-1,2-dihydro-3-pyridinyl)methyl]-3-methyl-1-(1-methylethyl)-6-[6-(methyloxy)-3-pyridinyl]-1H-indole-4-carboxamide;

N-[(4-ethyl-6-methyl-2-oxo-1,2-dihydro-3-pyridinyl)methyl]-3-methyl-1-(1-methylethyl)-6-(2-methyl-5-pyrimidinyl)-1H-indole-4-carboxamide;

6-(6-amino-3-pyridinyl)-N-[(4-ethyl-6-methyl-2-oxo-1,2-dihydro-3-pyridinyl)methyl]-3-methyl-1-(1-methylethyl)-1H-indole-4-carboxamide;

6-[6-(dimethylamino)-3-pyridinyl]-N-[(4-ethyl-6-methyl-2-oxo-1,2-dihydro-3-pyridinyl)methyl]-3-methyl-1-(1-methylethyl)-1H-indole-4-carboxamide;

N-[(4-ethyl-6-methyl-2-oxo-1,2-dihydro-3-pyridinyl)methyl]-3-methyl-1-(1-methylethyl)-6-(6-methyl-3-pyridinyl)-1H-indole-4-carboxamide;

N-[(4,6-dimethyl-2-oxo-1,2-dihydro-3-pyridinyl)methyl]-3-methyl-1-(1-methylethyl)-6-(1H-pyrazol-3-yl)-1H-indole-4-carboxamide;

N-[(4,6-dimethyl-2-oxo-1,2-dihydro-3-pyridinyl)methyl]-3-methyl-1-(1-methylethyl)-6-(1-methyl-1H-pyrazol-4-yl)-1H-indole-4-carboxamide;

N-[(4,6-dimethyl-2-oxo-1,2-dihydro-3-pyridinyl)methyl]-3-methyl-1-(1-methylethyl)-6-(1H-pyrazol-4-yl)-1H-indole-4-carboxamide;

N-[(4,6-dimethyl-2-oxo-1,2-dihydro-3-pyridinyl)methyl]-3-methyl-1-(1-methylethyl)-6-[1-(2-pyridinylmethyl)-1H-pyrazol-4-yl]-1H-indole-4-carboxamide;

N-[(4,6-dimethyl-2-oxo-1,2-dihydro-3-pyridinyl)methyl]-3-methyl-1-(1-methylethyl)-6-(1H-pyrrolo[2,3-b]pyridin-5-yl)-1H-indole-4-carboxamide;

N-[(4,6-dimethyl-2-oxo-1,2-dihydro-3-pyridinyl)methyl]-3-methyl-1-(1-methylethyl)-6-[1-(2-thienylmethyl)-1H-pyrazol-4-yl]-1H-indole-4-carboxamide;

N-((4,6-dimethyl-2-oxo-1,2-dihydropyridin-3-yl)methyl)-1-isopropyl-3-methyl-6-(3-(methylsulfonamidomethyl)phenyl)-1H-indole-4-carboxamide;

N-((4-benzyl-6-methyl-2-oxo-1,2-dihydropyridin-3-yl)methyl)-6-bromo-1-isopropyl-3-methyl-1H-indole-4-carboxamide;

6-(6-acetamidopyridin-3-yl)-N-((4,6-dimethyl-2-oxo-1,2-dihydropyridin-3-yl)methyl)-1-isopropyl-3-methyl-1H-indole-4-carboxamide;

6-(6-acetamidopyridin-3-yl)-1-isopropyl-3-methyl-N-((6-methyl-2-oxo-4-propyl-1,2-dihydropyridin-3-yl)methyl)-1H-indole-4-carboxamide;

1-isopropyl-3-methyl-N-((6-methyl-2-oxo-4-propyl-1,2-dihydropyridin-3-yl)methyl)-6-(1-(2-morpholinoethyl)-1H-pyrazol-4-yl)-1H-indole-4-carboxamide;

N-[(4,6-dimethyl-2-oxo-1,2-dihydro-3-pyridinyl)methyl]-3-methyl-1-(1-methylethyl)-6-(3-pyridinyl)-1H-indole-4-carboxamide;

6-bromo-3-methyl-1-(1-methylethyl)-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide;

3-methyl-1-(1-methylethyl)-N-[(6-methyl-2-oxo-4-propyl-1,2-dihydro-3-pyridinyl)methyl]-6-(2-methyl-3-pyridinyl)-1H-indole-4-carboxamide;

3-methyl-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide;

3-methyl-1-(1-methylethyl)-N-[(6-methyl-2-oxo-4-propyl-1,2-dihydro-3-pyridinyl)methyl]-6-[5-(4-methyl-1-piperazinyl)-3-pyridinyl]-1H-indole-4-carboxamide;

3-methyl-1-(1-methylethyl)-N-[(6-methyl-2-oxo-4-propyl-1,2-dihydro-3-pyridinyl)methyl]-6-(6-methyl-3-pyridinyl)-1H-indole-4-carboxamide;

6-{4-[(dimethylamino)methyl]phenyl}-3-methyl-1-(1-methylethyl)-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide;

N-[(4,6-dimethyl-2-oxo-1,2-dihydro-3-pyridinyl)methyl]-1-(1-methylethyl)-6-(3-pyridinyl)-1H-indole-4-carboxamide;

6-bromo-1-cyclopentyl-N-[(6-methyl-2-oxo-4-propyl-1,2-dihydro-3-pyridinyl)methyl]-1H-indole-4-carboxamide;

1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide;

6-bromo-1-cyclobutyl-N-[(6-methyl-2-oxo-4-propyl-1,2-dihydro-3-pyridinyl)methyl]-1H-indole-4-carboxamide;

1-cyclobutyl-6-{4-[(dimethylamino)methyl]phenyl}-N-[(6-methyl-2-oxo-4-propyl-1,2-dihydro-3-pyridinyl)methyl]-1H-indole-4-carboxamide;

1-cyclopropyl-6-{4-[(dimethylamino)methyl]phenyl}-N-[(4,6-dimethyl-2-oxo-1,2-dihydro-3-pyridinyl)methyl]-3-methyl-1H-indole-4-carboxamide;

1-cyclopropyl-N-[(4,6-dimethyl-2-oxo-1,2-dihydro-3-pyridinyl)methyl]-3-methyl-6-[6-(methyloxy)-3-pyridinyl]-1H-indole-4-carboxamide;

N-[(4,6-dimethyl-2-oxo-1,2-dihydro-3-pyridinyl)methyl]-3-methyl-1-(1-methylethyl)-6-[3-(methylsulfonyl)phenyl]-1H-indole-4-carboxamide;

6-bromo-1-cyclopentyl-N-[(4,6-dimethyl-2-oxo-1,2-dihydro-3-pyridinyl)methyl]-3-methyl-1H-indole-4-carboxamide;

1-cyclopentyl-6-{4-[(dimethylamino)methyl]phenyl}-N-[(4,6-dimethyl-2-oxo-1,2-dihydro-3-pyridinyl)methyl]-3-methyl-1H-indole-4-carboxamide;

3-methyl-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide;

N-((4,6-dimethyl-2-oxo-1,2-dihydropyridin-3-yl)methyl)-1-isopropyl-3-methyl-6-(2-(4-methylpiperazin-1-yl)pyrimidin-5-yl)-1H-indole-4-carboxamide;

6-bromo-1-(1-methylethyl)-N-[(6-methyl-2-oxo-1,2-dihydro-4,4'-bipyridin-3-yl)methyl]-1H-indole-4-carboxamide;

6-bromo-N-{[4-(ethylamino)-6-methyl-2-oxo-1,2-dihydro-3-pyridinyl]methyl}-1-(1-methylethyl)-1H-indole-4-carboxamide;

N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide;

6-bromo-1-(1-methylethyl)-N-{[6-methyl-2-oxo-4-(1-pyrrolidinyl)-1,2-dihydro-3-pyridinyl]methyl}-1H-indole-4-carboxamide;

1-(1-methylethyl)-N-{[6-methyl-2-oxo-4-(phenylamino)-1,2-dihydro-3-pyridinyl]methyl}-6-[6-(4-methyl-1-piperazinyl)-3-pyridinyl]-1H-indole-4-carboxamide;

6-bromo-N-[(4-ethyl-6-methyl-2-oxo-1,2-dihydro-3-pyridinyl)methyl]-1-(1-methylethyl)-1H-indole-4-carboxamide;

6-{4-[(dimethylamino)methyl]phenyl}-N-[(4-ethyl-6-methyl-2-oxo-1,2-dihydro-3-pyridinyl)methyl]-1-(1-methylethyl)-1H-indole-4-carboxamide;

N-[(4-ethyl-6-methyl-2-oxo-1,2-dihydro-3-pyridinyl)methyl]-1-(1-methylethyl)-6-[6-(4-methyl-1-piperazinyl)-3-pyridinyl]-1H-indole-4-carboxamide;

N-[(4-ethyl-6-methyl-2-oxo-1,2-dihydro-3-pyridinyl)methyl]-1-(1-methylethyl)-6-[6-(methyloxy)-3-pyridinyl]-1H-indole-4-carboxamide;

6-[6-(acetylamino)-3-pyridinyl]-1-(1-methylethyl)-N-[(6-methyl-2-oxo-4-propyl-1,2-dihydro-3-pyridinyl)methyl]-1H-indole-4-carboxamide;

6-(4-fluorophenyl)-1-(1-methylethyl)-N-[(6-methyl-2-oxo-4-propyl-1,2-dihydro-3-pyridinyl)methyl]-1H-indole-4-carboxamide;

6-[4-(acetylamino)phenyl]-1-(1-methylethyl)-N-[(6-methyl-2-oxo-4-propyl-1,2-dihydro-3-pyridinyl)methyl]-1H-indole-4-carboxamide;

methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate;

methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate;

methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate;

6-bromo-N-((6-ethyl-4-methyl-2-oxo-1,2-dihydropyridin-3-yl)methyl)-1-isopropyl-1H-indole-4-carboxamide;

N-((6-benzyl-4-methyl-2-oxo-1,2-dihydropyridin-3-yl)methyl)-6-bromo-1-isopropyl-1H-indole-4-carboxamide;

6-bromo-N-((6-cyclobutyl-4-methyl-2-oxo-1,2-dihydropyridin-3-yl)methyl)-1-isopropyl-1H-indole-4-carboxamide;

6-bromo-1-(1-methylethyl)-N-({6-methyl-4-[(methyloxy)methyl]-2-oxo-1,2-dihydro-3-pyridinyl}methyl)-1H-indole-4-carboxamide;

1-(1-methylethyl)-N-({6-methyl-4-[(methyloxy)methyl]-2-oxo-1,2-dihydro-3-pyridinyl}methyl)-6-[6-(4-methyl-1-piperazinyl)-3-pyridinyl]-1H-indole-4-carboxamide;

1-(1-methylethyl)-N-({6-methyl-4-[(methyloxy)methyl]-2-oxo-1,2-dihydro-3-pyridinyl}methyl)-6-[2-(4-methyl-1-piperazinyl)-4-pyridinyl]-1H-indole-4-carboxamide;

1-(1-methylethyl)-N-({6-methyl-4-[(methyloxy)methyl]-2-oxo-1,2-dihydro-3-pyridinyl}methyl)-6-(3-pyridinyl)-1H-indole-4-carboxamide;

1-(1-methylethyl)-N-({6-methyl-4-[(methyloxy)methyl]-2-oxo-1,2-dihydro-3-pyridinyl}methyl)-6-[6-(4-morpholinyl)-3-pyridinyl]-1H-indole-4-carboxamide;

6-bromo-1-cyclopropyl-N-[(6-methyl-2-oxo-4-propyl-1,2-dihydro-3-pyridinyl)methyl]-1H-indole-4-carboxamide;

1-cyclopropyl-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide;

1-cyclopropyl-N-[(6-methyl-2-oxo-4-propyl-1,2-dihydro-3-pyridinyl)methyl]-6-(3-pyridinyl)-1H-indole-4-carboxamide;

N-((4,6-dimethyl-2-oxo-1,2-dihydropyridin-3-yl)methyl)-1-isopropyl-3-methyl-6-(4-(piperazin-1-yl)phenyl)-1H-indole-4-carboxamide;

N-[(4-ethyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide;

1-isopropyl-3-methyl-N-((6-methyl-2-oxo-4-propyl-1,2-dihydropyridin-3-yl)methyl)-6-(2-(piperazin-1-yl)pyridin-4-yl)-1H-indole-4-carboxamide;

N-((4,6-dimethyl-2-oxo-1,2-dihydropyridin-3-yl)methyl)-1-isopropyl-3-methyl-6-(2-(piperazin-1-yl)pyridin-4-yl)-1H-indole-4-carboxamide;

1-cyclopropyl-N-[(4,6-dimethyl-2-oxo-1,2-dihydro-3-pyridinyl)methyl]-3-methyl-6-[6-(1-piperazinyl)-3-pyridinyl]-1H-indole-4-carboxamide;

methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate;

methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate;

methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate;

1-isopropyl-N-((6-methyl-2-oxo-4-propyl-1,2-dihydropyridin-3-yl)methyl)-6-(methylsulfonyl)-1H-indole-4-carboxamide;

N-((4,6-dimethyl-2-oxo-1,2-dihydropyridin-3-yl)methyl)-1-isopropyl-3-methyl-6-(methylsulfonyl)-1H-indole-4-carboxamide;

N-((4-ethyl-6-methyl-2-oxo-1,2-dihydropyridin-3-yl)methyl)-1-isopropyl-3-methyl-6-(methylsulfonyl)-1H-indole-4-carboxamide;

N-((4-benzyl-6-methyl-2-oxo-1,2-dihydropyridin-3-yl)methyl)-1-isopropyl-3-methyl-6-(methylsulfonyl)-1H-indole-4-carboxamide;

1-isopropyl-3-methyl-N-((6-methyl-2-oxo-4-propyl-1,2-dihydropyridin-3-yl)methyl)-6-(methylsulfonyl)-1H-indole-4-carboxamide;

3-({2-[6-(cyclopropylsulfonyl)-3-m ethyl-1-(1-methylethyl)-1H-indol-4-yl]-2-oxoethyl}amino)-4,6-dimethyl-2(1H)-pyridinone;

3-({2-[6-(cyclopropylsulfonyl)-3-methyl-1-(1-methylethyl)-1H-indol-4-yl]-2-oxoethyl}amino)-4,6-dimethyl-2(1H)-pyridinone;

3-methyl-1-(1-methylethyl)-N-{[6-methyl-2-oxo-4-(phenylmethyl)-1,2-dihydro-3-pyridinyl]methyl}-6-(methyloxy)-1H-indole-4-carboxamide;

N-[(4-ethyl-6-methyl-2-oxo-1,2-dihydro-3-pyridinyl)methyl]-3-methyl-1-(1-methylethyl)-6-(methyloxy)-1H-indole-4-carboxamide;

3-methyl-1-(1-methylethyl)-N-[(6-methyl-2-oxo-4-propyl-1,2-dihydro-3-pyridinyl)methyl]-6-(methyloxy)-1H-indole-4-carboxamide;

6-bromo-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-1-(1-methylethyl)-6-(methyloxy)-1H-indole-4-carboxamide;

N-[(4,6-dimethyl-2-oxo-1,2-dihydro-3-pyridinyl)methyl]-3-methyl-1-(1-methylethyl)-6-(methyloxy)-1H-indole-4-carboxamide;

6-chloro-N-[(4,6-dimethyl-2-oxo-1,2-dihydro-3-pyridinyl)methyl]-3-methyl-1-(1-methylethyl)-1H-indole-4-carboxamide;

6-{3-[(dimethylamino)methyl]phenyl}-N-[(4,6-dimethyl-2-oxo-1,2-dihydro-3-pyridinyl)methyl]-3-methyl-1-(1-methylethyl)-1H-indole-4-carboxamide;

6-bromo-3-methyl-1-(1-methylethyl)-N-{[6-methyl-4-(4-morpholinylmethyl)-2-oxo-1,2-dihydro-3-pyridinyl]methyl}-1H-indole-4-carboxamide;

N-[(4,6-dimethyl-2-oxo-1,2-dihydro-3-pyridinyl)methyl]-6-iodo-1-(1-methylethyl)-1H-indole-4-carboxamide;

6-iodo-1-(1-methylethyl)-N-[(6-methyl-2-oxo-4-propyl-1,2-dihydro-3-pyridinyl)methyl]-1H-indole-4-carboxamide;

6-bromo-1-ethyl-N-[(6-methyl-2-oxo-4-propyl-1,2-dihydro-3-pyridinyl)methyl]-1H-indole-4-carboxamide;

6-bromo-N-[(6-methyl-2-oxo-4-propyl-1,2-dihydro-3-pyridinyl)methyl]-1-propyl-1H-indole-4-carboxamide;

3-({2-[6-chloro-1-(1-methylethyl)-1H-indol-4-yl]-2-oxoethyl}amino)-4,6-dimethyl-2(1H)-pyridinone;

3-({2-[6-chloro-1-(1-methylethyl)-1H-indol-4-yl]-2-oxoethyl}amino)-6-methyl-4-propyl-2(1H)-pyridinone;

3-({2-[6-chloro-3-methyl-1-(1-methylethyl)-1H-indol-4-yl]-2-oxoethyl}amino)-6-methyl-4-propyl-2(1H)-pyridinone;

N-[(4,6-dimethyl-2-oxo-1,2-dihydro-3-pyridinyl)methyl]-6-fluoro-1-(1-methylethyl)-1H-indole-4-carboxamide;

3-({2-[6-fluoro-1-(1-methylethyl)-1H-indol-4-yl]-2-oxoethyl}amino)-6-methyl-4-propyl-2(1H)-pyridinone;

N-((4,6-dimethyl-2-oxo-1,2-dihydropyridin-3-yl)methyl)-1-isopropyl-3-methyl-6-(1H-tetrazol-5-yl)-1H-indole-4-carboxamide;

1-isopropyl-3-methyl-N-((6-methyl-2-oxo-4-propyl-1,2-dihydropyridin-3-yl)methyl)-6-(2H-tetrazol-5-yl)-1H-indole-4-carboxamide;

6-cyano-3-methyl-1-(1-methylethyl)-N-[(6-methyl-2-oxo-4-propyl-1,2-dihydro-3-pyridinyl)methyl]-1H-indole-4-carboxamide;

6-bromo-3-chloro-1-isopropyl-N-((6-methyl-2-oxo-4-propyl-1,2-dihydropyridin-3-yl)methyl)-1H-indole-4-carboxamide;

6-bromo-3-chloro-1-(1-methylethyl)-N-({6-methyl-4-[(methyloxy)methyl]-2-oxo-1,2-dihydro-3-pyridinyl}methyl)-1H-indole-4-carboxamide;

6-bromo-3-chloro-N-[(4,6-dimethyl-2-oxo-1,2-dihydro-3-pyridinyl)methyl]-1-(1-methylethyl)-1H-indole-4-carboxamide;

3-chloro-N-((4,6-dimethyl-2-oxo-1,2-dihydropyridin-3-yl)methyl)-1-isopropyl-6-(4-(morpholinomethyl)phenyl)-1H-indole-4-carboxamide;

3-chloro-N-((4,6-dimethyl-2-oxo-1,2-dihydropyridin-3-yl)methyl)-6-(3-fluoro-4-(morpholinomethyl)phenyl)-1-isopropyl-1H-indole-4-carboxamide;

6-(4-((1H-pyrazol-1-yl)methyl)phenyl)-3-chloro-N-((4,6-dimethyl-2-oxo-1,2-dihydropyridin-3-yl)methyl)-1-isopropyl-1H-indole-4-carboxamide;

3-chloro-N-((4,6-dimethyl-2-oxo-1,2-dihydropyridin-3-yl)methyl)-6-(2-fluorophenyl)-1-isopropyl-1H-indole-4-carboxamide;

3-chloro-6-{4-[(dimethylamino)methyl]phenyl}-N-[(4,6-dimethyl-2-oxo-1,2-dihydro-3-pyridinyl)methyl]-1-(1-methylethyl)-1H-indole-4-carboxamide;

3-chloro-N-[(4,6-dimethyl-2-oxo-1,2-dihydro-3-pyridinyl)methyl]-1-(1-methylethyl)-6-[6-(methyloxy)-3-pyridinyl]-1H-indole-4-carboxamide;

3-chloro-N-[(4,6-dimethyl-2-oxo-1,2-dihydro-3-pyridinyl)methyl]-1-(1-methylethyl)-6-(3-pyridinyl)-1H-indole-4-carboxamide;

3-chloro-6-{4-[(dimethylamino)methyl]phenyl}-1-(1-methylethyl)-N-[(6-methyl-2-oxo-4-propyl-1,2-dihydro-3-pyridinyl)methyl]-1H-indole-4-carboxamide;

3-chloro-1-(1-methylethyl)-N-[(6-methyl-2-oxo-4-propyl-1,2-dihydro-3-pyridinyl)methyl]-6-[6-(methyloxy)-3-pyridinyl]-1H-indole-4-carboxamide;

3-chloro-6-{4-[(dimethylamino)methyl]phenyl}-1-(1-methylethyl)-N-({6-methyl-4-[(methyloxy)methyl]-2-oxo-1,2-dihydro-3-pyridinyl}methyl)-1H-indole-4-carboxamide;

3-chloro-1-(1-methylethyl)-N-({6-methyl-4-[(methyloxy)methyl]-2-oxo-1,2-dihydro-3-pyridinyl}methyl)-6-[6-(methyloxy)-3-pyridinyl]-1H-indole-4-carboxamide;

3-chloro-1-isopropyl-N-((4-(methoxymethyl)-6-methyl-2-oxo-1,2-dihydropyridin-3-yl)methyl)-6-(pyridin-3-yl)-1H-indole-4-carboxamide;

3-chloro-1-isopropyl-N-((6-methyl-2-oxo-4-propyl-1,2-dihydropyridin-3-yl)methyl)-6-(6-(4-methylpiperazin-1-yl)pyridin-3-yl)-1H-indole-4-carboxamide;

3-chloro-N-((4-ethyl-6-methyl-2-oxo-1,2-dihydropyridin-3-yl)methyl)-1-isopropyl-6-(6-(4-methylpiperazin-1-yl)pyridin-3-yl)-1H-indole-4-carboxamide;

3-chloro-N-((4,6-dimethyl-2-oxo-1,2-dihydropyridin-3-yl)methyl)-1-isopropyl-6-(6-(4-methylpiperazin-1-yl)pyridin-3-yl)-1H-indole-4-carboxamide;

3-chloro-N-((4,6-dimethyl-2-oxo-1,2-dihydropyridin-3-yl)methyl)-1-isopropyl-6-(4-(trifluoromethyl)phenyl)-1H-indole-4-carboxamide;

3-chloro-N-((4,6-dimethyl-2-oxo-1,2-dihydropyridin-3-yl)methyl)-1-isopropyl-6-(6-(trifluoromethyl)pyridin-3-yl)-1H-indole-4-carboxamide;

3-chloro-N-((4,6-dimethyl-2-oxo-1,2-dihydropyridin-3-yl)methyl)-6-(3-fluorophenyl)-1-isopropyl-1H-indole-4-carboxamide;

3-chloro-6-(3,5-difluorophenyl)-N-((4,6-dimethyl-2-oxo-1,2-dihydropyridin-3-yl)methyl)-1-isopropyl-1H-indole-4-carboxamide;

3-chloro-6-(3,4-difluorophenyl)-N-((4,6-dimethyl-2-oxo-1,2-dihydropyridin-3-yl)methyl)-1-isopropyl-1H-indole-4-carboxamide;

3-chloro-N-((4,6-dimethyl-2-oxo-1,2-dihydropyridin-3-yl)methyl)-6-(4-fluoro-3-hydroxyphenyl)-1-isopropyl-1H-indole-4-carboxamide;

3-chloro-N-((4,6-dimethyl-2-oxo-1,2-dihydropyridin-3-yl)methyl)-6-(4-fluoro-3-methoxyphenyl)-1-isopropyl-1H-indole-4-carboxamide;

3-chloro-N-((4,6-dimethyl-2-oxo-1,2-dihydropyridin-3-yl)methyl)-1-isopropyl-6-(4-methoxyphenyl)-1H-indole-4-carboxamide;

3-chloro-N-((4,6-dimethyl-2-oxo-1,2-dihydropyridin-3-yl)methyl)-1-isopropyl-6-(3-methoxyphenyl)-1H-indole-4-carboxamide;

3-chloro-6-(3-cyano-4-fluorophenyl)-N-((4,6-dimethyl-2-oxo-1,2-dihydropyridin-3-yl)methyl)-1-isopropyl-1H-indole-4-carboxamide;

3-chloro-N-((4,6-dimethyl-2-oxo-1,2-dihydropyridin-3-yl)methyl)-1-isopropyl-6-phenyl-1H-indole-4-carboxamide;

3-chloro-N-((4,6-dimethyl-2-oxo-1,2-dihydropyridin-3-yl)methyl)-6-(4-fluorophenyl)-1-isopropyl-1H-indole-4-carboxamide;

3-chloro-N-((4,6-dimethyl-2-oxo-1,2-dihydropyridin-3-yl)methyl)-6-(3-fluoro-4-morpholinophenyl)-1-isopropyl-1H-indole-4-carboxamide;

3-chloro-N-((4,6-dimethyl-2-oxo-1,2-dihydropyridin-3-yl)methyl)-6-(6-fluoropyridin-3-yl)-1-isopropyl-1H-indole-4-carboxamide;

3-chloro-N-[(4,6-dimethyl-2-oxo-1,2-dihydro-3-pyridinyl)methyl]-1-(1-methylethyl)-6-(1H-pyrrolo[2,3-b]pyridin-5-yl)-1H-indole-4-carboxamide;

3-chloro-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide;

6-bromo-1-cyclopropyl-N-[(4,6-dimethyl-2-oxo-1,2-dihydro-3-pyridinyl)methyl]-3-methyl-1H-indole-4-carboxamide;

6-bromo-3-chloro-1-cyclopentyl-N-((4,6-dimethyl-2-oxo-1,2-dihydropyridin-3-yl)methyl)-1H-indole-4-carboxamide;

6-cyano-N-((4,6-dimethyl-2-oxo-1,2-dihydropyridin-3-yl)methyl)-1-isopropyl-3-methyl-1H-indole-4-carboxamide;

3-methyl-1-(1-methylethyl)-N-{[6-methyl-4-(1-methylethyl)-2-oxo-1,2-dihydro-3-pyridinyl]methyl}-6-[6-(4-methyl-1-piperazinyl)-3-pyridinyl]-1H-indole-4-carboxamide;

6-(4-{[2-(dimethylamino)ethyl]oxy}phenyl)-N-[(4,6-dimethyl-2-oxo-1,2-dihydro-3-pyridinyl)methyl]-3-methyl-1-(1-methylethyl)-1H-indole-4-carboxamide;

6-bromo-N-[(4,6-dimethyl-2-oxo-1,2-dihydro-3-pyridinyl)methyl]-3-fluoro-1-(1-methylethyl)-1H-indole-4-carboxamide;

6-bromo-3-fluoro-1-(1-methylethyl)-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-3-fluoro-1-(1-methylethyl)-6-[6-(4-methyl-1-piperazinyl)-3-pyridinyl]-1H-indole-4-carboxamide;

3-bromo-N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide;

3-fluoro-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide;

3-methyl-1-(1-methylethyl)-N-[(6-methyl-2-oxo-4-propyl-1,2-dihydro-3-pyridinyl)methyl]-6-(4-pyridazinyl)-1H-indole-4-carboxamide;

N-[(4,6-dimethyl-2-oxo-1,2-dihydro-3-pyridinyl)methyl]-3-methyl-1-(1-methylethyl)-6-(6-phenyl-3-pyridinyl)-1H-indole-4-carboxamide;

6-[3-(aminomethyl)phenyl]-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-[5-(4-morpholinylcarbonyl)-3-pyridinyl]-1H-indole-4-carboxamide;

3-methyl-1-(1-methylethyl)-N-{[6-methyl-4-(1-methylethyl)-2-oxo-1,2-dihydro-3-pyridinyl]methyl}-6-[6-(1-piperazinyl)-3-pyridinyl]-1H-indole-4-carboxamide;

N-[(4,6-dimethyl-2-oxo-1,2-dihydro-3-pyridinyl)methyl]-6-(6-formyl-3-pyridinyl)-3-methyl-1-(1-methylethyl)-1H-indole-4-carboxamide;

N-[(4-cyclopropyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide;

N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide;

6-(4-(2-(dimethylamino)ethyl)phenyl)-1-isopropyl-3-methyl-N-((6-methyl-2-oxo-4-propyl-1,2-dihydropyridin-3-yl)methyl)-1H-indole-4-carboxamide;

3,6-dibromo-N-[(4,6-dimethyl-2-oxo-1,2-dihydro-3-pyridinyl)methyl]-1-(1-methylethyl)-1H-indole-4-carboxamide;

N-{[(1,1-dimethylethyl)oxy]carbonyl}-4-[4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine;

N-[(4,6-dimethyl-2-oxo-1,2-dihydro-3-pyridinyl)methyl]-6-[6-(1H-imidazol-1-ylmethyl)-3-pyridinyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-(5,6,7,8-tetrahydro-1,6-naphthyridin-3-yl)-1H-indole-4-carboxamide;

N-[(4,6-dimethyl-2-oxo-1,2-dihydro-3-pyridinyl)methyl]-3-methyl-1-(1-methylethyl)-6-[2-(4-methyl-1-piperazinyl)-1,3-thiazol-5-yl]-1H-indole-4-carboxamide;

N-[(4,6-dimethyl-2-oxo-1,2-dihydro-3-pyridinyl)methyl]-6-{6-[(9aS)-hexahydropyrazino[2,1-c][1,4]oxazin-8(1H)-yl]-3-pyridinyl}-3-methyl-1-(1-methylethyl)-1H-indole-4-carboxamide;

3-methyl-1-(1-methylethyl)-N-[(6-methyl-2-oxo-4-propyl-1,2-dihydro-3-pyridinyl)methyl]-6-(5,6,7,8-tetrahydro-1,8-naphthyridin-3-yl)-1H-indole-4-carboxamide;

6-[6-(4-ethyl-1-piperazinyl)-3-pyridinyl]-3-methyl-1-(1-methylethyl)-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide;

3-methyl-1-(1-methylethyl)-6-{6-[4-(1-methylethyl)-1-piperazinyl]-3-pyridinyl}-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-3-methyl-1-(1-methylethyl)-6-[6-(4-morpholinylmethyl)-2-pyridinyl]-1H-indole-4-carboxamide;

N-[(4,6-dimethyl-2-oxo-1,2-dihydro-3-pyridinyl)methyl]-3-methyl-1-(1-methylethyl)-6-[6-(4-morpholinyl)-2-pyridinyl]-1H-indole-4-carboxamide;

N-[(4,6-dimethyl-2-oxo-1,2-dihydro-3-pyridinyl)methyl]-3-methyl-1-(1-methylethyl)-6-(6-methyl-2-pyridinyl)-1H-indole-4-carboxamide;

N-[(4,6-dimethyl-2-oxo-1,2-dihydro-3-pyridinyl)methyl]-3-methyl-1-(1-methylethyl)-6-[2-(4-morpholinyl)-4-pyrimidinyl]-1H-indole-4-carboxamide;

N-[(4,6-dimethyl-2-oxo-1,2-dihydro-3-pyridinyl)methyl]-3-methyl-1-(1-methylethyl)-6-(2-pyrimidinyl)-1H-indole-4-carboxamide;

6-{6-[(dimethylamino)methyl]-2-pyridinyl}-N-[(4,6-dimethyl-2-oxo-1,2-dihydro-3-pyridinyl)methyl]-3-methyl-1-(1-methylethyl)-1H-indole-4-carboxamide;

6-(6-amino-2-pyridinyl)-N-[(4,6-dimethyl-2-oxo-1,2-dihydro-3-pyridinyl)methyl]-3-methyl-1-(1-methylethyl)-1H-indole-4-carboxamide;

6-[2-amino-6-(4-morpholinyl)-4-pyrimidinyl]-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-6-[2-(methylamino)-4-pyrimidinyl]-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-(4-pyrimidinyl)-1H-indole-4-carboxamide;

N-[(4,6-dimethyl-2-oxo-1,2-dihydro-3-pyridinyl)methyl]-6-[2-(ethylamino)-4-pyrimidinyl]-3-methyl-1-(1-methylethyl)-1H-indole-4-carboxamide;

6-(2-amino-4-pyrimidinyl)-N-[(4,6-dimethyl-2-oxo-1,2-dihydro-3-pyridinyl)methyl]-3-methyl-1-(1-methylethyl)-1H-indole-4-carboxamide;

6-(1H-benzimidazol-5-yl)-N-[(4,6-dimethyl-2-oxo-1,2-dihydro-3-pyridinyl)methyl]-3-methyl-1-(1-methylethyl)-1H-indole-4-carboxamide;

6-(3-amino-1H-indazol-6-yl)-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-(1-methyl-1H-indazol-6-yl)-1H-indole-4-carboxamide;

N-[(4,6-dimethyl-2-oxo-1,2-dihydro-3-pyridinyl)methyl]-3-methyl-1-(1-methylethyl)-6-(5-methyl-1H-indazol-6-yl)-1H-indole-4-carboxamide;

N-[(4,6-dimethyl-2-oxo-1,2-dihydro-3-pyridinyl)methyl]-6-[6-(4-ethyl-1-piperazinyl)-3-pyridinyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-{6-[4-(1-methylethyl)-1-piperazinyl]-3-pyridinyl}-1H-indole-4-carboxamide;

6-chloro-3-methyl-1-(1-methylethyl)-N-{[6-methyl-4-(1-methylpropyl)-2-oxo-1,2-dihydro-3-pyridinyl]methyl}-1H-indole-4-carboxamide;

6-bromo-3-methyl-1-(1-methylethyl)-N-{[6-methyl-4-(1-methylpropyl)-2-oxo-1,2-dihydro-3-pyridinyl]methyl}-1H-indole-4-carboxamide;

3-methyl-1-(1-methylethyl)-N-{[6-methyl-4-(1-methylpropyl)-2-oxo-1,2-dihydro-3-pyridinyl]methyl}-6-[6-(4-methyl-1-piperazinyl)-3-pyridinyl]-1H-indole-4-carboxamide;

6-(6-chloro-3-pyridinyl)-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-6-[6-(1H-imidazol-1-yl)-3-pyridinyl]-3-methyl-1-(1-methylethyl)-1H-indole-4-carboxamide;

6-[6-(4-cyclopropyl-1-piperazinyl)-3-pyridinyl]-N-[(4,6-dimethyl-2-oxo-1,2-dihydro-3-pyridinyl)methyl]-3-methyl-1-(1-methylethyl)-1H-indole-4-carboxamide;

6-bromo-N-[(4,6-dimethyl-2-oxo-1,2-dihydro-3-pyridinyl)methyl]-3-methyl-1-(1-methylpropyl)-1H-indole-4-carboxamide;

6-{6-[2-(dimethylamino)ethyl]-3-pyridinyl}-N-[(4,6-dimethyl-2-oxo-1,2-dihydro-3-pyridinyl)methyl]-3-methyl-1-(1-methylethyl)-1H-indole-4-carboxamide;

6-{3-[(dimethylamino)methyl]phenyl}-N-[(4,6-dimethyl-2-oxo-1,2-dihydro-3-pyridinyl)methyl]-3-methyl-1-(1-methylpropyl)-1H-indole-4-carboxamide;

N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide;

N-[(4,6-dimethyl-2-oxo-1,2-dihydro-3-pyridinyl)methyl]-6-{6-[(3R,5S)-3,5-dimethyl-1-piperazinyl]-3-pyridinyl}-3-methyl-1-(1-methylethyl)-1H-indole-4-carboxamide;

6-{6-[3-(dimethylamino)-1-pyrrolidinyl]-3-pyridinyl}-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylpropyl)-6-[6-(1-piperazinyl)-3-pyridinyl]-1H-indole-4-carboxamide;

N-[(4,6-dimethyl-2-oxo-1,2-dihydro-3-pyridinyl)methyl]-3-methyl-1-(1-methylethyl)-6-[6-(4-methylhexahydro-1H-1,4-diazepin-1-yl)-3-pyridinyl]-1H-indole-4-carboxamide;

N-[(4,6-dimethyl-2-oxo-1,2-dihydro-3-pyridinyl)methyl]-3-methyl-1-(1-methylethyl)-6-[6-(4-piperidinyl)-3-pyridinyl]-1H-indole-4-carboxamide;

6-bromo-1-isopropyl-N-((6-methyl-2-oxo-4-((6-(trifluoromethyl)pyridin-2-yl)methyl)-1,2-dihydropyridin-3-yl)methyl)-1H-indole-4-carboxamide;

N-((4,6-dimethyl-2-oxo-1,2-dihydropyridin-3-yl)methyl)-1-isopropyl-3-methyl-6-(pyridazin-4-yl)-1H-indole-4-carboxamide;

N-[(6-amino-4-methyl-2-oxo-1,2-dihydro-3-pyridinyl)methyl]-6-chloro-3-methyl-1-(1-methylethyl)-1H-indole-4-carboxamide;

N-[(6-amino-4-methyl-2-oxo-1,2-dihydro-3-pyridinyl)methyl]-6-bromo-3-methyl-1-(1-methylethyl)-1H-indole-4-carboxamide;

6-bromo-N-[(4,6-dimethyl-2-oxo-1,2-dihydro-3-pyridinyl)methyl]-3-methyl-1-[(3R)-tetrahydro-3-furanyl]-1H-indole-4-carboxamide;

6-bromo-3-methyl-1-(1-methylethyl)-N-{[6-methyl-2-oxo-4-(1H-pyrazol-1-ylmethyl)-1,2-dihydro-3-pyridinyl]methyl}-1H-indole-4-carboxamide;

6-bromo-1-(1-methylethyl)-N-{[6-methyl-2-oxo-4-(1H-pyrazol-1-ylmethyl)-1,2-dihydro-3-pyridinyl]methyl}-1H-indole-4-carboxamide;

3-methyl-1-(1-methylethyl)-N-[(6-methyl-2-oxo-4-propyl-1,2-dihydro-3-pyridinyl)methyl]-6-(3-pyridinyl)-1H-indole-4-carboxamide;

6-[(aminocarbonyl)amino]-N-[(4,6-dimethyl-2-oxo-1,2-dihydro-3-pyridinyl)methyl]-3-methyl-1-(1-methylethyl)-1H-indole-4-carboxamide;

1-cyclopentyl-N-[(4,6-dimethyl-2-oxo-1,2-dihydro-3-pyridinyl)methyl]-3-methyl-6-[6-(4-methyl-1-piperazinyl)-3-pyridinyl]-1H-indole-4-carboxamide;

N-[(4,6-dimethyl-2-oxo-1,2-dihydro-3-pyridinyl)methyl]-3-methyl-1-(1-methylpropyl)-6-[6-(1-piperazinyl)-3-pyridinyl]-1H-indole-4-carboxamide;

N-[(4,6-dimethyl-2-oxo-1,2-dihydro-3-pyridinyl)methyl]-3-methyl-1-(1-methylpropyl)-6-[6-(1-piperazinyl)-3-pyridinyl]-1H-indole-4-carboxamide;

1-cyclopentyl-N-[(4,6-dimethyl-2-oxo-1,2-dihydro-3-pyridinyl)methyl]-3-methyl-6-[6-(1-piperazinyl)-3-pyridinyl]-1H-indole-4-carboxamide;

6-bromo-N-[(4,6-dimethyl-2-oxo-1,2-dihydro-3-pyridinyl)methyl]-3-methyl-1-[(1R)-1-methyl-2-(methyloxy)ethyl]-1H-indole-4-carboxamide;

N-[(4,6-dimethyl-2-oxo-1,2-dihydro-3-pyridinyl)methyl]-3-methyl-1-[(1S)-1-methyl-2-(methyloxy)ethyl]-6-[6-(1-piperazinyl)-3-pyridinyl]-1H-indole-4-carboxamide;

N-[(4,6-dimethyl-2-oxo-1,2-dihydro-3-pyridinyl)methyl]-3-methyl-1-[(1S)-1-methyl-2-(methyloxy)ethyl]-6-[6-(4-methyl-1-piperazinyl)-3-pyridinyl]-1H-indole-4-carboxamide;

6-bromo-N-[(4,6-dimethyl-2-oxo-1,2-dihydro-3-pyridinyl)methyl]-3-methyl-1-[(1S)-1-methyl-2-(methyloxy)ethyl]-1H-indole-4-carboxamide;

N-[(4,6-dimethyl-2-oxo-1,2-dihydro-3-pyridinyl)methyl]-3-methyl-6-{6-[(methylamino)methyl]-3-pyridinyl}-1-(1-methylethyl)-1H-indole-4-carboxamide;

6-[6-(2,6-dimethyl-4-morpholinyl)-3-pyridinyl]-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-[6-(2-methyl-4-morpholinyl)-3-pyridinyl]-1H-indole-4-carboxamide;

3-methyl-1-(1-methylethyl)-N-[(6-methyl-2-oxo-4-propyl-1,2-dihydro-3-pyridinyl)methyl]-6-(7-oxo-5,6,7,8-tetrahydro-1,8-naphthyridin-3-yl)-1H-indole-4-carboxamide;

N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide;

N-((4,6-dimethyl-2-oxo-1,2-dihydropyridin-3-yl)methyl)-1-isopropyl-3-methyl-6-(pyridazin-4-yl)-1H-indole-4-carboxamide;

N-((4,6-dimethyl-2-oxo-1,2-dihydropyridin-3-yl)methyl)-3-fluoro-1-isopropyl-6-(6-(4-methylpiperazin-1-yl)pyridin-3-yl)-1H-indole-4-carboxamide;

(R)—N-((4,6-dimethyl-2-oxo-1,2-dihydropyridin-3-yl)methyl)-3-methyl-6-(6-(4-methylpiperazin-1-yl)pyridin-3-yl)-1-(tetrahydrofuran-3-yl)-1H-indole-4-carboxamide;

(S)—N-((4,6-dimethyl-2-oxo-1,2-dihydropyridin-3-yl)methyl)-1-(1-methoxypropan-2-yl)-3-methyl-6-(6-(piperazin-1-yl)pyridin-3-yl)-1H-indole-4-carboxamide;

6-bromo-N-((4,6-dimethyl-2-oxo-1,2-dihydropyridin-3-yl)methyl)-1-(1-(dimethylamino)propan-2-yl)-3-methyl-1H-indole-4-carboxamide;

N-((4,6-dimethyl-2-oxo-1,2-dihydropyridin-3-yl)methyl)-1-isopropyl-3-methyl-6-(1H-pyrazolo[3,4-b]pyridin-5-yl)-1H-indole-4-carboxamide;

N-((4,6-dimethyl-2-oxo-1,2-dihydropyridin-3-yl)methyl)-1-(2-(dimethylamino)propyl)-3-methyl-6-(6-(piperazin-1-yl)pyridin-3-yl)-1H-indole-4-carboxamide;

6-bromo-N-((4,6-dimethyl-2-oxo-1,2-dihydropyridin-3-yl)methyl)-3-methyl-1-(pentan-2-yl)-1H-indole-4-carboxamide;

N-((4,6-dimethyl-2-oxo-1,2-dihydropyridin-3-yl)methyl)-1-isopropyl-6-(2-methoxypyrimidin-4-yl)-3-methyl-1H-indole-4-carboxamide;

N-((4,6-dimethyl-2-oxo-1,2-dihydropyridin-3-yl)methyl)-1-isopropyl-3-methyl-6-(1H-pyrazolo[4,3-c]pyridin-6-yl)-1H-indole-4-carboxamide;

6-methyl-3-({2-[3-methyl-1-(1-methylethyl)-6-(1,2,3,6-tetrahydro-4-pyridinyl)-1H-indol-4-yl]-2-oxoethyl}amino)-4-propyl-2(1H)-pyridinone;

6-(1H-benzo[d]imidazol-2-yl)-N-((4,6-dimethyl-2-oxo-1,2-dihydropyridin-3-yl)methyl)-1-isopropyl-3-methyl-1H-indole-4-carboxamide;

N-((4,6-dimethyl-2-oxo-1,2-dihydropyridin-3-yl)methyl)-1-(2-(dimethylamino)propyl)-3-methyl-6-(6-(4-methylpiperazin-1-yl)pyridin-3-yl)-1H-indole-4-carboxamide;

N-((4,6-dimethyl-2-oxo-1,2-dihydropyridin-3-yl)methyl)-1-isopropyl-3-methyl-6-(2-methylpyrimidin-4-yl)-1H-indole-4-carboxamide;

6-bromo-N-((4,6-dimethyl-2-oxo-1,2-dihydropyridin-3-yl)methyl)-3-methyl-1-(tetrahydro-2H-pyran-4-yl)-1H-indole-4-carboxamide;

6-bromo-N-((4,6-dimethyl-2-oxo-1,2-dihydropyridin-3-yl)methyl)-1-(2-(dimethylamino)propyl)-3-methyl-1H-indole-4-carboxamide;

N-((4,6-dimethyl-2-oxo-1,2-dihydropyridin-3-yl)methyl)-1-isopropyl-3-methyl-6-(6-(4-methylpiperazin-1-yl)pyridin-3-yl)-1H-indole-4-carboxamide;

N-[(4,6-dimethyl-2-oxo-1,2-dihydro-3-pyridinyl)methyl]-3-methyl-1-(1-methylethyl)-6-[6-(1-piperazinyl)-3-pyridinyl]-1H-indole-4-carboxamide;

6-bromo-1-(sec-butyl)-N-((4,6-dimethyl-2-oxo-1,2-dihydropyridin-3-yl)methyl)-3-methyl-1H-indole-4-carboxamide;

(R)-6-Bromo-1-(sec-butyl)-N-((4,6-dimethyl-2-oxo-1,2-dihydropyridin-3-yl)methyl)-3-methyl-1H-indole-4-carboxamide; and (S)-6-bromo-1-(sec-butyl)-N-((4,6-dimethyl-2-oxo-1,2-dihydropyridin-3-yl)methyl)-3-methyl-1H-indole-4-carboxamide;

1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide;

N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide;

N-[(4,6-dimethyl-2-oxo-1,2-dihydro-3-pyridinyl)methyl]-3-methyl-1-[(1R)-1-methylpropyl]-6-[6-(1-piperazinyl)-3-pyridinyl]-1H-indole-4-carboxamide;

1-(sec-Butyl)-N-((4,6-dimethyl-2-oxo-1,2-dihydropyridin-3-yl)methyl)-6-(3-((dimethylamino)methyl)phenyl)-3-methyl-1H-indole-4-carboxamide;

6-{3-[(Dimethylamino)methyl]phenyl}-N-[(4,6-dimethyl-2-oxo-1,2-dihydro-3-pyridinyl)methyl]-3-methyl-1-[(1S)-1-methylpropyl]-1H-indole-4-carboxamide;

6-{3-[(dimethylamino)methyl]phenyl}-N-[(4,6-dimethyl-2-oxo-1,2-dihydro-3-pyridinyl)methyl]-3-methyl-1-[(1R)-1-methylpropyl]-1H-indole-4-carboxamide;

1-cyclopentyl-N-((4,6-dimethyl-2-oxo-1,2-dihydropyridin-3-yl)methyl)-3-methyl-6-(6-(piperazin-1-yl)pyridin-3-yl)-1H-indole-4-carboxamide;

1-isopropyl-N-((6-methyl-2-oxo-4-propyl-1,2-dihydropyridin-3-yl)methyl)-6-(6-(piperazin-1-yl)pyridin-3-yl)-1H-indole-4-carboxamide;

1-isopropyl-3-methyl-N-((6-methyl-2-oxo-4-propyl-1,2-dihydropyridin-3-yl)methyl)-6-(4-(2-oxopiperazin-1-yl)phenyl)-1H-indole-4-carboxamide;

N-((4,6-dimethyl-2-oxo-1,2-dihydropyridin-3-yl)methyl)-1-isopropyl-3-methyl-6-(6-(piperazin-1-yl)pyridin-3-yl)-1H-indole-4-carboxamide;

N-((4,6-dimethyl-2-oxo-1,2-dihydropyridin-3-yl)methyl)-1-isopropyl-3-methyl-6-(1-(piperidin-4-yl)-1H-pyrazol-4-yl)-1H-indole-4-carboxamide;

6-methyl-3-[(2-{3-methyl-1-(1-methylethyl)-6-[6-(1-piperazinyl)-3-pyridinyl]-1H-indol-4-yl}-2-oxoethyl)amino]-4-propyl-2(1H)-pyridinone;

N-((4,6-dimethyl-2-oxo-1,2-dihydropyridin-3-yl)methyl)-1-isopropyl-3-methyl-6-(2-(piperazin-1-yl)pyrimidin-5-yl)-1H-indole-4-carboxamide;

3-methyl-1-(1-methylethyl)-N-[(6-methyl-2-oxo-4-propyl-1,2-dihydro-3-pyridinyl)methyl]-6-(1H-pyrazol-4-yl)-1H-indole-4-carboxamide;

N-((4,6-dimethyl-2-oxo-1,2-dihydropyridin-3-yl)methyl)-1-isopropyl-3-methyl-6-(5-(piperazin-1-yl)pyridin-3-yl)-1H-indole-4-carboxamide;

4-[4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine;

6-[6-(aminomethyl)-3-pyridinyl]-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-[6-(3-methyl-1-piperazinyl)-3-pyridinyl]-1H-indole-4-carboxamide;

4-[4-({[(4,6-dimethyl-2-oxo-1,2-dihydro-3-pyridinyl)methyl]amino}carbonyl)-3-methyl-1-(1-methylethyl)-1H-indol-6-yl]benzoic acid;

3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoic acid;

5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylic acid;

N-[(4,6-Dimethyl-2-oxo-1,2-dihydro-3-pyridinyl)methyl]-1-(1-methylethyl)-1H-indole-4-carboxamide;

N-((4-benzyl-6-methyl-2-oxo-1,2-dihydropyridin-3-yl)methyl)-1-isopropyl-1H-indole-4-carboxamide;

N-((4-benzyl-6-methyl-2-oxo-1,2-dihydropyridin-3-yl)methyl)-1-isopropyl-3-methyl-1H-indole-4-carboxamide;

1-cyclopentyl-N-((4,6-dimethyl-2-oxo-1,2-dihydropyridin-3-yl)methyl)-3-methyl-1H-indole-4-carboxamide;

6-methyl-3-({2-[3-methyl-1-(1-methylethyl)-6-(4-piperidinyl)-1H-indol-4-yl]-2-oxoethyl}amino)-4-propyl-2(1H)-pyridinone;

N-[(4,6-dimethyl-2-oxo-1,2-dihydro-3-pyridinyl)methyl]-3-methyl-1-(1-methylethyl)-6-[6-(2-piperidinyl)-3-pyridinyl]-1H-indole-4-carboxamide;

N-[(4,6-dimethyl-2-oxo-1,2-dihydro-3-pyridinyl)methyl]-3-methyl-1-(1-methylethyl)-1H-indole-4-carboxamide;

1-cyclopropyl-N-[(4,6-dimethyl-2-oxo-1,2-dihydro-3-pyridinyl)methyl]-3-methyl-6-(methylsulfonyl)-1H-indole-4-carboxamide;

1-cyclopentyl-6-(cyclopropylsulfonyl)-N-[(4,6-dimethyl-2-oxo-1,2-dihydro-3-pyridinyl)methyl]-3-methyl-1H-indole-4-carboxamide;

1-cyclopentyl-N-[(4,6-dimethyl-2-oxo-1,2-dihydro-3-pyridinyl)methyl]-3-methyl-6-(methylsulfonyl)-1H-indole-4-carboxamide;

3-({2-[6-(cyclopropylsulfonyl)-3-methyl-1-(1-methylethyl)-1H-indol-4-yl]-2-oxoethyl}amino)-4,6-dimethyl-2(1H)-pyridinone;

3-({2-[6-(cyclopropylsulfonyl)-3-methyl-1-(1-methylethyl)-1H-indol-4-yl]-2-oxoethyl}amino)-4,6-dimethyl-2(1H)-pyridinone;

1-cyclopentyl-6-(cyclopropylsulfonyl)-N-[(4,6-dimethyl-2-oxo-1,2-dihydro-3-pyridinyl)methyl]-3-methyl-1H-indole-4-carboxamide;

1-cyclopentyl-N-[(4,6-dimethyl-2-oxo-1,2-dihydro-3-pyridinyl)methyl]-3-methyl-6-(methylsulfonyl)-1H-indole-4-carboxamide;

N-[(4,6-dimethyl-2-oxo-1,2-dihydro-3-pyridinyl)methyl]-1-(1-methylethyl)-6-(trifluoromethyl)-1H-indole-4-carboxamide;

1-Isopropyl-N-((6-methyl-2-oxo-4-propyl-1,2-dihydropyridin-3-yl)methyl)-6-(trifluoromethyl)-1H-indole-4-carboxamide;

N-((4,6-dimethyl-2-oxo-1,2-dihydropyridin-3-yl)methyl)-6-(4-((dimethylamino)methyl)piperidin-1-yl)-1-isopropyl-3-methyl-1H-indole-4-carboxamide;

N-((4,6-dimethyl-2-oxo-1,2-dihydropyridin-3-yl)methyl)-6-(3-((dimethylamino)methyl)pyrrolidin-1-yl)-1-isopropyl-3-methyl-1H-indole-4-carboxamide;

1-cyclopentyl-N-((4,6-dimethyl-2-oxo-1,2-dihydropyridin-3-yl)methyl)-6-(pyrrolidin-1-yl)-1H-indole-4-carboxamide;

6-(1,1-dioxidothiomorpholino)-1-isopropyl-3-methyl-N-((6-methyl-2-oxo-4-propyl-1,2-dihydropyridin-3-yl)methyl)-1H-indole-4-carboxamide;

N-((4,6-dimethyl-2-oxo-1,2-dihydropyridin-3-yl)methyl)-1-isopropyl-3-methyl-6-(pyridin-3-ylamino)-1H-indole-4-carboxamide;

N-((4,6-dimethyl-2-oxo-1,2-dihydropyridin-3-yl)methyl)-6-(4-(4-fluorophenyl)piperidin-1-yl)-1-isopropyl-3-methyl-1H-indole-4-carboxamide;

N-((4,6-dimethyl-2-oxo-1,2-dihydropyridin-3-yl)methyl)-1-isopropyl-3-methyl-6-(4-(4-methylpiperazin-1-yl)piperidin-1-yl)-1H-indole-4-carboxamide;

N-((4,6-dimethyl-2-oxo-1,2-dihydropyridin-3-yl)methyl)-1-isopropyl-3-methyl-6-(4-(1-methylpiperidin-4-yl)piperazin-1-yl)-1H-indole-4-carboxamide;

N-((4,6-dimethyl-2-oxo-1,2-dihydropyridin-3-yl)methyl)-6-(4-fluoropiperidin-1-yl)-1-isopropyl-3-methyl-1H-indole-4-carboxamide;

N-((4,6-dimethyl-2-oxo-1,2-dihydropyridin-3-yl)methyl)-6-(4-(3-fluorophenyl)piperidin-1-yl)-1-isopropyl-3-methyl-1H-indole-4-carboxamide;

N-[(4-ethyl-6-methyl-2-oxo-1,2-dihydro-3-pyridinyl)methyl]-3-methyl-1-(1-methylethyl)-6-(4-morpholinyl)-1H-indole-4-carboxamide;

N-[(4,6-dimethyl-2-oxo-1,2-dihydro-3-pyridinyl)methyl]-3-methyl-1-(1-methylethyl)-6-(4-morpholinyl)-1H-indole-4-carboxamide;

N-[(4,6-dimethyl-2-oxo-1,2-dihydro-3-pyridinyl)methyl]-3-methyl-1-(1-methylethyl)-6-{[3-methyl-1-(1-methylethyl)-1H-pyrazol-5-yl]amino}-1H-indole-4-carboxamide;

6-(2-dimethylamino-ethoxy)-1-isopropyl-1H-indole-4-carboxylic acid (6-methyl-2-oxo-4-propyl-1,2-dihydro-pyridin-3-ylmethyl)-amide;

1-isopropyl-6-[2-(4-methyl-piperazin-1-yl)-ethoxy]-1H-indole-4-carboxylic acid (6-methyl-2-oxo-4-propyl-1,2-dihydro-pyridin-3-ylmethyl)-amide;

1-isopropyl-6-(2-morpholin-4-yl-ethoxy)-1H-indole-4-carboxylic acid (6-methyl-2-oxo-4-propyl-1,2-dihydro-pyridin-3-ylmethyl)-amide;

1-Isopropyl-6-(2-piperazin-1-yl-ethoxy)-1H-indole-4-carboxylic acid (6-methyl-2-oxo-4-propyl-1,2-dihydro-pyridin-3-ylmethyl)-amide;

N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide;

6-bromo-N-{[4-(ethylamino)-6-methyl-2-oxo-1,2-dihydro-3-pyridinyl]methyl}-1-(1-methylethyl)-1H-indole-4-carboxamide;

6-bromo-1-(1-methylethyl)-N-{[6-methyl-2-oxo-4-(1-pyrrolidinyl)-1,2-dihydro-3-pyridinyl]methyl}-1H-indole-4-carboxamide;

6-bromo-1-(1-methylethyl)-N-{[6-methyl-2-oxo-4-(phenylamino)-1,2-dihydro-3-pyridinyl]methyl}-1H-indole-4-carboxamide;

N-((6-amino-4-methyl-2-oxo-1,2-dihydropyridin-3-yl)methyl)-6-bromo-1-isopropyl-3-methyl-1H-indole-4-carboxamide;

N-((6-amino-4-methyl-2-oxo-1,2-dihydropyridin-3-yl)methyl)-6-chloro-1-isopropyl-3-methyl-1H-indole-4-carboxamide;

N-[(6-amino-4-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide;

N-[(6-amino-4-methyl-2-oxo-1,2-dihydro-3-pyridinyl)methyl]-6-{3-[(dimethylamino)methyl]phenyl}-3-methyl-1-(1-methylethyl)-1H-indole-4-carboxamide;

N-[(6-amino-4-methyl-2-oxo-1,2-dihydro-3-pyridinyl)methyl]-6-bromo-3-methyl-1-(1-methylpropyl)-1H-indole-4-carboxamide;

N-[(6-amino-4-methyl-2-oxo-1,2-dihydro-3-pyridinyl)methyl]-6-bromo-3-methyl-1-(1-methylpropyl)-1H-indole-4-carboxamide;

N-[(6-amino-4-methyl-2-oxo-1,2-dihydro-3-pyridinyl)methyl]-6-bromo-3-methyl-1-(1-methylpropyl)-1H-indole-4-carboxamide;

N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide;

N-((6-amino-2-oxo-4-propyl-1,2-dihydropyridin-3-yl)methyl)-6-bromo-1-isopropyl-3-methyl-1H-indole-4-carboxamide;

6-bromo-1-isopropyl-3-methyl-N-((4-methyl-6-(methylamino)-2-oxo-1,2-dihydropyridin-3-yl)methyl)-1H-indole-4-carboxamide;

N-[(4,6-dimethyl-2-oxo-1,2-dihydro-3-pyridinyl)methyl]-3-methyl-1-(1-methylethyl)-6-{6-[(2R)-2-methyl-1-piperazinyl]-3-pyridinyl}-1H-indole-4-carboxamide;

N-[(4,6-dimethyl-2-oxo-1,2-dihydro-3-pyridinyl)methyl]-6-[6-(3,4-dimethyl-1-piperazinyl)-3-pyridinyl]-3-methyl-1-(1-methylethyl)-1H-indole-4-carboxamide;

N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide;

N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide;

N-[(4,6-dimethyl-2-oxo-1,2-dihydro-3-pyridinyl)methyl]-6-[6-(3,3-dimethyl-1-piperazinyl)-3-pyridinyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-{6-[(2S)-2-methyl-1-piperazinyl]-3-pyridinyl}-1H-indole-4-carboxamide;

N-[(4,6-dimethyl-2-oxo-1,2-dihydro-3-pyridinyl)methyl]-6-[6-(hexahydropyrrolo[3,4-c]pyrrol-2(1H)-yl)-3-pyridinyl]-3-methyl-1-(1-methylethyl)-1H-indole-4-carboxamide;

6-{6-[(1S,4S)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide;

6-{6-[(1R,4R)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-6-{6-[(2S,5S)-2,5-dimethyl-1-piperazinyl]-3-pyridinyl}-3-methyl-1-(1-methylethyl)-1H-indole-4-carboxamide;

6-[6-(3,8-diazabicyclo[3.2.1]oct-3-yl)-3-pyridinyl]-N-[(4,6-dimethyl-2-oxo-1,2-dihydro-3-pyridinyl)methyl]-3-methyl-1-(1-methylethyl)-1H-indole-4-carboxamide;

N-((4,6-dimethyl-2-oxo-1,2-dihydropyridin-3-yl)methyl)-6-(6-((2R,5R)-2,5-dimethylpiperazin-1-yl)pyridin-3-yl)-1-isopropyl-3-methyl-1H-indole-4-carboxamide;

N-((4,6-dimethyl-2-oxo-1,2-dihydropyridin-3-yl)methyl)-1-isopropyl-3-methyl-6-(6-(pyrrolidin-1-ylmethyl)pyridin-3-yl)-1H-indole-4-carboxamide;

6-(6-{[(2R,6S)-2,6-dimethyl-4-morpholinyl]methyl}-3-pyridinyl)-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-{6-[(4-methyl-1-piperazinyl)methyl]-3-pyridinyl}-1H-indole-4-carboxamide;

N-[(4,6-dimethyl-2-oxo-1,2-dihydro-3-pyridinyl)methyl]-3-methyl-1-(1-methylethyl)-6-[6-(4-morpholinylmethyl)-3-pyridinyl]-1H-indole-4-carboxamide;

6-Bromo-N-((6-(hydroxymethyl)-4-methyl-2-oxo-1,2-dihydropyridin-3-yl)methyl)-1-isopropyl-3-methyl-1H-indole-4-carboxamide;

N-((6-(aminomethyl)-4-methyl-2-oxo-1,2-dihydropyridin-3-yl)methyl)-6-bromo-1-isopropyl-3-methyl-1H-indole-4-carboxamide;

3-Methyl-1-(1-methylethyl)-4-({[(6-methyl-2-oxo-4-propyl-1,2-dihydro-3-pyridinyl)methyl]amino}carbonyl)-1H-indole-6-carboxylic acid;

3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoic acid;

6-(2-Aminoethyl)-N-[(4,6-dimethyl-2-oxo-1,2-dihydro-3-pyridinyl)methyl]-3-methyl-1-(1-methylethyl)-1H-indole-4-carboxamide;

6-{3-[(dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide;

6-(4,5-Dihydro-1H-imidazol-2-yl)-N-((4,6-dimethyl-2-oxo-1,2-dihydropyridin-3-yl)methyl)-1-isopropyl-3-methyl-1H-indole-4-carboxamide;

[4-({[(4,6-dimethyl-2-oxo-1,2-dihydro-3-pyridinyl)methyl]amino}carbonyl)-3-methyl-1-(1-methylethyl)-1H-indol-6-yl]boronic acid;

N-[(4,6-dimethyl-2-oxo-1,2-dihydro-3-pyridinyl)methyl]-6-[6-(hydroxymethyl)-3-pyridinyl]-3-methyl-1-(1-methylethyl)-1H-indole-4-carboxamide;

N-[(4,6-dimethyl-2-oxo-1,2-dihydro-3-pyridinyl)methyl]-3-methyl-1-(1-methylethyl)-6-(3-oxetanyl)-1H-indole-4-carboxamide;

N-[(4,6-dimethyl-2-oxo-1,2-dihydro-3-pyridinyl)methyl]-3-methyl-1-(1-methylethyl)-6-{[6-(4-methyl-1-piperazinyl)-3-pyridinyl]amino}-1H-indole-4-carboxamide;

N-[(4,6-dimethyl-2-oxo-1,2-dihydro-3-pyridinyl)methyl]-3-methyl-1-(1-methylethyl)-6-{[(4-methyl-1-piperazinyl)carbonyl]amino}-1H-indole-4-carboxamide;

6-{[3-(dimethylamino)propyl]thio}-N-[(4,6-dimethyl-2-oxo-1,2-dihydro-3-pyridinyl)methyl]-3-methyl-1-(1-methylethyl)-1H-indole-4-carboxamide;

N-[(4,6-dimethyl-2-oxo-1,2-dihydro-3-pyridinyl)methyl]-6-(3-hydroxy-3-methyl-1-butyn-1-yl)-3-methyl-1-(1-methylethyl)-1H-indole-4-carboxamide;

6-(3-hydroxy-3-methyl-1-butyn-1-yl)-3-methyl-1-(1-methylethyl)-N-[(6-methyl-2-oxo-4-propyl-1,2-dihydro-3-pyridinyl)methyl]-1H-indole-4-carboxamide;

6-(cyclopropylethynyl)-3-methyl-1-(1-methylethyl)-N-[(6-methyl-2-oxo-4-propyl-1,2-dihydro-3-pyridinyl)methyl]-1H-indole-4-carboxamide;

N-[(4,6-dimethyl-2-oxo-1,2-dihydro-3-pyridinyl)methyl]-7-methyl-1-(1-methylethyl)-1H-indole-4-carboxamide;

7-Methyl-1-(1-methylethyl)-N-[(6-methyl-2-oxo-4-propyl-1,2-dihydro-3-pyridinyl)methyl]-1H-indole-4-carboxamide;

1-(1-Methylethyl)-N-[(6-methyl-2-oxo-4-propyl-1,2-dihydro-3-pyridinyl)methyl]-7-(methyloxy)-1H-indole-4-carboxamide;

N-[(4,6-dimethyl-2-oxo-1,2-dihydro-3-pyridinyl)methyl]-1-(1-methylethyl)-7-(methyloxy)-1H-indole-4-carboxamide;

6-chloro-1-isopropyl-2,3-dimethyl-N-((6-methyl-2-oxo-4-propyl-1,2-dihydropyridin-3-yl)methyl)-1H-indole-4-carboxamide;

6-Chloro-2-((dimethylamino)methyl)-1-isopropyl-3-methyl-N-((6-methyl-2-oxo-4-propyl-1,2-dihydropyridin-3-yl)methyl)-1H-indole-4-carboxamide; and 2-(2-aminoethyl)-6-chloro-1-isopropyl-3-methyl-N-((6-methyl-2-oxo-4-propyl-1,2-dihydropyridin-3-yl)methyl)-1H-indole-4-carboxamide, or a pharmaceutically acceptable salt thereof.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substituent group. The phrase should not be interpreted as duplicative of the substitutions herein described and depicted. Exemplary optional substituent groups include acyl, $C_1$-$C_6$alkyl, $C_1$-$C_3$alkylsulfonyl, $C_1$-$C_3$alkoxy, $C_1$-$C_3$alkoxycarbonyl, cyano, halogen, haloalkyl, hydroxyl, oxo, and nitro.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes.

The term "alkoxy" as used herein means —O($C_1$-$C_8$alkyl) including —OCH$_3$, —OCH$_2$CH$_3$ and —OC(CH$_3$)$_3$ and the like per the definition of alkyl above.

The term "alkylthio" as used herein is meant —S($C_1$-$C_8$alkyl) including —SCH$_3$, —SCH$_2$CH$_3$ and the like per the definition of alkyl above.

The term "acyloxy" means —OC(O)$C_1$-$C_8$alkyl and the like per the definition of alkyl above.

"Acylamino" means —N(H)C(O)$C_1$-$C_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "$C_3$-$C_8$cycloalkyl" refers to a non-aromatic cyclic hydrocarbon ring having from three to eight carbon atoms. Exemplary "$C_3$-$C_8$cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below.

As used herein, the term "aryl", unless otherwise defined, is meant aromatic, hydrocarbon, ring system. The ring system may be monocyclic or fused polycyclic (e.g., bicyclic, tricyclic, etc.), substituted or unsubstituted. In various embodiments, the monocyclic aryl ring is C5-C10, or C5-C7, or C5-C6, where these carbon numbers refer to the number of carbon atoms that form the ring system. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl, unless otherwise defined, are described below in the definition of "optionally substituted".

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. Suitable substituents for heteroaryl, unless otherwise defined are described below in the definition of "optionally substituted"

Provided herein are methods of treatment or prevention of autoimmune and inflammatory conditions and diseases that can be improved by inhibiting EZH1 and/or EZH2 and thereby, e.g., modulate the level of expression of methylation activated and methylation repressed target genes, or modulate the activity of signalling proteins. A method may comprise administering to a human, e.g. a human in need thereof, a therapeutically effective amount of an agent described herein.

Thus in one aspect there is provided the use of use of a compound or a pharmaceutically acceptable salt thereof which inhibits EZH2 and/or EZH1 (i.e. an EZH2 and/or EZH1 inhibitor) in the manufacture of a medicament for treating T cell mediated inflammatory immune diseases or T cell mediated hypersensitivity diseases.

In a further aspect there is provided a method of treatment of T cell mediated inflammatory immune diseases or T cell mediated hypersensitivity diseases in a human comprising administering a therapeutically effective amount of an EZH1 and/EZH2 inhibitor.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The agents may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated in this invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated in this invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated in this invention include arthrosclerosis, arthritis, phlebitis, vasculitis, and lymphangitis.

Examples of inflammatory conditions of the digestive system which may be treated in this invention include cholangitis, cholecystitis, enteritis, enterocolitis, gastritis, gastroenteritis, ileitis, and proctitis.

Examples of inflammatory conditions of the reproductive system which may be treated in this invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, Reiter's syndrome, Sjogren's syndrome, temporal arteritis, Wegener's granulomatosis, warm autoimmune haemolytic anemia, interstitial cystitis, lyme disease, morphea, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated in this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis.

Preferred treatments include any one of treatment of transplant rejection, psoriatic arthritis, multiple sclerosis, Type 1 diabetes, asthma, systemic lupus erythematosis, chronic pulmonary disease, and inflammation accompanying infectious conditions (e.g., sepsis).

Typically, but not absolutely, the salts of the compounds for use in the invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

Other salts, which are not pharmaceutically acceptable, may be useful in the preparation of compounds for use in this invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds for use in this invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound for use in this invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Experimentals

Chemical Background

The present compounds are automatically named by computer software, eg. ISISdraw, ChemDraw, or eLNB. A person skilled in the art understands that there might be slight differences in the chemical names generated by different software. The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. Also included in the present invention are fully or partially deuterated forms of the present compounds. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

EXAMPLES

General Experimental Methods

The following abbreviations are used throughout the experimental and have the following meaning:
aq aqueous
BINAP 2,2'-bis(diphenylphosphino)-1,1'-binapthyl
ca. circa
$CDCl_3$-d chloroform-d
$CD_3OD$-$d_4$ methanol-$d_4$
$Cs_2CO_3$ cesium carbonate
$CHCl_3$ chloroform ACN acetonitrile
CH$_3$CN acetonitrile
Celite® registered trademark of Celite Corp. brand of diatomaceous earth
DBU 1,8-diazabicyclo[5.4.0]undeca-7-ene
DCE dichloroethane
DCM methylene chloride
DME 1,2 dimethoxyethane
DMF N,N-dimethylformamide
DIEA diisopropyl ethylamine
DMSO-d$_6$ dimethylsulfoxide-d$_6$
EtOAc ethyl acetate
EDC 1-(3-dimethylaminopropyl)-3-ethylcarbodimide hydrochloride
h hour(s)
$^1$H NMR proton nuclear magnetic resonance
HCl hydrochloric acid
HOAT 1-hydroxy-7-azabenzotriazole
HPLC high performance liquid chromatography
IPA 2-propanol
K$_2$CO$_3$ potassium carbonate
KOH potassium hydroxide
LC/MS liquid chromatography/mass spectroscopy
MgSO$_4$ magnesium sulfate
MeOH methanol
min minute(s)
MTBE methyl tert-butyl ether
MS mass spectrometry
NaOH sodium hydroxide
Na$_2$SO$_4$ sodium sulfate
NH$_4$OH ammonium hydroxide
NMM 4-methylmorpholine
NMP N-Methyl-2-pyrrolidone
Pd/C Palladium (10% by wt) on carbon
PdCl$_2$(dppf)-CH$_2$Cl$_2$ 1,1'-Bis(diphenylphosphino)ferrocene-palladium(II)dichloride dichloromethane complex
Pd(Ph$_3$P)$_4$ tetrakis(triphenylphosphine)palladium(0)
SOCl$_2$ thionyl chloride
SPhos 2-Dicyclohexylphosphino-2',6'-dimethoxybiphenyl
TFA trifluoroacetic acid
THF tetrahydrofuran
TLC thin layer chromatography The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (acetonitrile-0.1% TFA): B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% (H$_2$O 0.02% TFA) in vessel A and 100% (CH$_3$CN 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% (H$_2$O 0.02% TFA) in vessel A and 100% (CH$_3$CN 0.018% TFA) in vessel B. The stationary phase was Zobax (C8) with a 3.5 um partical size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50×4.6 mm, 1.8 μm) eluting with CH$_3$CN: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal. All NMRs in DMSO unless otherwise noted.

Analytical HPLC: Products were analyzed by Agilent 1100 Analytical Chromatography system, with 4.5×75 mm Zorbax XDB-C18 column (3.5 um) at 2 mL/min with a 4 min gradient from 5% CH$_3$CN (0.1% formic acid) to 95% CH$_3$CN (0.1% formic acid) in H$_2$O (0.1% formic acid) and a 1 min hold.

The compounds of formula (I) can be made according to Scheme 1 or by analogous methods. Methyl 6-bromo-1H-indole-4-carboxylate (I) is alkylated with an alkyl halide in the presence of base (e.g. sodium hydride) or with an alcohol in the presence of (cyanomethyl)trimethylphosphonium chloride and base (e.g. sodium hydride) to give compounds of Formula II. Saponification of the ester with aqueous base provides compounds of Formula III, which are coupled to various aminomethylpyridones IV utilizing standard peptide coupling reagents (e.g. EDC, HOAT, NMM) to furnish compounds of Formula V. Palladium-mediated cross-coupling of various boronic acids (or boronates) with V provides compounds of Formula VI.

Scheme 1

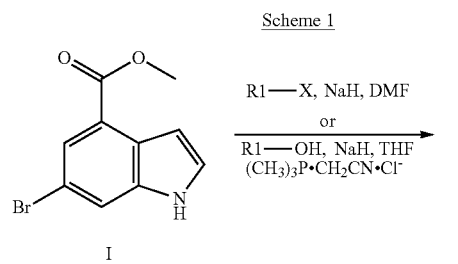

I

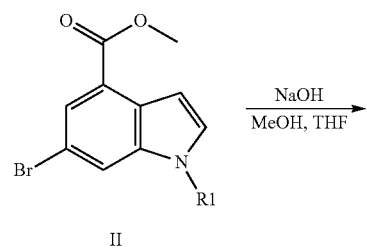

II

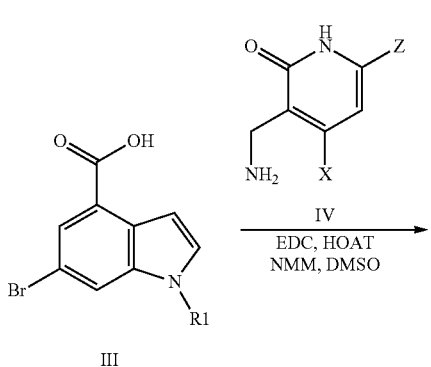

III

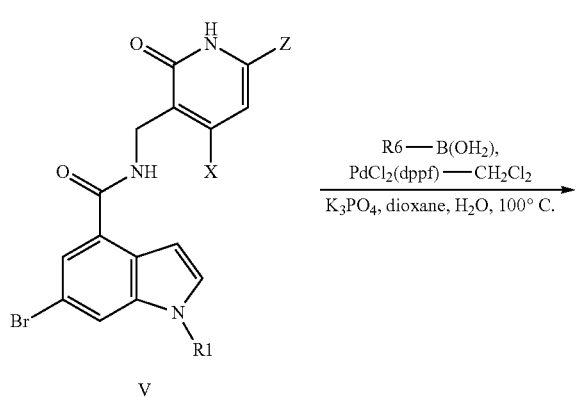

V

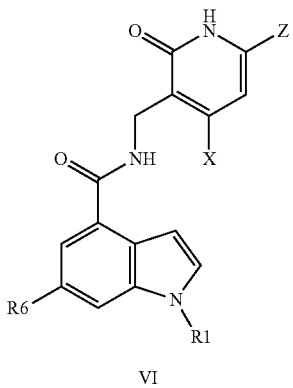

VI

The following examples are for illustrative purposes only and are not intended to limit the scope of the present invention. The compounds were named using ACD Name software [Advanced Chemistry Development, Inc., (ACD/Labs), Toronto, Canada. (http://www.acdlabs.com/products/name_lab/)].

Example 1

6-Bromo-N-[(4,6-dimethyl-2-oxo-1,2-dihydro-3-pyridinyl)methyl]-1-(1-methylethyl)-1H-indole-4-carboxamide

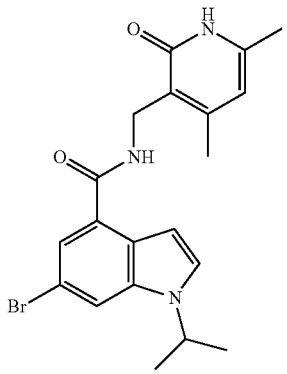

1a) Methyl 6-bromo-1-(1-methylethyl)-1H-indole-4-carboxylate

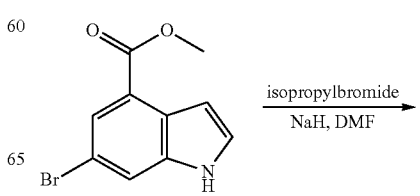

-continued

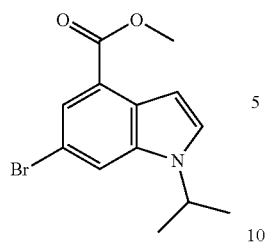

To a cooled (0° C.) solution of methyl 6-bromo-1H-indole-4-carboxylate (1.0 g, 3.94 mmol) solid in N,N-dimethylformamide (25 mL) was added sodium hydride (0.173 g, 4.33 mmol). The reaction was stirred for 15 min, at which time 2-bromopropane (0.554 mL, 5.90 mmol) was added. The reaction was then allowed to warm to RT and was maintained overnight. LCMS showed about 25% starting material remaining. The reaction was heated at 45° C. for 4 h, but no further conversion was noted. The reaction vessel was put back into an ice bath and stirred for 15 min. Then excess NaH (60%) was added, stirred for 10 min, and then 2-bromopropane (excess) was added. The ice bath was removed and the reaction stirred for 1 h. Approximately half of the reaction volume was removed in vacuo and poured into saturated $NH_4Cl$ (200 mL). This was extracted with ether (2×) and the combined organics were washed with brine, dried ($MgSO_4$), and concentrated. Purification by column chromatography (80 g Isco silica column; Gradient B: 5-25%, A: hexane, B: ethyl acetate) gave methyl 6-bromo-1-(1-methylethyl)-1H-indole-4-carboxylate (0.53 g, 1.718 mmol, 43.7% yield).

1b) 6-Bromo-1-(1-methylethyl)-1H-indole-4-carboxylic acid

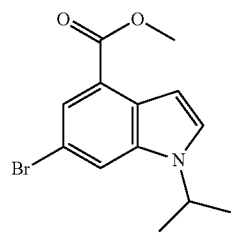

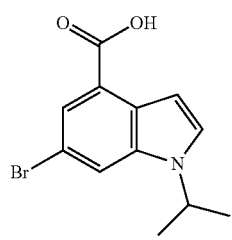

To a solution of methyl 6-bromo-1-(1-methylethyl)-1H-indole-4-carboxylate (0.52 g, 1.756 mmol) in methanol (15 mL) and tetrahydrofuran (3 mL) was added 3M NaOH (1.756 mL, 5.27 mmol) via syringe drop wise (over 2 min). The solution was maintained at RT for 2 h, at which time LCMS showed only 12% conversion to product. Then 1.5 mL 3M NaOH was added and the solution was maintained at RT overnight. LCMS showed complete conversion to product. Removed volatiles in vacuo and dissolved the residue in water and slowly acidified with 1M HCl (solids precipitated). Extracted with EtOAc (2×), combined organics and dried over $MgSO_4$. Filtered and concentrated in vacuo to give 6-bromo-1-(1-methylethyl)-1H-indole-4-carboxylic acid (0.50 g, 1.737 mmol, 99% yield) as a white solid.

1c) 6-Bromo-N-[(4,6-dimethyl-2-oxo-1,2-dihydro-3-pyridinyl)methyl]-1-(1-methylethyl)-1H-indole-4-carboxamide

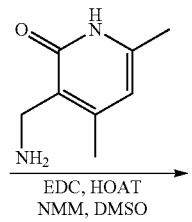

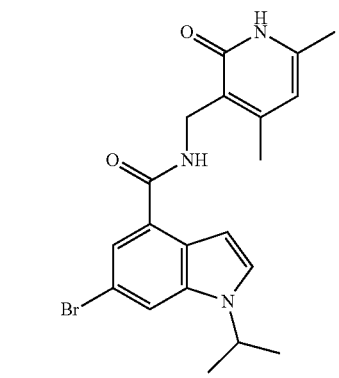 [SMILES: Cc1cc(C)c(CNC(=O)c2cc(Br)cc3c2ccn3C(C)C)c(=O)[nH]1]

To a mixture of 6-bromo-1-(1-methylethyl)-1H-indole-4-carboxylic acid (0.71 g, 2.52 mmol), 3-(aminomethyl)-4,6-dimethyl-2(1H)-pyridinone (0.575 g, 3.77 mmol), 1-hydroxy-7-azabenzotriazole (0.514 g, 3.77 mmol), and EDC (0.724 g, 3.77 mmol) in dimethylsulfoxide (20 mL) was added quickly N-methylmorpholine (1.107 mL, 10.07 mmol) via syringe. The solids slowly dissolved and the reaction was maintained at RT overnight. The reaction was slowly poured into ice-water (300 mL), stirred for 10 min, then allowed to sit for 10 min. The solids were filtered and washed with water (100 mL), airdried for 15 min, then dried in vacuum oven at 45° C. for 4 h to give 6-bromo-N-[(4,6-dimethyl-2-oxo-1,2-dihydro-3-pyridinyl)methyl]-1-(1-methylethyl)-1H-indole-4-carboxamide (0.82 g, 1.871 mmol, 74.4% yield). $^1$H NMR (400 MHz, DMSO-$d_6$) δ ppm 1.39-1.46 (m, 6H) 2.09-2.15 (m, 3H) 2.21 (s, 3H) 4.32 (d, J=5.05 Hz, 2H) 4.82 (quin, J=6.63 Hz, 1H) 5.88 (s, 1H) 6.86 (d, J=3.28 Hz, 1H) 7.51 (d, J=1.77 Hz, 1H) 7.62 (d, J=3.28 Hz, 1H) 7.92 (s, 1H) 8.31 (t, J=4.93 Hz, 1H) 11.55 (br. s., 1H). MS(ES) [M+H]+ 416.0.

Example 2

N-[(4,6-Dimethyl-2-oxo-1,2-dihydro-3-pyridinyl) methyl]-1-(1-methylethyl)-6-[6-(4-methyl-1-piperazinyl)-3-pyridinyl]-1H-indole-4-carboxamide

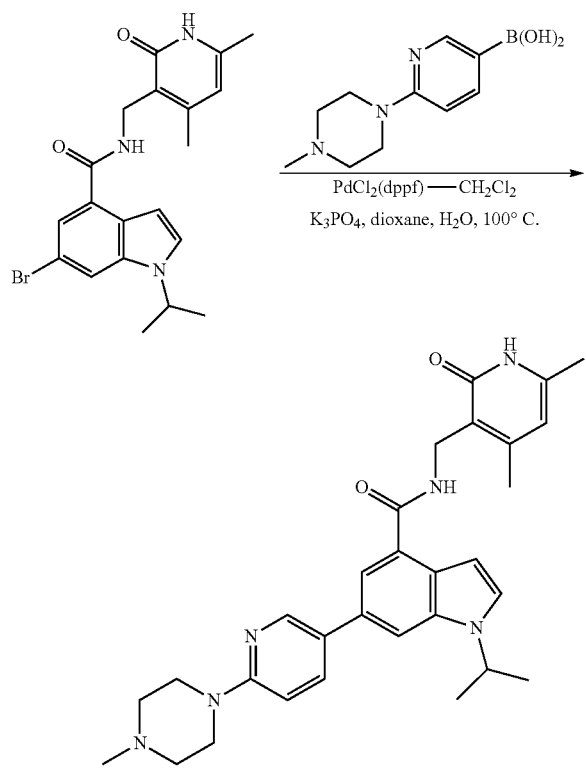

A mixture of 6-bromo-N-[(4,6-dimethyl-2-oxo-1,2-dihydro-3-pyridinyl)methyl]-1-(1-methylethyl)-1H-indole-4-carboxamide (0.10 g, 0.240 mmol), 1-methyl-4-[5-(4,4,5,5-tetramethyl-1,3,2-dioxaborolan-2-yl)-2-pyridinyl] piperazine (0.087 g, 0.288 mmol) and potassium phosphate (tribasic) (0.153 g, 0.721 mmol) in 1,4-dioxane (2 mL) and water (0.5 mL) was degassed with $N_2$ for 10 min, at which time $PdCl_2$(dppf)-$CH_2Cl_2$ (0.029 g, 0.036 mmol) was added. The reaction was sealed and heated at 100° C. for 2 h. The reaction was then allowed to cool to RT and sat overnight, at which time it was diluted with EtOAc, filtered through Celite, washed with EtOAc, and concentrated in vacuo. Purification of the residue by column chromatography (12 g Isco GOLD silica column; Gradient B: 5-90%; A: dichloromethane, B: 10% chloroform containing 2M ammonia in methanol) gave N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide (94 mg, 0.180 mmol, 74.8% yield). $^1$H NMR (400 MHz, DMSO-$d_6$) δ ppm 1.46 (d, J=6.57 Hz, 6H) 2.12 (s, 3H) 2.17-2.28 (m, 6H) 2.38-2.46 (m, 4H) 3.49-3.57 (m, 4H) 4.37 (d, J=5.05 Hz, 2H) 4.86-4.98 (m, 1H) 5.88 (s, 1H) 6.87 (d, J=3.03 Hz, 1H) 6.93 (d, J=8.84 Hz, 1H) 7.58 (d, J=3.28 Hz, 1H) 7.65 (d, J=1.26 Hz, 1H) 7.87 (s, 1H) 7.98 (dd, J=8.97, 2.65 Hz, 1H) 8.28 (t, J=5.05 Hz, 1H) 8.57 (d, J=2.27 Hz, 1H) 11.55 (s, 1H). MS(ES) [M+H]+ 513.3.

Examples 3-xx were prepared by the methods described above for Examples 1 and 2 or routine variations thereof, starting from the requisite 4-aminomethylpyridones and 6-substituted-4-indolecarboxylates. Routine variations include, but are not limited to, reversing the bromide and boronate coupling partners for the Suzuki type couplings or using a one pot procedure in which the borate is formed in situ.

| Ex | Structure | Name | $^1$H NMR (400 MHz, DMSO-$d_6$) δ ppm | MS(ES) [M + H]+ |
|---|---|---|---|---|
| 3 | 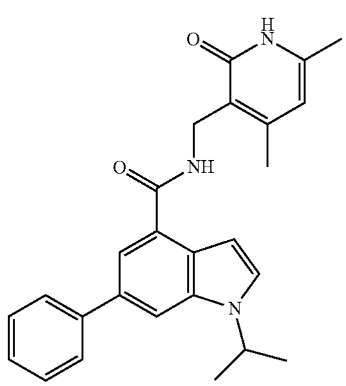 [SMILES: Cc1cc(C)c(CNC(=O)c2cc(-c3ccccc3)cc3c2ccn3C(C)C)c(=O)[nH]1] | N-[(4,6-Dimethyl-2-oxo-1,2-dihydro-3-pyridinyl)methyl]-1-(1-methylethyl)-6-phenyl-1H-indole-4-carboxamide | 1.45-1.51 (m, 6 H) 2.12 (s, 3 H) 2.23 (s, 3 H) 4.37 (d, J = 5.05 Hz, 2 H) 4.89-5.02 (m, 1 H) 5.88 (s, 1 H) 6.88 (d, J = 3.28 Hz, 1 H) 7.30-7.37 (m, 1 H) 7.47 (t, J = 7.71 Hz, 2 H) 7.62 (d, J = 3.28 Hz, 1 H) 7.71 (d, J = 1.52 Hz, 1 H) 7.76-7.84 (m, 2 H) 7.92 (s, 1 H) 8.32 (t, J = 5.05 Hz, 1 H) 11.55 (s, 1 H) | 414.1 |

| Ex | Structure | Name | ¹H NMR (400 MHz, DMSO-d₆) δ ppm | MS(ES) [M + H]⁺ |
|---|---|---|---|---|
| 4 | 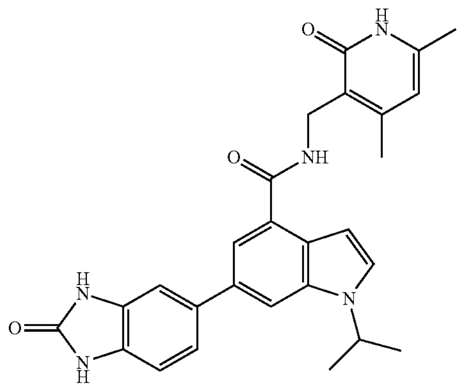 [SMILES: Cc1cc(C)c(CNC(=O)c2cc(-c3ccc4[nH]c(=O)[nH]c4c3)cc3c2ccn3C(C)C)c(=O)[nH]1] | N-[(4,6-Dimethyl-2-oxo-1,2-dihydro-3-pyridinyl)methyl]-1-(1-methylethyl)-6-(2-oxo-2,3-dihydro-1H-benzimidazol-5-yl)-1H-indole-4-carboxamide | 1.47 (d, J = 6.57 Hz, 6 H) 2.12 (s, 3 H) 2.23 (s, 3 H) 4.38 (d, J = 5.05 Hz, 2 H) 4.86-5.01 (m, 1 H) 5.89 (s, 1 H) 6.86 (d, J = 3.03 Hz, 1 H) 7.00 (d, J = 8.08 Hz, 1 H) 7.30 (s, 1 H) 7.36 (dd, J = 8.08, 1.77 Hz, 1 H) 7.59 (d, J = 3.28 Hz, 1 H) 7.65 (d, J = 1.26 Hz, 1 H) 7.83 (s, 1 H) 8.30 (t, J = 5.18 Hz, 1 H) 10.70 (s, 1 H) 10.66 (s, 1 H) 11.55 (s, 1 H) | 469.2 |
| 5 | 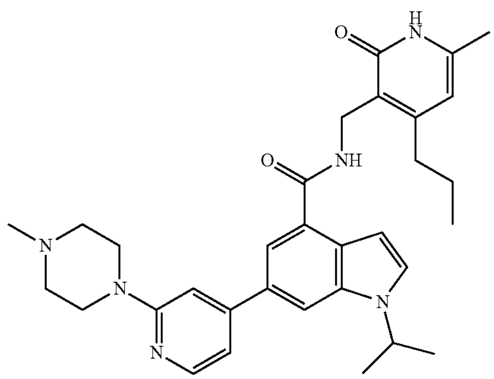 | 1-(1-methylethyl)-N-[(6-methyl-2-oxo-4-propyl-1,2-dihydro-3-pyridinyl)methyl]-6-[2-(4-methyl-1-piperazinyl)-4-pyridinyl]-1H-indole-4-carboxamide | 0.91 (t, J = 7.33 Hz, 3 H) 1.48 (d, J = 6.57 Hz, 6 H) 1.51-1.59 (m, 2 H) 2.13 (s, 3 H) 2.23 (s, 3 H) 2.43 (t, J = 4.93 Hz, 4 H) 2.52-2.59 (m, 2 H) 3.50-3.65 (m, 4 H) 4.41 (d, J = 5.05 Hz, 2 H) 4.91-5.09 (m, 1 H) 5.91 (s, 1 H) 6.89 (d, J = 3.03 Hz, 1 H) 7.05-7.21 (m, 2 H) 7.66-7.78 (m, 2 H) 8.05 (s, 1 H) 8.16 (d, J = 5.31 Hz, 1 H) 8.32 (t, J = 5.05 Hz, 1 H) 11.56 (s, 1 H) | 541.3 |
| 6 | 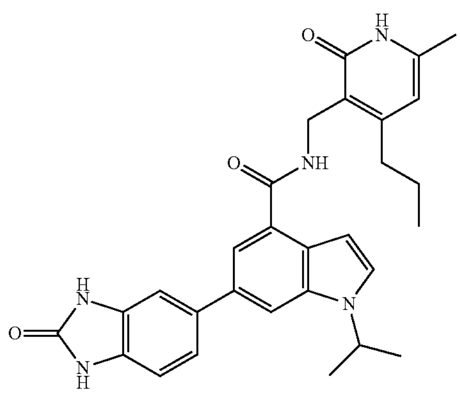 [SMILES: CCCc1cc(C)[nH]c(=O)c1CNC(=O)c1cc(-c2ccc3[nH]c(=O)[nH]c3c2)cc2c1ccn2C(C)C] | 1-(1-Methylethyl)-N-[(6-methyl-2-oxo-4-propyl-1,2-dihydro-3-pyridinyl)methyl]-6-(2-oxo-2,3-dihydro-1H-benzimidazol-5-yl)-1H-indole-4-carboxamide | 0.91 (t, J = 7.33 Hz, 3 H) 1.47 (d, J = 6.57 Hz, 6 H) 1.50-1.60 (m, 2 H) 2.13 (s, 3 H) 2.55 (t, J = 7.07 Hz, 2 H) 4.41 (d, J = 5.05 Hz, 2 H) 4.94 (quin, J = 6.63 Hz, 1 H) 5.91 (s, 1 H) 6.85 (d, J = 3.28 Hz, 1 H) 7.00 (d, J = 7.83 Hz, 1 H) 7.29 (s, 1 H) 7.35 (dd, J = 8.08, 1.77 Hz, 1 H) 7.57-7.69 (m, 2 H) 7.83 (s, 1 H) 8.30 (t, J = 5.05 Hz, 1 H) 10.70 (s, 1 H) 10.66 (s, 1 H) 11.56 (s, 1 H) | 498.3 |
| 7 | 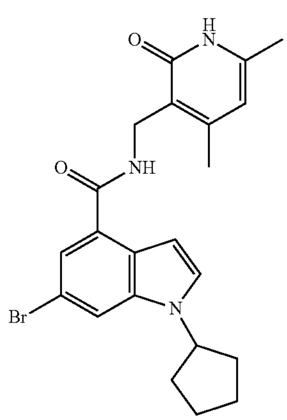 [SMILES: Cc1cc(C)c(CNC(=O)c2cc(Br)cc3c2ccn3C2CCCC2)c(=O)[nH]1] | 6-Bromo-1-cyclopentyl-N-[(4,6-dimethyl-2-oxo-1,2-dihydro-3-pyridinyl)methyl]-1H-indole-4-carboxamide | 1.64-1.87 (m, 6 H) 2.08-2.18 (m, 5 H) 2.21 (s, 3 H) 4.32 (d, J = 5.05 Hz, 2 H) 4.86-5.02 (m, 1 H) 5.88 (s, 1 H) 6.86 (d, J = 3.03 Hz, 1 H) 7.52 (d, J = 1.77 Hz, 1 H) 7.58 (d, J = 3.28 Hz, 1 H) 7.92 (s, 1 H) 8.24-8.38 (m, 1 H) 11.54 (s, 1 H) | 442.0, 444.2 |

| Ex | Structure | Name | ¹H NMR (400 MHz, DMSO-d$_6$) δ ppm | MS(ES) [M + H]$^+$ |
|---|---|---|---|---|
| 8 | 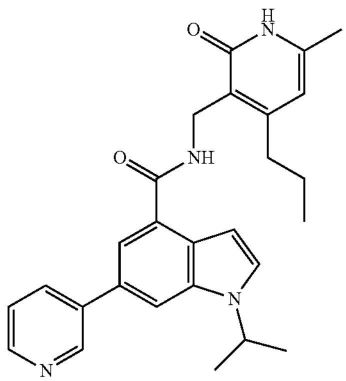 [SMILES: CCCc1cc(C)[nH]c(=O)c1CNC(=O)c1cc(-c2cccnc2)cc2c1ccn2C(C)C] | 1-(1-Methylethyl)-N-[(6-methyl-y)-2-oxo-4-propyl-1,2-dihydro-3-pyridinyl)methyl]-6-(3-pyridinyl)-1H-indole-4-carboxamide | 0.90 (t, J = 7.33 Hz, 3 H) 1.44-1.59 (m, 8 H) 2.13 (s, 3 H) 2.54 (dd, J = 8.59, 6.82 Hz, 2 H) 4.41 (d, J = 5.05 Hz, 2 H) 4.98 (quin, J = 6.63 Hz, 1 H) 5.91 (s, 1 H) 6.92 (d, J = 3.28 Hz, 1 H) 7.49 (dd, J = 7.33, 4.80 Hz, 1 H) 7.66 (d, J = 3.03 Hz, 1 H) 7.75 (d, J = 1.26 Hz, 1 H) 8.04 (s, 1 H) 8.20 (dt, J = 8.27, 1.80 Hz, 1 H) 8.34 (t, J = 5.05 Hz, 1 H) 8.54 (dd, J = 4.67, 1.64 Hz, 1 H) 9.04 (d, J = 1.77 Hz, 1 H) 11.56 (s, 1 H) | 443.2 |
| 9 | 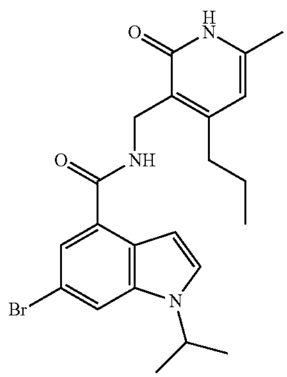 [SMILES: CCCc1cc(C)[nH]c(=O)c1CNC(=O)c1cc(Br)cc2c1ccn2C(C)C] | 6-Bromo-1-(1-methylethyl)-N-[(6-methyl-2-oxo-4-propyl-1,2-dihydro-3-pyridinyl)methyl]-1H-indole-4-carboxamide | 0.90 (t, J = 7.33 Hz, 3 H) 1.43 (d, J = 6.57 Hz, 6 H) 1.47-1.62 (m, 2 H) 2.13 (s, 3 H) 2.53 (d, J = 7.83 Hz, 2 H) 4.35 (d, J = 5.05 Hz, 2 H) 4.76-4.88 (m, 1 H) 5.91 (s, 1 H) 6.86 (d, J = 3.03 Hz, 1 H) 7.51 (d, J = 1.52 Hz, 1 H) 7.63 (d, J = 3.28 Hz, 1 H) 7.92 (s, 1 H) 8.29 (t, J = 5.05 Hz, 1 H) 11.56 (br. s., 1 H) | 444.2, 446.0 |
| 10 | 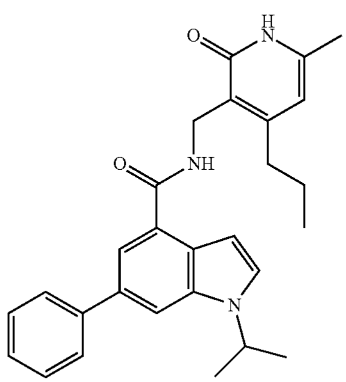 [SMILES: CCCc1cc(C)[nH]c(=O)c1CNC(=O)c1cc(-c2ccccc2)cc2c1ccn2C(C)C] | 1-(1-Methylethyl)-N-[(6-methyl-2-oxo-4-propyl-1,2-dihydro-3-pyridinyl)methyl]-6-phenyl-1H-indole-4-carboxamide | 0.91 (t, J = 7.33 Hz, 3 H) 1.48 (d, J = 6.57 Hz, 6 H) 1.50-1.60 (m, 2 H) 2.13 (s, 3 H) 2.54 (dd, J = 8.59, 6.82 Hz, 2 H) 4.41 (d, J = 5.05 Hz, 2 H) 4.88-5.02 (m, 1 H) 5.91 (s, 1 H) 6.88 (d, J = 3.03 Hz, 1 H) 7.28-7.38 (m, 1 H) 7.43-7.51 (m, 2 H) 7.63 (d, J = 3.28 Hz, 1 H) 7.71 (d, J = 1.26 Hz, 1 H) 7.75-7.83 (m, 2 H) 7.93 (s, 1 H) 8.32 (t, J = 5.05 Hz, 1 H) 11.57 (s, 1 H) | 442.1 |
| 11 | 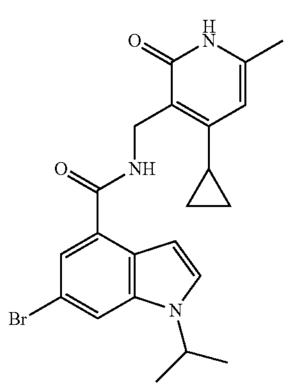 [SMILES: Cc1cc(C2CC2)c(CNC(=O)c2cc(Br)cc3c2ccn3C(C)C)c(=O)[nH]1] | 6-Bromo-N-[(4-cyclopropyl-6-methyl-2-oxo-1,2-dihydro-3-pyridinyl)methyl]-1-(1-methylethyl)-1H-indole-4-carboxamide | 11.48 (s, 1 H) 8.36 (t, J = 4.93 Hz, 1 H) 7.92 (s, 1 H) 7.63 (d, J = 3.28 Hz, 1 H) 7.52 (d, J = 1.52 Hz, 1 H) 6.84 (d, J = 3.28 Hz, 1 H) 5.52 (s, 1 H) 4.80-4.86 (m, 1 H) 4.52 (d, J = 5.05 Hz, 2 H) 2.14-2.19 (m, 1 H) 2.10 (s, 3 H) 1.43 (d, J = 6.57 Hz, 6 H) 0.91-0.98 (m, 2 H) 0.70-0.77 (m, 2 H) | 442.0, 444.1 |

-continued

| Ex | Structure | Name | ¹H NMR (400 MHz, DMSO-d₆) δ ppm | MS(ES) [M + H]⁺ |
|---|---|---|---|---|
| 12 | 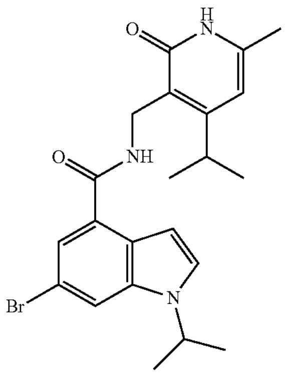 | 6-Bromo-1-(1-methylethyl)-N-{[6-methyl-4-(1-methylethyl)-2-oxo-1,2-dihydro-3-pyridinyl]methyl}-1H-indole-4-carboxamide | 11.54 (s, 1 H) 8.31 (t, J = 5.05 Hz, 1 H) 7.92 (s, 1 H) 7.63 (d, J = 3.28 Hz, 1 H) 7.51 (d, J = 1.52 Hz, 1 H) 6.86 (d, J = 3.28 Hz, 1 H) 6.02 (s, 1 H) 4.78-4.87 (m, 1 H) 4.40 (d, J = 4.80 Hz, 2 H) 3.36-3.40 (m, 1 H) 3.24-3.28 (m, 1 H) 2.16 (s, 3 H) 1.43 (d, J = 6.57 Hz, 6 H) 1.09-1.15 (m, 6 H) | 444.1, 446.0 |
| 13 | 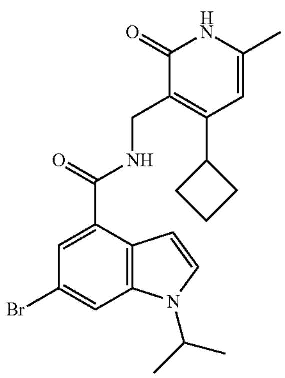 [SMILES: Cc1cc(C2CCC2)c(CNC(=O)c2cc(Br)cc3c2ccn3C(C)C)c(=O)[nH]1] | 6-Bromo-N-[(4-cyclobutyl-6-methyl-2-oxo-1,2-dihydro-3-pyridinyl)methyl]-1-(1-methylethyl)-1H-indole-4-carboxamide | 11.60 (s, 1 H) 8.26 (t, J = 4.80 Hz, 1 H) 7.92 (s, 1 H) 7.63 (d, J = 3.28 Hz, 1 H) 7.50 (d, J = 1.52 Hz, 1 H) 6.87 (d, J = 3.28 Hz, 1 H) 6.12 (s, 1 H) 4.78-4.86 (m, 1 H) 4.31 (d, J = 4.80 Hz, 2 H) 3.80 (m, 1 H) 2.21-2.26 (m, 2 H) 2.18 (s, 3 H) 2.05-2.13 (m, 2 H) 1.93-2.03 (m, 1 H) 1.78 (m, 1 H) 1.43 (d, J = 6.57 Hz, 6 H) | 455.9, 458.1 |
| 14 | 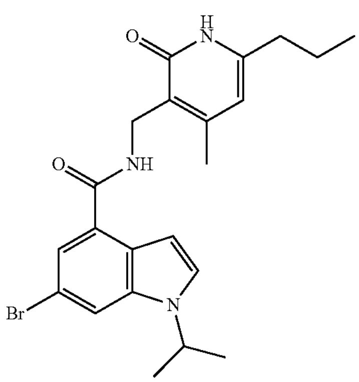 [SMILES: CCCc1cc(C)c(CNC(=O)c2cc(Br)cc3c2ccn3C(C)C)c(=O)[nH]1] | 6-Bromo-1-(1-methylethyl)-N-[(4-methyl-2-oxo-6-propyl-1,2-dihydro-3-pyridinyl)methyl]-1H-indole-4-carboxamide | 8.33 (br. s., 1H), 7.92 (s, 1H), 7.63 (d, J = 3.28 Hz, 1H), 7.52 (d, J = 1.52 Hz, 1H), 6.87 (d, J = 3.28 Hz, 1H), 5.90 (s, 1H), 4.78-4.87 (m, 1H), 4.33 (d, J = 5.05 Hz, 2H), 2.37 (t, J = 7.58 Hz, 2H), 2.23 (s, 3H), 1.58 (sxt, J = 7.43 Hz, 2H), 1.43 (d, J = 6.57 Hz, 6H), 0.88 (t, J = 7.33 Hz, 3H) | 444.2, 446.0 |
| 15 | 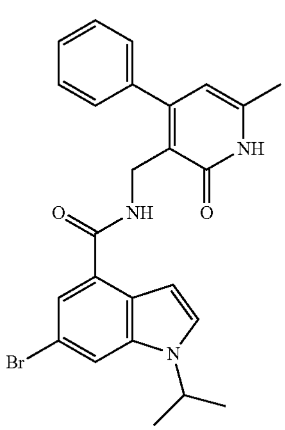 [SMILES: Cc1cc(-c2ccccc2)c(CNC(=O)c2cc(Br)cc3c2ccn3C(C)C)c(=O)[nH]1] | 6-Bromo-1-(1-methylethyl)-N-[(6-methyl-2-oxo-4-phenyl-1,2-dihydro-3-pyridinyl)methyl]-1H-indole-4-carboxamide | 11.88 (s, 1 H) 8.35 (t, J = 4.42 Hz, 1 H) 7.93 (s, 1 H) 7.63 (d, J = 3.28 Hz, 1 H) 7.40-7.50 (m, 6 H) 6.86 (d, J = 3.03 Hz, 1 H) 6.00 (s, 1 H) 4.78-4.87 (m, 1 H) 4.19 (d, J = 4.29 Hz, 2 H) 2.22 (s, 3 H) 1.44 (d, J = 6.57 Hz, 6 H) | 447.9, 479.7 |

-continued

| Ex | Structure | Name | ¹H NMR (400 MHz, DMSO-d₆) δ ppm | MS(ES) [M + H]⁺ |
|---|---|---|---|---|
| 16 | 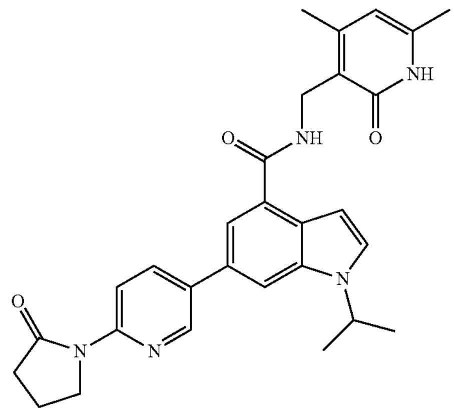 [SMILES: Cc1cc(C)c(CNC(=O)c2cc(-c3ccc(N4CCCC4=O)nc3)cc3c2ccn3C(C)C)c(=O)[nH]1] | N-((4,6-dimethyl-2-oxo-1,2-dihydropyridin-3-yl)methyl)-1-isopropyl-6-(6-(2-oxopyrrolidin-1-yl)pyridin-3-yl)-1H-indole-4-carboxamide | 1.49 (d, J = 4.00 Hz 6 H), 2.03-2.15 (m, 5 H), 2.24 (s, 3 H), 2.61 (t, J = 8.08 Hz, 2 H), 4.06 (t, J = 7.20 Hz, 2 H), 4.38 (d, J = 5.05 Hz, 2 H), 4.96 (quin, J = 6.69 Hz, 1 H), 5.89 (s, 1 H), 6.91 (d, J = 3.28 Hz, 1 H), 7.65 (d, J = 3.28 Hz, 1 H), 7.75 (d, J = 1.26 Hz, 1 H), 8.01 (s, 1 H), 8.25 (dd, J = 8.59, 2.53 Hz, 1 H), 8.32 (t, J = 5.05 Hz, 1 H), 8.39 (d, J = 8.84 Hz, 1 H), 8.85 (d, J = 2.02 Hz, 1 H), 11.55 (s, 1 H) | 498.3 |
| 17 | 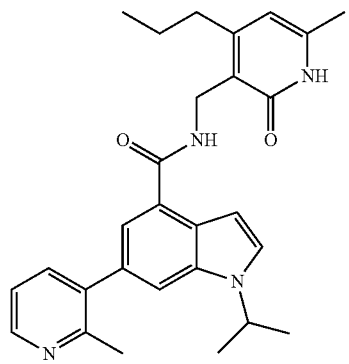 [SMILES: CCCc1cc(C)[nH]c(=O)c1CNC(=O)c1cc(-c2cccnc2C)cc2c1ccn2C(C)C] | 1-isopropyl-N-((6-methyl-2-oxo-4-propyl-1,2-dihydropyridin-3-yl)methyl)-6-(2-methylpyridin-3-yl)-1H-indole-4-carboxamide | 0.86-0.94 (m, 3 H), 1.46 (d, J = 6.57 Hz, 6 H), 1.50-1.59 (m, 2 H), 2.12 (s, 3 H), 4.38 (d, J = 5.31 Hz, 2 H), 4.80-4.94 (m, 1 H), 5.90 (s, 1 H), 6.92 (d, J = 3.03 Hz, 1 H), 7.31 (dd, J = 7.71, 4.93 Hz, 1 H), 7.42 (d, J = 1.26 Hz, 1 H), 7.66 (d, J = 3.28 Hz, 1 H), 7.67-7.72 (m, 3 H), 8.17 (s, 1 H), 8.24 (t, J = 5.18 Hz, 1 H), 8.46 (dd, J = 4.80, 1.77 Hz, 1 H) | 457.1 |
| 18 | 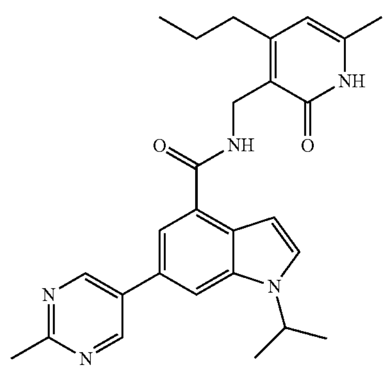 | 1-isopropyl-N-((6-methyl-2-oxo-4-propyl-1,2-dihydropyridin-3-yl)methyl)-6-(2-methylpyrimidin-5-yl)-1H-indole-4-carboxamide | 0.85-0.95 (m, 3 H), 1.44-1.60 (m, 8 H), 2.13 (s, 3 H), 3.33 (br. s., 2 H), 2.67 (s, 3H), 4.41 (d, J = 5.31 Hz, 2 H), 4.97 (quin, J = 6.63 Hz, 1 H), 5.92 (s, 1 H), 6.90 (d, J = 3.03 Hz, 1 H), 7.65 (d, J = 3.28 Hz, 1 H), 7.78 (d, J = 1.26 Hz, 2 H), 8.11 (s, 1 H), 8.32 (m, 1 H) | 458.2 |
| 19 | 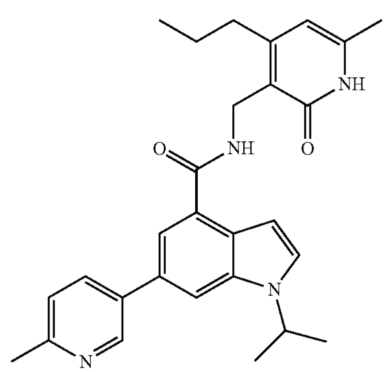 | 1-isopropyl-N-((6-methyl-2-oxo-4-propyl-1,2-dihydropyridin-3-yl)methyl)-6-(6-methylpyridin-3-yl)-1H-indole-4-carboxamide | 0.85-0.96 (m, 3 H), 1.48 (d, J = 8.00 Hz, 6 H), 1.55 (m, 2 H), 2.13 (s, 3 H), 3.33 (br. s., 1 H), 4.41 (d, J = 5.31 Hz, 2 H), 4.97 (quin, J = 6.63 Hz, 1 H), 5.92 (s, 1 H), 6.90 (d, J = 3.03 Hz, 1 H), 7.35 (d, J = 8.08 Hz, 1 H), 7.65 (d, J = 3.28 Hz, 1 H), 7.72 (d, J = 1.26 Hz, 1 H), 7.99 (s, 1 H), 8.09 (dd, J = 8.08, 2.53 Hz, 1 H), 8.15 (s, 1 H), 8.33 (t, J = 5.05 Hz, 1 H), 8.89 (d, J = 2.02 Hz, 1 H) | 457.1 |

-continued

| Ex | Structure | Name | ¹H NMR (400 MHz, DMSO-d₆) δ ppm | MS(ES) [M + H]⁺ |
|---|---|---|---|---|
| 20 | 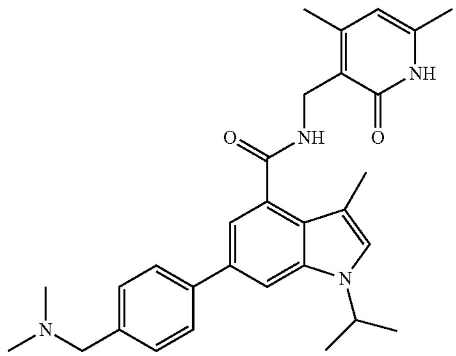 | N-((4,6-dimethyl-2-oxo-1,2-dihydropyridin-3-yl)methyl)-6-(4-((dimethylamino)methyl)phenyl)-1-isopropyl-3-methyl-1H-indole-4-carboxamide | 1.44 (m, 6 H), 1.73-1.80 (m, 2 H), 2.11 (s, 3 H), 2.17 (s, 3 H), 2.22-2.26 (m, 9 H), 3.58-3.65 (m, 2 H), 4.36 (d, J = 5.05 Hz, 2 H), 4.87 (quin, J = 6.69 Hz, 1 H), 5.87 (s, 1 H), 7.25 (d, J = 1.26 Hz, 1 H), 7.32 (d, J = 1.01 Hz, 1 H), 7.38 (d, J = 8.08 Hz, 2 H), 7.71 (d, J = 8.34 Hz, 2 H), 7.78 (d, J = 1.26 Hz, 1 H), 8.12-8.23 (m, 1 H) | 485.3 |
| 21 | 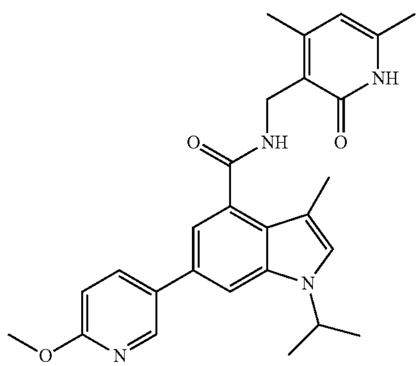 | N-((4,6-dimethyl-2-oxo-1,2-dihydropyridin-3-yl)methyl)-1-isopropyl-6-(6-methoxypyridin-3-yl)-3-methyl-1H-indole-4-carboxamide | 1.38-1.47 (m, 6 H), 2.11 (s, 3 H), 2.17 (s, 3 H), 2.24 (s, 3 H), 3.90 (s, 3 H), 4.35 (d, J = 5.05 Hz, 2 H), 4.86 (quin, J = 6.57 Hz, 1 H), 5.87 (s, 1 H), 6.88-6.96 (m, 1 H), 7.22 (d, J = 1.26 Hz, 1 H), 7.33 (d, J = 1.01 Hz, 1 H), 7.79 (d, J = 1.52 Hz, 1 H), 8.09 (dd, J = 8.59, 2.53 Hz, 1 H), 8.17 (t, J = 5.05 Hz, 1 H), 8.54 (d, J = 2.02 Hz, 1 H) | 459.3 |
| 22 | 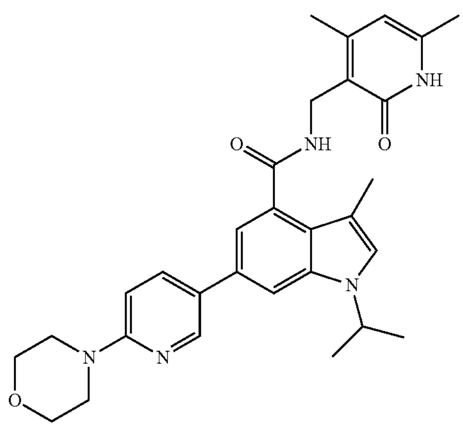 [SMILES: Cc1cc(C)c(CNC(=O)c2cc(-c3ccc(N4CCOCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(6-morpholinopyridin-3-yl)-1H-indole-4-carboxamide | 1.43 (m, 6 H), 2.11 (s, 3 H), 2.16 (s, 3 H), 2.24 (s, 3 H), 3.45-3.54 (m, 4 H), 3.70-3.79 (m, 4 H), 4.35 (d, J = 5.05 Hz, 2 H), 4.85 (quin, J = 6.63 Hz, 1 H), 5.87 (s, 1 H), 6.93 (d, J = 8.84 Hz, 1 H), 7.20 (d, J = 1.26 Hz, 1 H), 7.29 (s, 1 H), 7.69-7.77 (m, 1 H), 7.96 (dd, J = 8.97, 2.65 Hz, 1 H), 8.15 (t, J = 5.05 Hz, 1 H), 8.54 (d, J = 2.27 Hz, 1 H), 11.48 (s, 1 H) | 514.3 |
| 23 | 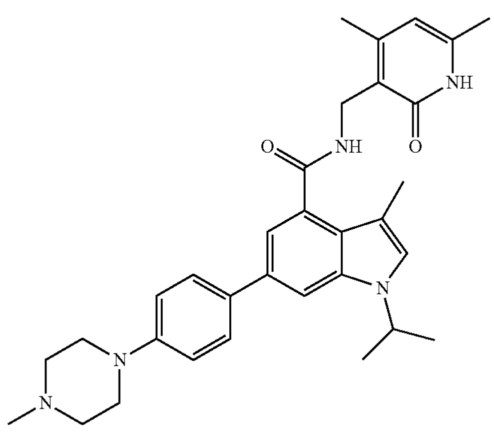 | N-((4,6-dimethyl-2-oxo-1,2-dihydropyridin-3-yl)methyl)-1-isopropyl-3-methyl-6-(4-(4-methylpiperazin-1-yl)phenyl)-1H-indole-4-carboxamide | 1.43 (m, 6 H), 2.11 (s, 3 H), 2.16 (s, 3 H), 2.24 (s, 3 H), 2.29 (s, 3 H), 2.53-2.58 (m, 4 H), 3.15-3.28 (m, 4 H), 4.35 (d, J = 5.05 Hz, 2 H), 4.84 (quin, J = 6.69 Hz, 1 H), 5.87 (s, 1 H), 7.02 (d, J = 8.84 Hz, 2 H), 7.19 (d, J = 1.26 Hz, 1 H), 7.27 (s, 1 H), 7.60 (d, J = 8.84 Hz, 2 H), 7.67 (d, J = 1.26 Hz, 1 H), 8.09-8.21 (m, 2 H) | 526.3 |

| Ex | Structure | Name | ¹H NMR (400 MHz, DMSO-d₆) δ ppm | MS(ES) [M + H]⁺ |
|---|---|---|---|---|
| 24 | 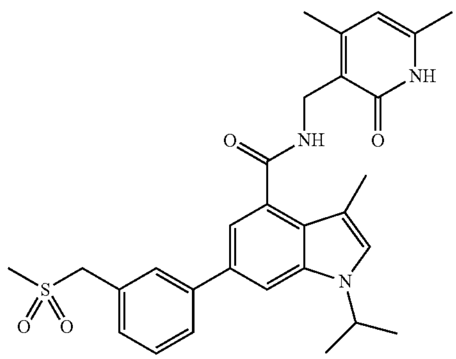 | N-((4,6-dimethyl-2-oxo-1,2-dihydropyridin-3-yl)methyl)-1-isopropyl-3-methyl-6-(3-((methylsulfonyl)methyl)phenyl)-1H-indole-4-carboxamide | 1.45 (m, 6 H), 2.11 (s, 3 H), 2.17 (s, 3 H), 2.24 (s, 3 H), 2.95 (s, 3 H), 4.36 (d, J = 5.05 Hz, 2 H), 4.57 (s, 2 H), 4.85 (quin, J = 6.63 Hz, 1 H), 5.87 (s, 1 H), 7.25 (d, J = 1.52 Hz, 1 H), 7.33-7.40 (m, 2 H), 7.49 (t, J = 7.71 Hz, 1 H), 7.72-7.82 (m, 3 H), 8.19 (t, J = 5.05 Hz, 1 H), 11.47 (s, 1 H) | 520.0 |
| 25 | 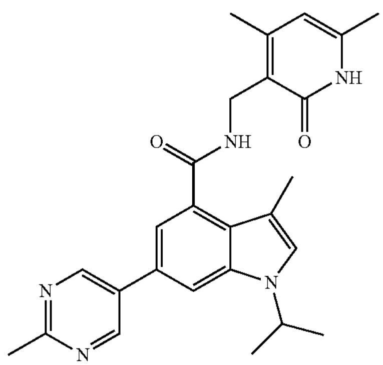 | N-((4,6-dimethyl-2-oxo-1,2-dihydropyridin-3-yl)methyl)-1-isopropyl-3-methyl-6-(2-methylpyrimidin-5-yl)-1H-indole-4-carboxamide | 1.44 (m, 6 H), 2.11 (s, 3 H), 2.17 (s, 3 H), 2.25 (s, 3 H), 2.67 (s, 3 H), 4.36 (d, J = 5.05 Hz, 2 H), 4.90 (quin, J = 6.63 Hz, 1 H), 5.87 (s, 1 H), 7.33 (d, J = 1.52 Hz, 1 H), 7.39 (d, J = 1.01 Hz, 1 H), 7.96 (d, J = 1.26 Hz, 1 H), 8.20 (t, J = 5.05 Hz, 1 H), 9.09 (s, 2 H), 11.49 (s, 1 H) | 444.2 |
| 26 | 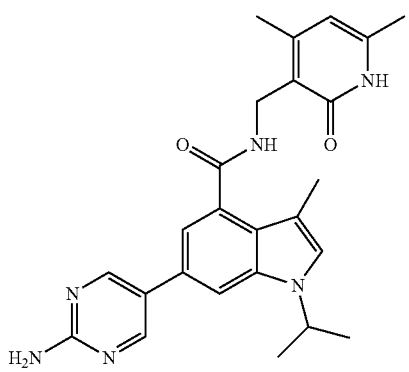 [SMILES: Cc1cc(C)c(CNC(=O)c2cc(-c3cnc(N)nc3)cc3c2c(C)cn3C(C)C)c(=O)[nH]1] | 6-(2-aminopyrimidin-5-yl)-N-((4,6-dimethyl-2-oxo-1,2-dihydropyridin-3-yl)methyl)-1-isopropyl-3-methyl-1H-indole-4-carboxamide | 1.43 (d, 6 H), 2.11 (s, 3 H), 2.15-2.20 (m, 3 H), 2.24 (s, 3 H), 4.35 (d, J = 5.05 Hz, 2 H), 4.85 (quin, J = 6.69 Hz, 1 H), 5.87 (s, 1 H), 6.70 (s, 2 H), 7.18 (d, J = 1.26 Hz, 1 H), 7.30 (s, 1 H), 7.75 (d, J = 1.26 Hz, 1 H), 8.10-8.19 (m, 1 H), 8.61-8.68 (m, 2H), 11.49 (br. s., 1 H) | 445.2 |
| 27 | 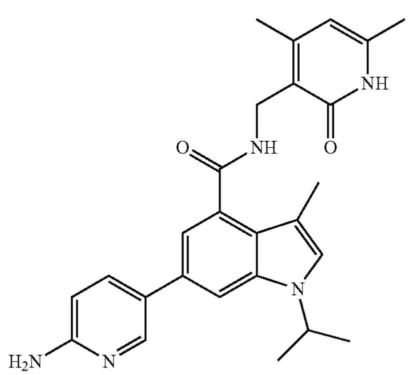 [SMILES: Cc1cc(C)c(CNC(=O)c2cc(-c3ccc(N)nc3)cc3c2c(C)cn3C(C)C)c(=O)[nH]1] | 6-(6-aminopyridin-3-yl)-N-((4,6-dimethyl-2-oxo-1,2-dihydropyridin-3-yl)methyl)-1-isopropyl-3-methyl-1H-indole-4-carboxamide | 1.42 (d, J = 8.00 Hz, 6 H), 2.11 (s, 3 H), 2.16 (s, 3 H), 2.24 (s, 3 H), 4.35 (d, J = 5.05 Hz, 2 H), 4.83 (quin, J = 6.63 Hz, 1 H), 5.87 (s, 1 H), 6.02 (s, 2 H), 6.54 (d, J = 8.59 Hz, 1 H), 7.14 (d, J = 1.52 Hz, 1 H), 7.27 (s, 1 H), 7.66 (d, J = 1.26 Hz, 1 H), 7.78 (dd, J = 8.59, 2.53 Hz, 1 H), 8.11-8.18 (m, 1 H), 8.30 (d, J = 2.02 Hz, 1 H) | 444.2 |

| Ex | Structure | Name | $^1$H NMR (400 MHz, DMSO-d$_6$) δ ppm | MS(ES) [M + H]$^+$ |
|---|---|---|---|---|
| 28 | 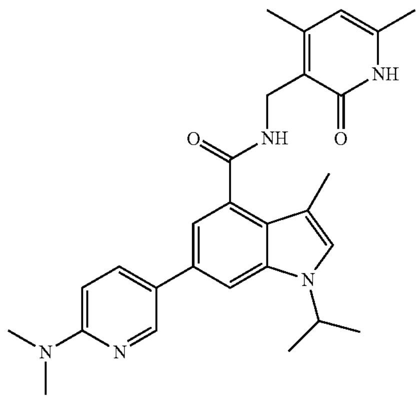 | N-((4,6-dimethyl-2-oxo-1,2-dihydropyridin-3-yl)methyl)-6-(6-(dimethylamino)pyridin-3-yl)-1-isopropyl-3-methyl-1H-indole-4-carboxamide | 1.43 (d, J = 8.00 Hz, 6 H), 2.11 (s, 3 H), 2.16 (s, 3 H), 2.24 (s, 3 H), 3.07 (s, 6 H), 4.35 (d, J = 5.05 Hz, 2 H), 4.84 (quin, J = 6.57 Hz, 1 H), 5.87 (s, 1 H), 6.73 (d, J = 8.59 Hz, 1 H), 7.17 (d, J = 1.52 Hz, 1 H), 7.28 (d, J = 1.01 Hz, 1 H), 7.68-7.74 (m, 1 H), 7.90 (dd, J = 8.84, 2.53 Hz, 1 H), 8.11-8.18 (m, 1 H), 8.48 (d, J = 2.02 Hz, 1 H) | 472.5 |
| 29 | 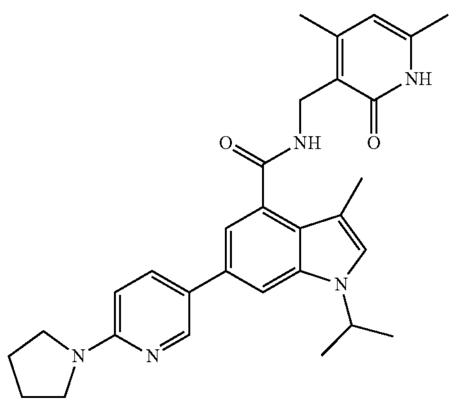 [SMILES: Cc1cc(C)c(CNC(=O)c2cc(-c3ccc(N4CCCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(6-(pyrrolidin-1-yl)pyridin-3-yl)-1H-indole-4-carboxamide | 1.39-1.47 (d, J = 8.00 Hz, 6 H), 1.93-2.01 (m, 4 H), 2.11 (s, 3 H), 2.16 (s, 3 H), 2.24 (s, 3 H), 3.41-3.48 (m, 4 H), 4.35 (d, J = 5.05 Hz, 2 H), 4.84 (quin, J = 6.63 Hz, 1 H), 5.87 (s, 1 H), 6.56 (d, J = 8.59 Hz, 1 H), 7.17 (d, J = 1.52 Hz, 1 H), 7.27 (d, J = 1.01 Hz, 1 H), 7.69 (d, J = 1.26 Hz, 1 H), 7.91 (dd, J = 8.72, 2.15 Hz, 1 H), 8.10-8.17 (m, 1 H), 8.45 (d, J = 2.27 Hz, 1 H) | 498.4 |
| 30 | 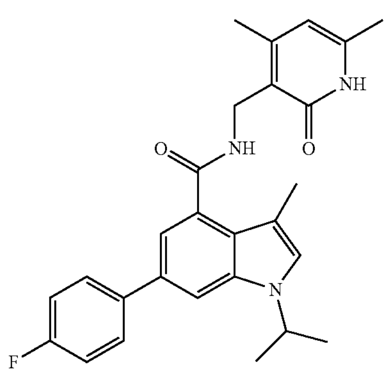 | N-((4,6-dimethyl-2-oxo-1,2-dihydropyridin-3-yl)methyl)-6-(4-fluorophenyl)-1-isopropyl-3-methyl-1H-indole-4-carboxamide | 1.43 (m, 6 H), 2.11 (s, 3 H), 2.17 (s, 3 H), 2.24 (s, 3 H), 4.31-4.41 (m, 2 H), 4.80-4.93 (m, 1 H), 5.87 (s, 1 H), 7.17-7.36 (m, 4 H), 7.74-7.84 (m, 3 H), 8.16-8.24 (m, 1 H), 11.43-11.55 (m, 1 H) | 446.0 |

-continued

| Ex | Structure | Name | ¹H NMR (400 MHz, DMSO-d₆) δ ppm | MS(ES) [M + H]⁺ |
|---|---|---|---|---|
| 31 | 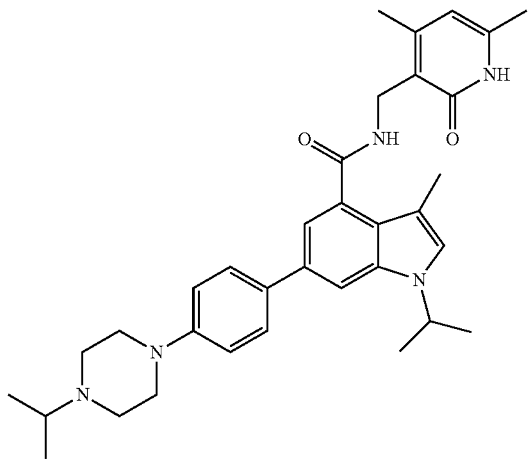 [SMILES: Cc1cc(C)c(CNC(=O)c2cc(-c3ccc(N4CCN(C(C)C)CC4)cc3)cc3c2c(C)cn3C(C)C)c(=O)[nH]1] | N-((4,6-dimethyl-2-oxo-1,2-dihydropyridin-3-yl)methyl)-1-isopropyl-6-(4-(4-isopropylpiperazin-1-yl)phenyl)-3-methyl-1H-indole-4-carboxamide | 1.01-1.11 (m, 6 H), 1.43 (d, J = 6.57 Hz, 6 H), 2.11 (s, 3 H), 2.16 (s, 3 H), 2.24 (s, 3 H), 2.68 (br. s., 4 H), 2.74-2.84 (m, 1 H), 3.15-3.26 (m, 4 H), 4.35 (d, J = 5.05 Hz, 2 H), 4.83 (quin, J = 6.57 Hz, 1 H), 5.87 (s, 1 H), 7.02 (d, J = 8.84 Hz, 2 H), 7.19 (d, J = 1.52 Hz, 1 H), 7.27 (s, 1 H), 7.60 (d, J = 8.84 Hz, 2 H), 7.67 (d, J = 1.26 Hz, 1 H), 8.11-8.21 (m, 2 H) | 554.2 |
| 32 | 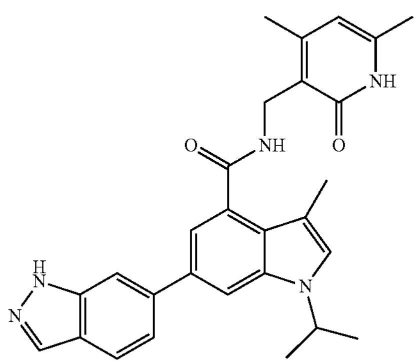 [SMILES: Cc1cc(C)c(CNC(=O)c2cc(-c3ccc4cn[nH]c4c3)cc3c2c(C)cn3C(C)C)c(=O)[nH]1] | N-((4,6-dimethyl-2-oxo-1,2-dihydropyridin-3-yl)methyl)-6-(1H-indazol-6-yl)-1-isopropyl-3-methyl-1H-indole-4-carboxamide | 1.40-1.51 (m, 6 H), 2.11 (s, 3 H), 2.19 (s, 3 H), 2.25 (s, 3 H), 4.33-4.46 (m, 2 H), 4.90 (quin, J = 6.63 Hz, 1 H), 5.87 (s, 1 H), 7.33 (dd, J = 12.76, 1.14 Hz, 2 H), 7.54 (dd, J = 8.46, 1.39 Hz, 1 H), 7.76-7.89 (m, 3 H), 8.09 (s, 1 H), 8.24 (t, J = 5.05 Hz, 1 H), 11.48 (br. s., 1 H), 13.07 (br. s., 1 H) | 468.3 |
| 33 | 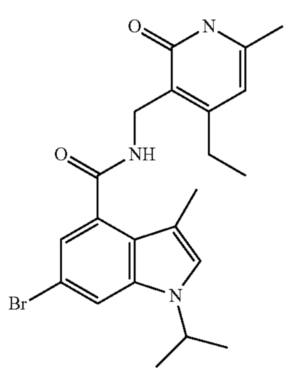 [SMILES: CCc1cc(C)[nH]c(=O)c1CNC(=O)c1cc(Br)cc2c1c(C)cn2C(C)C] | 6-bromo-N-[(4-ethyl-6-methyl-2-oxo-1,2-dihydro-3-pyridinyl)methyl]-3-methyl-1-(1-methylethyl)-1H-indole-4-carboxamide | 11.49 (s, 1 H) 8.23 (t, J = 5.05 Hz, 1 H) 7.77 (d, J = 1.77 Hz, 1 H) 7.33 (s, 1 H) 7.00 (d, J = 1.77 Hz, 1 H) 5.91 (s, 1 H) 4.74 (quin, J = 6.63 Hz, 1 H) 4.33 (s, 1 H) 4.32 (s, 1 H) 2.56 (q, J = 7.58 Hz, 2 H) 2.13 (s, 6 H) 1.40 (s, 3 H) 1.38 (s, 3 H) 1.13 (t, J = 7.58 Hz, 3 H) | 444.1/ 446.0 |

-continued

| Ex | Structure | Name | ¹H NMR (400 MHz, DMSO-d₆) δ ppm | MS(ES) [M + H]⁺ |
|---|---|---|---|---|
| 34 | 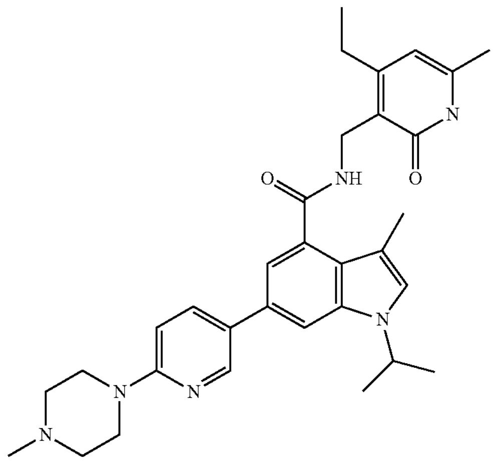 | N-[(4-ethyl-6-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide | 11.46 (br. s., 1 H) 8.50 (d, J = 2.27 Hz, 1 H) 8.10-8.18 (m, 1 H) 7.92 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.92 (d, J = 8.84 Hz, 1 H) 5.92 (s, 1 H) 4.84 (quin, J = 6.57 Hz, 1 H) 4.37 (d, J = 4.80 Hz, 2 H) 3.49-3.55 (m, 4 H) 2.59 (q, J = 7.41 Hz, 2 H) 2.40-2.44 (m, 4 H) 2.23 (s, 3 H) 2.17 (s, 3 H) 2.13 (s, 3 H) 1.44 (s, 3 H) 1.42 (s, 3 H) 1.14 (t, J = 7.58 Hz, 3 H) | 541.5 |
| 35 | 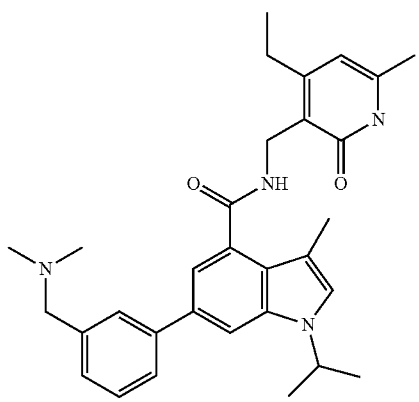 | 6-{3-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide | 11.48 (br. s., 1 H) 8.18 (t, J = 5.05 Hz, 1 H) 7.76 (d, J = 1.26 Hz, 1 H) 7.59-7.65 (m, 2 H) 7.40 (t, J = 7.58 Hz, 1 H) 7.33 (s, 1 H) 7.22-7.26 (m, 2 H) 5.92 (s, 1 H) 4.88 (dt, J = 13.33, 6.60 Hz, 1 H) 4.38 (s, 1 H) 4.37 (s, 1 H) 3.46 (s, 2 H) 2.59 (q, J = 7.58 Hz, 2 H) 2.18 (s, 9 H) 2.13 (s, 3 H) 1.45 (s, 3 H) 1.43 (s, 3 H) 1.15 (t, J = 7.58 Hz, 3 H) | 499.3 |
| 36 | 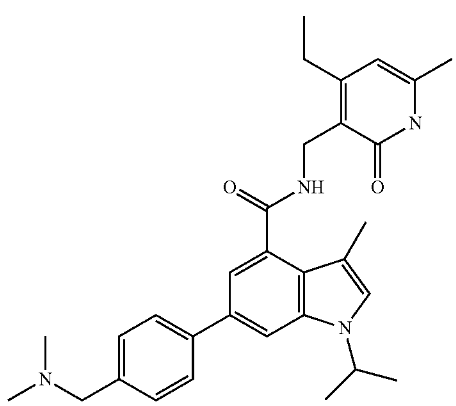 | 6-{4-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide | 11.48 (br. s., 1 H) 8.16 (t, J = 4.93 Hz, 1 H) 7.77 (s, 1 H) 7.70 (s, 1 H) 7.68 (s, 1 H) 7.37 (s, 1 H) 7.35 (s, 1 H) 7.32 (s, 1 H) 7.25 (s, 1 H) 5.92 (s, 1 H) 4.87 (dt, J = 13.14, 6.57 Hz, 1 H) 4.38 (br. s., 1 H) 4.37 (br. s., 1 H) 3.42 (s, 2 H) 2.59 (q, J = 7.58 Hz, 2 H) 2.17 (s, 9 H) 2.13 (s, 3 H) 1.44 (s, 3 H) 1.43 (s, 3 H) 1.15 (t, J = 7.45 Hz, 3 H) | 499.4 |

| Ex | Structure | Name | ¹H NMR (400 MHz, DMSO-d$_6$) δ ppm | MS(ES) [M + H]⁺ |
|---|---|---|---|---|
| 37 | 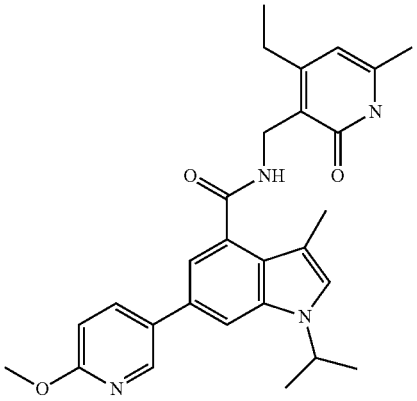 | N-[(4-ethyl-6-methyl-2-oxo-1,2-dihydro-3-pyridinyl)methyl]-3-methyl-1-(1-methylethyl)-6-[6-(methyloxy)-3-pyridinyl]-1H-indole-4-carboxamide | 11.49 (s, 1 H) 8.53 (d, J = 2.02 Hz, 1 H) 8.16 (t, J = 5.05 Hz, 1 H) 8.09 (dd, J = 8.59, 2.53 Hz, 1 H) 7.79 (d, J = 1.26 Hz, 1 H) 7.33 (s, 1 H) 7.22 (d, J = 1.26 Hz, 1 H) 6.91 (d, J = 8.59 Hz, 1 H) 5.92 (s, 1 H) 4.86 (quin, J = 6.63 Hz, 1 H) 4.38 (s, 1 H) 4.36 (s, 1 H) 3.90 (s, 3 H) 2.59 (q, J = 7.58 Hz, 2 H) 2.17 (s, 3 H) 2.13 (s, 3 H) 1.44 (s, 3 H) 1.43 (s, 3 H) 1.14 (t, J = 7.58 Hz, 3 H) | 473.1 |
| 38 | 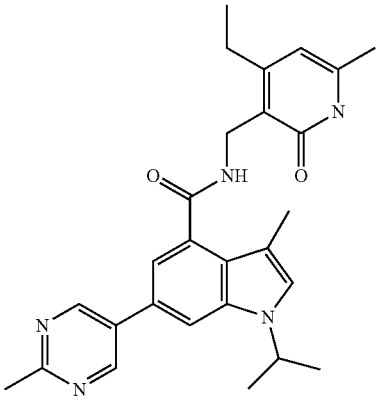 | N-[(4-ethyl-6-methyl-2-oxo-1,2-dihydro-3-pyridinyl)methyl]-3-methyl-1-(1-methylethyl)-6-(2-methyl-5-pyrimidinyl)-1H-indole-4-carboxamide | 11.50 (s, 1 H) 9.09 (s, 2 H) 8.18 (t, J = 5.05 Hz, 1 H) 7.96 (d, J = 1.26 Hz, 1 H) 7.39 (s, 1 H) 7.32 (d, J = 1.52 Hz, 1 H) 5.92 (s, 1 H) 4.90 (quin, J = 6.69 Hz, 1 H) 4.38 (s, 1 H) 4.37 (s, 1 H) 2.65-2.68 (m, 3 H) 2.60 (q, J = 7.58 Hz, 2 H) 2.18 (s, 3 H) 2.13 (s, 3 H) 1.45 (s, 3 H) 1.43 (s, 3 H) 1.14 (t, J = 7.58 Hz, 3 H) | 458.3 |
| 39 | 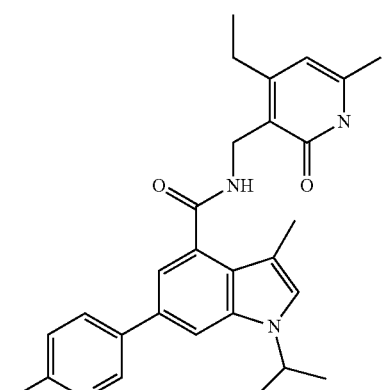 | 6-(6-amino-3-pyridinyl)-N-[(4-ethyl-6-methyl-2-oxo-1,2-dihydro-3-pyridinyl)methyl]-3-methyl-1-(1-methylethyl)-1H-indole-4-carboxamide | 11.50 (s, 1 H) 8.30 (d, J = 2.02 Hz, 1 H) 8.12 (t, J = 5.05 Hz, 1 H) 7.76 (dd, J = 8.59, 2.53 Hz, 1 H) 7.66 (d, J = 1.26 Hz, 1 H) 7.27 (s, 1 H) 7.14 (d, J = 1.52 Hz, 1 H) 6.53 (d, J = 8.59 Hz, 1 H) 5.98 (s, 2 H) 5.92 (s, 1 H) 4.83 (quin, J = 6.63 Hz, 1 H) 4.37 (s, 1 H) 4.36 (s, 1 H) 2.59 (q, J = 7.58 Hz, 2 H) 2.16 (s, 3 H) 2.13 (s, 3 H) 1.43 (s, 3 H) 1.41 (s, 3 H) 1.14 (t, J = 7.45 Hz, 3 H) | 458.2 |

| Ex | Structure | Name | $^1$H NMR (400 MHz, DMSO-d$_6$) δ ppm | MS(ES) [M + H]$^+$ |
|---|---|---|---|---|
| 40 | 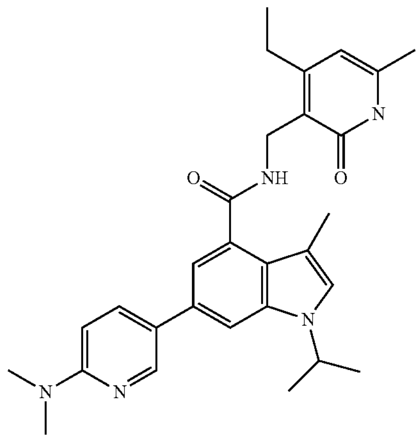 | 6-[6-(dimethylamino)-3-pyridinyl]-N-[(4-ethyl-6-methyl-2-oxo-1,2-dihydro-3-pyridinyl)methyl]-3-methyl-1-(1-methylethyl)-1H-indole-4-carboxamide | 11.47 (br. s., 1 H) 8.48 (d, J = 2.27 Hz, 1 H) 8.14 (t, J = 4.67 Hz, 1 H) 7.89 (dd, J = 8.72, 2.65 Hz, 1 H) 7.70 (d, J = 1.26 Hz, 1 H) 7.28 (s, 1 H) 7.17 (d, J = 1.52 Hz, 1 H) 6.73 (d, J = 8.84 Hz, 1 H) 5.92 (s, 1 H) 4.84 (quin, J = 6.57 Hz, 1 H) 4.37 (s, 1 H) 4.36 (s, 1 H) 3.07 (s, 6 H) 2.59 (q, J = 7.58 Hz, 2 H) 2.16 (s, 3 H) 2.13 (s, 3 H) 1.44 (s, 3 H) 1.42 (s, 3 H) 1.15 (t, J = 7.58 Hz, 3 H) | 486.3 |
| 41 | 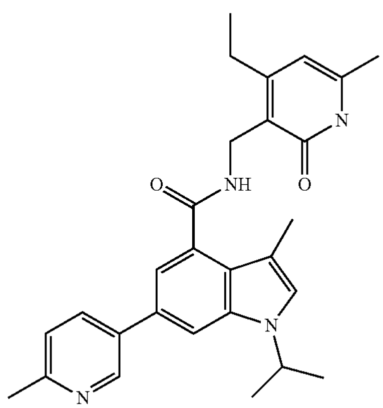 | N-[(4-ethyl-6-methyl-2-oxo-1,2-dihydro-3-pyridinyl)methyl]-3-methyl-1-(1-methylethyl)-6-(6-methyl-3-pyridinyl)-1H-indole-4-carboxamide | 11.44 (br. s., 1 H) 8.83 (d, J = 2.02 Hz, 1 H) 8.20 (t, J = 4.93 Hz, 1 H) 8.03 (dd, J = 8.08, 2.53 Hz, 1 H) 7.84 (d, J = 1.52 Hz, 1 H) 7.31-7.36 (m, 2 H) 7.26 (d, J = 1.52 Hz, 1 H) 5.92 (s, 1 H) 4.88 (quin, J = 6.63 Hz, 1 H) 4.38 (s, 1 H) 4.37 (s, 1 H) 2.59 (q, J = 7.58 Hz, 2 H) 2.18 (s, 3 H) 2.13 (s, 3 H) 1.44 (s, 3 H) 1.43 (s, 3 H) 1.14 (t, J = 7.58 Hz, 3 H) | 457.2 |
| 42 | 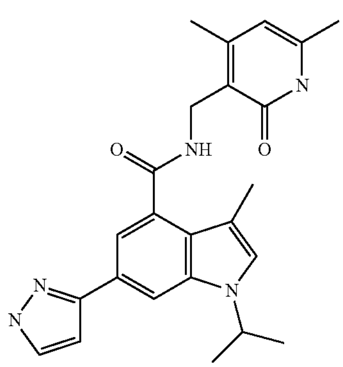 [SMILES: Cc1cc(C)c(CNC(=O)c2cc(-c3cc[nH]n3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrazol-3-yl)-1H-indole-4-carboxamide | 12.77 (br. s., 1 H) 11.48 (br. s., 1 H) 8.10 (br. s., 1 H) 7.89 (s, 1 H) 7.76 (br. s., 1 H) 7.46 (br. s., 1 H) 7.29 (br. s., 1 H) 6.75 (br. s., 1 H) 5.87 (s, 1 H) 4.79 (br. s., 1 H) 4.36 (s, 1 H) 4.35 (s, 1 H) 2.25 (s, 3 H) 2.15 (s, 3 H) 2.11 (s, 3 H) 1.45 (s, 3 H) 1.43 (s, 3 H) | 418.2 |

-continued

| Ex | Structure | Name | ¹H NMR (400 MHz, DMSO-d₆) δ ppm | MS(ES) [M + H]⁺ |
|---|---|---|---|---|
| 43 | 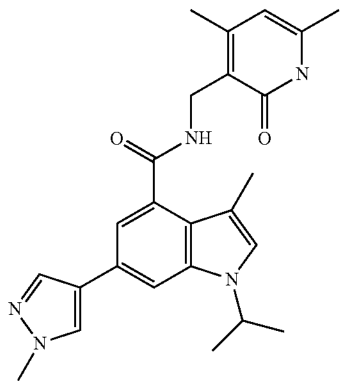 [SMILES: Cc1cc(C)c(CNC(=O)c2cc(-c3cnn(C)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1-methyl-1H-pyrazol-4-yl)-1H-indole-4-carboxamide | 11.47 (s, 1 H) 8.14 (s, 1 H) 8.05 (t, J = 5.18 Hz, 1 H) 7.89 (s, 1 H) 7.69 (d, J = 1.26 Hz, 1 H) 7.23 (s, 1 H) 7.15 (d, J = 1.52 Hz, 1 H) 5.87 (s, 1 H) 4.77 (quin, J = 6.69 Hz, 1 H) 4.35 (s, 1 H) 4.34 (s, 1 H) 3.86 (s, 3 H) 2.24 (s, 3 H) 2.13 (s, 3 H) 2.11 (s, 3 H) 1.43 (s, 3 H) 1.41 (s, 3 H) | 432.2 |
| 44 | 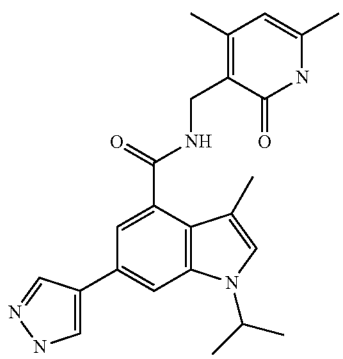 [SMILES: Cc1cc(C)c(CNC(=O)c2cc(-c3cn[nH]c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrazol-4-yl)-1H-indole-4-carboxamide | 11.50 (br. s., 1 H) 7.95-8.17 (m, 3 H) 7.72 (d, J = 1.01 Hz, 1 H) 7.23 (s, 1 H) 7.20 (d, J = 1.52 Hz, 1 H) 5.87 (s, 1 H) 4.79 (quin, J = 6.63 Hz, 1 H) 4.35 (s, 1 H) 4.34 (s, 1 H) 2.24 (s, 3 H) 2.13 (s, 3 H) 2.11 (s, 3 H) 1.43 (s, 3 H) 1.42 (s, 3 H) | 418.2 |
| 45 | 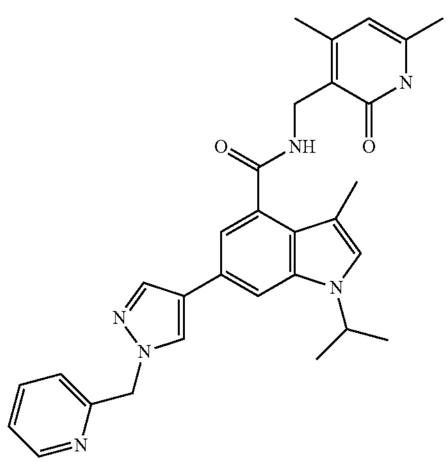 [SMILES: Cc1cc(C)c(CNC(=O)c2cc(-c3cnn(Cc4ccccn4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[1-(2-pyridinylmethyl)-1H-pyrazol-4-yl]-1H-indole-4-carboxamide | 11.47 (s, 1 H) 8.56 (d, J = 4.04 Hz, 1 H) 8.33 (s, 1 H) 8.07 (t, J = 5.05 Hz, 1 H) 7.99 (s, 1 H) 7.76-7.81 (m, 1 H) 7.73 (s, 1 H) 7.33 (dd, J = 6.69, 4.93 Hz, 1 H) 7.24 (s, 1 H) 7.18 (d, J = 1.26 Hz, 1 H) 7.10 (d, J = 7.83 Hz, 1 H) 5.87 (s, 1 H) 5.45 (s, 2 H) 4.79 (dt, J = 13.14, 6.57 Hz, 1 H) 4.35 (s, 1 H) 4.34 (s, 1 H) 2.24 (s, 3 H) 2.13 (s, 3 H) 2.11 (s, 3 H) 1.43 (s, 3 H) 1.41 (s, 3 H) | 509.0 |
| 46 | 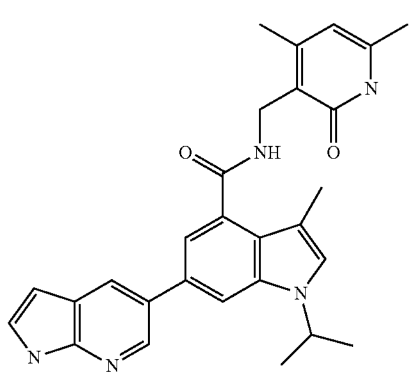 [SMILES: Cc1cc(C)c(CNC(=O)c2cc(-c3cnc4[nH]ccc4c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrrolo[2,3-b]pyridin-5-yl)-1H-indole-4-carboxamide | 11.67 (br. s., 1 H) 11.48 (s, 1 H) 8.60 (d, J = 2.27 Hz, 1 H) 8.27 (d, J = 2.02 Hz, 1 H) 8.20 (t, J = 5.05 Hz, 1 H) 7.82 (d, J = 1.26 Hz, 1 H) 7.49-7.52 (m, 1 H) 7.32 (s, 1 H) 7.29 (d, J = 1.52 Hz, 1 H) 6.51 (dd, J = 3.28, 1.77 Hz, 1 H) 5.87 (s, 1 H) 4.89 (dt, J = 13.33, 6.60 Hz, 1 H) 4.38 (s, 1 H) 4.36 (s, 1 H) 2.25 (s, 3 H) 2.19 (s, 3 H) 2.11 (s, 3 H) 1.45 (s, 3 H) 1.44 (s, 3 H) | 468.0 |

| Ex | Structure | Name | ¹H NMR (400 MHz, DMSO-d₆) δ ppm | MS(ES) [M + H]⁺ |
|---|---|---|---|---|
| 47 | 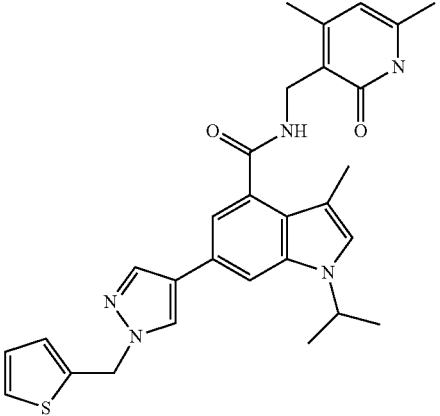 [SMILES: Cc1cc(C)c(CNC(=O)c2cc(-c3cnn(Cc4cccs4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[1-(2-thienylmethyl)-1H-pyrazol-4-yl]-1H-indole-4-carboxamide | 11.38 (br. s., 1 H) 8.26 (s, 1 H) 8.08 (t, J = 4.93 Hz, 1 H) 7.96 (s, 1 H) 7.70 (d, J = 1.26 Hz, 1 H) 7.48 (dd, J = 5.05, 1.26 Hz, 1 H) 7.23 (s, 1 H) 7.16 (s, 2 H) 7.01 (dd, J = 5.05, 3.28 Hz, 1 H) 5.87 (s, 1 H) 5.53 (s, 2 H) 4.78 (quin, J = 6.63 Hz, 1 H) 4.35 (s, 1 H) 4.33 (s, 1 H) 2.24 (s, 3 H) 2.13 (s, 3 H) 2.11 (s, 3 H) 1.42 (s, 3 H) 1.41 (s, 3 H) | 514.2 |
| 48 | 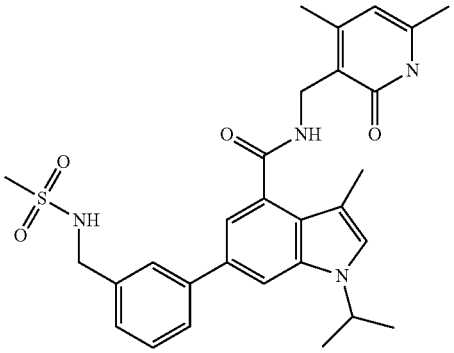 | N-((4,6-dimethyl-2-oxo-1,2-dihydropyridin-3-yl)methyl)-1-isopropyl-3-methyl-6-(3-(methylsulfonamidomethyl)phenyl)-1H-indole-4-carboxamide | 11.47 (s, 1 H) 8.18 (t, J = 4.93 Hz, 1 H) 7.70-7.78 (m, 2 H) 7.61-7.68 (m, 2 H) 7.44 (t, J = 7.71 Hz, 1 H) 7.30-7.35 (m, 2 H) 7.26 (d, J = 1.52 Hz, 1 H) 5.87 (s, 1 H) 4.86 (quin, J = 6.69 Hz, 1 H) 4.37 (br. s., 1 H) 4.35 (br. s., 1 H) 4.26 (s, 1 H) 4.24 (s, 1 H) 2.87-2.90 (m, 3 H) 2.22-2.26 (m, 3 H) 2.17 (s, 3 H) 2.11 (s, 3 H) 1.45 (s, 3 H) 1.41-1.45 (m, 3 H) | 534.9 |
| 49 | 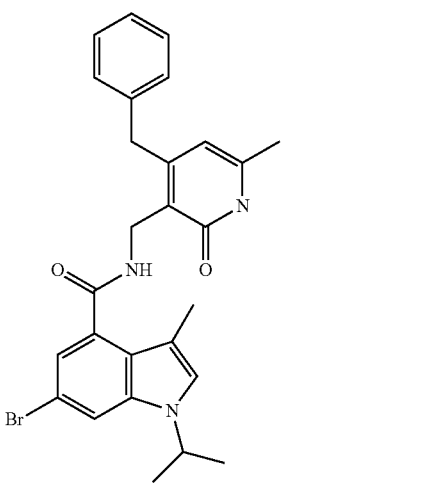 [SMILES: Cc1cc(Cc2ccccc2)c(CNC(=O)c2cc(Br)cc3c2c(C)cn3C(C)C)c(=O)[nH]1] | N-((4-benzyl-6-methyl-2-oxo-1,2-dihydropyridin-3-yl)methyl)-6-bromo-1-isopropyl-3-methyl-1H-indole-4-carboxamide | 11.56 (s, 1 H) 8.34 (t, J = 5.05 Hz, 1 H) 7.76 (d, J = 1.52 Hz, 1 H) 7.29-7.34 (m, 3 H) 7.20-7.26 (m, 3 H) 6.97 (d, J = 1.77 Hz, 1 H) 5.78 (s, 1 H) 4.74 (quin, J = 6.63 Hz, 1 H) 4.40 (s, 1 H) 4.39 (s, 1 H) 3.97 (s, 2 H) 2.13 (s, 3 H) 2.09 (s, 3 H) 1.40 (s, 3 H) 1.38 (s, 3 H) | 505.8/ 507.9 |

| Ex | Structure | Name | ¹H NMR (400 MHz, DMSO-d₆) δ ppm | MS(ES) [M + H]⁺ |
|---|---|---|---|---|
| 50 | 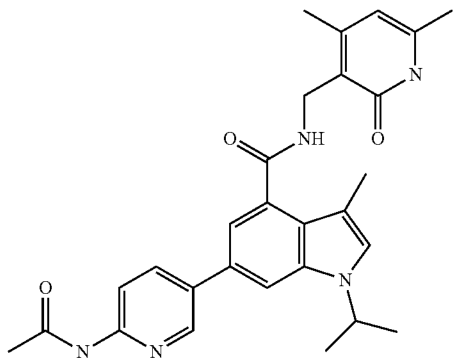 [SMILES: CC(=O)Nc1ccc(-c2cc(C(=O)NCc3c(C)cc(C)[nH]c3=O)c3c(C)cn(C(C)C)c3c2)cn1] | 6-(6-acetamidopyridin-3-yl)-N-((4,6-dimethyl-2-oxo-1,2-dihydropyridin-3-yl)methyl)-1-isopropyl-3-methyl-1H-indole-4-carboxamide | 11.48 (br. s., 1 H) 10.58 (s, 1 H) 8.71 (t, J = 1.64 Hz, 1 H) 8.12-8.21 (m, 3 H) 7.85 (d, J = 1.26 Hz, 1 H) 7.34 (s, 1 H) 7.27 (d, J = 1.52 Hz, 1 H) 5.87 (s, 1 H) 4.89 (quin, J = 6.57 Hz, 1 H) 4.36 (s, 1 H) 4.35 (s, 1 H) 2.25 (s, 3 H) 2.17 (s, 3 H) 2.12 (s, 3 H) 2.11 (s, 3 H) 1.45 (s, 3 H) 1.43 (s, 3 H) | 486.2 |
| 51 | 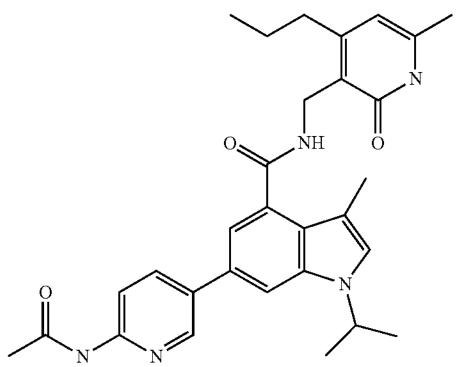 [SMILES: CCCc1cc(C)[nH]c(=O)c1CNC(=O)c1cc(-c2ccc(NC(C)=O)nc2)cc2c1c(C)cn2C(C)C] | 6-(6-acetamidopyridin-3-yl)-1-isopropyl-3-methyl-N-((6-methyl-2-oxo-4-propyl-1,2-dihydropyridin-3-yl)methyl)-1H-indole-4-carboxamide | 11.49 (s, 1 H) 10.58 (s, 1 H) 8.70 (s, 1 H) 8.13-8.18 (m, 3 H) 7.83-7.87 (m, 1 H) 7.35 (s, 1 H) 7.26 (d, J = 1.26 Hz, 1 H) 5.90 (s, 1 H) 4.89 (dt, J = 13.20, 6.66 Hz, 1 H) 4.38 (br. s., 1 H) 4.36 (br. s., 1 H) 2.53-2.58 (m, 2 H) 2.18 (s, 3 H) 2.12 (s, 5 H) 1.54-1.62 (m, 2 H) 1.45 (s, 3 H) 1.43 (s, 3 H) 0.94 (t, J = 7.33 Hz, 3 H) | 514.2 |
| 52 | 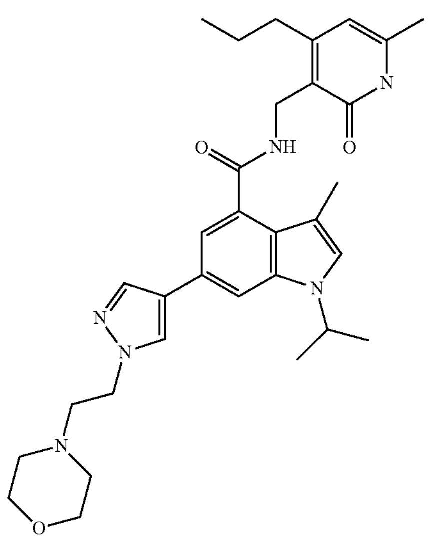 [SMILES: CCCc1cc(C)[nH]c(=O)c1CNC(=O)c1cc(-c2cnn(CCN3CCOCC3)c2)cc2c1c(C)cn2C(C)C] | 1-isopropyl-3-methyl-N-((6-methyl-2-oxo-4-propyl-1,2-dihydropyridin-3-yl)methyl)-6-(1-(2-morpholinoethyl)-1H-pyrazol-4-yl)-1H-indole-4-carboxamide | 11.47 (br. s., 1 H) 8.18 (s, 1 H) 8.03 (t, J = 5.05 Hz, 1 H) 7.89 (s, 1 H) 7.69 (d, J = 1.01 Hz, 1 H) 7.24 (d, J = 1.01 Hz, 1 H) 7.15 (d, J = 1.26 Hz, 1 H) 5.90 (s, 1 H) 4.78 (quin, J = 6.63 Hz, 1 H) 4.37 (s, 1 H) 4.35 (s, 1 H) 4.24 (t, J = 6.69 Hz, 2 H) 3.52-3.58 (m, 4 H) 2.75 (t, J = 6.69 Hz, 2 H) 2.52-2.58 (m, 2 H) 2.39-2.47 (m, 4 H) 2.13 (s, 3 H) 2.12 (s, 3 H) 1.53-1.62 (m, 2 H) 1.43 (s, 3 H) 1.42 (s, 3 H) 0.95 (t, J = 7.33 Hz, 3 H) | 559.0 |

| Ex | Structure | Name | ¹H NMR (400 MHz, DMSO-d$_6$) δ ppm | MS(ES) [M + H]⁺ |
|---|---|---|---|---|
| 53 | 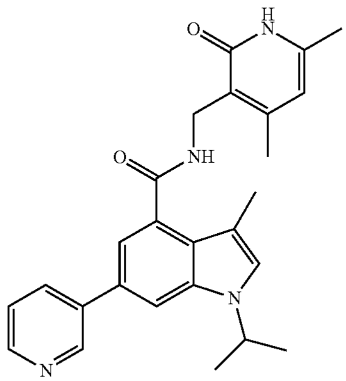 [SMILES: Cc1cc(C)c(CNC(=O)c2cc(-c3cccnc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(3-pyridinyl)-1H-indole-4-carboxamide | 1.44 (d, J = 6.57 Hz, 6 H), 2.10 (s, 3 H), 2.17 (s, 3 H), 2.24 (s, 3 H), 4.36 (d, J = 5.05 Hz, 2 H), 4.89 (dt, J = 13.14, 6.57 Hz, 1 H), 5.87 (s, 1 H), 7.35 (s, 1 H), 7.40 (s, 1 H), 7.73 (dd, J = 7.83, 5.31 Hz, 1 H), 7.98 (s, 1 H), 8.21 (t, J = 5.05 Hz, 1 H), 8.49 (d, J = 8.08 Hz, 1 H), 8.65 (d, J = 4.55 Hz, 1 H), 9.13 (s, 1 H), 11.48 (br. s., 1 H) | 429.0 |
| 54 | 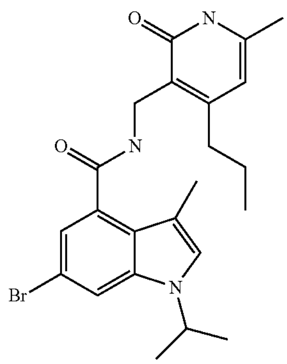 [SMILES: CCCc1cc(C)[nH]c(=O)c1CNC(=O)c1cc(Br)cc2c1c(C)cn2C(C)C] | 6-bromo-3-methyl-1-(1-methylethyl)-N-[(6-methyl-2-oxo-4-propyl-1,2-dihydro-3-pyridinyl)methyl]-1H-indole-4-carboxamide | 0.93 (t, 3 H), 1.38 (d, J = 6.57 Hz, 6 H), 1.44-1.67 (m, 2 H), 2.12 (d, J = 5.31 Hz, 6 H), 4.31 (d, J = 5.05 Hz, 2 H), 4.73 (dt, J = 13.14, 6.57 Hz, 1 H), 5.89 (s, 1 H), 6.99 (d, J = 1.52 Hz, 1 H), 7.33 (s, 1 H), 7.76 (d, J = 1.52 Hz, 1 H), 8.20 (t, J = 4.80 Hz, 1 H), 11.48 (s, 1 H) | 458.2/ 460.1 |
| 55 | 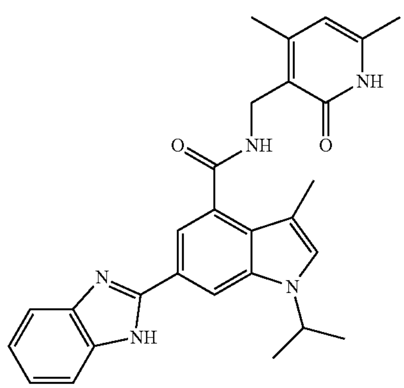 [SMILES: Cc1cc(C)c(CNC(=O)c2cc(-c3nc4ccccc4[nH]3)cc3c2c(C)cn3C(C)C)c(=O)[nH]1] | 6-(1H-benzo[d]imidazol-2-yl)-N-((4,6-dimethyl-2-oxo-1,2-dihydropyridin-3-yl)methyl)-1-isopropyl-3-methyl-1H-indole-4-carboxamide | 1.50 (d, J = 6.82 Hz, 6 H), 2.12 (s, 3 H), 2.19 (s, 3 H), 2.26 (s, 3 H), 4.39 (d, J = 5.05 Hz, 2 H), 4.82 (spt, J = 6.44 Hz, 1 H), 5.88 (s, 1 H), 7.12-7.24 (m, 2 H), 7.44 (s, 1 H), 7.51 (s, 1 H), 7.64 (d, J = 7.07 Hz, 1 H), 7.82 (d, J = 1.52 Hz, 1 H), 8.22 (t, J = 5.05 Hz, 1 H), 8.33 (d, J = 1.26 Hz, 1 H), 11.49 (br. s., 1 H), 12.83 (s, 1 H) | 468.4 |
| 56 | 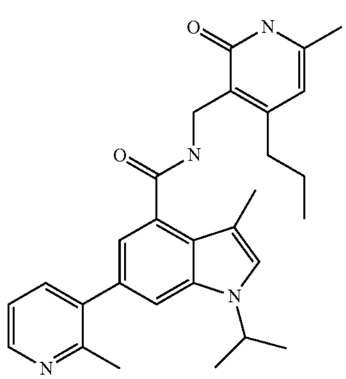 [SMILES: CCCc1cc(C)[nH]c(=O)c1CNC(=O)c1cc(-c2cccnc2C)cc2c1c(C)cn2C(C)C] | 3-methyl-1-(1-methylethyl)-N-[(6-methyl-2-oxo-4-propyl-1,2-dihydro-3-pyridinyl)methyl]-6-(2-methyl-3-pyridinyl)-1H-indole-4-carboxamide | 0.87-0.97 (m, 3 H), 1.41 (d, J = 6.57 Hz, 6 H), 1.55 (m, J = 15.16, 7.52, 7.36, 7.36 Hz, 2 H), 2.11 (s, 3 H), 2.19 (s, 3 H), 2.48 (s, 3 H), 3.17 (d, J = 5.31 Hz, 5 H), 4.34 (d, J = 5.05 Hz, 2 H), 4.78 (dt, J = 13.20, 6.66 Hz, 1 H), 5.88 (s, 1 H), 6.91 (d, J = 1.52 Hz, 1 H), 7.29 (dd, J = 7.58, 4.80 Hz, 2 H), 7.35 (s, 1 H), 7.54 (d, J = 1.26 Hz, 1 H), 7.65 (dd, J = 7.58, 1.52 Hz, 1 H), 8.11 (t, J = 5.05 Hz, 1 H), 8.44 (dd, J = 4.80, 1.52 Hz, 1 H), 11.47 (br. s., 1 H) | 471.4 |

| Ex | Structure | Name | ¹H NMR (400 MHz, DMSO-d₆) δ ppm | MS(ES) [M + H]⁺ |
|---|---|---|---|---|
| 57 | 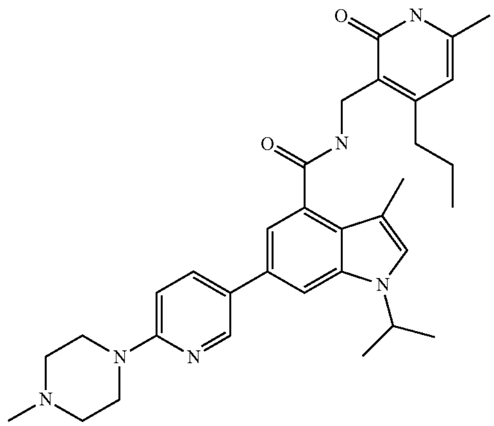 | 3-methyl-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 0.93 (t, J = 7.33 Hz, 3 H), 1.42 (d, J = 6.57 Hz, 5 H), 1.56 (m, J = 7.60, 7.60, 7.60, 7.39, 7.20 Hz, 2 H), 2.12 (s, 3 H), 2.16 (s, 3 H), 2.23 (s, 3 H), 2.43 (t, J = 4.93 Hz, 4 H), 3.44-3.61 (m, 5 H), 4.36 (d, J = 5.05 Hz, 2 H), 4.84 (ddd, J = 13.26, 6.57, 6.44 Hz, 1 H), 5.89 (s, 1 H), 6.92 (d, J = 8.84 Hz, 1 H), 7.17 (d, J = 1.52 Hz, 1 H), 7.28 (s, 1 H), 7.72 (d, J = 1.26 Hz, 1 H), 7.91 (dd, J = 8.84, 2.53 Hz, 1 H), 8.11 (t, J = 4.93 Hz, 1 H), 8.17 (s, 1 H), 8.49 (d, J = 2.53 Hz, 1 H), 11.49 (br. s., 1 H) | 555.1 |
| 58 | 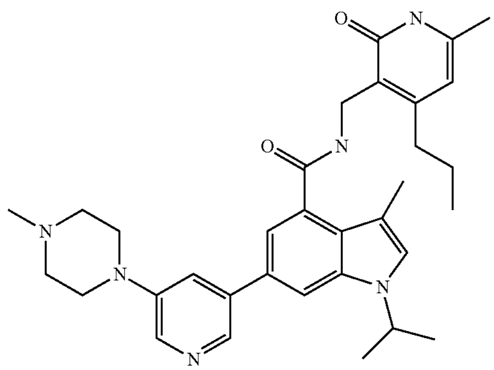 | 3-methyl-1-(1-methylethyl)-N-[(6-methyl-2-oxo-4-propyl-1,2-dihydro-3-pyridinyl)methyl]-6-[5-(4-methyl-1-piperazinyl)-3-pyridinyl]-1H-indole-4-carboxamide | 0.93 (t, J = 7.33 Hz, 3 H), 1.43 (d, J = 6.57 Hz, 6 H), 1.57 (m, J = 7.54, 7.54, 7.54, 7.33, 7.20 Hz, 2 H), 2.12 (s, 3 H), 2.17 (s, 3 H), 2.24 (s, 3 H), 2.44 (t, J = 4.80 Hz, 4 H), 2.52-2.58 (m, 2 H), 3.52-3.61 (m, 4 H), 4.36 (d, J = 4.80 Hz, 2 H), 4.92 (dt, J = 13.14, 6.57 Hz, 1 H), 5.90 (s, 1 H), 7.03 (d, J = 5.31 Hz, 1 H), 7.11 (s, 1 H), 7.30 (d, J = 1.26 Hz, 1 H), 7.38 (s, 1 H), 7.90 (d, J = 1.26 Hz, 1 H), 8.09-8.31 (m, 3 H) | 555.1 |
| 59 | 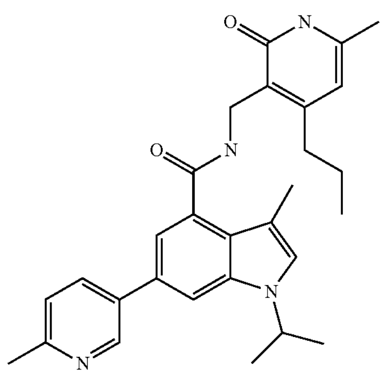 | 3-methyl-1-(1-methylethyl)-N-[(6-methyl-2-oxo-4-propyl-1,2-dihydro-3-pyridinyl)methyl]-6-(6-methyl-3-pyridinyl)-1H-indole-4-carboxamide | 0.93 (t, J = 7.33 Hz, 3 H), 1.45 (d, J = 6.57 Hz, 6 H), 1.57 (m, J = 15.16, 7.52, 7.36, 7.36 Hz, 2 H), 2.12 (s, 3 H), 2.17 (s, 3 H), 2.53-2.59 (m, 2 H), 2.68 (s, 3 H), 4.37 (d, J = 5.05 Hz, 2 H), 4.90 (dt, J = 13.33, 6.60 Hz, 1 H), 5.91 (s, 1 H), 7.11 (s, 1 H), 7.37 (d, J = 1.26 Hz, 1 H), 7.43 (s, 6 H), 7.81 (d, J = 8.34 Hz, 6 H), 8.02 (d, J = 1.26 Hz, 6 H), 8.17 (t, J = 5.05 Hz, 6 H), 8.66 (br. s., 6 H), 9.09 (d, J = 1.77 Hz, 1 H), 11.50 (br. s., 1 H) | 471.4 |
| 60 | 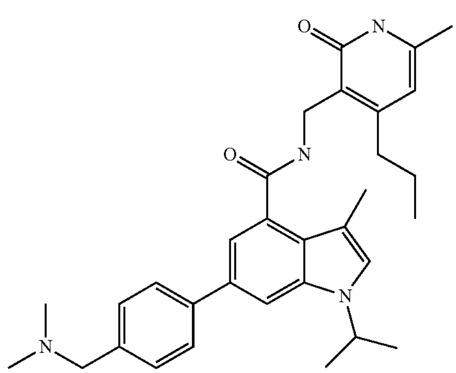 | 6-{4-[(dimethylamino)methyl]phenyl}-3-methyl-1-(1-methylethyl)-N-[(6-methyl-2-oxo-4-propyl-1,2-dihydro-3-pyridinyl)methyl]-1H-indole-4-carboxamide | 0.93 (t, J = 7.33 Hz, 3 H), 1.43 (d, J = 6.82 Hz, 6 H), 1.57 (dq, J = 15.06, 7.44 Hz, 2H), 2.12 (s, 3 H), 2.15-2.20 (m, 9 H), 2.53(1H), 3.41 (s, 2 H), 4.36 (d, J = 5.05 Hz, 2 H), 4.86 (quin, J = 6.63 Hz, 1 H), 5.89 (s, 1 H), 7.24 (d, J = 1.26 Hz, 1 H), 7.32 (s, 1 H), 7.35 (d, J = 8.34 Hz, 2 H), 7.68 (d, J = 8.08 Hz, 2 H), 7.76 (d, J = 1.26 Hz, 1 H), 8.15 (t, J = 4.93 Hz, 1 H), 11.47 (br. s., 1 H) | 513.4 |

-continued

| Ex | Name | ¹H NMR (400 MHz, DMSO-d₆) δ ppm | MS(ES) [M + H]⁺ |
|---|---|---|---|
| 61 | 6-methyl-3-({2-[3-methyl-1-(1-methylethyl)-6-(1,2,3,6-tetrahydro-4-pyridinyl)-1H-indol-4-yl]-2-oxoethyl}amino)-4-propyl-2(1H)-pyridinone | 0.93 (t, J = 7.33 Hz, 3 H), 1.40 (d, J = 6.57 Hz, 6 H), 1.50-1.65 (m, 2 H), 2.12 (d, J = 6.06 Hz, 6 H), 3.08 (br. s., 2 H), 3.52 (br. s., 2 H), 4.34 (d, J = 5.05 Hz, 2 H), 4.78 (dt, J = 13.20, 6.66 Hz, 1 H), 5.89 (s, 1 H), 6.18 (br. s., 1 H), 7.05 (d, J = 1.26 Hz, 1 H), 7.27 (s, 1 H), 7.50 (s, 3 H), 8.03 (t, J = 5.05 Hz, 1 H), 11.49 (br. s., 1 H) | 461.2 |
| 62 | N-[(4,6-dimethyl-2-oxo-1,2-dihydro-3-pyridinyl)methyl]-1-(1-methylethyl)-6-(3-pyridinyl)-1H-indole-4-carboxamide | 11.55 (br. s., 1 H), 9.11 (d, J = 1.8 Hz, 1 H), 8.60 (dd, J = 5.1, 1.5 Hz, 1 H), 8.36 (m, 2 H), 8.08 (s, 1 H), 7.78 (d, J = 1.5 Hz, 1 H), 7.68 (d, J = 3.3 Hz, 1 H), 7.61 (dd, J = 8.0, 4.9 Hz, 1 H), 6.93 (d, J = 3.3 Hz, 1 H), 5.89 (s, 1 H), 4.98 (quin, J = 6.6 Hz, 1 H), 4.38 (d, J = 5.1 Hz, 2 H), 2.23 (s, 3 H), 2.12 (s, 3 H), 1.49 (d, J = 6.8 Hz, 6 H) | 415.0 |
| 63 | 6-bromo-1-cyclopentyl-N-[(6-methyl-2-oxo-4-propyl-1,2-dihydro-3-pyridinyl)methyl]-1H-indole-4-carboxamide | 11.56 (s, 1 H), 8.30 (t, J = 5.2 Hz, 1 H), 7.93 (s, 1 H), 7.59 (d, J = 3.3 Hz, 1 H), 7.52 (d, J = 1.5 Hz, 1 H), 6.85 (d, J = 3.3 Hz, 1 H), 5.91 (s, 1 H), 4.94 (m, 1 H), 4.35 (d, J = 5.1 Hz, 2 H), 2.53 (d, J = 7.8 Hz, 2 H), 2.12 (m, 5 H), 1.80 (m, 4 H), 1.71 (m, 2 H), 1.52 (m, 2 H), 0.90 (t, J = 7.3 Hz, 3 H) | 470.1 |
| 64 | 1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.56 (s, 1 H), 8.56 (d, J = 2.5 Hz, 1 H), 8.27 (t, J = 5.2 Hz, 1 H), 7.97 (dd, J = 9.0, 2.7 Hz, 1 H), 7.87 (s, 1 H), 7.65 (d, J = 1.3 Hz, 1 H), 7.58 (d, J = 3.3 Hz, 1 H), 6.93 (d, J = 9.1 Hz, 1 H), 6.86 (d, J = 3.0 Hz, 1 H), 5.91 (s, 1 H), 4.92 (m, 1 H), 4.39 (d, J = 5.1 Hz, 2 H), 3.52 (m, 4 H), 2.54 (m, 2 H), 2.41 (m, 4 H), 2.22 (m, 3 H), 2.13 (s, 3 H), 1.53 (m, 2 H), 1.47 (d, J = 6.6 Hz, 6 H), 0.90 (t, J = 7.3 Hz, 3 H) | 541.5 |

-continued

| Ex | Structure | Name | ¹H NMR (400 MHz, DMSO-d₆) δ ppm | MS(ES) [M + H]⁺ |
|---|---|---|---|---|
| 65 | 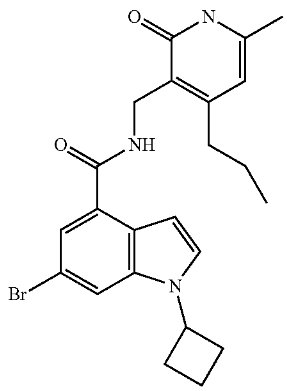 [SMILES: CCCc1cc(C)[nH]c(=O)c1CNC(=O)c1cc(Br)cc2c1ccn2C1CCC1] | 6-bromo-1-cyclobutyl-N-[(6-methyl-2-oxo-4-propyl-1,2-dihydro-3-pyridinyl)methyl]-1H-indole-4-carboxamide | 11.56 (s, 1 H), 8.31 (t, J = 5.1 Hz, 1 H), 7.87 (s, 1 H), 7.73 (d, J = 3.3 Hz, 1 H), 7.53 (d, J = 1.5 Hz, 1 H), 6.88 (d, J = 3.3 Hz, 1 H), 5.91 (s, 1 H), 5.04 (t, J = 8.3 Hz, 1 H), 4.35 (d, J = 5.1 Hz, 2 H), 2.54 (s, 1 H), 2.41 (m, 4 H), 2.13 (s, 3 H), 1.83 (m, 2 H), 1.52 (m, 2 H), 0.90 (t, J = 7.3 Hz, 3 H) | 445.9 |
| 66 | 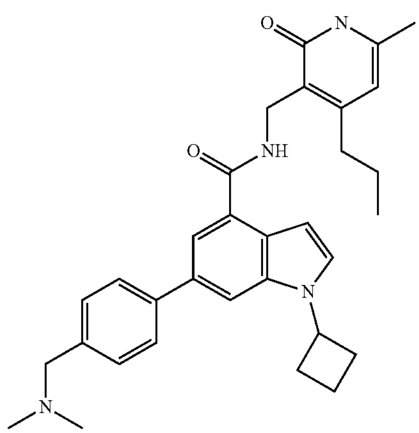 | 1-cyclobutyl-6-{4-[(dimethylamino)methyl]phenyl}-N-[(6-methyl-2-oxo-4-propyl-1,2-dihydro-3-pyridinyl)methyl]-1H-indole-4-carboxamide | 11.55 (s, 1 H), 8.32 (t, J = 5.1 Hz, 1 H), 7.89 (s, 1 H), 7.73 (m, 4 H), 7.37 (d, J = 8.1 Hz, 2 H), 6.90 (d, J = 3.0 Hz, 1 H), 5.91 (s, 1 H), 5.16 (t, J = 8.5 Hz, 1 H), 4.40 (d, J = 5.1 Hz, 2 H), 3.42 (s, 2 H), 2.55 (m, 3 H), 2.43 (m, 2 H), 2.15 (m, 9 H), 1.85 (dt, J = 9.8, 4.8 Hz, 2 H), 1.54 (m, 2 H), 0.90 (t, J = 7.3 Hz, 3 H) | 511.3 |
| 67 | 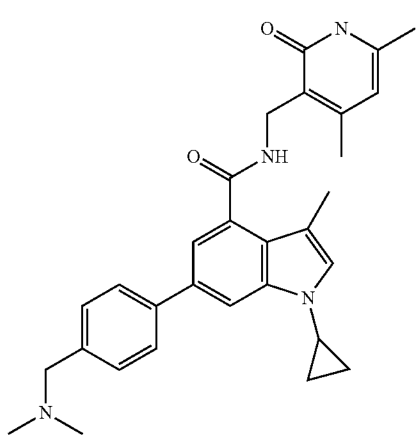 | 1-cyclopropyl-6-{4-[(dimethylamino)methyl]phenyl}-N-[(4,6-dimethyl-2-oxo-1,2-dihydro-3-pyridinyl)methyl]-3-methyl-1H-indole-4-carboxamide | 11.46 (s, 1 H), 8.19 (t, J = 5.1 Hz, 1 H), 7.76 (d, J = 1.5 Hz, 1 H), 7.67 (m, J = 8.1 Hz, 2 H), 7.37 (m, J = 8.1 Hz, 2 H), 7.28 (d, J = 1.5 Hz, 1 H), 7.14 (d, J = 1.0 Hz, 1 H), 5.86 (s, 1 H), 4.34 (d, J = 5.1 Hz, 2 H), 3.43 (m, 3 H), 2.23 (s, 3 H), 2.14 (m, 12 H), 1.06 (m, 2 H), 0.92 (m, 2 H) | 483.1 |

-continued

| Ex | Structure | Name | $^1$H NMR (400 MHz, DMSO-d$_6$) δ ppm | MS(ES) [M + H]$^+$ |
|---|---|---|---|---|
| 68 | 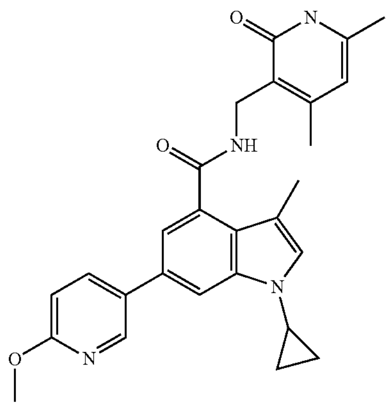 [SMILES: COc1ccc(-c2cc(C(=O)NCc3c(C)cc(C)[nH]c3=O)c3c(C)cn(C4CC4)c3c2)cn1] | 1-cyclopropyl-N-[(4,6-dimethyl-2-oxo-1,2-dihydro-3-pyridinyl)methyl]-3-methyl-6-[6-(methyloxy)-3-pyridinyl]-1H-indole-4-carboxamide | 11.46 (br. s., 1 H), 8.52 (d, J = 2.3 Hz, 1 H), 8.19 (t, J = 4.9 Hz, 1 H), 8.07 (dd, J = 8.6, 2.5 Hz, 1 H), 7.76 (d, J = 1.5 Hz, 1 H), 7.25 (d, J = 1.5 Hz, 1 H), 7.15 (d, J = 1.0 Hz, 1 H), 6.92 (d, J = 8.6 Hz, 1 H), 5.86 (s, 1 H), 4.34 (d, J = 5.1 Hz, 2 H), 3.90 (s, 3 H), 3.42 (m, 1 H), 2.22 (m, 3 H), 2.10 (s, 3 H), 2.13 (s, 3 H), 1.06 (m, 2 H), 0.92 (m, 2 H) | 457.1 |
| 69 | 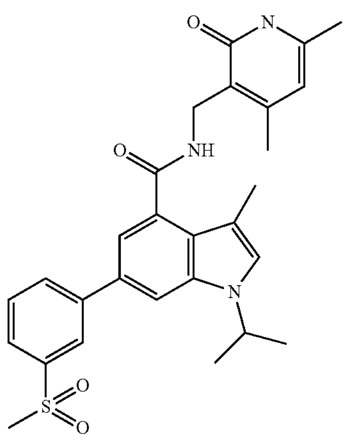 [SMILES: Cc1cc(C)c(CNC(=O)c2cc(-c3cccc(S(C)(=O)=O)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[3-(methylsulfonyl)phenyl]-1H-indole-4-carboxamide | 11.47 (s, 1 H), 8.23 (m, 2 H), 8.12 (d, J = 7.8 Hz, 1 H), 7.89 (m, 2 H), 7.73 (m, 1 H), 7.39 (s, 1 H), 7.32 (d, J = 1.5 Hz, 1 H), 5.87 (s, 1 H), 4.92 (m, 1 H), 4.36 (d, J = 4.8 Hz, 2 H), 3.31 (s, 3 H), 2.23 (m, 3 H), 2.18 (m, 3 H), 2.11 (s, 3 H), 1.42 (m, 6 H) | 505.9 |
| 70 | 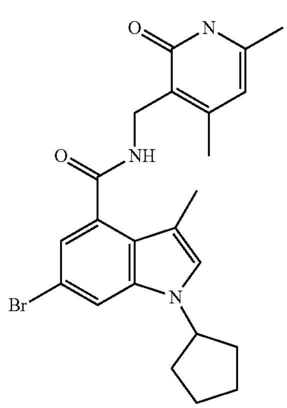 [SMILES: Cc1cc(C)c(CNC(=O)c2cc(Br)cc3c2c(C)cn3C2CCCC2)c(=O)[nH]1] | 6-bromo-1-cyclopentyl-N-[(4,6-dimethyl-2-oxo-1,2-dihydro-3-pyridinyl)methyl]-3-methyl-1H-indole-4-carboxamide | 11.48 (s, 1 H), 8.24 (t, J = 4.9 Hz, 1 H), 7.77 (d, J = 1.8 Hz, 1 H), 7.29 (s, 1 H), 7.00 (d, J = 1.8 Hz, 1 H), 5.86 (s, 1 H), 4.86 (t, J = 7.1 Hz, 1 H), 4.30 (d, J = 4.8 Hz, 2 H), 2.21 (s, 3 H), 2.08 (m, 8 H), 1.74 (m, 6 H) | 455.9 |

-continued

| Ex | Name | ¹H NMR (400 MHz, DMSO-d₆) δ ppm | MS(ES) [M + H]⁺ |
|---|---|---|---|
| 71 | 1-cyclopentyl-6-{4-[(dimethylamino)methyl]phenyl}-N-[(4,6-dimethyl-2-oxo-1,2-dihydro-3-pyridinyl)methyl]-3-methyl-1H-indole-4-carboxamide | 11.47 (s, 1 H), 8.18 (t, J = 5.1 Hz, 1 H), 7.78 (d, J = 1.5 Hz, 1 H), 7.69 (m, J = 8.1 Hz, 2 H), 7.36 (m, J = 8.3 Hz, 2 H), 7.26 (m, 2 H), 5.86 (s, 1 H), 5.00 (d, J = 7.1 Hz, 1 H), 4.35 (d, J = 5.1 Hz, 2 H), 3.41 (s, 2 H), 2.23 (s, 3 H), 2.14 (m, 14 H), 1.78 (m, 6 H) | 511.3 |
| 72 | 3-methyl-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide | 11.49 (s, 1 H), 8.12 (s, 1 H), 8.01 (t, J = 5.1 Hz, 1 H), 7.87 (s, 1 H), 7.69 (d, J = 1.3 Hz, 1 H), 7.23 (s, 1 H), 7.14 (d, J = 1.5 Hz, 1 H), 5.90 (s, 1 H), 4.77 (quin, J = 6.6 Hz, 1 H), 4.35 (d, J = 5.1 Hz, 2 H), 3.86 (s, 3 H), 2.54 (m, 2 H), 2.11 (m, 6 H), 1.57 (sxt, J = 7.5 Hz, 2 H), 1.42 (d, J = 6.6 Hz, 6 H), 0.94 (t, J = 7.3 Hz, 3 H) | 460.1 |
| 73 | N-((4,6-dimethyl-2-oxo-1,2-dihydropyridin-3-yl)methyl)-1-isopropyl-3-methyl-6-(2-(4-methylpiperazin-1-yl)pyrimidin-5-yl)-1H-indole-4-carboxamide | 11.48 (s, 1 H), 8.76 (s, 2 H), 8.13 (t, J = 5.2 Hz, 1 H), 7.77 (d, J = 1.5 Hz, 1 H), 7.30 (s, 1 H), 7.19 (d, J = 1.3 Hz, 1 H), 5.87 (s, 1 H), 4.83 (quin, J = 6.6 Hz, 1 H), 4.35 (d, J = 5.1 Hz, 2 H), 3.77 (m, 4 H), 2.38 (t, J = 5.1 Hz, 4 H), 2.23 (d, J = 6.3 Hz, 6 H), 2.16 (s, 3 H), 2.11 (s, 3 H), 1.42 (d, J = 6.6 Hz, 6 H) | 528.0 |

| Ex | Structure | Name | ¹H NMR (400 MHz, DMSO-d₆) δ ppm | MS(ES) [M + H]⁺ |
|---|---|---|---|---|
| 74 | 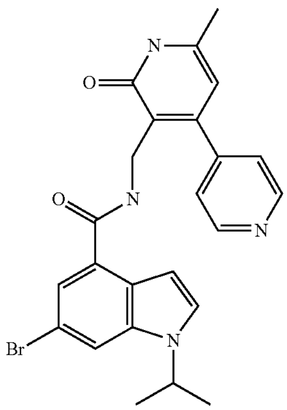 [SMILES: Cc1cc(-c2ccncc2)c(CNC(=O)c2cc(Br)cc3c2ccn3C(C)C)c(=O)[nH]1] | 6-bromo-1-(1-methylethyl)-N-[(6-methyl-2-oxo-1,2-dihydro-4,4'-bipyridin-3-yl)methyl]-1H-indole-4-carboxamide | 11.99 (br. s., 1 H) 8.66 (d, J = 6.06 Hz, 2 H) 8.33 (t, J = 4.42 Hz, 1 H) 7.93 (s, 1 H) 7.63 (d, J = 3.28 Hz, 1 H) 7.42-7.48 (m, 3 H) 6.84 (d, J = 3.03 Hz, 1 H) 6.00 (s, 1 H) 4.76-4.88 (m, 1 H) 4.16 (d, J = 4.29 Hz, 2 H) 2.23 (s, 3 H) 1.43 (d, J = 6.57 Hz, 6 H) | 480.7 |
| 75 | 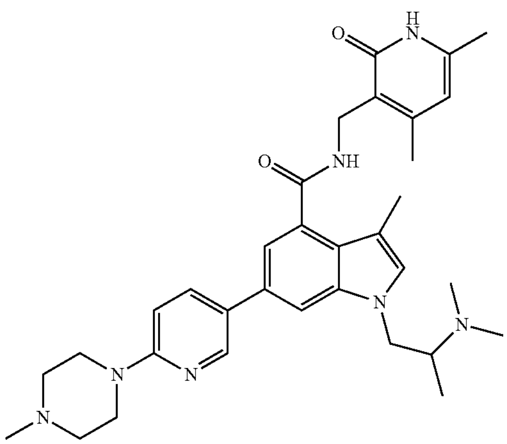 | N-((4,6-dimethyl-2-oxo-1,2-dihydropyridin-3-yl)methyl)-1-(2-(dimethylamino)propyl)-3-methyl-6-(6-(4-methylpiperazin-1-yl)pyridin-3-yl)-1H-indole-4-carboxamide | 0.82 (d, J = 6.57 Hz, 3 H), 2.10 (s, 3 H), 2.14 (s, 3 H), 2.20 (s, 6 H), 2.23 (d, J = 5.05 Hz, 6 H), 2.37-2.46 (m, 4 H), 2.98 (q, J = 6.82 Hz, 1 H), 3.48-3.58 (m, 4 H), 3.95-4.27 (m, 1 H), 4.34 (d, J = 5.05 Hz, 2 H), 5.86 (s, 1 H), 6.92 (d, J = 9.09 Hz, 1 H), 7.14 (s, 1 H), 7.17 (d, J = 1.26 Hz, 1 H), 7.68 (d, J = 1.26 Hz, 1 H), 7.90 (dd, J = 8.84, 2.78 Hz, 1 H), 8.17 (t, J = 5.05 Hz, 1 H), 8.50 (d, J = 2.27 Hz, 1 H), 11.47 (br. s., 1 H) | 570.6 |
| 76 | 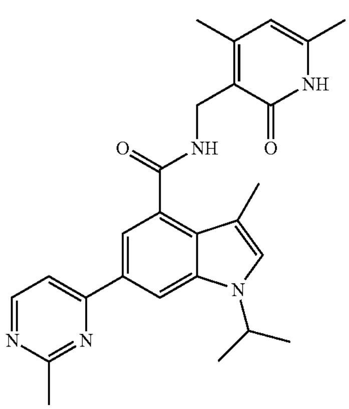 [SMILES: Cc1nccc(-c2cc(C(=O)NCc3c(C)cc(C)[nH]c3=O)c3c(C)cn(C(C)C)c3c2)n1] | N-((4,6-dimethyl-2-oxo-1,2-dihydropyridin-3-yl)methyl)-1-isopropyl-3-methyl-6-(2-methylpyrimidin-4-yl)-1H-indole-4-carboxamide | 1.46 (d, J = 6.57 Hz, 6 H), 2.12 (s, 3 H), 2.18 (s, 3 H), 2.25 (s, 3 H), 2.68 (s, 3 H), 4.37 (d, J = 4.80 Hz, 2 H), 4.92 (spt, J = 6.57 Hz, 1 H), 5.88 (s, 1 H), 7.48 (s, 1 H), 7.84 (d, J = 1.26 Hz, 1 H), 7.98 (d, J = 5.56 Hz, 1 H), 8.22 (t, J = 4.93 Hz, 1 H), 8.37 (d, J = 1.26 Hz, 1 H), 8.68 (d, J = 5.56 Hz, 1 H), 11.48 (s, 1 H) | 444.4 |

-continued

| Ex | Structure | Name | ¹H NMR (400 MHz, DMSO-d$_6$) δ ppm | MS(ES) [M + H]⁺ |
|---|---|---|---|---|
| 77 | 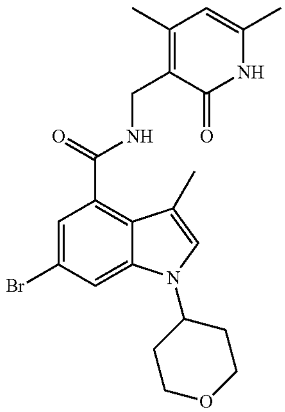 [SMILES: Cc1cc(C)c(CNC(=O)c2cc(Br)cc3c2c(C)cn3C2CCOCC2)c(=O)[nH]1] | 6-bromo-N-((4,6-dimethyl-2-oxo-1,2-dihydropyridin-3-yl)methyl)-3-methyl-1-(tetrahydro-2H-pyran-4-yl)-1H-indole-4-carboxamide | 1.76-1.86 (m, 2 H), 1.93 (dd, J = 12.00, 4.17 Hz, 2 H), 2.12 (d, J = 5.81 Hz, 6 H), 2.22 (s, 3 H), 3.49-3.62 (m, 2 H), 3.97 (dd, J = 11.12, 3.79 Hz, 2 H), 4.31 (d, J = 5.05 Hz, 2 H), 4.64 (br. s., 1 H), 5.86 (s, 1 H), 7.02 (d, J = 1.52 Hz, 1 H), 7.36 (s, 1 H), 7.88 (d, J = 1.52 Hz, 1 H), 8.24 (t, J = 4.93 Hz, 1 H), 11.47 (br. s., 1 H) | 472, 474 |
| 78 | 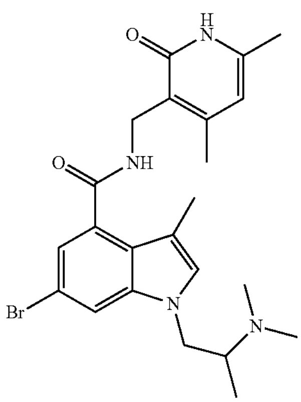 [SMILES: Cc1cc(C)c(CNC(=O)c2cc(Br)cc3c2c(C)cn3CC(C)N(C)C)c(=O)[nH]1] | 6-bromo-N-((4,6-dimethyl-2-oxo-1,2-dihydropyridin-3-yl)methyl)-1-(2-(dimethylamino)propyl)-3-methyl-1H-indole-4-carboxamide | (CHLOROFORM-d) 0.90 (d, J = 6.57 Hz, 3 H), 2.15 (s, 3 H), 2.22 (s, 3 H), 2.34 (s, 6 H), 2.39 (s, 3 H), 2.88-3.11 (m, 1 H), 3.81 (dd, J = 14.27, 8.46 Hz, 1 H), 4.19 (dd, J = 14.02, 4.42 Hz, 1 H), 4.57 (d, J = 5.56 Hz, 2 H), 5.93 (s, 1 H), 6.86 (s, 1 H), 7.20 (d, J = 1.52 Hz, 1 H), 7.45 (d, J = 1.52 Hz, 1 H), 12.52 (br. s., 1 H) | 473.2, 475.2 |
| 79 | 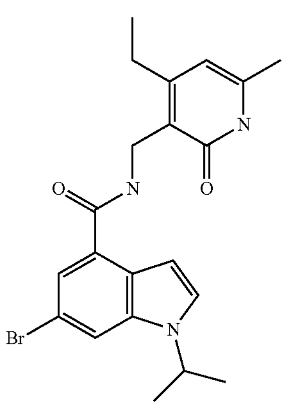 [SMILES: CCc1cc(C)[nH]c(=O)c1CNC(=O)c1cc(Br)cc2c1ccn2C(C)C] | 6-bromo-N-[(4-ethyl-6-methyl-2-oxo-1,2-dihydro-3-pyridinyl)methyl]-1-(1-methylethyl)-1H-indole-4-carboxamide | 11.56 (s, 1 H) 8.31 (t, J = 5.18 Hz, 1 H) 7.92 (s, 1 H) 7.63 (d, J = 3.03 Hz, 1 H) 7.52 (d, J = 1.52 Hz, 1 H) 6.86 (d, J = 3.28 Hz, 1 H) 5.93 (s, 1 H) 4.75-4.90 (m, 1 H) 4.35 (d, J = 5.05 Hz, 2 H) 2.54-2.60 (m, 2 H) 2.14 (s, 3 H) 1.43 (d, J = 6.57 Hz, 6 H) 1.11 (t, J = 7.33 Hz, 3 H) | |

-continued

| Ex | Structure | Name | ¹H NMR (400 MHz, DMSO-d₆) δ ppm | MS(ES) [M + H]⁺ |
|---|---|---|---|---|
| 80 | 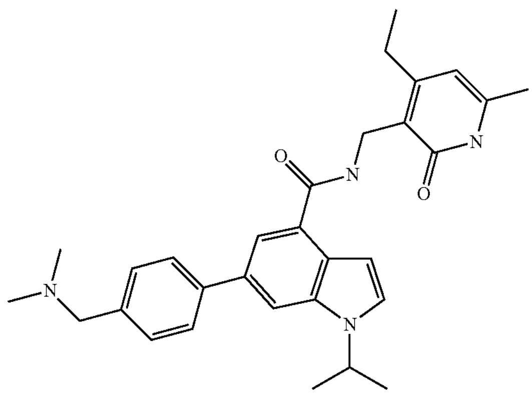 | 6-{4-[(dimethylamino)methyl]phenyl}-N-[(4-ethyl-6-methyl-2-oxo-1,2-dihydro-3-pyridinyl)methyl]-1-(1-methylethyl)-1H-indole-4-carboxamide | 11.56 (s, 1 H) 8.33 (t, J = 5.05 Hz, 1 H) 7.92 (s, 1 H) 7.70-7.78 (m, 3 H) 7.62 (d, J = 3.28 Hz, 1 H) 7.37 (d, J = 8.34 Hz, 2 H) 6.88 (d, J = 3.28 Hz, 1 H) 5.93 (s, 1 H) 4.87-5.04 (m, 1 H) 4.41 (d, J = 5.31 Hz, 2 H) 3.42 (s, 2 H) 2.59 (q, J = 7.58 Hz, 2 H) 2.17 (s, 6 H) 2.14 (s, 3 H) 1.48 (d, J = 6.82 Hz, 6 H) 1.12 (t, J = 7.33 Hz, 3 H) | 485.3 |
| 81 | 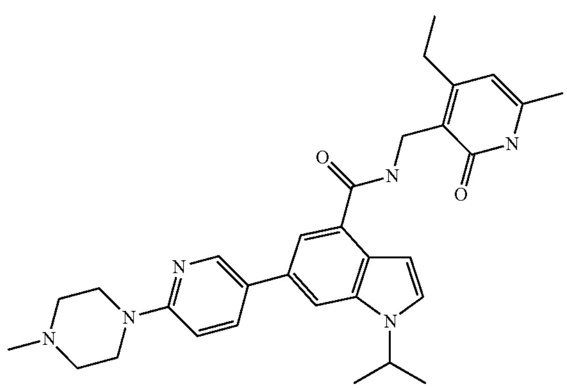 | N-[(4-ethyl-6-methyl-2-oxo-1,2-dihydro-3-pyridinyl)methyl]-1-(1-methylethyl)-6-[6-(4-methyl-1-piperazinyl)-3-pyridinyl]-1H-indole-4-carboxamide | 11.57 (br. s., 1 H) 8.57 (d, J = 2.27 Hz, 1 H) 8.30 (t, J = 5.05 Hz, 1 H) 7.98 (dd, J = 8.97, 2.65 Hz, 1 H) 7.88 (s, 1 H) 7.66 (d, J = 1.26 Hz, 1 H) 7.59 (d, J = 3.28 Hz, 1 H) 6.93 (d, J = 9.09 Hz, 1 H) 6.87 (d, J = 3.03 Hz, 1 H) 5.93 (s, 1 H) 4.88-4.98 (m, 1 H) 4.40 (d, J = 5.05 Hz, 2 H) 3.49-3.59 (m, 4 H) 2.58 (q, J = 7.58 Hz, 2 H) 2.37-2.45 (m, 4 H) 2.23 (s, 3 H) 2.14 (s, 3 H) 1.47 (d, J = 6.82 Hz, 6 H) 1.12 (t, J = 7.33 Hz, 3 H) | 527.2 |
| 82 | 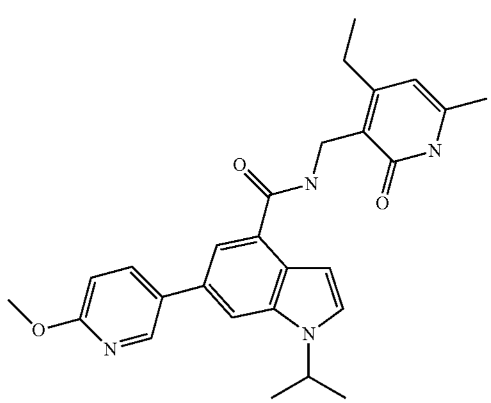 | N-[(4-ethyl-6-methyl-2-oxo-1,2-dihydro-3-pyridinyl)methyl]-1-(1-methylethyl)-6-[6-(methyloxy)-3-pyridinyl]-1H-indole-4-carboxamide | 11.57 (br. s., 1 H) 8.60 (br. s., 1 H) 8.31 (br. s., 1 H) 8.11-8.19 (m, 1 H) 7.94 (s, 1 H) 7.58-7.73 (m, 2 H) 6.85-6.99 (m, 2 H) 5.93 (s, 1 H) 4.87-5.02 (m, 1 H) 4.40 (d, J = 4.29 Hz, 2 H) 3.91 (s, 3 H) 2.55-2.64 (m, 2 H) 2.14 (s, 3 H) 1.48 (d, J = 6.57 Hz, 6 H) 1.12 (t, J = 7.33 Hz, 3 H) | 459.2 |

| Ex | Structure | Name | $^1$H NMR (400 MHz, DMSO-$d_6$) δ ppm | MS(ES) [M + H]$^+$ |
|---|---|---|---|---|
| 83 | 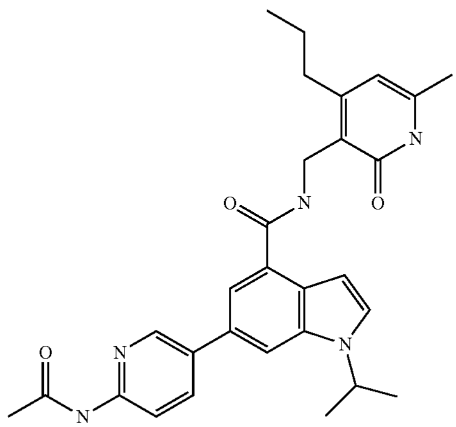 | 6-[6-(acetylamino)-3-pyridinyl]-1-(1-methylethyl)-N-[(6-methyl-2-oxo-4-propyl-1,2-dihydro-3-pyridinyl)methyl]-1H-indole-4-carboxamide | 11.56 (s, 1 H) 10.58 (s, 1 H) 8.76 (d, J = 2.02 Hz, 1 H) 8.32 (t, J = 4.93 Hz, 1 H) 8.14-8.23 (m, 2 H) 8.00 (s, 1 H) 7.73 (d, J = 1.26 Hz, 1 H) 7.65 (d, J = 3.03 Hz, 1 H) 6.90 (d, J = 3.28 Hz, 1 H) 5.92 (s, 1 H) 4.92-5.03 (m, 1 H) 4.41 (d, J = 5.05 Hz, 2 H) 2.53-2.58 (m, 2 H) 2.13 (d, J = 4.04 Hz, 6 H) 1.51-1.61 (m, 2 H) 1.48 (d, J = 6.57 Hz, 6 H) 0.91 (t, J = 7.33, 3 H) | 500.1 |
| 84 | 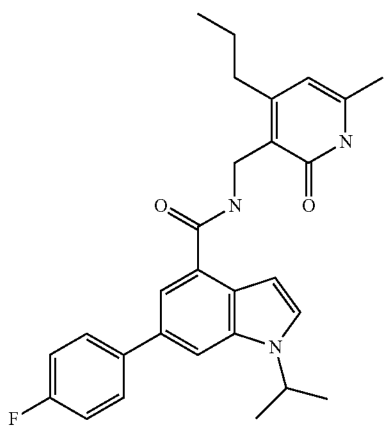 [SMILES: CCCc1cc(C)[nH]c(=O)c1CNC(=O)c1cc(-c2ccc(F)cc2)cc2c1ccn2C(C)C] | 6-(4-fluorophenyl)-1-(1-methylethyl)-N-[(6-methyl-2-oxo-4-propyl-1,2-dihydro-3-pyridinyl)methyl]-1H-indole-4-carboxamide | 11.56 (s, 1 H) 8.31 (t, J = 5.05 Hz, 1 H) 7.92 (s, 1 H) 7.80-7.86 (m, 2 H) 7.68 (d, J = 1.52 Hz, 1 H) 7.63 (d, J = 3.28 Hz, 1 H) 7.27-7.34 (m, 2 H) 6.88 (d, J = 3.03 Hz, 1 H) 5.92 (s, 1 H) 4.91-5.00 (m, 1 H) 4.41 (d, J = 5.05 Hz, 2 H) 2.53-2.58 (m, 2 H) 2.13 (s, 3 H) 1.51-1.59 (m, 2 H) 1.48 (d, J = 6.82 Hz, 6 H) 0.91 (t, J = 7.33 Hz, 3 H) | 460.1 |
| 85 | 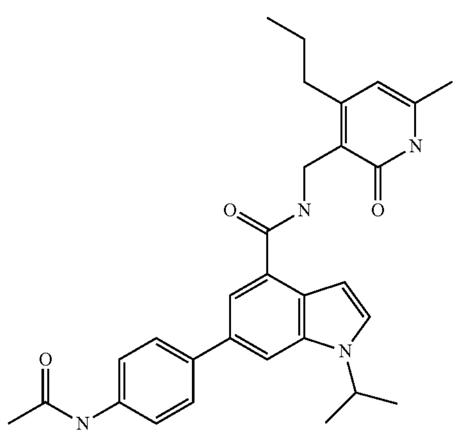 [SMILES: CCCc1cc(C)[nH]c(=O)c1CNC(=O)c1cc(-c2ccc(NC(C)=O)cc2)cc2c1ccn2C(C)C] | 6-[4-(acetylamino)phenyl]-1-(1-methylethyl)-N-[(6-methyl-2-oxo-4-propyl-1,2-dihydro-3-pyridinyl)methyl]-1H-indole-4-carboxamide | 11.56 (br. s., 1 H) 10.02 (s, 1 H) 8.29 (t, J = 5.05 Hz, 1 H) 7.89 (s, 1 H) 7.57-7.75 (m, 6 H) 6.86 (d, J = 3.28 Hz, 1 H) 5.92 (s, 1 H) 4.94 (quin, J = 6.57 Hz, 1 H) 4.41 (d, J = 5.05 Hz, 2 H) 2.57-2.53 (m, 2 H) 2.13 (s, 3 H) 2.07 (s, 3 H) 1.51-1.60 (m, 2 H) 1.48 (d, J = 6.57 Hz, 6 H) 0.91 (t, J = 7.33 Hz, 3 H) | 499.4 |

-continued

| Ex | Structure | Name | ¹H NMR (400 MHz, DMSO-d₆) δ ppm | MS(ES) [M + H]⁺ |
|---|---|---|---|---|
| 86 | 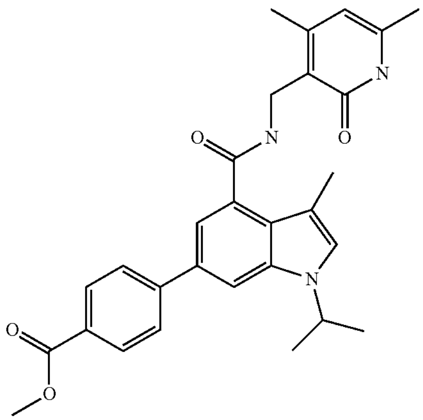 [SMILES: COC(=O)c1ccc(-c2cc(C(=O)NCc3c(C)cc(C)[nH]c3=O)c3c(C)cn(C(C)C)c3c2)cc1] | methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate | 11.48 (s, 1 H) 8.23 (t, J = 5.05 Hz, 1 H) 8.01-8.07 (m, 2 H) 7.90-7.96 (m, 3 H) 7.39 (s, 1 H) 7.33 (d, J = 1.26 Hz, 1 H) 5.87 (s, 1 H) 4.91 (t, J = 6.69 Hz, 1 H) 4.36 (d, J = 4.80 Hz, 2 H) 3.88(s, 3 H) 2.24 (s, 3 H) 2.18 (s, 3 H) 2.11 (s, 3 H) 1.44 (d, J = 6.57 Hz, 6 H) | 486.1 |
| 87 | 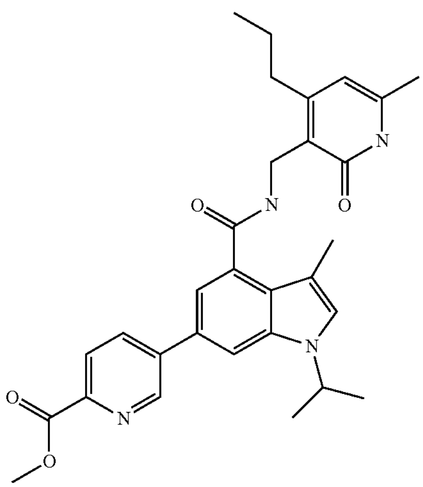 [SMILES: CCCc1cc(C)[nH]c(=O)c1CNC(=O)c1cc(-c2ccc(C(=O)OC)nc2)cc2c1c(C)cn2C(C)C] | methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate | 11.50 (s, 1 H) 9.13 (d, J = 1.77 Hz, 1 H) 8.36 (dd, J = 8.34, 2.27 Hz, 1 H) 8.23 (t, J = 5.05 Hz, 1 H) 8.13 (d, J = 8.34 Hz, 1 H) 8.02 (d, J = 1.52 Hz, 1 H) 7.43 (s, 1 H) 7.37 (d, J = 1.52 Hz, 1 H) 5.91 (s, 1 H) 4.88-4.99 (m, 1 H) 4.38 (d, J = 5.05 Hz, 2 H) 3.91 (s, 3 H) 2.53-2.59 (m, 2 H) 2.19 (s, 3 H) 2.13 (s, 3 H) 1.52-1.64 (m, 2 H) 1.45 (d, J = 6.57 Hz, 6 H) 0.94 (t, J = 7.33 Hz, 3 H) | 515.1 |
| 88 | 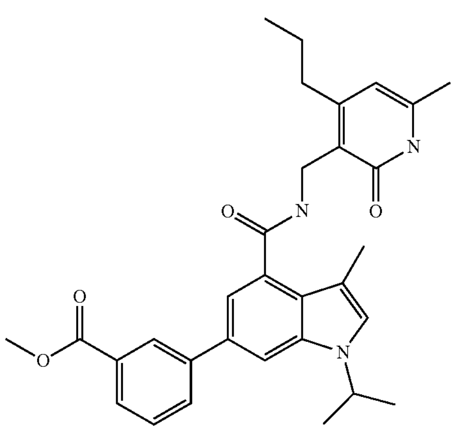 | methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate | 11.49 (br. s., 1 H) 8.19-8.31 (m, 2 H) 8.01-8.08 (m, 1 H) 7.95-7.90 (m, 1 H) 7.85 (s, 1 H) 7.59-7.65 (m, 1 H) 7.37 (s, 1 H) 7.26 (s, 1 H) 5.91 (br. s., 1 H) 4.87-4.97 (m, 1 H) 4.38 (d, J = 4.29 Hz, 2 H) 3.91 (s, 3 H) 2.55-2.62 (m, 2 H) 2.19 (s, 3 H) 2.12 (s, 3 H) 1.55-1.65 (m, 2 H) 1.44 (d, J = 6.57 Hz, 6 H) 0.94 (t, J = 7.2 Hz, 3 H) | 514.2 |

-continued

| Ex | Name | ¹H NMR (400 MHz, DMSO-d₆) δ ppm | MS(ES) [M + H]⁺ |
|---|---|---|---|
| 89 | 6-bromo-N-((6-ethyl-4-methyl-2-oxo-1,2-dihydropyridin-3-yl)methyl)-1-isopropyl-1H-indole-4-carboxamide | 8.36 (br. s., 1H), 7.92 (s, 1H), 7.63 (d, J = 3.28 Hz, 1H), 7.53 (d, J = 1.77 Hz, 1H), 6.88 (d, J = 3.28 Hz, 1H), 5.91 (s, 1H), 4.82 (dt, J = 6.60, 13.33 Hz, 1H), 4.33 (d, J = 5.05 Hz, 2H), 2.42 (q, J = 7.58 Hz, 2H), 2.23 (s, 3H), 1.43 (d, J = 6.57 Hz, 6H), 1.14 (t, J = 7.58 Hz, 3H) | 432.2 |
| 90 | N-((6-benzyl-4-methyl-2-oxo-1,2-dihydropyridin-3-yl)methyl)-6-bromo-1-isopropyl-1H-indole-4-carboxamide | 7.62 (d, J = 3.28 Hz, 1H), 7.51 (d, J = 1.52 Hz, 1H), 7.32 (s, 4H), 7.23 (td, J = 2.78, 5.56 Hz, 1H), 6.87 (d, J = 3.28 Hz, 1H), 5.89 (s, 1H), 4.82 (ddd, J = 6.44, 6.57, 13.26 Hz, 1H), 4.31 (d, J = 5.05 Hz, 2H), 3.74 (s, 2H), 2.19 (s, 3H), 1.43 (d, J = 6.82 Hz, 6H) | 494.2 |
| 91 | 6-bromo-N-((6-cyclobutyl-4-methyl-2-oxo-1,2-dihydropyridin-3-yl)methyl)-1-isopropyl-1H-indole-4-carboxamide | 8.40 (br. s., 1H), 7.92 (s, 1H), 7.63 (d, J = 3.28 Hz, 1H), 7.53 (d, J = 1.77 Hz, 1H), 6.88 (d, J = 3.28 Hz, 1H), 5.96 (s, 1H), 4.82 (quin, J = 6.63 Hz, 1H), 4.33 (d, J = 4.80 Hz, 2H), 3.25-3.38 (m, 2H), 2.25 (s, 3H), 2.06-2.22 (m, 4H), 1.84-1.99 (m, 1H), 1.70-1.82 (m, 1H), 1.43 (d, J = 6.57 Hz, 6H) | 455.9 |
| 92 | 6-bromo-1-(1-methylethyl)-N-({6-methyl-4-[(methyloxy)methyl]-2-oxo-1,2-dihydro-3-pyridinyl}methyl)-1H-indole-4-carboxamide | 11.70 (s, 1H), 8.32 (t, J = 5.05 Hz, 1H), 7.93 (s, 1H), 7.63 (d, J = 3.28 Hz, 1H), 7.51 (d, J = 1.52 Hz, 1H), 6.87 (d, J = 3.03 Hz, 1H), 6.09 (s, 1H), 4.82 (quin, J = 6.63 Hz, 1H), 4.49 (s, 2H), 4.30 (d, J = 5.05 Hz, 2H), 3.32 (s, 3H), 2.17 (s, 3H), 1.43 (d, J = 6.57 Hz, 6H) | 447.8 |

-continued

| Ex | Structure | Name | $^1$H NMR (400 MHz, DMSO-d$_6$) δ ppm | MS(ES) [M + H]$^+$ |
|---|---|---|---|---|
| 93 | 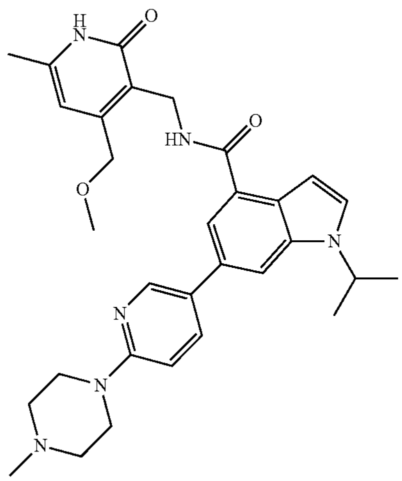 [SMILES: COCc1cc(C)[nH]c(=O)c1CNC(=O)c1cc(-c2ccc(N3CCN(C)CC3)nc2)cc2c1ccn2C(C)C] | 1-(1-methylethyl)-N-({6-methyl-4-[(methyloxy)methyl]-2-oxo-1,2-dihydro-3-pyridinyl}methyl)-6-[6-(4-methyl-1-piperazinyl)-3-pyridinyl]-1H-indole-4-carboxamide | 8.58 (d, J = 2.53 Hz, 1H), 8.31 (t, J = 5.05 Hz, 1H), 8.17 (s, 1H), 7.99 (dd, J = 2.53, 8.84 Hz, 1H), 7.88 (s, 1H), 7.66 (d, J = 1.26 Hz, 1H), 7.59 (d, J = 3.28 Hz, 1H), 6.94 (d, J = 8.84 Hz, 1H), 6.87 (d, J = 3.28 Hz, 1H), 6.10 (s, 1H), 4.93 (dq, J = 6.65, 6.82 Hz, 1H), 4.52 (s, 2H), 4.35 (d, J = 5.05 Hz, 2H), 3.50-3.58 (m, 4H), 3.32 (s, 3H), 2.45 (t, J = 4.93 Hz, 4H), 2.25 (s, 3H), 2.17 (s, 3H), 1.47 (d, J = 6.57 Hz, 6H) | 543.1 |
| 94 | 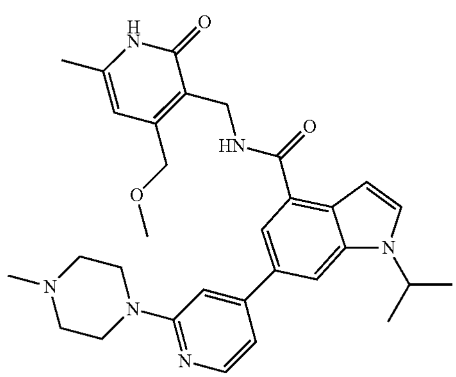 [SMILES: COCc1cc(C)[nH]c(=O)c1CNC(=O)c1cc(-c2ccnc(N3CCN(C)CC3)c2)cc2c1ccn2C(C)C] | 1-(1-methylethyl)-N-({6-methyl-4-[(methyloxy)methyl]-2-oxo-1,2-dihydro-3-pyridinyl}methyl)-6-[2-(4-methyl-1-piperazinyl)-4-pyridinyl]-1H-indole-4-carboxamide | 8.35 (t, J = 5.18 Hz, 1H), 8.18 (s, 1H), 8.16 (s, 2H), 8.05 (s, 1H), 7.74 (d, J = 1.26 Hz, 1H), 7.69 (d, J = 3.28 Hz, 1H), 7.17 (s, 1H), 7.11 (dd, J = 1.01, 5.31 Hz, 1H), 6.90 (d, J = 3.28 Hz, 1H), 6.10 (s, 1H), 5.01 (quin, J = 6.57 Hz, 1H), 4.53 (s, 2H), 4.35 (d, J = 5.31 Hz, 2H), 3.54-3.68 (m, 4H), 3.32 (s, 3H), 2.51-2.54 (m, 4H), 2.30 (s, 3H), 2.17 (s, 3H), 1.48 (d, J = 6.57 Hz, 6H) | 543.2 |
| 95 | 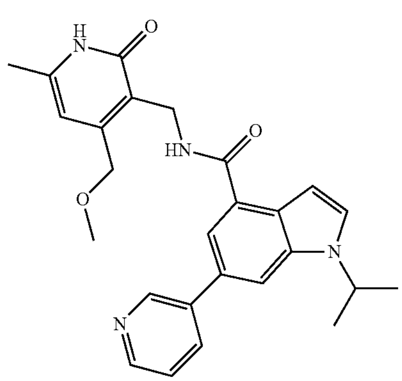 [SMILES: COCc1cc(C)[nH]c(=O)c1CNC(=O)c1cc(-c2cccnc2)cc2c1ccn2C(C)C] | 1-(1-methylethyl)-N-({6-methyl-4-[(methyloxy)methyl]-2-oxo-1,2-dihydro-3-pyridinyl}methyl)-6-(3-pyridinyl)-1H-indole-4-carboxamide | 11.75 (s, 1H), 9.05 (d, J = 2.02 Hz, 1H), 8.55 (dd, J = 1.52, 4.80 Hz, 1H), 8.39 (t, J = 5.18 Hz, 1H), 8.21 (dddd, J = 1.17, 1.52, 8.02 Hz, 1H), 8.15 (s, 1H), 8.05 (s, 1H), 7.76 (d, J = 1.52 Hz, 1H), 7.66 (d, J = 3.28 Hz, 1H), 7.49 (qd, 1H), 6.93 (d, J = 3.28 Hz, 1H), 6.10 (s, 1H), 4.98 (quin, J = 6.63 Hz, 1H), 4.52 (s, 2H), 4.36 (d, J = 5.05 Hz, 2H), 3.32 (s, 3H), 2.17 (s, 3H), 1.48 (d, J = 6.57 Hz, 6H) | 445.2 |

-continued

| Ex | Structure | Name | ¹H NMR (400 MHz, DMSO-d₆) δ ppm | MS(ES) [M + H]⁺ |
|---|---|---|---|---|
| 96 | 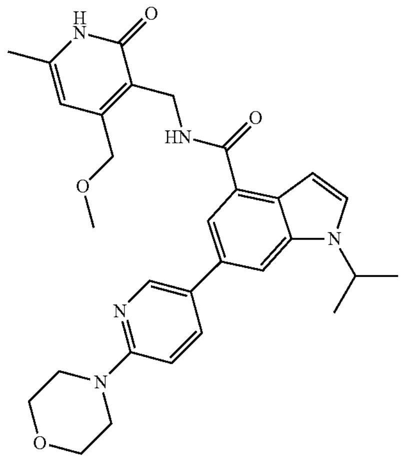 [SMILES: COCc1cc(C)[nH]c(=O)c1CNC(=O)c1cc(-c2ccc(N3CCOCC3)nc2)cc2c1ccn2C(C)C] | 1-(1-methylethyl)-N-({6-methyl-4-[(methyloxy)methyl]-2-oxo-1,2-dihydro-3-pyridinyl}methyl)-6-[6-(4-morpholinyl)-3-pyridinyl]-1H-indole-4-carboxamide | 11.71 (br. s., 1H), 8.60 (d, J = 2.53 Hz, 1H), 8.31 (t, J = 5.05 Hz, 1H), 8.15 (s, 1H), 8.02 (dd, J = 2.53, 8.84 Hz, 1H), 7.89 (s, 1H), 7.67 (d, J = 1.26 Hz, 1H), 7.59 (d, J = 3.28 Hz, 1H), 6.95 (d, J = 8.59 Hz, 1H), 6.88 (d, J = 3.28 Hz, 1H), 6.10 (s, 1H), 4.93 (quin, J = 6.63 Hz, 1H), 4.52 (s, 2H), 4.35 (d, J = 5.05 Hz, 2H), 3.70-3.77 (m, 4H), 3.46-3.52 (m, 4H), 3.32 (s, 3H), 2.17 (s, 3H), 1.47 (d, J = 6.57 Hz, 6H) | 530.9 |
| 97 | 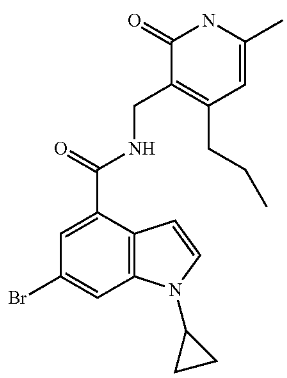 [SMILES: CCCc1cc(C)[nH]c(=O)c1CNC(=O)c1cc(Br)cc2c1ccn2C1CC1] | 6-bromo-1-cyclopropyl-N-[(6-methyl-2-oxo-4-propyl-1,2-dihydro-3-pyridinyl)methyl]-1H-indole-4-carboxamide | 11.56 (s, 1 H), 8.32 (t, J = 4.9 Hz, 1 H), 7.85 (s, 1 H), 7.56 (d, J = 1.8 Hz, 1 H), 7.45 (d, J = 3.3 Hz, 1 H), 6.78 (d, J = 3.0 Hz, 1 H), 5.90 (s, 1 H), 4.34 (d, J = 5.1 Hz, 2 H), 3.47 (dt, J = 7.0, 3.4 Hz, 1 H), 2.53 (br. s., 1 H), 2.13 (s, 3 H), 1.52 (m, 2 H), 1.07 (m, 2 H), 0.92 (m, 5 H) | 442.0 |
| 98 | 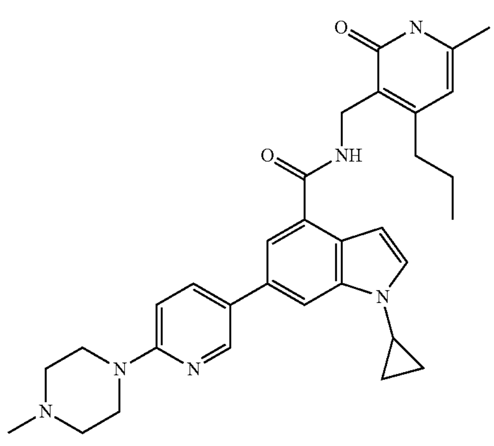 | 1-cyclopropyl-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.56 (s, 1 H), 8.54 (d, J = 2.5 Hz, 1 H), 8.30 (t, J = 5.1 Hz, 1 H), 7.95 (dd, J = 9.0, 2.7 Hz, 1 H), 7.85 (s, 1 H), 7.68 (d, J = 1.5 Hz, 1 H), 7.41 (d, J = 3.0 Hz, 1 H), 6.94 (d, J = 8.8 Hz, 1 H), 6.80 (d, J = 3.3 Hz, 1 H), 5.91 (s, 1 H), 4.39 (d, J = 5.1 Hz, 2 H), 3.51 (m, 5 H), 2.54 (m, 2 H), 2.41 (m, 4 H), 2.21 (m, 3 H), 2.13 (s, 3 H), 1.53 (m, 2 H), 1.09 (m, 2 H), 0.98 (m, 2 H), 0.89 (t, J = 7.3 Hz, 3 H) | 539.4 |

-continued

| Ex | Structure | Name | ¹H NMR (400 MHz, DMSO-d₆) δ ppm | MS(ES) [M + H]⁺ |
|---|---|---|---|---|
| 99 | 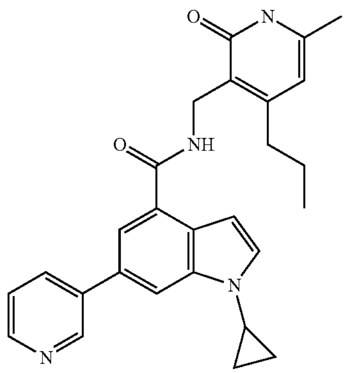 [SMILES: CCCc1cc(C)[nH]c(=O)c1CNC(=O)c1cc(-c2cccnc2)cc2c1ccn2C1CC1] | 1-cyclopropyl-N-[(6-methyl-2-oxo-4-propyl-1,2-dihydro-3-pyridinyl)methyl]-6-(3-pyridinyl)-1H-indole-4-carboxamide | 11.56 (s, 1 H), 9.02 (d, J = 1.8 Hz, 1 H), 8.56 (dd, J = 4.8, 1.5 Hz, 1 H), 8.37 (t, J = 5.1 Hz, 1 H), 8.18 (dt, J = 8.3, 1.9 Hz, 1 H), 7.99 (s, 1 H), 7.78 (d, J = 1.5 Hz, 1 H), 7.50 (m, 2 H), 6.85 (d, J = 3.3 Hz, 1 H), 5.91 (s, 1 H), 4.40 (d, J = 5.1 Hz, 2 H), 3.55 (tt, J = 7.0, 3.6 Hz, 1 H), 2.54 (m, 2 H), 2.13 (s, 3 H), 1.53 (m, 2 H), 1.11 (m, 2 H), 1.00 (m, 2 H), 0.89 (t, J = 7.3 Hz, 3 H) | 441.0 |
| 100 | 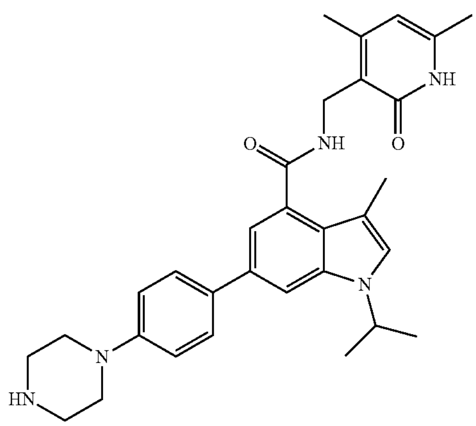 [SMILES: Cc1cc(C)c(CNC(=O)c2cc(-c3ccc(N4CCNCC4)cc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(4-(piperazin-1-yl)phenyl)-1H-indole-4-carboxamide | 1.43 (d, J = 6.57 Hz, 6 H), 2.11 (s, 3 H), 2.16 (s, 3 H), 2.24 (s, 3 H), 2.82-2.90 (m, 4 H), 3.04-3.12 (m, 4 H), 4.35 (d, J = 5.05 Hz, 2 H), 4.84 (quin, J = 6.63 Hz, 1 H), 5.87 (s, 1 H), 7.00 (d, J = 8.84 Hz, 2 H), 7.19 (d, J = 1.52 Hz, 1 H), 7.25-7.31 (m, 1 H), 7.59 (d, J = 8.84 Hz, 2 H), 7.67 (d, J = 1.26 Hz, 1 H), 8.14 (t, J = 5.05 Hz, 1 H) | 512.4 |
| 101 | 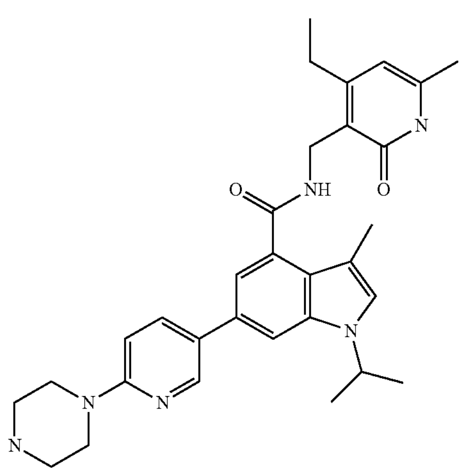 [SMILES: CCc1cc(C)[nH]c(=O)c1CNC(=O)c1cc(-c2ccc(N3CCNCC3)nc2)cc2c1c(C)cn2C(C)C] | N-[(4-ethyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide | 11.50 (br. s., 1 H) 8.50 (d, J = 2.53 Hz, 1 H) 8.13 (t, J = 4.80 Hz, 1 H) 7.91 (dd, J = 8.84, 2.53 Hz, 1 H) 7.69-7.76 (m, 1 H) 7.29 (s, 1 H) 7.18 (d, J = 1.26 Hz, 1 H) 6.88 (d, J = 8.84 Hz, 1 H) 5.92 (s, 1 H) 4.80-4.89 (m, 1 H) 4.38 (br. s., 1 H) 4.36 (br. s., 1 H) 3.39-3.51 (m, 4 H) 2.71-2.85 (m, 4 H) 2.53-2.63 (m, 3 H) 2.16 (s, 3 H) 2.13 (s, 3 H) 1.44 (s, 3 H) 1.42 (s, 3 H) 1.14 (t, J = 7.58 Hz, 3 H) | 527.2 |

-continued

| Ex | Structure | Name | ¹H NMR (400 MHz, DMSO-d$_6$) δ ppm | MS(ES) [M + H]⁺ |
|---|---|---|---|---|
| 102 | 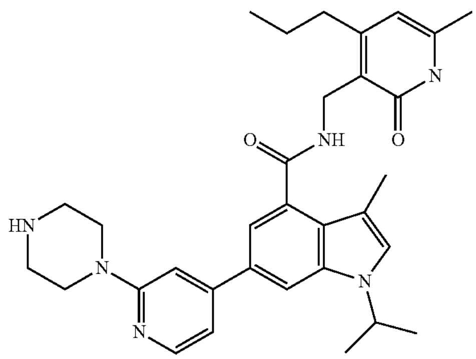 [SMILES: CCCc1cc(C)[nH]c(=O)c1CNC(=O)c1cc(-c2ccnc(N3CCNCC3)c2)cc2c1c(C)cn2C(C)C] | 1-isopropyl-3-methyl-N-((6-methyl-2-oxo-4-propyl-1,2-dihydropyridin-3-yl)methyl)-6-(2-(piperazin-1-yl)pyridin-4-yl)-1H-indole-4-carboxamide | 11.51 (br. s., 1 H) 8.18 (t, J = 5.05 Hz, 1 H) 8.11-8.16 (m, 1 H) 7.90 (d, J = 1.52 Hz, 1 H) 7.39 (s, 1 H) 7.30 (d, J = 1.52 Hz, 1 H) 6.99-7.12 (m, 2 H) 5.90 (s, 1 H) 4.93 (quin, J = 6.63 Hz, 1 H) 4.38 (br. s., 1 H) 4.36 (br. s., 1 H) 3.42-3.61 (m, 4 H) 2.79-2.83 (m, 3 H) 2.53-2.58 (m, 2 H) 2.17 (s, 3 H) 2.12 (s, 3 H) 1.53-1.62 (m, 2 H) 1.45 (s, 3 H) 1.43 (s, 3 H) 0.94 (t, J = 7.33 Hz, 3 H) | 541.4 |
| 103 | 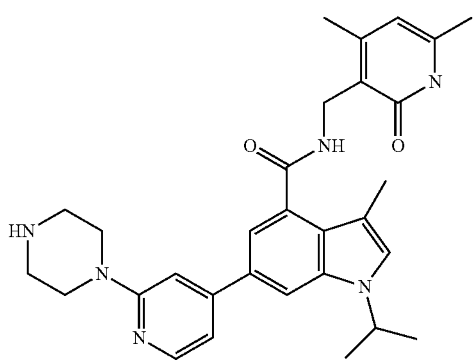 [SMILES: Cc1cc(C)c(CNC(=O)c2cc(-c3ccnc(N4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(2-(piperazin-1-yl)pyridin-4-yl)-1H-indole-4-carboxamide | 11.51 (br. s., 1 H) 8.21 (t, J = 4.93 Hz, 1 H) 8.14 (d, J = 5.05 Hz, 1 H) 7.90 (d, J = 1.52 Hz, 1 H) 7.38 (s, 1 H) 7.31 (d, J = 1.52 Hz, 1 H) 7.08 (s, 1 H) 7.02 (d, J = 4.80 Hz, 1 H) 5.87 (s, 1 H) 4.93 (quin, J = 6.57 Hz, 1 H) 4.36 (s, 1 H) 4.35 (s, 1 H) 3.43-3.52 (m, 4 H) 3.35 (br. s., 2 H) 2.79-2.84 (m, 3 H) 2.25 (s, 3 H) 2.16 (s, 3 H) 2.11 (s, 3 H) 1.44 (s, 3 H) 1.43 (s, 3 H) | 513.3 |
| 104 | 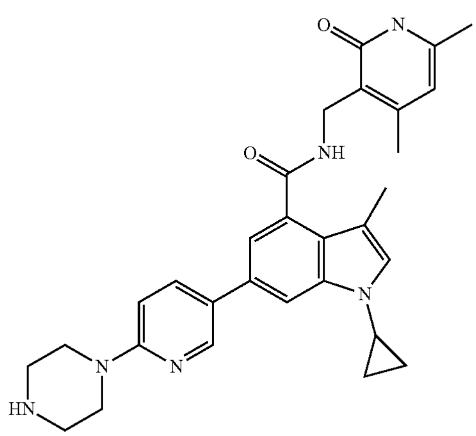 [SMILES: Cc1cc(C)c(CNC(=O)c2cc(-c3ccc(N4CCNCC4)nc3)cc3c2c(C)cn3C2CC2)c(=O)[nH]1] | 1-cyclopropyl-N-[(4,6-dimethyl-2-oxo-1,2-dihydro-3-pyridinyl)methyl]-3-methyl-6-[6-(1-piperazinyl)-3-pyridinyl]-1H-indole-4-carboxamide | 11.46 (br. s., 1 H), 8.48 (d, J = 2.3 Hz, 1 H), 8.16 (t, J = 5.1 Hz, 1 H), 7.89 (dd, J = 9.0, 2.7 Hz, 1 H), 7.70 (d, J = 1.5 Hz, 1 H), 7.22 (d, J = 1.5 Hz, 1 H), 7.11 (d, J = 1.0 Hz, 1 H), 6.89 (d, J = 8.8 Hz, 1 H), 5.86 (s, 1 H), 4.34 (d, J = 5.1 Hz, 2 H), 3.42 (m, 5 H), 2.80 (m, 4 H), 2.23 (s, 3 H), 2.12 (d, J = 7.1 Hz, 6 H), 1.05 (m, 2 H), 0.91 (m, 2 H) | 511.3 |

-continued

| Ex | Structure | Name | ¹H NMR (400 MHz, DMSO-d₆) δ ppm | MS(ES) [M + H]⁺ |
|---|---|---|---|---|
| 105 | 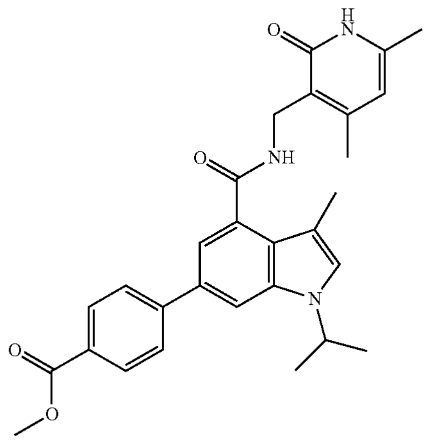 [SMILES: COC(=O)c1ccc(-c2cc(C(=O)NCc3c(C)cc(C)[nH]c3=O)c3c(C)cn(C(C)C)c3c2)cc1] | methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate | 11.48 (s, 1 H) 8.23 (t, J = 5.05 Hz, 1 H) 8.01-8.07 (m, 2 H) 7.90-7.96 (m, 3 H) 7.39 (s, 1 H) 7.33 (d, J = 1.26 Hz, 1 H) 5.87 (s, 1 H) 4.91 (t, J = 6.69 Hz, 1 H) 4.36 (d, J = 4.80 Hz, 2 H) 3.88 (s, 3 H) 2.24 (s, 3 H) 2.18 (s, 3 H) 2.11 (s, 3 H) 1.44 (d, J = 6.57 Hz, 6 H) | 486.1 |
| 106 | 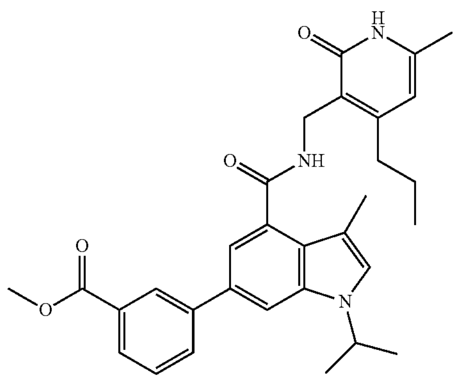 | methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate | 11.49 (br. s., 1 H) 8.19-8.31 (m, 2 H) 8.01-8.08 (m, 1 H) 7.95-7.90 (m, 1 H) 7.85 (s, 1 H) 7.59-7.65 (m, 1 H) 7.37 (s, 1 H) 7.26 (s, 1 H) 5.91 (br. s., 1 H) 4.87-4.97 (m, 1 H) 4.38 (d, J = 4.29 Hz, 2 H) 3.91 (s, 3 H) 2.55-2.62 (m, 2 H) 2.19 (s, 3 H) 2.12 (s, 3 H) 1.55-1.65 (m, 2 H) 1.44 (d, J = 6.57 Hz, 6 H) 0.94 (t, J = 7.2 Hz, 3 H) | 514.2 |
| 107 | 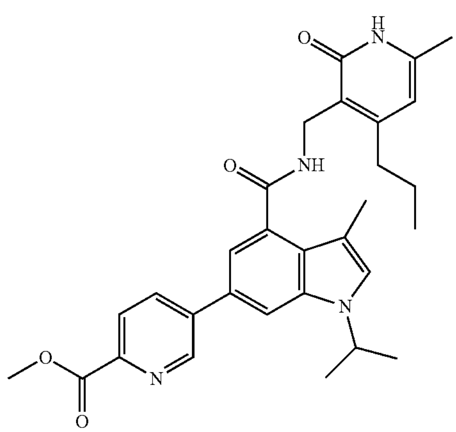 | methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate | 11.50 (s, 1 H) 9.13 (d, J = 1.77 Hz, 1 H) 8.36 (dd, J = 8.34, 2.27 Hz, 1 H) 8.23 (t, J = 5.05 Hz, 1 H) 8.13 (d, J = 8.34 Hz, 1 H) 8.02 (d, J = 1.52 Hz, 1 H) 7.43 (s, 1 H) 7.37 (d, J = 1.52 Hz, 1 H) 5.91 (s, 1 H) 4.88-4.99 (m, 1 H) 4.38 (d, J = 5.05 Hz, 2 H) 3.91 (s, 3 H) 2.53-2.59 (m, 2 H) 2.19 (s, 3 H) 2.13 (s, 3 H) 1.52-1.64 (m, 2 H) 1.45 (d, J = 6.57 Hz, 6 H) 0.94 (t, J = 7.33 Hz, 3 H) | 515.1 |

| Ex | Name | ¹H NMR (400 MHz, DMSO-d₆) δ ppm | MS(ES) [M + H]⁺ |
|---|---|---|---|
| 108 | 1-isopropyl-N-((6-methyl-2-oxo-4-propyl-1,2-dihydropyridin-3-yl)methyl)-6-(methylsulfonyl)-1H-indole-4-carboxamide | 0.91 (t, J = 8.00 Hz, 3 H), 1.45-1.60 (m, 8 H), 2.14 (s, 3 H), 3.23 (s, 3 H), 4.40 (d, J = 4.80 Hz, 2 H), 4.92-5.04 (m, 1 H), 5.92 (s, 1 H), 6.99 (d, J = 3.03 Hz, 1 H), 7.86 (d, J = 1.26 Hz, 1 H), 7.94 (d, J = 3.28 Hz, 1 H), 8.20 (s, 1 H), 8.44 (t, J = 4.80 Hz, 1 H), 11.58 (s, 1 H) | 444.2 |
| 109 | N-((4,6-dimethyl-2-oxo-1,2-dihydropyridin-3-yl)methyl)-1-isopropyl-3-methyl-6-(methylsulfonyl)-1H-indole-4-carboxamide | 1.42-1.51 (d, J = 8.00 Hz, 6 H), 2.12 (s, 3 H), 2.19 (s, 3 H), 2.24 (s, 3 H), 3.20 (s, 3 H), 4.35 (d, J = 5.05 Hz, 2 H), 4.89 (quin, J = 6.69 Hz, 1 H), 5.88 (s, 1 H), 7.41 (s, 1 H) 7.66 (s, 1 H), 8.07 (d, J = 1.52 Hz, 1 H), 8.37 (t, J = 4.93 Hz, 1 H), 11.50 (s, 1 H) | 430.0 |
| 110 | N-((4-ethyl-6-methyl-2-oxo-1,2-dihydropyridin-3-yl)methyl)-1-isopropyl-3-methyl-6-(methylsulfonyl)-1H-indole-4-carboxamide | 1.14 (m, 3 H), 1.45 (d, J = 6.57 Hz, 6 H), 2.13 (s, 3 H), 2.19 (s, 3 H), 2.54-2.65 (m, 3 H), 3.20 (s, 3 H), 4.37 (d, J = 5.05 Hz, 2 H), 4.89 (quin, J = 6.69 Hz, 1 H), 5.93 (s, 1 H), 7.40 (d, J = 1.52 Hz, 1 H), 7.66 (s, 1 H), 8.07 (d, J = 1.52 Hz, 1 H), 8.36 (t, J = 5.05 Hz, 1 H), 11.51 (s, 1 H) | 444.2 |
| 111 | N-((4-benzyl-6-methyl-2-oxo-1,2-dihydropyridin-3-yl)methyl)-1-isopropyl-3-methyl-6-(methylsulfonyl)-1H-indole-4-carboxamide | 1.45 (m, 6 H), 2.09 (s, 3 H), 2.18 (s, 3 H), 3.20 (s, 3 H), 3.99 (s, 2 H), 4.44 (d, J = 5.05 Hz, 2 H), 4.89 (quin, J = 6.69 Hz, 1 H), 5.79 (s, 1 H), 7.16-7.28 (m, 3 H), 7.30-7.36 (m, 2 H), 7.42 (d, J = 1.52 Hz, 1 H), 7.66 (s, 1 H), 8.08 (d, J = 1.52 Hz, 1 H), 8.50 (t, J = 5.05 Hz, 1 H), 11.58 (s, 1 H) | 505.9 |

| Ex | Structure | Name | ¹H NMR (400 MHz, DMSO-d₆) δ ppm | MS(ES) [M + H]⁺ |
|---|---|---|---|---|
| 112 | 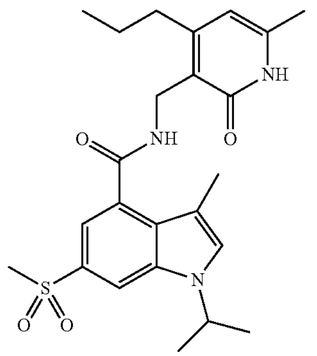 | 1-isopropyl-3-methyl-N-((6-methyl-2-oxo-4-propyl-1,2-dihydropyridin-3-yl)methyl)-6-(methylsulfonyl)-1H-indole-4-carboxamide | 0.94 (m, 3 H), 1.45 (d, J = 6.57 Hz, 6 H), 1.56 (sxt, J = 7.53 Hz, 2 H), 2.13 (s, 3 H), 2.19 (s, 3 H), 3.19 (s, 3 H), 4.37 (d, J = 4.80 Hz, 2 H), 4.89 (dt, J = 13.33, 6.60 Hz, 1 H), 5.91 (s, 1 H), 7.40 (d, J = 1.52 Hz, 1 H), 7.66 (s, 1 H), 8.08 (d, J = 1.26 Hz, 1 H), 8.35 (t, J = 4.67 Hz, 1 H), 11.51 (s, 1 H) | 458.2 |
| 113 | 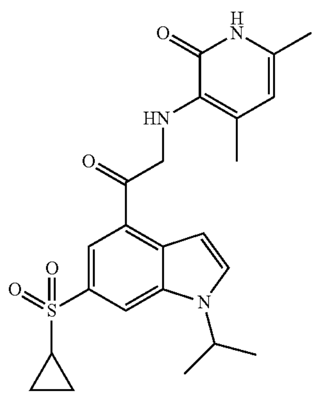 [SMILES: Cc1cc(C)c(NCC(=O)c2cc(S(=O)(=O)C3CC3)cc3c2ccn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 0.93-1.06 (m, 2 H), 1.11-1.25 (m, 2 H), 1.49 (d, J = 6.57 Hz, 6 H), 2.13 (s, 3 H), 2.24 (s, 3 H), 2.81-2.98 (m, 1 H), 4.37 (d, J = 5.05 Hz, 2 H), 4.99 (dt, J = 13.33, 6.60 Hz, 1 H), 5.90 (s, 1 H), 6.99 (d, J = 3.28 Hz, 1 H), 7.85 (d, J = 1.52 Hz, 1 H), 7.93 (d, J = 3.28 Hz, 1 H), 8.16 (s, 1 H), 8.49 (t, J = 4.93 Hz, 1 H), 11.57 (br. s., 1 H) | 442.0 |
| 114 | 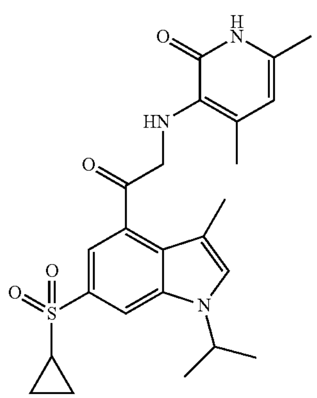 [SMILES: Cc1cc(C)c(NCC(=O)c2cc(S(=O)(=O)C3CC3)cc3c2c(C)cn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 1.00 (dd, J = 7.71, 2.65 Hz, 2 H), 1.13 (dd, J = 4.67, 2.40 Hz, 2 H), 1.45 (d, J = 6.57 Hz, 6 H), 2.12 (s, 3 H), 2.19 (s, 3 H), 2.23 (s, 3 H), 2.76-2.95 (m, 1 H), 4.35 (d, J = 5.05 Hz, 2 H), 4.91 (quin, J = 6.63 Hz, 1 H), 5.88 (s, 1 H), 7.36 (d, J = 1.52 Hz, 1 H), 7.66 (s, 1 H), 8.03 (d, J = 1.52 Hz, 1 H), 8.40 (t, J = 4.93 Hz, 1 H), 11.51 (s, 1 H) | 455.9 |
| 115 | 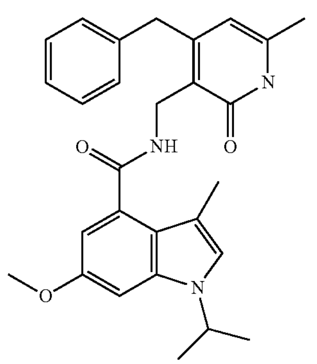 | 3-methyl-1-(1-methylethyl)-N-{[6-methyl-2-oxo-4-(phenylmethyl)-1,2-dihydro-3-pyridinyl]methyl}-6-(methyloxy)-1H-indole-4-carboxamide | 11.54 (br. s., 1 H) 8.13 (t, J = 5.18 Hz, 1 H) 7.29-7.33 (m, 2 H) 7.19-7.26 (m, 3 H) 7.12 (d, J = 1.01 Hz, 1 H) 7.03 (d, J = 2.27 Hz, 1 H) 6.58 (d, J = 2.27 Hz, 1 H) 5.78 (s, 1 H) 4.67 (quin, J = 6.63 Hz, 1 H) 4.40 (s, 1 H) 4.39 (s, 1 H) 3.98 (s, 2 H) 3.78-3.81 (m, 3 H) 2.10 (s, 3 H) 2.08 (s, 3 H) 1.40 (s, 3 H) 1.38 (s, 3 H) | 458.2 |

| Ex | Structure | Name | ¹H NMR (400 MHz, DMSO-d₆) δ ppm | MS(ES) [M + H]⁺ |
|---|---|---|---|---|
| 116 | 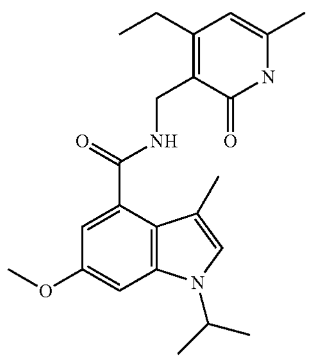 | N-[(4-ethyl-6-methyl-2-oxo-1,2-dihydro-3-pyridinyl)methyl]-3-methyl-1-(1-methylethyl)-6-(methyloxy)-1H-indole-4-carboxamide | 11.47 (br. s., 1 H) 8.00 (t, J = 4.93 Hz, 1 H) 7.12 (s, 1 H) 7.02 (d, J = 2.02 Hz, 1 H) 6.57 (d, J = 2.27 Hz, 1 H) 5.91 (s, 1 H) 4.67 (quin, J = 6.63 Hz, 1 H) 4.33 (s, 1 H) 4.32 (s, 1 H) 3.79 (s, 3 H) 2.53-2.60 (m, 2 H) 2.13 (s, 3 H) 2.10 (s, 3 H) 1.39 (s, 3 H) 1.38 (s, 3 H) 1.13 (t, J = 7.45 Hz, 3 H) | 395.8 |
| 117 | 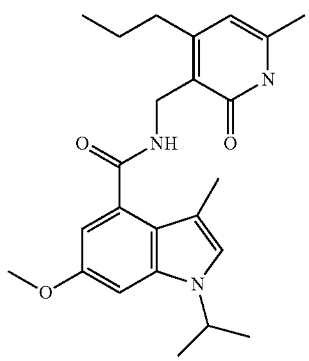 | 3-methyl-1-(1-methylethyl)-N-[(6-methyl-2-oxo-4-propyl-1,2-dihydro-3-pyridinyl)methyl]-6-(methyloxy)-1H-indole-4-carboxamide | 11.48 (br. s., 1 H) 7.98 (t, J = 5.05 Hz, 1 H) 7.10-7.13 (m, 1 H) 7.02 (d, J = 2.02 Hz, 1 H) 6.57 (d, J = 2.02 Hz, 1 H) 5.90 (s, 1 H) 4.66 (quin, J = 6.63 Hz, 1 H) 4.33 (s, 1 H) 4.32 (s, 1 H) 3.79 (s, 3 H) 2.55 (m, 2 H) 2.12 (s, 3 H) 2.10 (s, 3 H) 1.51-1.59 (m, 2 H) 1.39 (s, 3 H) 1.38 (s, 3 H) 0.93 (t, J = 7.33 Hz, 3 H) | 410.3 |
| 118 | 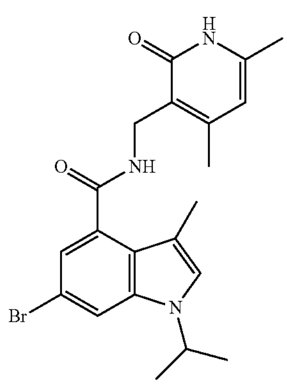 | 6-bromo-N-[(4,6-dimethyl-2-oxo-1,2-dihydro-3-pyridinyl)methyl]-3-methyl-1-(1-methylethyl)-1H-indole-4-carboxamide | 11.48 (br. s., 1H), 8.24 (t, J = 4.93 Hz, 1H), 7.76 (d, J = 1.52 Hz, 1H), 7.33 (d, J = 0.76 Hz, 1H), 7.00 (d, J = 1.77 Hz, 1H), 5.86 (s, 1H), 4.74 (quin, J = 6.63 Hz, 1H), 4.31 (d, J = 4.80 Hz, 2H), 2.22 (s, 3H), 2.12 (d, J = 7.07 Hz, 6H), 1.39 (d, J = 6.57 Hz, 6H) | 429.9 |
| 119 | 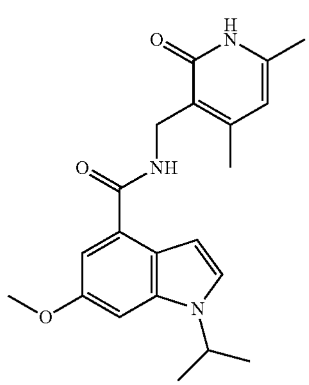 | N-[(4,6-dimethyl-2-oxo-1,2-dihydro-3-pyridinyl)methyl]-1-(1-methylethyl)-6-(methyloxy)-1H-indole-4-carboxamide | 11.55 (s, 1H), 8.12 (t, J = 5.18 Hz, 1H), 7.43 (d, J = 3.28 Hz, 1H), 7.19 (d, J = 2.02 Hz, 1H), 7.06 (d, J = 2.27 Hz, 1H), 6.74 (d, J = 3.28 Hz, 1H), 5.89 (s, 1H), 4.75 (quin, J = 6.63 Hz, 1H), 4.34 (d, J = 5.31 Hz, 2H), 3.82 (s, 3H), 2.23 (s, 3H), 2.12 (s, 3H), 1.43 (d, J = 6.57 Hz, 6H) | 368.1 |

-continued

| Ex | Structure | Name | ¹H NMR (400 MHz, DMSO-d₆) δ ppm | MS(ES) [M + H]⁺ |
|---|---|---|---|---|
| 120 | 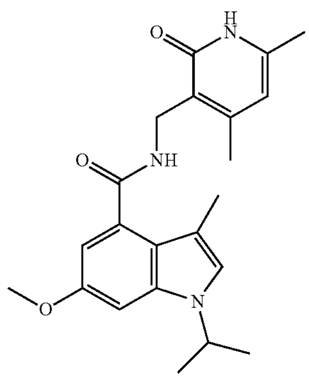 | N-[(4,6-dimethyl-2-oxo-1,2-dihydro-3-pyridinyl)methyl]-3-methyl-1-(1-methylethyl)-6-(methyloxy)-1H-indole-4-carboxamide | 11.47 (s, 1H), 8.02 (t, J = 5.05 Hz, 1H), 7.11 (s, 1H), 7.02 (d, J = 2.02 Hz, 1H), 6.57 (d, J = 2.02 Hz, 1H), 5.86 (s, 1H) 4.66 (quin, J = 6.63 Hz, 1H), 4.31 (d, J = 5.05 Hz, 2H), 3.79 (s, 3H), 2.22 (s, 3H), 2.10 (d, J = 4.80 Hz, 6H), 1.38 (d, J = 6.57 Hz, 6H) | 382.2 |
| 121 | 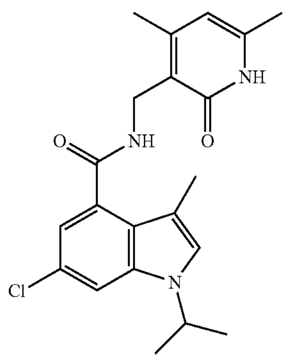 [SMILES: Cc1cc(C)c(CNC(=O)c2cc(Cl)cc3c2c(C)cn3C(C)C)c(=O)[nH]1] | 6-chloro-N-[(4,6-dimethyl-2-oxo-1,2-dihydro-3-pyridinyl)methyl]-3-methyl-1-(1-methylethyl)-1H-indole-4-carboxamide | 11.48 (br. s., 1H), 8.23 (t, J = 4.93 Hz, 1H), 7.63 (d, J = 1.77 Hz, 1H), 7.34 (d, J = 0.76 Hz, 1H), 6.90 (d, J = 2.02 Hz, 1H), 5.87 (s, 1H), 4.73 (quin, J = 6.63 Hz, 1H), 4.31 (d, J = 5.05 Hz, 2H), 2.22 (s, 3H), 2.12 (d, J = 7.07 Hz, 6H), 1.39 (d, J = 6.82 Hz, 6H) | 386.0 |
| 122 | 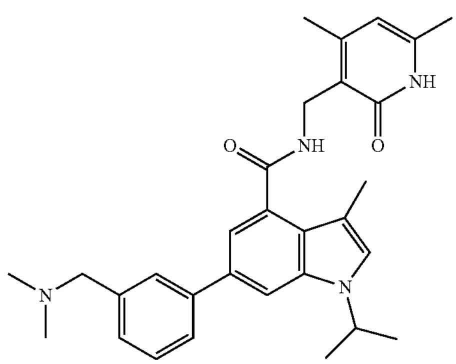 | 6-{3-[(dimethylamino)methyl]phenyl}-N-[(4,6-dimethyl-2-oxo-1,2-dihydro-3-pyridinyl)methyl]-3-methyl-1-(1-methylethyl)-1H-indole-4-carboxamide | 11.48 (s, 1H), 8.19 (t, J = 4.93 Hz, 1H), 7.77 (d, J = 1.26 Hz, 1H), 7.62-7.72 (m, 2H), 7.43 (t, J = 7.58 Hz, 1H), 7.33 (d, J = 0.76 Hz, 1H), 7.28 (d, J = 7.58 Hz, 1H), 7.24 (d, J = 1.52 Hz, 1H), 5.87 (s, 1H), 4.88 (quin, J = 6.63 Hz, 1H), 4.36 (d, J = 5.05 Hz, 2H), 3.62 (br. s., 2H), 2.28 (br. s., 6H), 2.24 (s, 3H), 2.17 (d, J = 1.01 Hz, 3H), 2.11 (s, 3H), 1.44 (d, J = 6.82 Hz, 6H) | 485.3 |
| 123 | 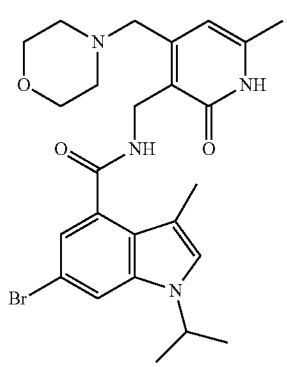 [SMILES: Cc1cc(CN2CCOCC2)c(CNC(=O)c2cc(Br)cc3c2c(C)cn3C(C)C)c(=O)[nH]1] | 6-bromo-3-methyl-1-(1-methylethyl)-N-{[6-methyl-4-(4-morpholinylmethyl)-2-oxo-1,2-dihydro-3-pyridinyl]methyl}-1H-indole-4-carboxamide | 11.64 (br. s., 1 H), 8.43 (br. s., 1 H), 7.78 (d, J = 1.3 Hz, 1 H), 7.33 (s, 1 H), 7.02 (d, J = 1.5 Hz, 1 H), 6.04 (s, 1 H), 4.75 (dt, J = 6.6, 13.0 Hz, 1 H), 4.41 (d, J = 4.8 Hz, 2 H), 3.40 (s, 2 H), 2.33 (br. s., 4 H), 2.25 (br. s., 4 H), 2.15 (s, 3 H), 2.11 (s, 3 H), 1.39 (d, J = 6.6 Hz, 6 H) | 515.2 |

| Ex | Structure | Name | $^1$H NMR (400 MHz, DMSO-d$_6$) δ ppm | MS(ES) [M + H]$^+$ |
|---|---|---|---|---|
| 124 | 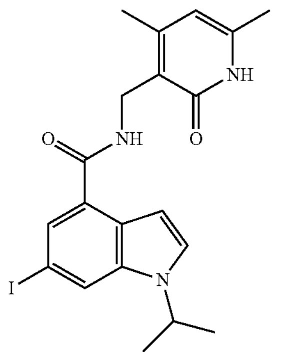 [SMILES: Cc1cc(C)c(CNC(=O)c2cc(I)cc3c2ccn3C(C)C)c(=O)[nH]1] | N-[(4,6-dimethyl-2-oxo-1,2-dihydro-3-pyridinyl)methyl]-6-iodo-1-(1-methylethyl)-1H-indole-4-carboxamide | 11.54 (s, 1 H), 8.27 (t, J = 5.1 Hz, 1 H), 8.05 (s, 1 H), 7.65 (d, J = 1.3 Hz, 1 H), 7.57 (d, J = 3.3 Hz, 1 H), 6.85 (d, J = 3.3 Hz, 1 H), 5.89 (s, 1 H), 4.81 (quin, J = 6.6 Hz, 1 H), 4.32 (d, J = 5.1 Hz, 2 H), 2.22 (s, 3 H), 2.12 (s, 3 H), 1.43 (d, J = 6.6 Hz, 6 H) | 464.0 |
| 125 | 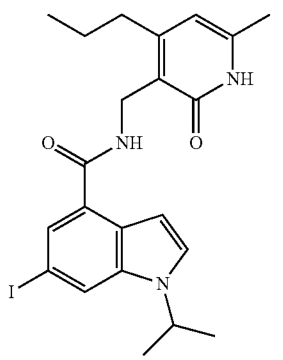 [SMILES: CCCc1cc(C)[nH]c(=O)c1CNC(=O)c1cc(I)cc2c1ccn2C(C)C] | 6-iodo-1-(1-methylethyl)-N-[(6-methyl-2-oxo-4-propyl-1,2-dihydro-3-pyridinyl)methyl]-1H-indole-4-carboxamide | 11.56 (s, 1 H), 8.27 (t, J = 5.1 Hz, 1 H), 8.05 (s, 1 H), 7.65 (d, J = 1.3 Hz, 1 H), 7.58 (d, J = 3.3 Hz, 1 H), 6.84 (d, J = 3.3 Hz, 1 H), 5.91 (s, 1 H), 4.82 (dt, J = 6.6, 13.3 Hz, 1 H), 4.35 (d, J = 5.3 Hz, 2 H), 2.52 (2 H under DMSO), 2.13 (s, 3 H), 1.53 (dq, J = 7.4, 15.1 Hz, 2 H), 0.91 (t, J = 7.3 Hz, 3 H) | 491.9 |
| 126 | 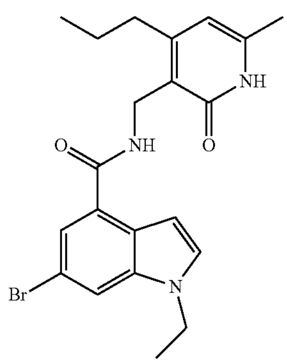 [SMILES: CCCc1cc(C)[nH]c(=O)c1CNC(=O)c1cc(Br)cc2c1ccn2CC] | 6-bromo-1-ethyl-N-[(6-methyl-2-oxo-4-propyl-1,2-dihydro-3-pyridinyl)methyl]-1H-indole-4-carboxamide | 0.92-0.88 (t, 3H), 1.34-1.31 (t, 3H), 1.53-1.49 (m, 2H), 2.13 (s, 3H), 2.54-2.49 (m, 2H), 4.25-4.20 (m, 2H), 4.35 (d, J = 4.8 Hz, 2H), 5.90 (s, 1H), 6.83 (d, J = 3.2 Hz, 1H), 7.51 (d, J = 3.2 Hz, 2H), 7.89 (s, 1H), 8.29-8.27 (t, 1H), 11.54 (s, 1H) | 432.15 |
| 127 | 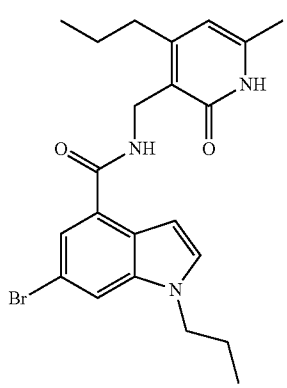 [SMILES: CCCc1cc(C)[nH]c(=O)c1CNC(=O)c1cc(Br)cc2c1ccn2CCC] | 6-bromo-N-[(6-methyl-2-oxo-4-propyl-1,2-dihydro-3-pyridinyl)methyl]-1-propyl-1H-indole-4-carboxamide | 0.83-0.79 δ (t, 3H), 0.92-0.88 (t, 3H), 1.55-1.51 (m, 2H), 1.74-1.71 (m, 2H), 1.76 (s, 3H), 2.54-2.45 (m, 2H), 4.17-4.14 (t, 2H), 4.35-4.34 (d, J = 5.2 Hz, 2H), 5.75 (s, 1H), 5.90 (s, 1H), 6.82 (d, J = 2.8 Hz), 7.51-7.49 (m, 2H), 7.90 (s, 1H), 8.28 (s, 1H), 11.54 (s, 1H) | 446.04 |

-continued

| Ex | Structure | Name | ¹H NMR (400 MHz, DMSO-d₆) δ ppm | MS(ES) [M + H]⁺ |
|---|---|---|---|---|
| 128 | 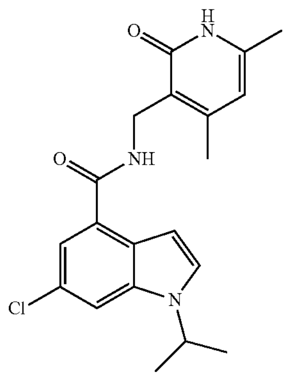 [SMILES: Cc1cc(C)c(CNC(=O)c2cc(Cl)cc3c2ccn3C(C)C)c(=O)[nH]1] | 3-({2-[6-chloro-1-(1-methylethyl)-1H-indol-4-yl]-2-oxoethyl}amino)-4,6-dimethyl-2(1H)-pyridinone | 1.43 (d, 6 H), 2.12 (s, 3 H), 2.21 (s, 3 H), 4.32 (d, J = 4.80 Hz, 2 H), 4.81 (dt, J = 13.33, 6.60 Hz, 1 H), 5.88 (s, 1 H), 6.86 (d, J = 3.03 Hz, 1 H), 7.40 (d, J = 1.52 Hz, 1 H), 7.63 (d, J = 3.28 Hz, 1 H), 7.79 (s, 1 H), 8.29 (t, J = 4.80 Hz, 1 H), 11.53 (br. s., 1 H) | 371.9 |
| 129 | 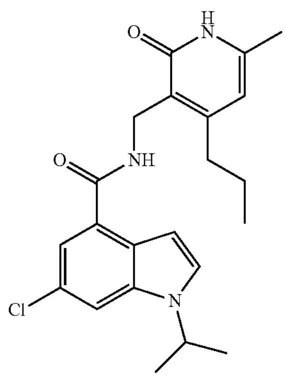 [SMILES: CCCc1cc(C)[nH]c(=O)c1CNC(=O)c1cc(Cl)cc2c1ccn2C(C)C] | 3-({2-[6-chloro-1-(1-methylethyl)-1H-indol-4-yl]-2-oxoethyl}amino)-6-methyl-4-propyl-2(1H)-pyridinone | 0.90 (t, J = 7.20 Hz, 3 H), 1.43 (d, J = 6.57 Hz, 6 H), 1.48-1.57 (m, 3 H), 2.13 (s, 3 H), 4.35 (d, J = 4.80 Hz, 2 H), 4.69-4.93 (m, 1 H), 5.90 (s, 1 H), 6.86 (d, J = 2.78 Hz, 1 H), 7.40 (s, 1 H), 7.64 (d, J = 3.28 Hz, 1 H), 7.79 (s, 1 H), 8.28 (br. s., 1 H), 11.55 (br. s., 1 H) | 399.8 |
| 130 | 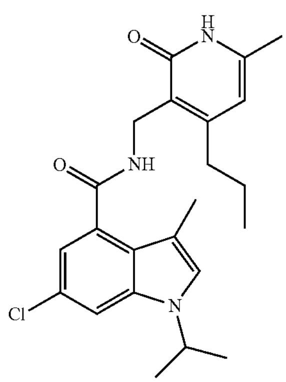 [SMILES: CCCc1cc(C)[nH]c(=O)c1CNC(=O)c1cc(Cl)cc2c1c(C)cn2C(C)C] | 3-({2-[6-chloro-3-methyl-1-(1-methylethyl)-1H-indol-4-yl]-2-oxoethyl}amino)-6-methyl-4-propyl-2(1H)-pyridinone | 0.93 (t, J = 7.33 Hz, 3 H), 1.39 (d, J = 6.57 Hz, 6 H), 1.47-1.67 (m, 2 H), 2.12 (d, J = 4.80 Hz, 6 H), 4.32 (d, J = 4.55 Hz, 2 H), 4.54-4.90 (m, 1 H), 5.89 (s, 1 H), 6.88 (s, 1 H), 7.34 (s, 1 H), 7.63 (s, 1 H), 8.20 (br. s., 1 H), 11.48 (br. s., 1 H) | 414.0 |
| 131 | 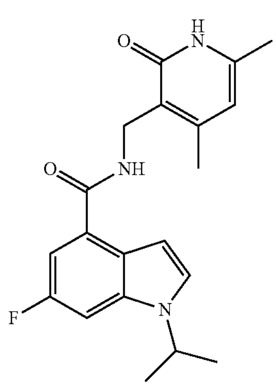 [SMILES: Cc1cc(C)c(CNC(=O)c2cc(F)cc3c2ccn3C(C)C)c(=O)[nH]1] | N-[(4,6-dimethyl-2-oxo-1,2-dihydro-3-pyridinyl)methyl]-6-fluoro-1-(1-methylethyl)-1H-indole-4-carboxamide | 1.42 (d, 6 H), 2.12 (s, 3 H), 2.22 (s, 3 H), 4.33 (d, J = 5.05 Hz, 2 H), 4.74 (dt, J = 13.14, 6.57 Hz, 1 H), 5.88 (s, 1 H), 6.85 (d, J = 3.03 Hz, 2 H), 7.25 (dd, J = 10.36, 1.77 Hz, 2 H), 7.51-7.67 (m, 4 H), 8.24 (t, J = 4.55 Hz, 2 H), 11.55 (br. s., 1 H) | 356.2 |

| Ex | Structure | Name | ¹H NMR (400 MHz, DMSO-d₆) δ ppm | MS(ES) [M + H]⁺ |
|---|---|---|---|---|
| 132 | 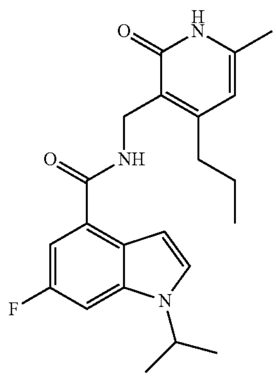 [SMILES: CCCc1cc(C)[nH]c(=O)c1CNC(=O)c1cc(F)cc2c1ccn2C(C)C] | 3-({2-[6-fluoro-1-(1-methylethyl)-1H-indol-4-yl]-2-oxoethyl}amino)-6-methyl-4-propyl-2(1H)-pyridinone | 0.90 (t, J = 7.20 Hz, 3 H), 1.43 (d, 6 H), 1.47-1.61 (m, 2 H), 2.13 (s, 3 H), 4.36 (d, J = 5.05 Hz, 2 H), 2.53 (2H), 4.75 (ddd, J = 13.20, 6.51, 6.32 Hz, 1 H), 5.91 (s, 1 H), 6.84 (d, J = 3.03 Hz, 1 H), 7.25 (dd, J = 10.36, 2.02 Hz, 1 H), 7.49-7.69 (m, 2 H), 8.23 (t, J = 4.93 Hz, 1 H), 11.57 (br. s., 1 H) | 384.0 |
| 133 | 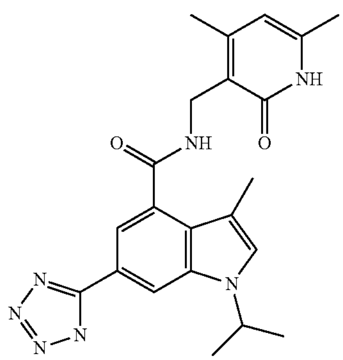 [SMILES: Cc1cc(C)c(CNC(=O)c2cc(-c3nnn[nH]3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1H-tetrazol-5-yl)-1H-indole-4-carboxamide | 11.50 (br. s., 1 H), 8.29 (t, J = 4.9 Hz, 1 H), 8.21 (s, 1 H), 7.62 (d, J = 1.3 Hz, 1 H), 7.51 (s, 1 H), 5.88 (s, 1 H), 4.80 (dt, J = 6.6, 13.1 Hz, 1 H), 4.37 (d, J = 5.1 Hz, 2 H), 2.25 (s, 3 H), 2.19 (s, 3 H), 2.12 (s, 3 H), 1.48 (d, J = 6.6 Hz, 6 H) | 419.9 |
| 134 | 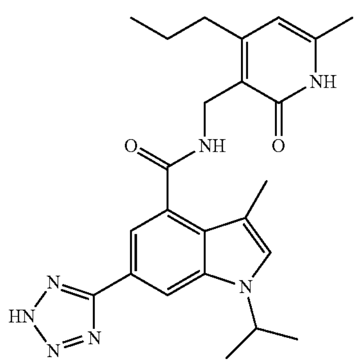 [SMILES: CCCc1cc(C)[nH]c(=O)c1CNC(=O)c1cc(-c2nn[nH]n2)cc2c1c(C)cn2C(C)C] | 1-isopropyl-3-methyl-N-((6-methyl-2-oxo-4-propyl-1,2-dihydropyridin-3-yl)methyl)-6-(2H-tetrazol-5-yl)-1H-indole-4-carboxamide | 11.50 (br. s., 1H), 8.25 (t, J = 4.93 Hz, 1H), 8.21 (d, J = 1.26 Hz, 1H), 7.63 (d, J = 0.76 Hz, 1H), 7.52 (s, 1H), 5.91 (s, 1H), 4.80 (qd, J = 6.19, 6.44 Hz, 1H), 4.38 (d, J = 5.05 Hz, 2H), 2.19 (s, 3H), 2.13 (s, 3H), 1.51-1.63 (m, 2H), 1.48 (d, J = 6.57 Hz, 6H), 1.10 (t, J = 6.95 Hz, 2H), 0.95 (t, J = 7.33 Hz, 3H) | 447.8 |
| 135 | 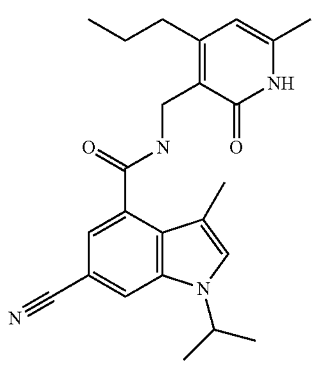 [SMILES: CCCc1cc(C)[nH]c(=O)c1CNC(=O)c1cc(C#N)cc2c1c(C)cn2C(C)C] | 6-cyano-3-methyl-1-(1-methylethyl)-N-[(6-methyl-2-oxo-4-propyl-1,2-dihydro-3-pyridinyl)methyl]-1H-indole-4-carboxamide | 11.50 (br. s., 1 H) 8.31 (t, J = 4.80 Hz, 1 H) 8.16 (d, J = 1.26 Hz, 1 H) 7.65 (s, 1 H) 7.19 (d, J = 1.26 Hz, 1 H) 5.90 (s, 1 H) 4.79-4.93 (m, 1 H) 4.33 (d, J = 5.05 Hz, 2 H) 2.55 (d, J = 1.52 Hz, 1 H) 2.17 (s, 3 H) 2.13 (s, 3 H) 1.51-1.61 (m, 2 H) 1.43 (d, J = 6.57 Hz, 6 H) 0.94 (t, J = 7.33 Hz, 3 H) | 405.1 |

-continued

| Ex | Structure | Name | ¹H NMR (400 MHz, DMSO-d₆) δ ppm | MS(ES) [M + H]⁺ |
|---|---|---|---|---|
| 136 | 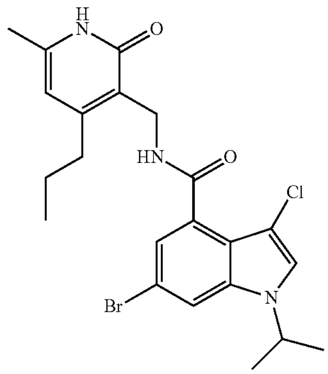 | 6-bromo-3-chloro-1-isopropyl-N-((6-methyl-2-oxo-4-propyl-1,2-dihydropyridin-3-yl)methyl)-1H-indole-4-carboxamide | 11.48 (s, 1H), 8.23 (t, J = 5.05 Hz, 1H), 7.93 (d, J = 1.52 Hz, 1H), 7.78 (s, 1H), 7.06 (d, J = 1.52 Hz, 1H), 5.89 (s, 1H), 4.84 (quin, J = 6.63 Hz, 1H), 4.33 (d, J = 5.05 Hz, 2H), 2.52-2.57 (m, 2H), 2.12 (s, 3H), 1.49-1.61 (m, J = 7.33, 7.52, 7.52, 7.52, 7.52 Hz, 2H), 1.41 (d, J = 6.82 Hz, 6H), 0.94 (t, J = 7.33 Hz, 3H) | 479.7 |
| 137 | 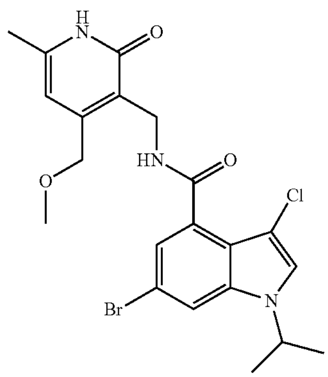 [SMILES: COCc1cc(C)[nH]c(=O)c1CNC(=O)c1cc(Br)cc2c1c(Cl)cn2C(C)C] | 6-bromo-3-chloro-1-(1-methylethyl)-N-({6-methyl-4-[(methyloxy)methyl]-2-oxo-1,2-dihydro-3-pyridinyl}methyl)-1H-indole-4-carboxamide | 8.32 (t, J = 4.80 Hz, 1H), 7.93 (s, 1H), 7.78 (s, 1H), 7.08 (s, 1H), 6.07 (s, 1H), 4.84 (q, J = 6.19, 6.38, 12.95 Hz, 1H), 4.48 (s, 2H), 4.29 (d, J = 5.05 Hz, 2H), 3.33 (br. s, 3H), 2.16 (s, 3H), 1.41 (d, J = 6.57 Hz, 6H) | 481.8 |
| 138 | 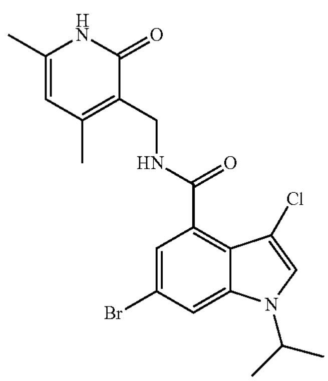 [SMILES: Cc1cc(C)c(CNC(=O)c2cc(Br)cc3c2c(Cl)cn3C(C)C)c(=O)[nH]1] | 6-bromo-3-chloro-N-[(4,6-dimethyl-2-oxo-1,2-dihydro-3-pyridinyl)methyl]-1-(1-methylethyl)-1H-indole-4-carboxamide | 8.27 (t, J = 4.93 Hz, 1H), 7.93 (d, J = 1.52 Hz, 1H), 7.78 (s, 1H), 7.07 (d, J = 1.77 Hz, 1H), 5.86 (s, 1H), 4.84 (quin, J = 6.63 Hz, 1H), 4.32 (d, J = 5.05 Hz, 2H), 2.21 (s, 3H), 2.11 (s, 3H), 1.41 (d, J = 6.57 Hz, 6H) | 451.8 |
| 139 | 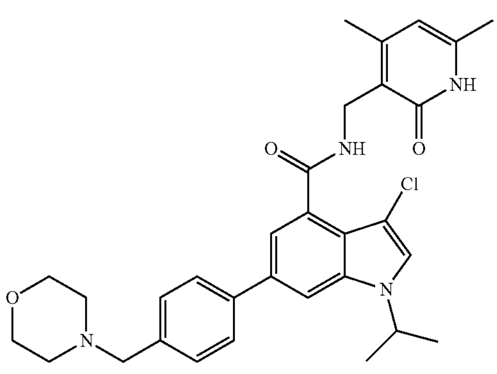 [SMILES: Cc1cc(C)c(CNC(=O)c2cc(-c3ccc(CN4CCOCC4)cc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-(4-(morpholinomethyl)phenyl)-1H-indole-4-carboxamide | 8.17 (t, J = 5.05 Hz, 1H), 8.15 (s, 1H), 7.90 (d, J = 1.26 Hz, 1H), 7.75 (s, 1H), 7.71 (d, J = 8.08 Hz, 2H), 7.40 (d, J = 8.34 Hz, 2H), 7.30 (d, J = 1.26 Hz, 1H), 5.87 (s, 1H), 4.96 (quin, J = 6.63 Hz, 1H), 4.37 (d, J = 5.05 Hz, 2H), 3.59 (t, J = 4.55 Hz, 4H), 3.51 (s, 2H), 2.39 (br. s., 4H), 2.24 (s, 3H), 2.11 (s, 3H), 1.46 (d, J = 6.82 Hz, 6H) | 547.0 |

-continued

| Ex | Structure | Name | ¹H NMR (400 MHz, DMSO-d₆) δ ppm | MS(ES) [M + H]⁺ |
|---|---|---|---|---|
| 140 | 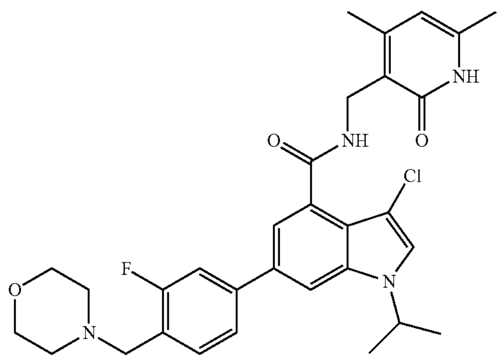 [SMILES: Cc1cc(C)c(CNC(=O)c2cc(-c3ccc(CN4CCOCC4)c(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluoro-4-(morpholinomethyl)phenyl)-1-isopropyl-1H-indole-4-carboxamide | 8.18 (t, J = 5.05 Hz, 1H), 8.14 (s, 1H), 7.98 (d, J = 1.26 Hz, 1H), 7.78 (s, 1H), 7.57-7.66 (m, 2H), 7.45-7.51 (m, 1H), 7.33 (d, J = 1.26 Hz, 1H), 5.87 (s, 1H), 4.99 (quin, J = 6.63 Hz, 1H), 4.37 (d, J = 5.05 Hz, 2H), 3.58 (dd, J = 4.04, 8.84 Hz, 6H), 2.42 (br. s., 4H), 2.24 (s, 3H), 2.11 (s, 3H), 1.46 (d, J = 6.57 Hz, 6H) | 565.3 |
| 141 | 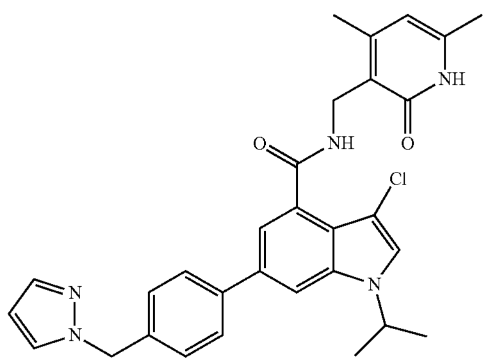 [SMILES: Cc1cc(C)c(CNC(=O)c2cc(-c3ccc(Cn4cccn4)cc3)cc3c2c(Cl)cn3C(C)C)c(=O)[nH]1] | 6-(4-((1H-pyrazol-1-yl)methyl)phenyl)-3-chloro-N-((4,6-dimethyl-2-oxo-1,2-dihydropyridin-3-yl)methyl)-1-isopropyl-1H-indole-4-carboxamide | 8.15 (s, 1H), 7.97 (s, 1H), 7.77 (s, 1H), 7.44 (s, 1H), 7.24-7.40 (m, 6H), 6.17 (br. s., 1H), 5.39 (s, 2H), 4.78-4.89 (m, 1H), 4.57 (br. s., 2H), 2.45 (s, 3H), 2.26 (br. s., 3H), 1.51 (d, J = 6.57 Hz, 6H) | 528.0 |
| 142 | 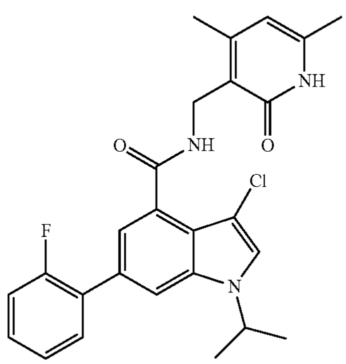 [SMILES: Cc1cc(C)c(CNC(=O)c2cc(-c3ccccc3F)cc3c2c(Cl)cn3C(C)C)c(=O)[nH]1] | 3-chloro-N-((4,6-dimethyl-2-oxo-1,2-dihydropyridin-3-yl)methyl)-6-(2-fluorophenyl)-1-isopropyl-1H-indole-4-carboxamide | 11.49 (br. s., 1H), 8.19 (t, J = 5.05 Hz, 1H), 7.76-7.83 (m, 2H), 7.56-7.68 (m, 1H), 7.38-7.46 (m, 1H), 7.29-7.36 (m, 2H), 7.17 (t, J = 1.39 Hz, 1H), 5.87 (s, 1H), 4.90 (quin, J = 6.63 Hz, 1H), 4.36 (d, J = 5.05 Hz, 2H), 2.23 (s, 3H), 2.11 (s, 3H), 1.45 (d, J = 6.82 Hz, 6H) | 465.9 |
| 143 | 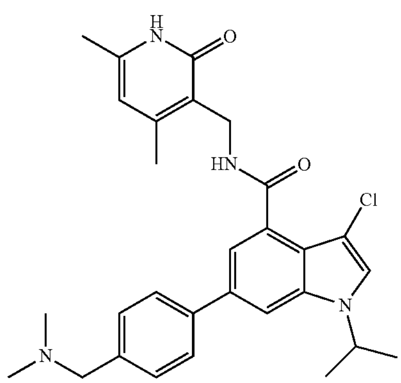 [SMILES: Cc1cc(C)c(CNC(=O)c2cc(-c3ccc(CN(C)C)cc3)cc3c2c(Cl)cn3C(C)C)c(=O)[nH]1] | 3-chloro-6-{4-[(dimethylamino)methyl]phenyl}-N-[(4,6-dimethyl-2-oxo-1,2-dihydro-3-pyridinyl)methyl]-1-(1-methylethyl)-1H-indole-4-carboxamide | 8.19 (s, 1H), 8.14-8.18 (m, 1H), 7.91 (d, J = 1.26 Hz, 1H), 7.75 (s, 1H), 7.73 (s, 1H), 7.71 (s, 1H), 7.39 (d, J = 8.08 Hz, 2H), 7.30 (d, J = 1.52 Hz, 1H), 5.87 (s, 1H), 4.97 (quin, J = 6.57 Hz, 1H), 4.37 (d, J = 5.05 Hz, 2H), 3.49 (s, 2H), 2.24 (s, 3H), 2.21 (s, 6H), 2.11 (s, 3H), 1.46 (d, J = 6.57 Hz, 6H) | 506.0 |

| Ex | Structure | Name | ¹H NMR (400 MHz, DMSO-d₆) δ ppm | MS(ES) [M + H]⁺ |
|---|---|---|---|---|
| 144 | 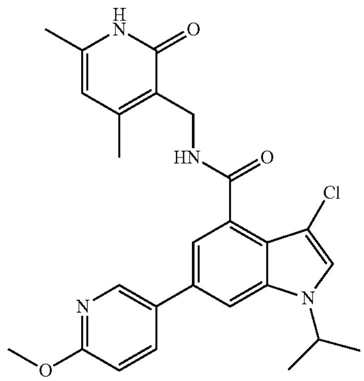 [SMILES: COc1ccc(-c2cc(C(=O)NCc3c(C)cc(C)[nH]c3=O)c3c(Cl)cn(C(C)C)c3c2)cn1] | 3-chloro-N-[(4,6-dimethyl-2-oxo-1,2-dihydro-3-pyridinyl)methyl]-1-(1-methylethyl)-6-[6-(methyloxy)-3-pyridinyl]-1H-indole-4-carboxamide | 11.46 (s, 1H), 8.56 (d, J = 2.02 Hz, 1H), 8.16 (t, J = 5.05 Hz, 1H), 8.11 (dd, J = 2.78, 8.59 Hz, 1H), 7.92 (d, J = 1.26 Hz, 1H), 7.75 (s, 1H), 7.28 (d, J = 1.26 Hz, 1H), 6.92 (d, J = 8.59 Hz, 1H), 5.87 (s, 1H), 4.96 (quin, J = 6.63 Hz, 1H), 4.36 (d, J = 5.05 Hz, 2H), 3.91 (s, 3H), 2.24 (s, 3H), 2.11 (s, 3H), 1.46 (d, J = 6.57 Hz, 6H) | 478.9 |
| 145 | 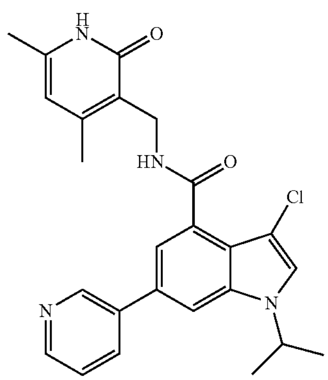 [SMILES: Cc1cc(C)c(CNC(=O)c2cc(-c3cccnc3)cc3c2c(Cl)cn3C(C)C)c(=O)[nH]1] | 3-chloro-N-[(4,6-dimethyl-2-oxo-1,2-dihydro-3-pyridinyl)methyl]-1-(1-methylethyl)-6-(3-pyridinyl)-1H-indole-4-carboxamide | 11.47 (br. s., 1H), 8.99 (d, J = 2.27 Hz, 1H), 8.56 (dd, J = 1.64, 4.67 Hz, 1H), 8.14-8.22 (m, 2H), 8.03 (d, J = 1.52 Hz, 1H), 7.80 (s, 1H), 7.49 (dd, J = 4.67, 7.96 Hz, 1H), 7.35 (d, J = 1.52 Hz, 1H), 5.87 (s, 1H), 4.94-5.05 (m, 1H), 4.37 (d, J = 5.05 Hz, 2H), 2.25 (s, 3H), 2.11 (s, 3H), 1.46 (d, J = 6.82 Hz, 6H) | 450.9 |
| 146 | 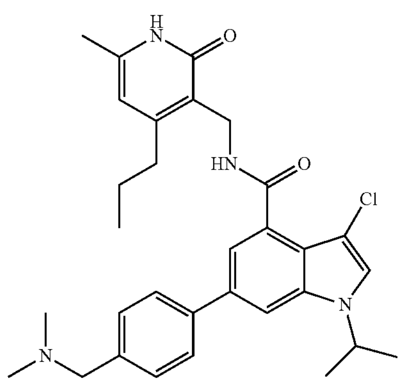 [SMILES: CCCc1cc(C)[nH]c(=O)c1CNC(=O)c1cc(-c2ccc(CN(C)C)cc2)cc2c1c(Cl)cn2C(C)C] | 3-chloro-6-{4-[(dimethylamino)methyl]phenyl}-1-(1-methylethyl)-N-[(6-methyl-2-oxo-4-propyl-1,2-dihydro-3-pyridinyl)methyl]-1H-indole-4-carboxamide | 11.48 (br. s., 1H), 8.14 (t, J = 4.80 Hz, 1H), 7.91 (d, J = 1.01 Hz, 1H), 7.75 (s, 1H), 7.71 (s, 1H), 7.69 (s, 1H), 7.39 (s, 1H), 7.37 (s, 1H), 7.29 (d, J = 1.01 Hz, 1H), 5.90 (s, 1H), 4.97 (qd, J = 6.44, 6.61 Hz, 1H), 4.38 (d, J = 5.05 Hz, 2H), 3.44 (s, 2H), 2.55 (dd, J = 6.95, 8.72 Hz, 2H), 2.18 (s, 6H), 2.12 (s, 3H), 1.57 (dq, J = 7.48, 15.19 Hz, 2H), 1.46 (d, J = 6.57 Hz, 6H), 0.95 (t, J = 7.33 Hz, 3H) | 534.4 |
| 147 | 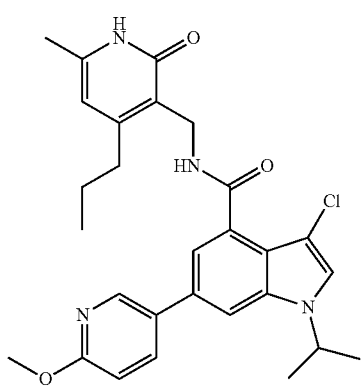 [SMILES: CCCc1cc(C)[nH]c(=O)c1CNC(=O)c1cc(-c2ccc(OC)nc2)cc2c1c(Cl)cn2C(C)C] | 3-chloro-1-(1-methylethyl)-N-[(6-methyl-2-oxo-4-propyl-1,2-dihydro-3-pyridinyl)methyl]-6-[6-(methyloxy)-3-pyridinyl]-1H-indole-4-carboxamide | 11.48 (s, 1H), 8.55 (d, J = 2.02 Hz, 1H), 8.13 (t, J = 5.05 Hz, 1H), 8.10 (dd, J = 2.53, 8.59 Hz, 1H), 7.93 (d, J = 1.52 Hz, 1H), 7.76 (s, 1H), 7.27 (d, J = 1.52 Hz, 1H), 6.93 (d, J = 8.59 Hz, 1H), 5.90 (s, 1H), 4.96 (quin, J = 6.63 Hz, 1H), 4.38 (d, J = 5.05 Hz, 2H), 3.91 (s, 3H), 2.55 (dd, J = 6.82, 8.84 Hz, 2H), 2.12 (s, 3H), 1.51-1.63 (m, 2H), 1.46 (d, J = 6.82 Hz, 6H), 0.94 (t, J = 7.33 Hz, 3H) | 509.0 |

| Ex | Structure | Name | ¹H NMR (400 MHz, DMSO-d₆) δ ppm | MS(ES) [M + H]⁺ |
|---|---|---|---|---|
| 148 | 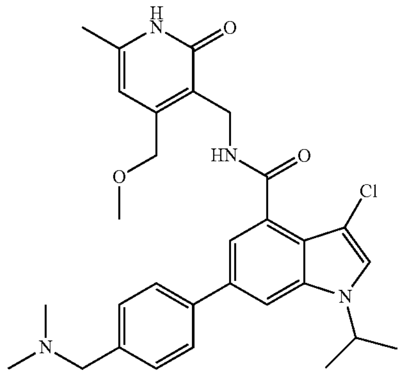 [SMILES: COCc1cc(C)[nH]c(=O)c1CNC(=O)c1cc(-c2ccc(CN(C)C)cc2)cc2c1c(Cl)cn2C(C)C] | 3-chloro-6-{4-[(dimethylamino)methyl]phenyl}-1-(1-methylethyl)-N-({6-methyl-4-[(methyloxy)methyl]-2-oxo-1,2-dihydro-3-pyridinyl}methyl)-1H-indole-4-carboxamide | 11.62 (br. s., 1H), 8.22 (t, J = 5.05 Hz, 1H), 8.16 (s, 1H), 7.90 (s, 1H), 7.74 (s, 1H), 7.72 (s, 1H), 7.70 (s, 1H), 7.39 (d, J = 8.34 Hz, 2H), 7.30 (s, 1H), 6.07 (s, 1H), 4.97 (dt, J = 6.69, 13.39 Hz, 1H), 4.51 (s, 2H), 4.33 (d, J = 5.05 Hz, 2H), 3.48 (s, 2H), 3.33 (s, 3H), 2.21 (s, 6H), 2.15 (s, 3H), 1.45 (d, J = 6.57 Hz, 6H) | 534.9 |
| 149 | 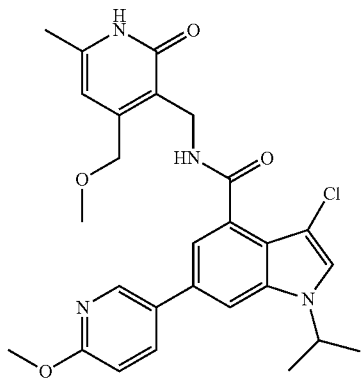 [SMILES: COCc1cc(C)[nH]c(=O)c1CNC(=O)c1cc(-c2ccc(OC)nc2)cc2c1c(Cl)cn2C(C)C] | 3-chloro-1-(1-methylethyl)-N-({6-methyl-4-[(methyloxy)methyl]-2-oxo-1,2-dihydro-3-pyridinyl}methyl)-6-[6-(methyloxy)-3-pyridinyl]-1H-indole-4-carboxamide | 11.63 (br. s., 1H), 8.56 (d, J = 2.02 Hz, 1H), 8.22 (t, J = 5.05 Hz, 1H), 8.11 (dd, J = 2.65, 8.72 Hz, 1H), 7.93 (d, J = 1.26 Hz, 1H), 7.75 (s, 1H), 7.29 (d, J = 1.52 Hz, 1H), 6.93 (d, J = 8.08 Hz, 1H), 6.08 (s, 1H), 4.96 (quin, J = 6.57 Hz, 1H), 4.52 (s, 2H), 4.34 (d, J = 5.31 Hz, 2H), 3.91 (s, 3H), 3.33 (br. s., 3H), 2.16 (s, 3H), 1.46 (d, J = 6.57 Hz, 6H) | 510.0 |
| 150 | 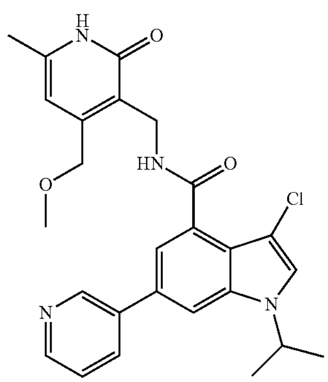 [SMILES: COCc1cc(C)[nH]c(=O)c1CNC(=O)c1cc(-c2cccnc2)cc2c1c(Cl)cn2C(C)C] | 3-chloro-1-isopropyl-N-((4-(methoxymethyl)-6-methyl-2-oxo-1,2-dihydropyridin-3-yl)methyl)-6-(pyridin-3-yl)-1H-indole-4-carboxamide | 11.63 (br. s., 1H), 9.00 (d, J = 1.77 Hz, 1H), 8.56 (dd, J = 1.52, 4.80 Hz, 1H), 8.26 (t, J = 5.18 Hz, 1H), 8.17 (ddd, J = 1.77, 2.02, 8.34 Hz, 1H), 8.04 (d, J = 1.52 Hz, 1H), 7.80 (s, 1H), 7.49 (ddd, J = 0.76, 4.74, 7.89 Hz, 1H), 7.36 (d, J = 1.26 Hz, 1H), 6.08 (s, 1H), 5.00 (quin, J = 6.63 Hz, 1H), 4.53 (s, 2H), 4.34 (d, J = 5.05 Hz, 2H), 3.33 (s, 3H), 2.16 (s, 3H), 1.46 (d, J = 6.57 Hz, 6H) | 479.0 |
| 151 | 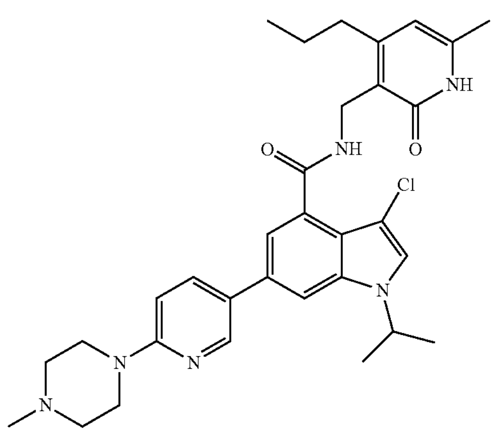 | 3-chloro-1-isopropyl-N-((6-methyl-2-oxo-4-propyl-1,2-dihydropyridin-3-yl)methyl)-6-(6-(4-methylpiperazin-1-yl)pyridin-3-yl)-1H-indole-4-carboxamide | 8.51 (d, J = 2.53 Hz, 1H), 8.13 (t, J = 4.55 Hz, 1H), 7.93 (dd, J = 2.53, 8.84 Hz, 1H), 7.86 (d, J = 1.26 Hz, 1H), 7.71 (s, 1H), 7.24 (d, J = 1.26 Hz, 1H), 6.93 (d, J = 9.09 Hz, 1H), 5.89 (s, 1H), 4.95 (quin, J = 6.63 Hz, 1H), 4.37 (d, J = 4.80 Hz, 2H), 3.51-3.57 (m, 4H), 2.52-2.58 (m, 2H), 2.37-2.45 (m, 4H), 2.23 (s, 3H), 2.12 (s, 3H), 1.57 (dddd, J = 7.20, 7.33, 7.48, 15.13 Hz, 2H), 1.45 (d, J = 6.57 Hz, 6H), 0.94 (t, J = 7.33 Hz, 3H) | 575.3 |

| Ex | Structure | Name | ¹H NMR (400 MHz, DMSO-d₆) δ ppm | MS(ES) [M + H]⁺ |
|---|---|---|---|---|
| 152 | 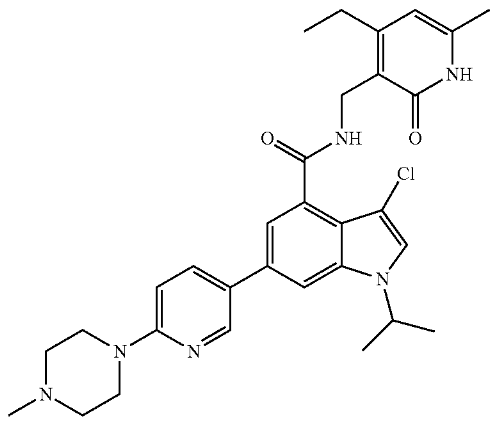 | 3-chloro-N-((4-ethyl-6-methyl-2-oxo-1,2-dihydropyridin-3-yl)methyl)-1-isopropyl-6-(6-(4-methylpiperazin-1-yl)pyridin-3-yl)-1H-indole-4-carboxamide | 8.52 (d, J = 2.53 Hz, 1H), 8.13 (t, J = 5.05 Hz, 1H), 7.94 (dd, J = 2.65, 8.97 Hz, 1H), 7.86 (d, J = 1.52 Hz, 1H), 7.71 (s, 1H), 7.24 (d, J = 1.52 Hz, 1H), 6.93 (d, J = 8.84 Hz, 1H), 5.91 (s, 1H), 4.94 (quin, J = 6.57 Hz, 1H), 4.38 (d, J = 5.05 Hz, 2H), 3.50-3.57 (m, 4H), 2.59 (q, J = 7.58 Hz, 2H), 2.39-2.45 (m, 4H), 2.23 (s, 3H), 2.13 (s, 3H), 1.45 (d, J = 6.82 Hz, 6H), 1.14 (t, J = 7.58 Hz, 3H) | 561.1 |
| 153 | 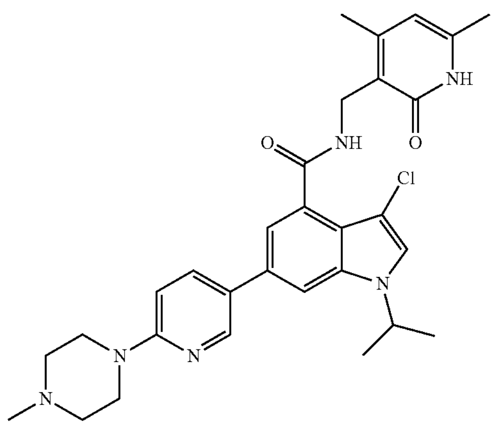 | 3-chloro-N-((4,6-dimethyl-2-oxo-1,2-dihydropyridin-3-yl)methyl)-1-isopropyl-6-(6-(4-methylpiperazin-1-yl)pyridin-3-yl)-1H-indole-4-carboxamide | 8.52 (d, J = 2.27 Hz, 1H), 8.15 (t, J = 4.55 Hz, 1H), 7.94 (dd, J = 2.53, 8.84 Hz, 1H), 7.85 (d, J = 1.26 Hz, 1H), 7.71 (s, 1H), 7.25 (d, J = 1.26 Hz, 1H), 6.93 (d, J = 8.84 Hz, 1H), 5.86 (s, 1H), 4.94 (quin, J = 6.63 Hz, 1H), 4.36 (d, J = 5.05 Hz, 2H), 3.50-3.57 (m, 4H), 2.38-2.45 (m, 4H), 2.23 (d, J = 3.03 Hz, 6H), 2.11 (s, 3H), 1.45 (d, J = 6.57 Hz, 6H) | 547.0 |
| 154 | 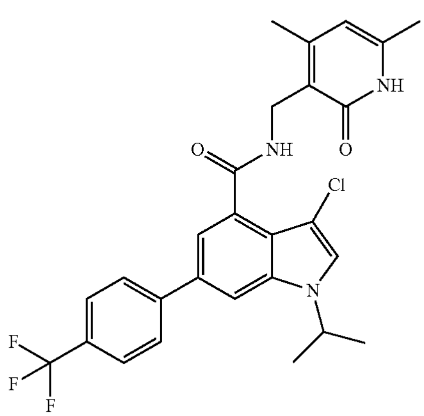 [SMILES: Cc1cc(C)c(CNC(=O)c2cc(-c3ccc(C(F)(F)F)cc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-(4-(trifluoromethyl)phenyl)-1H-indole-4-carboxamide | 11.47 (s, 1H), 8.23 (t, J = 4.93 Hz, 1H), 7.98-8.05 (m, 3H), 7.79-7.86 (m, 3H), 7.37 (d, J = 1.26 Hz, 1H), 5.87 (s, 1H), 5.00 (qd, J = 6.44, 6.61 Hz, 1H), 4.37 (d, J = 4.80 Hz, 2H), 2.24 (s, 3H), 2.11 (s, 3H), 1.47 (d, J = 6.57 Hz, 6H) | 516.0 |

-continued

| Ex | Structure | Name | ¹H NMR (400 MHz, DMSO-d₆) δ ppm | MS(ES) [M + H]⁺ |
|---|---|---|---|---|
| 155 | 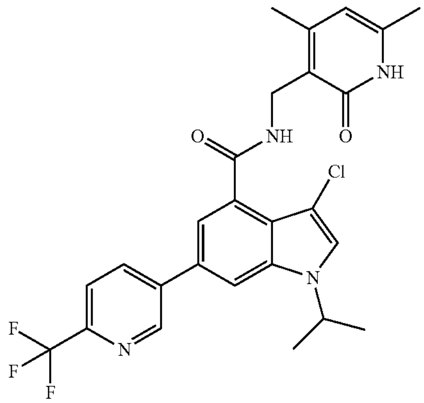 | 3-chloro-N-((4,6-dimethyl-2-oxo-1,2-dihydropyridin-3-yl)methyl)-1-isopropyl-6-(6-(trifluoromethyl)pyridin-3-yl)-1H-indole-4-carboxamide | 11.49 (br. s., 1H), 9.20 (d, J = 2.02 Hz, 1H), 8.47 (dd, J = 2.02, 8.08 Hz, 1H), 8.24 (t, J = 5.05 Hz, 1H), 8.16 (d, J = 1.26 Hz, 1H), 7.99 (d, J = 8.34 Hz, 1H), 7.86 (s, 1H), 7.45 (d, J = 1.52 Hz, 1H), 5.88 (s, 1H), 5.01 (quin, J = 6.63 Hz, 1H), 4.38 (d, J = 4.80 Hz, 2H), 2.25 (s, 3H), 2.11 (s, 3H), 1.47 (d, J = 6.57 Hz, 6H) | 517.0 |
| 156 | 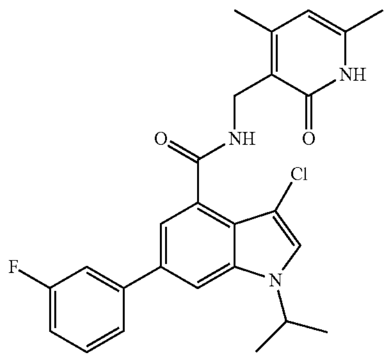 [SMILES: Cc1cc(C)c(CNC(=O)c2cc(-c3cccc(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluorophenyl)-1-isopropyl-1H-indole-4-carboxamide | 11.47 (br. s., 1H), 8.19 (t, J = 4.93 Hz, 1H), 7.99 (s, 1H), 7.79 (s, 1H), 7.44-7.69 (m, 4H), 7.34 (s, 1H), 7.18 (t, J = 7.33 Hz, 1H), 5.87 (s, 1H), 5.00 (dt, J = 6.66, 13.20 Hz, 1H), 4.37 (d, J = 4.80 Hz, 2H), 2.25 (s, 3H), 2.11 (s, 3H), 1.46 (d, J = 6.57 Hz, 6H) | 466.0 |
| 157 | 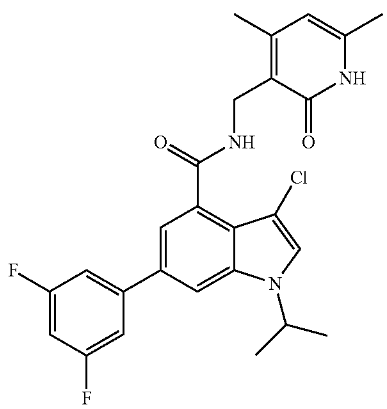 [SMILES: Cc1cc(C)c(CNC(=O)c2cc(-c3cc(F)cc(F)c3)cc3c2c(Cl)cn3C(C)C)c(=O)[nH]1] | 3-chloro-6-(3,5-difluorophenyl)-N-((4,6-dimethyl-2-oxo-1,2-dihydropyridin-3-yl)methyl)-1-isopropyl-1H-indole-4-carboxamide | 11.47 (s, 1H), 8.19 (t, J = 5.05 Hz, 1H), 8.06 (d, J = 1.52 Hz, 1H), 7.81 (s, 1H), 7.52-7.63 (m, 2H), 7.38 (d, J = 1.26 Hz, 1H), 7.20 (tt, J = 2.27, 9.35 Hz, 1H), 5.87 (s, 1H), 5.02 (quin, J = 6.63 Hz, 1H), 4.37 (d, J = 5.05 Hz, 2H), 2.25 (s, 3H), 2.11 (s, 3H), 1.46 (d, J = 6.57 Hz, 6H) | 484.0 |
| 158 | 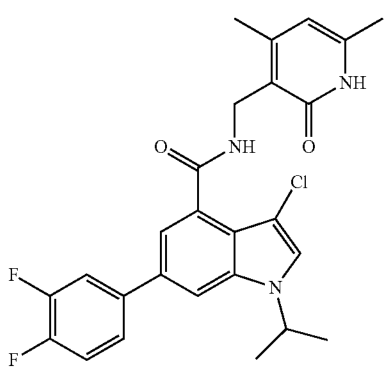 | 3-chloro-6-(3,4-difluorophenyl)-N-((4,6-dimethyl-2-oxo-1,2-dihydropyridin-3-yl)methyl)-1-isopropyl-1H-indole-4-carboxamide | 11.46 (s, 1H), 8.17 (t, J = 5.05 Hz, 1H), 7.98 (d, J = 1.52 Hz, 1H), 7.90 (ddd, J = 2.27, 7.83, 12.63 Hz, 1H), 7.78 (s, 1H), 7.59-7.69 (m, 1H), 7.52 (dt, J = 8.59, 10.61 Hz, 1H), 7.32 (d, J = 1.52 Hz, 1H), 5.87 (s, 1H), 4.99 (qd, J = 6.44, 6.61 Hz, 1H), 4.37 (d, J = 5.05 Hz, 2H), 2.24 (s, 3H), 2.11 (s, 3H), 1.46 (d, J = 6.57 Hz, 6H) | 484.0 |

-continued

| Ex | Structure | Name | $^1$H NMR (400 MHz, DMSO-d$_6$) δ ppm | MS(ES) [M + H]$^+$ |
|---|---|---|---|---|
| 159 | 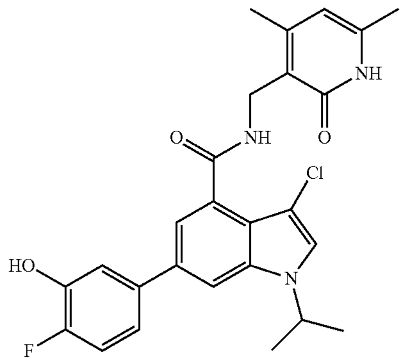 [SMILES: Cc1cc(C)c(CNC(=O)c2cc(-c3ccc(F)c(O)c3)cc3c2c(Cl)cn3C(C)C)c(=O)[nH]1] | 3-chloro-N-((4,6-dimethyl-2-oxo-1,2-dihydropyridin-3-yl)methyl)-6-(4-fluoro-3-hydroxyphenyl)-1-isopropyl-1H-indole-4-carboxamide | 11.46 (br. s., 1H), 9.94 (br. s., 1H), 8.18 (t, J = 5.05 Hz, 1H), 7.82 (d, J = 1.26 Hz, 1H), 7.74 (s, 1H), 7.29 (dd, J = 2.27, 8.59 Hz, 1H), 7.13-7.25 (m, 3H), 5.87 (s, 1H), 4.95 (quin, J = 6.63 Hz, 1H), 4.36 (d, J = 5.05 Hz, 2H), 2.24 (s, 3H), 2.11 (s, 3H), 1.45 (d, J = 6.82 Hz, 6H) | 481.8 |
| 160 | 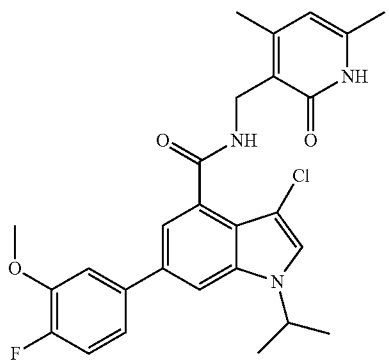 [SMILES: COc1cc(-c2cc(C(=O)NCc3c(C)cc(C)[nH]c3=O)c3c(Cl)cn(C(C)C)c3c2)ccc1F] | 3-chloro-N-((4,6-dimethyl-2-oxo-1,2-dihydropyridin-3-yl)methyl)-6-(4-fluoro-3-methoxyphenyl)-1-isopropyl-1H-indole-4-carboxamide | 11.46 (br. s., 1H), 8.16 (t, J = 5.05 Hz, 1H), 7.90 (s, 1H), 7.76 (s, 1H), 7.46 (d, J = 8.59 Hz, 1H), 7.24-7.34 (m, 3H), 5.87 (s, 1H), 4.98 (ddd, J = 6.44, 6.57, 13.26 Hz, 1H), 4.37 (d, J = 5.05 Hz, 2H), 3.97 (s, 3H), 2.25 (s, 3H), 2.11 (s, 3H), 1.46 (d, J = 6.57 Hz, 6H) | 496.1 |
| 161 | 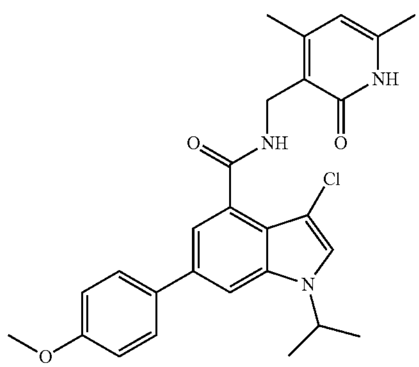 | 3-chloro-N-((4,6-dimethyl-2-oxo-1,2-dihydropyridin-3-yl)methyl)-1-isopropyl-6-(4-methoxyphenyl)-1H-indole-4-carboxamide | 11.48 (br. s., 1H), 8.16 (t, J = 5.05 Hz, 1H), 7.84 (d, J = 1.01 Hz, 1H), 7.64-7.75 (m, 3H), 7.26 (d, J = 1.01 Hz, 1H), 7.03 (d, J = 8.59 Hz, 2H), 5.87 (s, 1H), 4.95 (quin, J = 6.63 Hz, 1H), 4.36 (d, J = 5.05 Hz, 2H), 3.81 (s, 3H), 2.24 (s, 3H), 2.11 (s, 3H), 1.45 (d, J = 6.57 Hz, 6H) | 477.9 |
| 162 | 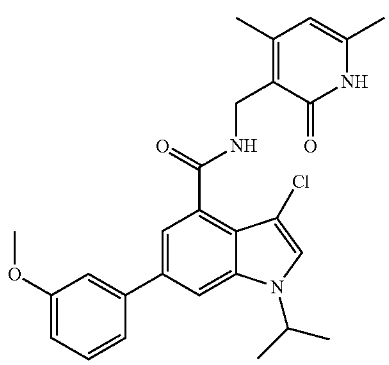 [SMILES: COc1cccc(-c2cc(C(=O)NCc3c(C)cc(C)[nH]c3=O)c3c(Cl)cn(C(C)C)c3c2)c1] | 3-chloro-N-((4,6-dimethyl-2-oxo-1,2-dihydropyridin-3-yl)methyl)-1-isopropyl-6-(3-methoxyphenyl)-1H-indole-4-carboxamide | 11.47 (br. s., 1H), 8.18 (t, J = 5.05 Hz, 1H), 7.91 (d, J = 1.01 Hz, 1H), 7.76 (s, 1H), 7.35-7.42 (m, 1H), 7.25-7.34 (m, 3H), 6.93 (dd, J = 1.77, 8.08 Hz, 1H), 5.87 (s, 1H), 4.99 (dt, J = 6.60, 13.33 Hz, 1H), 4.37 (d, J = 5.05 Hz, 2H), 3.85 (s, 3H), 2.24 (s, 3H), 2.11 (s, 3H), 1.46 (d, J = 6.57 Hz, 6H) | 477.9 |

-continued

| Ex | Structure | Name | ¹H NMR (400 MHz, DMSO-d₆) δ ppm | MS(ES) [M + H]⁺ |
|---|---|---|---|---|
| 163 | 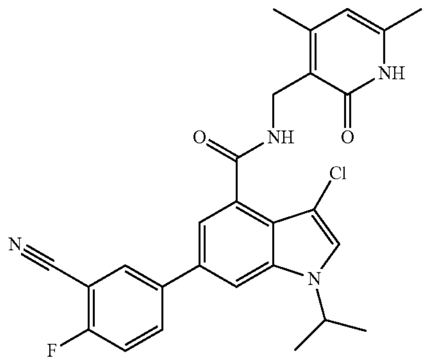 [SMILES: Cc1cc(C)c(CNC(=O)c2cc(-c3ccc(F)c(C#N)c3)cc3c2c(Cl)cn3C(C)C)c(=O)[nH]1] | 3-chloro-6-(3-cyano-4-fluorophenyl)-N-((4,6-dimethyl-2-oxo-1,2-dihydropyridin-3-yl)methyl)-1-isopropyl-1H-indole-4-carboxamide | 11.47 (s, 1H), 8.40 (dd, J = 2.40, 6.19 Hz, 1H), 8.15-8.24 (m, 2H), 8.06 (d, J = 1.52 Hz, 1H), 7.81 (s, 1H), 7.63 (t, J = 9.09 Hz, 1H), 7.38 (d, J = 1.52 Hz, 1H), 5.87 (s, 1H), 4.99 (quin, J = 6.63 Hz, 1H), 4.37 (d, J = 5.05 Hz, 2H), 2.25 (s, 3H), 2.11 (s, 3H), 1.47 (d, J = 6.57 Hz, 6H) | 491.0 |
| 164 | 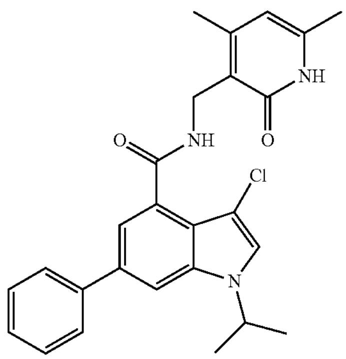 [SMILES: Cc1cc(C)c(CNC(=O)c2cc(-c3ccccc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-phenyl-1H-indole-4-carboxamide | 11.48 (br. s., 1H), 8.19 (t, J = 5.05 Hz, 1H), 7.91 (s, 1H), 7.72-7.80 (m, 3H), 7.47 (t, J = 7.58 Hz, 2H), 7.33-7.39 (m, 1H), 7.30 (d, J = 1.26 Hz, 1H), 5.87 (s, 1H), 4.97 (dt, J = 6.60, 13.33 Hz, 1H), 4.37 (d, J = 4.80 Hz, 2H), 2.24 (s, 3H), 2.11 (s, 3H), 1.46 (d, J = 6.82 Hz, 6H) | 447.8 |
| 165 | 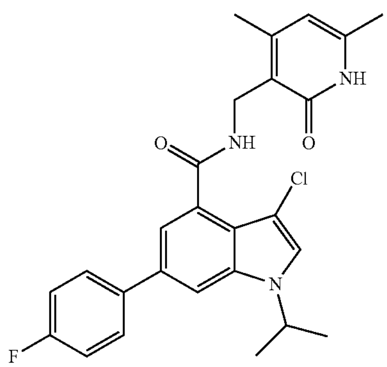 [SMILES: Cc1cc(C)c(CNC(=O)c2cc(-c3ccc(F)cc3)cc3c2c(Cl)cn3C(C)C)c(=O)[nH]1] | 3-chloro-N-((4,6-dimethyl-2-oxo-1,2-dihydropyridin-3-yl)methyl)-6-(4-fluorophenyl)-1-isopropyl-1H-indole-4-carboxamide | 11.47 (s, 1H), 8.18 (t, J = 5.05 Hz, 1H), 7.90 (d, J = 1.26 Hz, 1H), 7.80 (dd, J = 5.31, 8.84 Hz, 2H), 7.76 (s, 1H), 7.26-7.34 (m, 3H), 5.87 (s, 1H), 4.97 (quin, J = 6.57 Hz, 1H), 4.36 (d, J = 5.05 Hz, 2H), 2.24 (s, 3H), 2.11 (s, 3H), 1.45 (d, J = 6.57 Hz, 6H) | 466.0 |
| 166 | 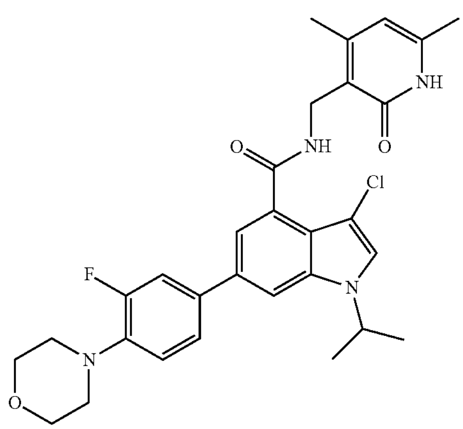 [SMILES: Cc1cc(C)c(CNC(=O)c2cc(-c3ccc(N4CCOCC4)c(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluoro-4-morpholinophenyl)-1-isopropyl-1H-indole-4-carboxamide | 11.48 (br. s., 1H), 8.16 (t, J = 4.93 Hz, 1H), 7.91 (d, J = 1.26 Hz, 1H), 7.74 (s, 1H), 7.63 (dd, J = 2.02, 14.65 Hz, 1H), 7.54 (dd, J = 1.77, 8.34 Hz, 1H), 7.30 (d, J = 1.01 Hz, 1H), 7.11 (t, J = 8.84 Hz, 1H), 5.87 (s, 1H), 4.98 (quin, J = 6.63 Hz, 1H), 4.36 (d, J = 5.05 Hz, 2H), 3.70-3.82 (m, 4H), 2.99-3.12 (m, 4H), 2.24 (s, 3H), 2.11 (s, 3H), 1.45 (d, J = 6.57 Hz, 6H) | 551.2 |

| Ex | Structure | Name | ¹H NMR (400 MHz, DMSO-d₆) δ ppm | MS(ES) [M + H]⁺ |
|---|---|---|---|---|
| 167 | 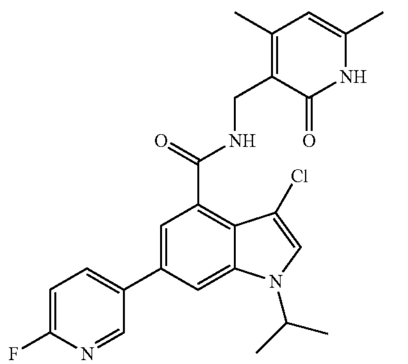 | 3-chloro-N-((4,6-dimethyl-2-oxo-1,2-dihydropyridin-3-yl)methyl)-6-(6-fluoropyridin-3-yl)-1-isopropyl-1H-indole-4-carboxamide | 11.47 (s, 1H), 8.64 (d, J = 2.53 Hz, 1H), 8.39 (td, J = 2.53, 8.21 Hz, 1H), 8.19 (t, J = 4.93 Hz, 1H), 8.03 (d, J = 1.52 Hz, 1H), 7.80 (s, 1H), 7.34 (d, J = 1.52 Hz, 1H), 7.30 (dd, J = 2.78, 8.59 Hz, 1H), 5.87 (s, 1H), 4.98 (ddd, J = 6.69, 6.82, 13.26 Hz, 1H), 4.37 (d, J = 5.05 Hz, 2H), 2.25 (s, 3H), 2.11 (s, 3H), 1.46 (d, J = 6.82 Hz, 6H) | 467.3 |
| 168 | 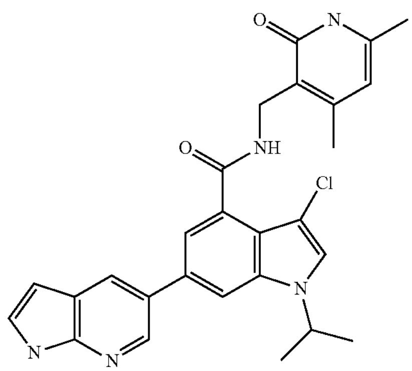 [SMILES: Cc1cc(C)c(CNC(=O)c2cc(-c3cnc4[nH]ccc4c3)cc3c2c(Cl)cn3C(C)C)c(=O)[nH]1] | 3-chloro-N-[(4,6-dimethyl-2-oxo-1,2-dihydro-3-pyridinyl)methyl]-1-(1-methylethyl)-6-(1H-pyrrolo[2,3-b]pyridin-5-yl)-1H-indole-4-carboxamide | 11.70 (br. s., 1 H) 11.42 (br. s., 1 H) 8.61 (d, J = 2.02 Hz, 1 H) 8.30 (d, J = 2.27 Hz, 1 H) 8.20 (t, J = 5.05 Hz, 1 H) 7.96 (d, J = 1.26 Hz, 1 H) 7.74 (s, 1 H) 7.52 (d, J = 3.54 Hz, 1 H) 7.35 (d, J = 1.26 Hz, 1 H) 6.51 (d, J = 3.54 Hz, 1 H) 5.87 (s, 1 H) 5.00 (quin, J = 6.63 Hz, 1 H) 4.38 (s, 1 H) 4.37 (s, 1 H) 2.25 (s, 3 H) 2.11 (s, 3 H) 1.48 (s, 3 H) 1.46 (s, 3 H) | 488.0 |
| 169 | 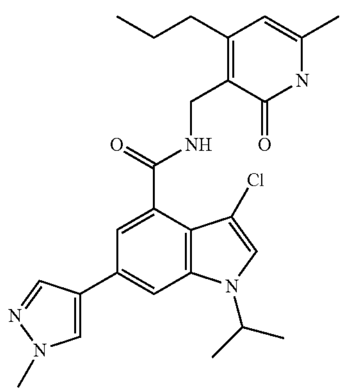 [SMILES: CCCc1cc(C)[nH]c(=O)c1CNC(=O)c1cc(-c2cnn(C)c2)cc2c1c(Cl)cn2C(C)C] | 3-chloro-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide | 11.47 (s, 1 H) 8.19 (s, 1 H) 8.02 (t, J = 5.05 Hz, 1 H) 7.92 (s, 1 H) 7.81-7.84 (m, 1 H) 7.66 (s, 1 H) 7.21 (d, J = 1.26 Hz, 1 H) 5.90 (s, 1 H) 4.87 (quin, J = 6.63 Hz, 1 H) 4.37 (s, 1 H) 4.36 (s, 1 H) 3.87 (s, 3 H) 2.53-2.58 (m, 2 H) 2.12 (s, 3 H) 1.53-1.61 (m, 2 H) 1.45 (s, 3 H) 1.44 (s, 3 H) 0.95 (t, J = 7.33 Hz, 3 H) | 479.8/ 481.9 |
| 170 | 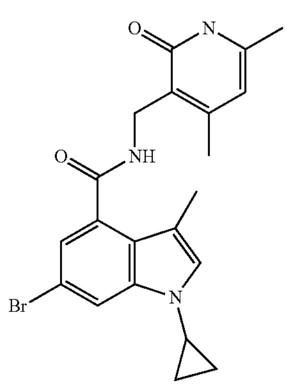 [SMILES: Cc1cc(C)c(CNC(=O)c2cc(Br)cc3c2c(C)cn3C2CC2)c(=O)[nH]1] | 6-bromo-1-cyclopropyl-N-[(4,6-dimethyl-2-oxo-1,2-dihydro-3-pyridinyl)methyl]-3-methyl-1H-indole-4-carboxamide | 11.48 (s, 1 H) 8.27 (t, J = 4.93 Hz, 1 H) 7.71 (d, J = 1.77 Hz, 1 H) 7.15 (s, 1 H) 7.06 (d, J = 1.52 Hz, 1 H) 5.86 (s, 1 H) 4.31 (s, 1 H) 4.29 (s, 1 H) 3.36-3.41 (m, 1 H) 2.21 (s, 3 H) 2.11 (s, 3 H) 2.10 (s, 3 H) 1.01-1.07 (m, 2 H) 0.86-0.91 (m, 2 H) | 427.7/ 429.9 |

-continued

| Ex | Structure | Name | $^1$H NMR (400 MHz, DMSO-d$_6$) δ ppm | MS(ES) [M + H]$^+$ |
|---|---|---|---|---|
| 171 | 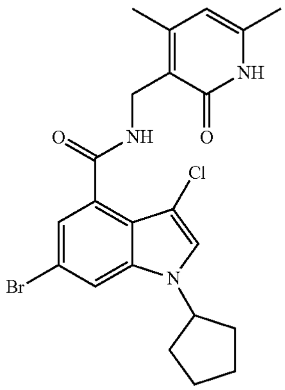 [SMILES: Cc1cc(C)c(CNC(=O)c2cc(Br)cc3c2c(Cl)cn3C2CCCC2)c(=O)[nH]1] | 6-bromo-3-chloro-1-cyclopentyl-N-((4,6-dimethyl-2-oxo-1,2-dihydropyridin-3-methyl)-1H-indole-4-carboxamide | 1.62-1.90 (m, 6 H), 2.08-2.15 (m, 5 H), 2.22 (s, 3 H), 2.22 (s, 3 H), 4.32 (d, J = 4.80 Hz, 2 H), 4.87-5.04 (m, 1 H), 5.86 (s, 1 H), 7.08 (m, 1 H), 7.72 (m, 1 H), 7.93 (d, J = 1.52 Hz, 1 H), 8.25 (t, J = 4.93 Hz, 1 H), 11.47 (br. s., 1 H) | 475.7 |
| 172 | 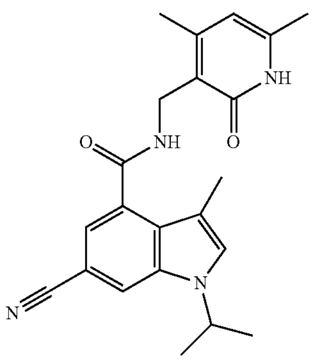 [SMILES: Cc1cc(C)c(CNC(=O)c2cc(C#N)cc3c2c(C)cn3C(C)C)c(=O)[nH]1] | 6-cyano-N-((4,6-dimethyl-2-oxo-1,2-dihydropyridin-3-yl)methyl)-1-isopropyl-3-methyl-1H-indole-4-carboxamide | 1.39-1.47 (m, 6 H), 2.12 (s, 3 H), 2.16 (s, 3 H), 2.22-2.26 (m, 3 H), 4.32 (d, J = 5.05 Hz, 2 H), 4.85 (quin, J = 6.63 Hz, 1 H), 5.87 (s, 1 H), 7.21 (d, J = 1.26 Hz, 1 H), 7.64 (s, 1 H), 8.16 (d, J = 1.26 Hz, 1 H), 8.33 (t, J = 5.05 Hz, 1 H), 11.48 (br. s., 1 H) | 377.2 |
| 173 | 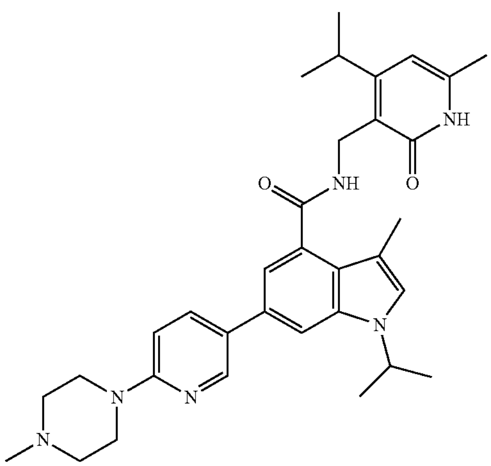 | 3-methyl-1-(1-methylethyl)-N-{[6-methyl-4-(1-methylethyl)-2-oxo-1,2-dihydro-3-pyridinyl]methyl}-6-[6-(4-methyl-1-piperazinyl)-3-pyridinyl]-1H-indole-4-carboxamide | 11.44 (br. s., 1 H) 8.50 (d, J = 2.27 Hz, 1 H) 8.18 (t, J = 4.80 Hz, 1 H) 7.92 (dd, J = 8.84, 2.53 Hz, 1 H) 7.72 (d, J = 1.26 Hz, 1 H) 7.29 (s, 1 H) 7.18 (d, J = 1.26 Hz, 1 H) 6.92 (d, J = 9.09 Hz, 1 H) 6.01 (s, 1 H) 4.84 (quin, J = 6.63 Hz, 1 H) 4.41 (br. s., 1 H) 4.40 (br. s., 1 H) 3.48-3.56 (m, 4 H) 3.24-3.31 (m, 1 H) 2.39-2.44 (m, 4 H) 2.23 (s, 3 H) 2.17 (s, 3 H) 2.14 (s, 3 H) 1.44 (s, 3 H) 1.42 (s, 3 H) 1.15 (s, 3 H) 1.13 (s, 3 H) | 555.4 |
| 174 | 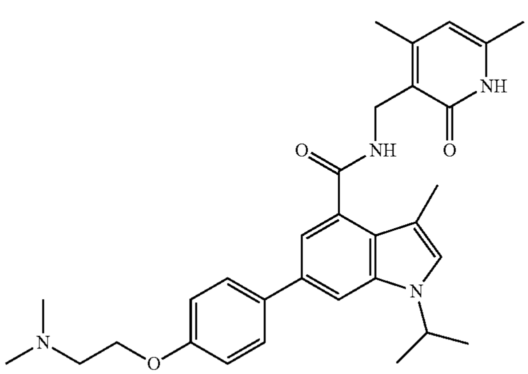 | 6-(4-{[2-(dimethylamino)ethyl]oxy}phenyl)-N-[(4,6-dimethyl-2-oxo-1,2-dihydro-3-pyridinyl)methyl]-3-methyl-1-(1-methylethyl)-1H-indole-4-carboxamide | 11.43 (br. s., 1 H) 8.09-8.27 (m, 1 H) 7.70 (d, J = 1.52 Hz, 1 H) 7.66-7.68 (m, 1 H) 7.63-7.66 (m, 1 H) 7.29 (d, J = 1.01 Hz, 1 H) 7.19 (d, J = 1.52 Hz, 1 H) 7.02-7.04 (m, 1 H) 7.00-7.02 (m, 1 H) 5.87 (s, 1 H) 4.85 (dt, J = 13.39, 6.69 Hz, 1 H) 4.36 (s, 1 H) 4.34 (s, 1 H) 4.09 (t, J = 5.81 Hz, 2 H) 2.61-2.67 (m, 2 H) 2.23 (s, 9 H) 2.17 (s, 3 H) 2.11 (s, 3 H) 1.44 (s, 3 H) 1.42 (s, 3 H) | 515.1 |

-continued

| Ex | Structure | Name | ¹H NMR (400 MHz, DMSO-d₆) δ ppm | MS(ES) [M + H]⁺ |
|---|---|---|---|---|
| 175 | 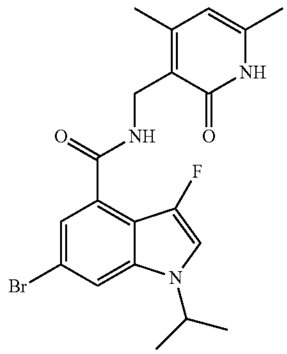 [SMILES: Cc1cc(C)c(CNC(=O)c2cc(Br)cc3c2c(F)cn3C(C)C)c(=O)[nH]1] | 6-bromo-N-[(4,6-dimethyl-2-oxo-1,2-dihydro-3-pyridinyl)methyl]-3-fluoro-1-(1-methylethyl)-1H-indole-4-carboxamide | 1H NMR (400 MHz, METHANOL-d4) δ 7.81 (t, J = 1.77 Hz, 1H), 7.40 (d, J = 1.52 Hz, 1H), 7.38 (d, J = 2.27 Hz, 1H), 6.13 (s, 1H), 4.71-4.81 (m, J = 1.52, 6.63, 6.63, 13.26 Hz, 1H), 4.54 (s, 2H), 2.40 (s, 3H), 2.26 (s, 3H), 1.47 (d, J = 6.82 Hz, 6H) | 434.1 |
| 176 | 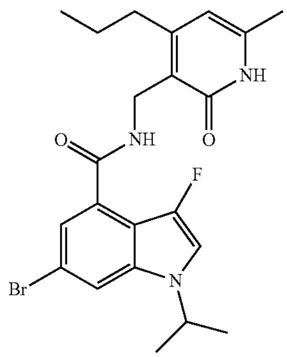 [SMILES: CCCc1cc(C)[nH]c(=O)c1CNC(=O)c1cc(Br)cc2c1c(F)cn2C(C)C] | 6-bromo-3-fluoro-1-(1-methylethyl)-N-[(6-methyl-2-oxo-4-propyl-1,2-dihydro-3-pyridinyl)methyl]-1H-indole-4-carboxamide | 11.49 (s, 1H), 8.20-8.28 (m, 1H), 7.94 (t, J = 1.77 Hz, 1H), 7.66 (d, J = 2.27 Hz, 1H), 7.24 (d, J = 1.52 Hz, 1H), 5.90 (s, 1H), 4.82 (dd, J = 1.52, 6.82 Hz, 1H), 4.33 (d, J = 5.05 Hz, 2H), 2.13 (s, 3H), 1.48-1.59 (m, 2H), 1.39 (d, J = 6.57 Hz, 6H), 0.92 (t, 3H) | 462.2 |
| 177 | 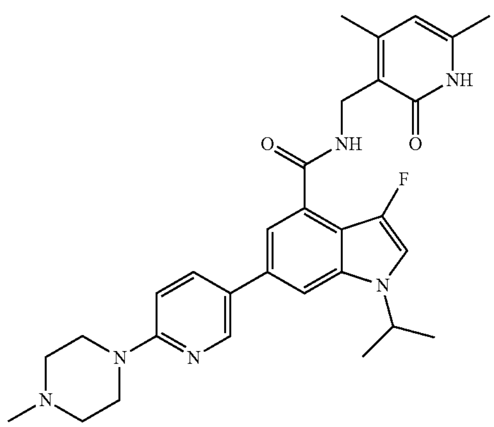 | N-[(4,6-dimethyl-2-oxo-1,2-dihydro-3-pyridinyl)methyl]-3-fluoro-1-(1-methylethyl)-6-[6-(4-methyl-1-piperazinyl)-3-pyridinyl]-1H-indole-4-carboxamide | 11.48 (d, J = 11.87 Hz, 1H), 8.54 (d, J = 2.53 Hz, 1H), 8.19 (t, J = 5.05 Hz, 1H), 8.16 (s, 1H), 7.96 (dd, J = 2.53, 8.84 Hz, 1H), 7.86 (s, 1H), 7.58 (d, J = 2.27 Hz, 1H), 7.43 (d, J = 1.01 Hz, 1H), 6.94 (d, J = 8.84 Hz, 1H), 5.88 (s, 1H), 4.86-5.03 (m, J = 7.07 Hz, 1H), 4.36 (d, J = 4.80 Hz, 2H), 3.48-3.59 (m, 4H), 2.44 (t, J = 4.93 Hz, 4H), 2.23 (d, J = 10.36 Hz, 6H), 2.12 (s, 3H), 1.42 (d, 6H) | 531.4 |
| 178 | 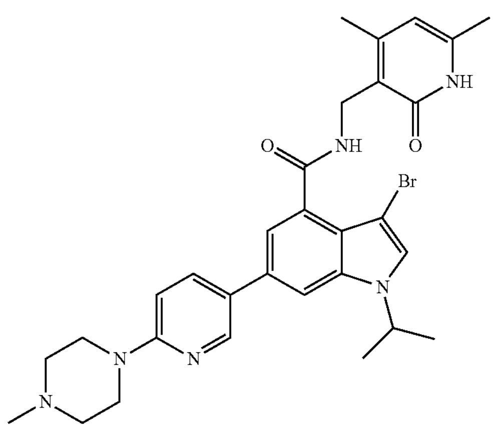 | 3-bromo-N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide | 1H NMR (400 MHz, METHANOL-d4) δ 8.49 (d, J = 2.27 Hz, 1H), 7.97 (dd, J = 2.53, 8.84 Hz, 1H), 7.77 (d, J = 1.26 Hz, 1H), 7.55 (s, 1H), 7.37 (d, J = 1.26 Hz, 1H), 6.99 (d, J = 8.84 Hz, 1H), 6.14 (s, 1H), 4.60 (s, 2H), 3.74 (br. s., 4H), 2.96 (t, J = 4.55 Hz, 4H), 2.65 (s, 3H), 2.47 (s, 3H), 2.26 (s, 3H), 1.54 (d, J = 6.57 Hz, 6H) | 592.2 |

| Ex | Structure | Name | ¹H NMR (400 MHz, DMSO-d$_6$) δ ppm | MS(ES) [M + H]⁺ |
|---|---|---|---|---|
| 179 | 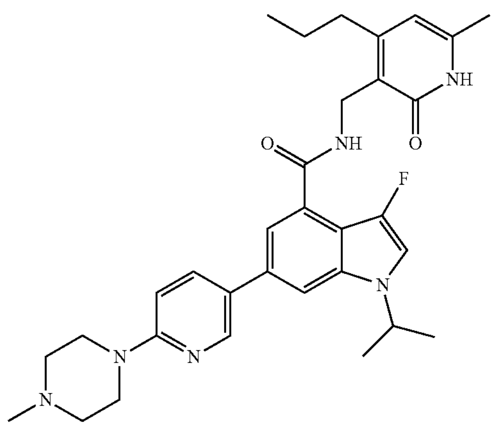 | 3-fluoro-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.50 (br. s., 1H), 8.53 (d, J = 2.53 Hz, 1H), 8.12-8.21 (m, 1H), 7.95 (dd, J = 2.53, 8.84 Hz, 1H), 7.86 (s, 1H), 7.59 (d, J = 2.27 Hz, 1H), 7.43 (d, J = 1.26 Hz, 1H), 6.94 (d, J = 8.84 Hz, 1H), 5.90 (s, 1H), 4.86-5.03 (m, 1H), 4.37 (d, J = 5.05 Hz, 2H), 3.49-3.58 (m, 4H), 2.37-2.47 (m, 4H), 2.24 (s, 3H), 2.13 (s, 3H), 1.55 (sxt, J = 7.53 Hz, 2H), 1.42 (d, J = 6.57 Hz, 6H), 0.92 (t, J = 7.33 Hz, 3H) | 559.7 |
| 180 | 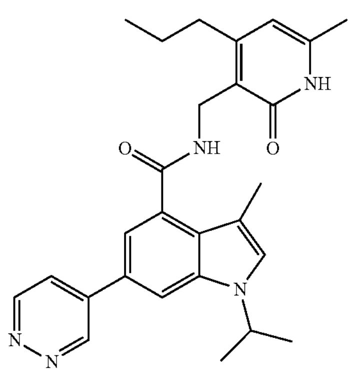 [SMILES: CCCc1cc(C)[nH]c(=O)c1CNC(=O)c1cc(-c2ccnnc2)cc2c1c(C)cn2C(C)C] | 3-methyl-1-(1-methylethyl)-N-[(6-methyl-2-oxo-4-propyl-1,2-dihydro-3-pyridinyl)methyl]-6-(4-pyridazinyl)-1H-indole-4-carboxamide | 11.00-11.70 (bs, 1H), 9.70-9.79 (m, 1H), 9.16-9.27 (m, 1H), 8.25 (t, J = 4.80 Hz, 1H), 8.19 (d, J = 1.52 Hz, 1H), 8.08 (dd, J = 2.53, 5.56 Hz, 1H), 7.48 (s, 2H), 5.91 (s, 1H), 4.96 (quin, J = 6.63 Hz, 1H), 4.38 (d, J = 4.80 Hz, 2H), 2.53-2.59 (m, 2H), 2.19 (s, 3H), 2.12 (s, 3H), 1.58 (sxt, J = 7.43 Hz, 2H), 1.46 (d, J = 6.82 Hz, 6H), 0.94 (t, J = 7.45 Hz, 3H) | 458.3 |
| 181 | 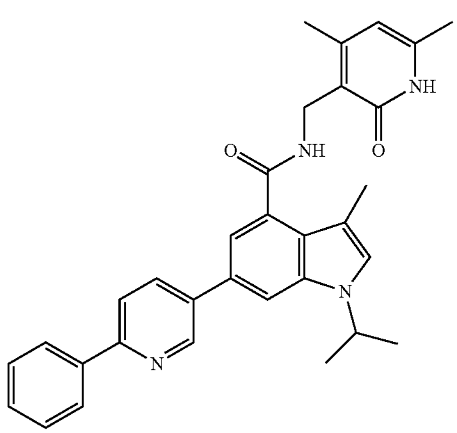 [SMILES: Cc1cc(C)c(CNC(=O)c2cc(-c3ccc(-c4ccccc4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(6-phenyl-3-pyridinyl)-1H-indole-4-carboxamide | 11.52 (br. s., 1 H) 9.10 (d, J = 2.27 Hz, 1 H) 8.31 (dd, J = 8.21, 2.15 Hz, 1 H) 8.25 (t, J = 5.05 Hz, 1 H) 8.16 (d, J = 7.33 Hz, 2 H) 8.09 (d, J = 8.34 Hz, 1 H) 7.98 (d, J = 1.26 Hz, 1 H) 7.51-7.56 (m, 2 H) 7.45-7.49 (m, 1 H) 7.37-7.40 (m, 2 H) 5.89 (s, 1 H) 4.89-4.96 (m, 1 H) 4.37 (d, J = 5.05 Hz, 2 H) 2.26 (s, 3 H) 2.19 (s, 3 H) 2.12 (s, 3 H) 1.46 (d, J = 6.57 Hz, 6 H) | |

| Ex | Structure | Name | ¹H NMR (400 MHz, DMSO-d₆) δ ppm | MS(ES) [M + H]⁺ |
|---|---|---|---|---|
| 182 | 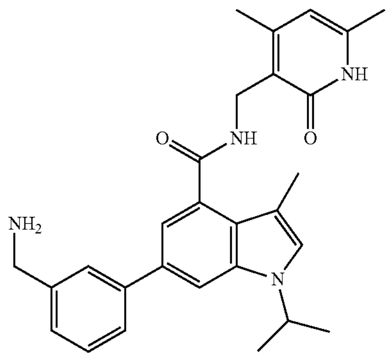 [SMILES: Cc1cc(C)c(CNC(=O)c2cc(-c3cccc(CN)c3)cc3c2c(C)cn3C(C)C)c(=O)[nH]1] | 6-[3-(aminomethyl)phenyl]-N-[(4,6-dimethyl-2-oxo-1,2-dihydro-3-pyridinyl)methyl]-3-methyl-1-(1-methylethyl)-1H-indole-4-carboxamide | 8.17 (br. s., 1 H) 7.78 (br. s., 2 H) 7.65 (br. s., 1 H) 7.43 (t, J = 7.83 Hz, 1 H) 7.33 (br. s., 2 H) 7.20-7.31 (m, 1 H) 5.87 (s, 1 H) 4.85 (d, J = 6.57 Hz, 1 H) 4.36 (br. s., 1 H) 4.35 (br. s., 1 H) 3.92 (s, 1 H) 2.24 (s, 3 H) 2.17 (s, 3 H) 2.11 (s, 3 H) 1.45 (br. s., 3 H) 1.44 (br. s., 3 H) | 457.3 |
| 183 | 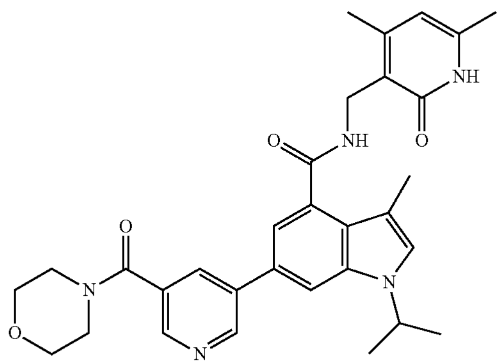 [SMILES: Cc1cc(C)c(CNC(=O)c2cc(-c3cncc(C(=O)N4CCOCC4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[5-(4-morpholinylcarbonyl)-3-pyridinyl]-1H-indole-4-carboxamide | 11.48 (s, 1 H) 9.07 (d, J = 2.27 Hz, 1 H) 8.56 (d, J = 1.77 Hz, 1 H) 8.18-8.25 (m, 2 H) 7.96 (d, J = 1.26 Hz, 1 H) 7.39 (s, 1 H) 7.34 (d, J = 1.52 Hz, 1 H) 5.87 (s, 1 H) 4.92 (quin, J = 6.63 Hz, 1 H) 4.36 (d, J = 5.05 Hz, 2 H) 3.69 (br. s., 4 H) 3.54-3.62 (m, 2 H) 3.43 (br. s., 2 H) 2.25 (s, 3 H) 2.18 (s, 3 H) 2.11 (s, 3 H) 1.44 (d, J = 6.57 Hz, 6 H) | 542.4 |
| 184 | 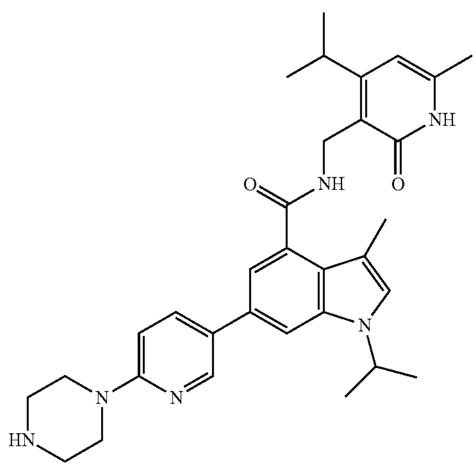 [SMILES: Cc1cc(C(C)C)c(CNC(=O)c2cc(-c3ccc(N4CCNCC4)nc3)cc3c2c(C)cn3C(C)C)c(=O)[nH]1] | 3-methyl-1-(1-methylethyl)-N-{[6-methyl-4-(1-methylethyl)-2-oxo-1,2-dihydro-3-pyridinyl]methyl}-6-[6-(1-piperazinyl)-3-pyridinyl]-1H-indole-4-carboxamide | 11.49 (br. s., 1 H) 8.49 (d, J = 2.27 Hz, 1 H) 8.18 (t, J = 4.67 Hz, 1 H) 7.90 (dd, J = 8.84, 2.27 Hz, 1 H) 7.72 (s, 1 H) 7.29 (s, 1 H) 7.18 (s, 1 H) 6.88 (d, J = 8.84 Hz, 1 H) 6.01 (s, 1 H) 4.79-4.90 (m, 1 H) 4.41 (br. s., 1 H) 4.40 (br. s., 1 H) 3.41-3.57 (m, 4 H) 3.22-3.30 (m, 1 H) 2.62-2.90 (m, 4 H) 2.55 (s, 1 H) 2.17 (s, 3 H) 2.14 (s, 3 H) 1.43 (s, 3 H) 1.42 (s, 3 H) 1.15 (s, 3 H) 1.13 (s, 3 H) | 541.3 |
| 185 | 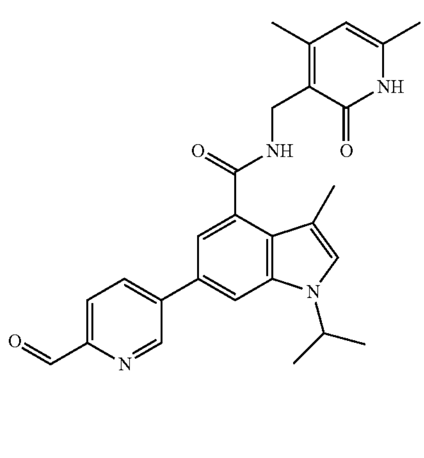 [SMILES: Cc1cc(C)c(CNC(=O)c2cc(-c3ccc(C=O)nc3)cc3c2c(C)cn3C(C)C)c(=O)[nH]1] | N-[(4,6-dimethyl-2-oxo-1,2-dihydro-3-pyridinyl)methyl]-6-(6-formyl-3-pyridinyl)-3-methyl-1-(1-methylethyl)-1H-indole-4-carboxamide | 11.50 (br. s., 1 H) 10.04 (s, 1 H) 9.27 (d, J = 1.52 Hz, 1 H) 8.44 (dd, J = 8.08, 1.77 Hz, 1 H) 8.27 (t, J = 5.05 Hz, 1 H) 8.07 (d, J = 1.26 Hz, 1 H) 8.01 (d, J = 8.08 Hz, 1 H) 7.42-7.45 (m, 2 H) 5.88 (s, 1 H) 4.89-4.99 (m, 1 H) 4.37 (d, J = 5.05 Hz, 2 H) 2.25 (s, 3 H) 2.18 (s, 3 H) 2.11 (s, 3 H) 1.45 (d, J = 6.57 Hz, 6 H) | 457.2 |

| Ex | Structure | Name | ¹H NMR (400 MHz, DMSO-d₆) δ ppm | MS(ES) [M + H]⁺ |
|---|---|---|---|---|
| 186 | 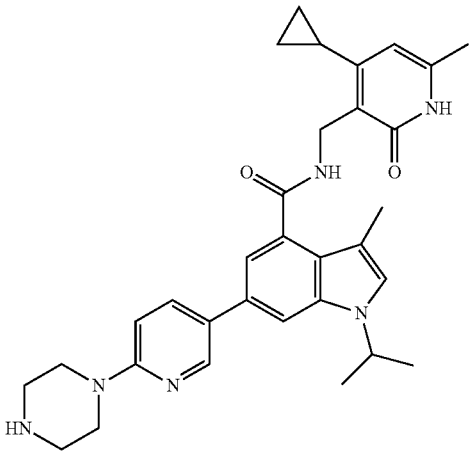 [SMILES: Cc1cc(C2CC2)c(CNC(=O)c2cc(-c3ccc(N4CCNCC4)nc3)cc3c2c(C)cn3C(C)C)c(=O)[nH]1] | N-[(4-cyclopropyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide | 11.42 (br. s., 1 H) 8.50 (d, J = 2.02 Hz, 1 H) 8.23 (t, J = 4.93 Hz, 1 H) 7.91 (dd, J = 8.84, 2.53 Hz, 1 H) 7.72 (s, 1 H) 7.29 (s, 1 H) 7.20 (s, 1 H) 6.88 (d, J = 9.09 Hz, 1 H) 5.49 (s, 1 H) 4.79-4.89 (m, 1 H) 4.54 (br. s., 1 H) 4.53 (br. s., 1 H) 3.42-3.50 (m, 4 H) 2.74-2.88 (m, 4 H) 2.15-2.23 (m, 4 H) 2.09 (s, 3 H) 1.44 (s, 3 H) 1.42 (s, 3 H) 0.94-1.01 (m, 2 H) 0.76 (d, J = 3.54 Hz, 2 H) | 539.3 |
| 187 | 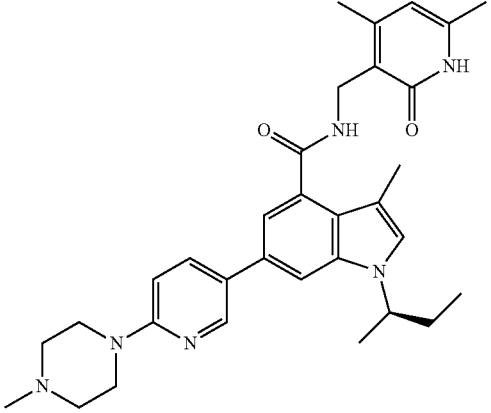 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.73 (d, J = 1.26 Hz, 1 H) 7.26 (s, 1 H) 7.17 (d, J = 1.52 Hz, 1 H) 6.92 (d, J = 9.09 Hz, 1 H) 5.87 (s, 1 H) 4.56-4.65 (m, 1 H) 4.36 (s, 1 H) 4.34 (s, 1 H) 3.49-3.55 (m, 4 H) 2.40-2.44 (m, 4 H) 2.24 (s, 3 H) 2.23 (s, 3 H) 2.16 (s, 3 H) 2.11 (s, 3 H) 1.76-1.87 (m, 2 H) 1.41 (d, J = 6.57 Hz, 3 H) 0.73 (t, J = 7.33 Hz, 3 H) | 541.6 |
| 188 | 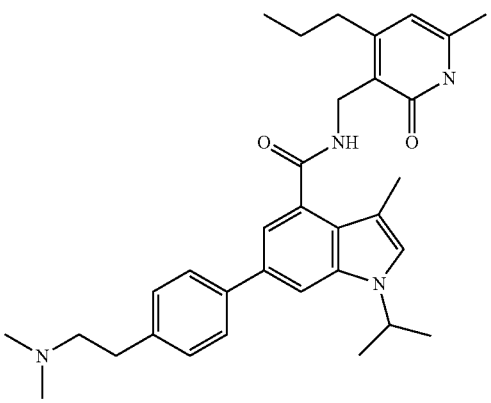 | 6-(4-(2-(dimethylamino)ethyl)phenyl)-1-isopropyl-3-methyl-N-((6-methyl-2-oxo-4-propyl-1,2-dihydropyridin-3-yl)methyl)-1H-indole-4-carboxamide | 11.50 (br. s., 1 H) 8.15 (t, J = 4.93 Hz, 1 H) 7.73-7.76 (m, 1 H) 7.61-7.66 (m, 2 H) 7.31 (d, J = 2.78 Hz, 2 H) 7.29 (s, 1 H) 7.22 (d, J = 1.26 Hz, 1 H) 5.90 (s, 1 H) 4.86 (quin, J = 6.63 Hz, 1 H) 4.37 (s, 1 H) 4.36 (br. s., 1 H) 2.72-2.78 (m, 2 H) 2.55 (d, J = 7.33 Hz, 2 H) 2.47 (d, J = 7.07 Hz, 2 H) 2.14-2.23 (m, 9 H) 2.12 (s, 3 H) 1.53-1.62 (m, 2 H) 1.44 (s, 3 H) 1.43 (s, 3 H) 0.94 (t, J = 7.45 Hz, 3 H) | 527.1 |

-continued

| Ex | Structure | Name | ¹H NMR (400 MHz, DMSO-d₆) δ ppm | MS(ES) [M + H]⁺ |
|---|---|---|---|---|
| 189 | 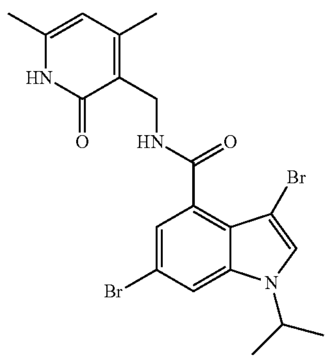 [SMILES: Cc1cc(C)c(CNC(=O)c2cc(Br)cc3c2c(Br)cn3C(C)C)c(=O)[nH]1] | 3,6-dibromo-N-[(4,6-dimethyl-2-oxo-1,2-dihydro-3-pyridinyl)methyl]-1-(1-methylethyl)-1H-indole-4-carboxamide | 1H NMR (400 MHz, METHANOL-d4) δ 7.81 (d, J = 1.52 Hz, 1H), 7.54 (s, 1H), 7.23 (d, J = 1.52 Hz, 1H), 6.12 (s, 1H), 4.77 (quin, J = 6.69 Hz, 1H), 4.55 (s, 2H), 2.44 (s, 3H), 2.25 (s, 3H), 1.50 (d, J = 6.57 Hz, 6H) | 495.8 |
| 190 | 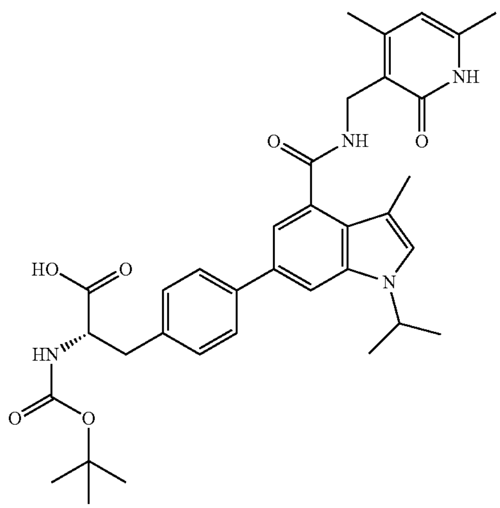 [SMILES: Cc1cc(C)c(CNC(=O)c2cc(-c3ccc(C[C@H](NC(=O)OC(C)(C)C)C(=O)O)cc3)cc3c2c(C)cn3C(C)C)c(=O)[nH]1] | N-{[(1,1-dimethylethyl)oxy]carbonyl}-4-[4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine | 12.61 (br. s., 1 H) 11.49 (br. s., 1 H) 8.18 (t, J = 5.05 Hz, 1 H) 7.75 (s, 1 H) 7.65 (d, J = 8.34 Hz, 2 H) 7.34 (s, 1 H) 7.32 (s, 2 H) 7.23 (s, 1 H) 7.15 (s, 1 H) 5.87 (s, 1 H) 4.82-4.90 (m, 1 H) 4.35 (d, J = 5.31 Hz, 2 H) 4.12-4.08 (m, 1 H) 3.08-2.88 (m, 2 H) 2.24 (s, 3 H) 2.17 (s, 3 H) 2.11 (s, 3 H) 1.43 (d, J = 6.57 Hz, 6H | 615.4 |
| 191 | 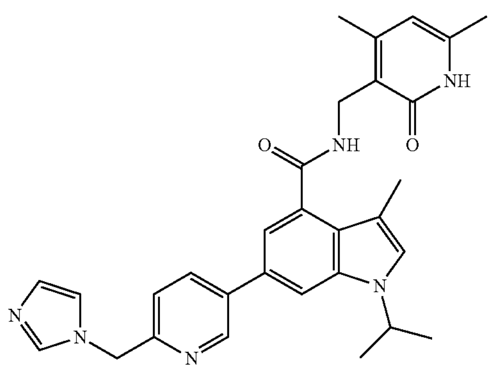 [SMILES: Cc1cc(C)c(CNC(=O)c2cc(-c3ccc(Cn4ccnc4)nc3)cc3c2c(C)cn3C(C)C)c(=O)[nH]1] | N-[(4,6-dimethyl-2-oxo-1,2-dihydro-3-pyridinyl)methyl]-6-[6-(1H-imidazol-1-ylmethyl)-3-pyridinyl]-3-methyl-1-(1-methylethyl)-1H-indole-4-carboxamide | 9.31 (br. s., 1 H) 9.04 (br. s., 1 H) 8.39 (d, J = 2.53 Hz, 1 H) 7.97 (br. s., 1 H) 7.70-7.86 (m, 3 H) 7.39 (br. s., 2 H) 6.25 (br. s., 1 H) 5.68 (br. s., 2 H) 4.80-4.95 (m, 1 H) 4.42 (br. s., 2 H) 2.34 (br. s., 3 H) 2.22 (br. s., 3 H) 2.15 (br. s., 3 H) 1.44 (br. s., 6 H); spiked with d-TFA | 509.6 |

-continued

| Ex | Structure | Name | ¹H NMR (400 MHz, DMSO-d₆) δ ppm | MS(ES) [M + H]⁺ |
|---|---|---|---|---|
| 192 | 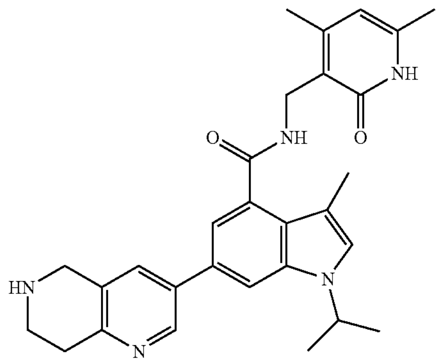 [SMILES: Cc1cc(C)c(CNC(=O)c2cc(-c3cnc4c(c3)CNCC4)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(5,6,7,8-tetrahydro-1,6-naphthyridin-3-yl)-1H-indole-4-carboxamide | 11.49 (br. s., 1 H) 8.71 (d, J = 2.02 Hz, 1 H) 8.19 (t, J = 5.05 Hz, 1 H) 7.82 (dd, J = 11.49, 1.64 Hz, 2 H) 7.34 (s, 1 H) 7.26 (d, J = 1.52 Hz, 1 H) 5.87 (s, 1 H) 4.88 (quin, J = 6.63 Hz, 1 H) 4.36 (d, J = 5.05 Hz, 2 H) 3.94 (s, 2 H) 3.05 (t, J = 5.81 Hz, 2 H) 2.75-2.86 (m, 2 H) 2.24 (s, 3 H) 2.17 (s, 3 H) 2.11 (s, 3 H) 1.43 (d, J = 6.57 Hz, 6 H) | 484.3 |
| 193 | 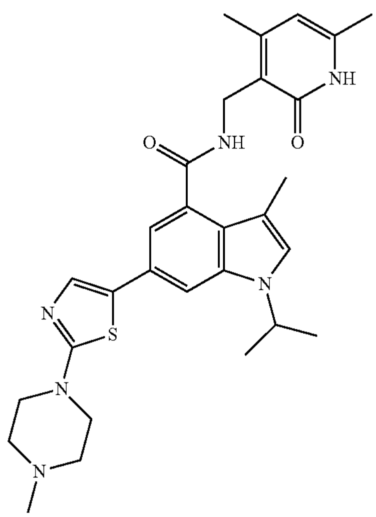 [SMILES: Cc1cc(C)c(CNC(=O)c2cc(-c3cnc(N4CCN(C)CC4)s3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[2-(4-methyl-1-piperazinyl)-1,3-thiazol-5-yl]-1H-indole-4-carboxamide | 11.47 (s, 1 H) 8.15 (t, J = 5.05 Hz, 1 H) 7.57 (s, 1 H) 7.56 (d, J = 1.26 Hz, 1 H) 7.28 (d, J = 1.01 Hz, 1 H) 7.05 (d, J = 1.26 Hz, 1 H) 5.87 (s, 1 H) 4.77 (quin, J = 6.63 Hz, 1 H) 4.34 (s, 1 H) 4.33 (s, 1 H) 3.41-3.47 (m, 4 H) 2.41-2.47 (m, 4 H) 2.23 (s, 6 H) 2.13 (s, 3 H) 2.11 (s, 3 H) 1.42 (s, 3 H) 1.40 (s, 3 H) | 533.6 |
| 194 | 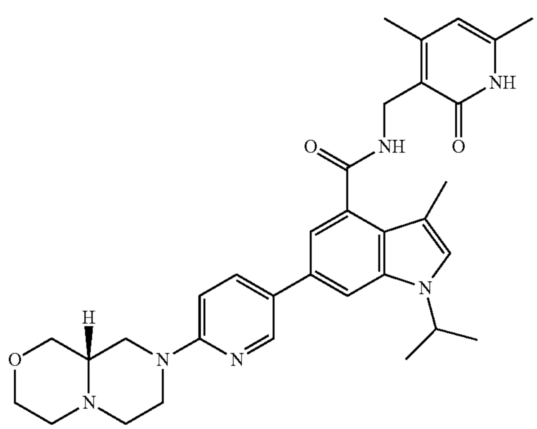 [SMILES: Cc1cc(C)c(CNC(=O)c2cc(-c3ccc(N4CCN5CCOC[C@@H]5C4)nc3)cc3c2c(C)cn3C(C)C)c(=O)[nH]1] | N-[(4,6-dimethyl-2-oxo-1,2-dihydro-3-pyridinyl)methyl]-6-{6-[(9aS)-hexahydropyrazino[2,1-c][1,4]oxazin-8(1H)-yl]-3-pyridinyl}-3-methyl-1-(1-methylethyl)-1H-indole-4-carboxamide | 11.44 (br. s., 1 H) 8.50 (d, J = 2.53 Hz, 1 H) 8.16 (t, J = 5.05 Hz, 1 H) 7.94 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.93 (d, J = 8.84 Hz, 1 H) 5.87 (s, 1 H) 4.84 (quin, J = 6.63 Hz, 1 H) 4.35 (s, 1 H) 4.34 (s, 1 H) 4.24 (d, J = 12.63 Hz, 1 H) 4.14 (d, J = 11.62 Hz, 1 H) 3.78-3.82 (m, 1 H) 3.77 (br. s., 1 H) 3.56 (td, J = 11.37, 2.27 Hz, 1 H) 3.19 (t, J = 10.48 Hz, 1 H) 2.80-2.95 (m, 2 H) 2.69 (d, J = 11.87 Hz, 1 H) 2.39-2.46 (m, 1 H) 2.14-2.27 (m, 9 H) 2.11 (s, 3 H) 1.43 (s, 3 H) 1.42 (s, 3 H) | 569.5 |

| Ex | Structure | Name | ¹H NMR (400 MHz, DMSO-d₆) δ ppm | MS(ES) [M + H]⁺ |
|---|---|---|---|---|
| 195 | 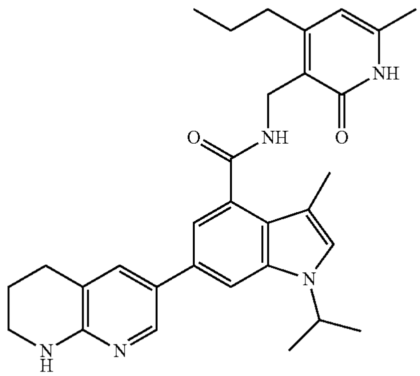 [SMILES: CCCc1cc(C)[nH]c(=O)c1CNC(=O)c1cc(-c2cnc3c(c2)CCCN3)cc2c1c(C)cn2C(C)C] | 3-methyl-1-(1-methylethyl)-N-[(6-methyl-2-oxo-4-propyl-1,2-dihydro-3-pyridinyl)methyl]-6-(5,6,7,8-tetrahydro-1,8-naphthyridin-3-yl)-1H-indole-4-carboxamide | 11.49 (s, 1 H) 8.14 (d, J = 2.27 Hz, 1 H) 8.09 (t, J = 5.05 Hz, 1 H) 7.64 (d, J = 1.26 Hz, 1 H) 7.56 (d, J = 1.77 Hz, 1 H) 7.26 (s, 1 H) 7.14 (d, J = 1.26 Hz, 1 H) 6.51 (s, 1 H) 5.90 (s, 1 H) 4.83 (quin, J = 6.57 Hz, 1 H) 4.37 (br. s., 1 H) 4.35 (br. s., 1 H) 3.30 (br. s., 2 H) 2.76 (t, J = 6.06 Hz, 2 H) 2.56 (d, J = 7.33 Hz, 2 H) 2.16 (s, 3 H) 2.12 (s, 3 H) 1.78-1.85 (m, 2 H) 1.53-1.62 (m, 2 H) 1.43 (s, 3 H) 1.41 (s, 3 H) 0.94 (t, J = 7.33 Hz, 3 H) | 512.4 |
| 196 | 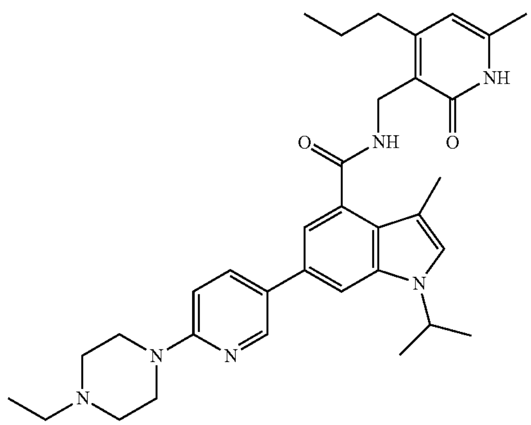 [SMILES: CCCc1cc(C)[nH]c(=O)c1CNC(=O)c1cc(-c2ccc(N3CCN(CC)CC3)nc2)cc2c1c(C)cn2C(C)C] | 6-[6-(4-ethyl-1-piperazinyl)-3-pyridinyl]-3-methyl-1-(1-methylethyl)-N-[(6-methyl-2-oxo-4-propyl-1,2-dihydro-3-pyridinyl)methyl]-1H-indole-4-carboxamide | 11.49 (s, 1 H) 8.50 (d, J = 2.53 Hz, 1 H) 8.12 (t, J = 5.05 Hz, 1 H) 7.91 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.92 (d, J = 8.84 Hz, 1 H) 5.90 (s, 1 H) 4.84 (quin, J = 6.63 Hz, 1 H) 4.37 (s, 1 H) 4.36 (s, 1 H) 3.48-3.56 (m, 4 H) 2.55 (dd, J = 8.72, 6.95 Hz, 2 H) 2.44-2.49 (m, 4 H) 2.38 (q, J = 7.24 Hz, 2 H) 2.17 (s, 3 H) 2.12 (s, 3 H) 1.53-1.62 (m, 2 H) 1.44 (s, 3 H) 1.42 (s, 3 H) 1.05 (t, J = 7.07 Hz, 3 H) 0.94 (t, J = 7.33 Hz, 3 H) | 569.8 |
| 197 | 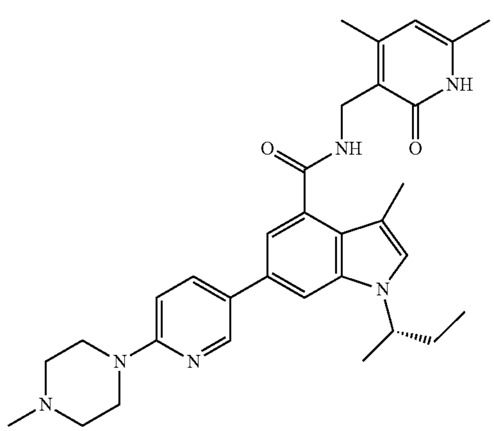 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.72-7.75 (m, 1 H) 7.26 (s, 1 H) 7.17 (d, J = 1.26 Hz, 1 H) 6.92 (d, J = 8.84 Hz, 1 H) 5.87 (s, 1 H) 4.56-4.65 (m, 1 H) 4.36 (s, 1 H) 4.34 (s, 1 H) 3.50-3.55 (m, 4 H) 2.40-2.44 (m, 4 H) 2.24 (s, 3 H) 2.23 (s, 3 H) 2.16 (s, 3 H) 2.11 (s, 3 H) 1.81 (dq, J = 9.85, 7.16 Hz, 2 H) 1.41 (d, J = 6.57 Hz, 3 H) 0.73 (t, J = 7.33 Hz, 3 H) | 541.8 |

| Ex | Structure | Name | ¹H NMR (400 MHz, DMSO-d₆) δ ppm | MS(ES) [M + H]⁺ |
|---|---|---|---|---|
| 198 | 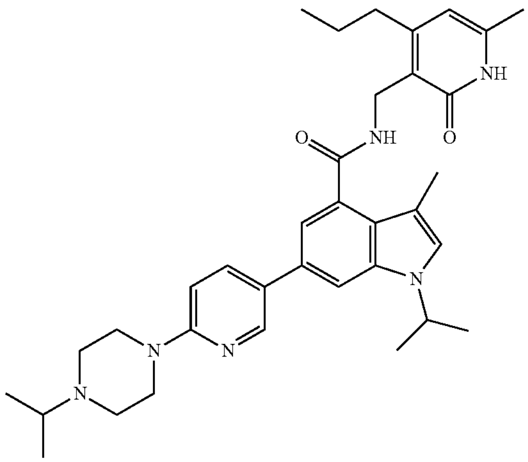 [SMILES: CCCc1cc(C)[nH]c(=O)c1CNC(=O)c1cc(-c2ccc(N3CCN(C(C)C)CC3)nc2)cc2c1c(C)cn2C(C)C] | 3-methyl-1-(1-methylethyl)-6-{6-[4-(1-methylethyl)-1-piperazinyl]-3-pyridinyl}-N-[(6-methyl-2-oxo-4-propyl-1,2-dihydro-3-pyridinyl)methyl]-1H-indole-4-carboxamide | 11.49 (br. s., 1 H) 8.50 (d, J = 2.53 Hz, 1 H) 8.12 (t, J = 5.05 Hz, 1 H) 7.91 (dd, J = 8.84, 2.53 Hz, 1 H) 7.72 (d, J = 1.26 Hz, 1 H) 7.29 (s, 1 H) 7.18 (d, J = 1.26 Hz, 1 H) 5.90 (s, 1 H) 4.84 (quin, J = 6.69 Hz, 1 H) 4.37 (br. s., 1 H) 4.36 (br. s., 1 H) 3.46-3.55 (m, 4 H) 2.66-2.73 (m, 1 H) 2.52-2.57 (m, 6 H) 2.17 (s, 3 H) 2.12 (s, 3 H) 1.53-1.62 (m, 2 H) 1.44 (s, 3 H) 1.42 (s, 3 H) 1.02 (s, 3 H) 1.01 (s, 3 H) 0.99 (d, J = 6.57 Hz, 1 H) 0.94 (t, J = 7.33 Hz, 3 H) | 583.6 |
| 199 | 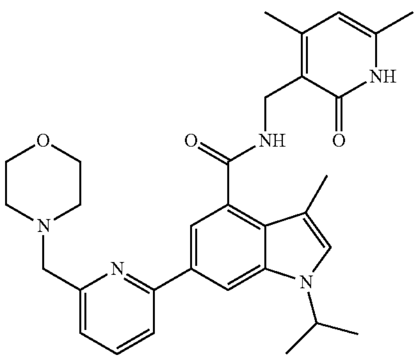 [SMILES: Cc1cc(C)c(CNC(=O)c2cc(-c3cccc(CN4CCOCC4)n3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(4-morpholinylmethyl)-2-pyridinyl]-1H-indole-4-carboxamide | 1.45 (d, J = 6.82 Hz, 6 H), 2.11 (s, 3 H), 2.18 (s, 3 H), 2.25 (s, 3 H), 3.57-3.66 (m, 4 H), 3.69 (s, 2 H), 4.37 (d, J = 5.05 Hz, 2 H), 4.87 (spt, J = 6.40 Hz, 1 H), 5.87 (s, 1 H), 7.33-7.41 (m, 2 H), 7.74 (d, J = 1.52 Hz, 1 H), 7.83 (t, J = 7.71 Hz, 1 H), 7.93 (d, J = 7.83 Hz, 1 H), 8.15 (t, J = 5.05 Hz, 1 H), 8.19 (d, J = 1.26 Hz, 1 H), 11.47 (s, 1 H) | 528.4 |
| 200 | 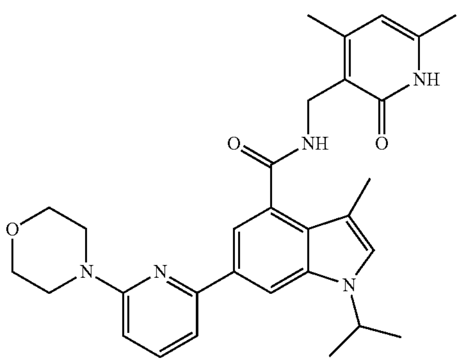 [SMILES: Cc1cc(C)c(CNC(=O)c2cc(-c3cccc(N4CCOCC4)n3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(4-morpholinyl)-2-pyridinyl]-1H-indole-4-carboxamide | 1.45 (d, J = 6.57 Hz, 6 H), 2.12 (s, 3 H), 2.17 (s, 3 H), 2.25 (s, 3 H), 3.48-3.61 (m, 4 H), 3.70-3.83 (m, 4 H), 4.36 (d, J = 5.05 Hz, 2 H), 4.86 (spt, J = 6.57 Hz, 1 H), 5.88 (s, 1 H), 6.75 (d, J = 8.59 Hz, 1 H), 7.30-7.43 (m, 2 H), 7.63 (t, J = 7.95 Hz, 1 H), 7.71 (d, J = 1.52 Hz, 1 H), 8.09-8.21 (m, 2 H), 11.46 (s, 1 H) | 514 |
| 201 | 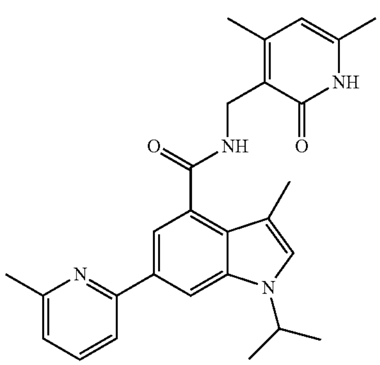 | N-[(4,6-dimethyl-2-oxo-1,2-dihydro-3-pyridinyl)methyl]-3-methyl-1-(1-methylethyl)-6-(6-methyl-2-pyridinyl)-1H-indole-4-carboxamide | 1.45 (d, J = 6.82 Hz, 6 H), 2.11 (s, 3 H), 2.18 (s, 3 H), 2.25 (s, 3 H), 2.55 (s, 3 H), 4.37 (d, J = 5.05 Hz, 2 H), 4.87 (spt, J = 6.57 Hz, 1 H), 5.87 (s, 1 H), 7.16 (d, J = 7.33 Hz, 1 H), 7.37 (d, J = 1.01 Hz, 1 H), 7.70-7.78 (m, 2 H), 7.85 (d, J = 8.08 Hz, 1 H), 8.15 (t, J = 4.93 Hz, 1 H), 8.19 (d, J = 1.52 Hz, 1 H), 11.48 (s, 1 H) | 443 |

| Ex | Structure | Name | ¹H NMR (400 MHz, DMSO-d₆) δ ppm | MS(ES) [M + H]⁺ |
|---|---|---|---|---|
| 202 | 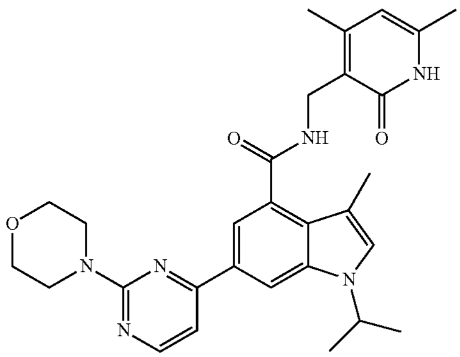 [SMILES: Cc1cc(C)c(CNC(=O)c2cc(-c3ccnc(N4CCOCC4)n3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[2-(4-morpholinyl)-4-pyrimidinyl]-1H-indole-4-carboxamide | 1.45 (d, J = 6.57 Hz, 6 H), 2.12 (s, 3 H), 2.17 (s, 3 H), 2.25 (s, 3 H), 3.68-3.76 (m, 4 H), 3.76-3.86 (m, 4 H), 4.36 (d, J = 5.05 Hz, 2 H), 4.92 (spt, J = 6.48 Hz, 1 H), 5.88 (s, 1 H), 7.38 (d, J = 5.31 Hz, 1 H), 7.45 (s, 1 H), 7.79 (d, J = 1.26 Hz, 1 H), 8.20 (t, J = 5.05 Hz, 1 H), 8.29 (d, J = 1.26 Hz, 1 H), 8.41 (d, J = 5.31 Hz, 1 H), 11.46 (s, 1 H) | 515 |
| 203 | 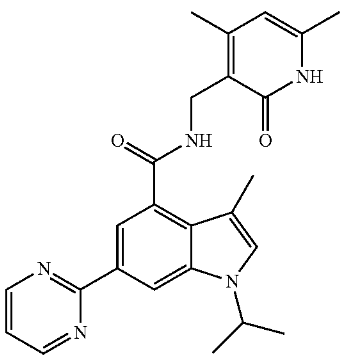 [SMILES: Cc1cc(C)c(CNC(=O)c2cc(-c3ncccn3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(2-pyrimidinyl)-1H-indole-4-carboxamide | 1.47 (d, J = 6.57 Hz, 6 H), 2.12 (s, 3 H), 2.19 (s, 3 H), 2.25 (s, 3 H), 4.37 (d, J = 5.05 Hz, 2 H), 4.84 (spt, J = 6.61 Hz, 1 H), 5.88 (s, 1 H), 7.38 (t, J = 4.80 Hz, 1 H), 7.46 (s, 1 H), 8.06 (d, J = 1.26 Hz, 1 H), 8.18 (t, J = 5.05 Hz, 1 H), 8.52 (d, J = 1.26 Hz, 1 H), 8.87 (d, J = 4.80 Hz, 2 H), 11.48 (s, 1 H) | |
| 204 | 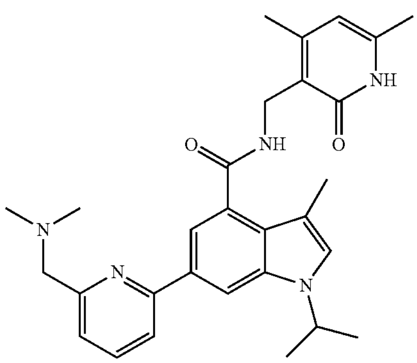 | 6-{6-[(dimethylamino)methyl]-2-pyridinyl}-N-[(4,6-dimethyl-2-oxo-1,2-dihydro-3-pyridinyl)methyl]-3-methyl-1-(1-methylethyl)-1H-indole-4-carboxamide | 1.45 (d, J = 6.82 Hz, 6 H), 2.11 (s, 3 H), 2.17 (s, 3 H), 2.25 (s, 9 H), 3.62 (s, 2 H), 4.37 (d, J = 4.80 Hz, 2 H), 4.87 (spt, J = 6.36 Hz, 1 H), 5.87 (s, 1 H), 7.33 (d, J = 7.58 Hz, 1 H), 7.37 (s, 1 H), 7.75 (d, J = 1.26 Hz, 1 H), 7.83 (t, J = 7.71 Hz, 1 H), 7.92 (d, J = 7.83 Hz, 1 H), 8.15 (t, J = 4.93 Hz, 1 H), 8.19 (d, J = 1.26 Hz, 1 H), 11.47 (s, 1 H) | |
| 205 | 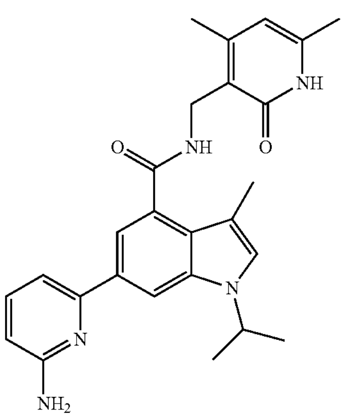 [SMILES: Cc1cc(C)c(CNC(=O)c2cc(-c3cccc(N)n3)cc3c2c(C)cn3C(C)C)c(=O)[nH]1] | 6-(6-amino-2-pyridinyl)-N-[(4,6-dimethyl-2-oxo-1,2-dihydro-3-pyridinyl)methyl]-3-methyl-1-(1-methylethyl)-1H-indole-4-carboxamide | 1.44 (d, J = 6.57 Hz, 6 H), 2.11 (s, 3 H), 2.16 (s, 3 H), 2.24 (s, 3 H), 4.35 (d, J = 5.05 Hz, 2 H), 4.74-4.87 (m, 1 H), 5.87 (s, 1 H), 5.96 (s, 2 H), 6.37 (d, J = 7.83 Hz, 1 H), 7.14 (d, J = 7.33 Hz, 1 H), 7.34 (s, 1 H), 7.44 (t, J = 7.83 Hz, 1 H), 7.65 (d, J = 1.26 Hz, 1 H), 8.04-8.13 (m, 2 H), 11.47 (s, 1 H). | 444 |

-continued

| Ex | Structure | Name | ¹H NMR (400 MHz, DMSO-d₆) δ ppm | MS(ES) [M + H]⁺ |
|---|---|---|---|---|
| 206 | 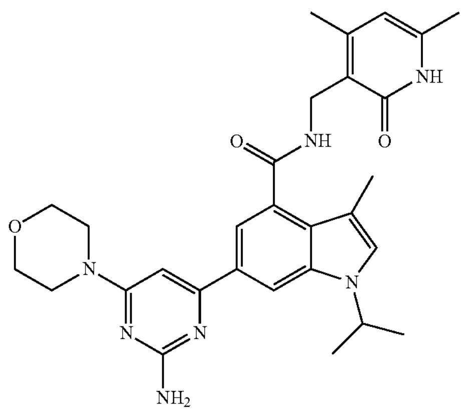 [SMILES: Cc1cc(C)c(CNC(=O)c2cc(-c3cc(N4CCOCC4)nc(N)n3)cc3c2c(C)cn3C(C)C)c(=O)[nH]1] | 6-[2-amino-6-(4-morpholinyl)-4-pyrimidinyl]-N-[(4,6-dimethyl-2-oxo-1,2-dihydro-3-pyridinyl)methyl]-3-methyl-1-(1-methylethyl)-1H-indole-4-carboxamide | 1.44 (d, 6 H), 2.11 (s, 3 H), 2.15 (s, 3 H), 2.24 (s, 3 H), 3.53-3.79 (m, 8 H), 4.35 (d, J = 4.29 Hz, 2 H), 4.80-4.95 (m, 1 H), 5.87 (s, 1 H), 6.10 (br. s., 2 H), 6.68 (s, 1 H), 7.38 (s, 1 H), 7.76 (s, 1 H), 8.06 (br. s., 1 H), 8.18 (s, 1 H), 11.46 (br. s., 1 H). | 530 |
| 207 | 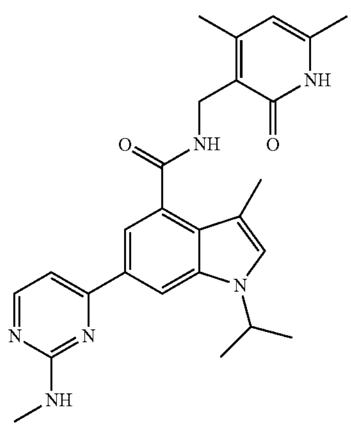 [SMILES: CNc1nccc(-c2cc(C(=O)NCc3c(C)cc(C)[nH]c3=O)c3c(C)cn(C(C)C)c3c2)n1] | N-[(4,6-dimethyl-2-oxo-1,2-dihydro-3-pyridinyl)methyl]-3-methyl-6-[2-(methylamino)-4-pyrimidinyl]-1-(1-methylethyl)-1H-indole-4-carboxamide | 1.45 (d, J = 6.82 Hz, 6 H), 2.11 (s, 3 H), 2.17 (s, 3 H), 2.25 (s, 3 H), 2.88 (br. s., 3 H), 4.36 (d, J = 5.05 Hz, 2 H), 4.81-4.94 (spt, J = 6.57 Hz, 1 H), 5.87 (s, 1 H), 7.07 (br. s., 1 H), 7.25 (d, J = 5.31 Hz, 1 H), 7.44 (s, 1 H), 7.78 (s, 1 H), 8.16 (t, J = 4.93 Hz, 1 H), 8.26 (s, 1 H), 8.31 (d, J = 4.80 Hz, 1 H), 11.47 (s, 1 H) | 459.1 |
| 208 | 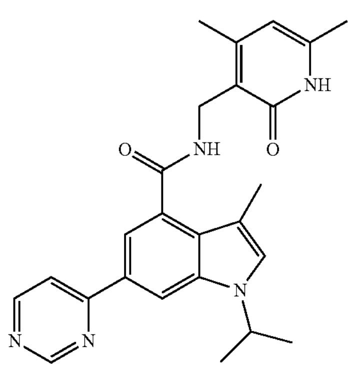 [SMILES: Cc1cc(C)c(CNC(=O)c2cc(-c3ccncn3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(4-pyrimidinyl)-1H-indole-4-carboxamide | 1.46 (d, J = 6.57 Hz, 6 H), 2.12 (s, 3 H), 2.19 (s, 3 H), 2.25 (s, 3 H), 4.37 (d, J = 5.05 Hz, 2 H), 4.92 (spt, J = 6.65 Hz, 1 H), 5.88 (s, 1 H), 7.49 (s, 1 H), 7.85 (d, J = 1.26 Hz, 1 H), 8.17-8.27 (m, 2 H), 8.42 (d, J = 1.52 Hz, 1 H), 8.80 (d, J = 5.31 Hz, 1 H), 9.19 (d, J = 1.01 Hz, 1 H), 11.48 (s, 1 H) | 430.0 |

| Ex | Structure | Name | $^1$H NMR (400 MHz, DMSO-d$_6$) δ ppm | MS(ES) [M + H]$^+$ |
|---|---|---|---|---|
| 209 | 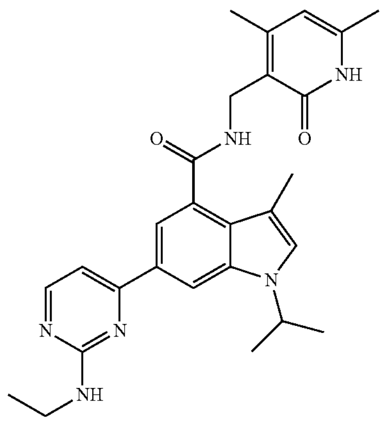 [SMILES: CCNc1nccc(-c2cc(C(=O)NCc3c(C)cc(C)[nH]c3=O)c3c(C)cn(C(C)C)c3c2)n1] | N-[(4,6-dimethyl-2-oxo-1,2-dihydro-3-pyridinyl)methyl]-6-[2-(ethylamino)-4-pyrimidinyl]-3-methyl-1-(1-methylethyl)-1H-indole-4-carboxamide | 1.17 (t, J = 7.07 Hz, 3 H), 1.45 (d, J = 6.57 Hz, 6 H), 2.11 (s, 3 H), 2.17 (s, 3 H), 2.24 (s, 3 H), 3.34-3.45 (m, 2 H), 4.36 (d, J = 5.05 Hz, 2 H), 4.86 (spt, J = 6.61 Hz, 1 H), 5.87 (s, 1 H), 7.12 (br. s., 1 H), 7.23 (d, J = 5.31 Hz, 1 H), 7.43 (s, 1 H), 7.76 (d, J = 1.26 Hz, 1 H), 8.16 (t, J = 4.93 Hz, 1 H), 8.25 (s, 1 H), 8.30 (d, J = 5.05 Hz, 1 H), 11.47 (s, 1 H) | 473.0 |
| 210 | 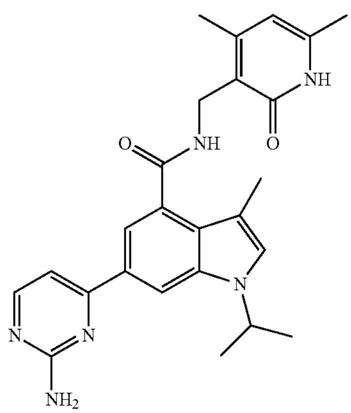 [SMILES: Cc1cc(C)c(CNC(=O)c2cc(-c3ccnc(N)n3)cc3c2c(C)cn3C(C)C)c(=O)[nH]1] | 6-(2-amino-4-pyrimidinyl)-N-[(4,6-dimethyl-2-oxo-1,2-dihydro-3-pyridinyl)methyl]-3-methyl-1-(1-methylethyl)-1H-indole-4-carboxamide | 1.45 (d, J = 6.57 Hz, 6 H), 2.11 (s, 3 H), 2.17 (s, 3 H), 2.24 (s, 3 H), 4.35 (d, J = 5.05 Hz, 2 H), 4.80-4.92 (m, 1 H), 5.87 (s, 1 H), 6.61 (s, 2 H), 7.25 (d, J = 5.31 Hz, 1 H), 7.44 (s, 1 H), 7.75 (d, J = 1.26 Hz, 1 H), 8.15 (t, J = 5.05 Hz, 1 H), 8.23 (d, J = 1.01 Hz, 1 H), 8.27 (d, J = 5.31 Hz, 1 H), 11.47 (s, 1 H) | 445 |
| 211 | 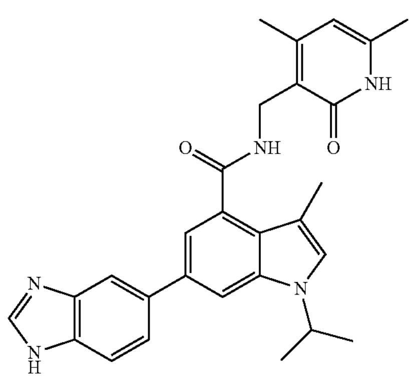 [SMILES: Cc1cc(C)c(CNC(=O)c2cc(-c3ccc4[nH]cnc4c3)cc3c2c(C)cn3C(C)C)c(=O)[nH]1] | 6-(1H-benzimidazol-5-yl)-N-[(4,6-dimethyl-2-oxo-1,2-dihydro-3-pyridinyl)methyl]-3-methyl-1-(1-methylethyl)-1H-indole-4-carboxamide | 1.45 (d, J = 6.57 Hz, 6 H), 2.11 (s, 3 H), 2.19 (s, 3 H), 2.25 (s, 3 H), 4.37 (d, J = 5.05 Hz, 2 H), 4.82-4.95 (m, 1 H), 5.87 (s, 1 H), 7.24-7.30 (m, 1 H), 7.30 (s, 1 H), 7.53-7.64 and 7.66-7.75 (m, 2 H), 7.79 (s, 1 H), 7.80-7.84 and 7.98-8.06 (m, 1 H), 8.20 (t, J = 5.05 Hz, 1 H), 8.23 (s, 1 H), 11.47 (br. s., 1 H), 12.45 (br. s., 1 H) | |

| Ex | Structure | Name | ¹H NMR (400 MHz, DMSO-d₆) δ ppm | MS(ES) [M + H]⁺ |
|---|---|---|---|---|
| 212 | 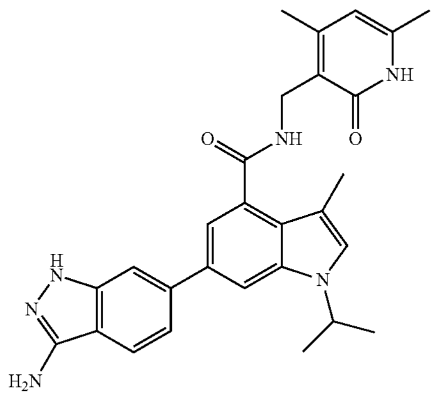 [SMILES: Cc1cc(C)c(CNC(=O)c2cc(-c3ccc4c(N)n[nH]c4c3)cc3c2c(C)cn3C(C)C)c(=O)[nH]1] | 6-(3-amino-1H-indazol-6-yl)-N-[(4,6-dimethyl-2-oxo-1,2-dihydro-3-pyridinyl)methyl]-3-methyl-1-(1-methylethyl)-1H-indole-4-carboxamide | 1.44 (d, J = 6.82 Hz, 6 H), 2.11 (s, 3 H), 2.18 (s, 3 H), 2.24 (s, 3 H), 4.37 (d, J = 4.80 Hz, 2 H), 4.89 (spt, J = 6.48 Hz, 1 H), 5.35 (s, 2 H), 5.87 (s, 1 H), 7.25-7.35 (m, 3 H), 7.50 (s, 1 H), 7.74 (d, J = 8.34 Hz, 1 H), 7.80 (d, J = 1.26 Hz, 1 H), 8.21 (t, J = 5.05 Hz, 1 H), 11.37 (br. s., 1 H), 11.47 (br. s., 1 H) | 483 |
| 213 | 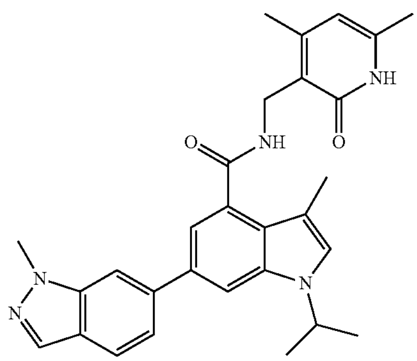 | N-[(4,6-dimethyl-2-oxo-1,2-dihydro-3-pyridinyl)methyl]-3-methyl-1-(1-methylethyl)-6-(1-methyl-1H-indazol-6-yl)-1H-indole-4-carboxamide | 1.46 (d, J = 6.57 Hz, 6 H), 2.11 (s, 3 H), 2.18 (s, 3 H), 2.26 (s, 3 H), 4.13 (s, 3 H), 4.37 (d, J = 5.05 Hz, 2 H), 4.91 (spt, J = 6.57 Hz, 1 H), 5.87 (s, 1 H), 7.35 (s, 1 H), 7.39 (d, J = 1.26 Hz, 1 H), 7.57 (dd, J = 8.46, 1.39 Hz, 1 H), 7.81 (d, J = 8.59 Hz, 1 H), 7.90 (d, J = 1.52 Hz, 1 H), 7.96 (s, 1 H), 8.04 (s, 1 H), 8.18 (t, J = 5.05 Hz, 1 H), 11.47 (s, 1 H) | |
| 214 | 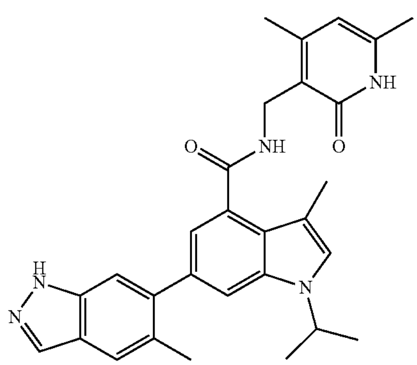 [SMILES: Cc1cc(C)c(CNC(=O)c2cc(-c3cc4[nH]ncc4cc3C)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(5-methyl-1H-indazol-6-yl)-1H-indole-4-carboxamide | 1.42 (d, J = 6.57 Hz, 6 H), 2.09 (s, 3 H), 2.20 (s, 3 H), 2.22 (s, 3 H), 2.31 (s, 3 H), 4.34 (d, J = 5.05 Hz, 2 H), 4.78 (spt, J = 6.53 Hz, 1 H), 5.85 (s, 1 H), 6.93 (d, J = 1.52 Hz, 1 H), 7.33 (s, 1 H), 7.37 (s, 1 H), 7.50 (d, J = 1.26 Hz, 1 H), 7.65 (s, 1 H), 8.01 (s, 1 H), 8.13 (t, J = 5.05 Hz, 1 H), 11.45 (br. s., 1 H), 12.92 (br. s., 1 H) | |
| 215 | 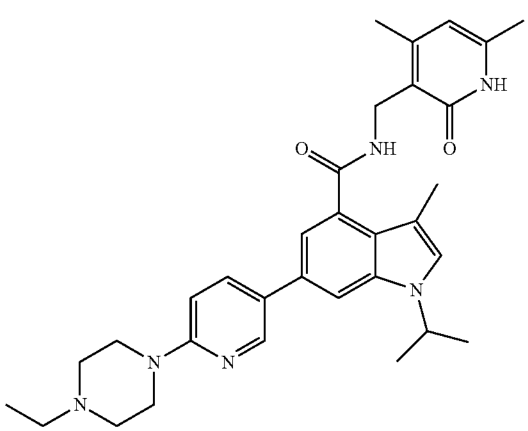 [SMILES: CCN1CCN(c2ccc(-c3cc(C(=O)NCc4c(C)cc(C)[nH]c4=O)c4c(C)cn(C(C)C)c4c3)cn2)CC1] | N-[(4,6-dimethyl-2-oxo-1,2-dihydro-3-pyridinyl)methyl]-6-[6-(4-ethyl-1-piperazinyl)-3-pyridinyl]-3-methyl-1-(1-methylethyl)-1H-indole-4-carboxamide | 1.05 (t, J = 7.20 Hz, 3 H) 1.43 (d, J = 6.57 Hz, 6 H) 2.11 (s, 3 H) 2.16 (s, 3 H) 2.24 (s, 3 H) 2.37 (q, J = 7.07 Hz, 2 H) 2.45-2.49 (m, 4 H) 3.49-3.55 (m, 4 H) 4.35 (d, J = 5.05 Hz, 2 H) 4.78-4.90 (m, 1 H) 5.87 (s, 1 H) 6.92 (d, J = 8.84 Hz, 1 H) 7.18 (d, J = 1.52 Hz, 1 H) 7.29 (s, 1 H) 7.72 (d, J = 1.26 Hz, 1 H) 7.92 (dd, J = 8.84, 2.78 Hz, 1 H) 8.15 (t, J = 5.05 Hz, 1 H) 8.51 (d, J = 2.53 Hz, 1 H) 11.48 (br. s., 1 H) | 541.6 |

-continued

| Ex | Structure | Name | ¹H NMR (400 MHz, DMSO-d₆) δ ppm | MS(ES) [M + H]⁺ |
|---|---|---|---|---|
| 216 | 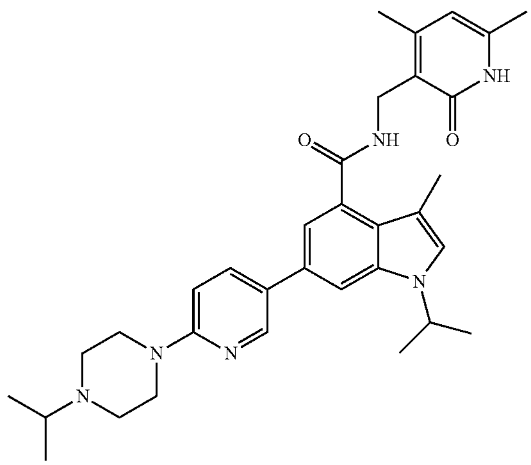 | N-[(4,6-dimethyl-2-oxo-1,2-dihydro-3-pyridinyl)methyl]-3-methyl-1-(1-methylethyl)-6-{6-[4-(1-methylethyl)-1-piperazinyl]-3-pyridinyl}-1H-indole-4-carboxamide | 1.01 (d, J = 6.57 Hz, 6 H) 1.43 (d, J = 6.57 Hz, 6 H) 2.11 (s, 3 H) 2.16 (s, 3 H) 2.24 (s, 3 H) 2.53-2.57 (m, 4 H) 2.67-2.73 (m, 1 H) 3.47-3.54 (m, 4 H) 4.35 (d, J = 5.31 Hz, 2 H) 4.84 (s, 1 H) 5.87 (s, 1 H) 6.91 (d, J = 8.84 Hz, 1 H) 7.18 (d, J = 1.26 Hz, 1 H) 7.29 (s, 1 H) 7.72 (d, J = 1.52 Hz, 1 H) 7.92 (dd, J = 8.84, 2.53 Hz, 1 H) 8.14 (s, 1 H) 8.50 (d, J = 2.27 Hz, 1 H) 11.48 (s, 1 H) | 555.8 |
| 217 | 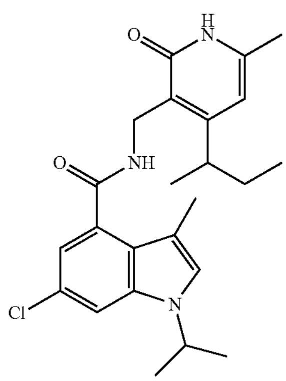 | 6-chloro-3-methyl-1-(1-methylethyl)-N-{[6-methyl-4-(1-methylpropyl)-2-oxo-1,2-dihydro-3-pyridinyl]methyl}-1H-indole-4-carboxamide | 0.79 (t, J = 7.33 Hz, 3 H) 1.11 (d, J = 6.82 Hz, 3 H) 1.39 (d, J = 6.57 Hz, 6 H) 1.50 (quin, J = 7.33 Hz, 2 H) 2.14 (s, 6 H) 2.98 (q, J = 6.91 Hz, 1 H) 4.36 (d, J = 5.05 Hz, 2 H) 4.73 (quin, J = 6.63 Hz, 1 H) 5.95 (s, 1 H) 6.88 (d, J = 1.77 Hz, 1 H) 7.34 (s, 1 H) 7.64 (d, J = 1.77 Hz, 1 H) 8.23 (t, J = 4.93 Hz, 1 H) 11.48 (s, 1 H) | 428.2 |
| 218 | 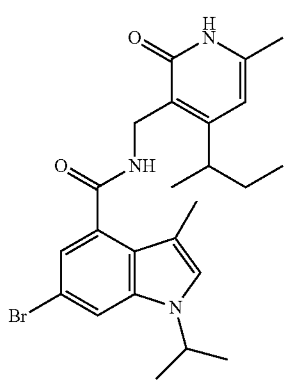 [SMILES: CCC(C)c1cc(C)[nH]c(=O)c1CNC(=O)c1cc(Cl)cc2c1c(C)cn2C(C)C] | 6-bromo-3-methyl-1-(1-methylethyl)-N-{[6-methyl-4-(1-methylpropyl)-2-oxo-1,2-dihydro-3-pyridinyl]methyl}-1H-indole-4-carboxamide | 0.79 (t, J = 7.33 Hz, 3 H) 1.11 (d, J = 6.82 Hz, 3 H) 1.33-1.44 (m, 6 H) 1.50 (quin, J = 7.33 Hz, 2 H) 2.07-2.20 (m, 6 H) 2.91-3.05 (m, 1 H) 4.36 (d, J = 5.05 Hz, 2 H) 4.74 (dt, J = 13.33, 6.60 Hz, 1 H) 5.95 (s, 1 H) 6.99 (d, J = 1.52 Hz, 1 H) 7.34 (s, 1 H) 7.76 (d, J = 1.52 Hz, 1 H) 8.24 (t, J = 4.80 Hz, 1 H) 11.48 (br. s., 1 H) | 474.2 |

-continued

| Ex | Structure | Name | ¹H NMR (400 MHz, DMSO-d₆) δ ppm | MS(ES) [M + H]⁺ |
|---|---|---|---|---|
| 219 | 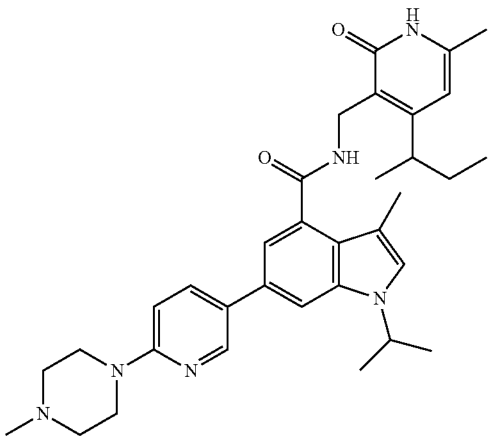 [SMILES: CCC(C)c1cc(C)[nH]c(=O)c1CNC(=O)c1cc(-c2ccc(N3CCN(C)CC3)nc2)cc2c1c(C)cn2C(C)C] | 3-methyl-1-(1-methylethyl)-N-{[6-methyl-4-(1-methylpropyl)-2-oxo-1,2-dihydro-3-pyridinyl]methyl}-6-[6-(4-methyl-1-piperazinyl)-3-pyridinyl]-1H-indole-4-carboxamide | 0.80 (t, J = 7.33 Hz, 3 H) 1.10-1.15 (m, 3 H) 1.34-1.47 (m, 6 H) 1.51 (quin, J = 7.33 Hz, 2 H) 2.10-2.28 (m, 9 H) 2.35-2.44 (m, 4 H) 3.01 (sxt, J = 6.92 Hz, 1 H) 3.45-3.58 (m, 4 H) 4.33-4.50 (m, 2 H) 4.84 (quin, J = 6.63 Hz, 1 H) 5.96 (s, 1 H) 6.92 (d, J = 8.84 Hz, 1 H) 7.18 (d, J = 1.26 Hz, 1 H) 7.29 (s, 1 H) 7.72 (d, J = 1.26 Hz, 1 H) 7.90 (dd, J = 8.84, 2.53 Hz, 1 H) 8.16 (t, J = 4.93 Hz, 1 H) 8.49 (d, J = 2.53 Hz, 1 H) 11.48 (br. s., 1 H) | 569.4 |
| 220 | 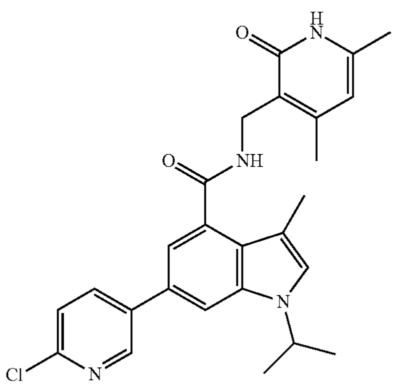 [SMILES: Cc1cc(C)c(CNC(=O)c2cc(-c3ccc(Cl)nc3)cc3c2c(C)cn3C(C)C)c(=O)[nH]1] | 6-(6-chloro-3-pyridinyl)-N-[(4,6-dimethyl-2-oxo-1,2-dihydro-3-pyridinyl)methyl]-3-methyl-1-(1-methylethyl)-1H-indole-4-carboxamide | 1.36-1.52 (m, 6 H) 2.11 (s, 3 H) 2.16-2.20 (m, 3 H) 2.21-2.28 (m, 3 H) 4.35 (d, J = 5.05 Hz, 2 H) 4.89 (quin, J = 6.63 Hz, 1 H) 5.87 (s, 1 H) 7.30 (d, J = 1.26 Hz, 1 H) 7.39 (s, 1 H) 7.59 (d, J = 8.34 Hz, 1 H) 7.92 (d, J = 1.52 Hz, 1 H) 8.18-8.29 (m, 2 H) 8.83 (d, J = 2.27 Hz, 1 H) 11.49 (s, 1 H) | 463.2 |
| 221 | 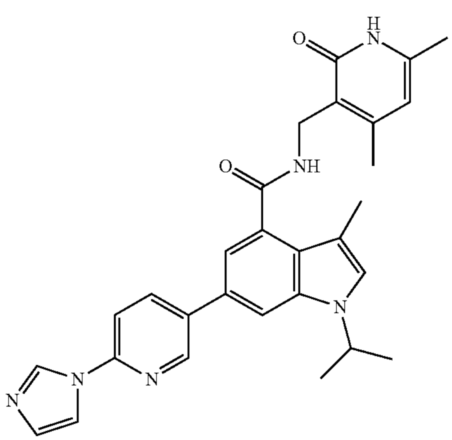 [SMILES: Cc1cc(C)c(CNC(=O)c2cc(-c3ccc(-n4ccnc4)nc3)cc3c2c(C)cn3C(C)C)c(=O)[nH]1] | N-[(4,6-dimethyl-2-oxo-1,2-dihydro-3-pyridinyl)methyl]-6-[6-(1H-imidazol-1-yl)-3-pyridinyl]-3-methyl-1-(1-methylethyl)-1H-indole-4-carboxamide | 1.42-1.48 (m, 6 H) 2.11 (s, 3 H) 2.18 (s, 3 H) 2.22-2.30 (m, 3 H) 4.36 (d, J = 5.05 Hz, 2 H) 4.84-4.97 (m, 1 H) 5.87 (s, 1 H) 7.16 (s, 1 H) 7.33-7.41 (m, 2 H) 7.91 (d, J = 8.34 Hz, 1 H) 7.95 (d, J = 1.26 Hz, 1 H) 8.02 (s, 1 H) 8.22 (t, J = 5.05 Hz, 1 H) 8.39 (dd, J = 8.59, 2.53 Hz, 1 H) 8.60 (s, 1 H) 8.90 (d, J = 2.27 Hz, 1 H) 11.49 (s, 1 H) | 495.2 |

| Ex | Structure | Name | ¹H NMR (400 MHz, DMSO-d₆) δ ppm | MS(ES) [M + H]⁺ |
|---|---|---|---|---|
| 222 | 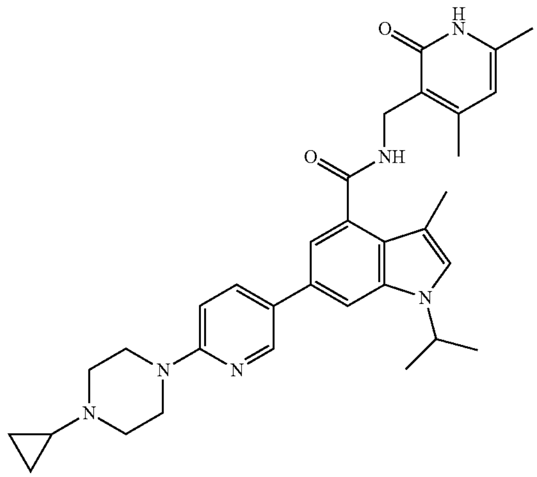 [SMILES: Cc1cc(C)c(CNC(=O)c2cc(-c3ccc(N4CCN(C5CC5)CC4)nc3)cc3c2c(C)cn3C(C)C)c(=O)[nH]1] | 6-[6-(4-cyclopropyl-1-piperazinyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 0.34-0.49 (m, 4 H) 1.42 (d, J = 6.57 Hz, 6 H) 1.65 (tt, J = 6.57, 3.41 Hz, 1 H) 2.11 (s, 3 H) 2.16 (s, 3 H) 2.24 (s, 3 H) 2.59-2.69 (m, 4 H) 3.42-3.56 (m, 4 H) 4.34 (d, J = 5.05 Hz, 2 H) 4.84 (quin, J = 6.63 Hz, 1 H) 5.87 (s, 1 H) 6.91 (d, J = 8.84 Hz, 1 H) 7.18 (d, J = 1.26 Hz, 1 H) 7.28 (s, 1 H) 7.71 (d, J = 1.26 Hz, 1 H) 7.92 (dd, J = 8.84, 2.53 Hz, 1 H) 8.15 (t, J = 5.05 Hz, 1 H) 8.50 (d, J = 2.27 Hz, 1 H) 11.48 (s, 1 H) | 553.8 |
| 223 | 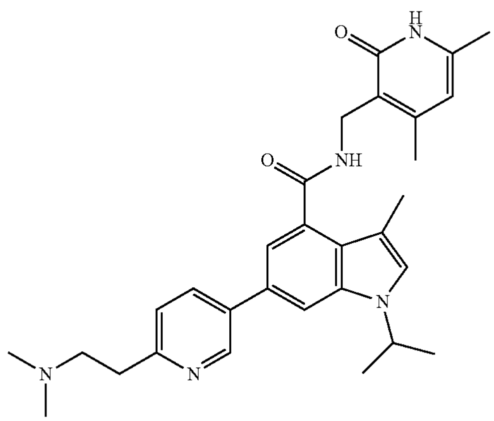 | 6-{6-[2-(dimethylamino)ethyl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, J = 6.57 Hz, 6 H) 2.11 (s, 3 H) 2.14-2.22 (m, 9 H) 2.24 (s, 3 H) 2.61 (t, J = 7.58 Hz, 2 H) 2.89 (t, J = 7.45 Hz, 2 H) 4.35 (d, J = 5.05 Hz, 2 H) 4.81-4.94 (m, 1 H) 5.87 (s, 1 H) 7.25 (d, J = 1.26 Hz, 1 H) 7.32-7.40 (m, 2 H) 7.84 (d, J = 1.26 Hz, 1 H) 8.03 (dd, J = 8.08, 2.53 Hz, 1 H) 8.19 (t, J = 5.05 Hz, 1 H) 8.84 (d, J = 2.02 Hz, 1 H) 11.48 (s, 1 H) | 500.3 |
| 224 | 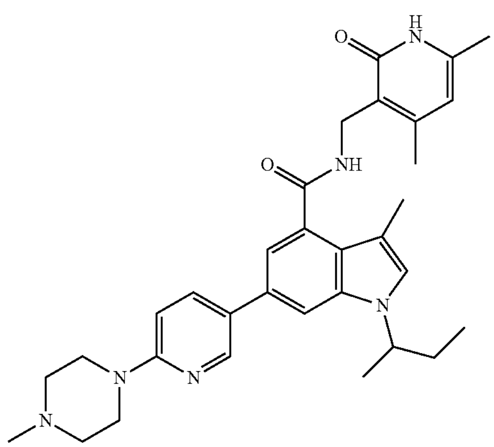 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 0.72 (t, J = 7.33 Hz, 3 H) 1.40 (d, J = 6.82 Hz, 3 H) 1.80 (td, J = 7.26, 2.91 Hz, 2 H) 2.11 (s, 3 H) 2.16 (s, 3 H) 2.23 (d, J = 5.31 Hz, 6 H) 2.37-2.46 (m, 4 H) 3.46-3.56 (m, 4 H) 4.35 (d, J = 5.05 Hz, 2 H) 4.60 (d, J = 7.07 Hz, 1 H) 5.86 (s, 1 H) 6.91 (d, J = 8.84 Hz, 1 H) 7.17 (d, J = 1.26 Hz, 1 H) 7.26 (s, 1 H) 7.73 (d, J = 1.26 Hz, 1 H) 7.91 (dd, J = 8.84, 2.53 Hz, 1 H) 8.16 (t, J = 4.93 Hz, 1 H) 8.50 (d, J = 2.53 Hz, 1 H) 11.48 (s, 1 H) | 541.7 |

| Ex | Name | ¹H NMR (400 MHz, DMSO-d₆) δ ppm | MS(ES) [M + H]⁺ |
|---|---|---|---|
| 225 | N-[(4,6-dimethyl-2-oxo-1,2-dihydro-3-pyridinyl)methyl]-6-{6-[(3R,5S)-3,5-dimethyl-1-piperazinyl]-3-pyridinyl}-3-methyl-1-(1-methylethyl)-1H-indole-4-carboxamide | 1.00-1.07 (m, 6 H) 1.39-1.46 (m, 6 H) 2.11 (s, 3 H) 2.16 (s, 3 H) 2.21-2.34 (m, 6 H) 2.70-2.82 (m, 2 H) 4.17 (dd, J = 12.25, 2.15 Hz, 2 H) 4.35 (d, J = 5.05 Hz, 2 H) 4.83 (quin, J = 6.57 Hz, 1 H) 5.87 (s, 1 H) 6.89 (d, J = 9.09 Hz, 1 H) 7.17 (d, J = 1.26 Hz, 1 H) 7.28 (s, 1 H) 7.70 (d, J = 1.52 Hz, 1 H) 7.89 (dd, J = 8.84, 2.53 Hz, 1 H) 8.15 (t, J = 5.18 Hz, 1 H) 8.47 (d, J = 2.27 Hz, 1 H) 11.48 (br. s., 1 H) | 541.4 |
| 226 | 6-{6-[3-(dimethylamino)-1-pyrrolidinyl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.35-1.49 (m, 6 H) 1.75-1.88 (m, 1 H) 2.11 (s, 3 H) 2.13-2.19 (m, 4 H) 2.20-2.27 (m, 9 H) 2.72-2.84 (m, 1 H) 3.14 (dd, J = 9.85, 8.34 Hz, 1 H) 3.34-3.41 (m, 1 H) 3.61 (t, J = 8.59 Hz, 1 H) 3.71 (dd, J = 10.11, 7.07 Hz, 1 H) 4.35 (d, J = 5.05 Hz, 2 H) 4.83 (quin, J = 6.63 Hz, 1 H) 5.87 (s, 1 H) 6.54 (d, J = 8.84 Hz, 1 H) 7.16 (d, J = 1.52 Hz, 1 H) 7.27 (s, 1 H) 7.68 (d, J = 1.26 Hz, 1 H) 7.88 (dd, J = 8.59, 2.53 Hz, 1 H) 8.14 (t, J = 5.05 Hz, 1 H) 8.45 (d, J = 2.27 Hz, 1 H) 11.48 (s, 1 H) | 541.7 |
| 227 | N-[(4,6-dimethyl-2-oxo-1,2-dihydro-3-pyridinyl)methyl]-3-methyl-1-(1-methylethyl)-6-[6-(4-methylhexahydro-1H-1,4-diazepin-1-yl)-3-pyridinyl]-1H-indole-4-carboxamide | 1.42 (d, J = 6.57 Hz, 6 H) 1.87-1.97 (m, 2 H) 2.16 (s, 3 H) 2.11 (s, 3 H) 2.20-2.32 (m, 6 H) 2.59-2.72 (m, 2 H) 3.63 (t, J = 6.19 Hz, 2 H) 3.78 (br. s., 2 H) 4.34 (d, J = 5.05 Hz, 2 H) 4.76-4.89 (m, 1 H) 5.87 (s, 1 H) 6.70 (d, J = 8.84 Hz, 1 H) 7.16 (d, J = 1.52 Hz, 1 H) 7.27 (s, 1 H) 7.69 (d, J = 1.26 Hz, 1 H) 7.87 (dd, J = 8.84, 2.53 Hz, 1 H) 8.14 (t, J = 5.05 Hz, 1 H) 8.45 (d, J = 2.27 Hz, 1 H) 11.48 (s, 1 H) | 541.3 |

-continued

| Ex | Structure | Name | ¹H NMR (400 MHz, DMSO-d₆) δ ppm | MS(ES) [M + H]⁺ |
|---|---|---|---|---|
| 228 | 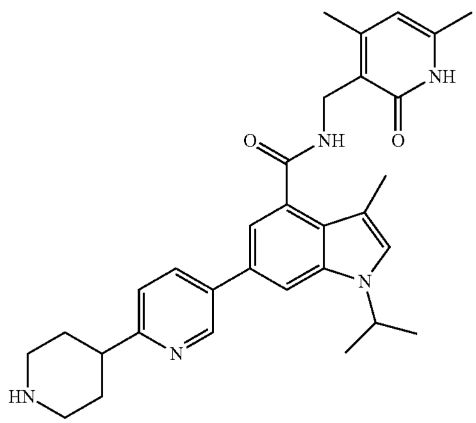 [SMILES: Cc1cc(C)c(CNC(=O)c2cc(-c3ccc(C4CCNCC4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(4-piperidinyl)-3-pyridinyl]-1H-indole-4-carboxamide | 1H NMR (400 MHz, MeOH-d4) 1.55 (d, J = 6.82 Hz, 6 H) 2.14-2.29 (m, 5 H) 2.35 (br. s., 2 H) 2.47 (s, 3 H) 2.60 (s, 3 H) 3.23-3.31 (m, 1 H) 3.47-3.59 (m, 1 H) 3.64 (br. s., 2 H) 4.68 (s, 2 H) 6.77 (br. s., 1 H) 7.45 (s, 1 H) 7.65 (s, 1 H) 8.08-8.17 (m, 2 H) 9.03 (d, J = 8.34 Hz, 1 H) 9.22 (d, J = 1.77 Hz, 1 H) | 585 |
| 229 | 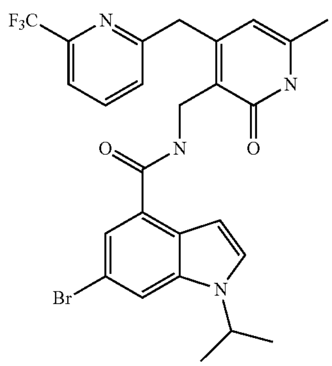 [SMILES: Cc1cc(Cc2cccc(C(F)(F)F)n2)c(CNC(=O)c2cc(Br)cc3c2ccn3C(C)C)c(=O)[nH]1] | 6-bromo-1-isopropyl-N-((6-methyl-2-oxo-4-((6-(trifluoromethyl)pyridin-2-yl)methyl)-1,2-dihydropyridin-3-yl)methyl)-1H-indole-4-carboxamide | 1.42 (s, 3 H), 1.44 (s, 3 H), 2.11 (s, 3 H), 4.27 (s, 2 H), 4.44 (d, J = 5.05 Hz, 2 H), 4.74-4.88 (m, 1 H), 5.88 (s, 1 H), 6.84 (d, J = 3.03 Hz, 1 H), 7.45 (d, J = 1.77 Hz, 1 H), 7.54-7.64 (m, 2 H), 7.71 (d, J = 7.58 Hz, 1 H), 7.91 (s, 1 H), 7.93-8.00 (m, 1 H), 8.35 (t, J = 5.05 Hz, 1 H), 11.68 (s, 1 H) | 461, 463 |
| 230 | 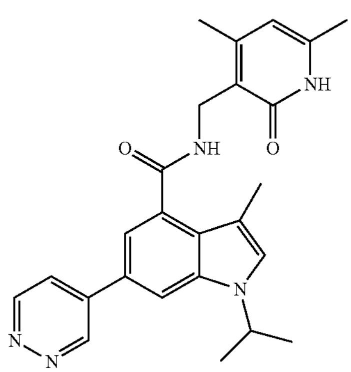 [SMILES: Cc1cc(C)c(CNC(=O)c2cc(-c3ccnnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridazin-4-yl)-1H-indole-4-carboxamide | 11.10-11.70 (br. s, 1H), 9.77 (dd, J = 1.26, 2.53 Hz, 1H), 9.22 (dd, J = 1.14, 5.43 Hz, 1H), 8.30 (br. s., 1H), 8.19 (d, J = 1.52 Hz, 1H), 8.09 (dd, J = 2.53, 5.56 Hz, 1H), 7.42-7.54 (m, 2H), 5.87 (s, 1H), 4.96 (quin, J = 6.63 Hz, 1H), 4.36 (d, J = 5.05 Hz, 2H), 2.25 (s, 3H), 2.18 (s, 3H), 2.11 (s, 3H), 1.45 (d, 6H) | 430.3 |
| 231 | 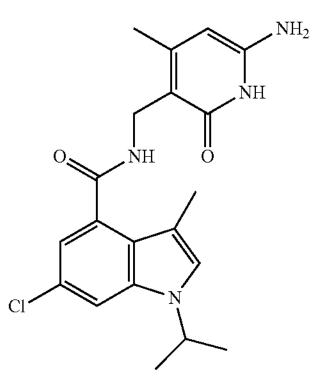 [SMILES: Cc1cc(N)[nH]c(=O)c1CNC(=O)c1cc(Cl)cc2c1c(C)cn2C(C)C] | N-[(6-amino-4-methyl-2-oxo-1,2-dihydro-3-pyridinyl)methyl]-6-chloro-3-methyl-1-(1-methylethyl)-1H-indole-4-carboxamide | 10.62 (br. s., 1 H), 8.14 (t, J = 4.4 Hz, 1 H), 7.63 (d, J = 1.8 Hz, 1 H), 7.34 (s, 1 H), 6.89 (d, J = 1.8 Hz, 1 H), 5.85 (br. s., 2 H), 5.20 (s, 1 H), 4.73 (dt, J = 6.7, 13.2 Hz, 1 H), 4.22 (d, J = 4.8 Hz, 2 H), 2.14 (s, 3 H), 2.12 (s, 3 H), 1.39 (d, J = 6.6 Hz, 6 H) | 387.2 |

-continued

| Ex | Name | ¹H NMR (400 MHz, DMSO-d₆) δ ppm | MS(ES) [M + H]⁺ |
|---|---|---|---|
| 232 | N-[(6-amino-4-methyl-2-oxo-1,2-dihydro-3-pyridinyl)methyl]-6-bromo-3-methyl-1-(1-methylethyl)-1H-indole-4-carboxamide | 10.59 (br. s., 1 H), 8.13 (t, J = 4.4 Hz, 1 H), 7.76 (d, J = 1.5 Hz, 1 H), 7.33 (s, 1 H), 6.99 (d, J = 1.5 Hz, 1 H), 5.83 (br. s., 2 H), 5.19 (s, 1 H), 4.74 (dt, J = 6.6, 13.3 Hz, 1 H), 4.22 (d, J = 4.8 Hz, 2 H), 2.14 (s, 3 H), 2.11 (s, 3 H), 1.39 (d, J = 6.6 Hz, 6 H) | 431.1 |
| 233 | 6-bromo-N-[(4,6-dimethyl-2-oxo-1,2-dihydro-3-pyridinyl)methyl]-3-methyl-1-[(3R)-tetrahydro-3-furanyl]-1H-indole-4-carboxamide | 1.94-2.07 (m, 1 H), 2.11, (s, 3 H), 2.12 (s, 3 H), 2.22 (s, 3 H), 2.40-2.48 (m, 1 H), 3.75-3.87 (m, 2 H), 3.88-3.96 (m, 1 H), 3.98-4.11 (m, 1 H), 4.31 (d, J = 5.05 Hz, 2 H), 5.17-5.32 (m, 1 H), 5.86 (s, 1 H), 7.04 (d, J = 1.52 Hz, 1 H), 7.23 (s, 1 H), 7.84 (d, J = 1.77 Hz, 1 H), 8.25 (t, J = 4.93 Hz, 1 H), 11.47 (s, 1 H) | 458, 460 |
| 234 | 6-bromo-3-methyl-1-(1-methylethyl)-N-{[6-methyl-2-oxo-4-(1H-pyrazol-1-ylmethyl)-1,2-dihydro-3-pyridinyl]methyl}-1H-indole-4-carboxamide | 1.39 (d, J = 6.8 Hz, 6 H), 2.06 (s, 3 H), 2.11 (s, 3 H), 4.44 (d, J = 5.3 Hz, 2 H), 4.75 (dt, J = 13.3, 6.6 Hz, 1 H), 5.41 (s, 1 H), 5.44 (s, 2 H), 7.07 (d, J = 1.8 Hz, 1 H), 7.33 (s, 1 H), 7.47 (d, J = 1.3 Hz, 1 H), 7.78 (d, J = 1.5 Hz, 1 H), 7.84 (d, J = 1.8 Hz, 1 H), 8.52 (t, J = 5.2 Hz, 1 H), 11.67 (br. s., 1 H) | 496.3 |
| 235 | 6-bromo-1-(1-methylethyl)-N-{[6-methyl-2-oxo-4-(1H-pyrazol-1-ylmethyl)-1,2-dihydro-3-pyridinyl]methyl}-1H-indole-4-carboxamide | 1.44 (d, J = 6.6 Hz, 6 H), 2.06 (s, 3 H), 4.46 (d, J = 5.3 Hz, 2 H), 4.83 (dt, J = 13.2, 6.7 Hz, 1 H), 5.45 (s, 3 H), 6.31 (t, J = 2.0 Hz, 1 H), 6.90 (d, J = 3.0 Hz, 1 H), 7.51 (d, J = 1.8 Hz, 1 H), 7.57 (d, J = 1.5 Hz, 1 H), 7.64 (d, J = 3.3 Hz, 1 H), 7.87 (d, J = 2.3 Hz, 1 H), 7.94 (s, 1 H), 8.56 (t, J = 5.1 Hz, 1 H), 11.73 (br. s., 1 H) | 484.2 |

-continued

| Ex | Structure | Name | ¹H NMR (400 MHz, DMSO-d₆) δ ppm | MS(ES) [M + H]⁺ |
|---|---|---|---|---|
| 236 | 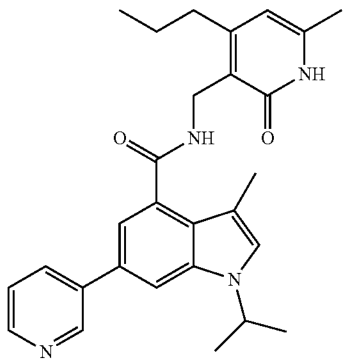 [SMILES: CCCc1cc(C)[nH]c(=O)c1CNC(=O)c1cc(-c2cccnc2)cc2c1c(C)cn2C(C)C] | 3-methyl-1-(1-methylethyl)-N-[(6-methyl-2-oxo-4-propyl-1,2-dihydro-3-pyridinyl)methyl]-6-(3-pyridinyl)-1H-indole-4-carboxamide | 0.94 (t, J = 7.3 Hz, 3 H), 1.44 (d, J = 6.6 Hz, 6 H), 1.51-1.67 (m, 2 H), 2.12 (s, 3 H), 2.19 (s, 3 H), 2.52-2.59 (m, 2 H), 4.38 (d, J = 4.0 Hz, 2 H), 4.81-4.98 (m, 1 H), 5.90 (s, 1 H), 7.28 (s, 1 H), 7.37 (s, 1 H), 7.47 (dd, J = 7.8, 4.5 Hz, 1 H), 7.89 (s, 1 H), 8.14 (d, J = 8.1 Hz, 1 H), 8.18 (br. s., 1 H), 8.53 (dd, J = 4.8, 1.3 Hz, 1 H), 8.97 (d, J = 1.8 Hz, 1 H), 11.49 (s, 1 H) | 457.3 |
| 237 | 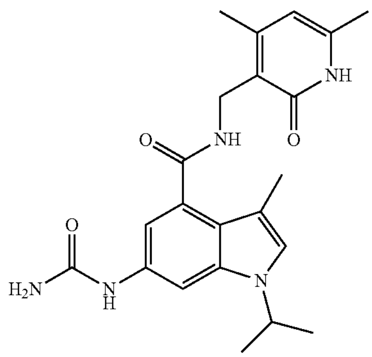 [SMILES: Cc1cc(C)c(CNC(=O)c2cc(NC(N)=O)cc3c2c(C)cn3C(C)C)c(=O)[nH]1] | 6-[(aminocarbonyl)amino]-N-[(4,6-dimethyl-2-oxo-1,2-dihydro-3-pyridinyl)methyl]-3-methyl-1-(1-methylethyl)-1H-indole-4-carboxamide | 1.39 (m, 6 H), 2.08-2.12 (m, 6 H), 2.22 (s, 3 H), 4.32 (d, J = 5.05 Hz, 2 H), 4.44-4.59 (m, 1 H), 5.76 (s, 2 H), 5.87 (s, 1 H), 6.79 (d, J = 1.77 Hz, 1 H), 7.11 (s, 1 H), 7.71 (d, J = 1.52 Hz, 1 H), 7.98 (t, J = 5.05 Hz, 1 H), 8.47 (s, 1 H), 11.46 (s, 1 H) | 410.3 |
| 238 | 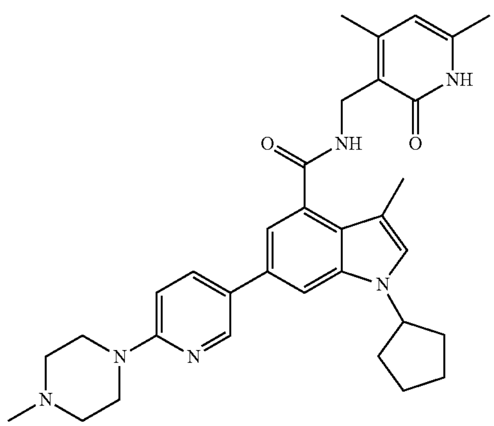 | 1-cyclopentyl-N-[(4,6-dimethyl-2-oxo-1,2-dihydro-3-pyridinyl)methyl]-3-methyl-6-[6-(4-methyl-1-piperazinyl)-3-pyridinyl]-1H-indole-4-carboxamide | 1.66-1.89 (m, 6 H), 2.05-2.20 (m, 8 H), 2.25 (d, J = 7.07 Hz, 6 H), 3.49-3.58 (m, 4 H), 2.47 (m, 4 H), 4.35 (d, J = 5.05 Hz, 2 H), 4.97 (quin, J = 6.88 Hz, 1 H), 5.87 (s, 1 H), 6.93 (d, J = 8.84 Hz, 1 H), 7.19 (d, J = 1.26 Hz, 1 H), 7.25 (s, 1 H), 7.74 (d, J = 1.26 Hz, 1 H), 7.93 (dd, J = 8.84, 2.53 Hz, 1 H), 8.14-8.21 (m, 1 H), 8.51 (d, J = 2.53 Hz, 1 H) | 553.8 |
| 239 | 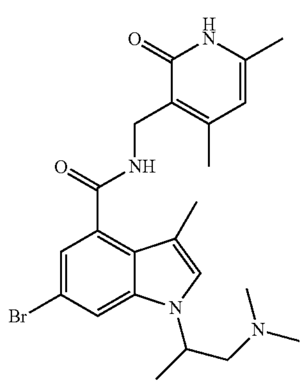 [SMILES: Cc1cc(C)c(CNC(=O)c2cc(Br)cc3c2c(C)cn3C(C)CN(C)C)c(=O)[nH]1] | 6-bromo-N-((4,6-dimethyl-2-oxo-1,2-dihydropyridin-3-yl)methyl)-1-(1-(dimethylamino)propan-2-yl)-3-methyl-1H-indole-4-carboxamide | (600 MHz, CHLOROFORM-d) 1.44 (d, J = 6.42 Hz, 3 H) 2.14 (s, 3 H) 2.22 (br. s., 9 H) 2.38 (s, 3 H) 2.55-2.60 (m, 1 H) 2.65-2.74 (m, 1 H) 4.45-4.54 (m, 1 H) 4.57 (d, J = 5.29 Hz, 2 H) 5.92 (s, 1 H) 6.93 (s, 1 H) 7.19 (s, 1 H) 7.23 (br. s., 1 H) 7.48 (s, 1 H) 12.53 (br. s., 1 H) | 473.2, 475.2 |

| Ex | Structure | Name | ¹H NMR (400 MHz, DMSO-d$_6$) δ ppm | MS(ES) [M + H]⁺ |
|---|---|---|---|---|
| 240 | 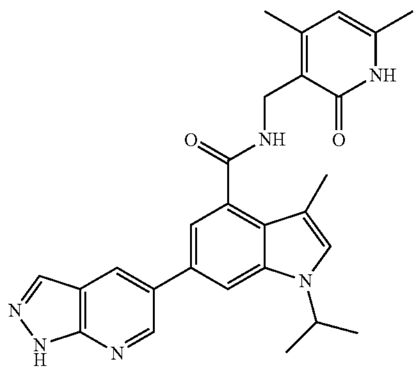 [SMILES: Cc1cc(C)c(CNC(=O)c2cc(-c3cnc4[nH]ncc4c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1H-pyrazolo[3,4-b]pyridin-5-yl)-1H-indole-4-carboxamide | 1.45 (d, J = 6.82 Hz, 6 H), 2.11 (s, 3 H), 2.19 (s, 3 H), 2.25 (s, 3 H), 4.37 (d, J = 5.05 Hz, 2 H), 4.84-4.96 (m, J = 13.29, 6.59, 6.59, 6.59, 6.59 Hz, 1 H), 5.87 (s, 1 H), 7.32 (d, J = 1.52 Hz, 1 H), 7.35 (s, 1 H), 7.90 (d, J = 1.26 Hz, 1 H), 8.16-8.25 (m, 2 H), 8.53 (d, J = 2.02 Hz, 1 H), 8.94 (d, J = 2.02 Hz, 1 H), 11.47 (s, 1 H), 13.67 (s, 1 H) | 469 |
| 241 | 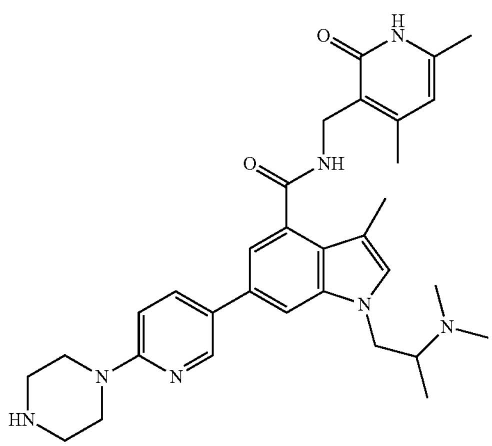 [SMILES: Cc1cc(C)c(CNC(=O)c2cc(-c3ccc(N4CCNCC4)nc3)cc3c2c(C)cn3CC(C)N(C)C)c(=O)[nH]1] | N-((4,6-dimethyl-2-oxo-1,2-dihydropyridin-3-yl)methyl)-1-(2-(dimethylamino)propyl)-3-methyl-6-(6-(piperazin-1-yl)pyridin-3-yl)-1H-indole-4-carboxamide | 0.82 (d, 3 H), 2.10 (s, 3 H), 2.14 (s, 3 H), 2.20 (s, 6 H), 2.23 (s, 3 H), 2.75-2.84 (m, 4 H), 2.91-3.04 (m, 1 H), 3.39-3.50 (m, 4 H), 4.03 (dd, J = 14.40, 7.07 Hz, 1 H), 4.20 (dd, J = 14.15, 7.07 Hz, 1 H), 4.34 (d, J = 5.05 Hz, 2 H), 5.86 (s, 1 H), 6.88 (d, J = 8.84 Hz, 1 H), 7.14 (s, 1 H), 7.17 (d, J = 1.26 Hz, 1 H), 7.67 (d, J = 1.26 Hz, 1 H), 7.89 (dd, J = 8.84, 2.53 Hz, 1 H), 8.17 (t, J = 4.93 Hz, 1 H), 8.49 (d, J = 2.27 Hz, 1 H), 11.48 (br. s., 1 H) | 556.7 |
| 242 | 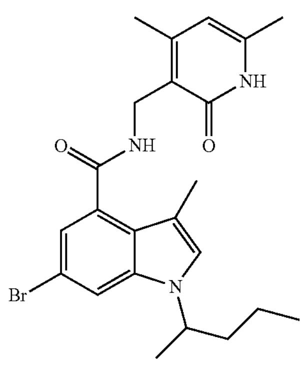 [SMILES: CCCC(C)n1cc(C)c2c(C(=O)NCc3c(C)cc(C)[nH]c3=O)cc(Br)cc21] | 6-bromo-N-((4,6-dimethyl-2-oxo-1,2-dihydropyridin-3-yl)methyl)-3-methyl-1-(pentan-2-yl)-1H-indole-4-carboxamide | 0.76-0.86 (m, 3 H), 0.92-1.20 (m, 2 H), 1.36 (d, J = 6.82 Hz, 3 H), 1.63-1.86 (m, 2 H), 2.08-2.15 (m, 6 H), 2.19-2.26 (m, 3 H), 4.30 (d, J = 5.05 Hz, 2 H), 4.51-4.68 (m, 1 H), 5.86 (s, 1 H), 6.99 (d, J = 1.52 Hz, 1 H), 7.31 (s, 1 H), 7.78 (d, J = 1.77 Hz, 1 H), 8.25 (t, J = 4.93 Hz, 1 H), 11.48 (s, 1 H) | |

-continued

| Ex | Structure | Name | ¹H NMR (400 MHz, DMSO-d₆) δ ppm | MS(ES) [M + H]⁺ |
|---|---|---|---|---|
| 243 | 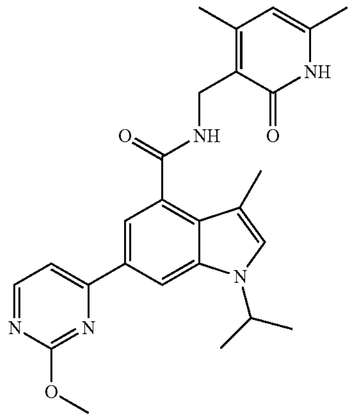 [SMILES: COc1nccc(-c2cc(C(=O)NCc3c(C)cc(C)[nH]c3=O)c3c(C)cn(C(C)C)c3c2)n1] | N-((4,6-dimethyl-2-oxo-1,2-dihydropyridin-3-yl)methyl)-1-isopropyl-6-(2-methoxypyrimidin-4-yl)-3-methyl-1H-indole-4-carboxamide | 1.46 (d, J = 6.57 Hz, 6 H), 2.12 (s, 3 H), 2.18 (s, 3 H), 2.25 (s, 3 H), 4.00 (s, 3 H), 4.37 (d, J = 4.80 Hz, 2 H), 4.92 (spt, J = 6.61 Hz, 1 H), 5.87 (s, 1 H), 7.49 (s, 1 H), 7.79-7.86 (m, 2 H), 8.22 (t, J = 5.05 Hz, 1 H), 8.38 (d, J = 1.26 Hz, 1 H), 8.60 (d, J = 5.30 Hz, 1 H), 11.48 (s, 1 H) | 460.4 |
| 244 | 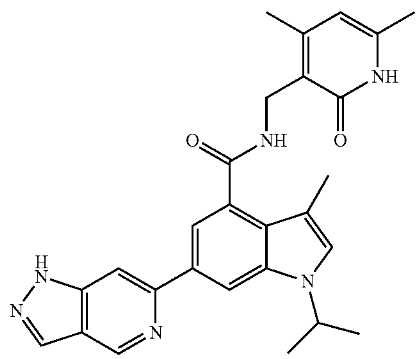 [SMILES: Cc1cc(C)c(CNC(=O)c2cc(-c3cc4[nH]ncc4cn3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1H-pyrazolo[4,3-c]pyridin-6-yl)-1H-indole-4-carboxamide | 1.46 (d, J = 6.57 Hz, 6 H), 2.12 (s, 3 H), 2.19 (s, 3 H), 2.26 (s, 3 H), 4.38 (d, J = 5.05 Hz, 2 H), 4.90 (spt, J = 6.61 Hz, 1 H), 5.88 (s, 1 H), 7.37 (s, 1 H), 7.79 (d, J = 1.26 Hz, 1 H), 8.08 (s, 1 H), 8.19 (t, J = 4.93 Hz, 1 H), 8.27-8.35 (m, 2 H), 9.18 (d, J = 1.01 Hz, 1 H), 11.48 (br. s., 1 H), 13.45 (br. s., 1 H) | 469.4 |
| 245 | 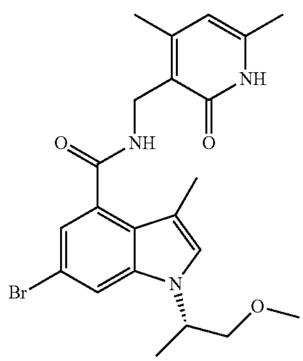 [SMILES: COC[C@H](C)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-3-methyl-1-[(1R)-1-methyl-2-(methyloxy)ethyl]-1H-indole-4-carboxamide | 1.33-1.40 (m, 3 H), 2.12 (d, J = 4.80 Hz, 6 H), 2.22 (s, 3 H), 3.15-3.21 (m, 3 H), 3.49-3.65 (m, 2 H), 4.31 (d, J = 5.05 Hz, 2 H), 4.73-4.90 (m, 1 H), 5.87 (s, 1 H), 6.97-7.06 (m, 1 H), 7.31 (s, 1 H), 7.78 (d, J = 1.52 Hz, 1 H), 8.26 (t, J = 4.93 Hz, 1 H), 11.48 (s, 1 H) | 460.2 |
| 246 | 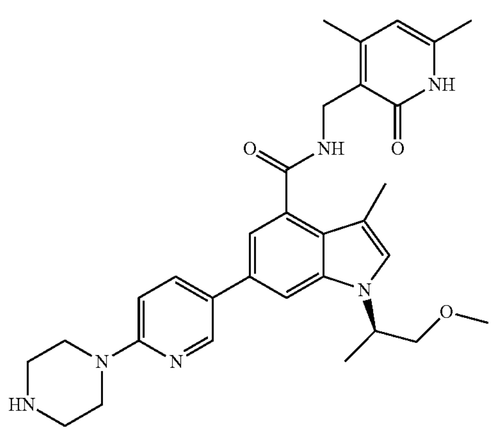 [SMILES: COC[C@@H](C)n1cc(C)c2c(C(=O)NCc3c(C)cc(C)[nH]c3=O)cc(-c3ccc(N4CCNCC4)nc3)cc21] | N-[(4,6-dimethyl-2-oxo-1,2-dihydro-3-pyridinyl)methyl]-3-methyl-1-[(1S)-1-methyl-2-(methyloxy)ethyl]-6-[6-(1-piperazinyl)-3-pyridinyl]-1H-indole-4-carboxamide | 1.41 (m, 3 H), 2.11 (s, 3 H), 2.15 (s, 3 H), 2.24 (s, 3 H), 2.77-2.83 (m, 3 H), 3.13-3.26 (m, 3 H), 3.41-3.48 (m, 3 H), 3.53-3.69 (m, 2 H), 4.35 (d, J = 5.05 Hz, 2 H), 4.85-4.99 (m, 1 H), 5.87 (s, 1 H), 6.85-6.93 (m, 1 H), 7.18 (d, J = 1.26 Hz, 1 H), 7.27 (s, 1 H), 7.74 (d, J = 1.26 Hz, 1 H), 7.88-7.96 (m, 1 H), 8.17 (t, J = 4.93 Hz, 1 H), 8.45-8.54 (m, 1 H) | 543.7 |

-continued

| Ex | Structure | Name | ¹H NMR (400 MHz, DMSO-d₆) δ ppm | MS(ES) [M + H]⁺ |
|---|---|---|---|---|
| 247 | 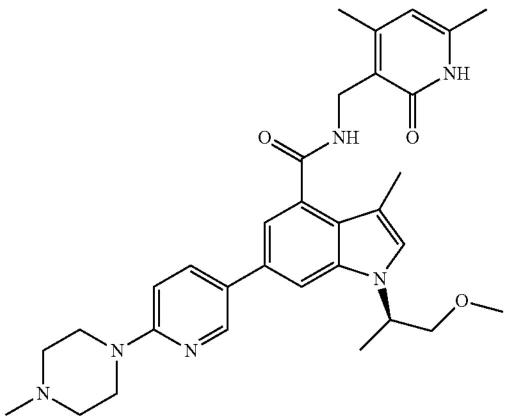 | N-[(4,6-dimethyl-2-oxo-1,2-dihydro-3-pyridinyl)methyl]-3-methyl-1-[(1S)-1-methyl-2-(methyloxy)ethyl]-6-[6-(4-methyl-1-piperazinyl)-3-pyridinyl]-1H-indole-4-carboxamide | 1.41 (d, J = 6.82 Hz, 3 H), 2.11 (s, 3 H), 2.16 (s, 3 H), 2.23 (d, J = 4.04 Hz, 5 H), 2.39-2.45 (m, 4 H), 3.31-3.38 (m, 1 H), 3.47-3.70 (m, 6 H), 4.35 (d, J = 5.05 Hz, 2 H), 4.84-4.99 (m, 1 H), 5.87 (s, 1 H), 6.92 (d, J = 8.84 Hz, 1 H), 7.19 (d, J = 1.52 Hz, 1 H), 7.27 (s, 1 H), 7.75 (d, J = 1.26 Hz, 1 H), 7.92 (dd, J = 8.84, 2.78 Hz, 1 H), 8.19 (t, J = 4.93 Hz, 1 H), 8.51 (d, J = 2.53 Hz, 1 H) | 557.8 |
| 248 | 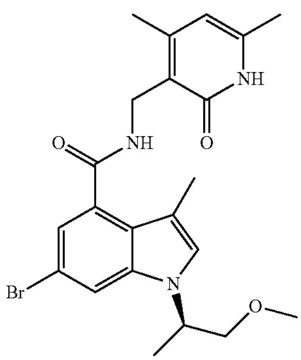 [SMILES: COC[C@@H](C)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-3-methyl-1-[(1S)-1-methyl-2-(methyloxy)ethyl]-1H-indole-4-carboxamide | 1.37 (m, 3 H), 2.12 (d, J = 4.55 Hz, 6 H), 2.22 (s, 3 H), 3.18 (s, 3 H), 3.50-3.66 (m, 2 H), 4.30 (d, J = 5.05 Hz, 2 H), 4.72-4.87 (m, 1 H), 5.80-5.92 (m, 1 H), 7.00 (d, J = 1.52 Hz, 1 H), 7.31 (s, 1 H), 7.78 (d, J = 1.52 Hz, 1 H), 8.26 (t, J = 4.80 Hz, 1 H), 11.48 (s, 1 H) | 460.2 |
| 249 | 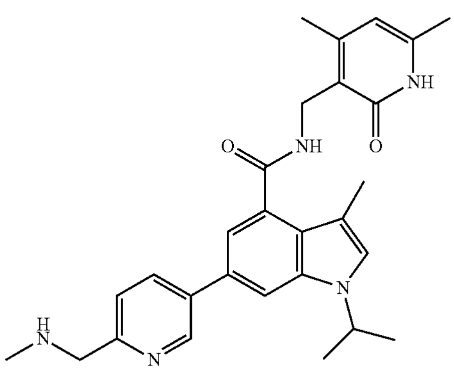 | N-[(4,6-dimethyl-2-oxo-1,2-dihydro-3-pyridinyl)methyl]-3-methyl-6-{6-[(methylamino)methyl]-3-pyridinyl}-1-(1-methylethyl)-1H-indole-4-carboxamide | 11.52 (s, 1H) 8.87 (d, J = 2.27 Hz, 1 H) 8.21 (t, J = 5.05 Hz, 1 H) 8.08-8.14 (m, 1 H) 7.86 (d, J = 1.26 Hz, 1 H) 7.49 (d, J = 8.08 Hz, 1 H) 7.36 (s, 1 H) 7.28 (d, J = 1.26 Hz, 1 H) 5.87 (s, 1 H) 4.89 (dt, J = 13.33, 6.60 Hz, 1 H) 4.36 (s, 1 H) 4.35 (s, 1 H) 3.78 (s, 2 H) 2.29-2.38 (m, 3 H) 2.24 (s, 3 H) 2.18 (s, 3 H) 2.11 (s, 3 H) 1.45 (s, 3 H) 1.43 (s, 3 H) | 472.3 |

-continued

| Ex | Structure | Name | $^1$H NMR (400 MHz, DMSO-d$_6$) δ ppm | MS(ES) [M + H]$^+$ |
|---|---|---|---|---|
| 250 | 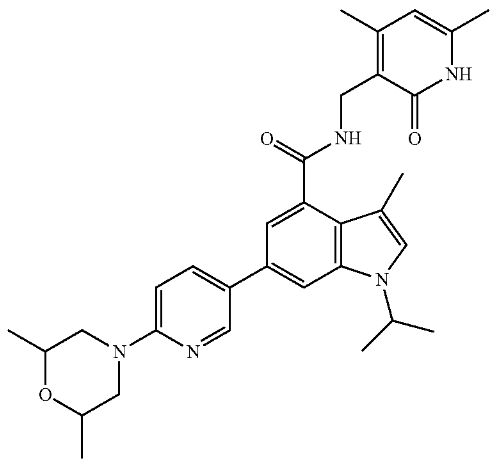 | 6-[6-(2,6-dimethyl-4-morpholinyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 11.47 (s, 1 H) 8.51 (d, J = 2.27 Hz, 1 H) 8.15 (t, J = 4.93 Hz, 1 H) 7.94 (dd, J = 8.84, 2.53 Hz, 1 H) 7.72 (d, J = 1.26 Hz, 1 H) 7.27-7.31 (m, 1 H) 7.19 (d, J = 1.26 Hz, 1 H) 6.94 (d, J = 8.84 Hz, 1 H) 5.87 (s, 1 H) 4.85 (quin, J = 6.63 Hz, 1 H) 4.36 (s, 1 H) 4.34 (s, 1 H) 4.19-4.22 (m, 1 H) 4.17 (s, 1 H) 3.60-3.68 (m, 2 H) 2.42 (dd, J = 12.63, 10.61 Hz, 2 H) 2.24 (s, 3 H) 2.16 (s, 3 H) 2.11 (s, 3 H) 1.44 (s, 3 H) 1.42 (s, 3 H) 1.19 (s, 3 H) 1.18 (s, 3 H) | 542.5 |
| 251 | 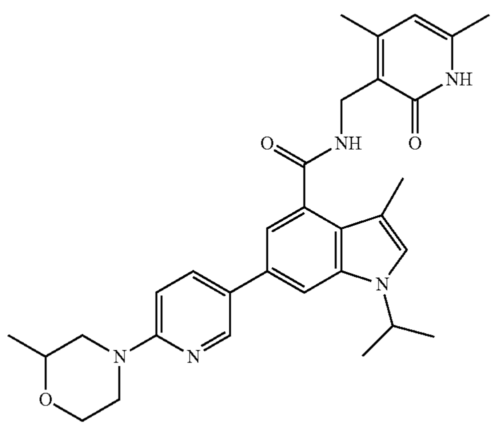 | N-[(4,6-dimethyl-2-oxo-1,2-dihydro-3-pyridinyl)methyl]-3-methyl-1-(1-methylethyl)-6-[6-(2-methyl-4-morpholinyl)-3-pyridinyl]-1H-indole-4-carboxamide | 11.48 (s, 1 H) 8.52 (d, J = 2.53 Hz, 1 H) 8.16 (t, J = 5.05 Hz, 1 H) 7.95 (dd, J = 8.84, 2.53 Hz, 1 H) 7.73 (d, J = 1.26 Hz, 1 H) 7.29 (s, 1 H) 7.19 (d, J = 1.26 Hz, 1 H) 6.93 (d, J = 8.84 Hz, 1 H) 5.87 (s, 1 H) 4.85 (dt, J = 13.20, 6.66 Hz, 1 H) 4.35 (s, 1 H) 4.34 (s, 1 H) 4.18 (d, J = 12.38 Hz, 1 H) 4.07 (s, 1 H) 3.93 (dd, J = 11.37, 2.27 Hz, 1 H) 3.54-3.64 (m, 2 H) 2.82 (td, J = 12.25, 3.54 Hz, 1 H) 2.52-2.56 (m, 1 H) 2.22-2.26 (m, 3 H) 2.16 (s, 3 H) 2.11 (s, 3 H) 1.44 (s, 3 H) 1.42 (s, 3 H) 1.18 (d, J = 6.32 Hz, 3 H) | 528.3 |
| 252 | 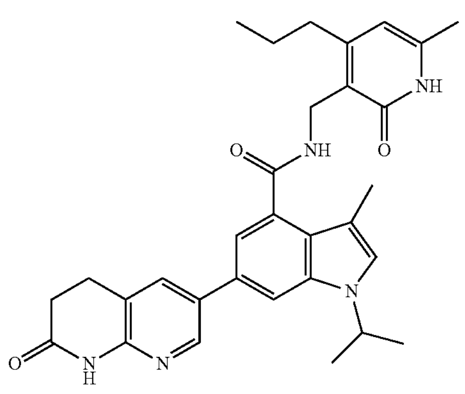 [SMILES: CCCc1cc(C)[nH]c(=O)c1CNC(=O)c1cc(-c2cnc3c(c2)CCC(=O)N3)cc2c1c(C)cn2C(C)C] | 3-methyl-1-(1-methylethyl)-N-[(6-methyl-2-oxo-4-propyl-1,2-dihydro-3-pyridinyl)methyl]-6-(7-oxo-5,6,7,8-tetrahydro-1,8-naphthyridin-3-yl)-1H-indole-4-carboxamide | 11.44 (br. s., 1 H) 10.53 (br. s., 1 H) 8.48 (d, J = 2.27 Hz, 1 H) 8.11-8.22 (m, 1 H) 8.01 (d, J = 2.27 Hz , 17 H) 7.82 (d, J = 1.26 Hz, 1 H) 7.34 (s, 1 H) 7.25 (d, J = 1.26 Hz, 1 H) 5.90 (s, 1 H) 4.88 (quin, J = 6.69 Hz, 1 H) 4.37 (br. s., 1 H) 4.36 (br. s., 1 H) 2.98 (t, J = 7.58 Hz, 2 H) 2.53-2.57 (m, 4 H) 2.17 (s, 3 H) 2.12 (s, 3 H) 1.53-1.62 (m, 2 H) 1.45 (s, 3 H) 1.43 (s, 3 H) 0.94 (t, J = 7.45 Hz, 3 H) | 526.2 |

| Ex | Structure | Name | ¹H NMR (400 MHz, DMSO-d₆) δ ppm | MS(ES) [M + H]⁺ |
|---|---|---|---|---|
| 253 | 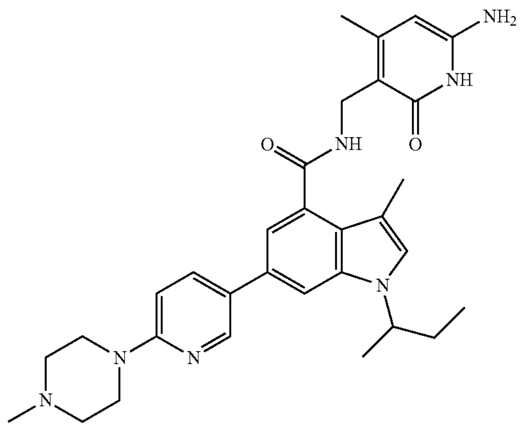 [SMILES: CCC(C)n1cc(C)c2c(C(=O)NCc3c(C)cc(N)[nH]c3=O)cc(-c3ccc(N4CCN(C)CC4)nc3)cc21] | N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 10.47 (br. s., 1 H) 8.50 (d, J = 2.53 Hz, 1 H) 7.98 (br. s., 1 H) 7.92 (dd, J = 8.84, 2.53 Hz, 1 H) 7.71-7.74 (m, 1 H) 7.26 (s, 1 H) 7.16 (d, J = 1.26 Hz, 1 H) 6.92 (d, J = 9.09 Hz, 1 H) 5.76 (s, 2 H) 5.16 (br. s., 1 H) 4.57-4.65 (m, 1 H) 4.26 (br. s., 1 H) 4.25 (br. s., 1 H) 3.52 (br. s., 4 H) 2.42 (br. s., 4 H) 2.23 (s, 3 H) 2.18 (s, 3 H) 2.13 (s, 3 H) 1.81 (td, J = 7.20, 3.03 Hz, 2 H) 1.41 (d, J = 6.82 Hz, 3 H) 0.73 (t, J = 7.20 Hz, 3 H) | 542.6 |
| 254 | 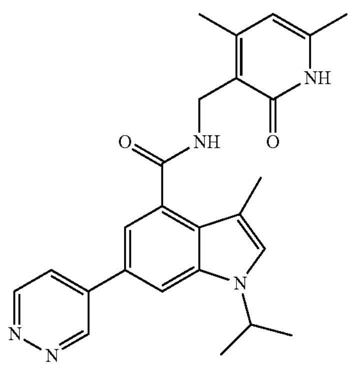 [SMILES: Cc1cc(C)c(CNC(=O)c2cc(-c3ccnnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridazin-4-yl)-1H-indole-4-carboxamide | 11.10-11.70 (br. s, 1H), 9.77 (dd, J = 1.26, 2.53 Hz, 1H), 9.22 (dd, J = 1.14, 5.43 Hz, 1H), 8.30 (br. s., 1H), 8.19 (d, J = 1.52 Hz, 1H), 8.09 (dd, J = 2.53, 5.56 Hz, 1H), 7.42-7.54 (m, 2H), 5.87 (s, 1H), 4.96 (quin, J = 6.63 Hz, 1H), 4.36 (d, J = 5.05 Hz, 2H), 2.25 (s, 3H), 2.18 (s, 3H), 2.11 (s, 3H), 1.45 (d, 6H) | 430.3 |
| 255 | 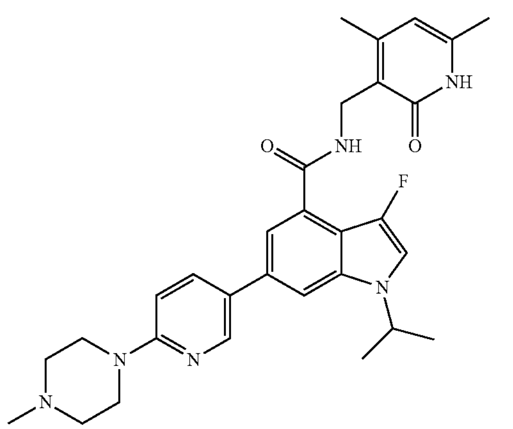 | N-((4,6-dimethyl-2-oxo-1,2-dihydropyridin-3-yl)methyl)-3-fluoro-1-isopropyl-6-(6-(4-methylpiperazin-1-yl)pyridin-3-yl)-1H-indole-4-carboxamide | 11.48 (d, J = 11.87 Hz, 1H), 8.54 (d, J = 2.53 Hz, 1H), 8.19 (t, J = 5.05 Hz, 1H), 8.16 (s, 1H), 7.96 (dd, J = 2.53, 8.84 Hz, 1H), 7.86 (s, 1H), 7.58 (d, J = 2.27 Hz, 1H), 7.43 (d, J = 1.01 Hz, 1H), 6.94 (d, J = 8.84 Hz, 1H), 5.88 (s, 1H), 4.86-5.03 (m, J = 7.07 Hz, 1H), 4.36 (d, J = 4.80 Hz, 2H), 3.48-3.59 (m, 4H), 2.44 (t, J = 4.93 Hz, 4H), 2.23 (d, J = 10.36 Hz, 6H), 2.12 (s, 3H), 1.42 (d, 6H) | 531.4 |

| Ex | Structure | Name | ¹H NMR (400 MHz, DMSO-d$_6$) δ ppm | MS(ES) [M + H]$^+$ |
|---|---|---|---|---|
| 256 | 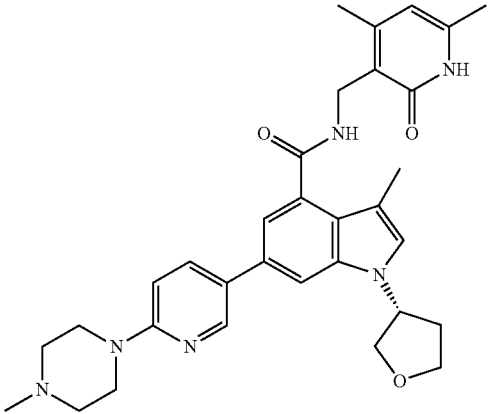 | (R)-N-((4,6-dimethyl-2-oxo-1,2-dihydropyridin-3-yl)methyl)-3-methyl-6-(6-(4-methylpiperazin-1-yl)pyridin-3-yl)-1-(tetrahydrofuran-3-yl)-1H-indole-4-carboxamide | 2.02-2.13 (m, 4 H), 2.15 (s, 3 H), 2.19-2.28 (m, 6 H), 2.37-2.49 (m, 5 H), 3.45-3.59 (m, 4 H), 3.77-3.89 (m, 2 H), 3.94-4.01 (m, 1 H), 4.01-4.11 (m, 1 H), 4.35 (d, J = 5.05 Hz, 2 H), 5.33 (dd, J = 7.96, 5.68 Hz, 1 H), 5.87 (s, 1 H), 6.93 (d, J = 8.84 Hz, 1 H), 7.15-7.26 (m, 2 H), 7.81 (d, J = 1.26 Hz, 1 H), 7.93 (dd, J = 8.84, 2.53 Hz, 1 H), 8.16 (t, J = 5.05 Hz, 1 H), 8.52 (d, J = 2.53 Hz, 1 H), 11.47 (s, 1 H) | 555.6 |
| 257 | 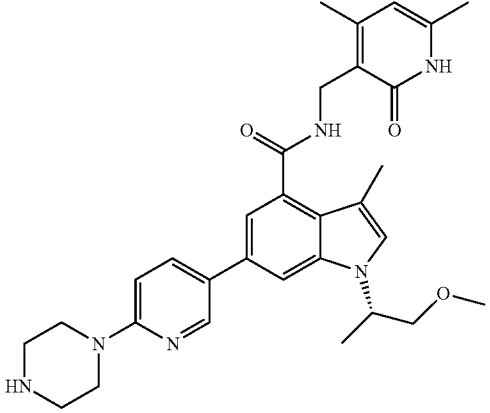 [SMILES: COC[C@H](C)n1cc(C)c2c(C(=O)NCc3c(C)cc(C)[nH]c3=O)cc(-c3ccc(N4CCNCC4)nc3)cc21] | (S)-N-((4,6-dimethyl-2-oxo-1,2-dihydropyridin-3-yl)methyl)-1-(1-methoxypropan-2-yl)-3-methyl-6-(6-(piperazin-1-yl)pyridin-3-yl)-1H-indole-4-carboxamide | 1.34-1.48 (m, 3 H), 2.11 (s, 3 H), 2.16 (s, 3 H), 2.24 (s, 3 H), 2.76-2.86 (m, 4 H), 3.34 (s, 3 H), 3.40-3.48 (m, 4 H), 3.53-3.69 (m, 2 H), 4.35 (d, J = 5.05 Hz, 2 H) 4.84-4.98 (m, 1 H), 5.87 (s, 1 H), 6.88 (d, J = 8.84 Hz, 1 H), 7.18 (d, J = 1.26 Hz, 1 H), 7.27 (d, J = 1.01 Hz, 1 H), 7.74 (d, J = 1.26 Hz, 1 H), 7.87-7.96 (m, 1 H), 8.17 (t, J = 5.05 Hz, 1 H), 8.44-8.54 (m, 1 H) | 543.5 |
| 258 | 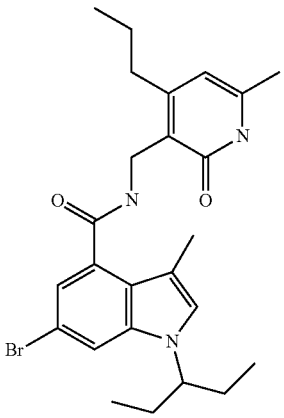 [SMILES: CCCc1cc(C)[nH]c(=O)c1CNC(=O)c1cc(Br)cc2c1c(C)cn2C(CC)CC] | 6-bromo-1-(1-ethylpropyl)-3-methyl-N-[(6-methyl-2-oxo-4-propyl-1,2-dihydro-3-pyridinyl)methyl]-1H-indole-4-carboxamide | 11.48 (br. s., 1 H) 8.24 (br. s., 1 H) 7.79 (s, 1 H) 7.28 (s, 1 H) 6.98 (s, 1 H) 5.89 (s, 1 H) 4.33 (d, J = 4.29 Hz, 2 H) 4.21-4.29 (m, 1 H) 2.58-2.55 (m, 2 H) 2.14 (d, J = 9.85 Hz, 6 H) 1.74-1.82 (m, 4 H) 1.55 (br. s., 2 H) 0.94 (t, J = 7.07 Hz, 3 H) 0.64 (t, J = 7.07 Hz, 6 H) | 486.3 |

-continued

| Ex | Structure | Name | ¹H NMR (400 MHz, DMSO-d$_6$) δ ppm | MS(ES) [M + H]⁺ |
|---|---|---|---|---|
| 259 | 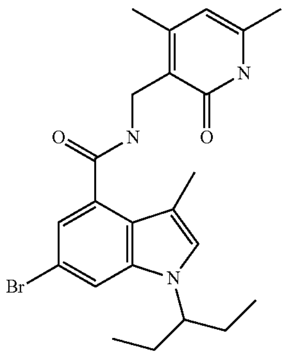 [SMILES: CCC(CC)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-1-(1-ethylpropyl)-3-methyl-1H-indole-4-carboxamide | 11.47 (br. s., 1 H) 8.26 (t, J = 4.80 Hz, 1 H) 7.79 (d, J = 1.26 Hz, 1 H) 7.27 (s, 1 H) 6.99 (d, J = 1.52 Hz, 1 H) 5.86 (s, 1 H) 4.31 (d, J = 4.80 Hz, 2 H) 4.23-4.29 (m, 1 H) 2.22 (s, 3 H) 2.13 (d, J = 11.62 Hz, 6 H) 1.73-1.83 (m, 4 H) 0.64 (t, J = 7.33 Hz, 6 H) | 458.2 |
| 260 | 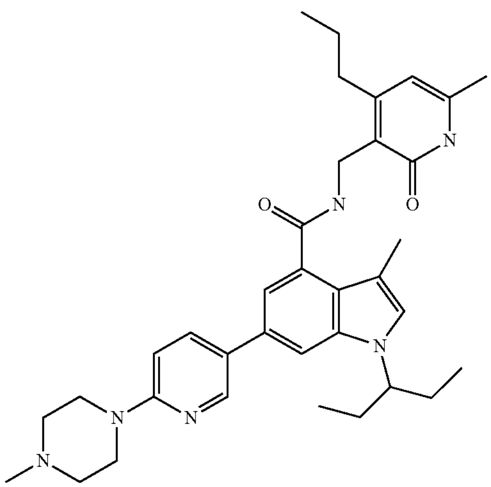 | 1-(1-ethylpropyl)-3-methyl-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.49 (br. s., 1 H) 8.49 (br. s., 1 H) 8.15 (br. s., 1 H) 7.90 (br. s., 1 H) 7.75 (br. s., 1 H) 7.11-7.26 (m, 2 H) 6.93 (br. s., 1 H) 5.90 (br. s., 1 H) 4.37 (br. s., 3 H) 3.47-3.57 (m, 4 H) 2.36-2.45 (m, 6 H) 2.10-2.25 (m, 9 H) 1.81 (br. s., 4 H) 1.58 (br. s., 2 H) 0.94 (br. s., 3 H) 0.67 (br. s., 6 H) | 583.8 |
| 261 | 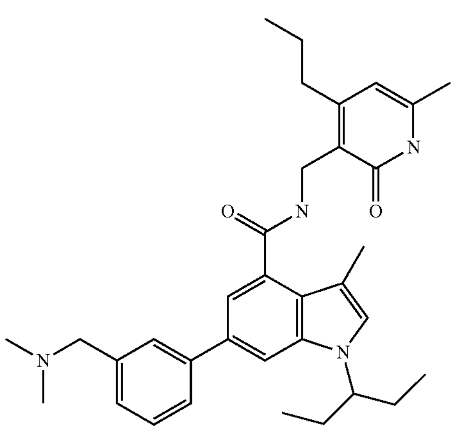 | 6-{3-[(dimethylamino)methyl]phenyl}-1-(1-ethylpropyl)-3-methyl-N-[(6-methyl-2-oxo-4-propyl-1,2-dihydro-3-pyridinyl)methyl]-1H-indole-4-carboxamide | 11.37 (br. s., 1 H) 7.39-7.58 (m, 7 H) 6.95 (br. s., 1 H) 5.89 (br. s., 1 H) 4.66 (d, J = 5.31 Hz, 2 H) 4.16 (br. s., 1 H) 3.53 (br. s., 2 H) 2.68-2.18 (m, 2 H) 2.31 (br. s., 9 H) 2.09 (br. s., 3 H) 1.80-1.96 (m, 4 H) 1.60-1.72 (m, 2 H) 0.98-1.09 (m, 3 H) 0.79 (d, J = 6.06 Hz, 6 H) | 541.2 |

| Ex | Structure | Name | $^1$H NMR (400 MHz, DMSO-$d_6$) δ ppm | MS(ES) [M + H]$^+$ |
|---|---|---|---|---|
| 262 | 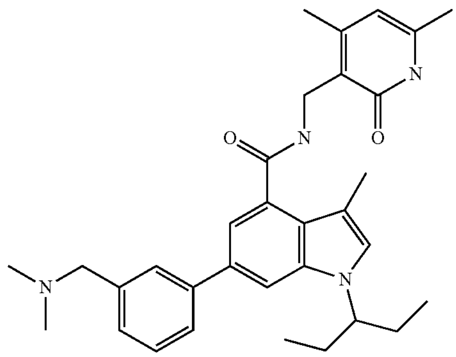 | 6-{3-[(dimethylamino)methyl]phenyl}-N-[(4,6-dimethyl-2-oxo-1,2-dihydro-3-pyridinyl)methyl]-1-(1-ethylpropyl)-3-methyl-1H-indole-4-carboxamide | 11.47 (br. s., 1 H) 8.23 (br. s., 1 H) 7.78 (br. s., 1 H) 7.61 (br. s., 2 H) 7.40 (br. s., 1 H) 7.19-7.29 (m, 3 H) 5.87 (br. s., 1 H) 4.33-4.45 (m, 3 H) 3.47 (br. s., 2 H) 2.24 (br. s., 3 H) 2.18 (br. s., 9 H) 2.11 (br. s., 3 H) 1.75-1.90 (m, 4 H) 0.68 (br. s., 6 H) | 513.4 |
| 263 | 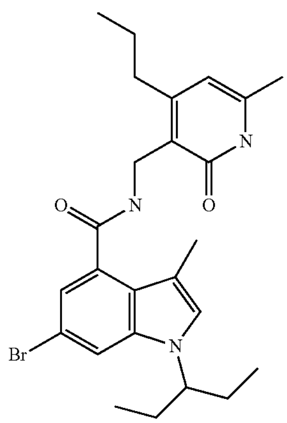 [SMILES: CCCc1cc(C)[nH]c(=O)c1CNC(=O)c1cc(Br)cc2c1c(C)cn2C(CC)CC] | 6-bromo-1-(1-ethylpropyl)-3-methyl-N-[(6-methyl-2-oxo-4-propyl-1,2-dihydro-3-pyridinyl)methyl]-1H-indole-4-carboxamide | 11.48 (br. s., 1 H) 8.24 (br. s., 1 H) 7.79 (s, 1 H) 7.28 (s, 1 H) 6.98 (s, 1 H) 5.89 (s, 1 H) 4.33 (d, J = 4.29 Hz, 2 H) 4.21-4.29 (m, 1 H) 2.58-2.55 (m, 2 H) 2.14 (d, J = 9.85 Hz, 6 H) 1.74-1.82 (m, 4 H) 1.55 (br. s., 2 H) 0.94 (t, J = 7.07 Hz, 3 H) 0.64 (t, J = 7.07 Hz, 6 H) | 486.3 |

Example 264

N-((4,6-dimethyl-2-oxo-1,2-dihydropyridin-3-yl)methyl)-1-isopropyl-3-methyl-6-(6-(4-methylpiperazin-1-yl)pyridin-3-yl)-1H-indole-4-carboxamide

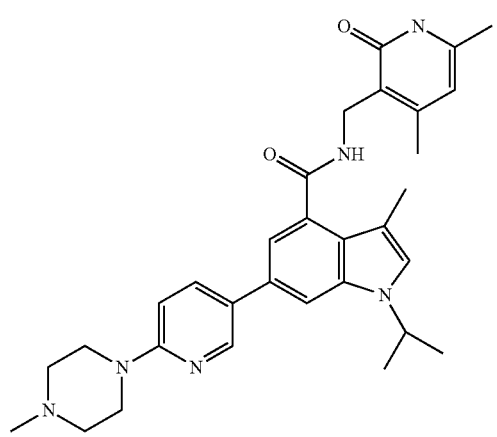

To a stirred solution of 6-bromo-N-((1,2-dihydro-4,6-dimethyl-2-oxopyridin-3-yl)methyl)-1-isopropyl-3-methyl-1H-indole-4-carboxamide (2 g, 4.65 mmol) in DMF (100 mL) was added 1-methyl-4-(5-(4,4,5,5-tetramethyl-1,3,2-dioxaborolan-2-yl)pyridin-2-yl)piperazine (1.55 g, 5.12 mmol) followed by a solution of sodium carbonate (1.23 g, 11.62 mmol) in water (10 mL) and the contents were degassed with argon for 30 min. After that PdCl$_2$(PPh$_3$)$_2$ (326 mg, 0.464 mmol) was added and the contents again degassed with argon for 10 min. The reaction mixture was stirred at reflux for 3 h. The reaction mixture was diluted with water (100 mL) and extracted with ethyl acetate (3×150 mL). The combined organic layers were dried over anhydrous Na$_2$SO$_4$, filtered, and concentrated to afford the crude product (2.8 g). The crude compound was purified by column chromatography over silica gel (100-200 mesh, eluent: 0-10% MeOH: DCM), and the obtained product was further triturated with diethyl ether (100 mL) to afford the title compound as an off white solid (1.2 g, 50%). $^1$H NMR (DMSO-$d_6$, 400 MHz): δ 1.493 (d, J=6.4 Hz, 6H), 2.092 (s, 3H), 2.286 (s, 3H), 2.409 (s, 3H), 2.424 (s, 3H), 2.632 (s, 4H), 3.621 (s, 4H), 4.603-4.685 (m, 3H), 5.880 (s, 1H), 6.606 (d, J=8.8 Hz, 1H), 7.016 (s, 1H), 7.261 (s, 1H), 7.433 (s, 1H), 7.675-7.704 (dd, J=9 Hz, 2.4 Hz, 1H), 8.425 (d, J=2.0 Hz, 1H), 11.699 (brs, 1H); LCMS (ES+): 525.23 [M−H].

Example 265

N-[(4,6-dimethyl-2-oxo-1,2-dihydro-3-pyridinyl)methyl]-3-methyl-1-(1-methylethyl)-6-[6-(1-piperazinyl)-3-pyridinyl]-1H-indole-4-carboxamide

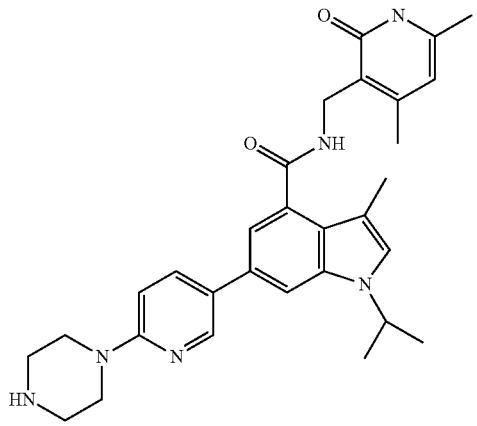 [SMILES: Cc1cc(C)c(CNC(=O)c2cc(-c3ccc(N4CCNCC4)nc3)cc3c2c(C)cn3C(C)C)c(=O)[nH]1]

6-Bromo-N-[(4,6-dimethyl-2-oxo-1,2-dihydro-3-pyridinyl)methyl]-3-methyl-1-(1-methylethyl)-1H-indole-4-carboxamide (1.9 g, 4.42 mmol), 1-[5-(4,4,5,5-tetramethyl-1,3,2-dioxaborolan-2-yl)-2-pyridinyl]piperazine (1.277 g, 4.42 mmol) and potassium phosphate (tribasic) (2.81 g, 13.25 mmol) were placed in a 150 mL pressure vessel followed by addition of 1,4-dioxane (40 mL) and water (10.00 mL). The suspension was stirred and degassed under $N_2$ for 15 min. (emulsion). Next added in $PdCl_2(dppf)$-$CH_2Cl_2$ adduct (0.361 g, 0.442 mmol) and degassed for 2 min. The reaction flask was sealed and the contents heated at reflux for 2 h. The suspension was filtered, and dioxane was removed in vacuo. The resultant oil was partitioned between 300 mL of ethyl acetate and 100 mL of water, and the layers were separated. Decolorizing carbon was added, and after 10 min, the organic layer was filtered through short pad of silica. 300 mL of 1M HCl was added and neutralized with NaOH (to pH ~9). The contents were extracted with ethyl acetate. The organic layer was separated, washed with brine, dried over $MgSO_4$, filtered and concentrated in vacuo. The product was suspended in diethyl ether and filtered. The title compound was isolated as a yellow solid (950 mg, 41% yield). $^1$H NMR (400 MHz, DMSO-$d_6$) δ 11.49 (br. s., 1H), 8.52 (d, J=2.27 Hz, 1H), 8.15 (t, J=5.05 Hz, 1H), 7.95 (dd, J=2.53, 8.84 Hz, 1H), 7.73 (d, J=1.26 Hz, 1H), 7.29 (s, 1H), 7.19 (d, J=1.52 Hz, 1H), 6.93 (d, J=9.09 Hz, 1H), 5.87 (s, 1H), 4.85 (quin, J=6.63 Hz, 1H), 4.35 (d, J=5.05 Hz, 2H), 3.49-3.63 (m, 4H), 2.81-3.02 (m, 4H), 2.24 (s, 3H), 2.16 (s, 3H), 2.11 (s, 3H), 1.43 (d, J=6.57 Hz, 6H); LCMS=513.3 (MH+).

Example 266

6-bromo-1-(sec-butyl)-N-((4,6-dimethyl-2-oxo-1,2-dihydropyridin-3-yl)methyl)-3-methyl-1H-indole-4-carboxamide

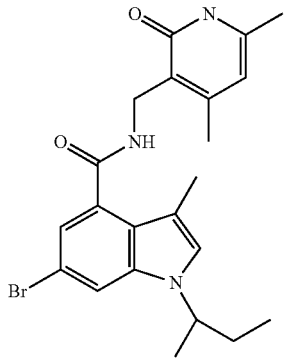 [SMILES: CCC(C)n1cc(C)c2c(C(=O)NCc3c(C)cc(C)[nH]c3=O)cc(Br)cc21]

Added sequentially to a reaction flask were 6-bromo-1-(sec-butyl)-3-methyl-1H-indole-4-carboxylic acid (1.33 g, 4.29 mmol), 3-(aminomethyl)-4,6-dimethyl-2(1H)-pyridinone (1.213 g, 6.43 mmol), 1-hydroxy-7-azabenzotriazole (0.875 g, 6.43 mmol), EDC (1.233 g, 6.43 mmol), followed by DMSO (30 mL, via syringe) and then N-methylmorpholine (1.886 mL, 17.15 mmol, via syringe). The contents were sealed and stirred at room temperature and the solids gradually dissolved. The contents were stirred at room temperature for 32 h, and then slowly diluted into 220 mL of ice-water with stirring. The contents were stirred for 10 min, and then allowed to stand for an additional 10 min. The contents were filtered and the filtered solid was washed with additional water (50 mL). The solid was then air dried for 10 min, and then in a vacuum oven at 50° C. for 23 h total. The product was collected as 1.75 g (87%). $^1$H NMR (400 MHz, DMSO-d6) δ ppm 0.69 (t, J=7.33 Hz, 3H), 1.36 (d, J=6.57 Hz, 3H), 1.77 (dq, J=10.29, 7.09 Hz, 2H), 2.12 (d, J=9.09 Hz, 6H), 2.21 (s, 3H), 4.30 (d, J=5.05 Hz, 2H), 4.43-4.56 (m, 1H), 5.86 (s, 1H), 6.99 (d, J=1.52 Hz, 1H), 7.30 (s, 1H), 7.77 (d, J=1.77 Hz, 1H), 8.25 (t, J=4.93 Hz, 1H), 11.49 (br. s., 1H); LCMS=444.1 (MH+).

Examples 267 and 268

(S)-6-bromo-1-(sec-butyl)-N-((4,6-dimethyl-2-oxo-1,2-dihydropyridin-3-yl)methyl)-3-methyl-1H-indole-4-carboxamide (Ex 267) and (R)-6-Bromo-1-(sec-butyl)-N-((4,6-dimethyl-2-oxo-1,2-dihydropyridin-3-yl)methyl)-3-methyl-1H-indole-4-carboxamide (Ex 268)

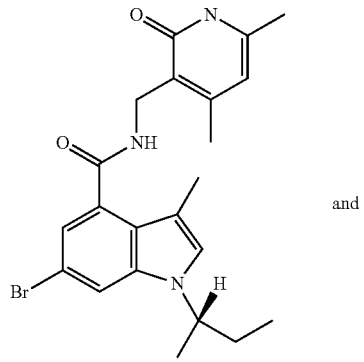

and

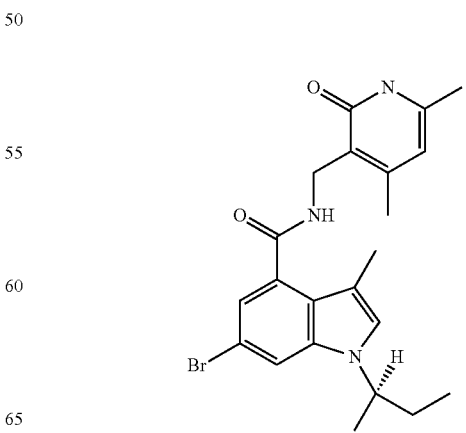

6-Bromo-1-(sec-butyl)-N-((4,6-dimethyl-2-oxo-1,2-dihydropyridin-3-yl)methyl)-3-methyl-1H-indole-4-carboxamide (racemic mixture, 1.9 g) was resolved by chiral HPLC (column: Chiralpak AD-H, 5 microns, 50 mm×250 mm, UV detection: 240 nM, flow rate: 100 mL/min, T=20 deg C., eluent: 60:40:0.1 n-heptane:ethanol:isopropylamine (isocratic)). For each run, 100 mg of the racemic compound was dissolved in 30 volumes (3.0 mL) of warm ethanol with a few drops of isopropylamine added. A total of 19 runs were performed. Baseline resolution was observed for each run. The isomer that eluted at 8.3-10.1 min was collected (following concentration) as a white solid, which was dried at 50° C. (<5 mm Hg) to afford 901 mg, and was determined to be the S isomer* (Ex. 267; chiral HPLC: >99.5% ee (no R isomer detected). The isomer that eluted at 10.8-13.0 min was collected as a white solid, which was dried at 50° C. (<5 mm Hg) to afford 865 mg, and was determined to be the R isomer* (Ex. 268; chiral HPLC: 99.2% ee; 0.4% S isomer detected). $^1$H NMR and LCMS were consistent with the parent racemate. * The absolute configuration was determined by an independent synthesis of each enantiomer from the corresponding commercially available homochiral alcohols via Mitsunobu reaction. The stereochemical assignments were also consistent by vibrational circular dichroism (VCD) analysis.

Example 269

1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide

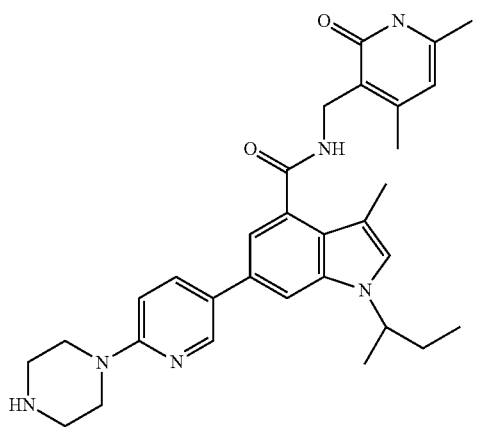 [SMILES: CCC(C)n1cc(C)c2c(C(=O)NCc3c(C)cc(C)[nH]c3=O)cc(-c3ccc(N4CCNCC4)nc3)cc21]

Added sequentially to a reaction vial were 6-bromo-1-(sec-butyl)-N-((4,6-dimethyl-2-oxo-1,2-dihydropyridin-3-yl)methyl)-3-methyl-1H-indole-4-carboxamide (0.15 g, 0.338 mmol), 1-(5-(4,4,5,5-tetramethyl-1,3,2-dioxaborolan-2-yl)pyridin-2-yl)piperazine (0.127 g, 0.439 mmol), and potassium phosphate (tribasic) (0.287 g, 1.350 mmol), followed by 1,4-Dioxane (3 mL) and water (0.75 mL). The suspension was stirred under N$_2$ degassing for 10 min., and then added PdCl$_2$(dppf)-CH$_2$Cl$_2$ adduct (0.028 g, 0.034 mmol). The reaction vial was sealed, placed into a heat block at 95° C., and stirred for 1.5 h. The contents were removed from heating and allowed to cool to room temperature. The aq layer was removed from bottom of the reaction vial via pipette. The reaction mixture was diluted into EtOAc (20 mL) followed by addition of 0.2 g each of Thiol-3 silicycle resin and silica gel.

The volatiles were removed in vacuo and the residue dried on hi-vac for 1 h. The contents were purified by silica gel chromatography (dry loaded, eluent: A: Dichloromethane, B: 10% (2M Ammonia in Methanol) in Chloroform, Gradient B: 8-95%). The obtained solid was concentrated from TBME and dried in vacuum oven at 45° C. for 18 h. The product was collected as 129 mg (70%). $^1$H NMR (400 MHz, DMSO-d6) δ ppm 0.73 (t, J=7.33 Hz, 3H), 1.40 (d, J=6.57 Hz, 3H), 1.80 (dq, J=10.07, 7.08 Hz, 2H), 2.11 (s, 3H), 2.14-2.19 (m, 3H), 2.24 (s, 3H), 2.76-2.85 (m, 4H), 3.41-3.49 (m, 4H), 4.35 (d, J=5.05 Hz, 2H), 4.54-4.67 (m, 1H), 5.87 (s, 1H), 6.88 (d, J=8.84 Hz, 1H), 7.17 (d, J=1.26 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.53 Hz, 1H), 11.48 (br. s., 1H); LCMS MH+=527.3.

Example 270

N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide

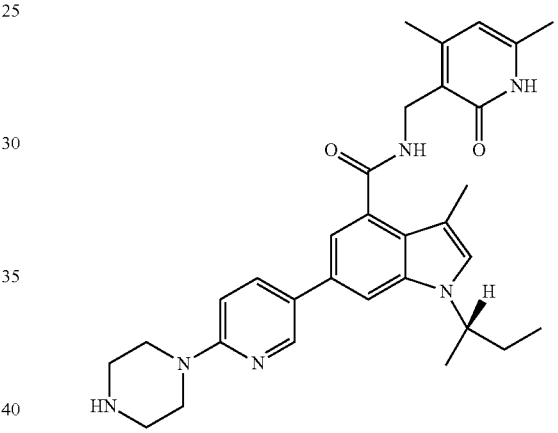

To a 30 mL microwave vial were added (S)-6-bromo-1-(sec-butyl)-N-((4,6-dimethyl-2-oxo-1,2-dihydropyridin-3-yl)methyl)-3-methyl-1H-indole-4-carboxamide (100 mg, 0.225 mmol), 1-(5-(4,4,5,5-tetramethyl-1,3,2-dioxaborolan-2-yl)pyridin-2-yl)piperazine (85 mg, 0.293 mmol), 1,2-Dimethoxyethane (DME) (3 mL), water (1.000 mL) and sodium carbonate (0.338 mL, 0.675 mmol), and the mixture was degassed for 5 min by bubbling nitrogen. PdCl$_2$(dppf)-CH$_2$Cl$_2$ adduct (14.70 mg, 0.018 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/H$_2$O, 0.1% NH$_4$OH to 60% ACN/H$_2$O, 0.1% NH$_4$OH) to give 91 mg of product as off-white solid. $^1$H NMR (400 MHz, DMSO-d6) δ ppm 0.70-0.78 (m, 3H), 1.37-1.44 (m, 3H), 1.75-1.87 (m, 2H), 2.11 (s, 3H), 2.16 (s, 3H), 2.22-2.27 (m, 3H), 2.77-2.85 (m, 4H), 3.41-3.49 (m, 4H), 4.35 (d, J=5.31 Hz, 2H), 4.56-4.68 (m, 1H), 5.87 (s, 1H), 6.88 (d, J=8.84 Hz, 1H), 7.17 (d, J=1.52 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.53 Hz, 1H); LCMS: 527.8 (MH+).

Example 271

N-[(4,6-dimethyl-2-oxo-1,2-dihydro-3-pyridinyl)methyl]-3-methyl-1-[(1R)-1-methylpropyl]-6-[6-(1-piperazinyl)-3-pyridinyl]-1H-indole-4-carboxamide

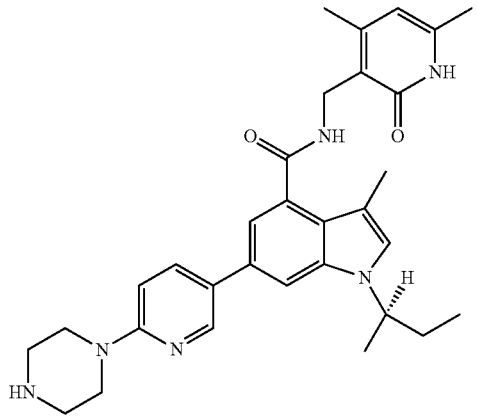 [SMILES: CC[C@@H](C)n1cc(C)c2c(C(=O)NCc3c(C)cc(C)[nH]c3=O)cc(-c3ccc(N4CCNCC4)nc3)cc21]

To a 30 mL microwave vial were added (R)-6-bromo-1-(sec-butyl)-N-((4,6-dimethyl-2-oxo-1,2-dihydropyridin-3-yl)methyl)-3-methyl-1H-indole-4-carboxamide (100 mg, 0.225 mmol), 1-(5-(4,4,5,5-tetramethyl-1,3,2-dioxaborolan-2-yl)pyridin-2-yl)piperazine (85 mg, 0.293 mmol), 1,2-Dimethoxyethane (DME) (3 mL), water (1.000 mL) and sodium carbonate (0.338 mL, 0.675 mmol), and the mixture was degassed for 5 min by bubbling nitrogen. PdCl$_2$(dppf)-CH$_2$Cl$_2$ adduct (14.70 mg, 0.018 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/H$_2$O, 0.1% NH$_4$OH to 60% ACN/H$_2$O, 0.1% NH$_4$OH) to give 90 mg of product as off-white solid. $^1$H NMR (400 MHz, DMSO-d6) δ ppm 0.73 (m, 3H), 1.41 (d, J=6.57 Hz, 3H), 1.81 (td, J=7.14, 2.91 Hz, 2H), 2.11 (s, 3H), 2.15-2.20 (m, 3H), 2.24 (s, 3H), 2.77-2.83 (m, 4H), 3.41-3.49 (m, 4H), 4.35 (d, J=5.05 Hz, 2H), 4.54-4.68 (m, 1H), 5.87 (s, 1H), 6.88 (d, J=8.84 Hz, 1H), 7.17 (d, J=1.52 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.27 Hz, 1H); LCMS: 527.7 (MH+).

Example 272

1-(sec-Butyl)-N-((4,6-dimethyl-2-oxo-1,2-dihydropyridin-3-yl)methyl)-6-(3-((dimethylamino)methyl)phenyl)-3-methyl-1H-indole-4-carboxamide

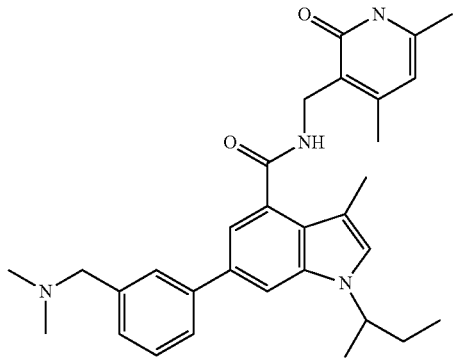

Added sequentially to a reaction vial were 6-bromo-1-(sec-butyl)-N-((4,6-dimethyl-2-oxo-1,2-dihydropyridin-3-yl)methyl)-3-methyl-1H-indole-4-carboxamide (0.15 g, 0.338 mmol), N,N-dimethyl-1-(3-(4,4,5,5-tetramethyl-1,3,2-dioxaborolan-2-yl)phenyl)methanamine-hydrochloride (0.131 g, 0.439 mmol) and potassium phosphate (tribasic) (0.287 g, 1.350 mmol), followed by 1,4-Dioxane (4 mL) and water (0.75 mL). The suspension was stirred under N$_2$ degassing for 10 min., and then added PdCl$_2$(dppf)-CH$_2$Cl$_2$ adduct (0.028 g, 0.034 mmol). The reaction vial was sealed, placed into a heat block at 95° C., and stirred for 1.5 h. The contents were removed from heating and allowed to cool to room temperature. The aq layer was removed from bottom of the reaction vial via pipette. The reaction mixture was diluted into EtOAc (20 mL) followed by addition of 0.2 g each of Thiol-3 silicycle resin and silica gel. The volatiles were removed in vacuo and the residue dried on hi-vac for 1 h. The contents were purified by silica gel chromatography (dry loaded, eluent: A: Dichloromethane, B: 10% (2M Ammonia in Methanol) in Chloroform; Gradient B: 8-95%). The obtained solid was concentrated from TBME to afford a foam, and was dried in vacuum oven at 45° C. for 18 h. The product was collected as 116 mg (65%). $^1$H NMR (400 MHz, DMSO-d6) δ ppm 0.73 (t, J=7.33 Hz, 3H), 1.41 (d, J=6.57 Hz, 3H), 1.82 (dq, J=9.85, 7.16 Hz, 2H), 2.08-2.12 (m, 3H), 2.15-2.21 (m, 9H), 2.24 (s, 3H), 3.44-3.49 (m, 2H), 4.35 (d, J=5.05 Hz, 2H), 4.57-4.70 (m, 1H), 5.86 (s, 1H), 7.19-7.26 (m, 2H), 7.30 (s, 1H), 7.36-7.44 (m, 1H), 7.58-7.65 (m, 2H), 7.76 (d, J=1.26 Hz, H), 8.21 (t, J=5.05 Hz, 1H), 11.47 (s, 1H); LCMS M+H=499.3.

Example 273

6-{3-[(Dimethylamino)methyl]phenyl}-N-[(4,6-dimethyl-2-oxo-1,2-dihydro-3-pyridinyl)methyl]-3-methyl-1-[(1S)-1-methylpropyl]-1H-indole-4-carboxamide

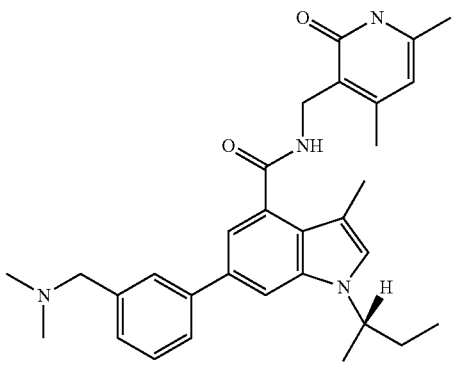

(S)-6-bromo-1-(sec-butyl)-N-((4,6-dimethyl-2-oxo-1,2-dihydropyridin-3-yl)methyl)-3-methyl-1H-indole-4-carboxamide (100 mg, 0.23 mmol), N,N-dimethyl-1-(3-(4,4,5,5-tetramethyl-1,3,2-dioxaborolan-2-yl)phenyl)methanamine, HCl (100 mg, 0.34 mmol) and Palladium Tetrakis (26 mg, 0.023 mmol) in DMF/water (3 ml:1 ml) were stirred for 10 min under nitrogen. Cesium carbonate (220 mg, 0.68 mmol) was added and the insoluble mixture was irradiated (microwave) at 150° C. for 15 min. The contents were evaporated, dissolved in DCM/MeOH (1:1), and pre-absorbed on silica gel and purified using silica gel chromatography (eluent: DCM/MeOH/NH$_4$OH, gradient 0 to 80:20:2 in DCM). The isolated product was first treated with EtOAc along with some hexanes. The product was then dissolved in MeOH and purified by reverse-phase HPLC (30×100 Varian Polaris C18 column, eluent: 10-80% gradient of MeCN in water with 0.1% TFA). The product fractions were combined, most of the solvent was evaporated, and a sat. solution of NaHCO₃ was added. Solids that crashed out were filtered, air-dried for 15 min, and dried in vacuum-oven overnight. The solid product was collected as 87 mg (75%). ¹H NMR (400 MHz, DMSO-d6) δ ppm 11.38 (br. s., 1H), 8.23 (t, J=4.67 Hz, 1H), 7.77 (d, J=1.01 Hz, 1H), 7.60-7.64 (m, 2H), 7.40 (t, J=7.58 Hz, 1H), 7.30 (s, 1H), 7.20-7.26 (m, 2H), 5.87 (s, 1H), 4.59-4.68 (m, 1H), 4.36 (s, 1H), 4.35 (s, 1H), 3.46 (s, 2H), 2.24 (s, 3H), 2.18 (s, 9H), 2.11 (s, 3H), 1.76-1.88 (m, 2H), 1.41 (d, J=6.57 Hz, 3H), 0.74 (t, J=7.33 Hz, 3H); LCMS: 499.4 (MH+).

Example 274

6-{3-[(dimethylamino)methyl]phenyl}-N-[(4,6-dimethyl-2-oxo-1,2-dihydro-3-pyridinyl)methyl]-3-methyl-1-[(1R)-1-methylpropyl]-1H-indole-4-carboxamide

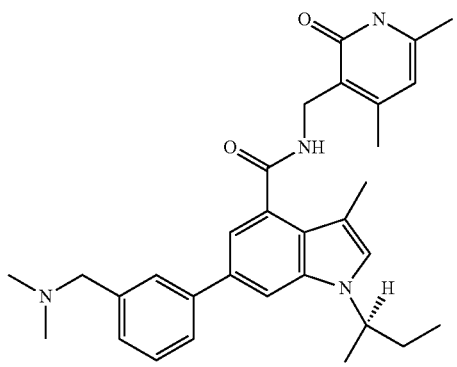

(R)-6-bromo-1-(sec-butyl)-N-((4,6-dimethyl-2-oxo-1,2-dihydropyridin-3-yl)methyl)-3-methyl-1H-indole-4-carboxamide (100 mg, 0.23 mmol), N,N-dimethyl-1-(3-(4,4,5,5-tetramethyl-1,3,2-dioxaborolan-2-yl)phenyl)methanamine, HCl (100 mg, 0.34 mmol) and Palladium Tetrakis (26 mg, 0.023 mmol) in DMF/water (3 mL:1 mL) were stirred for 10 min under nitrogen. Cesium carbonate (220 mg, 0.68 mmol) was added and the insoluble mixture was irradiated (microwave) at 150° C. for 15 min. The contents were evaporated, dissolved in DCM/MeOH (1:1), and pre-absorbed on silica gel and purified using silica gel chromatography (eluent: DCM/MeOH/NH₄OH, gradient 0 to 80:20:2 in DCM). The isolated product was first treated with EtOAc along with some hexanes. The product was then dissolved in MeOH and purified by reversed-phase HPLC (30× 100 Varian Polaris C18 column, eluent: 10-80% gradient of MeCN in water with 0.1% TFA). The product fractions were combined, most of the solvent was evaporated, and a sat. solution of NaHCO₃ was added. Solids that crashed out were filtered, air-dried for 15 min, and dried in vacuum-oven overnight. The solid product was collected as 85 mg (75%). ¹H NMR (400 MHz, DMSO-d6) δ ppm 11.48 (s, 1H) 8.21 (t, J=5.05 Hz, 1H) 7.77 (d, J=1.26 Hz, 1H) 7.60-7.66 (m, 2H) 7.41 (t, J=7.58 Hz, 1H) 7.30 (s, 1H) 7.25 (d, J=7.58 Hz, 1H) 7.22 (d, J=1.52 Hz, 1H) 5.87 (s, 1H) 4.60-4.68 (m, 1H) 4.36 (s, 1H) 4.35 (s, 1H) 3.49 (br. s., 2H) 2.24 (s, 3H) 2.19 (d, J=8.84 Hz, 9H) 2.11 (s, 3H) 1.77-1.88 (m, 2H) 1.41 (d, J=6.57 Hz, 3H) 0.74 (t, J=7.33 Hz, 3H); LCMS: 499.4 (MH+).

Example 275

1-cyclopentyl-N-((4,6-dimethyl-2-oxo-1,2-dihydropyridin-3-yl)methyl)-3-methyl-6-(6-(piperazin-1-yl)pyridin-3-yl)-1H-indole-4-carboxamide

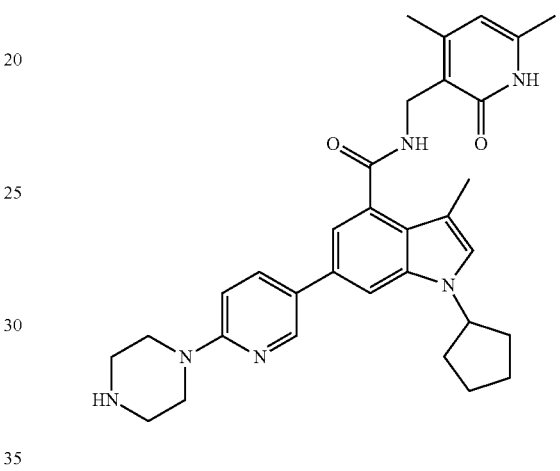

To a 30 mL microwave vial were added 6-bromo-1-cyclopentyl-N-((4,6-dimethyl-2-oxo-1,2-dihydropyridin-3-yl)methyl)-3-methyl-1H-indole-4-carboxamide (80 mg, 0.175 mmol), 1-(5-(4,4,5,5-tetramethyl-1,3,2-dioxaborolan-2-yl)pyridin-2-yl)piperazine (65.9 mg, 0.228 mmol), 1,2-Dimethoxyethane (DME) (3 mL), Water (1.000 mL) and sodium carbonate (0.263 mL, 0.526 mmol), and the mixture was degassed for 5 min by bubbling nitrogen. PdCl₂(dppf)-CH₂Cl₂ adduct (11.45 mg, 0.014 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/H₂O, 0.1% NH₄OH to 60% ACN/H₂O, 0.1% NH₄OH) to give 72 mg of product as off-white solid. ¹H NMR (400 MHz, DMSO-d6) δppm 1.65-1.89 (m, 6H), 2.08-2.19 (m, 8H), 2.24 (s, 3H), 2.76-2.84 (m, 4H), 3.40-3.48 (m, 4H), 4.35 (d, J=5.05 Hz, 2H), 4.92-5.04 (m, 1H), 5.87 (s, 1H), 6.88 (d, J=8.84 Hz, 1H), 7.19 (d, J=1.26 Hz, 1H), 7.25 (s, 1H), 7.74 (d, J=1.26 Hz, 1H), 7.91 (dd, J=8.84, 2.53 Hz, 1H), 8.15 (t, J=5.05 Hz, 1H), 8.51 (d, J=2.53 Hz, 1H); LCMS: 539.8 (MH+).

Some examples were prepared as above from a boronic acid (or boronate) containing a Boc-protected amine. These examples required removal of the Boc-protecting group to provide the title compounds.

Example 276

1-isopropyl-N-((6-methyl-2-oxo-4-propyl-1,2-dihydropyridin-3-yl)methyl)-6-(6-(piperazin-1-yl)pyridin-3-yl)-1H-indole-4-carboxamide

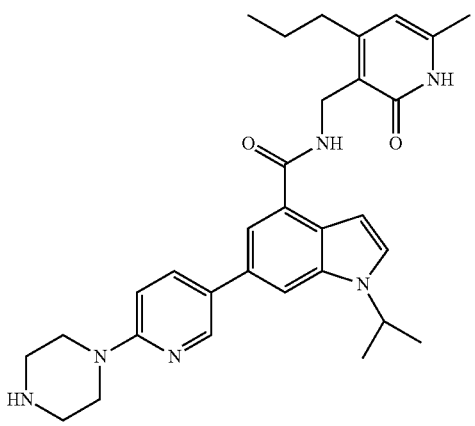 [SMILES: CCCc1cc(C)[nH]c(=O)c1CNC(=O)c1cc(-c2ccc(N3CCNCC3)nc2)cc2c1ccn2C(C)C]

To a suspension of 1,1-dimethylethyl 4-{5-[1-(1-methylethyl)-4-({[(6-methyl-2-oxo-4-propyl-1,2-dihydro-3-pyridinyl)methyl]amino}carbonyl)-1H-indol-6-yl]-2-pyridinyl}-1-piperazinecarboxylate (70 mg, 0.112 mmol) in dichloromethane (2 mL) was added TFA (0.5 ml, 6.49 mmol), and the mixture was stirred for 1 h. The mixture was concentrated and the residue was treated with saturated aqueous NaHCO$_3$ solution and filtered. The solid was purified using column chromatography (silica gel, 0 to 15% (9:1 MeOH/NH$_4$OH)/CH$_2$Cl$_2$) to give 1-isopropyl-N-((6-methyl-2-oxo-4-propyl-1,2-dihydropyridin-3-yl)methyl)-6-(6-(piperazin-1-yl)pyridin-3-yl)-1H-indole-4-carboxamide (51 mg, 84%) as off-white solid. $^1$H NMR (400 MHz, DMSO-d$_6$) δ ppm 0.91 (m, 3H), 1.47 (d, J=4.00 Hz, 6H), 1.53-1.60 (m, 2H), 2.14 (s, 3H), 2.89-2.98 (m, 4H), 3.51-3.59 (m, 4H), 4.40 (d, J=5.05 Hz, 2H), 4.93 (quin, J=6.63 Hz, 1H), 5.92 (s, 1H), 6.87 (d, J=3.03 Hz, 1H), 6.94 (d, J=8.84 Hz, 1H), 7.60 (d, J=3.03 Hz, 1H), 7.66 (d, J=1.26 Hz, 1H), 7.88 (s, 1H), 8.00 (dd, J=8.84, 2.53 Hz, 1H), 8.28 (t, J=5.05 Hz, 1H), 8.58 (d, J=2.27 Hz, 1H). MS: (M+H)$^+$=527.2.

Examples 277-285 were prepared by the methods described above for Examples 276 or routine variations thereof, starting from the requisite N-Boc protected material:

| Ex | Structure | Name | $^1$H NMR (400 MHz, DMSO-d$_6$) δ ppm | MS(ES) [M + H]$^+$ |
|---|---|---|---|---|
| 277 | 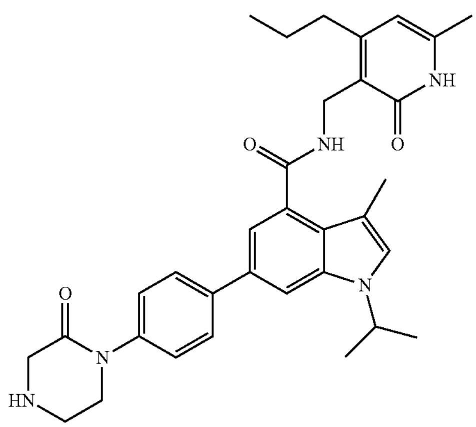 [SMILES: CCCc1cc(C)[nH]c(=O)c1CNC(=O)c1cc(-c2ccc(N3CCNCC3=O)cc2)cc2c1c(C)cn2C(C)C] | 1-isopropyl-3-methyl-N-((6-methyl-2-oxo-4-propyl-1,2-dihydropyridin-3-yl)methyl)-6-(4-(2-oxopiperazin-1-yl)phenyl)-1H-indole-4-carboxamide | 0.94 (m, 3 H), 1.44 (d, J = 6.57 Hz, 6 H), 1.54-1.63 (m, 2 H), 2.12 (s, 3 H), 2.18 (s, 3 H), 3.04 (t, J = 5.31 Hz, 2 H), 3.41 (s, 2 H), 3.64 (t, J = 5.31 Hz, 2 H), 4.37 (d, J = 5.05 Hz, 2 H), 4.87 (quin, J = 6.63 Hz, 1 H), 5.90 (s, 1 H), 7.25 (d, J = 1.26 Hz, 1 H), 7.34 (s, 1 H), 7.40 (d, J = 8.59 Hz, 2 H), 7.70-7.83 (m, 3 H), 8.18 (t, J = 5.05 Hz, 1 H) | 554.4 |
| 278 | 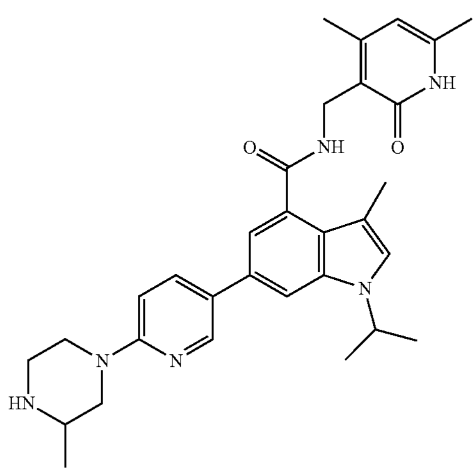 [SMILES: Cc1cc(C)c(CNC(=O)c2cc(-c3ccc(N4CCNC(C)C4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(3-methyl-1-piperazinyl)-3-pyridinyl]-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.73 (d, J = 1.26 Hz, 1 H) 7.26 (s, 1 H) 7.17 (d, J = 1.52 Hz, 1 H) 6.92 (d, J = 9.09 Hz, 1 H) 5.87 (s, 1 H) 4.56-4.65 m, 1 H) 4.36 (s, 1 H) 4.34 (s, 1 H) 3.49-3.55 (m, 4 H) 2.40-2.44 (m, 4 H) 2.24 (s, 3 H) 2.23 (s, 3 H) 2.16 (s, 3 H) 2.11 (s, 3 H) 1.76-1.87 (m, 2 H) 1.41 (d, J = 6.57 Hz, 3 H) 0.73 (t, J = 7.33 Hz, 3 H) | 527.3 |

| Ex | Structure | Name | ¹H NMR (400 MHz, DMSO-d₆) δ ppm | MS(ES) [M + H]⁺ |
|---|---|---|---|---|
| 279 | 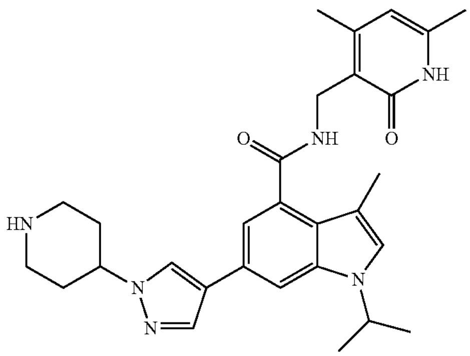 [SMILES: Cc1cc(C)c(CNC(=O)c2cc(-c3cnn(C4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1-(piperidin-4-yl)-1H-pyrazol-4-yl)-1H-indole-4-carboxamide | 1.42 (m, 6 H), 1.81 (qd, J = 11.96, 4.04 Hz, 2 H), 1.98 (m, 2 H), 2.12 (d, J = 6.57 Hz, 6 H), 2.24 (s, 3 H), 2.55-2.66 (m, 2 H), 3.05 (d, J = 12.63 Hz, 2 H), 4.18 (tt, J = 11.49, 4.04 Hz, 1 H), 4.34 (d, J = 5.05 Hz, 2 H), 4.78 (quin, J = 6.69 Hz, 1 H), 5.87 (s, 1 H), 7.18 (d, J = 1.26 Hz, 1 H), 7.22 (d, J = 1.01 Hz, 1 H), 7.71 (d, J = 1.01 Hz, 1 H), 7.89 (s, 1 H), 8.03 (t, J = 5.18 Hz, 1 H), 8.24 (s, 1 H) | 501.1 |
| 280 | 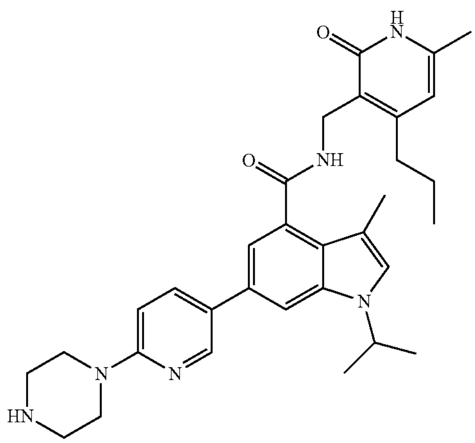 [SMILES: CCCc1cc(C)[nH]c(=O)c1CNC(=O)c1cc(-c2ccc(N3CCNCC3)nc2)cc2c1c(C)cn2C(C)C] | 6-methyl-3-[(2-{3-methyl-1-(1-methylethyl)-6-[6-(1-piperazinyl)-3-pyridinyl]-1H-indol-4-yl}-2-oxoethyl)amino]-4-propyl-2(1H)-pyridinone | 0.93 (t, J = 7.33 Hz, 3 H), 1.42 (d, J = 6.57 Hz, 6 H), 1.56 (qt, J = 7.56, 7.36 Hz, 2 H), 2.12 (s, 3 H), 2.16 (s, 3 H), 2.52-2.58 (m, 2 H), 2.77-2.90 (m, 4 H), 3.42-3.51 (m, 4 H), 4.36 (d, J = 5.05 Hz, 2 H), 4.84 (dt, J = 13.20, 6.66 Hz, 1 H), 5.90 (s, 1 H), 6.89 (d, J = 8.84 Hz, 1 H), 7.17 (d, J = 1.26 Hz, 1 H), 7.29 (s, 1 H), 7.72 (s, 1 H), 7.91 (dd, J = 8.84, 2.53 Hz, 1 H), 8.12 (t, J = 4.93 Hz, 1 H), 8.49 (d, J = 2.27 Hz, 1 H), 11.49 (br. s., 1 H) | 541.5 |
| 281 | 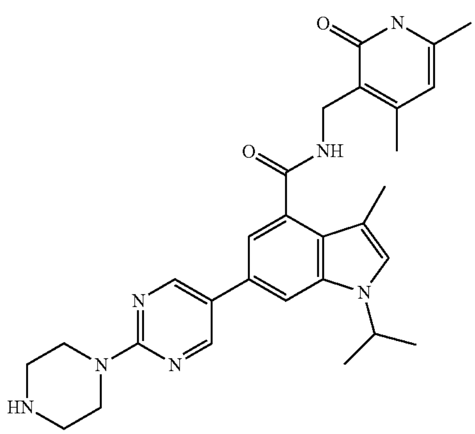 [SMILES: Cc1cc(C)c(CNC(=O)c2cc(-c3cnc(N4CCNCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(2-(piperazin-1-yl)pyrimidin-5-yl)-1H-indole-4-carboxamide | 11.47 (br. s., 1 H), 8.75 (s, 2 H), 8.13 (t, J = 5.1 Hz, 1 H), 7.76 (d, J = 1.5 Hz, 1 H), 7.30 (s, 1 H), 7.19 (d, J = 1.3 Hz, 1 H), 5.87 (s, 1 H), 4.83 (m, 1 H), 4.34 (d, J = 5.1 Hz, 2 H), 3.71 (m, 4 H), 2.77 (m, 4 H), 2.24 (s, 3 H), 2.15 (s, 3 H), 2.11 (s, 3 H), 1.42 (d, J = 6.6 Hz, 6 H) | 514.2 |
| 282 | 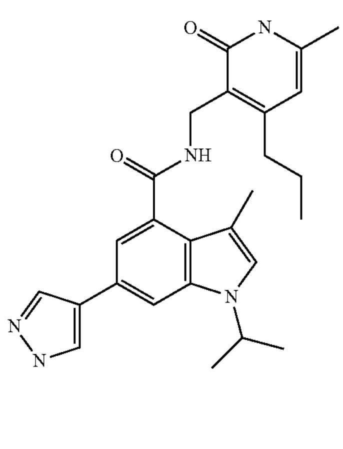 [SMILES: CCCc1cc(C)[nH]c(=O)c1CNC(=O)c1cc(-c2cn[nH]c2)cc2c1c(C)cn2C(C)C] | 3-methyl-1-(1-methylethyl)-N-[(6-methyl-2-oxo-4-propyl-1,2-dihydro-3-pyridinyl)methyl]-6-(1H-pyrazol-4-yl)-1H-indole-4-carboxamide | 12.85 (br. s., 1 H), 11.49 (br. s., 1 H), 8.01 (t, J = 5.2 Hz, 3 H), 7.72 (d, J = 1.3 Hz, 1 H), 7.20 (m, 2 H), 5.90 (s, 1 H), 4.78 (quin, J = 6.6 Hz, 1 H), 4.35 (d, J = 5.1 Hz, 2 H), 2.55 (m, 2 H), 2.11 (m, 6 H), 1.57 (sxt, J = 7.5 Hz, 2 H), 1.42 (d, J = 6.6 Hz, 6 H), 0.94 (m, 3 H) | 446.0 |

-continued

| Ex | Structure | Name | ¹H NMR (400 MHz, DMSO-d₆) δ ppm | MS(ES) [M + H]⁺ |
|---|---|---|---|---|
| 283 | 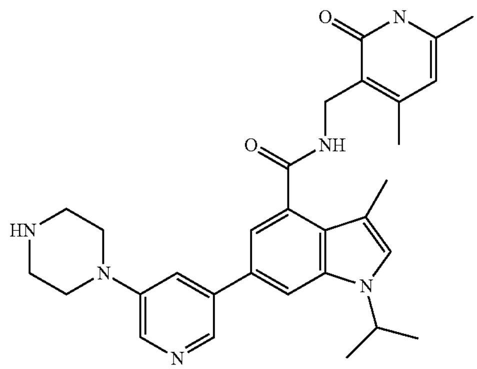 [SMILES: Cc1cc(C)c(CNC(=O)c2cc(-c3cncc(N4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(5-(piperazin-1-yl)pyridin-3-yl)-1H-indole-4-carboxamide | 11.48 (br. s., 1 H), 8.36 (d, J = 1.8 Hz, 1 H), 8.20 (m, 2 H), 7.84 (d, J = 1.3 Hz, 1 H), 7.55 (t, J = 2.3 Hz, 1 H), 7.35 (d, J = 1.0 Hz, 1 H), 7.26 (d, J = 1.5 Hz, 1 H), 5.87 (s, 1 H), 4.91 (quin, J = 6.6 Hz, 1 H), 4.35 (d, J = 5.1 Hz, 2 H), 3.19 (m, 4 H), 2.88 (m, 4 H), 2.24 (s, 3 H), 2.16 (s, 3 H), 2.11 (s, 3 H), 1.43 (d, J = 6.6 Hz, 6 H) | 513.3 |
| 284 | 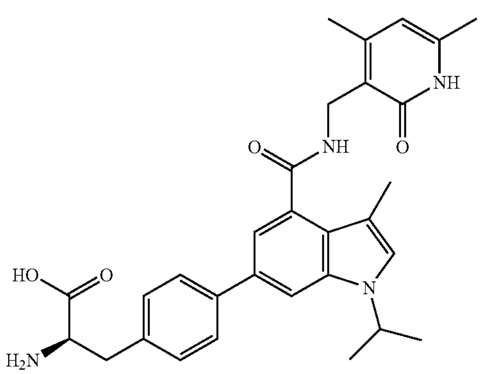 [SMILES: Cc1cc(C)c(CNC(=O)c2cc(-c3ccc(C[C@@H](N)C(=O)O)cc3)cc3c2c(C)cn3C(C)C)c(=O)[nH]1] | 4-(4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine | 11.48 (br. s., 1 H) 8.18 (t, J = 4.93 Hz, 1 H) 7.75 (s, 1 H) 7.70 (d, J = 8.08 Hz, 2 H) 7.31-7.37 (m, 3 H) 7.24 (s, 1 H) 5.87 (s, 1 H) 4.89-4.82 (m, 1 H) 4.35 (d, J = 4.80 Hz, 2 H) 3.85 (br. s., 1 H) 2.97-3.22 (m, 2 H) 2.24 (s, 3 H) 2.17 (s, 3 H) 2.11 (s, 3 H) 1.43 (d, J = 6.57 Hz, 6 H) | 515.3 |
| 285 | 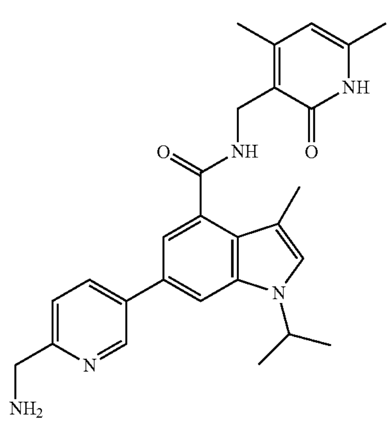 [SMILES: Cc1cc(C)c(CNC(=O)c2cc(-c3ccc(CN)nc3)cc3c2c(C)cn3C(C)C)c(=O)[nH]1] | 6-[6-(aminomethyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 11.47 (br. s., 1 H) 8.37 (s, 1 H) 8.13 (br. s., 1 H) 7.79-7.76 (m, 1 H) 7.66 (s, 1 H) 7.26 (s, 1 H) 7.14 (s, 1 H) 6.53 (d, J = 8.34 Hz, 2 H) 5.87 (br. s., 1 H) 4.88-4.75 (m, 1 H) 4.35 (d, J = 4.04 Hz, 2 H) 2.81 (d, J = 4.29 Hz, 3 H) 2.24 (s, 3 H) 2.16 (s, 3 H) 2.11 (s, 3 H) 1.43 (d, J = 6.32 Hz, 6 H) | 458.3 |

Some examples were prepared as above from a boronic acid (or boronate) containing an alkyl ester. These examples required saponification of the ester to provide the corresponding carboxylic acids.

Example 286

4-[4-({[(4,6-Dimethyl-2-oxo-1,2-dihydro-3-pyridinyl)methyl]amino}carbonyl)-3-methyl-1-(1-methylethyl)-1H-indol-6-yl]benzoic acid

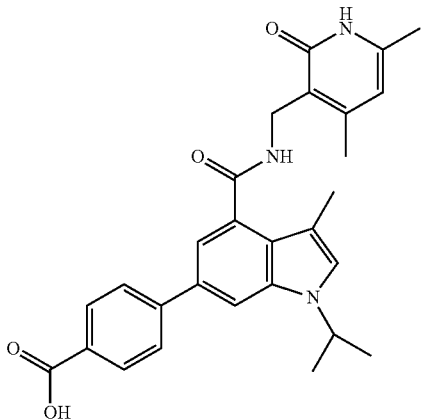 [SMILES: Cc1cc(C)c(CNC(=O)c2cc(-c3ccc(C(=O)O)cc3)cc3c2c(C)cn3C(C)C)c(=O)[nH]1]

To a solution of methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate (30 mg, 0.062 mmol) in MeOH (2 mL) and THF (1 mL) was 3N NaOH (0.031 mL, 0.185 mmol). The reaction was heated at 50° C. for 12 h, at which time it was allowed to cool to ambient temperature and treated with acidic ice water to bring pH to 6. The solid was filtered and washed several times with water and an 8:2 mixture of acidic (pH2) ice water:MeOH. Purification by reverse phase Gilson HPLC (10-80%, acetonitrile/water+0.1% TFA, YMC ODS-A C18 Column 75×30 mm ID S-5 um, 12 nM Column 7 minutes) provided the title compound (12 mg, 0.024 mmol, 39.5% yield) as an off-white solid. $^1$H NMR (400 MHz, DMSO-$d_6$) δ ppm 12.91 (br. s., 1H) 11.48 (br. s., 1H) 8.23 (t, J=5.05 Hz, 1H) 8.02 (d, J=8.34 Hz, 3H) 7.87-7.94 (m, 4H) 7.38 (s, 1H) 7.32 (d, J=1.52 Hz, 1H) 5.87 (s, 1H) 4.91 (quin, J=6.63 Hz, 1H) 4.36 (d, J=4.80 Hz, 2H) 2.24 (s, 3H) 2.18 (s, 3H) 2.11 (s, 3H) 1.44 (d, J=6.57 Hz, 6H). MS(ES) [M+H]$^+$ 486.1.

Examples 287-288 were prepared by the methods described above for Example 286, or routine variations thereof, starting from the requisite alkylester:

| Ex | Structure | Name | $^1$H NMR (400 MHz, DMSO-$d_6$) δ ppm | MS(ES) [M + H]$^+$ |
|---|---|---|---|---|
| 287 | 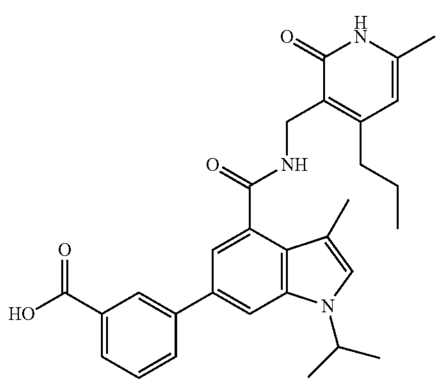 [SMILES: CCCc1cc(C)[nH]c(=O)c1CNC(=O)c1cc(-c2cccc(C(=O)O)c2)cc2c1c(C)cn2C(C)C] | 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoic acid | 13.07 (br. s., 1 H) 11.49 (br. s., 1 H) 8.27 (s, 1 H) 8.23 (t, J = 4.67 Hz, 1 H) 8.00 (d, J = 8.08 Hz, 1 H) 7.90 (d, J = 7.58 Hz, 1 H) 7.84 (s, 1 H) 7.59 (t, J = 7.71 Hz, 1 H) 7.36 (s, 1 H) 7.26 (s, 1 H) 5.90 (s, 1 H) 4.98-4.95 (m, 1 H) 4.38 (d, J = 5.05 Hz, 2 H) 2.56 (d, J = 7.58 Hz, 2 H) 2.19 (s, 3 H) 2.12 (s, 3H) 1.54-1.62 (m, 2 H) 1.44 (d, J = 6.57 Hz, 6 H) 0.94 (t, J = 7.33 Hz, 3 H) | 500.1 |
| 288 | 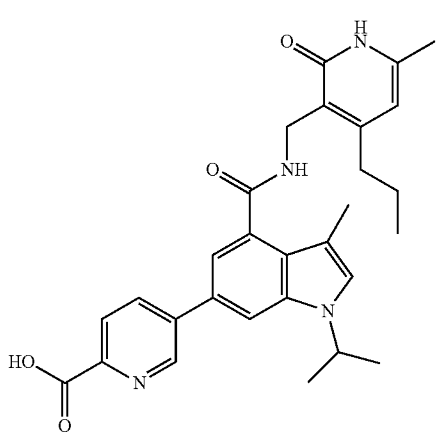 [SMILES: CCCc1cc(C)[nH]c(=O)c1CNC(=O)c1cc(-c2ccc(C(=O)O)nc2)cc2c1c(C)cn2C(C)C] | 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylic acid | 13.22 (br. s., 1 H) 11.51 (br. s., 1 H) 9.11 (br. s., 1 H) 8.31-8.38 (m, 1 H) 8.23 (br. s., 1 H) 8.12 (br. s., 1 H) 8.02 (br. s., 1 H) 7.42 (br. s., 1 H) 7.37 (br.s., 1 H) 5.91 (br. s., 1 H) 4.88-4.98 (m, 1 H) 4.38 (br. s., 2 H) 2.55-2.61 (m, 2 H) 2.19 (br. s., 3 H) 2.12 (br. s., 3 H) 1.54-1.62 (m, 2 H) 1.46 (br. s., 6 H) 0.90-0.99 (m, 3 H) | 501.1 |

Example 289

N-[(4,6-Dimethyl-2-oxo-1,2-dihydro-3-pyridinyl)methyl]-1-(1-methylethyl)-1H-indole-4-carboxamide

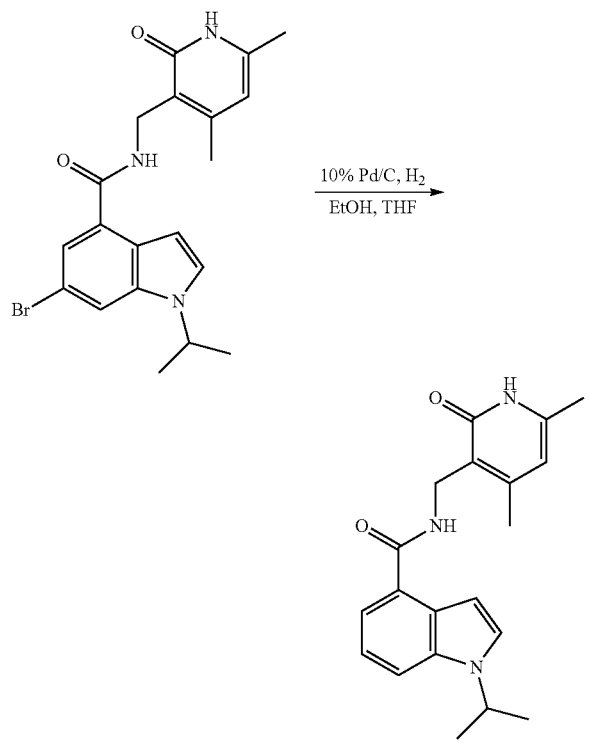

To a flask under $N_2$ atmosphere was added 10% palladium on carbon (0.028 g, 0.026 mmol) and ethanol (1 mL) (to wet catalyst). The flask was then charged with 6-bromo-N-[(4,6-dimethyl-2-oxo-1,2-dihydro-3-pyridinyl)methyl]-1-(1-methylethyl)-1H-indole-4-carboxamide (0.11 g, 0.264 mmol), ethanol (4 mL) and tetrahydrofuran (1 mL). The suspension was stirred under $N_2$, then evacuated and refilled with $H_2$ (balloon) and stirred overnight. The reaction was then placed back under $N_2$ and diluted with 10% methanol/dichloromethane. Celite was added and the mixture was stirred for 15 min, filtered through a pad of Celite, washed with 10% methanol/dichloromethane, and concentrated. The residue was dissolved in dimethylsulfoxide and acetonitrile (with 0.1% trifluoroacetic acid and purified by Gilson prep HPLC (Sunfire 30×75 mm; Gradient B: 15-75%; A: water+0.1% TFA; B: acetonitrile+0.1% TFA). The resulting residue was dissolved in 10% methanol/dichloromethane and treated with Silicycle carbonate resin (1.5 g). The mixture was stirred for 30 min, filtered through Celite, washed with 10% methanol/dichloromethane, and concentrated. The residue was dissolved in dichloromethane and treated with methyl-t-butylether. The solvents were removed by via $N_2$ stream and the solids dried in a vacuum oven at 45° C. for 18 h to give N-[(4,6-dimethyl-2-oxo-1,2-dihydro-3-pyridinyl)methyl]-1-(1-methylethyl)-1H-indole-4-carboxamide (56 mg, 0.159 mmol, 60% yield). $^1$H NMR (400 MHz, DMSO-$d_6$) δ ppm 1.41-1.48 (m, 6H) 2.09-2.15 (m, 3H) 2.24 (s, 3H) 4.35 (d, J=5.31 Hz, 2H) 4.79 (quin, J=6.63 Hz, 1H) 5.88 (s, 1H) 6.84 (d, J=3.03 Hz, 1H) 7.11-7.18 (m, 1H) 7.39 (d, J=6.57 Hz, 1H) 7.58 (d, J=3.28 Hz, 1H) 7.65 (d, J=8.34 Hz, 1H) 8.08 (t, J=5.31 Hz, 1H) 11.54 (br. s., 1H). MS(ES) [M+H]$^+$ 338.6.

Examples 290-295 were prepared by the methods described above for Example 289, or routine variations thereof, starting from the requisite 6-haloindole, alkene, or CBz-protected amine:

| Ex | Structure | Name | $^1$H NMR (400 MHz, DMSO-$d_6$) δ ppm | MS(ES) [M + H]$^+$ |
|---|---|---|---|---|
| 290 | 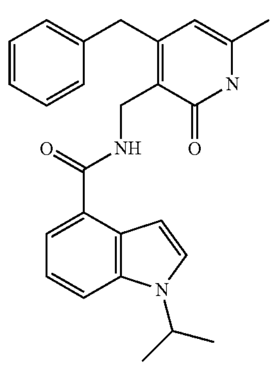 [SMILES: Cc1cc(Cc2ccccc2)c(CNC(=O)c2cccc3c2ccn3C(C)C)c(=O)[nH]1] | N-((4-benzyl-6-methyl-2-oxo-1,2-dihydropyridin-3-yl)methyl)-1-isopropyl-1H-indole-4-carboxamide | 11.60 (br. s., 1 H) 8.10-8.20 (m, 1 H) 7.66 (d, J = 8.34 Hz, 1 H) 7.59 (d, J = 3.28 Hz, 1 H) 7.40 (d, J = 7.07 Hz, 1 H) 7.14-7.31 (m, 6 H) 6.85 (d, J = 3.03 Hz, 1 H) 5.82 (s, 1 H) 4.80 (quin, J = 6.69 Hz, 1 H) 4.44 (s, 1 H) 4.42 (s, 1 H) 4.01 (s, 2 H) 2.10 (s, 3 H) 1.47 (s, 3 H) 1.45 (s, 3 H) | 413.9 |

-continued

| Ex | Structure | Name | $^1$H NMR (400 MHz, DMSO-$d_6$) δ ppm | MS(ES) [M + H]$^+$ |
|---|---|---|---|---|
| 291 | 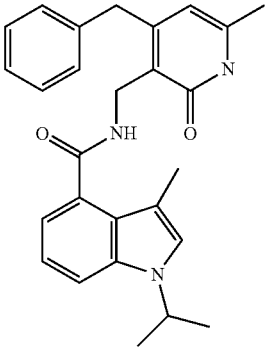 [SMILES: Cc1cc(Cc2ccccc2)c(CNC(=O)c2cccc3c2c(C)cn3C(C)C)c(=O)[nH]1] | N-((4-benzyl-6-methyl-2-oxo-1,2-dihydropyridin-3-yl)methyl)-1-isopropyl-3-methyl-1H-indole-4-carboxamide | 11.55 (s, 1 H) 8.08 (t, J = 5.18 Hz, 1 H) 7.50 (d, J = 7.83 Hz, 1 H) 7.20-7.33 (m, 6 H) 7.04-7.08 (m, 1 H) 6.90 (d, J = 7.07 Hz, 1 H) 5.79 (s, 1 H) 4.72 (quin, J = 6.63 Hz, 1 H) 4.41 (d, J = 5.31 Hz, 2 H) 3.99 (s, 2 H) 2.15 (s, 3 H) 2.09 (s, 3 H) 1.42 (s, 3 H) 1.40 (s, 3 H) | 427.8 |
| 292 | 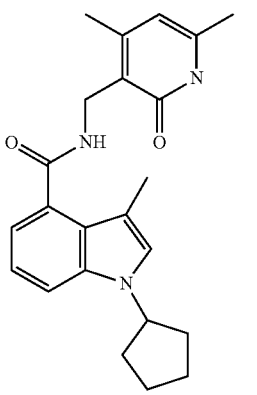 [SMILES: Cc1cc(C)c(CNC(=O)c2cccc3c2c(C)cn3C2CCCC2)c(=O)[nH]1] | 1-cyclopentyl-N-((4,6-dimethyl-2-oxo-1,2-dihydropyridin-3-yl)methyl)-3-methyl-1H-indole-4-carboxamide | 11.47 (br. s., 1 H) 7.99 (t, J = 4.93 Hz, 1 H) 7.51 (d, J = 7.83 Hz, 1 H) 7.24 (s, 1 H) 7.06 (t, J = 7.71 Hz, 1 H) 6.93 (d, J = 6.82 Hz, 1 H) 5.87 (s, 1 H) 4.86 (d, J = 7.33 Hz, 1 H) 4.33 (s, 1 H) 4.32 (s, 1 H) 2.23 (s, 3 H) 2.07-2.16 (m, 8 H) 1.76-1.86 (m, 4 H) 1.69 (d, J = 3.54 Hz, 2 H) | 378.3 |
| 293 | 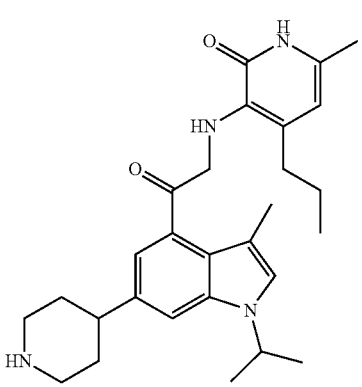 [SMILES: CCCc1cc(C)[nH]c(=O)c1NCC(=O)c1cc(C2CCNCC2)cc2c1c(C)cn2C(C)C] | 6-methyl-3-({2-[3-methyl-1-(1-methylethyl)-6-(4-piperidinyl)-1H-indol-4-yl]-2-oxoethyl}amino)-4-propyl-2(1H)-pyridinone | 0.93 (t, J = 7.33 Hz, 3 H), 1.39 (d, J = 6.57 Hz, 6 H), 1.48-1.64 (m, 4 H), 1.68 (br. s., 2 H), 2.12 (s, 6 H), 2.54 (m, 4 H), 3.01 (d, J = 11.87 Hz, 2 H), 3.16 (d, J = 4.55 Hz, 1 H), 4.33 (d, J = 5.05 Hz, 2 H), 4.70 (dt, J = 13.20, 6.66 Hz, 1 H), 5.89 (s, 1 H), 6.82 (s, 1 H), 7.19 (s, 1 H), 7.30 (s, 1 H), 7.93 (t, J = 4.80 Hz, 1 H), 8.55 (s, 1 H) | 463.1 |
| 294 | 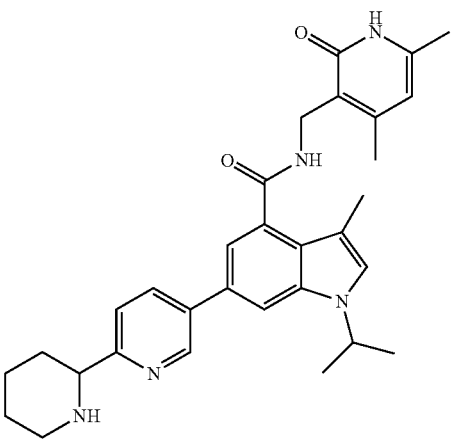 [SMILES: Cc1cc(C)c(CNC(=O)c2cc(-c3ccc(C4CCCCN4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(2-piperidinyl)-3-pyridinyl]-1H-indole-4-carboxamide | 1H NMR (400 MHz, METHANOL-d4) δppm 1.51-1.53 (d, 6 H) 1.82-1.84 (m, 3 H) 1.99-2.05 (m, 2 H) 2.24-2.26 (d, J = 7.83 Hz, 6 H) 2.26-2.31 (m, 1 H) 2.46 (s, 3 H) 3.13-3.25 (m, 1 H) 3.52-3.55 (m, 1 H) 4.36-4.49 (m, 1 H) 4.58 (s, 2 H) 4.83-4.89 (m, 1 H) 6.15 (s, 1 H) 7.30 (s, 1 H) 7.39 (s, 1 H) 7.52-7.54 (d, J = 8.08 Hz, 1 H) 7.80 (s, 1 H) 8.19-8.22 (dd, J = 8.08, 2.02 Hz, 1 H) 8.99-9.00 (d, J = 1.77 Hz, 1 H) | 512.3 |

| Ex | Structure | Name | ¹H NMR (400 MHz, DMSO-d₆) δ ppm | MS(ES) [M + H]⁺ |
|---|---|---|---|---|
| 295 | 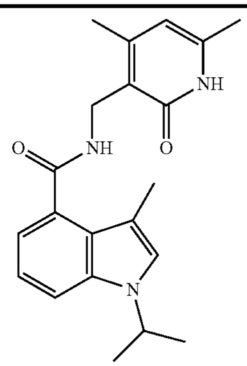 | N-[(4,6-dimethyl-2-oxo-1,2-dihydro-3-pyridinyl)methyl]-3-methyl-1-(1-methylethyl)-1H-indole-4-carboxamide | 11.47 (s, 1 H) 7.99 (t, J = 5.05 Hz, 1 H) 7.49 (d, J = 8.08 Hz, 1 H) 7.28 (s, 1 H) 7.04-7.09 (m, 1 H) 6.92 (d, J = 6.32 Hz, 1 H) 5.87 (s, 1 H) 4.71 (quin, J = 6.63 Hz, 1 H) 4.33 (s, 1 H) 4.32 (s, 1 H) 2.23 (s, 3 H) 2.14 (s, 3 H) 2.11 (s, 3 H) 1.42 (s, 3 H) 1.40 (s, 3 H) | 352.2 |

Example 296

1-Cyclopropyl-N-[(4,6-dimethyl-2-oxo-1,2-dihydro-3-pyridinyl)methyl]-3-methyl-6-(methylsulfonyl)-1H-indole-4-carboxamide

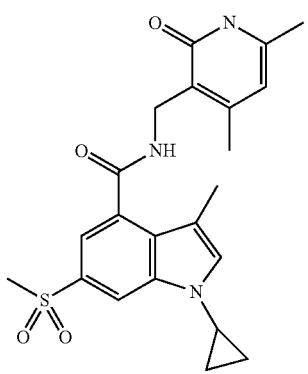

To a vial under a stream of N2 was added copper(II) trifluoromethanesulfonate (0.084 g, 0.233 mmol), sodium methanesulfinate (0.056 g, 0.467 mmol), DMSO (1.3 mL), and N,N-dimethylethylene diamine (0.053 mL, 0.490 mmol). The deep blue reaction was stirred for 5 min, then was added 6-bromo-1-cyclopropyl-N-[(4,6-dimethyl-2-oxo-1,2-dihydro-3-pyridinyl)methyl]-3-methyl-1H-indole-4-carboxamide (0.10 g, 0.233 mmol). The vial was sealed and heated at 120° C. for 3 h, at which time it was diluted with water (50 ml). The mixture was extracted with 30% THF/EtOAc (2×) (needed to warm to break up emulsion). Combined organics, dried over magnesium sulfate, filtered through Celite, and concentrated. Purification of the residue by column chromatography (12 gram Isco GOLD silica column; gradient B: 5-85%; A: dichloromethane, B: 10% (2M ammonia in MeOH) in chloroform) provided 1-cyclopropyl-N-[(4,6-dimethyl-2-oxo-1,2-dihydro-3-pyridinyl)methyl]-3-methyl-6-(methylsulfonyl)-1H-indole-4-carboxamide (83 mg, 0.184 mmol, 79% yield) as a white solid. ¹H NMR (400 MHz, DMSO-d₆) δ ppm 11.50 (s, 1H), 8.38 (t, J=5.1 Hz, 1H), 8.06 (d, J=1.8 Hz, 1H), 7.46 (dd, J=7.8, 1.3 Hz, 2H), 5.87 (s, 1H), 4.34 (d, J=5.1 Hz, 2H), 3.52 (tt, J=7.0, 3.6 Hz, 1H), 3.20 (s, 3H), 2.23 (s, 3H), 2.11 (s, 3H), 2.14 (s, 3H), 1.09 (m, 2H), 0.96 (m, 2H). MS(ES) [M+H]⁺ 427.8.

Examples 297-302 were prepared by the methods described above for Example 296, or routine variations thereof, starting from the requisite 6-bromoindole:

| Ex | Structure | Name | ¹H NMR (400 MHz, DMSO-d₆) δ ppm | MS(ES) [M + H]⁺ |
|---|---|---|---|---|
| 297 | 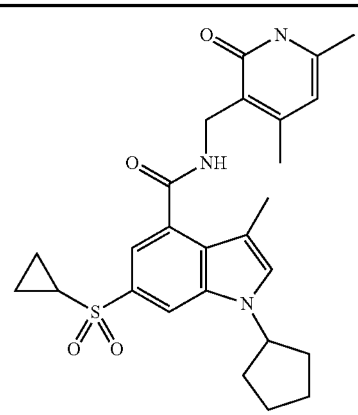 | 1-cycloypentyl-6-(cyclopropylsulfonyl)-N-[(4,6-dimethyl-2-oxo-1,2-dihydro-3-pyridinyl)methyl]-3-methyl-1H-indole-4-carboxamide | 11.49 (s, 1 H), 8.39 (t, J = 4.9 Hz, 1 H), 8.04 (d, J = 1.5 Hz, 1 H), 7.61 (s, 1 H), 7.35 (d, J = 1.5 Hz, 1 H), 5.87 (s, 1 H), 5.03 (t, J = 6.9 Hz, 1 H), 4.34 (d, J = 4.8 Hz, 2 H), 2.85 (m, 1 H), 2.23 (s, 3 H), 2.14 (m, 8 H), 1.81 (m, 4 H), 1.74 (m, 2 H), 1.13 (m, 2 H), 1.00 (m, 2 H) | 481.9 |

| Ex | Structure | Name | ¹H NMR (400 MHz, DMSO-d₆) δ ppm | MS(ES) [M + H]⁺ |
|---|---|---|---|---|
| 298 | 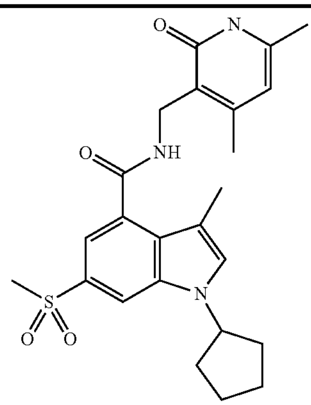 | 1-cyclopentyl-N-[(4,6-dimethyl-2-oxo-1,2-dihydro-3-pyridinyl)methyl]-3-methyl-6-(methylsulfonyl)-1H-indole-4-carboxamide | 11.50 (s, 1 H), 8.36 (t, J = 4.9 Hz, 1 H), 8.09 (d, J = 1.5 Hz, 1 H), 7.61 (s, 1 H), 7.40 (d, J = 1.5 Hz, 1 H), 5.87 (s, 1 H), 5.01 (t, J = 7.1 Hz, 1 H), 4.35 (d, J = 5.1 Hz, 2 H), 3.19 (s, 3 H), 2.23 (s, 3 H), 2.15 (m, 8 H), 1.78 (m, 6 H) | 455.9 |
| 299 | 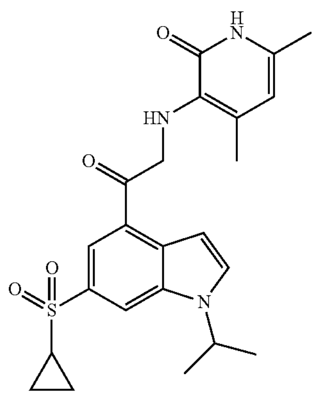 [SMILES: Cc1cc(C)c(NCC(=O)c2cc(S(=O)(=O)C3CC3)cc3c2ccn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 0.93-1.06 (m, 2 H), 1.11-1.25 (m, 2 H), 1.49 (d, J = 6.57 Hz, 6 H), 2.13 (s, 3 H), 2.24 (s, 3 H), 2.81-2.98 (m, 1 H), 4.37 (d, J = 5.05 Hz, 2 H), 4.99 (dt, J = 13.33, 6.60 Hz, 1 H), 5.90 (s, 1 H), 6.99 (d, J = 3.28 Hz, 1 H), 7.85 (d, J = 1.52 Hz, 1 H), 7.93 (d, J = 3.28 Hz, 1 H), 8.16 (s, 1 H), 8.49 (t, J = 4.93 Hz, 1 H), 11.57 (br. s., 1 H) | 442.0 |
| 300 | 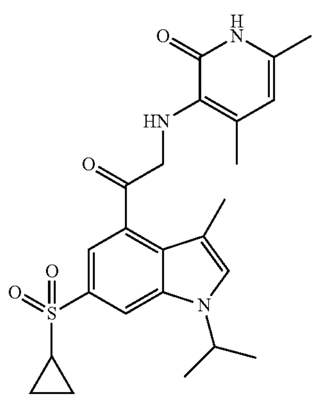 [SMILES: Cc1cc(C)c(NCC(=O)c2cc(S(=O)(=O)C3CC3)cc3c2c(C)cn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 1.00 (dd, J = 7.71, 2.65 Hz, 2 H), 1.13 (dd, J = 4.67, 2.40 Hz, 2 H), 1.45 (d, J = 6.57 Hz, 6 H), 2.12 (s, 3 H), 2.19 (s, 3 H), 2.23 (s, 3 H), 2.76-2.95 (m, 1 H), 4.35 (d, J = 5.05 Hz, 2 H), 4.91 (quin, J = 6.63 Hz, 1 H), 5.88 (s, 1 H), 7.36 (d, J = 1.52 Hz, 1 H), 7.66 (s, 1 H), 8.03 (d, J = 1.52 Hz, 1 H), 8.40 (t, J = 4.93 Hz, 1 H), 11.51 (s, 1 H) | 455.9 |
| 301 | 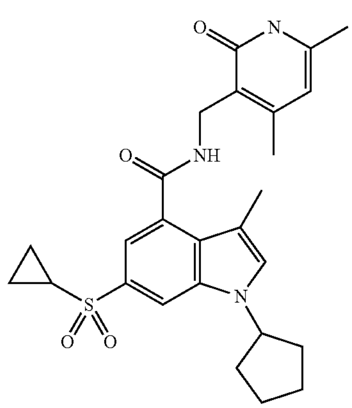 [SMILES: Cc1cc(C)c(CNC(=O)c2cc(S(=O)(=O)C3CC3)cc3c2c(C)cn3C2CCCC2)c(=O)[nH]1] | 1-cyclopentyl-6-(cyclopropylsulfonyl)-N-[(4,6-dimethyl-2-oxo-1,2-dihydro-3-pyridinyl)methyl]-3-methyl-1H-indole-4-carboxamide | 11.49 (s, 1 H), 8.39 (t, J = 4.9 Hz, 1 H), 8.04 (d, J = 1.5 Hz, 1 H), 7.61 (s, 1 H), 7.35 (d, J = 1.5 Hz, 1 H), 5.87 (s, 1 H), 5.03 (t, J = 6.9 Hz, 1 H), 4.34 (d, J = 4.8 Hz, 2 H), 2.85 (m, 1 H), 2.23 (s, 3 H), 2.14 (m, 8 H), 1.81 (m, 4 H), 1.74 (m, 2 H), 1.13 (m, 2 H), 1.00 (m, 2 H) | 481.9 |

-continued
| Ex | Structure | Name | $^{1}$H NMR (400 MHz, DMSO-$d_6$) δ ppm | MS(ES) [M + H]$^+$ |
|---|---|---|---|---|
| 302 | 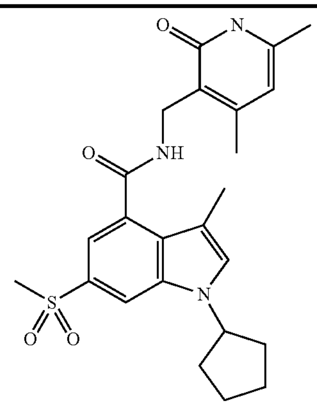 | 1-cyclopentyl-N-[(4,6-dimethyl-2-oxo-1,2-dihydro-3-pyridinyl)methyl]-3-methyl-6-(methylsulfonyl)-1H-indole-4-carboxamide | 11.50 (s, 1 H), 8.36 (t, J = 4.9 Hz, 1 H), 8.09 (d, J = 1.5 Hz, 1 H), 7.61 (s, 1 H), 7.40 (d, J = 1.5 Hz, 1 H), 5.87 (s, 1 H), 5.01 (t, J = 7.1 Hz, 1 H), 4.35 (d, J = 5.1 Hz, 2 H), 3.19 (s, 3 H), 2.23 (s, 3 H), 2.15 (m, 8 H), 1.78 (m, 6 H) | 455.9 |
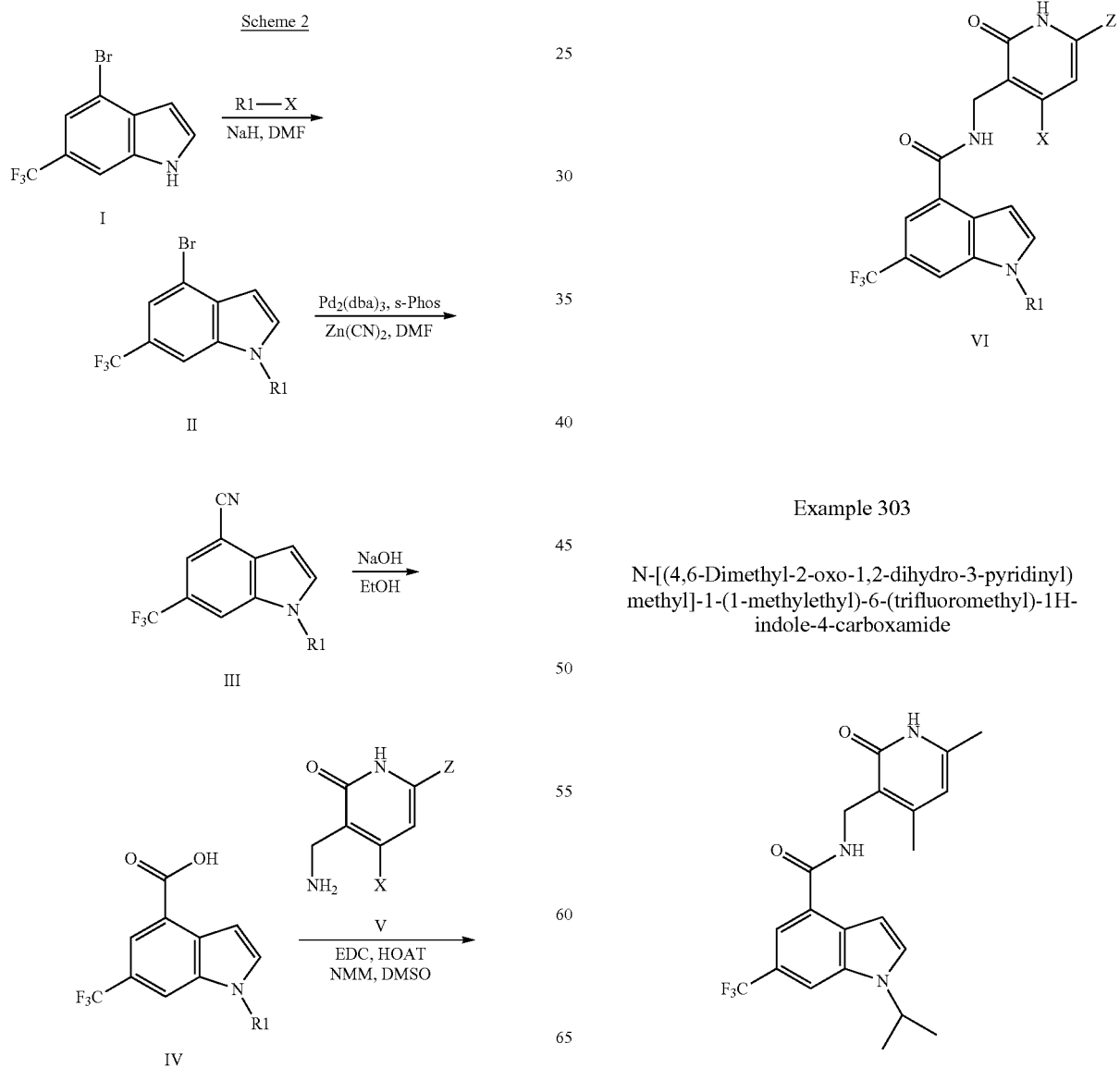
Example 303
N-[(4,6-Dimethyl-2-oxo-1,2-dihydro-3-pyridinyl)methyl]-1-(1-methylethyl)-6-(trifluoromethyl)-1H-indole-4-carboxamide a) 4-Bromo-1-(1-methylethyl)-6-(trifluoromethyl)-1H-indole

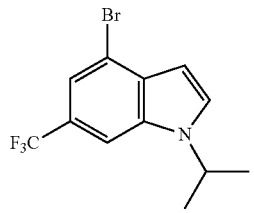 [SMILES: CC(C)n1ccc2c(Br)cc(C(F)(F)F)cc21]

To a solution of 4-bromo-6-(trifluoromethyl)-1H-indole (1 g, 3.79 mmol) in DMF (6 mL) was added 60% sodium hydride (0.182 g, 4.54 mmol), and the mixture was stirred for 30 min. 2-bromopropane (0.533 mL, 5.68 mmol) was added and the mixture was stirred overnight. The reaction was then quenched with 10% NaHCO$_3$ and extracted with EtOAc (3×). The extract was dried over Na$_2$SO$_4$ and concentrated. The residue was purified using column chromatography (Silica gel, 0 to 100% EtOAc/hexanes) to give the title compound (460 mg, 40%) as white solid. $^1$H NMR (400 MHz, CHLOROFORM-d) δ ppm 1.56-1.61 (m, 6H), 4.66-4.79 (m, 1H), 6.65 (d, J=3.03 Hz, 1H), 7.27-7.31 (m, 1H), 7.45 (d, J=3.03 Hz, 1H), 7.54 (s, 1H), 7.63 (s, 1H). MS: (M+H)$^+$=306.2.

b) 1-Isopropyl-6-(trifluoromethyl)-1H-indole-4-carbonitrile

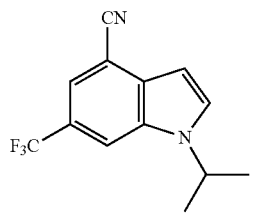 [SMILES: CC(C)n1ccc2c(C#N)cc(C(F)(F)F)cc21]

To a 10-mL microwave tube were added 4-bromo-1-(1-methylethyl)-6-(trifluoromethyl)-1H-indole (330 mg, 1.078 mmol), dicyanozinc (146 mg, 1.240 mmol), DMF (4 mL) and water (0.040 mL), and the mixture was degassed for 5 min by bubbling N$_2$. s-Phos (48.7 mg, 0.119 mmol) and tris(dibenzylideneacetone)dipalladium(0) (49.4 mg, 0.054 mmol) were added. The tube was sealed and the mixture was heated at 120° C. for 2.5 h. 1N NaOH (3 mL) was added and the mixture was extracted with EtOAc (3×). The extract was dried over Na$_2$SO$_4$ and concentrated. The residue was purified using column chromatography (Silica gel, 0 to 70% EtOAc/hexanes) to give the title compound (210 mg, 77%) as white solid. $^1$H NMR (400 MHz, CHLOROFORM-d) δ ppm 1.61 (m, 6H), 4.79 (spt, J=6.69 Hz, 1H), 6.84 (d, J=3.28 Hz, 1H), 7.59 (d, J=3.28 Hz, 1H), 7.73 (s, 1H), 7.88 (s, 1H). MS: (M+H)$^+$=253.2.

c) 1-Isopropyl-6-(trifluoromethyl)-1H-indole-4-carboxylic acid

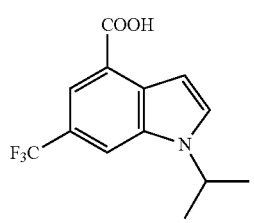 [SMILES: CC(C)n1ccc2c(C(=O)O)cc(C(F)(F)F)cc21]

To a solution of 1-(1-methylethyl)-6-(trifluoromethyl)-1H-indole-4-carbonitrile (180 mg, 0.714 mmol) in ethanol (5 mL) was added 10% sodium hydroxide (5 mL, 0.714 mmol), and the mixture was heated at reflux overnight. The mixture was concentrated to remove EtOH and the aqueous phase was acidified using 1N HCl to ~pH 4. The precipitate was collected by filtration and dried under high vacuum to give the title compound (167 mg, 86%) as brown solid. $^1$H NMR (400 MHz, DMSO-d$_6$) δ ppm 1.43-1.60 (m, 6H), 4.96-5.13 (m, 1H), 7.11 (d, J=3.28 Hz, 1H), 7.89-8.05 (m, 2H), 8.25 (s, 1H), 13.15 (br. s., 1H). MS: (M+H)$^+$=272.0.

d) N-((4,6-Dimethyl-2-oxo-1,2-dihydropyridin-3-yl)methyl)-1-isopropyl-6-(trifluoromethyl)-1H-indole-4-carboxamide

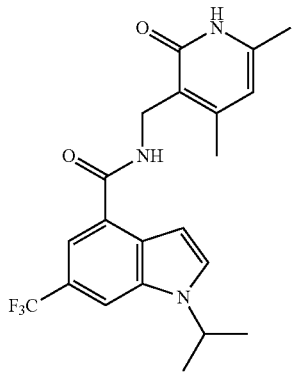 [SMILES: Cc1cc(C)c(CNC(=O)c2cc(C(F)(F)F)cc3c2ccn3C(C)C)c(=O)[nH]1]

To a solution of 1-(1-methylethyl)-6-(trifluoromethyl)-1H-indole-4-carboxylic acid (40 mg, 0.147 mmol) in dimethyl sulfoxide (1 mL) were added 3-(aminomethyl)-4,6-dimethyl-2(1H)-pyridinone (41.7 mg, 0.221 mmol), N-methylmorpholine (0.065 mL, 0.590 mmol), 1-hydroxy-7-azabenzotriazole (40.1 mg, 0.295 mmol) and EDC (56.5 mg, 0.295 mmol), and the mixture was stirred overnight. The mixture was quenched with water (5 mL) and stirred for 10 min. The precipitate was collected by filtration and dried under high vacuum to give the title compound (39 mg, 63%) as an off-white solid. $^1$H NMR (400 MHz, DMSO-d$_6$) δ ppm 1.47 (m, 6H), 2.13 (s, 3H), 2.23 (s, 3H), 4.36 (d, J=5.05 Hz, 2H), 4.99 (dt, J=13.20, 6.66 Hz, 1H), 5.89 (s, 1H), 6.98 (d, J=3.03 Hz, 1H), 7.68 (s, 1H), 7.86 (d, J=3.28 Hz, 1H), 8.08 (s, 1H), 8.45 (t, J=4.93 Hz, 1H), 11.56 (s, 1H). MS: (M+H)$^+$=406.1.

Example 304

1-Isopropyl-N-((6-methyl-2-oxo-4-propyl-1,2-dihydropyridin-3-yl)methyl)-6-(trifluoromethyl)-1H-indole-4-carboxamide

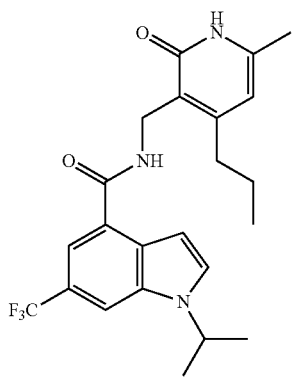 [SMILES: CCCc1cc(C)[nH]c(=O)c1CNC(=O)c1cc(C(F)(F)F)cc2c1ccn2C(C)C]

The title compound was prepared using procedures as described for N-((4,6-dimethyl-2-oxo-1,2-dihydropyridin-3-yl)methyl)-1-isopropyl-6-(trifluoromethyl)-1H-indole-4-carboxamide. $^1$H NMR (400 MHz, DMSO-$d_6$) δ ppm 0.91 (t, J=8.00 Hz 3H), 1.39-1.63 (m, 8H), 2.14 (s, 3H), 4.39 (d, J=5.05 Hz, 2H), 4.99 (dt, J=13.26, 6.76 Hz, 1H), 5.92 (s, 1H), 6.98 (d, J=3.28 Hz, 1H), 7.68 (s, 1H), 7.87 (d, J=3.03 Hz, 1H), 8.08 (s, 1H), 8.44 (t, J=5.05 Hz, 1H), 11.57 (s, 1H). MS: (M+H)$^+$=434.1.

Scheme 3

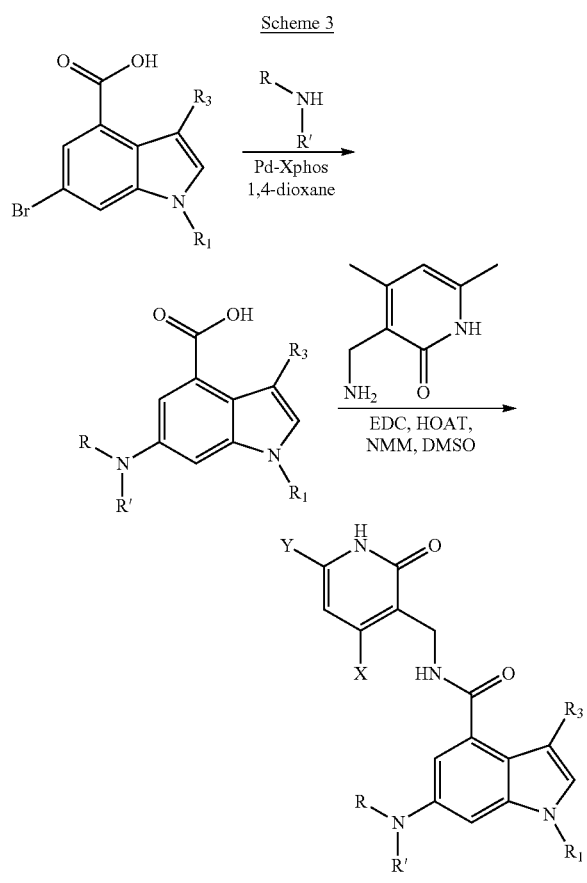

Example 305

N-((4,6-dimethyl-2-oxo-1,2-dihydropyridin-3-yl)methyl)-6-(4-((dimethylamino)methyl)piperidin-1-yl)-1-isopropyl-3-methyl-1H-indole-4-carboxamide

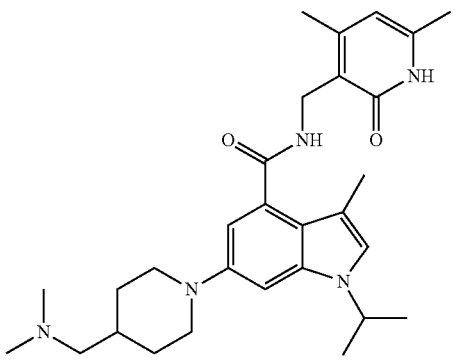

a) 6-(4-((Dimethylamino)methyl)piperidin-1-yl)-1-isopropyl-3-methyl-1H-indole-4-carboxylic acid

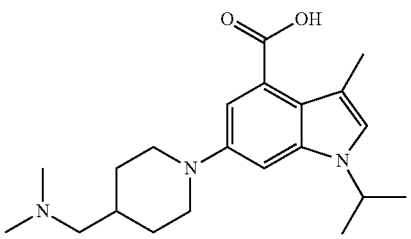 [SMILES: Cc1cn(C(C)C)c2cc(N3CCC(CN(C)C)CC3)cc(C(=O)O)c12]

To a 10-mL microwave tube were added 6-bromo-3-methyl-1-(1-methylethyl)-1H-indole-4-carboxylic acid (100 mg, 0.338 mmol), 1,4-dioxane (2 mL), N,N-dimethyl-1-(4-piperidinyl)methanamine (52.8 mg, 0.371 mmol) and sodium tert-butoxide (71.4 mg, 0.743 mmol), and the mixture was degassed for 5 min. Chloro(2-dicyclohexylphosphino-2',4',6'-tri-1-propyl-1,1'-biphenyl)[2-(2-aminoethyl)phenyl]Pd(II)Me-t-butylether adduct (13.96 mg, 0.017 mmol) was added and the tube was sealed. The mixture was stirred at 98° C. with stirring for 20 h. The mixture was then concentrated and the residue was purified using reverse-phase HPLC (Gemini 5u C18(2) 100A, AXIA; 30×100 mm 5 micron; (30 mL/min, 7% ACN/H2O, 0.1% formic acid to 37% ACN/H2O, 0.1% formic acid) to give the title compound (65 mg, 54%) as pale yellow solid. $^1$H NMR (400 MHz, DMSO-$d_6$) δ ppm 1.19-1.34 (m, 2H), 1.39 (d, J=6.57 Hz, 6H), 1.58-1.71 (m, 1H), 1.82 (d, J=11.87 Hz, 2H), 2.23-2.31 (m, 10H), 2.66 (td, J=11.94, 1.89 Hz, 2H), 3.57-3.71 (m, 2H), 4.70 (quin, J=6.63 Hz, 1H), 7.09 (d, J=2.02 Hz, 1H), 7.15 (dd, J=9.60, 1.52 Hz, 2H). MS: (M+H)$^+$=358.2.

b) N-((4,6-Dimethyl-2-oxo-1,2-dihydropyridin-3-yl)methyl)-6-(4-((dimethylamino)methyl)piperidin-1-yl)-1-isopropyl-3-methyl-1H-indole-4-carboxamide

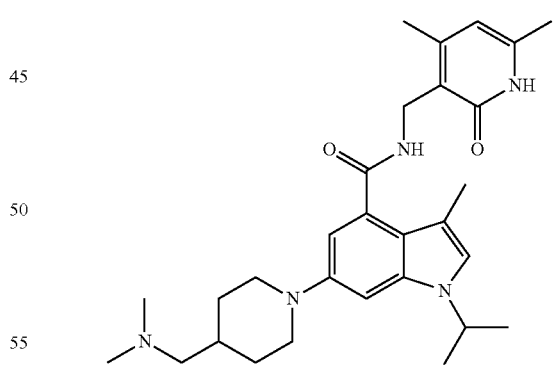

To a solution of 6-{4-[(dimethylamino)methyl]-1-piperidinyl}-3-methyl-1-(1-methylethyl)-1H-indole-4-carboxylic acid (62 mg, 0.173 mmol) in dimethyl sulfoxide (1 mL) were added 3-(aminomethyl)-4,6-dimethyl-2(1H)-pyridinone (42.5 mg, 0.225 mmol), N-methylmorpholine (0.095 mL, 0.867 mmol), 1-hydroxy-7-azabenzotriazole (47.2 mg, 0.347 mmol) and EDC (66.5 mg, 0.347 mmol), and the mixture was stirred overnight. The mixture was purified using reverse-phase HPLC (Gemini 5u C18(2) 100A, AXIA; 30×100 mm 5 micron; 30 mL/min, 8% ACN/H2O, 0.1% formic acid to 38% ACN/H2O, 0.1% formic acid) to give the title compound (52 mg, 55%) as an off-white solid. $^1$H NMR (400 MHz, DMSO-$d_6$) ppm 1.26 (m, 2H), 1.35-1.41 (m, 6H), 1.57-1.71 (m, 1H), 1.80 (d, J=11.12 Hz, 2H), 2.10 (d, J=10.36 Hz, 6H), 2.22 (s, 3H), 2.26-2.33 (m, 8H), 2.57-2.72 (m, 2H), 3.61 (d, J=12.13 Hz, 2H), 4.31 (d, J=5.05 Hz, 2H), 4.58-4.72 (m, 1H), 5.86 (s, 1H), 6.69 (d, J=2.02 Hz, 1H), 6.92 (d, J=1.77 Hz, 1H), 7.05 (d, J=1.01 Hz, 1H), 7.92-7.99 (m, 1H). MS: (M+H)$^+$=492.1.

Examples 306-317 were prepared by the methods described above for Example 305, or routine variations thereof, using the requisite amine:

| Ex | Structure | Name | $^1$H NMR (400 MHz, DMSO-$d_6$) δ ppm | MS(ES) [M + H]$^+$ |
|---|---|---|---|---|
| 306 | 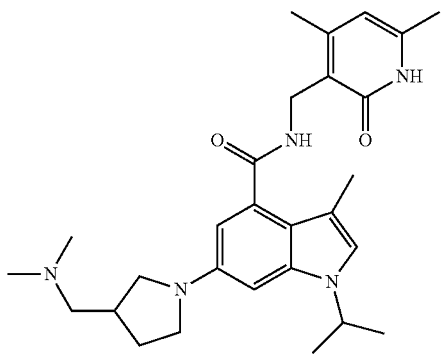 | N-((4,6-dimethyl-2-oxo-1,2-dihydropyridin-3-yl)methyl)-6-(3-((dimethylamino)methyl)pyrrolidin-1-yl)-1-isopropyl-3-methyl-1H-indole-4-carboxamide | 1.36 (m, 6 H), 1.68 (dd, J = 12.13, 7.58 Hz, 1 H), 2.01-2.38 (m, 20 H), 2.99 (dd, J = 9.09, 6.57 Hz, 1 H), 3.20-3.30 (m, 1 H), 3.35-3.44 (m, 1 H), 4.31 (d, J = 5.05 Hz, 2 H), 4.53-4.67 (m, 1 H), 5.87 (s, 1 H), 6.35 (d, J = 2.02 Hz, 1 H), 6.45 (d, J = 1.77 Hz, 1 H), 6.93 (d, J = 1.01 Hz, 1 H), 7.88 (t, J = 5.18 Hz, 1 H), 11.47 (s, 1 H) | 478.0 |
| 307 | 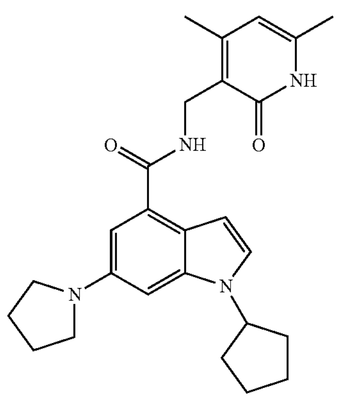 [SMILES: Cc1cc(C)c(CNC(=O)c2cc(N3CCCC3)cc3c2ccn3C2CCCC2)c(=O)[nH]1] | 1-cyclopentyl-N-((4,6-dimethyl-2-oxo-1,2-dihydropyridin-3-yl)methyl)-6-(pyrrolidin-1-yl)-1H-indole-4-carboxamide | 1.65-1.88 (m, 7 H), 1.95-2.02 (m, 5 H), 2.08-2.18 (m, 6 H), 2.24 (s, 3 H), 3.29 (t, J = 6.32 Hz, 4 H), 4.34 (d, J = 5.31 Hz, 2 H), 4.74-4.90 (m, 1 H), 5.89 (s, 1 H), 6.59-6.70 (m, 2 H), 6.83 (d, J = 1.77 Hz, 1 H), 7.22 (d, J = 3.28 Hz, 1 H), 8.03 (t, J = 5.31 Hz, 1 H) | 433.2 |
| 308 | 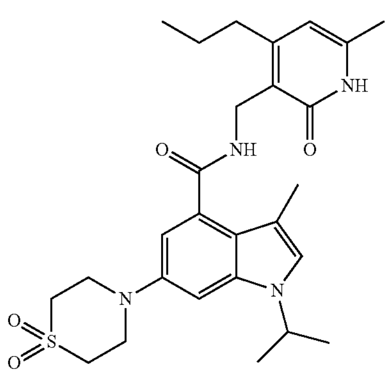 [SMILES: CCCc1cc(C)[nH]c(=O)c1CNC(=O)c1cc(N2CCS(=O)(=O)CC2)cc2c1c(C)cn2C(C)C] | 6-(1,1-dioxidothiomorpholino)-1-isopropyl-3-methyl-N-((6-methyl-2-oxo-4-propyl-1,2-dihydropyridin-3-yl)methyl)-1H-indole-4-carboxamide | 1.06 (m, 3 H), 1.43-1.54 (m, 6 H), 1.68 (sxt, J = 7.58 Hz, 2 H), 2.19 (s, 3 H), 2.27 (s, 3 H), 2.69-2.82 (m, 2 H), 3.17-3.26 (m, 4 H), 3.76-3.86 (m, 4 H), 4.52-4.58 (m, 2 H), 4.69 (dt, J = 13.39, 6.69 Hz, 1 H), 6.11-6.21 (m, 1 H), 6.88 (d, J = 2.02 Hz, 1 H), 7.09 (dd, J = 11.75, 1.64 Hz, 2H) | 513.2 |

| Ex | Structure | Name | ¹H NMR (400 MHz, DMSO-d₆) δ ppm | MS(ES) [M + H]⁺ |
|---|---|---|---|---|
| 309 | 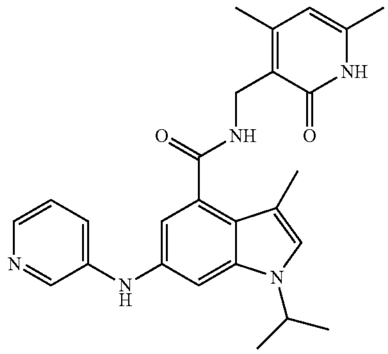 [SMILES: Cc1cc(C)c(CNC(=O)c2cc(Nc3cccnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridin-3-ylamino)-1H-indole-4-carboxamide | 1.39 (m, 6 H), 2.11 (d, J = 3.28 Hz, 6 H), 2.22 (s, 3 H), 4.32 (d, J = 4.80 Hz, 2 H), 4.59 (dt, J = 13.14, 6.57 Hz, 1 H), 5.86 (s, 1 H), 6.76 (d, J = 1.26 Hz, 1 H), 7.12-7.25 (m, 3 H), 7.41 (d, J = 8.34 Hz, 1 H), 7.95 (d, J = 3.54 Hz, 1 H), 8.10 (t, J = 4.80 Hz, 1 H), 8.25 (s, 1 H), 8.30-8.39 (m, 1 H), 11.47 (br. s., 1 H) | 444.1 |
| 310 | 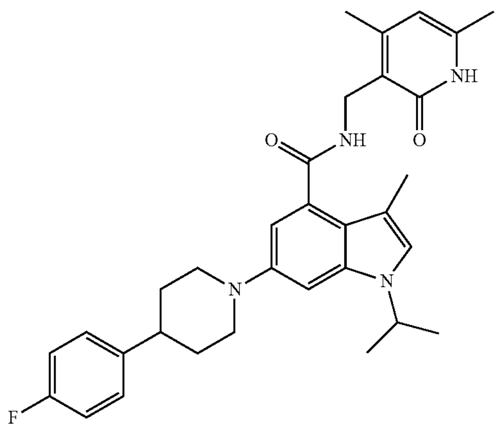 [SMILES: Cc1cc(C)c(CNC(=O)c2cc(N3CCC(c4ccc(F)cc4)CC3)cc3c2c(C)cn3C(C)C)c(=O)[nH]1] | N-((4,6-dimethyl-2-oxo-1,2-dihydropyridin-3-yl)methyl)-6-(4-(4-fluorophenyl)piperidin-1-yl)-1-isopropyl-3-methyl-1H-indole-4-carboxamide | 11.48 (s, 1H), 8.01 (br. s., 1H), 6.48-7.39 (m, 6H), 5.87 (s, 1H), 4.68 (dt, J = 6.09, 12.32 Hz, 1H), 4.33 (d, J = 5.05 Hz, 2H), 3.74 (d, J = 12.13 Hz, 2H), 2.23 (s, 3H), 2.11 (s, 6H), 1.89 (br. s., 3H), 1.39 (d, J = 6.32 Hz, 6H) | 528.9 |
| 311 | 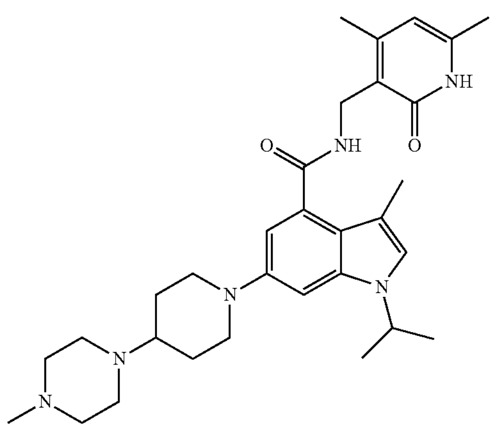 | N-((4,6-dimethyl-2-oxo-1,2-dihydropyridin-3-yl)methyl)-1-isopropyl-3-methyl-6-(4-(4-methylpiperazin-1-yl)piperidin-1-yl)-1H-indole-4-carboxamide | 7.97 (br. s., 1H), 7.05 (s, 1H), 6.92 (d, J = 1.77 Hz, 1H), 6.68 (d, J = 2.02 Hz, 1H), 5.86 (s, 1H), 4.60-4.69 (m, J = 6.44, 6.44 Hz, 1H), 4.31 (d, J = 4.80 Hz, 2H), 3.65 (d, J = 11.37 Hz, 2H), 3.25-3.32 (m, 4H), 2.68 (ddd, J = 1.89, 2.02, 3.66 Hz, 2H), 2.62 (dd, J = 1.14, 11.24 Hz, 2H), 2.33 (dt, J = 1.77, 3.54 Hz, 1H), 2.22 (s, 3H), 2.14 (s, 3H), 2.11 (s, 5H), 2.08 (s, 4H), 1.80-1.91 (m, J = 10.36 Hz, 2H), 1.55 (br. s., 1H), 1.37 (d, J = 6.57 Hz, 6H) | 533.0 |

-continued

| Ex | Structure | Name | ¹H NMR (400 MHz, DMSO-d₆) δ ppm | MS(ES) [M + H]⁺ |
|---|---|---|---|---|
| 312 | 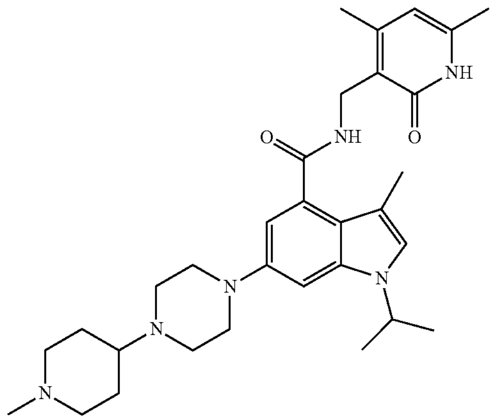 | N-((4,6-dimethyl-2-oxo-1,2-dihydropyridin-3-yl)methyl)-1-isopropyl-3-methyl-6-(4-(1-methylpiperidin-4-yl)piperazin-1-yl)-1H-indole-4-carboxamide | 7.04 (s, 1H), 7.00 (d, J = 1.77 Hz, 1H), 6.87 (d, J = 2.02 Hz, 1H), 6.13 (s, 1H), 4.66 (quin, J = 6.69 Hz, 1H), 4.54 (s, 2H), 3.18-3.29 (m, 4H), 3.11-3.18 (m, 1H), 2.98 (d, J = 11.87 Hz, 2H), 2.76-2.85 (m, 4H), 2.43 (s, 3H), 2.27-2.35 (m, 5H), 2.26 (s, 3H), 2.17 (s, 3H), 2.04-2.14 (m, 2H), 1.93-2.02 (m, 2H), 1.54-1.72 (m, 2H), 1.45 (d, J = 6.57 Hz, 6H) | 533.0 |
| 313 | 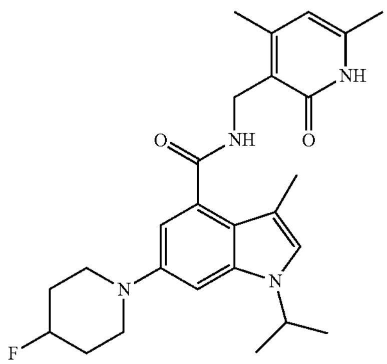 [SMILES: Cc1cc(C)c(CNC(=O)c2cc(N3CCC(F)CC3)cc3c2c(C)cn3C(C)C)c(=O)[nH]1] | N-((4,6-dimethyl-2-oxo-1,2-dihydropyridin-3-yl)methyl)-6-(4-fluoropiperidin-1-yl)-1-isopropyl-3-methyl-1H-indole-4-carboxamide | 7.01-7.06 (m, 2H), 6.88 (d, J = 2.02 Hz, 1H), 6.14 (s, 1H), 4.81-4.88 (m, 1H), 4.59-4.71 (m, 1H), 4.54 (s, 2H), 3.09-3.19 (m, 2H), 2.44 (s, 3H), 2.26 (s, 3H), 2.17 (s, 3H), 1.88-2.15 (m, 4H), 1.46 (d, J = 6.82 Hz, 6H) | 452.8 |
| 314 | 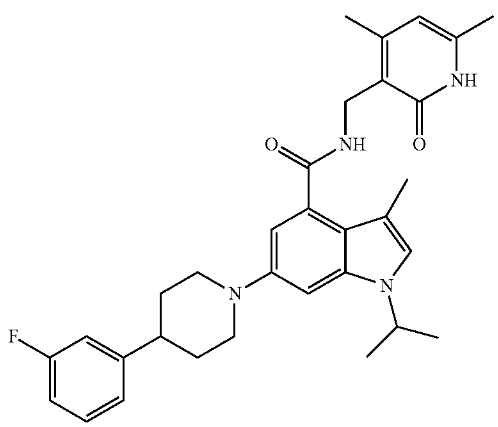 [SMILES: Cc1cc(C)c(CNC(=O)c2cc(N3CCC(c4cccc(F)c4)CC3)cc3c2c(C)cn3C(C)C)c(=O)[nH]1] | N-((4,6-dimethyl-2-oxo-1,2-dihydropyridin-3-yl)methyl)-6-(4-(3-fluorophenyl)piperidin-1-yl)-1-isopropyl-3-methyl-1H-indole-4-carboxamide | 8.01 (t, 1H), 7.36 (td, J = 6.32, 7.96 Hz, 1H), 7.12-7.19 (m, 2H), 7.07 (d, J = 1.01 Hz, 1H), 7.00-7.06 (m, 1 H), 6.98 (d, J = 1.77 Hz, 1H), 6.74 (d, J = 2.02 Hz, 1H), 5.87 (s, 1H), 4.68 (quin, J = 6.57 Hz, 1H), 4.32 (d, J = 5.05 Hz, 2H), 3.75 (d, J = 11.87 Hz, 2H), 2.65-2.82 (m, 3H), 2.23 (s, 3H), 2.10 (d, J = 4.04 Hz, 6H), 1.75-1.96 (m, 4H), 1.38 (d, J = 6.57 Hz, 6H) | 529.0 |
| 315 | 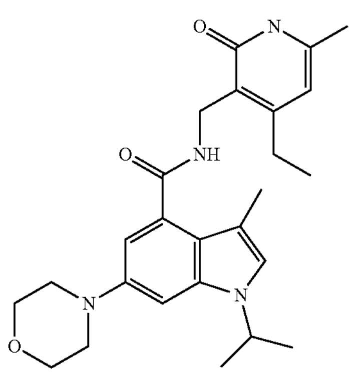 [SMILES: CCc1cc(C)[nH]c(=O)c1CNC(=O)c1cc(N2CCOCC2)cc2c1c(C)cn2C(C)C] | N-[(4-ethyl-6-methyl-2-oxo-1,2-dihydro-3-pyridinyl)methyl]-3-methyl-1-(1-methylethyl)-6-(4-morpholinyl)-1H-indole-4-carboxamide | 11.43 (br. s., 1 H) 7.96 (t, J = 5.05 Hz, 1 H) 7.08 (d, J = 1.01 Hz, 1 H) 6.95 (d, J = 2.02 Hz, 1 H) 6.70 (d, J = 2.02 Hz, 1 H) 5.91 (s, 1 H) 4.67 (quin, J = 6.63 Hz, 1 H) 4.34 (s, 1 H) 4.32 (s, 1 H) 3.74-3.77 (m, 4 H) 3.07-3.11 (m, 4 H) 2.54-2.60 (m, 2 H) 2.13 (s, 3 H) 2.09 (s, 3 H) 1.38 (s, 3 H) 1.37 (s, 3 H) 1.13 (t, J = 7.58 Hz, 3 H) | 451.0 |

| Ex | Structure | Name | $^1$H NMR (400 MHz, DMSO-$d_6$) δ ppm | MS(ES) [M + H]$^+$ |
|---|---|---|---|---|
| 316 | 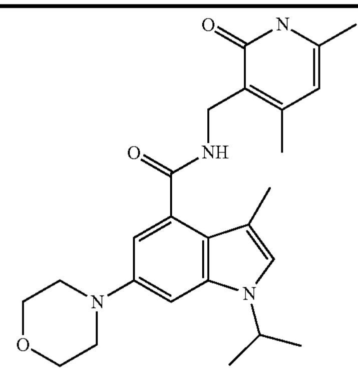 | N-[(4,6-dimethyl-2-oxo-1,2-dihydro-3-pyridinyl)methyl]-3-methyl-1-(1-methylethyl)-6-(4-morpholinyl)-1H-indole-4-carboxamide | 11.34 (br. s., 1 H) 7.99 (t, J = 4.93 Hz, 1 H) 7.08 (s, 1 H) 6.94 (d, J = 2.02 Hz, 1 H) 6.70 (d, J = 1.77 Hz, 1 H) 5.86 (s, 1 H) 4.67 (quin, J = 6.57 Hz, 1 H) 4.32 (s, 1 H) 4.30 (s, 1 H) 3.72-3.80 (m, 4 H) 3.06-3.13 (m, 4 H) 2.22 (s, 3 H) 2.11 (s, 3 H) 2.09 (s, 3 H) 1.38 (s, 3 H) 1.37 (s, 3 H) | 437.1 |
| 317 | 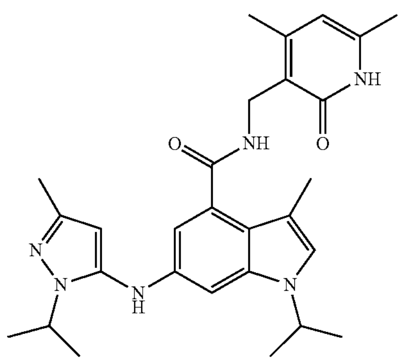 [SMILES: Cc1cc(Nc2cc(C(=O)NCc3c(C)cc(C)[nH]c3=O)c3c(C)cn(C(C)C)c3c2)n(C(C)C)n1] | N-[(4,6-dimethyl-2-oxo-1,2-dihydro-3-pyridinyl)methyl]-3-methyl-1-(1-methylethyl)-6-{[3-methyl-1-(1-methylethyl)-1H-pyrazol-5-yl]amino}-1H-indole-4-carboxamide | 1.30 (m, 6 H), 1.35 (d, J = 6.82 Hz, 6 H), 2.08 (s, 3 H), 2.11 (s, 3 H), 2.13 (s, 3 H) 2.21 (s, 3 H), 4.31 (d, J = 5.05 Hz, 2 H), 4.37-4.49 (m, 2 H), 5.70-5.77 (m, 1 H), 5.86 (s, 1 H), 6.60 (d, J = 1.77 Hz, 1 H), 6.71 (d, J = 1.77 Hz, 1 H), 6.99-7.07 (m, 1 H), 7.67 (s, 1 H), 7.93-8.03 (m, 1 H), 11.46 (br. s., 1 H) | 489.0 |

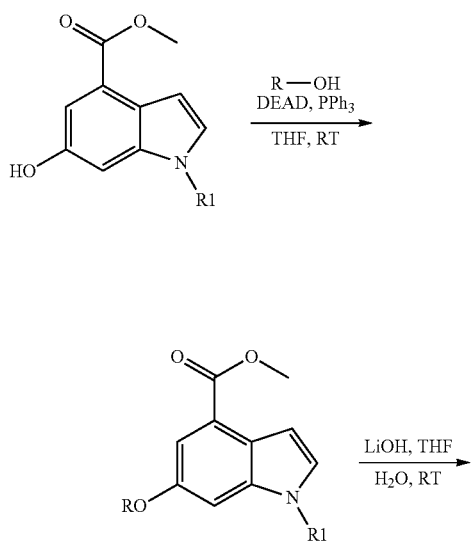

Scheme 4

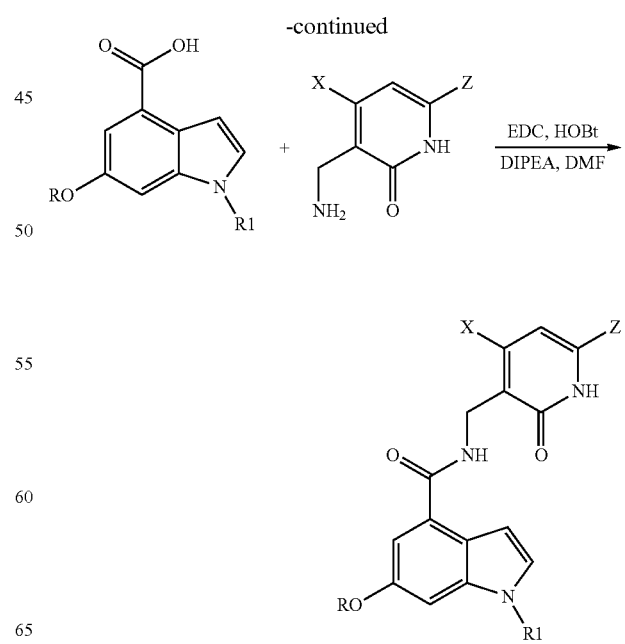

Example 318

6-(2-Dimethylamino-ethoxy)-1-isopropyl-1H-indole-4-carboxylic acid (6-methyl-2-oxo-4-propyl-1,2-dihydro-pyridin-3-ylmethyl)-amide

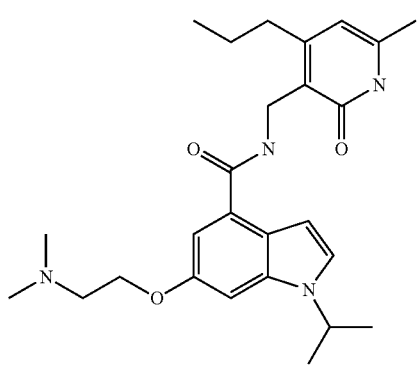

a) 6-(2-Dimethylamino-ethoxy)-1-isopropyl-1H-indole-4-carboxylic acid methyl ester

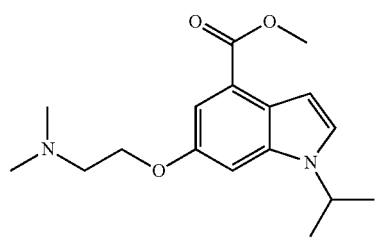 [SMILES: COC(=O)c1cc(OCCN(C)C)cc2c1ccn2C(C)C]

To a cooled (0° C.) mixture of 6-hydroxy-1-isopropyl-1H-indole-4-carboxylic acid methyl ester (700 mg, 3 mmol), 2-dimethylamino-ethanol (320 mg, 3.60 mmol) and PPh₃ (948 mg, 3.60 mmol) in THF (10 mL) was added DEAD (620 mg, 3.60 mmol) and stirred for 16 h at RT. Reaction mixture was concentrated under reduced pressure and the residue was purified by column chromatography by eluting with 2% MeOH in chloroform to afford the title compound (550 mg, 60%) as colorless gum. LCMS (ES+): m/z=305.36 [M+H].

b) 6-(2-Dimethylamino-ethoxy)-1-isopropyl-1H-indole-4-carboxylic acid

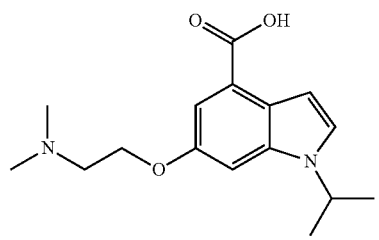 [SMILES: CC(C)n1ccc2c(C(=O)O)cc(OCCN(C)C)cc21]

To a solution of 6-(2-dimethylamino-ethoxy)-1-isopropyl-1H-indole-4-carboxylic acid methyl ester (500 mg, 1.64 mmol) in THF (5 mL) was added LiOH.H₂O (200 mg, 4.93 mmol) in water (5 mL). the reaction was heated at reflux for 5 h, at which time the THF was removed under reduced pressure. The remaining mixture was acidified with 1N HCl (pH ~6) and extracted with 10% MeOH in chloroform (4×30 mL). The combined organic layer was dried over anhydrous Na₂SO₄ and concentrated to yield 6-(2-dimethylamino-ethoxy)-1-isopropyl-1H-indole-4-carboxylic acid (400 mg), which was used in the next stage without further purification. LCMS (ES+): m/z=291.30 [M+H].

c) 6-(2-Dimethylamino-ethoxy)-1-isopropyl-1H-indole-4-carboxylic acid (6-methyl-2-oxo-4-propyl-1,2-dihydro-pyridin-3-ylmethyl)-amide

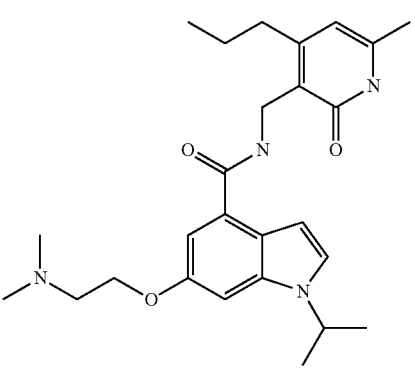

To a cooled (0° C.) mixture of 6-(2-dimethylamino-ethoxy)-1-isopropyl-1H-indole-4-carboxylic acid (400 mg, 1.37 mmol) in DMF (10 mL) was added EDC.HCl (310 mg, 1.65 mmol) and HOBt.H₂O (250 mg, 1.65 mmol). The reaction was stirred for 15 min, then DIPEA (1.2 mL, 6.89 mmol) and 3-aminomethyl-6-methyl-4-propyl-1H-pyridin-2-one (240 mg, 1.37 mmol) were added. The reaction was allowed to warm to RT and stirred for 16 h, at which time it was diluted with water (20 mL) and extracted with DCM (2×15 mL). The combined DCM layer was dried over Na₂SO₄ and concentrated. The residue was purified by flash column chromatography eluting with 3% MeOH in chloroform and then further purified by preparative HPLC to furnish 6-(2-dimethylamino-ethoxy)-1-isopropyl-1H-indole-4-carboxylic acid (6-methyl-2-oxo-4-propyl-1,2-dihydro-pyridin-3-ylmethyl)-amide (120 mg, 19%) as an off white solid. ¹H NMR (400 MHz, DMSO-d₆): δ 0.92-0.88 (t, 3H), 1.43-1.41 (d, J=6.8 Hz, 6H), 1.56 (m, 2H), 2.12 (s, 3H), 2.22 (s, 6H), 2.55-2.53 (m, 2H), 2.06 (m, 2H), 4.11-4.09 (t, 2H), 4.36-4.34 (d, J=4.8 Hz, 2H), 4.76-4.73 (m, 1H), 5.90 (s, 1H), 6.74-6.73 (d, J=2.8 Hz, 1H), 7.04 (s, 1H), 7.20 (s, 1H), 7.43-7.42 (d, J=3.2 Hz, 1H), 8.10-8.07 (bs, 1H), 11.55 (bs, 1H). LCMS (ES+): m/z=453.23 [M+H].

Examples 319-320 were prepared by the methods described above for Example 318, or routine variations thereof, using the requisite alcohol (Mitsunobu reaction) and aminomethylpyridone:

| Ex | Structure | Name | $^1$H NMR (400 MHz, DMSO-$d_6$) δ ppm | MS(ES) [M + H]$^+$ |
|---|---|---|---|---|
| 319 | 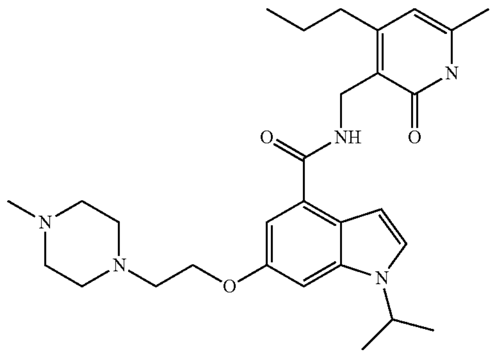 | 1-isopropyl-6-[2-(4-methyl-piperazin-1-yl)-ethoxy]-1H-indole-4-carboxylic acid (6-methyl-2-oxo-4-propyl-1,2-dihydro-pyridin-3-ylmethyl)-amide | 0.92 (t, 3H), 1.42 (d, J = 6.8 Hz, 6H), 1.57 (m, 2H), 2.14 (d, 6H), 2.32 (m, 8H), 2.54 (m, 2H), 2.71 (t, 2H), 4.13-4.11 (m, 2H), 4.35 (d, J = 5.2 Hz, 2H), 4.78-4.72 (m, 1H), 5.90 (s, 1H), 6.74 (d, J = 3.2 Hz, 1H), 7.05 (s, 1H), 7.22 (s, 1H), 7.42 (d, J = 3.2 Hz, 1H), 8.12 (t, 1H), 11.55 (bs, 1H) | 506.26 |
| 320 | 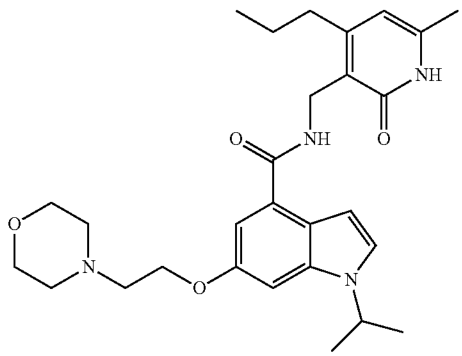 [SMILES: CCCc1cc(C)[nH]c(=O)c1CNC(=O)c1cc(OCCN2CCOCC2)cc2c1ccn2C(C)C] | 1-isopropyl-6-(2-morpholin-4-yl-ethoxy)-1H-indole-4-carboxylic acid (6-methyl-2-oxo-4-propyl-1,2-dihydro-pyridin-3-ylmethyl)-amide | 0.94 (t, 3H), 1.42 (d, J = 6.8 Hz, 6H), 1.57 (m, 2H), 2.14 (s, 3H), 2.46-2.50 (m, 4H), 2.75 (t, 2H), 2.68-2.75 (t, 4H), 4.15-4.19 (m, 2H), 4.35 (d, 2H), 4.78-4.72 (m, 1 H), 5.91 (s, 1H), 6.73 (d, 1H), 7.10 (s, 1H), 7.25 (s, 1H), 7.62 (d, 1H), 8.12 (t, 1H), 11.55 (bs, 1H) | 495.22 |

Example 321

1-Isopropyl-6-(2-piperazin-1-ylethoxy)-1H-indole-4-carboxylic acid (6-methyl-2-oxo-4-propyl-1,2-dihydro-pyridin-3-ylmethyl)-amide

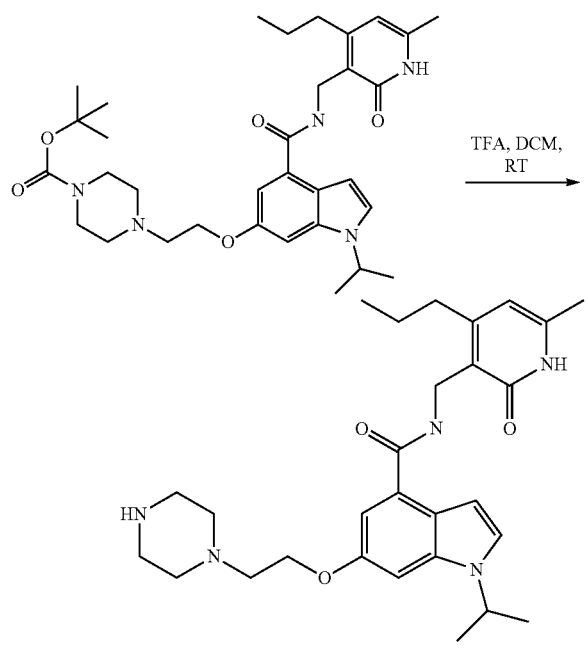

To a stirred solution of 4-(2-{1-isopropyl-4-[(6-methyl-2-oxo-4-propyl-1,2-dihydro-pyridin-3-ylmethyl)-carbamoyl]-1H-indol-6-yloxy}-ethyl)-piperazine-1-carboxylic acid tert-butyl ester (280 mg, 0.472 mmol; prepared following the procedure of Example xx) in dichloromethane (15 mL) was added TFA (1.5 mL) at room temperature and then stirred for 3 h at room temperature. Reaction mixture was concentrated under reduced pressure, diluted with water (20 mL) and washed the resulting aqueous layer with diethyl ether (2×15 mL). The aqueous layer was basified with (pH ~8) with saturated aqueous NaHCO$_3$ solution and extracted with dichloromethane (3×20 mL). The combined organic layer was washed with brine solution (2×25 mL) and concentrated. Purification by preparative HPLC afforded 1-isopropyl-6-(2-piperazin-1-yl-ethoxy)-1H-indole-4-carboxylic acid (6-methyl-2-oxo-4-propyl-1,2-dihydro-pyridin-3-ylmethyl)-amide (48 mg, 20%) as an off white solid. $^1$H NMR (400 MHz, DMSO-$d_6$): δ 0.93 (t, 3H), 1.42 (d, 6H, J=6.8 Hz), 1.57 (m, 2H), 2.14 (s, 3H), 2.45-2.2 (m, 4H), 2.68 (t, 2H), 2.75 (t, 4H), 4.15-4.19 (m, 2H), 4.35 (d, 2H), 4.78-4.72 (m, 1H), 5.91 (s, 1H), 6.73 (d, 1H), 7.03 (s, 1H), 7.24 (s, 1H), 7.42 (d, 1H), 8.12 (t, 1H), 11.58 (bs, 1H). LCMS (ES+): m/z=494.57 [M+H].

Scheme 5

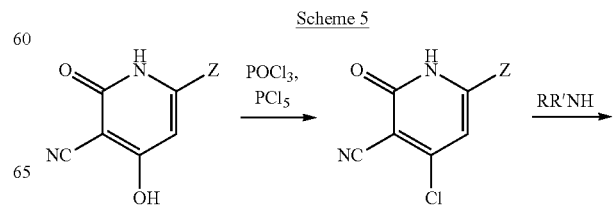

237

-continued

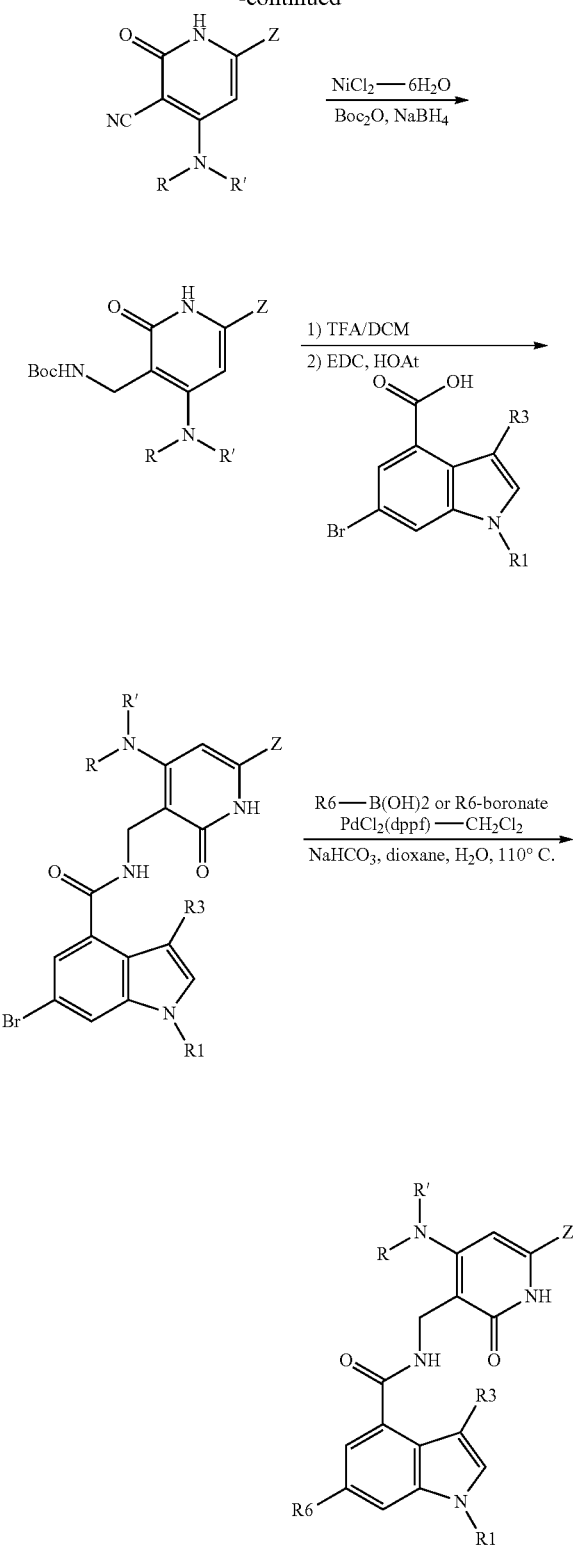

see: Heterocycles, vol. 60, No. 6, 2003, 1461-1468

238

Example 322

N-{[4-(ethylamino)-6-methyl-2-oxo-1,2-dihydro-3-pyridinyl]methyl}-1-(1-methylethyl)-6-[6-(4-methyl-1 perazinyl)-3-pyridinyl]-1H-indole-4-carboxamide a) 4-Chloro-6-methyl-2-oxo-1,2-dihydro-3-pyridinecarbonitrile

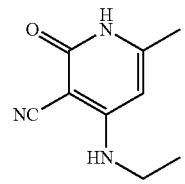

Using a 100 ml round bottom with reflux condenser, PCl$_5$ (6.7 g, 32 mmol), POCl$_3$ (3.0 mL, 32 mmol) and 30 ml CHCl$_3$ (dry) were stirred for 5 min (see: Heterocycles, vol. 60, No. 6, 2003, 1461-1468). Added 4-hydroxy-6-methyl-2-oxo-1,2-dihydro-3-pyridinecarbonitrile (4 g, 26.6 mmol) and stirred for 2 h at 80° C. Quenched reaction while hot and poured into 1 L beaker with 100 "g" ice, 24 mL NH$_4$OH, pH by paper was 8-9. Stirred 5 min and filtered. Washed solid with water. Suspended solid in ethanol and filtered and washed with ethanol. Gave: 4-chloro-6-methyl-2-oxo-1,2-dihydro-3-pyridinecarbonitrile (1.7 g, 9.58 mmol, 40% yield) $^1$H NMR (400 MHz, DMSO-d$_6$) δ ppm 12.85 (br. s., 1H) 6.53 (s, 1H) 2.28 (s, 3H) MS(ES) [M+H]$^+$ 168.9.

b) 4-(Ethylamino)-6-methyl-2-oxo-1,2-dihydro-3-pyridinecarbonitrile

To a 10 ml microwave vial added 4-chloro-6-methyl-2-oxo-1,2-dihydro-3-pyridinecarbonitrile (750 mg, 4.45 mmol) and methanol (1 mL) then added ethylamine (5.56 mL, 11.12 mmol). One drop on conc. HCl was added and the vial was capped and the reaction was microwaved to 120° C. for 1 hr. The reaction was cooled and the solid was filtered and washed with cold MeOH. Gave 4-(ethylamino)-6-methyl-2-oxo-1,2-dihydro-3-pyridinecarbonitrile (500 mg, 2.77 mmol, 62.2% yield) $^1$H NMR (400 MHz, DMSO-d$_6$) δ ppm 11.05 (br. s., 1H) 7.11 (br. s., 1H) 5.78 (br. s., 1H) 3.22-3.32 (m, 2H) 2.11 (s, 3H) 1.10 (t, J=7.07 Hz, 3H)_MS(ES) [M+H]$^+$ 177.8.

c) 1,1-Dimethylethyl {[4-(ethylamino)-6-methyl-2-oxo-1,2-dihydro-3-pyridinyl]methyl}carbamate

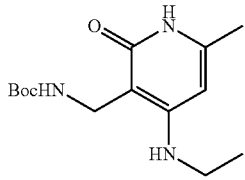 [SMILES: CCNc1cc(C)[nH]c(=O)c1CNC(=O)OC(C)(C)C]

In a 250 ml, round bottom flask under $N_2$ added 4-(ethylamino)-6-methyl-2-oxo-1,2-dihydro-3-pyridinecarbonitrile (500 mg, 2.82 mmol) as a solid then added Methanol (50 mL) and cooled to 0° C. in an ice bath. Next di-tert-butyl dicarbonate (1.310 mL, 5.64 mmol) was added and the suspension stirred for 5 min. Nickel Chloride-hexahydrate (335 mg, 1.411 mmol) solid was added followed by $NaBH_4$ (747 mg, 19.75 mmol) as a solid (in 3 portions—allowed 1 min in between portions b/c it turns black and there is gas evolution). After addition and stirring at 0° C. for ~10 min the ice bath was removed and the mix stirred at rt ON. The next morning the reaction was quenched with—Diethylene triamine (0.613 mL, 5.64 mmol) via syringe and the mix continued to stir 20 min. The reaction was diluted with EtOAc and was treated with sat $NaHCO_3$ and stirred 10 min. The mixture was transferred to a sep. funnel and the organic layer was separated out and washed (2xs) with sat $NaHCO_3$. The organic layer was concentrated in vacuo to a solid. The solid was stirred with 5% MeOH/Water (50 mL) then filtered. The solid was washed with 5% MeOH/Water and water (2xs) and dried to give 1,1-dimethylethyl {[4-(ethylamino)-6-methyl-2-oxo-1,2-dihydro-3-pyridinyl]methyl}carbamate (500 mg, 1.599 mmol, 56.7% yield). $^1$H NMR (400 MHz, DMSO-$d_6$) δ ppm 10.64 (br. s., 1H) 7.08 (br. s., 1H) 6.25 (br. s., 1H) 5.64 (s, 1H) 3.96 (d, J=6.06 Hz, 2H) 3.09-3.18 (m, 2H) 2.06 (s, 3H) 1.38 (s, 9H) 1.14 (t, 3H) [M+H]$^+$ 282.5.

d) 6-Bromo-N-{[4-(ethylamino)-6-methyl-2-oxo-1,2-dihydro-3-pyridinyl]methyl}-1-(1-methylethyl)-1H-indole-4-carboxamide

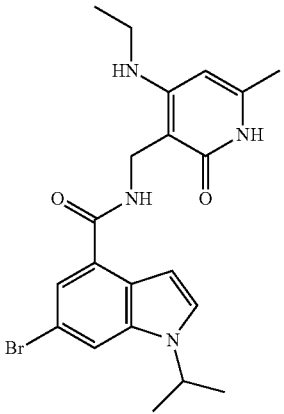 [SMILES: CCNc1cc(C)[nH]c(=O)c1CNC(=O)c1cc(Br)cc2c1ccn2C(C)C]

In a 50 mL round bottom was added 1,1-dimethylethyl {[4-(ethylamino)-6-methyl-2-oxo-1,2-dihydro-3-pyridinyl]methyl}carbamate (500 mg, 1.777 mmol) and Dichloromethane (DCM) (20.00 mL). TFA (1.095 mL, 14.22 mmol) was added and the reaction stirred at rt for 3.5 h. The LCMS indicated deprotection. The reaction was evaporated and evaporated from DCM. Dimethyl Sulfoxide (DMSO) (20 mL) was added to the round bottom followed by 6-bromo-1-(1-methylethyl)-1H-indole-4-carboxylic acid (501 mg, 1.777 mmol), to the solution was added N-methylmorpholine (1.172 mL, 10.66 mmol) 1-hydroxy-7-azabenzotriazole (363 mg, 2.67 mmol) and EDC (511 mg, 2.67 mmol). The reaction stirred at rt for 12 hr. The reaction was poured onto Ice water (10 mL) and was stirred for 20 min let it rest for 10 min and filter. Rinse solid with water (10 mL). Purification of solid by reverse phase Gilson HPLC (10-90% acetonitrile/water+0.1% TFA, YMC ODS-A C18 Column 75×30 mm ID S-5 um, 12 nM Column 7 minutes) provided the desired product as a white solid after neutralization with 0.1N NaOH and evaporation and precipitation from water. 6-bromo-N-{[4-(ethylamino)-6-methyl-2-oxo-1,2-dihydro-3-pyridinyl]methyl}-1-(1-methylethyl)-1H-indole-4-carboxamide (240 mg, 0.523 mmol, 29.4% yield). $^1$H NMR (400 MHz, DMSO-$d_6$) δ ppm 10.70 (s, 1H) 8.87 (m, 1H) 7.93 (s, 1H) 7.57-7.71 (m, 2H) 6.89 (d, J=3.28 Hz, 1H) 6.71 (m, 1H) 5.66 (s, 1H) 4.82 (m, 1H) 4.34 (d, J=5.81 Hz, 2H) 3.12-3.23 (m, 2H) 2.08 (s, 3H) 1.43 (d, J=6.57 Hz, 6H) 1.18 (t, 3H) MS(ES) [M+H]$^+$ 445.1.

e) N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide

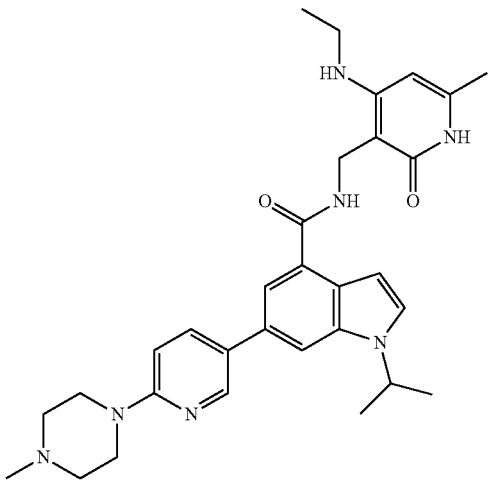

To a 20 mL microwave vial was added 6-bromo-N-{[4-(ethylamino)-6-methyl-2-oxo-1,2-dihydro-3-pyridinyl]methyl}-1-(1-methylethyl)-1H-indole-4-carboxamide (70 mg, 0.170 mmol), and 1-methyl-4-[5-(4,4,5,5-tetramethyl-1,3,2-dioxaborolan-2-yl)-2-pyridinyl]piperazine (59.9 mg, 0.198 mmol). $PdCl_2$(dppf)-$CH_2Cl_2$ adduct (14.67 mg, 0.018 mmol) and sodium bicarbonate (45.3 mg, 0.539 mmol) were added followed by 1,2-Dimethoxyethane (DME) (5 mL) and Water (2 mL). The vial was sealed and the reaction was heated to 85° C. for 1 hr. The reaction was cooled and evaporated. The material was taken into Methanol/DMSO and was filtered through an acrodisk and purified by reverse phase Gilson HPLC (5-80% acetonitrile/water+0.1% TFA, YMC ODS-A C18 Column 75×30 mm ID S-5 um, 12 nM Column, 6 minutes) the desired fractions were collected and evaporated from 0.1N NaOH which provided the desired product N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide (57 mg, 0.101 mmol, 56.2% yield). $^1$H NMR (400 MHz, DMSO-$d_6$) δ ppm 10.68 (s, 1H) 8.89 (t, J=5.94 Hz, 1H) 8.66 (d, J=2.02 Hz, 1H) 8.09 (dd, J=8.59, 2.02 Hz, 1H) 7.91 (s, 1H) 7.80 (s, 1H) 7.60 (d, J=3.03 Hz, 1H) 6.99 (d, J=8.84 Hz, 1H) 6.89-6.96 (m, 2H) 5.66 (s, 1H) 4.85-4.98 (m, 1H) 4.39 (d, J=5.81 Hz, 2H) 3.63 (br. s., 4H) 3.11-3.24 (m, 2H) 2.7 (bs, 4H) 2.08 (s, 3H) 1.47 (d, J=6.57 Hz, 6H) 1.20 (t, 3H). MS(ES) [M+H]$^+$ 542.4.

Examples 323-324 were prepared by the methods described above for Example 322, or routine variations thereof, using the requisite amine:

| Ex | Structure | Name | ¹H NMR (400 MHz, DMSO-d₆) δ ppm | MS(ES) [M + H]⁺ |
|---|---|---|---|---|
| 323 | 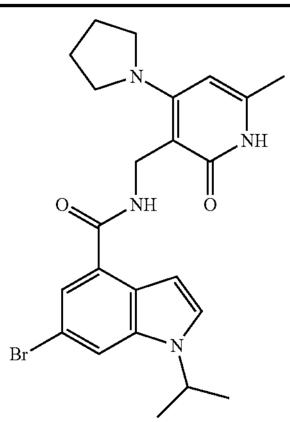 | 6-bromo-1-(1-methylethyl)-N-{[6-methyl-2-oxo-4-(1-pyrrolidinyl)-1,2-dihydro-3-pyridinyl]methyl}-1H-indole-4-carboxamide | 10.86 (s, 1 H) 8.22 (t, J = 4.29 Hz, 1 H) 7.93 (s, 1 H) 7.64 (d, J = 3.28 Hz, 1 H) 7.53 (d, J = 1.77 Hz, 1 H) 6.85 (d, J = 3.28 Hz, 1 H) 5.74 (s, 1 H) 4.78-4.89 (m, 1 H) 4.42 (d, J = 4.29 Hz, 2 H) 3.43-3.54 (m, 4 H) 2.09 (s, 3 H) 1.80-1.89 (m, 4 H) 1.44 (d, J = 6.57 Hz, 6 H) | 473.0 |
| 324 | 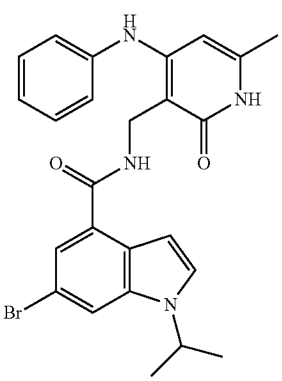 [SMILES: Cc1cc(Nc2ccccc2)c(CNC(=O)c2cc(Br)cc3c2ccn3C(C)C)c(=O)[nH]1] | 6-bromo-1-(1-methylethyl)-N-{[6-methyl-2-oxo-4-(phenylamino)-1,2-dihydro-3-pyridinyl]methyl}-1H-indole-4-carboxamide | 11.02 (s, 1 H) 9.45 (s, 1 H) 9.15-9.21 (m, 1 H) 7.96 (s, 1 H) 7.67 (dd, J = 10.11, 2.53 Hz, 2 H) 7.34-7.40 (m, 2 H) 7.15 (d, J = 7.33 Hz, 2 H) 7.04-7.09 (m, 1 H) 6.91 (d, J = 3.03 Hz, 1 H) 5.91 (s, 1 H) 4.80-4.87 (m, 1 H) 4.39 (d, J = 5.81 Hz, 2 H) 2.06 (s, 3 H) 1.44 (d, J = 6.57 Hz, 6 H) | 493.0 |

Example 325

N-((6-Amino-4-methyl-2-oxo-1,2-dihydropyridin-3-yl)methyl)-6-bromo-1-isopropyl-3-methyl-1H-indole-4-carboxamide

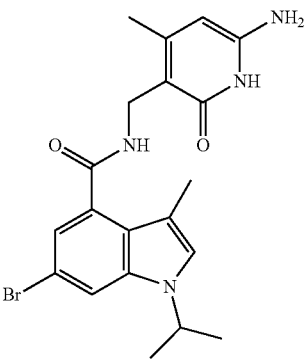 [SMILES: Cc1cc(N)[nH]c(=O)c1CNC(=O)c1cc(Cl)cc2c1c(C)cn2C(C)C]

a) tert-Butyl (5-((6-bromo-1-isopropyl-3-methyl-1H-indole-4-carboxamido)methyl)-6-methoxy-4-methylpyridin-2-yl)carbamate

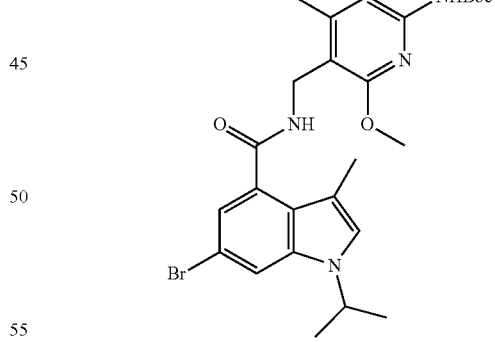

To a stirred solution of tert-butyl (5-(aminomethyl)-6-methoxy-4-methylpyridin-2-yl)carbamate (0.40 g, 1.496 mmol), 6-bromo-1-isopropyl-3-methyl-1H-indole-4-carboxylic acid (0.44 g, 1.486 mmol), and HOAt (0.21 g, 1.543 mmol) in DMF (25 mL) was added EDC free base (0.25 g, 1.610 mmol). The reaction was stirred at RT overnight then evaporated to dryness under vacuum. The remaining was purified by silica gel chromatography (Analogix, SF25-60g, 0 to 30% EtOAc in hexanes) to give the product tert-butyl (5-(((6-bromo-1-isopropyl-3-methyl- 1H-indole-4-carboxamido)methyl)-6-methoxy-4-methylpyridin-2-yl)carbamate (0.81 g, 1.485 mmol, 99% yield) as a white solid. ¹H NMR (400 MHz, DMSO-d₆) δ=9.42 (s, 1H), 8.41 (t, J=4.8 Hz, 1H), 7.77 (d, J=1.5 Hz, 1H), 7.33 (s, 1H), 7.21 (s, 1H), 6.99 (d, J=1.8 Hz, 1H), 4.40 (d, J=5.1 Hz, 2H), 3.81 (s, 3H), 2.35 (s, 3H), 2.10 (d, J=1.0 Hz, 3H), 1.47 (s, 9H), 1.38 (d, J=6.6 Hz, 6H). MS(ES)+ m/e 545.2 [M+H]⁺.

b) N-((6-Amino-4-methyl-2-oxo-1,2-dihydropyridin-3-yl)methyl)-6-bromo-1-isopropyl-3-methyl-1H-indole-4-carboxamide

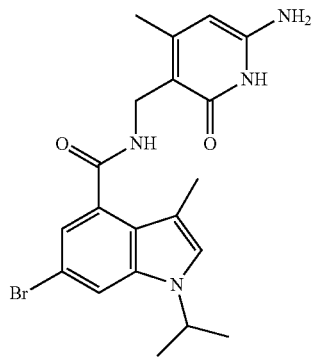

To a stirred solution of tert-butyl (5-((6-bromo-1-isopropyl-3-methyl-1H-indole-4-carboxamido)methyl)-6-methoxy-4-methylpyridin-2-yl)carbamate (0.80 g, 1.467 mmol) in acetonitrile (20 mL) was added dropwise at RT TMSI (0.50 ml, 3.67 mmol). A reflux condenser was attached and the reaction was purged with N₂ and heated to 70° C. After stirring for 30 minutes LCMS indicated that the reaction was complete (89% pure with 11% possible iodinated side product as the only other impurity). After 1 hr the reaction was quenched with MeOH (5 mL) and stirred for 30 minutes. The clear brown solution was evaporated to dryness under vacuum, taken up in CH₂Cl₂, washed with aq. Na₂S₂O₃, (a ppt. formed that was filtered off), dried (Na₂SO₄), filtered, and concentrated under vacuum. Purification by silica gel chromatography (Analogix, SF25-10g, 0 to 7% (5% NH₄OH/MeOH) in CH₂Cl₂) gave the product N-((6-amino-4-methyl-2-oxo-1,2-dihydropyridin-3-yl)methyl)-6-bromo-1-isopropyl-3-methyl-1H-indole-4-carboxamide (59.6 mg, 0.138 mmol, 9.4% yield) as a white solid. Note: The ppt. that was filtered off during the aq. Na₂S₂O₃ wash was later shown to contain product. This solid was washed with water and dried under vacuum to give additional product as an off-white solid (602 mg, 1.4 mmol, 95%, 100% pure by LCMS). ¹H NMR (400 MHz, DMSO-d₆) δ=10.59 (br. s., 1H), 8.13 (t, J=4.4 Hz, 1H), 7.76 (d, J=1.5 Hz, 1H), 7.33 (s, 1H), 6.99 (d, J=1.5 Hz, 1H), 5.83 (br. s., 2H), 5.19 (s, 1H), 4.74 (dt, J=6.6, 13.3 Hz, 1H), 4.22 (d, J=4.8 Hz, 2H), 2.14 (s, 3H), 2.11 (s, 3H), 1.39 (d, J=6.6 Hz, 6H). MS(ES)+ m/e 431.1 [M+H]⁺.

Examples 326-334 were prepared by the methods described above for Example 325, or routine variations thereof, using the requisite amine:

| Ex | Structure | Name | ¹H NMR (400 MHz, DMSO-d₆) δ ppm | MS(ES) [M + H]⁺ |
|---|---|---|---|---|
| 326 | 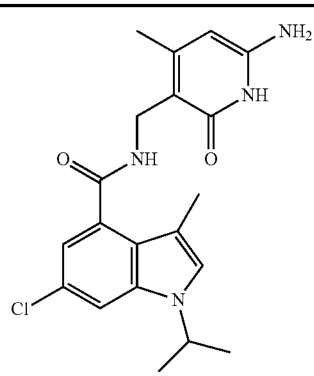 | N-((6-amino-4-methyl-2-oxo-1,2-dihydropyridin-3-yl)methyl)-6-chloro-1-isopropyl-3-methyl-1H-indole-4-carboxamide | 10.62 (br. s., 1 H), 8.14 (t, J = 4.4 Hz, 1 H), 7.63 (d, J = 1.8 Hz, 1 H), 7.34 (s, 1 H), 6.89 (d, J = 1.8 Hz, 1 H), 5.85 (br. s., 2 H), 5.20 (s, 1 H), 4.73 (dt, J = 6.7, 13.2 Hz, 1 H), 4.22 (d, J = 4.8 Hz, 2 H), 2.14 (s, 3 H), 2.12 (s, 3 H), 1.39 (d, J = 6.6 Hz, 6 H) | 387.2 |
| 327 | 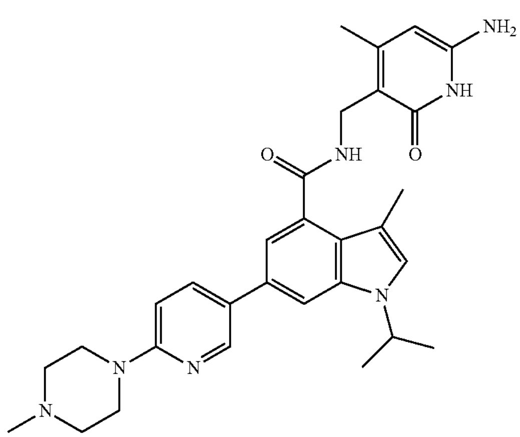 [SMILES: Cc1cc(N)[nH]c(=O)c1CNC(=O)c1cc(-c2ccc(N3CCN(C)CC3)nc2)cc2c1c(C)cn2C(C)C] | N-[(6-amino-4-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide | 10.49 (br. s., 1 H), 8.51 (d, J = 2.5 Hz, 1 H), 7.98 (t, J = 4.8 Hz, 1 H), 7.93 (dd, J = 2.5, 8.8 Hz, 1 H), 7.71 (d, J = 1.3 Hz, 1 H), 7.29 (s, 1 H), 7.17 (d, J = 1.5 Hz, 1 H), 6.92 (d, J = 8.8 Hz, 1 H), 5.77 (s, 2 H), 5.16 (s, 1 H), 4.84 (quin, J = 6.6 Hz, 1 H), 4.26 (d, J = 5.1 Hz, 2 H), 3.61-3.46 (m, 4 H), 2.43 (t, J = 4.7 Hz, 4 H), 2.24 (s, 3 H), 2.18 (s, 3 H), 2.13 (s, 3 H), 1.43 (d, J = 6.6 Hz, 6 H) | 528.6 |

| Ex | Structure | Name | ¹H NMR (400 MHz, DMSO-d₆) δ ppm | MS(ES) [M + H]⁺ |
|---|---|---|---|---|
| 328 | 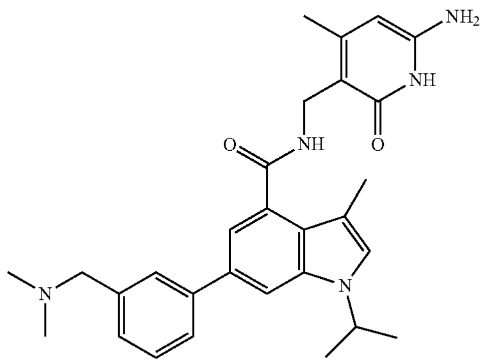 [SMILES: Cc1cc(N)[nH]c(=O)c1CNC(=O)c1cc(-c2cccc(CN(C)C)c2)cc2c1c(C)cn2C(C)C] | N-[(6-amino-4-methyl-2-oxo-1,2-dihydro-3-pyridinyl)methyl]-6-{3-[(dimethylamino)methyl]phenyl}-3-methyl-1-(1-methylethyl)-1H-indole-4-carboxamide | 10.48 (br. s., 1 H), 8.03 (t, J = 4.9 Hz, 1 H), 7.75 (d, J = 1.3 Hz, 1 H), 7.64 (s, 1 H), 7.63 (d, 1 H), 7.40 (t, J = 7.6 Hz, 1 H), 7.33 (s, 1 H), 7.24 (d, J = 7.6 Hz, 1 H), 7.22 (d, J = 1.5 Hz, 1 H), 5.77 (s, 2 H), 5.16 (s, 1 H), 4.88 (quin, J = 6.6 Hz, 1 H), 4.26 (d, J = 5.1 Hz, 2 H), 3.48 (s, 2 H), 2.19 (s, 9 H), 2.13 (s, 3 H), 1.44 (d, J = 6.6 Hz, 6 H) | 486.3 |
| 329 | 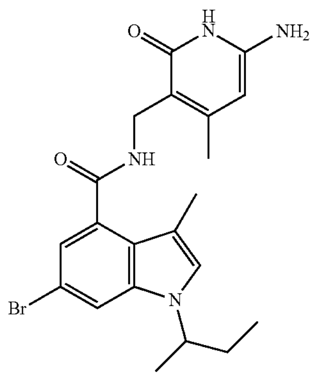 [SMILES: CCC(C)n1cc(C)c2c(C(=O)NCc3c(C)cc(N)[nH]c3=O)cc(Br)cc21] | N-[(6-amino-4-methyl-2-oxo-1,2-dihydro-3-pyridinyl)methyl]-6-bromo-3-methyl-1-(1-methylpropyl)-1H-indole-4-carboxamide | 0.70 (t, J = 7.33 Hz, 3 H) 1.36 (d, J = 6.82 Hz, 3 H) 1.69-1.84 (m, 2 H) 2.15 (s, 2 H) 2.10 (s, 4 H) 4.21 (d, J = 4.80 Hz, 2 H) 4.41-4.58 (m, 1 H) 5.15 (s, 1 H) 5.77 (s, 2 H) 6.97 (d, J = 1.52 Hz, 1 H) 7.29 (s, 1 H) 7.76 (d, J = 1.77 Hz, 1 H) 8.06 (t, J = 4.80 Hz, 1 H) 10.47 (br. s., 1 H) | 447.2 |
| 330 | 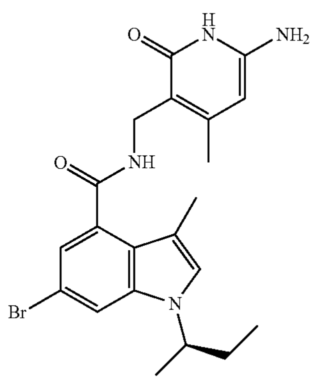 [SMILES: CC[C@@H](C)n1cc(C)c2c(C(=O)NCc3c(C)cc(N)[nH]c3=O)cc(Br)cc21] | N-[(6-amino-4-methyl-2-oxo-1,2-dihydro-3-pyridinyl)methyl]-6-bromo-3-methyl-1-(1-methylpropyl)-1H-indole-4-carboxamide | 0.668 (t, J = 7.4 Hz, 3H), 1.36 (d, J = 6.8 Hz, 3H), 1.76-1.78 (m, 2H), 2.11 (s, 3H), 2.15 (s, 3H), 4.21 (d, J = 4.8 Hz, 2H), 4.35-4.38 (m, 1H), 5.15 (s, 1H), 5.78 (s, 2H), 6.97 (s, 1H), 7.30 (s, 1H), 7.76 (s, 1H), 8.07-8,.09 (m, 1H), 10.4-10.5 (br s, 1H) | 445.2 |
| 331 | 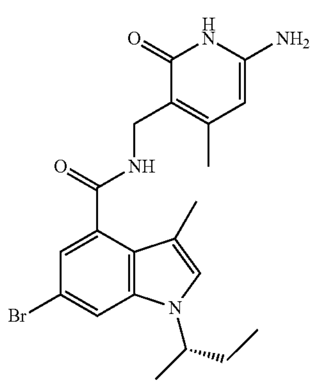 [SMILES: CC[C@H](C)n1cc(C)c2c(C(=O)NCc3c(C)cc(N)[nH]c3=O)cc(Br)cc21] | N-[(6-amino-4-methyl-2-oxo-1,2-dihydro-3-pyridinyl)methyl]-6-bromo-3-methyl-1-(1-methylpropyl)-1H-indole-4-carboxamide | 0.668 (t, J = 7.4 Hz, 3H), 1.36 (d, J = 6.8 Hz, 3H), 1.76-1.78 (m, 2H), 2.11 (s, 3H), 2.15 (s, 3H), 4.21 (d, J = 4.8 Hz, 2H), 4.35-4.38 (m, 1H), 5.15 (s, 1H), 5.78 (s, 2H), 6.97 (s, 1H), 7.30 (s, 1H), 7.76 (s, 1H), 8.07-8,.09 (m, 1H), 10.4-10.5 (br s, 1H) | 445.2 |

| Ex | Structure | Name | ¹H NMR (400 MHz, DMSO-d₆) δ ppm | MS(ES) [M + H]⁺ |
|---|---|---|---|---|
| 332 | 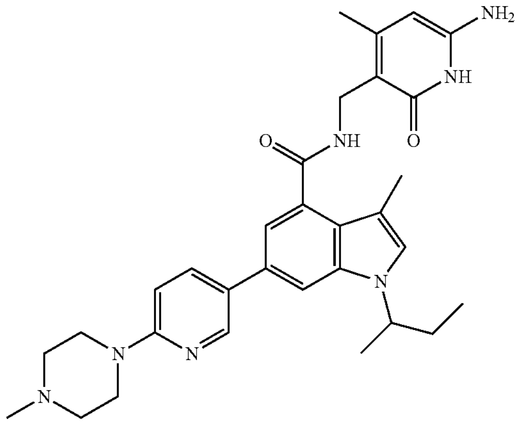 [SMILES: CCC(C)n1cc(C)c2c(C(=O)NCc3c(C)cc(N)[nH]c3=O)cc(-c3ccc(N4CCN(C)CC4)nc3)cc21] | N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 10.47 (br. s., 1 H) 8.50 (d, J = 2.53 Hz, 1 H) 7.98 (br. s., 1 H) 7.92 (dd, J = 8.84, 2.53 Hz, 1 H) 7.71-7.74 (m, 1 H) 7.26 (s, 1 H) 7.16 (d, J = 1.26 Hz, 1 H) 6.92 (d, J = 9.09 Hz, 1 H) 5.76 (s, 2 H) 5.16 (br. s., 1 H) 4.57-4.65 (m, 1 H) 4.26 (br. s., 1 H) 4.25 (br. s., 1 H) 3.52 (br. s., 4 H) 2.42 (br. s., 4 H) 2.23 (s, 3 H) 2.18 (s, 3 H) 2.13 (s, 3 H) 1.81 (td, J = 7.20, 3.03 Hz, 2 H) 1.41 (d, J = 6.82 Hz, 3 H) 0.73 (t, J = 7.20 Hz, 3 H) | 542.6 |
| 333 | 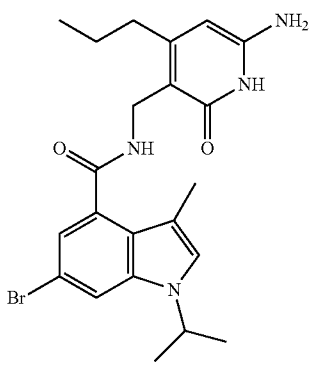 [SMILES: CCCc1cc(N)[nH]c(=O)c1CNC(=O)c1cc(Br)cc2c1c(C)cn2C(C)C] | N-((6-amino-2-oxo-4-propyl-1,2-dihydropyridin-3-yl)methyl)-6-bromo-1-isopropyl-3-methyl-1H-indole-4-carboxamide | 10.52 (br. s., 1 H), 8.04 (t, J = 4.7 Hz, 1 H), 7.76 (d, J = 1.8 Hz, 1 H), 7.33 (s, 1 H), 6.98 (d, J = 1.8 Hz, 1 H), 5.77 (s, 2 H), 5.17 (s, 1 H), 4.74 (quin, J = 6.6 Hz, 1 H), 4.23 (d, J = 4.8 Hz, 2 H), 2.45-2.34 (m, 2 H), 2.15 (s, 3 H), 1.52 (dq, J = 7.4, 15.1 Hz, 2 H), 1.39 (d, J = 6.6 Hz, 6 H), 0.93 (t, J = 7.3 Hz, 3 H) | 459.2 |
| 334 | 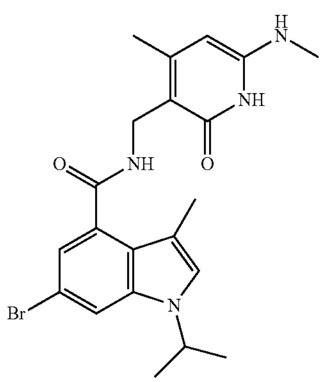 [SMILES: CNc1cc(C)c(CNC(=O)c2cc(Br)cc3c2c(C)cn3C(C)C)c(=O)[nH]1] | 6-bromo-1-isopropyl-3-methyl-N-((4-methyl-6-(methylamino)-2-oxo-1,2-dihydropyridin-3-yl)methyl)-1H-indole-4-carboxamide | 10.48 (br. s., 1 H), 8.11 (t, J = 4.5 Hz, 1 H), 7.75 (d, J = 1.5 Hz, 1 H), 7.33 (s, 1 H), 6.99 (d, J = 1.5 Hz, 1 H), 5.76 (q, J = 4.4 Hz, 1 H), 5.13 (br. s., 1 H), 4.74 (quin, J = 6.6 Hz, 1 H), 4.24 (d, J = 4.8 Hz, 2 H), 2.67 (d, J = 5.1 Hz, 3 H), 2.17 (s, 3 H), 2.15 (s, 3 H), 1.39 (d, J = 6.6 Hz, 6 H) | 445.2 |

Example 335

N-[(4,6-Dimethyl-2-oxo-1,2-dihydro-3-pyridinyl)methyl]-3-methyl-1-(1-methylethyl)-6-{6-[(2R)-2-methyl-1-piperazinyl]-3-pyridinyl}-1H-indole-4-carboxamide

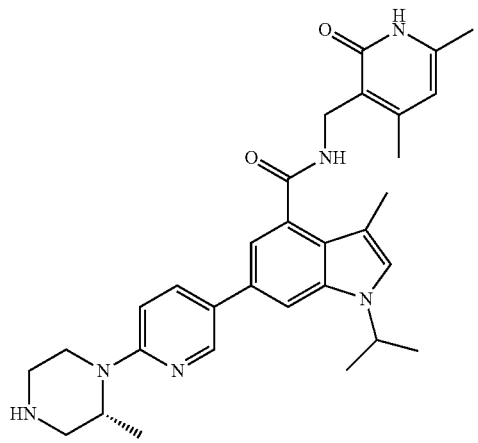 [SMILES: Cc1cc(C)c(CNC(=O)c2cc(-c3ccc(N4CCNC[C@H]4C)nc3)cc3c2c(C)cn3C(C)C)c(=O)[nH]1]

a) (R)-tert-Butyl 4-(5-(4-(((4,6-dimethyl-2-oxo-1,2-dihydropyridin-3-yl)methyl)carbamoyl)-1-isopropyl-3-methyl-1H-indol-6-yl)pyridin-2-yl)-3-methylpiperazine-1-carboxylate

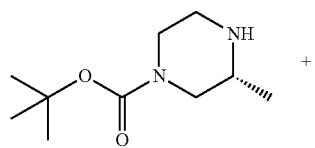 +

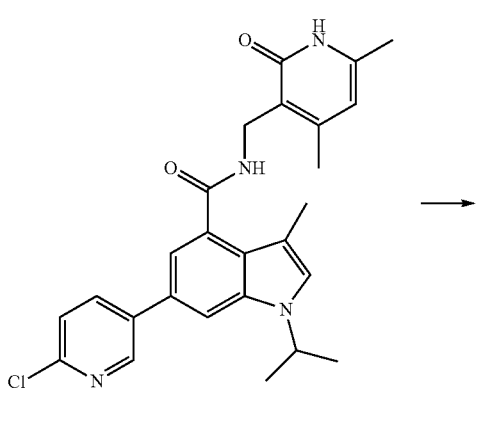 →

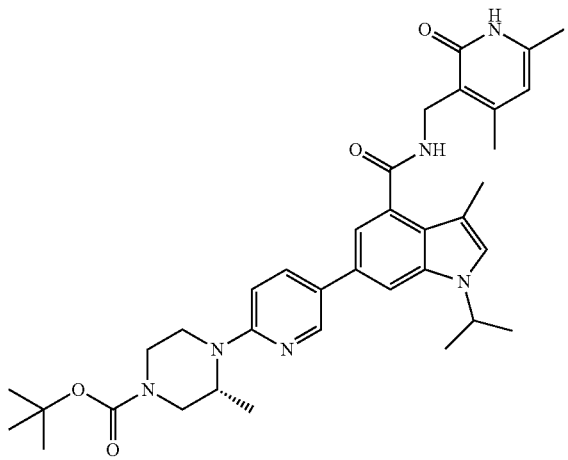

Added 6-(6-chloropyridin-3-yl)-N-((4,6-dimethyl-2-oxo-1,2-dihydropyridin-3-yl)methyl)-1-isopropyl-3-methyl-1H-indole-4-carboxamide (131 mg, 0.283 mmol), (R)-tert-butyl 3-methylpiperazine-1-carboxylate (70.8 mg, 0.354 mmol), sodium tert-butoxide (59.8 mg, 0.623 mmol) and 1,4-Dioxane (2 mL) to a microwave vial and degassed for 10 minutes. Added Pd XPhos (10.45 mg, 0.014 mmol) and heated to 100° C. for 16 hours. Concentrated, added DCM and water. Filtered, separated phases. Extracted aqueous phase twice more with DCM. Combined DCM extracts and washed with water, brine, dried (MgSO$_4$), filtered and rotovapped off DCM. The residue was purified via Biotage (0% to 5% MeOH:DCM; 10 g-HP-silica gel column). Obtained 28 mg of the title compound. $^1$H NMR (400 MHz, CHLOROFORM-d) δ ppm 1.16 (d, J=6.32 Hz, 3H), 1.44-1.57 (m, 15H), 2.06 (s, 3H), 2.28 (s, 3H), 2.39 (s, 3H), 2.87-3.36 (m, 3H), 3.57 (s, 1H), 3.86-4.30 (m, 3H), 4.50 (d, J=9.35 Hz, 1H), 4.58-4.79 (m, 3H), 5.87 (s, 1H), 6.64 (d, J=8.59 Hz, 1H), 7.01 (s, 1H), 7.45 (s, 1H), 7.76 (d, J=8.08 Hz, 1H), 8.46 (d, J=2.27 Hz, 1H), 12.42 (br. s., 1H). LCMS: [M+H]$^+$ 627.5.

b) N-[(4,6-Dimethyl-2-oxo-1,2-dihydro-3-pyridinyl)methyl]-3-methyl-1-(1-methylethyl)-6-{6-[(2R)-2-methyl-1-piperazinyl]-3-pyridinyl}-1H-indole-4-carboxamide

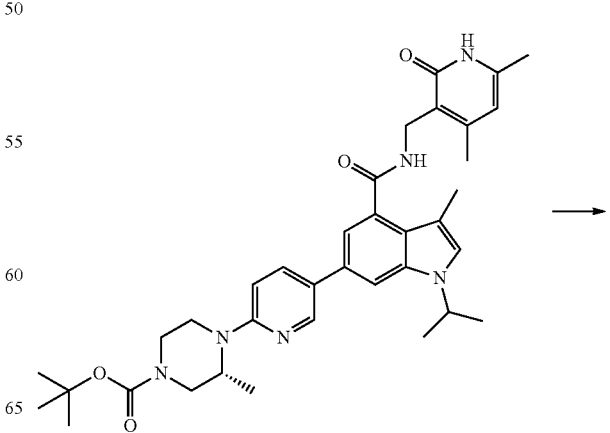 →

251
-continued

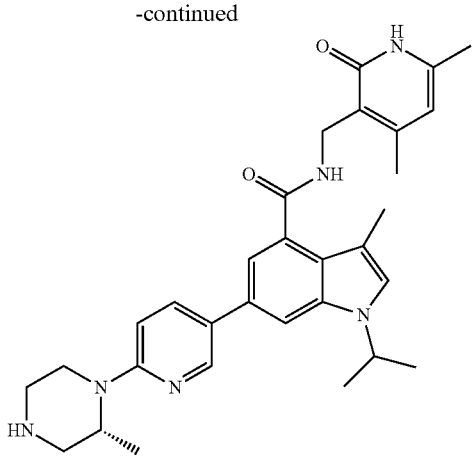

252

Added trifluoroacetic acid (1 ml, 12.98 mmol) to a solution of (R)-tert-butyl 4-(5-(4-(((4,6-dimethyl-2-oxo-1,2-dihydropyridin-3-yl)methyl)carbamoyl)-1-isopropyl-3-methyl-1H-indol-6-yl)pyridin-2-yl)-3-methylpiperazine-1-carboxylate (57 mg, 0.091 mmol) in DCM (3 mL) and let stir at RT for 1 hour. Concentrated on rotovap. Partitioned between DCM and sat'd $Na_2CO_3$, separated and washed DCM phase with water, brine, dried ($MgSO_4$), filtered and rotovapped off DCM. Obtained 25 mg of the title compound as a tan solid. $^1$H NMR (400 MHz, CHLOROFORM-d) δ ppm 1.19 (d, 2H), 1.46-1.59 (m, 6H), 2.21 (s, 3H), 2.27 (s, 3H), 2.44 (s, 3H), 2.83 (dd, J=12.13, 3.54 Hz, 1H), 2.96-3.29 (m, 4H), 3.90 (br. s., 1H), 4.47-4.76 (m, 5H), 6.00 (s, 1H), 6.51 (d, J=8.59 Hz, 1H), 7.05 (s, 1H), 7.45 (s, 1H), 7.68 (dd, J=8.72, 2.40 Hz, 1H), 8.43 (d, J=2.27 Hz, 1H), 10.11-12.70 (m, 1H). LCMS: [M+H]$^+$ 527.5.

Examples 336-346 were prepared by the methods described above for Example 335, or routine variations thereof, using the requisite amine:

| Ex | Structure | Name | $^1$H NMR (400 MHz, DMSO-$d_6$) δ ppm | MS(ES) [M + H]$^+$ |
|---|---|---|---|---|
| 336 | 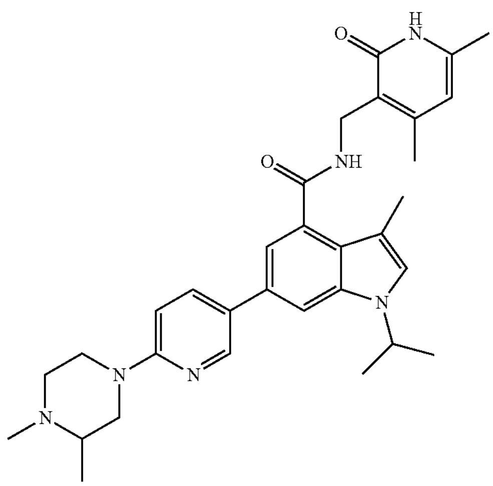 | N-[(4,6-dimethyl-2-oxo-1,2-dihydro-3-pyridinyl)methyl]-6-[6-(3,4-dimethyl-1-piperazinyl)-3-pyridinyl]-3-methyl-1-(1-methylethyl)-1H-indole-4-carboxamide | (CHLOROFORM-d) 1.16 (d, J = 6.06 Hz, 3 H), 1.47 (d, J = 6.57 Hz, 6 H), 2.03 (s, 3 H), 2.14-2.29 (m, 4 H), 2.30-2.42 (m, 7 H), 2.69 (dd, J = 12.25, 10.74 Hz, 1 H), 2.91 (d, J = 11.62 Hz, 1 H), 3.00-3.13 (m, 1 H), 4.06 (d, J = 12.63 Hz, 2 H), 4.38-4.75 (m, 3 H), 5.85 (s, 1 H), 6.64 (d, J = 8.59 Hz, 1 H), 6.99 (s, 1 H), 7.42 (d, J = 1.52 Hz, 1 H), 7.70 (dd, J = 8.84, 2.53 Hz, 1 H), 8.43 (d, J = 2.27 Hz, 1 H), 12.55 (br. s., 1 H) | 541.3 |
| 337 | 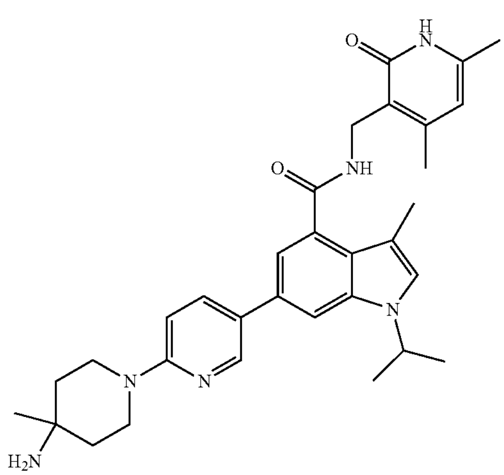 | N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide | (CHLOROFORM-d) 1.24 (s, 3 H), 1.49 (d, J = 6.57 Hz, 6 H), 1.60-1.73 (m, 4 H), 2.10 (s, 3 H), 2.28 (s, 3 H), 2.38 (s, 2 H), 3.39-3.53 (m, 2 H), 3.57-3.70 (m, 2 H), 4.54-4.75 (m, 3 H), 5.88 (s, 1 H), 6.61 (d, J = 8.84 Hz, 1 H), 7.01 (s, 1 H), 7.26 (br. s., 1 H), 7.29 (d, J = 5.81 Hz, 1 H), 7.44 (s, 1 H), 7.66 (dd, J = 8.84, 2.27 Hz, 2 H), 8.41 (d, J = 2.02 Hz, 2 H), 10.07-13.76 (m, 1 H) | 541.5 |

-continued

| Ex | Structure | Name | ¹H NMR (400 MHz, DMSO-d₆) δ ppm | MS(ES) [M + H]⁺ |
|---|---|---|---|---|
| 338 | 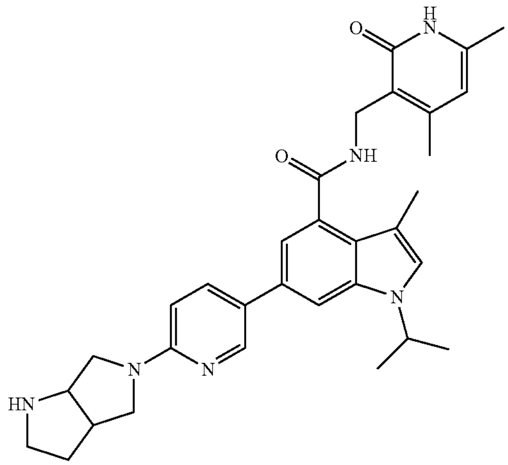 [SMILES: Cc1cc(C)c(CNC(=O)c2cc(-c3ccc(N4CC5CCNC5C4)nc3)cc3c2c(C)cn3C(C)C)c(=O)[nH]1] | N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide | (CHLOROFORM-d) 1.48 (t, J = 6.57 Hz, 6 H), 1.54-1.69 (m, 1 H), 2.10 (s, 3 H), 2.31 (s, 3 H), 2.42 (s, 3 H), 2.77-3.05 (m, 3 H), 3.22 (dd, J = 10.86, 4.55 Hz, 1 H), 3.31-3.46 (m, 2 H), 3.46-3.58 (m, 1 H), 4.03 (d, J = 5.56 Hz, 1 H), 4.39-4.86 (m, 3 H), 5.90 (s, 1 H), 6.16 (d, J = 8.59 Hz, 1 H), 7.03 (s, 1 H), 7.21 (s, 1 H), 7.41 (s, 1 H), 7.53 (d, J = 6.32 Hz, 2 H), 8.32 (d, J = 2.02 Hz, 1 H) | 539.5 |
| 339 | 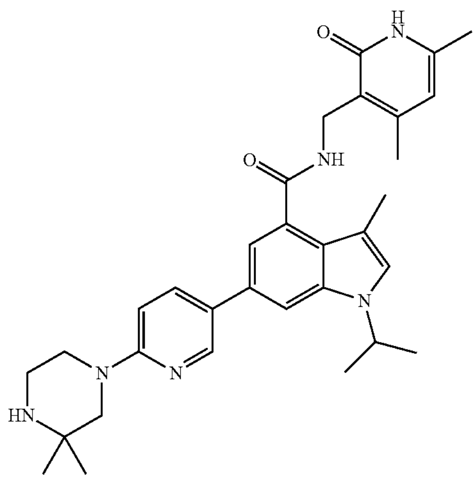 [SMILES: Cc1cc(C)c(CNC(=O)c2cc(-c3ccc(N4CCNC(C)(C)C4)nc3)cc3c2c(C)cn3C(C)C)c(=O)[nH]1] | N-[(4,6-dimethyl-2-oxo-1,2-dihydro-3-pyridinyl)methyl]-6-[6-(3,3-dimethyl-1-piperazinyl)-3-pyridinyl]-3-methyl-1-(1-methylethyl)-1H-indole-4-carboxamide | (CHLOROFORM-d) 1.21 (s, 6 H), 1.49 (d, J = 6.82 Hz, 6 H), 2.09 (s, 3 H), 2.28 (s, 3 H), 2.40 (s, 3 H), 2.99-3.12 (m, 2 H), 3.33 (s, 2 H), 3.45-3.60 (m, 2 H), 4.55-4.77 (m, 3 H), 5.89 (s, 1 H), 6.63 (d, J = 8.84 Hz, 1 H), 7.01 (s, 1 H), 7.22-7.26 (m, 1 H), 7.28 (d, J = 1.26 Hz, 1 H), 7.44 (d, J = 1.01 Hz, 1 H), 7.70 (dd, J = 8.84, 2.53 Hz, 1 H), 8.42 (d, J = 2.27 Hz, 1 H) | 541.6 |
| 340 | 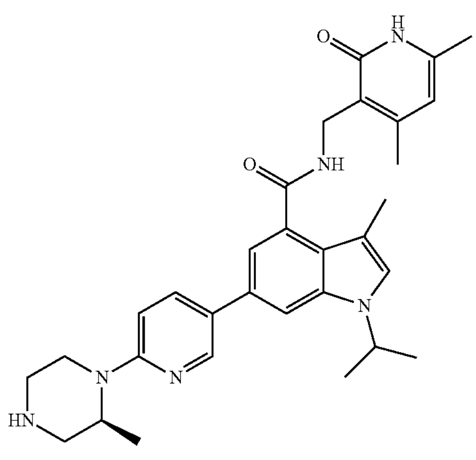 [SMILES: Cc1cc(C)c(CNC(=O)c2cc(-c3ccc(N4CCNC[C@@H]4C)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-{6-[(2S)-2-methyl-1-piperazinyl]-3-pyridinyl}-1H-indole-4-carboxamide | (CHLOROFORM-d) 1.21 (d, J = 6.57 Hz, 3 H), 1.49 (d, J = 6.82 Hz, 6 H), 2.07 (s, 3 H), 2.28 (s, 3 H), 2.39 (s, 3 H), 2.76-2.99 (m, 2 H), 3.02-3.21 (m, 3 H), 3.94 (d, J = 12.63 Hz, 1 H), 4.38-4.48 (m, 1 H), 4.56-4.77 (m, 3 H), 5.88 (s, 1 H), 6.59 (d, J = 9.09 Hz, 1 H), 7.01 (s, 1 H), 7.30 (d, 1 H), 7.45 (d, J = 1.01 Hz, 1 H), 7.71 (dd, J = 8.84, 2.53 Hz, 1 H), 8.45 (d, J = 2.27 Hz, 1 H) | 527.5 |

-continued

| Ex | Structure | Name | ¹H NMR (400 MHz, DMSO-d₆) δ ppm | MS(ES) [M + H]⁺ |
|---|---|---|---|---|
| 341 | 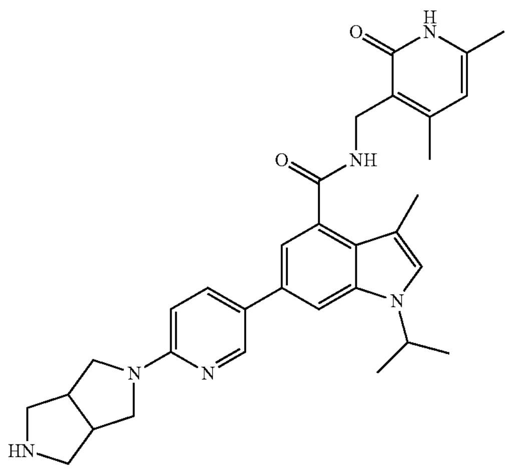 [SMILES: Cc1cc(C)c(CNC(=O)c2cc(-c3ccc(N4CC5CNCC5C4)nc3)cc3c2c(C)cn3C(C)C)c(=O)[nH]1] | N-[(4,6-dimethyl-2-oxo-1,2-dihydro-3-pyridinyl)methyl]-6-[6-(hexahydropyrrolo[3,4-c]pyrrol-2(1H)-yl)-3-pyridinyl]-3-methyl-1-(1-methylethyl)-1H-indole-4-carboxamide | (CHLOROFORM-d) 1.49 (d, 6 H), 2.18 (s, 3 H), 2.33 (s, 3 H), 2.44 (s, 3 H), 2.63 (d, J = 6.32 Hz, 2 H), 2.89 (br. s., 2 H), 3.02 (d, J = 9.60 Hz, 2 H), 3.24 (dd, J = 10.99, 6.19 Hz, 2 H), 3.35 (dd, J = 9.85, 7.07 Hz, 2 H), 4.55-4.72 (m, 3 H), 5.91-6.01 (m, 2 H), 7.09 (s, 1 H), 7.13 (s, 1 H), 7.35-7.49 (m, 2 H), 7.60-7.81 (m, 1 H), 8.26 (d, J = 2.02 Hz, 1 H) | 539.5 |
| 342 | 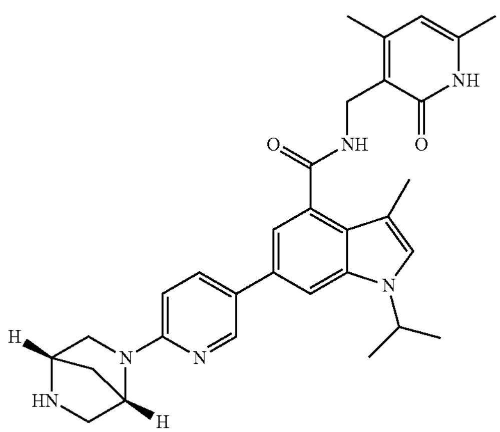 [SMILES: Cc1cc(C)c(CNC(=O)c2cc(-c3ccc(N4C[C@@H]5C[C@H]4CN5)nc3)cc3c2c(C)cn3C(C)C)c(=O)[nH]1] | 6-{6-[(1S,4S)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, J = 6.57 Hz, 6 H), 1.68 (d, J = 9.35 Hz, 1 H), 1.80 (d, J = 8.84 Hz, 1 H), 2.11 (s, 3 H), 2.16 (s, 3 H), 2.24 (s, 3 H), 2.82 (d, J = 9.35 Hz, 1 H), 2.89-2.97 (m, 1 H), 3.16-3.25 (m, 2 H), 3.49 (d, J = 8.34 Hz, 1 H), 3.69 (br. s., 1 H), 4.35 (d, J = 4.80 Hz, 2 H), 4.69 (s, 1 H), 4.83 (quin, J = 6.63 Hz, 1 H), 5.87 (s, 1 H), 6.56 (d, J = 8.84 Hz, 1 H), 7.16 (d, J = 1.26 Hz, 1 H), 7.27 (s, 1 H), 7.68 (d, J = 1.26 Hz, 1 H), 7.86 (dd, J = 8.72, 2.40 Hz, 1 H), 8.14 (t, J = 5.05 Hz, 1 H), 8.44 (d, J = 2.27 Hz, 1 H) | 525.3 |
| 343 | 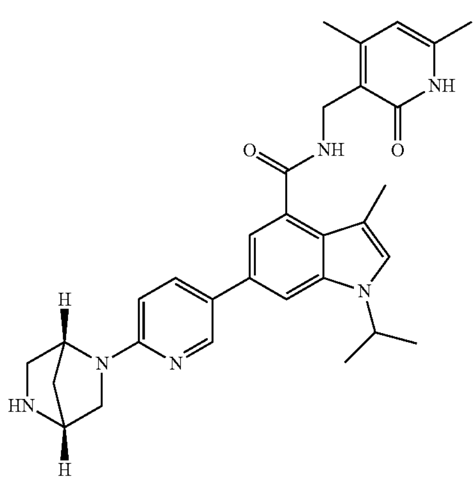 [SMILES: Cc1cc(C)c(CNC(=O)c2cc(-c3ccc(N4C[C@H]5C[C@@H]4CN5)nc3)cc3c2c(C)cn3C(C)C)c(=O)[nH]1] | 6-{6-[(1R,4R)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, 6 H), 1.70 (m, 1 H), 1.80 (m, 1 H), 2.11 (s, 3 H), 2.16 (s, 3 H), 2.24 (s, 3 H), 2.80-2.87 (m, 1 H), 2.91-2.98 (m, 1 H,) 3.23 (d, J = 9.35 Hz, 1 H), 3.49 (dd, J = 9.35, 2.02 Hz, 1 H), 3.72 (s, 1 H), 4.35 (d, J = 5.05 Hz, 2 H), 4.70 (s, 1 H), 4.83 (quin, J = 6.63 Hz, 1 H), 5.87 (s, 1 H), 6.56 (d, J = 8.84 Hz, 1 H), 7.16 (d, J = 1.52 Hz, 1 H), 7.27 (s, 1 H), 7.68 (d, J = 1.26 Hz, 1 H), 7.87 (dd, J = 8.84, 2.53 Hz, 1 H), 8.14 (t, J = 4.93 Hz, 1 H), 8.44 (d, J = 2.27 Hz, 1H) | 525.7 |

| Ex | Structure | Name | ¹H NMR (400 MHz, DMSO-d₆) δ ppm | MS(ES) [M + H]⁺ |
|---|---|---|---|---|
| 344 | 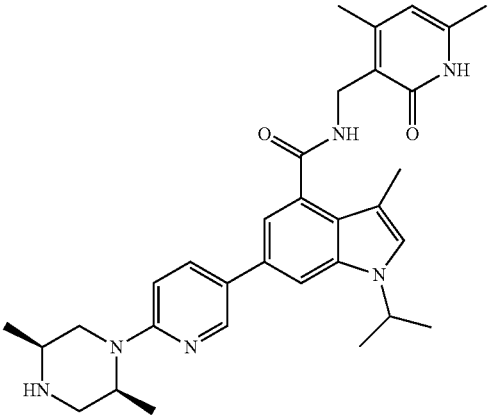 | N-[(4,6-dimethyl-2-oxo-1,2-dihydro-3-pyridinyl)methyl]-6-{6-[(2S,5S)-2,5-dimethyl-1-piperazinyl]-3-pyridinyl}-3-methyl-1-(1-methylethyl)-1H-indole-4-carboxamide | 1.10 (m, 6 H), 1.43 (d, J = 6.82 Hz, 6 H), 2.11 (s, 3 H), 2.14-2.19 (m, 3 H), 2.24 (s, 3 H), 2.61-2.74 (m, 1 H), 2.79-2.96 (m, 2 H), 3.93-4.04 (m, 1 H), 4.35 (d, J = 5.05 Hz, 3 H), 4.76-4.90 (m, 1 H), 5.87 (s, 1 H), 6.82 (d, J = 8.84 Hz, 1 H), 7.17 (d, J = 1.52 Hz, 1 H), 7.28 (s, 1 H), 7.70 (d, J = 1.26 Hz, 1 H), 7.89 (dd, J = 8.84, 2.53 Hz, 1 H), 8.14 (t, J = 5.05 Hz, 1 H), 8.49 (d, J = 2.53 Hz, 1 H) | 541.6 |
| 345 | 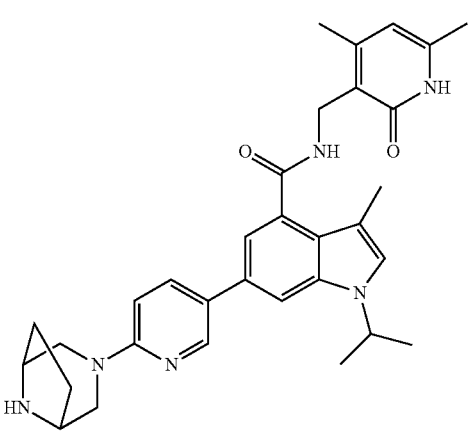 [SMILES: Cc1cc(C)c(CNC(=O)c2cc(-c3ccc(N4CC5CCC(C4)N5)nc3)cc3c2c(C)cn3C(C)C)c(=O)[nH]1] | 6-[6-(3,8-diazabicyclo[3.2.1]oct-3-yl)-3-pyridinyl]-N-[(4,6-dimethyl-2-oxo-1,2-dihydro-3-pyridinyl)methyl]-3-methyl-1-(1-methylethyl)-1H-indole-4-carboxamide | 1.38-1.48 (m, 6 H), 1.60-1.74 (m, 4 H), 2.11 (s, 3 H), 2.16 (s, 3 H), 2.24 (s, 3 H), 2.79-2.95 (m, 2 H), 3.35 (d, J = 1.26 Hz, 5 H), 3.54 (br. s., 2 H), 3.83-3.91 (m, 2 H), 4.35 (d, J = 5.05 Hz, 2 H), 4.83 (quin, J = 6.57 Hz, 1 H), 5.87 (s, 1 H), 6.75 (d, J = 8.84 Hz, 1 H), 7.17 (d, J = 1.52 Hz, 1 H), 7.28 (s, 1 H), 7.70 (d, J = 1.26 Hz, 1 H), 7.89 (dd, J = 8.84, 2.53 Hz, 1 H), 8.15 (t, J = 5.05 Hz, 1 H), 8.45-8.51 (m, 1 H) | 539.6 |
| 346 | 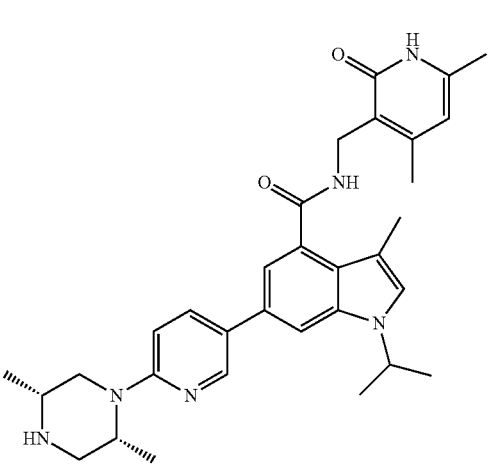 | N-((4,6-dimethyl-2-oxo-1,2-dihydropyridin-3-yl)methyl)-6-(6-((2R,5R)-2,5-dimethylpiperazin-1-yl)pyridin-3-yl)-1-isopropyl-3-methyl-1H-indole-4-carboxamide | (METHANOL-d4) 1.25 (d, 3 H), 1.31 (d, J = 6.32 Hz, 3 H), 1.49 (d, J = 6.57 Hz, 6 H), 2.23 (d, J = 10.11 Hz, 6 H), 2.43 (s, 3 H), 2.81 (dd, J = 13.39, 11.37 Hz, 1 H), 2.92-3.28 (m, 3 H), 4.16 (dd, J = 13.52, 3.16 Hz, 1 H), 4.62 (br. s., 1 H), 4.80 (quin, J = 6.69 Hz, 1 H), 6.12 (s, 1 H), 6.90 (d, J = 8.84 Hz, 1 H), 7.20 (s, 1 H), 7.27 (d, J = 1.52 Hz, 1 H), 7.63 (d, J = 1.26 Hz, 1 H), 7.92 (dd, J = 8.84, 2.53 Hz, 1 H), 8.44 (d, J = 2.27 Hz, 1 H) | 541.3 |

Example 347

N-((4,6-Dimethyl-2-oxo-1,2-dihydropyridin-3-yl)methyl)-1-isopropyl-3-methyl-6-(6-(pyrrolidin-1-ylmethyl)pyridin-3-yl)-1H-indole-4-carboxamide

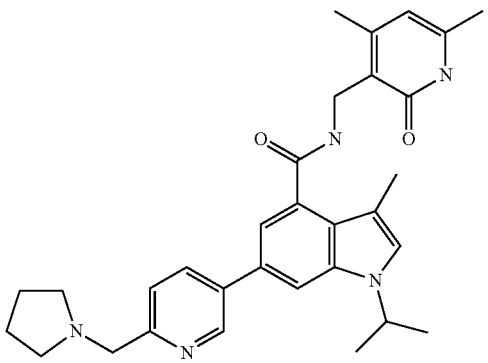 [SMILES: Cc1cc(C)c(CNC(=O)c2cc(-c3ccc(CN4CCCC4)nc3)cc3c2c(C)cn3C(C)C)c(=O)[nH]1]

To a solution of N-((4,6-dimethyl-2-oxo-1,2-dihydropyridin-3-yl)methyl)-6-(6-formylpyridin-3-yl)-1-isopropyl-3-methyl-1H-indole-4-carboxamide (100 mg, 0.219 mmol), in DCM (10 mL) and methanol (2 mL) was added pyrrolidine (0.035 mL, 0.438 mmol), followed by sodium sulfate (31.1 mg, 0.219 mmol). The reaction stirred at rt for 12 h, at which time sodium borohydride (16.57 mg, 0.438 mmol) was added and the reaction stirred rt for 2 h and 45° C. for 2 h. The reaction was quenched with water and extracted with EtOAc. The organic layer was evaporated. Purification by reverse phase Gilson HPLC (10-60% acetonitrile/water+0.1% TFA, YMC ODS-A C18 Column 75×30 mm ID S-5 um, 12 nM Column 7 minutes), followed by isolation and extraction with EtOAc/0.1N NaOH provided N-((4,6-dimethyl-2-oxo-1,2-dihydropyridin-3-yl)methyl)-1-isopropyl-3-methyl-6-(6-(pyrrolidin-1-ylmethyl)pyridin-3-yl)-1H-indole-4-carboxamide, which was evaporated from the organic layer as a yellow foam solid (68 mg, 0.125 mmol, 57.0% yield). $^1$H NMR (400 MHz, DMSO-$d_6$) δ ppm 11.48 (br. s., 1H) 9.06 (d, J=2.02 Hz, 1H) 8.30 (dd, J=8.08, 2.27 Hz, 1H) 8.20 (t, J=5.18 Hz, 1H) 7.94 (d, J=1.26 Hz, 1H) 7.60 (d, J=8.08 Hz, 1H) 7.40 (s, 1H) 7.32 (s, 1H) 5.88 (s, 1H) 4.92-4.89 (m, 1H) 4.59 (d, J=5.56 Hz, 2H) 4.36 (d, J=5.05 Hz, 2H) 3.34 (br. s., 4H) 2.25 (s, 3H) 2.17 (d, J=1.01 Hz, 3H) 2.11 (s, 3H) 1.99 (br.s., 4H) 1.45 (d, J=6.57 Hz, 6H). LCMS: [M+H]$^+$=512.3.

Examples 348-350 were prepared by the methods described above for Example 347, or routine variations thereof, using the requisite amine:

| Ex | Structure | Name | $^1$H NMR (400 MHz, DMSO-$d_6$) δ ppm | MS(ES) [M + H]$^+$ | EZH2 pIC50 |
|---|---|---|---|---|---|
| 348 | 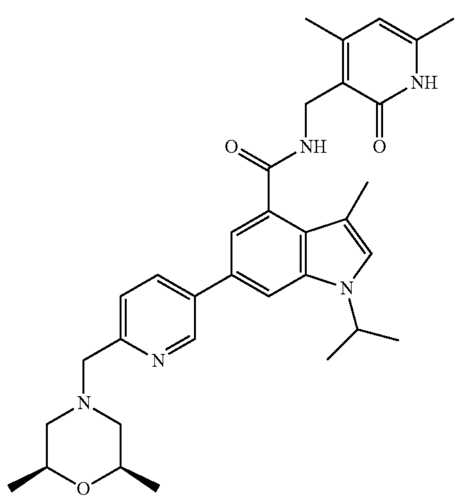 | 6-(6-{[(2R,6S)-2,6-dimethyl-4-morpholinyl]methyl}-3-pyridinyl)-N-[(4,6-dimethyl-2-oxo-1,2-dihydro-3-pyridinyl)methyl]-3-methyl-1-(1-methylethyl)-1H-indole-4-carboxamide | 11.48 (br. s., 1 H) 9.09 (d, J = 2.02 Hz, 1 H) 8.32 (dd, J = 8.08, 2.27 Hz, 1 H) 8.19 (t, J = 5.05 Hz, 1 H) 7.94 (d, J = 1.26 Hz, 1 H) 7.62 (d, J = 8.08 Hz, 1 H) 7.41 (s, 1 H) 7.33 (d, J = 1.52 Hz, 1 H) 5.88 (s, 1 H) 4.87-4.94 (m, 1 H) 4.52 (br. s., 2 H) 4.36 (d, J = 4.80 Hz, 2 H) 3.87-3.96 (m, 2 H) 3.35-3.45 (m, 2 H) 2.75-2.85 (m, 2 H) 2.25 (s, 3 H) 2.17 (s, 3 H) 2.11 (s, 3 H) 1.45 (d, J = 6.57 Hz, 6 H) 1.14 (d, J = 6.06 Hz, 6 H) | 556.4 | 7.44 |

| Ex | Structure | Name | ¹H NMR (400 MHz, DMSO-$d_6$) δ ppm | MS(ES) [M + H]⁺ | EZH2 pIC50 |
|---|---|---|---|---|---|
| 349 | 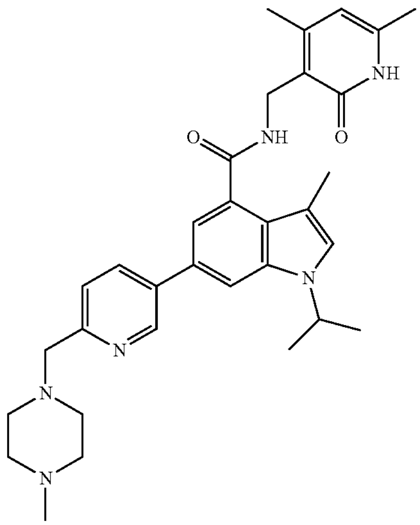 [SMILES: Cc1cc(C)c(CNC(=O)c2cc(-c3ccc(CN4CCN(C)CC4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-{6-[(4-methyl-1-piperazinyl)methyl]-3-pyridinyl}-1H-indole-4-carboxamide | 11.50 (br. s., 1 H) 9.03 (d, J = 2.02 Hz, 1 H) 8.37 (dd, J = 8.08, 2.02 Hz, 1 H) 8.21 (t, J = 5.05 Hz, 1 H) 7.93 (d, J = 1.26 Hz, 1 H) 7.65 (d, J = 8.08 Hz, 1 H) 7.41 (s, 1 H) 7.32 (d, J = 1.52 Hz, 1 H) 5.88 (s, 1 H) 4.90 (quin, J = 6.63 Hz, 1 H) 4.36 (d, J = 5.05 Hz, 2 H) 4.08 (br. s., 2 H) 3.07-3.56 (m, 8 H) 2.83 (s, 3 H) 2.24-2.28 (m, 3 H) 2.17 (s, 3 H) 2.12 (s, 3 H) 1.45 (d, J = 6.57 Hz, 6 H) | 541.3 | 7.6 |
| 350 | 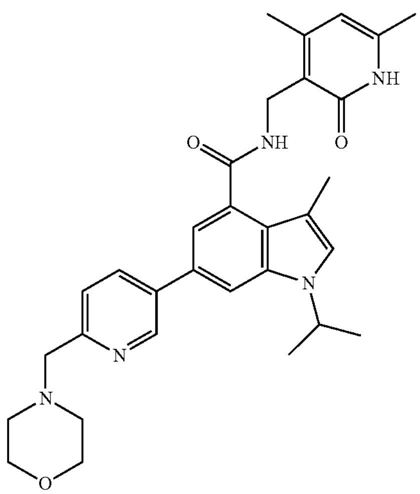 [SMILES: Cc1cc(C)c(CNC(=O)c2cc(-c3ccc(CN4CCOCC4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(4-morpholinylmethyl)-3-pyridinyl]-1H-indole-4-carboxamide | 11.49 (br. s., 1 H) 8.88 (d, J = 2.02 Hz, 1 H) 8.21 (t, J = 4.93 Hz, 1 H) 8.12 (dd, J = 8.08, 2.27 Hz, 1 H) 7.86 (d, J = 1.26 Hz, 1 H) 7.51 (d, J = 8.08 Hz, 1 H) 7.36 (s, 1 H) 7.27 (d, J = 1.52 Hz, 1 H) 5.87 (s, 1 H) 4.85-4.93 (m, 1 H) 4.36 (d, J = 4.80 Hz, 2 H) 3.62 (dd, J = 9.47, 4.93 Hz, 6 H) 2.45 (br. s., 4 H) 2.24 (s, 3 H) 2.18 (s, 3 H) 2.11 (s, 3 H) 1.44 (d, J = 6.57 Hz, 6 H) | 528.3 | 7.64 |

Example 351

6-Bromo-N-((6-(hydroxymethyl)-4-methyl-2-oxo-1,2-dihydropyridin-3-yl)methyl)-1-isopropyl-3-methyl-1H-indole-4-carboxamide

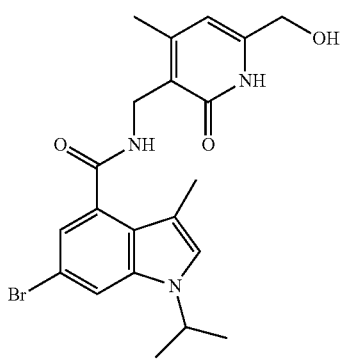 [SMILES: Cc1cc(CO)[nH]c(=O)c1CNC(=O)c1cc(Br)cc2c1c(C)cn2C(C)C]

a) 6-Bromo-N-((6-(hydroxymethyl)-2-methoxy-4-methylpyridin-3-yl)methyl)-1-isopropyl-3-methyl-1H-indole-4-carboxamide

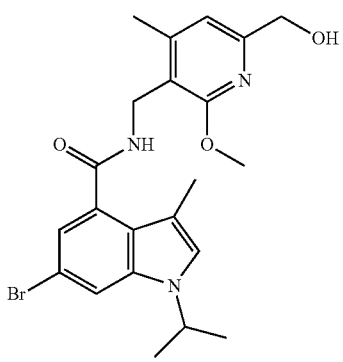 [SMILES: COc1nc(CO)cc(C)c1CNC(=O)c1cc(Br)cc2c1c(C)cn2C(C)C]

To a stirred solution of (5-(aminomethyl)-6-methoxy-4-methylpyridin-2-yl)methanol (0.29 g, 1.591 mmol), 6-bromo-1-isopropyl-3-methyl-1H-indole-4-carboxylic acid (0.48 g, 1.621 mmol), and HOAt (0.22 g, 1.616 mmol) in Dichloromethane (15 mL) and DMF (5 mL) was added EDC free base (0.30 g, 1.932 mmol). The reaction was stirred at RT for 3 h then evaporated to dryness under vacuum. The remaining was purified by silica gel chromatography (Analogix, SF25-60g, 0 to 20% EtOAc in CH$_2$Cl$_2$) to give the product 6-bromo-N-((6-(hydroxymethyl)-2-methoxy-4-methylpyridin-3-yl)methyl)-1-isopropyl-3-methyl-1H-indole-4-carboxamide (0.73 g, 1.586 mmol, 100% yield) as a white solid. $^1$H NMR (400 MHz, DMSO-d$_6$) δ=8.46 (t, J=4.9 Hz, 1H), 7.77 (d, J=1.8 Hz, 1H), 7.33 (d, J=1.0 Hz, 1H), 6.99 (d, J=1.5 Hz, 1H), 6.90 (s, 1H), 5.31 (t, J=5.9 Hz, 1H), 4.74 (quin, J=6.6 Hz, 1H), 4.45 (d, J=5.1 Hz, 1H), 4.43 (d, J=5.8 Hz, 2H), 3.83 (s, 3H), 2.40 (s, 3H), 2.10 (s, 3H), 1.38 (d, J=6.8 Hz, 6H). MS(ES)+ m/e 460.2 [M+H]$^+$.

b) 6-Bromo-N-((6-(hydroxymethyl)-4-methyl-2-oxo-1,2-dihydropyridin-3-yl)methyl)-1-isopropyl-3-methyl-1H-indole-4-carboxamide

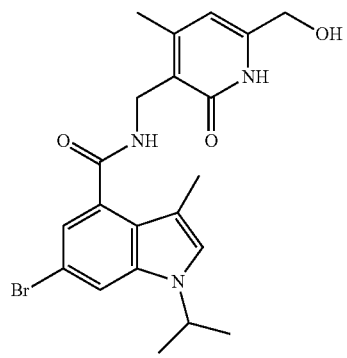 [SMILES: Cc1cc(CO)[nH]c(=O)c1CNC(=O)c1cc(Br)cc2c1c(C)cn2C(C)C]

To a stirred solution of 6-bromo-N-((6-(hydroxymethyl)-2-methoxy-4-methylpyridin-3-yl)methyl)-1-isopropyl-3-methyl-1H-indole-4-carboxamide (500 mg, 1.086 mmol) in tetrahydrofuran (5 mL) was added 6N HCl (15 mL, 15.00 mmol). The reaction was stirred under N$_2$ with heating at 80° C. for 18 hr. The reaction was cooled to RT and evaporated to dryness under vacuum. The remaining was purified by silica gel chromatography (Analogix, SF25-60g, 4% MeOH in CH$_2$Cl$_2$). The pure fractions were combined and evaporated to dryness under vacuum. Triturated with a small volume of water, filtered, washed with water and dried under vacuum to give the product 6-bromo-N-((6-(hydroxymethyl)-4-methyl-2-oxo-1,2-dihydropyridin-3-yl)methyl)-1-isopropyl-3-methyl-1H-indole-4-carboxamide (189 mg, 0.423 mmol, 39.0% yield) as a white solid. $^1$H NMR (400 MHz, DMSO-d$_6$) δ=11.30 (s, 1H), 8.27 (t, J=4.9 Hz, 1H), 7.76 (d, J=1.8 Hz, 1H), 7.33 (s, 1H), 7.01 (d, J=1.8 Hz, 1H), 6.05 (s, 1H), 5.38 (t, J=5.9 Hz, 1H), 4.74 (dt, J=6.7, 13.2 Hz, 1H), 4.32 (d, J=5.1 Hz, 2H), 4.25 (d, J=5.8 Hz, 2H), 2.26 (s, 3H), 2.13 (s, 3H), 1.39 (d, J=6.6 Hz, 6H). MS(ES)+ m/e 446.1 [M+H]$^+$.

Example 352

N-((6-(aminomethyl)-4-methyl-2-oxo-1,2-dihydropyridin-3-yl)methyl)-6-bromo-1-isopropyl-3-methyl-1H-indole-4-carboxamide

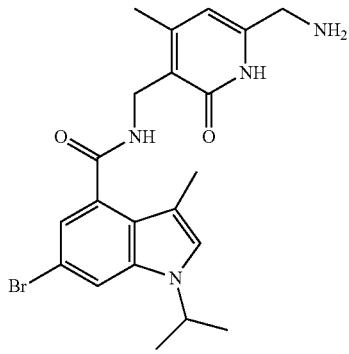 [SMILES: Cc1cc(CN)[nH]c(=O)c1CNC(=O)c1cc(Br)cc2c1c(C)cn2C(C)C]

a) tert-Butyl ((5-(((6-bromo-1-isopropyl-3-methyl-1H-indole-4-carboxamido)methyl)-6-methoxy-4-methylpyridin-2-yl)methyl)carbamate

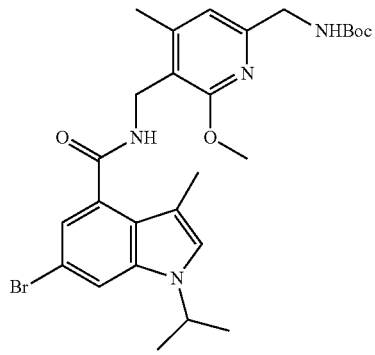 [SMILES: COc1nc(CNC(=O)OC(C)(C)C)cc(C)c1CNC(=O)c1cc(Br)cc2c1c(C)cn2C(C)C]

To a stirred solution of tert-butyl ((5-(aminomethyl)-6-methoxy-4-methylpyridin-2-yl)methyl)carbamate (0.55 g, 1.955 mmol), 6-bromo-1-isopropyl-3-methyl-1H-indole-4-carboxylic acid (0.63 g, 2.127 mmol), and HOAt (0.27 g, 1.984 mmol) in Dichloromethane (20 mL) and DMF (5 mL) was added EDC free base (0.34 g, 2.190 mmol). The reaction was stirred at RT for 2 hr then evaporated to dryness under vacuum. The remaining was purified by silica gel chromatography (Analogix, SF25-60g, 0 to 40% EtOAc in hexanes) to give the product tert-butyl ((5-(((6-bromo-1-isopropyl-3-methyl-1H-indole-4-carboxamido)methyl)-6-methoxy-4-methylpyridin-2-yl)methyl)carbamate (1.07 g, 1.912 mmol, 98% yield) as a white solid. $^1$H NMR (400 MHz, DMSO-d$_6$) δ=8.47 (t, J=4.8 Hz, 1H), 7.76 (d, J=1.8 Hz, 1H), 7.35 (t, 1H), 7.33 (d, J=1.0 Hz, 1H), 6.99 (d, J=1.5 Hz, 1H), 6.67 (s, 1H), 4.74 (quin, J=6.6 Hz, 1H), 4.44 (d, J=4.8 Hz, 2H), 4.08 (d, J=6.3 Hz, 2H), 3.85 (s, 3H), 2.37 (s, 3H), 2.10 (s, 3H), 1.41 (s, 9H), 1.38 (d, J=6.6 Hz, 6H). MS(ES)+ m/e 559.3 [M+H]$^+$.

b) N-((6-(Aminomethyl)-4-methyl-2-oxo-1,2-dihydropyridin-3-yl)methyl)-6-bromo-1-isopropyl-3-methyl-1H-indole-4-carboxamide

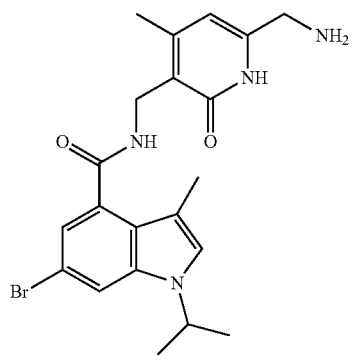 [SMILES: Cc1cc(CN)[nH]c(=O)c1CNC(=O)c1cc(Br)cc2c1c(C)cn2C(C)C]

To a stirred solution of tert-butyl ((5-(((6-bromo-1-isopropyl-3-methyl-1H-indole-4-carboxamido)methyl)-6-methoxy-4-methylpyridin-2-yl)methyl)carbamate (500 mg, 0.894 mmol) in Tetrahydrofuran (THF) (5 mL) was added 6N HCl (15 mL, 15.00 mmol). The reaction was stirred under N2 with heating at 80° C. for 18 hr. The reaction was cooled to RT and evaporated to dryness under vacuum. The remaining was purified by silica gel chromatography (Analogix, SF25-40 g, 0 to 10% (5% NH4OH in MeOH) in CH2Cl2). The pure fractions were combined and evaporated to dryness under vacuum. Dissolved with a small volume of CH2Cl2, scratched out by slowly adding hexanes, filtered, washed with hexanes and dried under vacuum to give the product N-((6-(aminomethyl)-4-methyl-2-oxo-1,2-dihydropyridin-3-yl)methyl)-6-bromo-1-isopropyl-3-methyl-1H-indole-4-carboxamide (328 mg, 0.736 mmol, 82% yield) as an off-white solid. $^1$H NMR (400 MHz, DMSO-$d_6$) δ=8.26 (t, J=5.1 Hz, 1H), 7.76 (d, J=1.8 Hz, 1H), 7.33 (d, J=1.0 Hz, 1H), 7.01 (d, J=1.5 Hz, 1H), 6.01 (s, 1H), 5.77 (s, 0H), 4.74 (quin, J=6.6 Hz, 1H), 4.32 (d, J=5.1 Hz, 2H), 3.46 (s, 2H), 2.25 (s, 3H), 2.14 (s, 3H), 1.39 (d, J=6.8 Hz, 6H). MS(ES)+ m/e 445.2 [M+H]$^+$.

Example 353

3-Methyl-1-(1-methylethyl)-4-({[(6-methyl-2-oxo-4-propyl-1,2-dihydro-3-pyridinyl)methyl]amino}carbonyl)-1H-indole-6-carboxylic acid

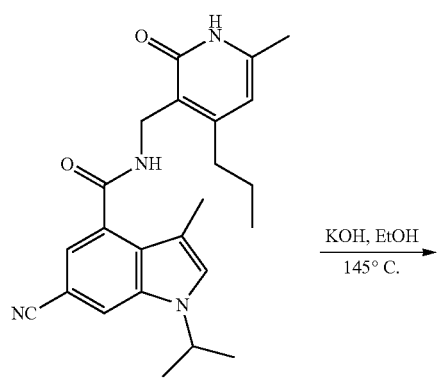

KOH, EtOH
145° C.

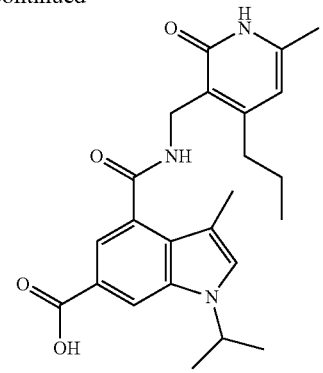

To a 5 ml microwave vial was added, 6-cyano-3-methyl-1-(1-methylethyl)-N-[(6-methyl-2-oxo-4-propyl-1,2-dihydro-3-pyridinyl)methyl]-1H-indole-4-carboxamide (100 mg, 0.247 mmol), KOH (41.6 mg, 0.742 mmol) was ground and added followed by Ethanol (8 mL) the reaction was microwaved at 145° C. for 22 hr. The reaction was poured onto acidic Ice water (20 mL) and was stirred for 20 min. EtOAc was added and the mix was stirred an additional 10 min. The layers were separated and the majority of the product was in the EtOAc which was evaporated. The residue was dissolved in MeOH (1 mL) and material was crashed out with ice and was filtered to give product 3-methyl-1-(1-methylethyl)-4-({[(6-methyl-2-oxo-4-propyl-1,2-dihydro-3-pyridinyl)methyl]amino}carbonyl)-1H-indole-6-carboxylic acid (70 mg, 0.160 mmol, 64.9% yield) $^1$H NMR (400 MHz, DMSO-$d_6$) δ ppm 11.49 (br. s., 1H) 8.18 (s, 1H) 8.10 (s, 1H) 7.53 (d, J=7.58 Hz, 2H) 5.90 (s, 1H) 4.76-4.90 (m, 1H) 4.36 (d, J=4.80 Hz, 2H) 2.55 (br. s., 1H) 2.18 (s, 3H) 2.13 (s, 3H) 1.52-1.61 (m, 2H) 1.44 (d, J=6.57 Hz, 6H) 0.94 (t, J=7.33 Hz, 3H) MS(ES) [M+H]$^+$ 423.8

Example 354

3-[3-Methyl-1-(1-methylethyl)-4-({[(6-methyl-2-oxo-4-propyl-1,2-dihydro-3-pyridinyl)methyl]amino}carbonyl)-1H-indol-6-yl]propanoic acid

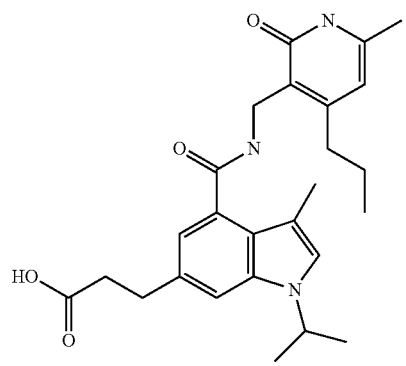 [SMILES: CCCc1cc(C)[nH]c(=O)c1CNC(=O)c1cc(CCC(=O)O)cc2c1c(C)cn2C(C)C]

267 a) Ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate

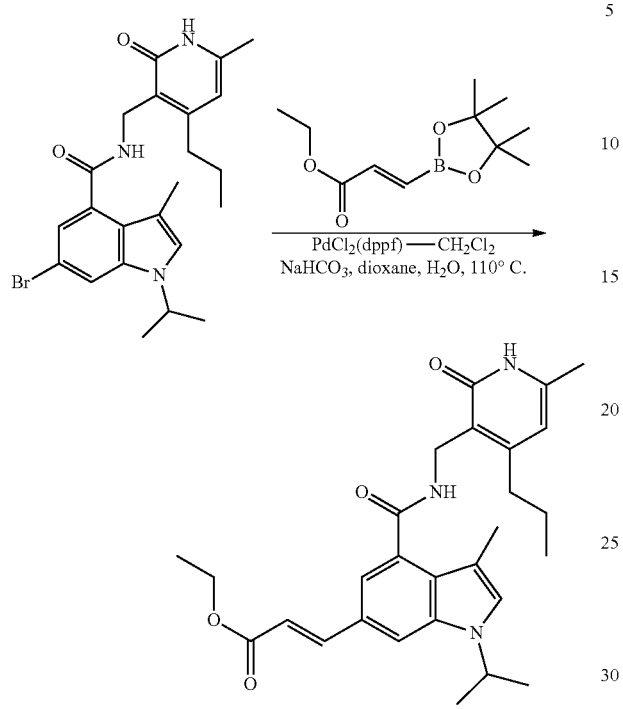

Following the general procedure detailed above for Suzuki cross-couplings (see Example 2), ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate (120 mg, 0.234 mmol, 53.6% yield) was prepared. $^1$H NMR (400 MHz, DMSO-$d_6$) δ ppm 11.49 (s, 1H) 8.12 (t, J=4.93 Hz, 1H) 7.97 (d, J=1.01 Hz, 1H) 7.74 (d, J=15.92 Hz, 1H) 7.43 (s, 1H) 7.27 (d, J=1.26 Hz, 1H) 6.61 (d, J=15.92 Hz, 1H) 5.90 (s, 1H) 4.78-4.86 (m, 1H) 4.35 (d, J=5.05 Hz, 2H) 4.19 (q, J=7.07 Hz, 2H) 2.53-2.58 (m, 2H) 2.14 (d, J=11.12 Hz, 6H) 1.53-1.62 (m, 2H) 1.43 (d, J=6.82 Hz, 6H) 1.27 (t, J=7.07 Hz, 3H) 0.93-0.97 (m, 3H). MS(ES) [M+H]$^+$ 477.9 b) Ethyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoate

268

-continued

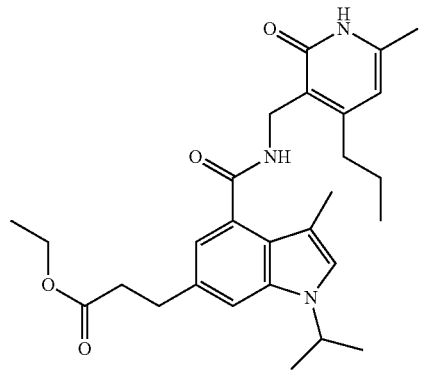

In a 50 ml flask was added ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate (120 mg, 0.251 mmol), and Ethanol (10 mL). PdOH2 (70.6 mg, 0.503 mmol) was added and the reaction was degassed with N2 for 15 min then H2 was bubbled in (via balloon) and the reaction stirred for 12 hr. The reaction was purged with N2 for 30 min and then filtered through an acro disc and evaporated. The residue was suspended in MeOH/Water (2 mL/4 mL) and filtered and washed with water to give a white solid. ethyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoate (70 mg, 0.146 mmol, 58.1% yield). $^1$H NMR (400 MHz, DMSO-$d_6$) δ ppm 11.49 (br. s., 1H) 7.90 (br. s., 1H) 7.34 (s, 1H) 7.21 (s, 1H) 6.82 (s, 1H) 5.90 (s, 1H) 4.63-4.73 (m, 1H) 4.34 (d, J=4.55 Hz, 2H) 4.04 (q, J=7.07 Hz, 2H) 2.92 (t, J=7.33 Hz, 2H) 2.64 (t, J=7.45 Hz, 2H) 2.55-2.62 (m, 2H) 2.12 (s, 6H) 1.52-1.62 (m, 2H) 1.40 (d, J=6.32 Hz, 6H) 1.16 (t, J=7.07 Hz, 3H) 0.94 (t, J=7.20 Hz, 3H). MS(ES) [M+H]$^+$ 479.8.

c) 3-[3-Methyl-1-(1-methylethyl)-4-({[(6-methyl-2-oxo-4-propyl-1,2-dihydro-3-pyridinyl)methyl]amino}carbonyl)-1H-indol-6-yl]propanoic acid

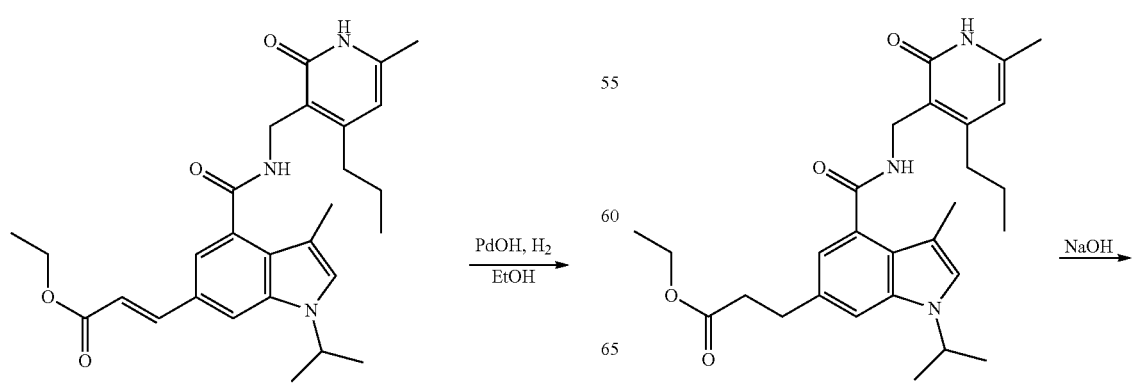

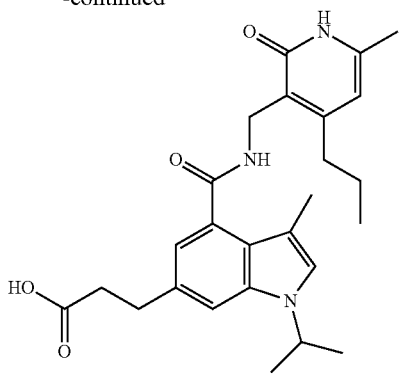

Following the general procedure detailed above for Suzuki cross-couplings (see Example 2), 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoic acid (45 mg, 0.095 mmol, 64.9% yield) was prepared. $^1$H NMR (400 MHz, DMSO-$d_6$) δ ppm 12.05 (br.s, 1H) 11.49 (br. s., 1H) 7.88-7.95 (m, 1H) 7.34 (s, 1H) 7.20 (s, 1H) 6.82 (s, 1H) 5.90 (s, 1H) 4.64-4.73 (m, 1H) 4.34 (d, J=4.80 Hz, 2H) 2.89 (t, J=7.71 Hz, 2H) 2.55-2.60 (m, 4H) 2.12 (s, 6H) 1.53-1.61 (m, 2H) 1.40 (d, J=6.57 Hz, 6H) 0.92-0.96 (m, 3H). MS(ES) [M+H]$^+$ 451.9.

Example 355

6-(2-Aminoethyl)-N-[(4,6-dimethyl-2-oxo-1,2-dihydro-3-pyridinyl)methyl]-3-methyl-1-(1-methylethyl)-1H-indole-4-carboxamide

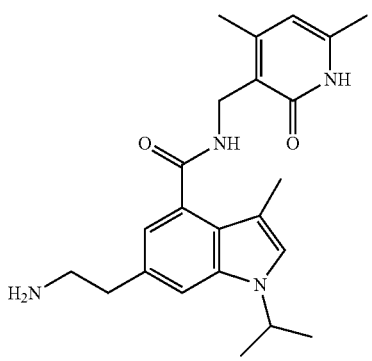 [SMILES: Cc1cc(C)c(CNC(=O)c2cc(CCN)cc3c2c(C)cn3C(C)C)c(=O)[nH]1]

a) 6-[2-({[(1,1-Dimethylethyl)oxy]carbonyl}amino)ethyl]-3-methyl-1-(1-methylethyl)-1H-indole-4-carboxylic acid

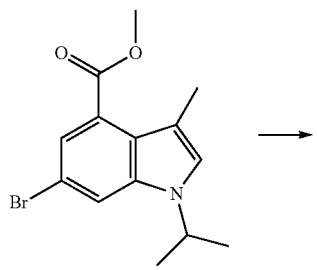

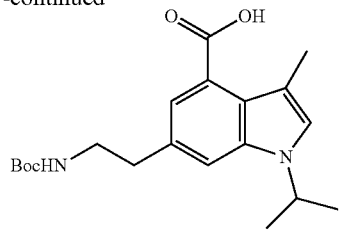

In a glass pressure bottle was added methyl 6-bromo-3-methyl-1-(1-methylethyl)-1H-indole-4-carboxylate (1.00 g, 2.77 mmol), potassium t-butyl-N-[2-(trifluoroboranuidyl)ethyl]carbamate (900 mg, 3.58 mmol), cesium carbonate (3.2 g, 9.82 mmol), toluene (24 mL) and water (8 mL). The mixture was stirred and purged with N2. To the reaction was added palladium(II) acetate (40 mg, 0.178 mmol) and RuPhos (160 mg, 0.342 mmol), the reaction capped and stirred at 95° C. for 18 hr. LCMS showed that the reaction was complete. The reaction was taken up in EtOAc, diluted with water, and filtered to remove insolubles. The organic phase was removed, dried (MgSO$_4$), filtered and concentrated under vacuum. Purification by silica gel chromatography (Analogix, SF25-60g, 0 to 20% EtOAc in hexanes gave the methyl ester.

To the ester in THF (10 mL) and MeOH (30 mL) was added 1N NaOH (10 mL, 10 mmol). The solution was stirred at reflux 80° C. for 24 hr (slow saponification). After cooling to RT the reaction was concentrated under vacuum, neutralized with 1N HCl (10 mL), triturated with water, filtered and dried under vacuum to give the product 6-[2-({[(1,1-dimethylethyl)oxy]carbonyl}amino)ethyl]-3-methyl-1-(1-methylethyl)-1H-indole-4-carboxylic acid (865 mg, 2.31 mmol, 83.0% yield) as a white solid. $^1$H NMR (400 MHz, DMSO-$d_6$) δ 12.69 (br. s., 1H), 7.43 (s, 1H), 7.31 (s, 1H), 7.25 (s, 1H), 6.89 (t, J=5.6 Hz, 1H), 4.71 (dt, J=6.6, 13.3 Hz, 1H), 3.23-3.10 (m, 2H), 2.80 (t, J=7.3 Hz, 2H), 2.30 (s, 3H), 1.42 (d, J=6.6 Hz, 6H), 1.37 (s, 9H). MS(ES)+ m/e 361.2 [M+H]$^+$.

b) 6-(2-Aminoethyl)-N-[(4,6-dimethyl-2-oxo-1,2-dihydro-3-pyridinyl)methyl]-3-methyl-1-(1-methylethyl)-1H-indole-4-carboxamide hydrochloride salt

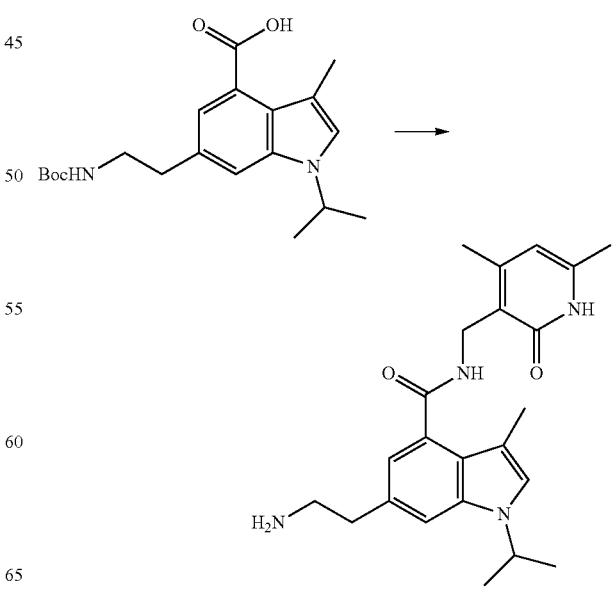

To a stirred suspension of 6-[2-({[(1,1-dimethylethyl)oxy]carbonyl}amino)ethyl]-3-methyl-1-(1-methylethyl)-1H-indole-4-carboxylic acid (500 mg, 1.387 mmol), 3-(aminomethyl)-4,6-dimethyl-2(1H)-pyridinone HCl salt (340 mg, 1.802 mmol), HOAt (245 mg, 1.800 mmol) in DMF (20 mL) was added N-methylmorpholine (200 µL, 1.819 mmol) and EDC free base (280 mg, 1.804 mmol). The reaction was stirred overnight at RT. LCMS showed that the reaction was complete. The reaction was evaporated to dryness and purified by silica gel chromatography (Analogix, SF25-40g, 0 to 10% CH$_2$Cl$_2$/20% (5% NH$_4$OH in MeOH) in CH$_2$Cl$_2$). The pure fractions were combined and evaporated to dryness. Triturated with 50% MeOH in water, filtered and dried under vacuum to give the Boc protected product as an off-white solid. The Boc protected product was suspended in a small volume of MeOH (2 mL) and treated with 4N HCl in dioxane (25 mL) and stirred at RT for 1 hr. LCMS showed that the reaction was complete. The reaction was evaporated to dryness, triturated with Et$_2$O, filtered and dried under vacuum to give the product 6-(2-aminoethyl)-N-[(4,6-dimethyl-2-oxo-1,2-dihydro-3-pyridinyl)methyl]-3-methyl-1-(1-methylethyl)-1H-indole-4-carboxamide (460 mg, 1.067 mmol, 77% yield) as an off-white solid. $^1$H NMR (400 MHz, DMSO-d$_6$+D$_2$O) δ 8.05 (t, J=5.2 Hz, 1H), 8.00 (br. s., 2H), 7.39 (d, J=1.0 Hz, 1H), 7.25 (s, 1H), 6.86 (d, J=1.3 Hz, 1H), 5.93 (s, 1H), 4.69 (dt, J=6.6, 13.3 Hz, 1H), 4.34 (d, J=5.1 Hz, 2H), 3.06 (dd, J=5.8, 7.6 Hz, 2H), 3.01-2.91 (m, 2H), 2.25 (s, 3H), 2.13 (s, 3H), 2.12 (s, 3H), 1.41 (d, J=6.8 Hz, 6H). MS(ES)+ m/e 394.9 [M+H]$^+$.

Example 356

6-{3-[(Dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide

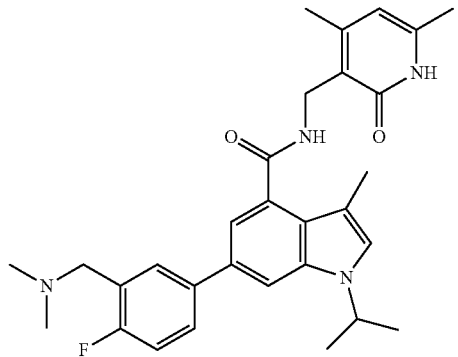

a) Methyl 6-(4-fluoro-3-formylphenyl)-3-methyl-1-(1-methylethyl)-1H-indole-4-carboxylate

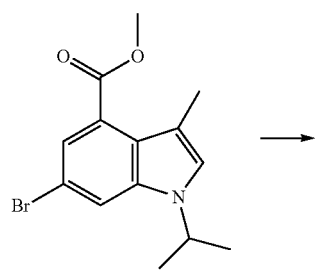

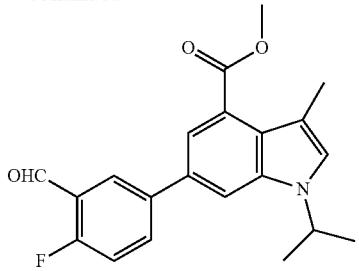

To a glass pressure vessel was added methyl 6-bromo-3-methyl-1-(1-methylethyl)-1H-indole-4-carboxylate (500 mg, 1.612 mmol), 4-fluoro-3-formylbenzeneboronic acid (375 mg, 2.233 mmol), Potassium phosphate (1.1 g, 5.18 mmol), dioxane (12 mL) and water (3 mL). The reaction was purged with N$_2$ and charged with PdCl$_2$(dppf)-CH$_2$Cl$_2$ adduct (120 mg, 0.147 mmol). The reaction was capped and stirred at 110° C. for 4 hr. LCMS showed that the reaction was complete. The reaction was diluted with water, extracted with EtOAc, washed with brine, dried (MgSO$_4$), filtered, and concentrated under vacuum. Purification by silica gel chromatography (Analogix, SF25-60g, 0 to 50% EtOAc in hexanes) gave the product methyl 6-(4-fluoro-3-formylphenyl)-3-methyl-1-(1-methylethyl)-1H-indole-4-carboxylate (560 mg, 1.585 mmol, 98% yield) as an off-white solid. $^1$H NMR (400 MHz, DMSO-d$_6$) δ=10.30 (s, 1H), 8.24-8.13 (m, 2H), 8.10 (d, J=1.5 Hz, 1H), 7.75 (d, J=1.8 Hz, 1H), 7.57-7.46 (m, 2H), 4.98 (quin, J=6.6 Hz, 1H), 3.91 (s, 3H), 2.31 (s, 3H), 1.46 (d, J=6.6 Hz, 6H). MS(ES)+ m/e 354.2 [M+H]$^+$.

b) 6-{3-[(Dimethylamino)methyl]-4-fluorophenyl}-3-methyl-1-(1-methylethyl)-1H-indole-4-carboxylic acid

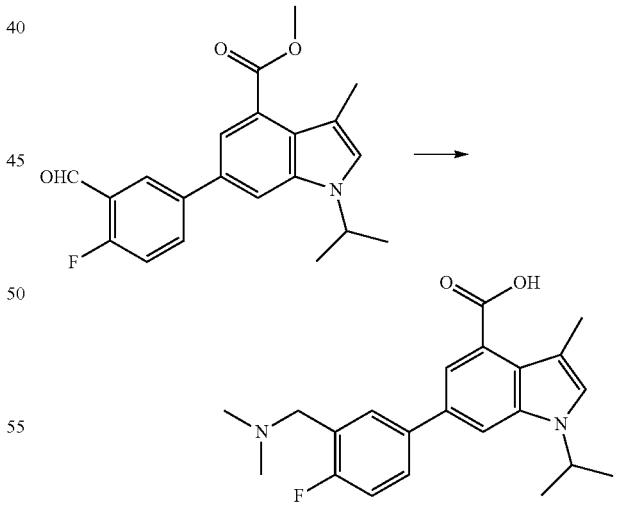

To a stirred solution of methyl 6-(4-fluoro-3-formylphenyl)-3-methyl-1-(1-methylethyl)-1H-indole-4-carboxylate (550 mg, 1.556 mmol) in CH$_2$Cl$_2$ (25 mL) was added 2N dimethylamine in THF (3.0 mL, 6.00 mmol) and acetic acid (170 µL, 2.97 mmol). After stirring at RT for 1 hr sodium triacetoxyborohydride (1.0 g, 4.72 mmol) was added portion-wise over 10 minutes. The reaction was stirred at RT overnight. LCMS showed the product as well as a substantial amount of the alcohol and one unidentifiable side product. The reaction was purified by silica gel chromatography (Analogix, SF25-60g, 0 to 50% CH₂Cl₂/20% (5% NH₄OH in MeOH) in CH₂Cl₂). The last fraction contained the desired product and was combined and evaporated to dryness. Trituration with hexanes, filtration and drying under vacuum gave the methyl ester product (0.25 g, 0.65 mMol, 41%) as an off-white solid.

The ester was taken up in THF (15 mL) and MeOH (5 mL) and treated with 1N NaOH (4 mL). The reaction was refluxed (80° C. oil bath) overnight. LCMS showed that the reaction was complete. The reaction was cooled to RT and concentrated under vacuum. Neutralization with 1N HCl (4 mL) ppt. out the product, which was triturated with a small amount of cold water, filtered, and dried under vacuum to give the product 6-{3-[(dimethylamino)methyl]-4-fluorophenyl}-3-methyl-1-(1-methylethyl)-1H-indole-4-carboxylic acid (210 mg, 0.570 mmol, 36.6% yield) as a white solid. ¹H NMR (400 MHz, DMSO-d₆) δ=12.84 (br. s., 1H), 10.80 (br. s., 1H), 8.18 (dd, J=2.0, 7.1 Hz, 1H), 8.12 (s, 1H), 8.01-7.85 (m, 1H), 7.76 (d, J=1.3 Hz, 1H), 7.49 (s, 1H), 7.43 (t, J=9.1 Hz, 1H), 4.95 (dt, J=6.6, 13.1 Hz, 1H), 4.43 (br. s., 2H), 2.80 (s, 6H), 2.34 (s, 3H), 1.46 (d, J=6.6 Hz, 6H). MS(ES)+ m/e 369.0 [M+H]⁺.

c) 6-{3-[(Dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide To a stirred suspension of 6-{3-[(dimethylamino)methyl]-4-fluorophenyl}-3-methyl-1-(1-methylethyl)- 1H-indole-4-carboxylic acid (210 mg, 0.570 mmol), 3-(aminomethyl)-4,6-dimethyl-2(1H)-pyridinone HCl salt (140 mg, 0.742 mmol) and HOAt (100 mg, 0.735 mmol) in DMF (15 mL) was added N-methylmorpholine (82 μl, 0.746 mmol) and EDC free base (110 mg, 0.709 mmol). The reaction was stirred for 4 h at RT and concentrated to near dryness under vacuum. Water was added till the product ppt. out. The suspension was triturated, filtered, rinsed with cold water then dried under vacuum to give the product 6-{3-[(dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide (186 mg, 0.370 mmol, 64.9% yield) as a light tan solid. ¹H NMR (400 MHz, DMSO-d₆) δ=11.47 (br. s., 1H), 8.15 (t, J=4.9 Hz, 1H), 8.04 (d, J=5.3 Hz, 1H), 7.90-7.86 (m, 1H), 7.39 (t, J=9.2 Hz, 1H), 7.35 (s, 1H), 7.27 (d, J=1.3 Hz, 1H), 5.87 (s, 1H), 4.88 (dt, J=6.6, 13.3 Hz, 1H), 4.36 (d, J=5.1 Hz, 2H), 4.26 (br. s., 2H), 2.69 (s, 6H), 2.24 (s, 3H), 2.17 (s, 3H), 2.11 (s, 3H), 1.44 (d, J=6.6 Hz, 6H). MS(ES)+ m/e 503.0 [M+H]⁺.

Example 357

6-(4,5-Dihydro-1H-imidazol-2-yl)-N-((4,6-dimethyl-2-oxo-1,2-dihydropyridin-3-yl)methyl)-1-isopropyl-3-methyl-1H-indole-4-carboxamide

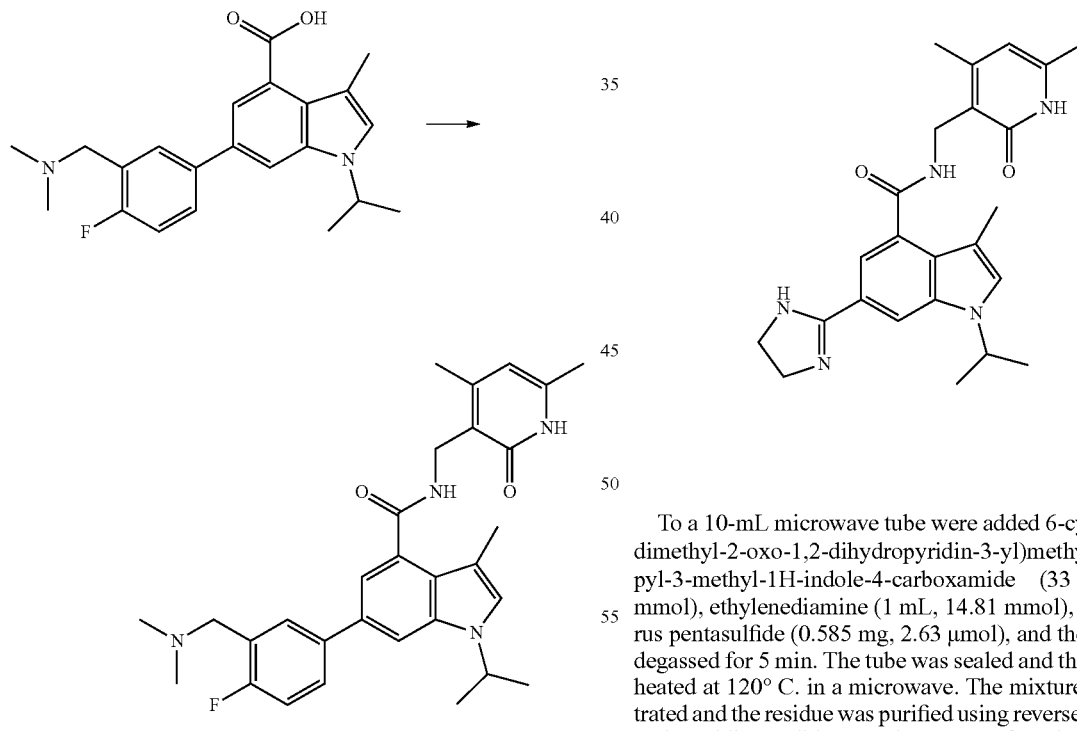

To a 10-mL microwave tube were added 6-cyano-N-((4,6-dimethyl-2-oxo-1,2-dihydropyridin-3-yl)methyl)-1-isopropyl-3-methyl-1H-indole-4-carboxamide (33 mg, 0.088 mmol), ethylenediamine (1 mL, 14.81 mmol), and phosphorus pentasulfide (0.585 mg, 2.63 μmol), and the mixture was degassed for 5 min. The tube was sealed and the mixture was heated at 120° C. in a microwave. The mixture was concentrated and the residue was purified using reverse-phase HPLC under acidic conditions to give 32 mg of product as off-white solid. ¹H NMR (400 MHz, DMSO-d₆) ppm 1.46 (m, 6H), 2.11 (s, 3H), 2.17 (s, 3H), 2.24 (s, 3H), 4.35 (d, J=5.05 Hz, 2H), 4.75 (quin, J=6.69 Hz, 1H), 5.87 (s, 1H), 7.49-7.60 (m, 2H), 8.16-8.26 (m, 2H), 8.39 (s, 1H). MS: (M+H)⁺=419.9.

Examples 358-366 were prepared following the general methods described above and/or well established synthetic procedures:

| Ex | Name | ¹H NMR (400 MHz, DMSO-d₆) δ ppm | MS(ES) [M + H]⁺ | EZH2 pIC50 |
|---|---|---|---|---|
| 358 | [4-({[(4,6-dimethyl-2-oxo-1,2-dihydro-3-pyridinyl)methyl]amino}carbonyl)-3-methyl-1-(1-methylethyl)-1H-indol-6-yl]boronic acid | 11.48 (br. s., 1H), 8.04 (s, 2H), 7.95 (s, 1H), 7.88 (t, J = 5.05 Hz, 1H), 7.40 (s, 1H), 7.31 (s, 1 H), 5.87 (s, 1H), 4.64-4.76 (m, 1H), 4.34 (d, J = 5.05 Hz, 2H), 2.23 (s, 3H), 2.15 (s, 3H), 2.11 (s, 3H), 1.44 (d, J = 6.57 Hz, 6H) | 396.3 | 6.33 |
| 359 | N-[(4,6-dimethyl-2-oxo-1,2-dihydro-3-pyridinyl)methyl]-6-[6-(hydroxymethyl)-3-pyridinyl]-3-methyl-1-(1-methylethyl)-1H-indole-4-carboxamide | 11.51 (br. s., 1 H) 9.01 (br. s., 1 H) 8.55 (br. s., 1 H) 8.23 (t, J = 5.18 Hz, 1 H) 7.99 (s, 1 H) 7.79 (d, J = 8.08 Hz, 1 H) 7.41 (s, 1 H) 7.35 (d, J = 1.26 Hz, 1 H) 5.88 (s, 1 H) 4.86-4.98 (m, 1 H) 4.76 (s, 2 H) 4.36 (d, J = 5.05 Hz, 2 H) 2.25 (s, 3 H) 2.17 (s, 3 H) 2.11 (s, 3 H) 1.45 (d, J = 6.57 Hz, 6 H) | 459.1 | 7.23 |
| 360 | N-[(4,6-dimethyl-2-oxo-1,2-dihydro-3-pyridinyl)methyl]-3-methyl-1-(1-methylethyl)-6-(3-oxetanyl)-1H-indole-4-carboxamide | 1.41 (d, J = 6.57 Hz, 6 H), 2.11 (s, 3 H), 2.14 (s, 3 H), 2.23 (s, 3 H), 4.30-4.39 (m, 3 H), 4.67-4.81 (m, 3 H), 4.96 (dd, J = 8.46, 5.68 Hz, 2 H), 5.87 (s, 1 H), 7.03 (d, J = 1.26 Hz, 1 H), 7.25 (d, J = 1.01 Hz, 1 H), 7.48 (d, J = 1.26 Hz, 1 H), 8.05 (t, J = 5.05 Hz, 1 H), 11.47 (br. s., 1 H). | 408 | 6.54 |
| 361 | N-[(4,6-dimethyl-2-oxo-1,2-dihydro-3-pyridinyl)methyl]-3-methyl-1-(1-methylethyl)-6-{[6-(4-methyl-1-piperazinyl)-3-pyridinyl]amino}-1H-indole-4-carboxamide | 1.36 (m, 6 H), 2.08 (s, 3 H), 2.11 (s, 3 H), 2.21 (s, 3 H), 2.24 (s, 3 H), 2.40-2.47 (m, 4 H), 3.33-3.42 (m, 4 H), 4.30 (d, J = 5.05 Hz, 2 H), 4.47 (quin, J = 6.63 Hz, 1 H), 5.86 (s, 1 H), 6.60 (d, J = 2.02 Hz, 1 H), 6.81 (d, J = 8.84 Hz, 1 H), 6.88 (d, J = 1.77 Hz, 1 H), 7.02 (d, J = 1.01 Hz, 1 H), 7.39 (dd, J = 8.84, 2.78 Hz, 1 H), 7.66 (s, 1 H), 7.95-8.04 (m, 2 H) | 542.1 | 7.26 |

-continued

| Ex | Structure | Name | ¹H NMR (400 MHz, DMSO-d₆) δ ppm | MS(ES) [M + H]⁺ | EZH2 pIC50 |
|---|---|---|---|---|---|
| 362 | 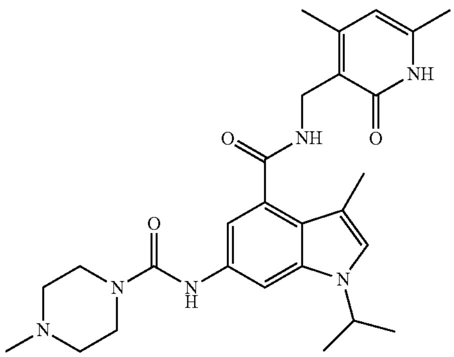 | N-[(4,6-dimethyl-2-oxo-1,2-dihydro-3-pyridinyl)methyl]-3-methyl-1-(1-methylethyl)-6-{[(4-methyl-1-piperazinyl)carbonyl]amino}-1H-indole-4-carboxamide | 1.40 (m, 6 H), 2.11 (s, 6 H), 2.21 (d, J = 9.09 Hz, 6 H), 2.28-2.35 (m, 4 H), 3.40-3.47 (m, 4 H), 4.32 (d, J = 5.31 Hz, 2 H), 4.51 (quin, J = 6.63 Hz, 1 H), 5.87 (s, 1 H), 7.03 (d, J = 1.77 Hz, 1 H), 7.12 (d, J = 1.01 Hz, 1 H), 7.73 (d, J = 1.77 Hz, 1 H), 7.90 (t, J = 5.05 Hz, 1 H), 8.47 (s, 3 H) 11.47 (br. s., 2 H) | 493.3 | 6.89 |
| 363 | 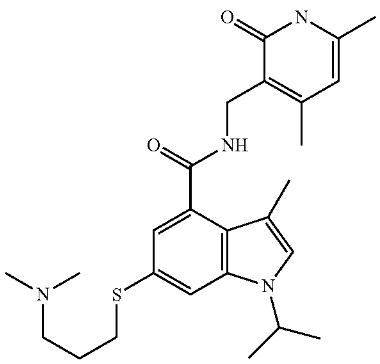 | 6-{[3-(dimethylamino)prop-yl]thio}-N-[(4,6-dimethyl-2-oxo-1,2-dihydro-3-pyridinyl)methyl]-3-methyl-1-(1-methylethyl)-1H-indole-4-carboxamide | 11.47 (s, 1 H), 8.12 (t, J = 5.1 Hz, 1 H), 7.51 (d, J = 1.5 Hz, 1 H), 7.27 (s, 1 H), 6.91 (d, J = 1.3 Hz, 1 H), 5.86 (s, 1 H), 4.74 (m, 1 H), 4.31 (d, J = 5.1 Hz, 2 H), 2.95 (t, J = 7.2 Hz, 2 H), 2.29 (t, J = 7.1 Hz, 2 H), 2.22 (s, 3 H), 2.10 (m, 12 H), 1.65 (quin, J = 7.1 Hz, 2 H), 1.39 (d, J = 6.6 Hz, 6 H) | 469.1 | |
| 364 | 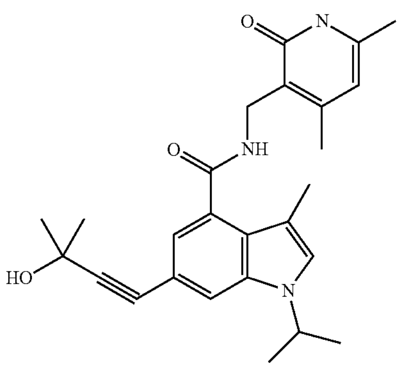 [SMILES: Cc1cc(C)c(CNC(=O)c2cc(C#CC(C)(C)O)cc3c2c(C)cn3C(C)C)c(=O)[nH]1] | N-[(4,6-dimethyl-2-oxo-1,2-dihydro-3-pyridinyl)methyl]-6-(3-hydroxy-3-methyl-1-butyn-1-yl)-3-methyl-1-(1-methylethyl)-1H-indole-4-carboxamide | 11.46 (s, 1 H), 8.16 (t, J = 5.1 Hz, 1 H), 7.54 (d, J = 1.3 Hz, 1 H), 7.37 (s, 1 H), 6.90 (d, J = 1.3 Hz, 1 H), 5.86 (s, 1 H), 5.41 (s, 1 H), 4.75 (m, 1 H), 4.31 (d, J = 5.1 Hz, 2 H), 2.21 (s, 3 H), 2.11 (s, 3 H), 2.14 (s, 3 H), 1.47 (s, 6 H), 1.39 (d, J = 6.6 Hz, 6 H) | 434.0 | |
| 365 | 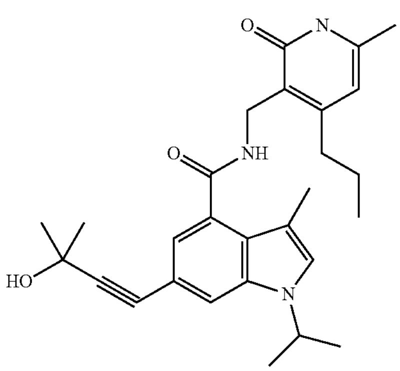 [SMILES: CCCc1cc(C)[nH]c(=O)c1CNC(=O)c1cc(C#CC(C)(C)O)cc2c1c(C)cn2C(C)C] | 6-(3-hydroxy-3-methyl-1-butyn-1-yl)-3-methyl-1-(1-methylethyl)-N-[(6-methyl-2-oxo-4-propyl-1,2-dihydro-3-pyridinyl)methyl]-1H-indole-4-carboxamide | 11.48 (s, 1 H), 8.12 (t, J = 5.1 Hz, 1 H), 7.55 (d, J = 1.3 Hz, 1 H), 7.38 (s, 1 H), 6.90 (d, J = 1.3 Hz, 1 H), 5.89 (s, 1 H), 5.41 (s, 1 H), 4.76 (m, 1 H), 4.32 (d, J = 4.8 Hz, 2 H), 2.54 (s, 1 H), 2.13 (d, J = 9.3 Hz, 6 H), 1.55 (m, 2 H), 1.47 (s, 6 H), 1.40 (m, 6 H), 0.93 (t, J = 7.3 Hz, 3 H) | 462.1 | |

-continued

| Ex | Structure | Name | $^1$H NMR (400 MHz, DMSO-d$_6$) δ ppm | MS(ES) [M + H]$^+$ | EZH2 pIC50 |
|---|---|---|---|---|---|
| 366 | 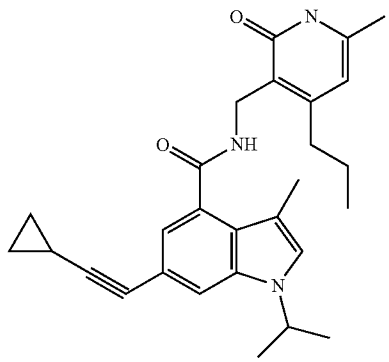 [SMILES: CCCc1cc(C)[nH]c(=O)c1CNC(=O)c1cc(C#CC2CC2)cc2c1c(C)cn2C(C)C] | 6-(cyclopropylethynyl)-3-methyl-1-(1-methylethyl)-N-[(6-methyl-2-oxo-4-propyl-1,2-dihydro-3-pyridinyl)methyl]-1H-indole-4-carboxamide | 11.48 (s, 1 H), 8.09 (t, J = 4.9 Hz, 1 H), 7.54 (d, J = 1.3 Hz, 1 H), 7.35 (s, 1 H), 6.87 (d, J = 1.3 Hz, 1 H), 5.89 (s, 1 H), 4.72 (quin, J = 6.6 Hz, 1 H), 4.31 (d, J = 5.1 Hz, 2 H), 2.13 (d, J = 4.0 Hz, 6 H), 1.54 (m, 3 H), 1.38 (d, J = 6.6 Hz,6H), 0.93 (t, J = 7.3 Hz, 3 H), 0.87 (m, 2 H), 0.71 (m, 2 H) | 444.1 | |

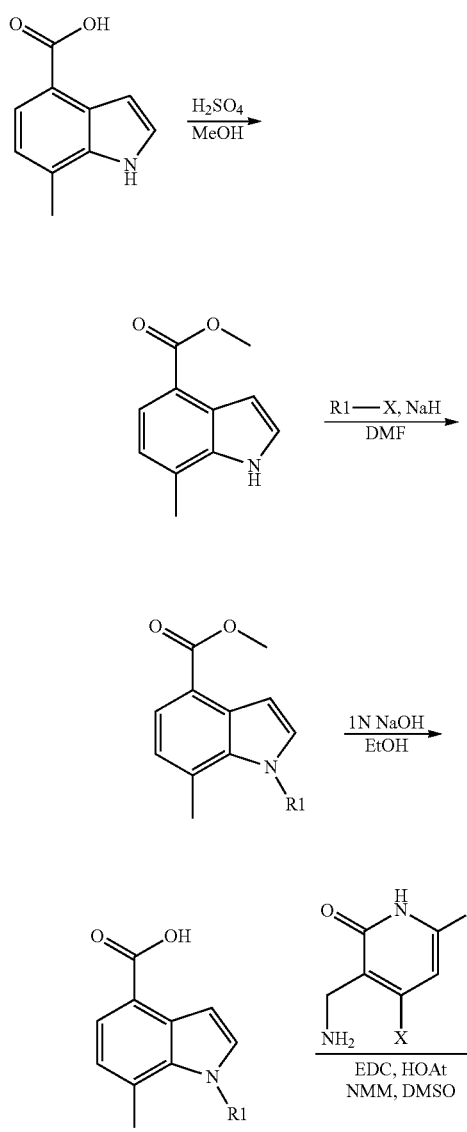

Scheme 6

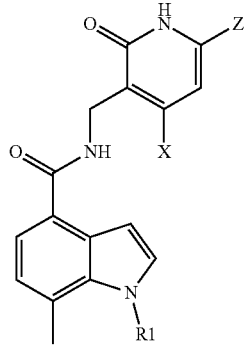

-continued

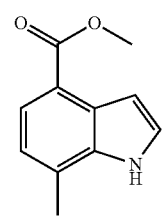

Example 367

N-[(4,6-Dimethyl-2-oxo-1,2-dihydro-3-pyridinyl)methyl]-7-methyl-1-(1-methylethyl)-1H-indole-4-carboxamide a) Methyl 7-methyl-1H-indole-4-carboxylate Under N2 atmosphere, 7-methyl-1H-indole-4-carboxylic acid (1 g, 5.71 mmol), sulfuric acid (300 µL, 5.63 mmol) and methanol (50 mL) were heated at reflux for 10 h. The MeOH was removed in vacuo and the residue dissolved in 30 mL DCM. The solution was washed with water and saturated NaHCO$_3$, dried over MgSO$_4$, filtered and concentrated. The residue was purified by column chromatography (Biotage; 0% to 100% EtOAc:Hex; 25 g-HP-silica gel column) to give the title compound. $^1$H NMR (400 MHz, CHLOROFORM-d)

δ ppm 2.59 (s, 3H), 4.00 (s, 3H), 7.08 (d, J=7.58 Hz, 1H), 7.20-7.26 (m, 1H), 7.38 (t, J=2.78 Hz, 1H), 7.88 (d, J=7.58 Hz, 1H), 8.32 (br. s., 1H).

b) Methyl 7-methyl-1-(1-methylethyl)-1H-indole-4-carboxylate

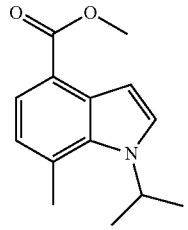 [SMILES: COC(=O)c1ccc(C)c2c1ccn2C(C)C]

A cooled (ice/water bath) solution of methyl methyl 7-methyl-1H-indole-4-carboxylate (260 mg, 1.374 mmol) in DMF (20 mL) was added sodium hydride (43.4 mg, 1.718 mmol). After 10 minutes 2-iodopropane (0.151 mL, 1.512 mmol) was added and the reaction was stirred for 16 h. LCMS showed reaction only 10% complete. Added sodium hydride (43.4 mg, 1.718 mmol) followed by 2-iodopropane (0.151 mL, 1.512 mmol). After 2 hours LCMS showed reaction was 15% compete. Added more sodium hydride (43.4 mg, 1.718 mmol) and let stir for 5 minutes, then added more 2-bromopropane (0.142 mL, 1.512 mmol). Heated to 70° C. for 16 h. LCMS showed reaction 50% complete. Concentrated reaction mixture. Added DCM and washed with water and brine, dried over MgSO$_4$, filtered and concentrated. The residue was purified by column chromatography (Biotage; 0% to 100% DCM:Hex; 25 g-HP-silica gel column) to give 137 mg of the title compound. $^1$H NMR (400 MHz, CHLOROFORM-d) δ ppm 1.48-1.60 (m, 6H), 2.78 (s, 3H), 3.94-4.02 (m, 3H), 5.17 (dt, J=13.20, 6.66 Hz, 1H), 6.96 (d, J=7.83 Hz, 1H), 7.28 1H, 7.40 (d, J=3.28 Hz, 1H), 7.81 (d, J=7.58 Hz, 1H). MS(ES) [M+H]$^+$ 232.1 c) 7-Methyl-1-(1-methylethyl)-1H-indole-4-carboxylic acid

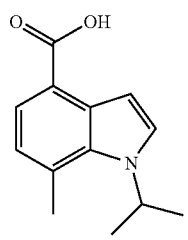 [SMILES: Cc1ccc(C(=O)O)c2ccn(C(C)C)c12]

To a solution of methyl 7-methyl-1-(1-methylethyl)-1H-indole-4-carboxylate (137 mg, 0.592 mmol) in ethanol (30 mL) was added 1N sodium hydroxide (2.369 mL, 2.369 mmol). The mixture was heated at reflux for 2 h, at which time it was concentrated. The residue was dissolved in water (20 mL) and acidified by addition of 1N HCl. The mixture was extracted with DCM (4×30 mL) and the combined extracts and washed with water and brine, dried over MgSO$_4$, filtered and concentrated to give 104 mg of the title compound. $^1$H NMR (400 MHz, CHLOROFORM-d) δ ppm 1.55 (d, 6H), 2.82 (s, 3H), 5.11-5.28 (m, 1H), 7.00 (d, J=7.83 Hz, 1H), 7.31 (d, J=3.54 Hz, 1H), 7.44 (d, J=3.28 Hz, 1H), 7.89 (d, J=7.58 Hz, 1H). MS(ES) [M+H]$^+$ 218.3.

d) N-[(4,6-Dimethyl-2-oxo-1,2-dihydro-3-pyridinyl)methyl]-7-methyl-1-(1-methylethyl)-1H-indole-4-carboxamide

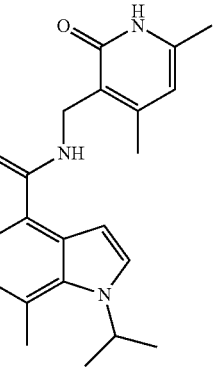

Added 7-methyl-1-(1-methylethyl)-1H-indole-4-carboxylic acid (52 mg, 0.239 mmol), 3-(aminomethyl)-4,6-dimethyl-2(1H)-pyridinone (56.4 mg, 0.299 mmol), 1-hydroxy-7-azabenzotriazole (65.2 mg, 0.479 mmol), EDC (92 mg, 0.479 mmol) and N-methylmorpholine (0.105 mL, 0.957 mmol) to Dimethyl Sulfoxide (DMSO) (10 mL) and stirred at RT for 16 h. Added 25 ml of water and let stir for 10 minutes. Filtered off solids. Dissolved solids in DCM, washed with water, dried over MgSO$_4$, filtered and concentrated. The residue was purified by column chromatography (Biotage; 0% to 20% gradient MeOH:DCM; 10 g-HP-silica gel column) to give 55 mg of N-[(4,6-Dimethyl-2-oxo-1,2-dihydro-3-pyridinyl)methyl]-7-methyl-1-(1-methylethyl)-1H-indole-4-carboxamide. $^1$H NMR (400 MHz, CHLOROFORM-d) δ ppm 1.49 (d, 6H), 2.24 (s, 3H), 2.44 (s, 3H), 2.75 (s, 3H), 4.63 (d, J=4.55 Hz, 2H), 5.17 (dt, J=13.20, 6.66 Hz, 1H), 5.97 (s, 1H), 6.91 (d, J=7.58 Hz, 1H), 7.01 (d, J=3.54 Hz, 1H), 7.29 (d, J=3.28 Hz, 1H), 7.39 (d, J=7.33 Hz, 1H), 7.69 (br. s., 1H), 12.59 (br. s., 1H). MS(ES) [M+H]$^+$ 352.4.

Example 368

7-Methyl-1-(1-methylethyl)-N-[(6-methyl-2-oxo-4-propyl-1,2-dihydro-3-pyridinyl)methyl]-1H-indole-4-carboxamide

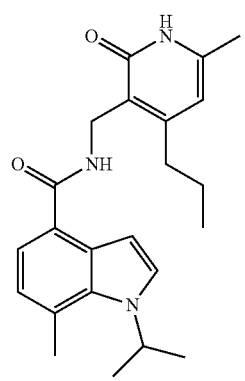 [SMILES: CCCc1cc(C)[nH]c(=O)c1CNC(=O)c1ccc(C)c2c1ccn2C(C)C]

7-Methyl-1-(1-methylethyl)-N-[(6-methyl-2-oxo-4-propyl-1,2-dihydro-3-pyridinyl)methyl]-1H-indole-4-carboxamide was prepared following the procedure of Example 367. ¹H NMR (400 MHz, CHLOROFORM-d) δ ppm 0.95-1.07 (m, 3H), 1.50 (d, J=6.57 Hz, 6H), 1.63 (qt, J=7.56, 7.36 Hz, 2H), 2.27 (s, 3H), 2.68-2.82 (m, 5H), 4.64 (d, J=2.53 Hz, 2H), 5.17 (dq, J=6.82, 6.65 Hz, 1H), 6.04 (s, 1H), 6.91 (d, J=7.58 Hz, 1H), 7.00 (d, J=3.54 Hz, 1H), 7.31 (d, J=3.54 Hz, 1H), 7.39 (d, J=7.33 Hz, 1H), 7.64 (br. s., 1H), 12.13 (br. s., 1H). MS(ES) [M+H]⁺ 380.2.

Scheme 7

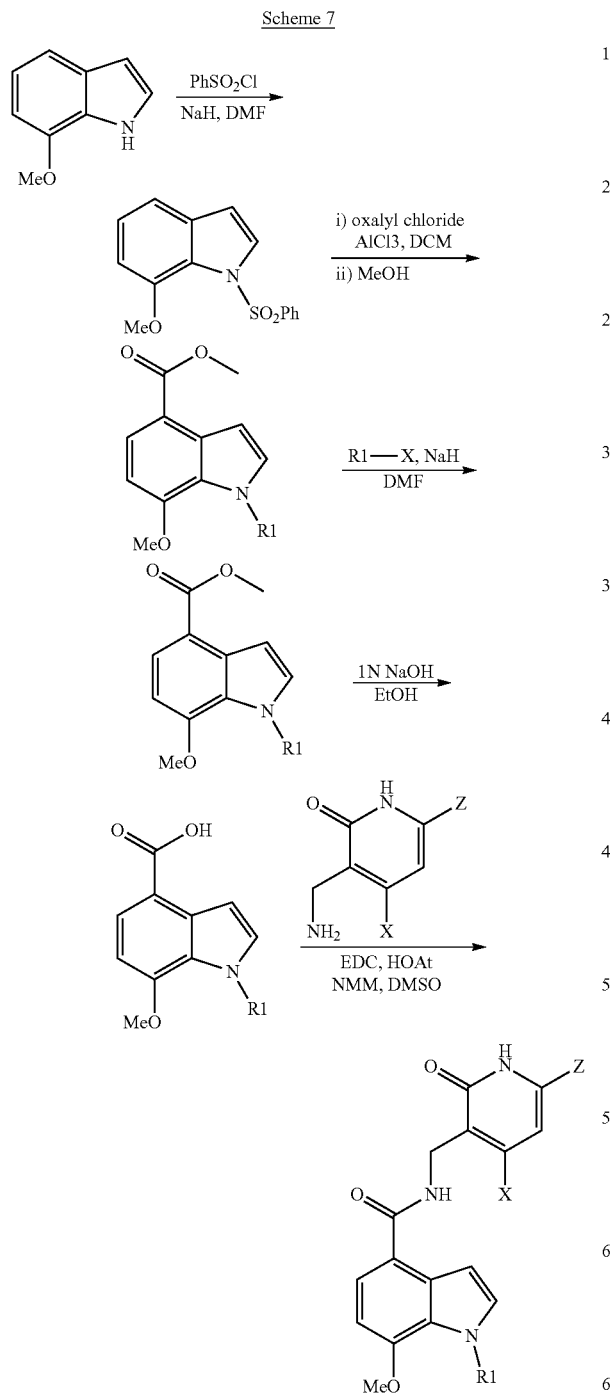

Example 369

1-(1-Methylethyl)-N-[(6-methyl-2-oxo-4-propyl-1,2-dihydro-3-pyridinyl)methyl]-7-(methyloxy)-1H-indole-4-carboxamide

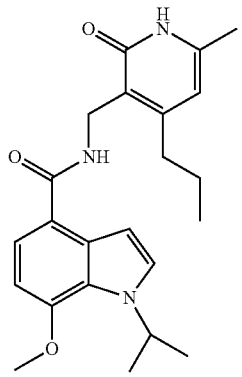

a) 7-(Methyloxy)-1-(phenylsulfonyl)-1H-indole

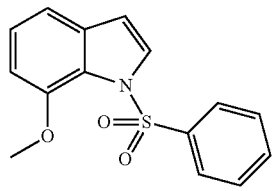 [SMILES: COc1cccc2ccn(S(=O)(=O)c3ccccc3)c12]

To a cooled (ice water bath) solution of 7-(methyloxy)-1H-indole (3 g, 20.38 mmol) in DMF (100 mL) was added sodium hydride (0.618 g, 24.46 mmol) portionwise. After 15 minutes a solution of benzenesulfonyl chloride (3.94 mL, 30.6 mmol) in 20 ml of DMF was added dropwise. The reaction mixture was stirred at RT for 24 h, at which time it was concentrated. The residue was dissolved in DCM (100 ml) and washed with water and brine, dried over MgSO₄, filtered and concentrated. The residue was purified by column chromatography (Biotage; 0% to 100% DCM:Hex; 50 g-HP-silica gel column) to give 3.65 g of the title compound. ¹H NMR (400 MHz, CHLOROFORM-d) δ ppm 3.65 (s, 3H), 6.60-6.75 (m, 2H), 7.08-7.22 (m, 2H), 7.40-7.62 (m, 3H), 7.77-7.92 (m, 3H). MS(ES) [M+H]⁺ 288.0.

b) Methyl 7-(methyloxy)-1-(phenylsulfonyl)-1H-indole-4-carboxylate

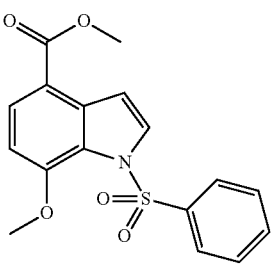 [SMILES: COC(=O)c1ccc(OC)c2c1ccn2S(=O)(=O)c1ccccc1]

To a cooled (0° C.) suspension of aluminium chloride (8.47 g, 63.5 mmol) in DCM (100 mL) was added oxalyl chloride (5.56 mL, 63.5 mmol) dropwise. After stirring for 30 minutes a solution of 7-(methyloxy)-1-(phenylsulfonyl)-1H-indole (3.65 g, 12.70 mmol) in DCM (15 ml) was added dropwise. The reaction was stirred at RT for 1 h, at which time it was poured into brine and extracted with DCM. The DCM extracts were dried over MgSO$_4$, filtered, and evaporated to dryness. Added 100 ml of MeOH to the residue and heated at reflux for 3 h. The mixture was concentrated and the residue purified by column chromatography (Biotage; 0% to 100% DCM:Hex; 50 g-HP-silica gel column) to give 2.3 g of the title compound. $^1$H NMR (400 MHz, CHLOROFORM-d) δ ppm 3.70 (s, 3H), 3.95 (s, 3H), 6.67 (d, J=8.59 Hz, 1H), 7.41 (d, J=3.79 Hz, 1H), 7.46-7.53 (m, 2H), 7.54-7.62 (m, 1H), 7.79-7.86 (m, 2H), 7.94 (d, J=8.59 Hz, 1H), 7.98 (d, J=3.54 Hz, 1H). MS(ES) [M+H]$^+$ 346.0.

c) Methyl 1-(1-methylethyl)-7-(methyloxy)-1H-indole-4-carboxylate

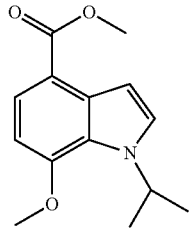 [SMILES: COC(=O)c1ccc(OC)c2c1ccn2C(C)C]

To a cooled (ice/water bath) solution of methyl 7-(methyloxy)-1H-indole-4-carboxylate (350 mg, 1.706 mmol) in DMF (20 mL) was added sodium hydride (56.0 mg, 2.217 mmol). After 10 minutes added 2-iodopropane (0.188 mL, 1.876 mmol). The reaction was stirred at RT for 1 h, followed by heating at 50° C. for 2 h. The reaction was then cooled in an ice water bath and more sodium hydride (56.0 mg, 2.217 mmol) and 2-iodopropane (0.188 mL, 1.876 mmol) were added. The reaction was heated at 50° C. for 3 h, at which time it was concentrated. The residue was dissolved in DCM and washed with water and brine, dried over MgSO$_4$, filtered and concentrated to give 400 mg of the title compound. $^1$H NMR (400 MHz, CHLOROFORM-d) δ ppm 1.49 (d, 6H), 3.95 (s, 3H), 4.01 (s, 3H), 5.46 (dt, J=13.39, 6.69 Hz, 1H), 6.66 (d, J=8.34 Hz, 1H), 7.15 (d, J=3.03 Hz, 1H), 7.34 (d, J=3.28 Hz, 1H), 7.87 (d, J=8.34 Hz, 1H). MS(ES) [M+H]$^+$248.2.

d) 1-(1-Methylethyl)-7-(methyloxy)-1H-indole-4-carboxylic acid

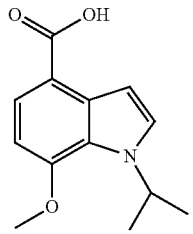 [SMILES: COc1ccc(C(=O)O)c2ccn(C(C)C)c12]

Added 1N sodium hydroxide (6.47 mL, 6.47 mmol) to a solution of methyl 1-(1-methylethyl)-7-(methyloxy)-1H-indole-4-carboxylate (400 mg, 1.618 mmol) in ethanol (30 mL) and heated at reflux for 3 h. The EtOH was removed in vacuo and the residue dissolved in 20 ml of water. Acidified solution by addition of 1N HCl and extracted with DCM. the combined DCM extracts were washed with water and brine, dried over MgSO$_4$, filtered and concentrated to give 350 mg of the title compound. $^1$H NMR (400 MHz, CHLOROFORM-d) δ ppm 1.51 (d, 6H), 4.03 (s, 3H), 5.47 (dt, J=13.39, 6.69 Hz, 2H), 6.70 (d, J=8.34 Hz, 2H), 7.23 (d, J=3.28 Hz, 2H), 7.37 (d, J=3.03 Hz, 2H), 7.99 (d, J=8.34 Hz, 2H). MS(ES) [M+H]$^+$ 234.0.

e) 1-(1-Methylethyl)-N-[(6-methyl-2-oxo-4-propyl-1,2-dihydro-3-pyridinyl)methyl]-7-(methyloxy)-1H-indole-4-carboxamide

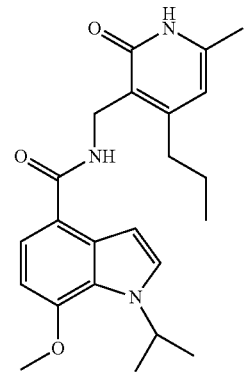 [SMILES: CCCc1cc(C)[nH]c(=O)c1CNC(=O)c1ccc(OC)c2c1ccn2C(C)C]

Added 1-(1-methylethyl)-7-(methyloxy)-1H-indole-4-carboxylic acid (160 mg, 0.686 mmol), 3-(aminomethyl)-6-methyl-4-propyl-2(1H)-pyridinone (186 mg, 0.857 mmol), 1-hydroxy-7-azabenzotriazole (187 mg, 1.372 mmol), EDC (263 mg, 1.372 mmol) and N-methylmorpholine (0.302 mL, 2.74 mmol) to DMSO (10 mL) and stirred mixture at RT for 16 h. Added 25 ml of water and stirred for 10 minutes. Filtered off solids and dried in vacuo. The solids were purified by column chromatography (Biotage; 0% to 15% gradient MeOH:DCM; 10 g-HP-silica gel column) to give 165 mg of 1-(1-methylethyl)-N-[(6-methyl-2-oxo-4-propyl-1,2-dihydro-3-pyridinyl)methyl]-7-(methyloxy)-1H-indole-4-carboxamide. $^1$H NMR (400 MHz, CHLOROFORM-d) δ ppm 1.01 (t, 3H), 1.45 (d, J=6.57 Hz, 6H), 1.63 (m, J=7.45, 7.45, 7.45, 7.45, 7.33 Hz, 2H), 2.24 (s, 3H), 2.74 (t, J=7.58 Hz, 2H), 3.96 (s, 3H), 4.64 (br. s., 2H), 5.45 (quin, J=6.63 Hz, 1H), 5.97 (s, 1H), 6.62 (d, J=8.08 Hz, 1H), 6.94 (d, J=3.28 Hz, 1H), 7.24 (d, J=3.28 Hz, 1H), 7.53 (d, J=8.08 Hz, 1H), 7.74 (br. s., 1H), 12.46 (br. s., 1H). MS(ES) [M+H]$^+$ 395.7.

Example 370

N-[(4,6-Dimethyl-2-oxo-1,2-dihydro-3-pyridinyl)methyl]-1-(1-methylethyl)-7-(methyloxy)-1H-indole-4-carboxamide

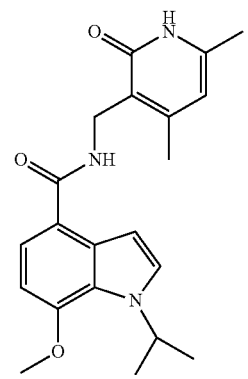 [SMILES: COc1ccc(C(=O)NCc2c(C)cc(C)[nH]c2=O)c2ccn(C(C)C)c12]

N-[(4,6-Dimethyl-2-oxo-1,2-dihydro-3-pyridinyl)methyl]-1-(1-methylethyl)-7-(methyloxy)-1H-indole-4-carboxamide was prepared following the procedure of Example 369. $^1$H NMR (400 MHz, CHLOROFORM-d) δ ppm 1.45 (d, 6H), 2.21 (s, 3H), 2.43 (s, 3H), 3.96 (s, 3H), 4.63 (d, J=5.56 Hz, 2H), 5.35-5.57 (m, 1H), 5.94 (s, 1H), 6.61 (d, J=8.34 Hz, 1H), 6.94 (d, J=3.28 Hz, 1H), 7.23 (d, J=3.03 Hz, 1H), 7.52 (d, J=8.08 Hz, 1H), 7.66 (br. s., 1H), 12.73 (br. s., 1H). MS(ES) [M+H]$^+$ 368.1.

Example 371

6-chloro-1-isopropyl-2,3-dimethyl-N-((6-methyl-2-oxo-4-propyl-1,2-dihydropyridin-3-yl)methyl)-1H-indole-4-carboxamide

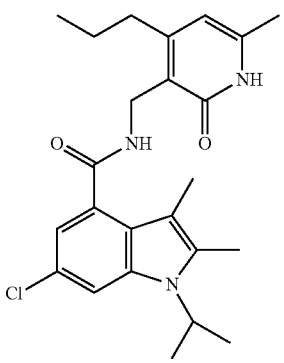 [SMILES: CCCc1cc(C)[nH]c(=O)c1CNC(=O)c1cc(Cl)cc2c1c(C)c(C)n2C(C)C]

a) Methyl 6-chloro-1-isopropyl-2,3-dimethyl-1H-indole-4-carboxylate

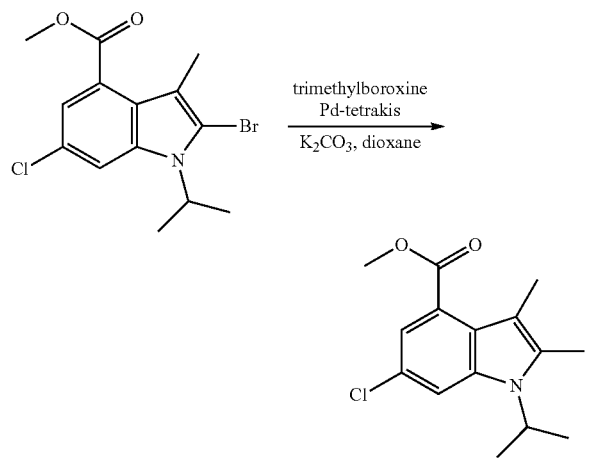

To a stirred solution of methyl 2-bromo-6-chloro-1-isopropyl-3-methyl-1H-indole-4-carboxylate (0.50 g, 1.451 mmol), Trimethylboroxine (0.30 mL, 2.146 mmol) and potassium carbonate (0.31 g, 2.243 mmol) in 1,4-Dioxane (20 mL) under N$_2$ was added palladium tetrakis (0.18 g, 0.156 mmol). The reaction was heated to 110° C. and stirred for 18 hr. After 3 hr an additional 100 uL Trimethylboroxine was added. The reaction was concentrated under vacuum, taken up in EtOAc, washed with water, dried (MgSO$_4$), filtered and concentrated under vacuum. Purification by silica gel chromatography (Analogix, SF25-60g, 0 to 10% EtOAc in hexanes) gave the product methyl 6-chloro-1-isopropyl-2,3-dimethyl-1H-indole-4-carboxylate (0.33 g, 1.180 mmol, 81% yield) as a clear thick oil. $^1$H NMR (400 MHz, DMSO-d$_6$) δ=7.80 (d, J=2.0 Hz, 1H), 7.28 (d, J=1.8 Hz, 1H), 4.81 (dt, J=6.9, 13.9 Hz, 1H), 3.87 (s, 3H), 2.39 (s, 3H), 2.13 (s, 3H), 1.51 (d, J=7.1 Hz, 6H) MS(ES)+ m/e 280.1 [M+H]$^+$.

b) 6-Chloro-1-isopropyl-2,3-dimethyl-N-((6-methyl-2-oxo-4-propyl-1,2-dihydropyridin-3-yl)methyl)-1H-indole-4-carboxamide

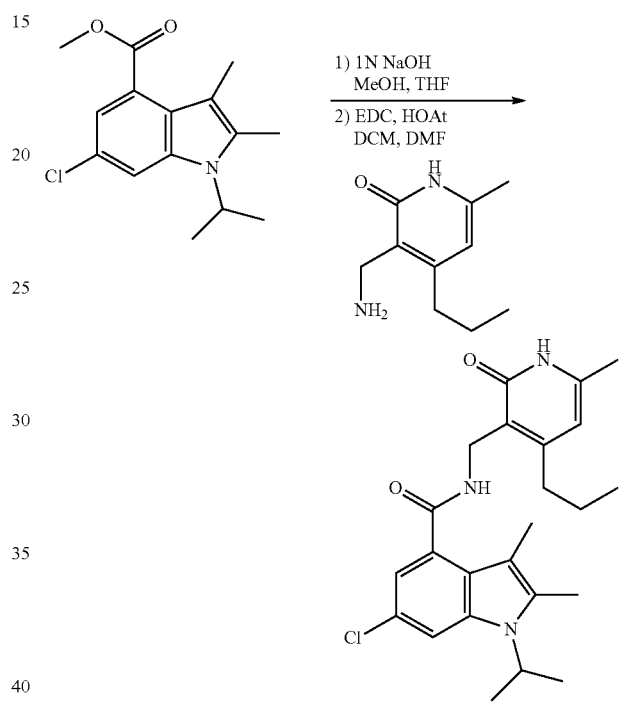

To a stirred solution of methyl 6-chloro-1-isopropyl-2,3-dimethyl-1H-indole-4-carboxylate (320 mg, 1.144 mmol) in Methanol (12 mL) and Tetrahydrofuran (THF) (4 mL) was added 1N NaOH (4 mL, 4.00 mmol). The reaction was refluxed (70° C. oil bath) for 18 h. The reaction was concentrated under vacuum, diluted with water, acidified with 1N HCl (4 mL), filtered, washed with water and dried under vacuum to give the carboxylic acid (0.30 g, 1.14 mmol, 100%) as a light yellow solid. MS(ES)+ m/e 266.1 [M+H]$^+$.

To the carboxylic acid above was added 3-(aminomethyl)-6-methyl-4-propylpyridin-2(1H)-one (230 mg, 1.276 mmol), HOAt (160 mg, 1.176 mmol), Dichloromethane (12 mL) and N,N-Dimethylformamide (4.00 mL) to dissolve. With stirring was added EDC free base (210 mg, 1.353 mmol) and the reaction stirred at RT for 3 hr. LCMS showed that the reaction was complete. The reaction was evaporated to dryness under vacuum then purified by silica gel chromatography (SF25-40g, 50 to 100% EtOAc in CH$_2$Cl$_2$) (streaked off). The pure fractions were combined and evaporated under vacuum. The remaining solid was triturated with 25% CH$_2$Cl$_2$ in hexanes, filtered, washed with hexanes and dried under vacuum to give the product 6-chloro-1-isopropyl-2,3-dimethyl-N-((6-methyl-2-oxo-4-propyl-1,2-dihydropyridin-3-yl)methyl)-1H-indole-4-carboxamide (431 mg, 1.007 mmol, 88% yield) as an off-white solid. $^1$H NMR (400 MHz, DMSO-d$_6$) δ=11.49

(s, 1H), 8.16 (t, J=5.1 Hz, 1H), 7.58 (d, J=1.8 Hz, 1H), 6.82 (d, J=1.8 Hz, 1H), 5.89 (s, 1H), 4.75 (dt, J=6.9, 13.9 Hz, 1H), 4.31 (d, J=5.1 Hz, 2H), 2.52 (2H under DMSO), 2.33 (s, 3H), 2.12 (s, 3H), 2.04 (s, 3H), 1.61-1.51 (m, 2H), 1.49 (d, J=6.8 Hz, 6H), 0.94 (t, J=7.3 Hz, 3H). MS(ES)+ m/e 428.3 [M+H]+.

Example 372

6-Chloro-2-((dimethylamino)methyl)-1-isopropyl-3-methyl-N-((6-methyl-2-oxo-4-propyl-1,2-dihydropyridin-3-yl)methyl)-1H-indole-4-carboxamide

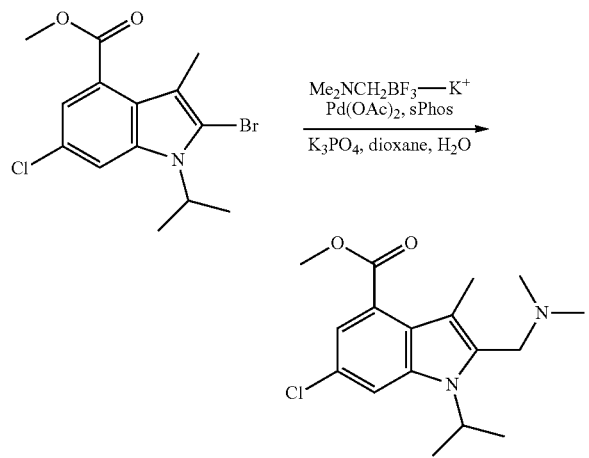

a) Methyl 6-chloro-2-((dimethylamino)methyl)-1-isopropyl-3-methyl-1H-indole-4-carboxylate

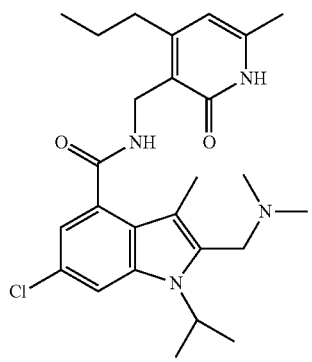 [SMILES: CCCc1cc(C)[nH]c(=O)c1CNC(=O)c1cc(Cl)cc2c1c(C)c(CN(C)C)n2C(C)C]

To a stirred mixture of methyl 2-bromo-6-chloro-1-isopropyl-3-methyl-1H-indole-4-carboxylate (1.0 g, 2.90 mmol), potassium ((dimethylamino)methyl)trifluoroborate (0.5 g, 3.03 mmol) and Potassium phosphate (1.9 g, 8.95 mmol) (purged with N₂)) in dioxane (3 mL) and water (3 mL) was added palladium(II) acetate (25 mg, 0.111 mmol) and sPhos (90 mg, 0.219 mmol). The reaction was heated to 100° C. and stirred for 18 hr under N₂. LCMS showed that the reaction was complete. The reaction was diluted with EtOAc and water, and filtered to remove insolubles. The EtOAc phase was removed, dried (Na₂SO₄), filtered, and concentrated under vacuum. The crude was purified by silica gel chromatography (Analogix, SF25-40g, 0 to 2% (5% NH₄OH/MeOH) in CH₂Cl₂). The product fractions were combined, evaporated to dryness under vacuum to give the product methyl 6-chloro-2-((dimethylamino)methyl)-1-isopropyl-3-methyl-1H-indole-4-carboxylate (0.45 g, 1.394 mmol, 48.0% yield) as a light yellow oil (Only 84% pure by LCMS). This was used as is in the next reaction. ¹H NMR (400 MHz, DMSO-d₆) δ=7.82 (d, J=1.8 Hz, 1H), 7.28 (d, J=1.8 Hz, 1H), 4.96 (dt, J=7.1, 14.1 Hz, 1H), 3.88 (s, 3H), 3.52 (s, 2H), 2.17 (s, 3H), 2.16 (s, 6H), 1.53 (d, J=7.1 Hz, 6H). MS(ES)+ m/e 323.2 [M+H]+, 278.1 [M+H]+ −45 (HNMe₂).

b) 6-Chloro-2-((dimethylamino)methyl)-1-isopropyl-3-methyl-1H-indole-4-carboxylic acid hydrochloride salt

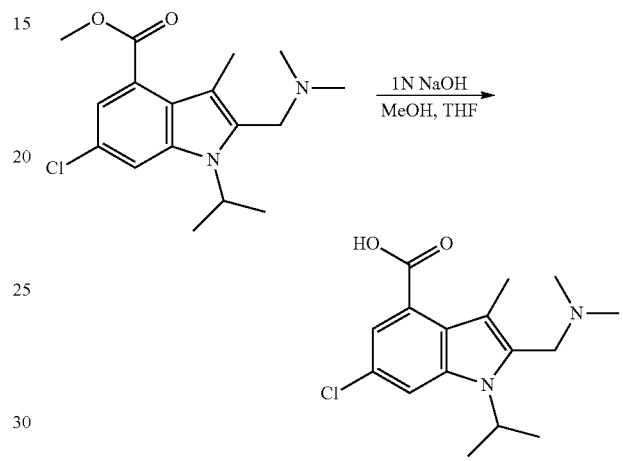

To methyl 6-chloro-2-((dimethylamino)methyl)-1-isopropyl-3-methyl-1H-indole-4-carboxylate (0.44 g, 1.363 mmol) was added 6N HCl (20 ml, 120 mmol). The reaction was purged with N₂, attached a reflux condensor, heated to 80° C., and stirred for 18 hr. LCMS showed that the reaction was complete. The reaction was cooled to RT, diluted with an equal volume of water, washed with EtOAc, and evaporated to dryness under vacuum to give the product 6-chloro-2-((dimethylamino)methyl)-1-isopropyl-3-methyl-1H-indole-4-carboxylic acid hydrochloride salt (0.42 g, 1.216 mmol, 89% yield) as a beige solid. (86% pure by LCMS, contains ~10% of the des-chloro side product from the previous reaction.) Used as is in the next step. ¹H NMR (400 MHz, DMSO-d₆) δ=13.19 (br. s., 1H), 10.45 (br. s., 1H), 7.90 (d, J=1.8 Hz, 1H), 7.33 (d, J=1.8 Hz, 1H), 4.91 (quin, J=6.9 Hz, 1H), 4.58 (d, J=5.6 Hz, 2H), 2.79 (d, J=4.8 Hz, 6H), 2.34 (s, 3H), 1.58 (d, J=6.8 Hz, 6H). MS(ES)+ m/e 309.2 [M+H]+, 264.1 [M+H]+ −45 (HNMe₂).

c) 6-Chloro-2-((dimethylamino)methyl)-1-isopropyl-3-methyl-N-((6-methyl-2-oxo-4-propyl-1,2-dihydropyridin-3-yl)methyl)-1H-indole-4-carboxamide

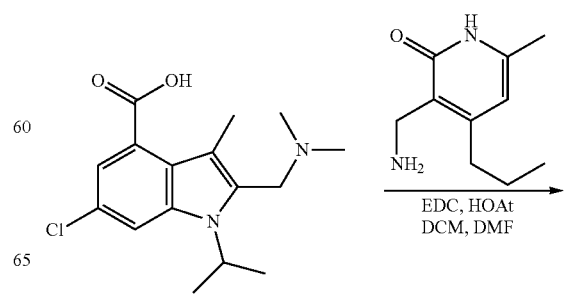

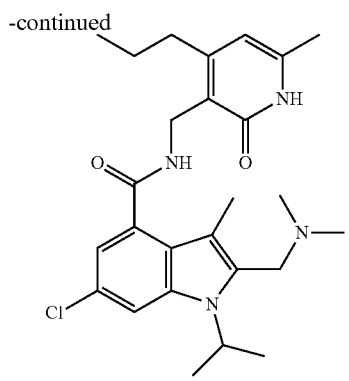

To 6-chloro-2-((dimethylamino)methyl)-1-isopropyl-3-methyl-1H-indole-4-carboxylic acid hydrochloride salt (0.42 g, 1.216 mmol), 3-(aminomethyl)-6-methyl-4-propylpyridin-2(1H)-one (0.22 g, 1.221 mmol), HOAt (0.17 g, 1.249 mmol) was added Dichloromethane (16 mL), N,N-Dimethylformamide (4 mL) and N-methylmorpholine (135 µL, 1.228 mmol). The mixture was stirred and EDC free base (0.20 g, 1.288 mmol) was added. After stirring for 2 hr LCMS showed that the reaction was complete. The reaction was evaporated to dryness under vacuum and purified by silica gel chromatography (Analogix, SF25-60g, 0 to 8% (5% NH$_4$OH in MeOH) in CH$_2$Cl$_2$). The pure fractions were combined, evaporated to dryness then taken up in 20% EtOAc in hexanes. Scratching crystallized out the product which was filtered and washed with hexanes to give the product 6-chloro-2-((dimethylamino)methyl)-1-isopropyl-3-methyl-N-((6-methyl-2-oxo-4-propyl-1,2-dihydropyridin-3-yl)methyl)-1H-indole-4-carboxamide (362 mg, 0.769 mmol, 63.2% yield) as an off-white solid. $^1$H NMR (400 MHz, DMSO-d$_6$) δ=11.49 (s, 1H), 8.24 (t, J=4.9 Hz, 1H), 7.61 (d, J=1.8 Hz, 1H), 6.83 (d, J=1.8 Hz, 1H), 5.89 (s, 1H), 4.91 (quin, J=7.0 Hz, 1H), 4.31 (d, J=5.1 Hz, 2H), 3.47 (s, 2H), 2.52 (2H under DMSO), 2.14 (s, 6H), 2.12 (s, 3H), 2.10 (s, 3H), 1.62-1.53 (m, 2H), 1.51 (d, J=7.1 Hz, 6H), 0.94 (t, J=7.3 Hz, 3H). MS(ES)+ m/e 471.3 [M+H]$^+$.

Example 373

2-(2-Aminoethyl)-6-chloro-1-isopropyl-3-methyl-N-((6-methyl-2-oxo-4-propyl-1,2-dihydropyridin-3-yl)methyl)-1H-indole-4-carboxamide

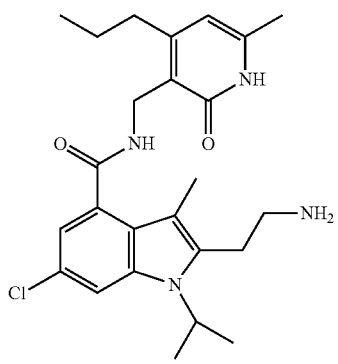 [SMILES: CCCc1cc(C)[nH]c(=O)c1CNC(=O)c1cc(Cl)cc2c1c(C)c(CCN)n2C(C)C]

a) Methyl 2-(2-((tert-butoxycarbonyl)amino)ethyl)-6-chloro-1-isopropyl-3-methyl-1H-indole-4-carboxylate

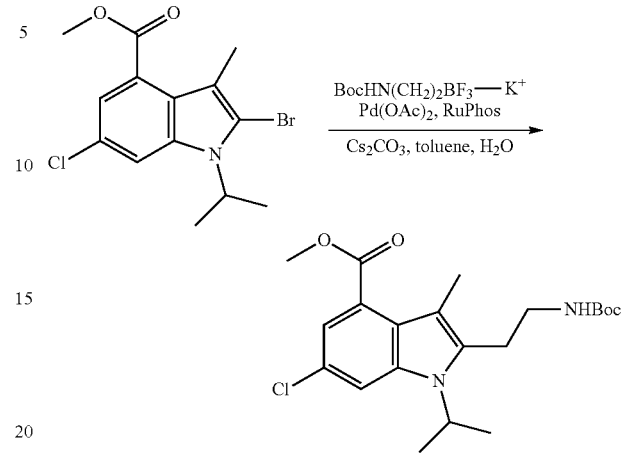

To a stirred mixture of methyl 2-bromo-6-chloro-1-isopropyl-3-methyl-1H-indole-4-carboxylate (0.37 g, 1.074 mmol), potassium (2-((tert-butoxycarbonyl)amino)ethyl)trifluoroborate (0.30 g, 1.195 mmol) and Cs$_2$CO$_3$ (1.0 g, 3.07 mmol) (purged with N$_2$) in toluene (12 mL) and water (4 mL) was added palladium(II) acetate (20 mg, 0.089 mmol) and RuPhos (80 mg, 0.171 mmol). The reaction was heated to 95° C. and stirred for 18 hr under N$_2$. LCMS still showed SM. Another portion of palladium(II) acetate (20 mg, 0.089 mmol) and RuPhos (80 mg, 0.171 mmol) was added and the reaction stirred at 95° C. for another 18 hr. LCMS showed that the reaction was now mostly done. The reaction was diluted with EtOAc and water, and filtered to remove insolubles. The EtOAc phase was removed, dried (MgSO$_4$), filtered, and concentrated under vacuum. The crude was purified by silica gel chromatography (Analogix, SF25-60g, 0 to 25% EtOAc in hexanes). Three fractions were collected. The first fraction contained a significant amount of the desbromo product, the second fraction was a mixture of unknowns, and the last fraction contained product (Note; opposite order from the TLC). The product fractions were combined, evaporated to dryness under vacuum, triturated with hexanes, filtered and dried under vacuum to give the product methyl 2-(2-((tert-butoxycarbonyl)amino)ethyl)-6-chloro-1-isopropyl-3-methyl-1H-indole-4-carboxylate (148 mg, 0.362 mmol, 33.7% yield) as a white solid. $^1$H NMR (400 MHz, DMSO-d$_6$) δ=7.81 (d, J=1.5 Hz, 1H), 7.28 (d, J=1.8 Hz, 1H), 7.00 (t, J=5.6 Hz, 1H), 3.87 (s, 3H), 3.07 (q, J=6.7 Hz, 2H), 2.97-2.85 (m, 2H), 2.13 (s, 3H), 1.56 (d, J=7.1 Hz, 6H), 1.36 (s, 9H). MS(ES)+ m/e 409.2 [M+H]$^+$.

b) 2-(2-Aminoethyl)-6-chloro-1-isopropyl-3-methyl-N-((6-methyl-2-oxo-4-propyl-1,2-dihydropyridin-3-yl)methyl)-1H-indole-4-carboxamide

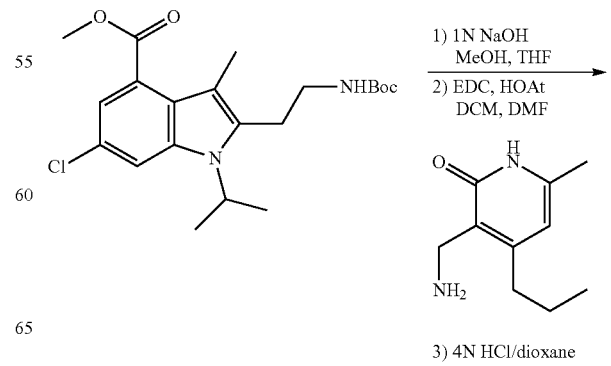

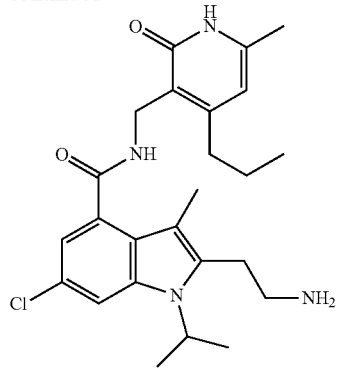

3-Methyl-1H-indole-4-carboxylate (140 mg, 0.342 mmol) in Methanol (9 mL) and Tetrahydrofuran (3 mL) was added 1N NaOH (2 mL, 2.000 mmol). The reaction was refluxed (70° C. oil bath) for 18 h (reaction proceeded very slowly at 60° C. with only 1 mL 1N NaOH). The reaction was concentrated under vacuum, diluted with water, acidified with 1N HCl (2 mL), filtered, washed with water and dried under vacuum to give the carboxylic acid (0.14 g, 0.354 mmol, 100%) as a white solid. MS(ES)+ m/e 395.0 [M+H]$^+$.

To the carboxylic acid above was added 3-(aminomethyl)-6-methyl-4-propylpyridin-2(1H)-one (80 mg, 0.444 mmol), HOAt (60 mg, 0.441 mmol), Dichloromethane (12 mL) and N,N-Dimethylformamide (3.00 mL) to dissolve. With stirring was added EDC free base (70 mg, 0.451 mmol) and the reaction stirred at RT overnight. LCMS showed that the reaction was complete. The reaction was evaporated to dryness under vacuum then purified by silica gel chromatography (SF25-40g, 50 to 100% EtOAc in CH$_2$Cl$_2$) to give the Boc protected final product (0.20 g, 3.59 mmol, 100%) as a white solid. MS(ES)+ m/e 557.3 [M+H]$^+$.

The above was dissolved with MeOH (5 mL) then treated, while stirring, with a solution of 4N HCl in dioxane (10 mL, 40.0 mmol). The reaction was stirred for 30 minutes then evaporated to dryness under vacuum. The solid was triturated with Et$_2$O, filtered, washed with hexanes and dried under vacuum to give the product 2-(2-aminoethyl)-6-chloro-1-isopropyl-3-methyl-N-((6-methyl-2-oxo-4-propyl-1,2-dihydropyridin-3-yl)methyl)-1H-indole-4-carboxamide hydrochloride salt (161 mg, 0.326 mmol, 95% yield) as a light yellow solid. MS(ES)+ m/e 457.2 [M+H]$^+$.

INTERMEDIATES

Intermediate 1

3-(Aminomethyl)-4,6-dimethyl-2(1H)-pyridinone hydrochloride

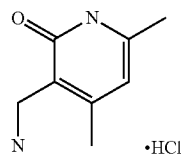

Palladium on carbon (10%) (3.24 g) was charged into a 2L dry Parr bottle and a small amount of acetic acid was added. Next added 4,6-dimethyl-2-oxo-1,2-dihydro-pyridine-3-carbonitrile (30 g, 202.7 mmol), sodium acetate (30.75 g, 375.0 mmol), platinum oxide (0.218 g), and acetic acid (1 L). The bottle was capped, placed on Parr apparatus, and shaken under an atmosphere of H$_2$ (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, ether, and dried. The product was collected as 36 g. This batch was combined with other batches prepared on smaller scales and triturated with ether to give 51 g of pure compound. $^1$H NMR (400 MHz, DMSO-d$_6$) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(Aminomethyl)-6-methyl-4-(trifluoromethyl)-2(1H)-pyridinone

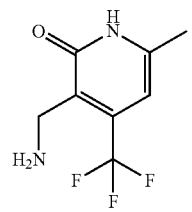

To a dried 500 mL Parr bottle equipped with nitrogen inlet were added sodium acetate (1.502 g, 18.30 mmol), 10% palladium on carbon (1.579 g, 0.742 mmol), platinum(IV) oxide (0.011 g, 0.049 mmol) and a small amount of acetic acid to wet the catalysts, under nitrogen stream. Next was added 2-hydroxy-6-methyl-4-(trifluoromethyl)-3-pyridinecarbonitrile (2.0 g, 9.89 mmol) followed by acetic acid (175 mL) while under nitrogen atmosphere. The contents were sealed, placed on a Parr shaker, and reacted at 40 psi of H$_2$ for ca. 6 hr, keeping the H$_2$ psi between 20 and 40 psi (vessel was refilled twice). The vessel was purged with nitrogen and the reaction mixture filtered through Celite, and the filter pad was further washed with a small amount of acetic acid. The volatiles were removed in vacuo to afford a residue, which was dried under high vacuum for 45 min. The solid was suspended in conc. HCl (12 mL), stirred, and filtered. The clear filtrate was concentrated in vacuo and the residue dried under high vacuum. The collected solid was suspended in conc. HCl (2 mL) and diluted with EtOH (13 mL). The contents were agitated and stored at ca. 0° C. (freezer) for 30 min to give a white solid. The solid was filtered and washed with cold ethanol (5 mL). The solid was filtered and dried in vacuum oven for 1 h to give 3-(aminomethyl)-6-methyl-4-(trifluoromethyl)-2(1H)-pyridinone (0.95 g, 40%). LCMS E-S (M+H)=206.9. $^1$H NMR (400 MHz, DMSO-$d_6$) δ ppm 2.31 (s, 3H), 3.40-3.62 (m, 2H), 3.87 (d, J=5.05 Hz, 2H), 8.12-8.37 (m, 3H).

Intermediate 3

3-(Aminomethyl)-4-cyclohexyl-6-methyl-2(1H)-pyridinone

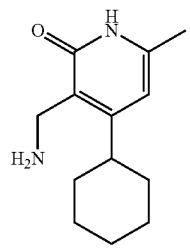 [SMILES: Cc1cc(C2CCCCC2)c(CN)c(=O)[nH]1]

3a) 4-Cyclohexyl-6-methyl-2-oxo-1,2-dihydro-3-pyridinecarbonitrile

To a stirred suspension of $CrCl_2$ (58 g, 472.8 mmol) in THF (1500 mL) was added a THF solution (500 mL) of 1,1-dichloro-2-propanone (10 g, 78.8 mmol) and cyclohexanecarbaldehyde (8.84 g, 78.8 mmol). The reaction mixture was heated at reflux for 2 h, and then quenched by the addition of 1.0M HCl. The reaction mixture was filtered through a pad of Celite and concentrated in vacuo. The crude residue (10 g) was added to a solution of DMSO (150 mL) containing t-BuOK (7.5 g, 65.7 mmol) and cyanoacetamide (6.1 g, 72.3 mmol) and stirred at room temperature for 30 min. Additional t-BuOK (22.5 g, 197.1 mmol) was added and the reaction mixture was stirred under an atmosphere of oxygen for an additional 1 h. The contents were purged with argon, diluted with 4 volumes of $H_2O$, and then 5 volumes of 4N HCl, which were added slowly. The reaction mixture was filtered, washed with water and dried to give 4-cyclohexyl-6-methyl-2-oxo-1,2-dihydro-3-pyridinecarbonitrile (4.5 g, 32%). $^1$H NMR (400 MHz, DMSO-$d_6$) δ ppm 6.25 (s, 1H), 2.61-2.65 (m, 1H), 2.22 (s, 3H), 1.66-1.79 (m, 4H), 1.24-1.46 (m, 6H).

3b) 3-(Aminomethyl)-4-cyclohexyl-6-methyl-2(1H)-pyridinone

To an ice-bath cooled THF (100 mL) solution of the product from step 1 (2 g, 9.26 mmol) was added $NaBH_4$ (0.81 g, 21.3 mmol) and $I_2$ (2.3 g, 9.26 mmol), and the mixture stirred for 30 min. The reaction mixture was then heated at reflux for 3 h, and then allowed to cool to room temperature. After cooling to 0° C., the reaction mixture was acidified by slow addition of 3N HCl (1 mL). The reaction mixture was concentrated in vacuo and the crude product purified by reverse phase HPLC to give 3-(aminomethyl)-4-cyclohexyl-6-methyl-2(1H)-pyridinone as a solid (0.5 g, 25%). LCMS E-S (M+H)=221.1. $^1$H NMR (400 MHz, DMSO-$d_6$) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 4

3-(Aminomethyl)-4-cyclopropyl-6-methyl-2(1H)-pyridinone

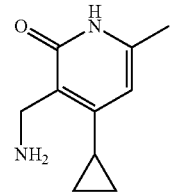

The title compound was prepared in the same manner as described for 3-(aminomethyl)-4-cyclohexyl-6-methyl-2(1H)-pyridinone (Intermediate 3) using 4-cyclopropyl-6-methyl-2-oxo-1,2-dihydro-3-pyridinecarbonitrile (5 g, 28.7 mmol). Obtained: 0.50 g (10%). LCMS E-S (M+H)=179.1. $^1$H NMR (400 MHz, DMSO-$d_6$) δ ppm 11.76-11.78 (br s, 1H), 7.82-7.92 (br s, 3H), 5.61 (s, 1H), 3.94-3.99 (m, 2H), 2.11 (s, 3H), 1.98-2.05 (m, 1H), 0.95-1.01 (m, 2H), 0.74-0.79 (m, 2H).

Intermediate 5

3-(Aminomethyl)-6-methyl-4-propyl-2(1H)-pyridinone

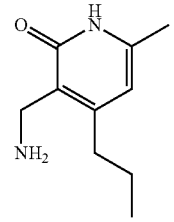

5a) 6-Methyl-2-oxo-4-propyl-1,2-dihydro-3-pyridinecarbonitrile

To a solution of DMSO (300 mL) containing t-BuOK (20 g, 178 mmol) and cyanoacetamide (16.5 g, 196 mmol) was added (3E)-3-hepten-2-one (20 g, 178 mmol), and the contents were stirred at room temperature for 30 min. Additional t-BuOK (60 g, 534 mmol) was added and the reaction mixture was placed under an atmosphere of oxygen for an additional 1 h. The reaction mixture was purged with argon, diluted with 4 volumes of $H_2O$, and then 5 volumes of 4N HCl, which were added slowly. The reaction mixture was filtered, washed with water, and dried to give 6-methyl-2-oxo-4-propyl-1,2-dihydro-3-pyridinecarbonitrile (10 g, 32%). $^1$H NMR (400 MHz, DMSO-$d_6$) δ ppm 12.25-12.40 (br s, 1H), 6.18 (s, 1H), 2.53 (t, 2H), 2.22 (s, 3H), 1.57-1.64 (m, 2H), 0.84 (t, 3H).

5b) 3-(Aminomethyl)-6-methyl-4-propyl-2(1H)-pyridinone

The title compound was prepared in the same manner as described for 3-(aminomethyl)-4-cyclohexyl-6-methyl-2(1H)-pyridinone (Intermediate 3) using 6-methyl-2-oxo-4-propyl-1,2-dihydro-3-pyridinecarbonitrile (2 g, 11.2 mmol). Obtained: 1.2 g (60%). LCMS E-S (M+H)=181.1. $^1$H NMR (400 MHz, DMSO-$d_6$) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 6

3-(Aminomethyl)-6-methyl-4-phenyl-2(1H)-pyridinone

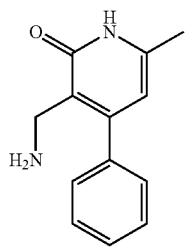 [SMILES: Cc1cc(-c2ccccc2)c(CN)c(=O)[nH]1]

The title compound was prepared in the same manner as described for 3-(aminomethyl)-6-methyl-4-propyl-2(1H)-pyridinone (Intermediate 5) using (3E)-4-phenyl-3-buten-2-one (20 g, 137 mmol). LCMS E-S (M+H)=215.0. $^1$H NMR (400 MHz, DMSO-d$_6$) δ ppm 12.2-12.3 (br s, 1H), 7.88-8.00 (br s, 3H), 7.43-7.51 (m, 3H), 7.29-7.38 (m, 2H), 6.08 (s, 1H), 3.67-3.70 (m, 2H), 2.23 (s, 3H).

Intermediate 7

3-(Aminomethyl)-6-methyl-4-(1-methylethyl)-2(1H)-pyridinone

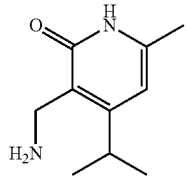

The title compound was prepared in the same manner as described for 3-(aminomethyl)-6-methyl-4-propyl-2(1H)-pyridinone (Intermediate 5) using (3E)-5-methyl-3-hexen-2-one (20 g, 137 mmol). LCMS E-S (M+H)=181.1. $^1$H NMR (400 MHz, DMSO-d$_6$) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 8

3-(Aminomethyl)-4-methyl-6-propyl-2(1H)-pyridinone

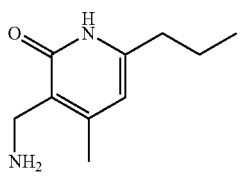

8a) 4-Methyl-2-oxo-6-propyl-1,2-dihydro-3-pyridinecarbonitrile

To a solution of NaNH$_2$ (32.5 g, 862 mmol) in anhydrous ether (500 mL) at 30° C. was added dropwise a mixture of butyric acid ethyl ester (50 g, 431 mmol) and acetone (37.5 g, 646.5 mol). After addition, the reaction mixture was stirred for 4 h. The reaction mixture was poured onto ice water with stirring. Additional ether was added, and the layers were separated. The aqueous layer was acidified to pH 5.0 with 2N HCl and then to pH 7.5 with Na$_2$CO$_3$. The aqueous layer was then extracted with ether. The combined organic layers were dried over Na$_2$SO$_4$, filtered, and concentrated in vacuo. The crude product, 2,4-heptanedione (20 g, 156 mmol), and 2-cyanoacetamide (13.12 g, 156 mmol) were suspended in EtOH (160 mL) at 75° C., followed by addition of piperidine (13.2 g, 156 mmol). The contents were stirred and heated at reflux for 1 h. The mixture was cooled to room temperature and filtered. The collected solid was suspended in water and stirred for 1 h. The mixture was filtered and dried to give 4-methyl-2-oxo-6-propyl-1,2-dihydro-3-pyridinecarbonitrile (11 g, 40%). LCMS E-S (M+H)=181.1. $^1$H NMR (400 MHz, DMSO-d$_6$) δ ppm 12.3-12.4 (br s, 1H), 6.25 (s, 1H), 3.64 (s, 3H), 2.50 (t, 2H), 1.63 (m, 2H), 0.94 (t, 3H).

8b) 3-(Aminomethyl)-4-methyl-6-propyl-2(1H)-pyridinone

Sodium acetate (3.5 g, 42.6 mmol), palladium on carbon (0.81 g) and platinum oxide (0.1 g) were placed in a dried Parr bottle flushed with nitrogen, followed by addition of a small amount of acetic acid (to wet the catalysts). A solution of 4-methyl-2-oxo-6-propyl-1,2-dihydro-pyridine-3-carbonitrile (5 g, 28 mmol) in acetic acid was added to the Parr bottle followed by additional acetic acid (200 mL). The vessel was capped, placed on Parr apparatus and hydrogenated at 45 psi for 12 h. The reaction mixture was filtered and the filtrate concentrated in vacuo. The crude product was purified by preparative HPLC to afford the title compound (TFA salt) as 4.1 g (87%). LCMS E-S (M+H))=181.1. $^1$H NMR (400 MHz, DMSO-d$_6$) δ ppm 11.8-11.9 (br s, 1H), 7.83-7.88 (br s, 3H), 5.99 (s, 1H), 3.77-3.81 (m, 2H), 2.37 (t, 2H), 1.53 (m, 2H), 0.83 (t, 3H).

Intermediate 9

3-(Aminomethyl)-6-cyclopropyl-4-methyl-2(1H)-pyridinone hydrochloride

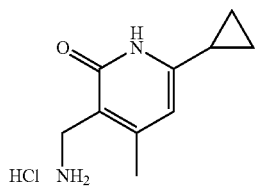

9a) 1-cyclopropyl-1,3-butanedione

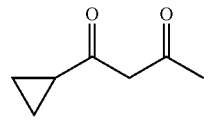

To a stirring solution of THF (100 mL) was added potassium tert-butoxide (5.60 g, 49.5 mmol), followed by a mixture of cyclopropyl methyl ketone (3.27 mL, 33 mmol) and ethyl acetate (9.69 mL, 99 mmol) in 30 mL THF at 35° C., via addition funnel over a 25 min period. The contents were heated and stirred at 60° C. After 3 h, the contents were removed from heating, and allowed to cool to room temperature. The reaction mixture was carefully diluted with 30 mL 2N HCl and stirred for 10 min. The mixture was extracted with diethyl ether (3×50 mL), and the combined organic layers washed with brine (1×50 mL). The organic layer was dried over MgSO$_4$, filtered, and concentrated in vacuo. Purification by chromatography on silica gel (eluent: 0 to 15% EtOAc in hexanes) with good separation afforded 1-cyclopropyl-1,3-butanedione as a light yellow colored oil, 3.9 g in ~75% purity (residual solvent), for an overall yield of 70%. $^1$H NMR (400 MHz, CDCl$_3$) δ ppm 0.89-0.96 (m, 2H), 1.09-1.15 (m, 2H), 1.59-1.69 (m, 1H), 2.04 (s, 3H), 5.63 (s, 1H), 15.5-16.0 (br s, 1H).

9b) 6-Cyclopropyl-4-methyl-2-oxo-1,2-dihydro-3-pyridinecarbonitrile

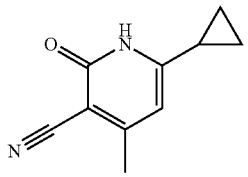

To a stirred solution of ethanol (5 mL) were added 1-cyclopropyl-1,3-butanedione (505 mg, 3.00 mmol) and cyanoacetamide (252 mg, 3.00 mmol), and the heterogenous contents heated until homogenous (ca. 75° C.). Piperidine was added (0.395 mL, 4.00 mmol) and the mixture was heated at reflux for 30 min. The reaction mixture was allowed to cool to room temperature, wherein precipitation ensued. The solid precipitate was filtered and set aside. The filtrate was concentrated in vacuo and the oily residue treated with minimal EtOAc and then 10 mL hexanes to afford a second crop of solid. The solid product crops were combined, suspended in water (7 mL), vigorously stirred, and vacuum filtered to afford 6-cyclopropyl-4-methyl-2-oxo-1,2-dihydro-3-pyridinecarbonitrile as a nearly white solid (380 mg, 73%). LCMS E-S (M+H)=175.1. $^1$H NMR (400 MHz, CDCl$_3$) δ ppm 1.01-1.09 (m, 2H), 1.28 (dd, J=8.59, 2.27 Hz, 2H), 1.95-2.01 (m, 1H), 2.43 (s, 3H), 5.82 (s, 1H).

9c) 1,1-Dimethylethyl [(6-cyclopropyl-4-methyl-2-oxo-1,2-dihydro-3-pyridinyl)methyl]carbamate

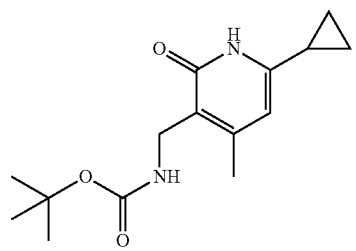 [SMILES: Cc1cc(C2CC2)[nH]c(=O)c1CNC(=O)OC(C)(C)C]

6-Cyclopropyl-4-methyl-2-oxo-1,2-dihydro-3-pyridinecarbonitrile (0.35 g, 2.01 mmol) was added to methanol (20 mL) and the stirred contents cooled to −10° C. Next was added di-tert-butyloxycarbonyl (0.933 mL, 4.02 mmol) and the suspension stirred for 15 min. Next was added in NiCl$_2$-6H$_2$O (0.055 g, 0.201 mmol) as a solid and stirred for 5 min. Then NaBH$_4$ (0.532 g, 14.06 mmol) was added in 6 portions with 5 min. increments between each portion. Then the ice bath was removed and the contents were stirred with warming to room temperature overnight. The reaction mixture was returned to −10° C., followed by addition of 3 more portions of NaBH$_4$ (0.532 g, 14.06 mmol). The ice bath was removed and the mixture stirred at room temperature for 1 h. The contents were quenched by addition of diethylethylene amine (0.218 mL, 2.01 mmol) and stirred for 45 min at room temperature. The volatiles were removed in vacuo and the residue suspended in EtOAc and saturated NaHCO$_3$. The organic layer was washed with additional NaHCO$_3$. The layers were separated, and the organic layer dried over MgSO$_4$, filtered, and concentrated in vacuo. The crude product was purified by silica gel chromatography (eluent: 10% methanol in dichloromethane). The collected product was dried under hi-vacuum for 1 h, and then treated with ether and filtered. After drying in vacuum oven at 45° C. for 2 h, 1,1-dimethylethyl[(6-cyclopropyl-4-methyl-2-oxo-1,2-dihydro-3-pyridinyl)methyl]carbamate was collected (0.28 g, 50%). $^1$H NMR (400 MHz, DMSO-d$_6$) δ ppm 0.73-0.80 (m, 2H), 0.88-0.96 (m, 2H), 1.36 (s, 9H), 1.70-1.82 (m, 1H), 2.11 (s, 3H), 3.95 (d, J=5.31 Hz, 2H), 5.66 (s, 1H), 6.51 (t, J=4.80 Hz, 1H), 11.50 (br. s., 1H).

9d) 3-(Aminomethyl)-6-cyclopropyl-4-methyl-2(1H)-pyridinone hydrochloride 1,1-Dimethylethyl[(6-cyclopropyl-4-methyl-2-oxo-1,2-dihydro-3-pyridinyl)methyl]carbamate (0.28 g, 1.006 mmol) was added to EtOAc (9 mL) and methanol (1.0 mL). The suspension was stirred at room temperature for 5 min, followed by addition of 4M HCl in dioxane (5.03 mL, 20.12 mmol), and the contents were stirred at room temperature overnight. The volatiles were then removed in vacuo to afford a solid. The solid was triturated with ether, filtered, and dried in a vacuum oven at 45° C. for 4 h. The title compound was collected (0.22 g, 100% yield). $^1$H NMR (400 MHz, DMSO-d$_6$) δ ppm 0.78-0.86 (m, 2H), 0.95-1.03 (m, 2H), 1.83 (tt, J=8.46, 5.05 Hz, 1H), 2.16-2.22 (m, 3H), 3.75 (q, J=5.47 Hz, 2H), 5.79 (s, 1H), 8.02 (br. s., 3H), 11.92 (br. s., 1H).

Intermediate 10

3-(Aminomethyl)-4-ethyl-6-methyl-2(1H)-pyridinone hydrochloride

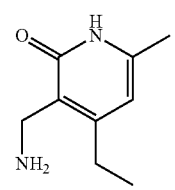

10a) Hex-3-en-2-one

To a stirred solution of 1-(triphenylphosphoranylidene)-2-propanone (100 g, 307 mmol) in DCM (500 mL) was added propionaldehyde (140 mL, 1929 mmol) at room temperature. The reaction mixture was then stirred at room temperature for 18 hours. The reaction was monitored by TLC. The solvent (DCM) was distilled off using ordinary distillation. The residue was then distilled using fractional distillation under vacuum (~450 mbar) and the desired product was isolated. The title compound, hex-3-en-2-one (20 g, 66%), was collected at 110° C. $^1$H NMR (CDCl$_3$, 400 MHz) δ ppm 1.071-1.121 (t, 3H, J=7.4 Hz), 2.250-2.299 (m, 5H), 6.054-6.094 (d, 1H, J=16 Hz), 6.823-6.895 (m, 1H).

10b) 4-Ethyl-1,2-dihydro-6-methyl-2-oxopyridine-3-carbonitrile

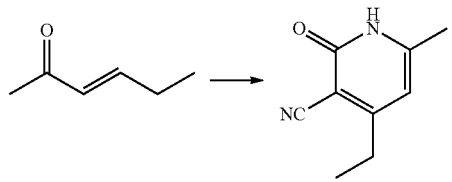

To a stirred solution of t-BuOK (22.85 g, 204.08 mmol) and cyanoacetamide (18.8 g, 224.1 mmol) in DMSO (300 mL) was added hex-3-en-2-one (20 g, 204.08 mmol) under argon atmosphere at room temperature. The reaction mixture was then stirred at room temperature for 30 min and then added additional t-BuOK (68.5 g, 612.05 mmol) was added. Argon gas was displaced by oxygen gas and the mixture stirred for 48 hrs at room temperature in presence of oxygen. Reaction was monitored by TLC. The reaction mixture was cooled to 0° C. and diluted with water (100 mL) followed by 4N HCl (120 mL). The mixture was stirred for 15 min and the resulting solid was filtered. The solid was washed with water (1 L) and dried to afford the title compound, 4-ethyl-1,2-dihydro-6-methyl-2-oxopyridine-3-carbonitrile (10.5 g, 31%), as an off white solid. $^1$H NMR (CDCl$_3$, 400 MHz): δ ppm 1.148-1.185 (t, 3H, J=7.4 Hz), 2.237 (s, 3H), 2.557-2.614 (m, 2H), 6.211 (s, 1H), 12.330 (broad s, 1H). MS(ES) [M+H]$^+$ 161.06.

10c) 3-(Amino methyl)-4-ethyl-6-methylpyridin-2(1H)-one

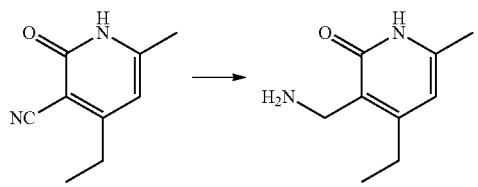

To a suspension of Raney Nickel (6 g) in methanol (200 mL) was added 4-ethyl-1,2-dihydro-6-methyl-2-oxopyridine-3-carbonitrile (10 g, 61.7 mmol) and methanolic ammonia (750 mL). The reaction mixture was stirred at room temperature under hydrogen pressure (80 psi) for 48 hrs. The reaction mixture was filtered through Celite and washed with methanol (250 mL). The filtrate was concentrated under reduced pressure and the residue purified by filter column using silica gel (60-120 mesh), eluted with 10% MeOH in CHCl$_3$, to afford 3-(amino methyl)-4-ethyl-6-methylpyridin-2(1H)-one (5.6 g, 54%) as an off white solid. $^1$H NMR (DMSO-D$_6$, 400 MHz) (free amine): δ ppm 1.063-1.101 (t, 3H, J=7.6 Hz), 2.101 (s, 3H), 2.412-2.449 (m, 2H), 3.448 (s, 2H), 5.835 (s, 1H). MS(ES) [M+H]$^+$ 167.06.

10d) 3-(Aminomethyl)-4-ethyl-6-methylpyridin-2(1H)-one hydrochloride

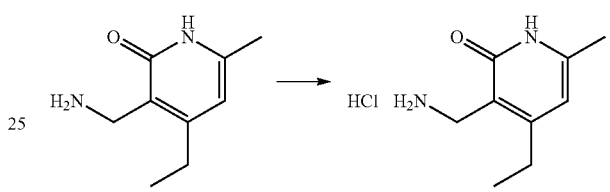

3-(Amino methyl)-4-ethyl-6-methylpyridin-2(1H)-one, (5.6 g, 33 mmol) was suspended in DCM (560 mL) and the insoluble contents/particles were filtered. The filtrate was concentrated and dried. The residue was dissolved in DCM (10 mL) and 4M HCl in 1,4-dioxane (16 mL, 66 mmol) was added at 0° C. and stirred for 10 min, at which time the reaction mixture was concentrated under high-vacuum and dried. The resulting crude solid was triturated with hexane (150 mL) and filtered. The solid was dried under vacuum. Collected 3-(amino methyl)-4-ethyl-6-methylpyridin-2(1H)-one hydrochloride (5.9 g, 86%). $^1$H NMR (400 MHz, DMSO-d$_6$) δ ppm 1.082-1.120 (t, 3H, J=7.6 Hz), 2.179 (s, 3H), 2.503-2.544 (m, 2H), 3.785-3.798 (d, 2H, J=5.2 Hz), 6.024 (s, 1H), 7.985 (broad s, 2H), 11.858 (broad s, 1H). MS(ES) [M+H]$^+$ 167.2.

Intermediate 11

3-(aminomethyl)-6-ethyl-4-methyl-2(1H)-pyridinone

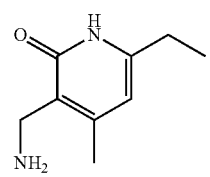

11a) 4-ethyl-6-methyl-2-oxo-1,2-dihydro-3-pyridinecarbonitrile

To a solution of t-BuOK (17.2 g, 153 mmol) and cyanoacetamide (13 g, 153 mmol) in CH$_3$CN (225 mL) was added (3E)-3-hexen-2-one (15 g, 153 mmol) at room temperature under N$_2$ atmosphere. The reaction mixture was stirred for 30 min. To the reaction mixture was added additional t-BuOK (51.4 g), and the N₂ was displaced by oxygen. After stirring for 1 h without external cooling, the mixture was diluted with 4N HCl, which was added slowly and with good stirring. The mixture was filtered, washed with EtOH, dried to give 6-ethyl-4-methyl-2-oxo-1,2-dihydro-3-pyridinecarbonitrile (5 g, 21%). ¹H NMR (400 MHz, DMSO-d₆) δ 12.33 (br. s., 1H), 6.18 (s, 1H), 2.45 (q, 2H), 2.30 (s, 3H), 1.11 (t, 3H).

11b) 3-(aminomethyl)-6-ethyl-4-methyl-2(1H)-pyridinone

To an ice bath cooled THF solution (200 mL) of 6-ethyl-4-methyl-2-oxo-1,2-dihydro-3-pyridinecarbonitrile (7 g, 43.2 mmol) was added NaBH₄(4.2 g, 108 mmol), and I₂ (11.2 g, 43.2 mmol), and the contents were stirred for 30 min. The reaction mixture was then heated at reflux overnight. The reaction mixture was cooled, and carefully neutralized by slow addition of 4N HCl at 0° C. The mixture was dried over MgSO₄, filtered, and concentrated in vacuo. The product was purified by HPLC to give 3-(aminomethyl)-6-ethyl-4-methyl-2(1H)-pyridinone as a TFA salt (1.9 g, 26.4%). LCMS MH+=167.1 ¹H NMR (400 MHz, DMSO-d₆) δ 11.82 (br. s., 1H), 7.82 (br s, 3H), 5.97 (s, 1H), 3.75-3.77 (m, 2H), 2.39 (q, 2H), 2.17 (s, 3H), 1.09 (t, 3H).

Intermediate 12

3-(aminomethyl)-6-methyl-4,4'-bipyridin-2(1H)-one

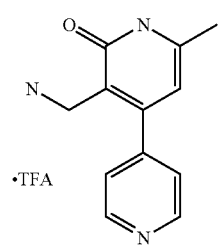 [SMILES: Cc1cc(-c2ccncc2)c(CN)c(=O)[nH]1]

12a) (2Z)-3-Hydroxy-1-(4-pyridinyl)-2-buten-1-one

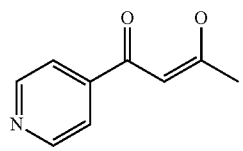

To a solution of ethyl 4-pyridinecarboxylate (30 g, 198 mmol) and acetone (34.58 g, 595 mmol) in THF (150 mL) was slowly added NaOMe (12.87 g, 238 mmol) at 35-40° C. The mixture was stirred at room temperature for 0.5 h, and then heated at reflux for 3 h. The mixture was cooled to room temperature and filtered to give a solid, which was washed with t-BuOMe, and dissolved in H₂O. The solution was acidified with acetic acid and the resulting oily product was extracted with CHCl₃. The solvent was removed in vacuo, and the crude product was obtained (12 g, 37%) and used without further purification. ¹H NMR (400 MHz, DMSO-d₆) δ 8.73 (d, 2H), 7.76 (d, 2H), 6.63 (s, 1H), 2.21 (s, 3H); note: enolic OH does not appear.

12b) 6-Methyl-2-oxo-1,2-dihydro-4,4'-bipyridine-3-carbonitrile and 4-methyl-6-oxo-1,6-dihydro-2,4'-bipyridine-5-carbonitrile

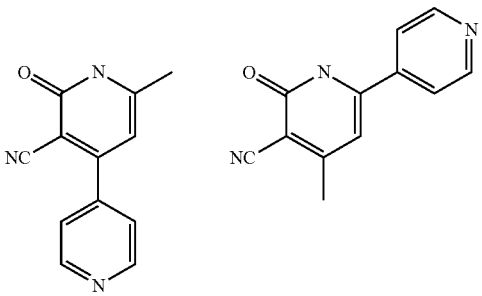 [SMILES: Cc1cc(-c2ccncc2)c(C#N)c(=O)[nH]1 ; Cc1cc(-c2ccncc2)[nH]c(=O)c1C#N]

To a solution of (2Z)-3-hydroxy-1-(4-pyridinyl)-2-buten-1-one (8 g, crude, 49 mmol) and cyanoacetamide (4.12 g, 49 mmol) in anhydrous EtOH (100 mL) was added piperidine (4.17 g, 49 mmol) under N₂ at 75° C. The mixture was heated at reflux for 1 h, and then cooled to room temperature. After filtration, the solid was collected and washed with H₂O to give the crude product (4 g) as two isomers. After separation by HPLC, 1.8 g of 6-methyl-2-oxo-1,2-dihydro-4,4'-bipyridine-3-carbonitrile and 1.2 g of 4-methyl-6-oxo-1,6-dihydro-2,4'-bipyridine-5-carbonitrile were obtained. The identity of 6-methyl-2-oxo-1,2-dihydro-4,4'-bipyridine-3-carbonitrile was established by nOE analysis. ¹H NMR (400 MHz, DMSO-d₆) δ 12.79 (br. s., 1H), 8.75 (d, 2H), 7.58 (d, 2H), 6.37 (s, 1H), 2.31 (s, 3H).

12c) 3-(Aminomethyl)-6-methyl-4,4'-bipyridin-2(1H)-one

To an ice bath cooled THF (100 mL) solution of 6-methyl-2-oxo-1,2-dihydro-4,4'-bipyridine-3-carbonitrile (4 g, 18.9 mmol) was added NaBH₄ (1.43 g, 37.9 mmol), and I₂ (4.81 g, 18.9 mmol), and the mixture was stirred for 0.5 h. The reaction mixture was then heated at reflux for 4 h. After cooling to 0° C., the reaction mixture was adjusted to pH 5 with 4N HCl. The mixture was concentrated in vacuo to give the crude compound, which was purified by HPLC to give 3-(aminomethyl)-6-methyl-4,4'-bipyridin-2(1H)-one (1.9 g, 31%) as a TFA salt. LCMS MH+=216.0 ¹H NMR (400 MHz, DMSO-d₆ in D₂O) δ 8.87 (d, 2H), 7.87 (d, 2H), 6.13 (s, 1H), 3.65 (br s, 2H), 2.17 (s, 3H).

Intermediate 13

3-(Aminomethyl)-6-cyclobutyl-4-methyl-2(1H)-pyridinone

13a) Ethyl cyclobutanecarboxylate

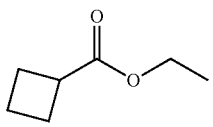

To a solution of cyclobutanecarboxylic acid (50 g, 500 mmol) in EtOH (1.2 L) was slowly added H₂SO₄ (20 mL) at room temperature. The solution was stirred at reflux overnight, and then cooled and poured into H₂O. The aqueous layer was extracted with ether. The combined organic layers were washed with brine, dried over Na₂SO₄, and concentrated in vacuo to give ethyl cyclobutanecarboxylate as a colorless oil (44 g, 69%). ¹H NMR (400 MHz, CDCl₃-d₃) δ 4.04 (q, 2H), 3.04 (m, 1H), 2.12 (m, 4H), 1.88 (m, 2H), 1.18 (t, 3H).

13b) 1-Cyclobutyl-1,3-butanedione

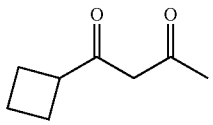

To a solution of NaNH₂ (11.7 g, 91 mmol) in anhydrous ether (150 mL) under N₂ at 30° C. was added dropwise a mixture of ethyl cyclobutanecarboxylate (19.2 g, 150 mmol) and acetone (21.75 g, 375 mmol). After addition, the reaction mixture was stirred for 4 h, then poured onto ice water with stirring. Ether was added and the unreacted components were extracted into the organic phase. The clear aqueous extract was acidified to pH 5.0 with 2N HCl, and then to pH 7.5 with Na₂CO₃. The solution was extracted with ether. The combined organic layers were dried (Na₂SO₄), filtered, and concentrated to give the crude product of 1-cyclobutyl-1,3-butanedione (9.7 g, 76%), which was used in the next step without further purification. ¹H NMR (400 MHz, CDCl₃-d₃) δ 5.42 (s, 1H), 3.66 (s, 1H), 2.11-2.23 (m, 4H), 2.02 (s, 3H), 1.93-1.99 (m, 2H).

13c) 6-Cyclobutyl-4-methyl-2-oxo-1,2-dihydro-3-pyridinecarbonitrile and 4-cyclobutyl-6-methyl-2-oxo-1,2-dihydro-3-pyridinecarbonitrile

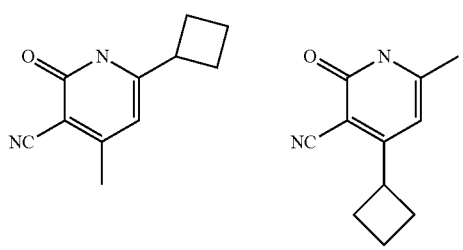

To a solution of 1-cyclobutyl-1,3-butanedione (1.5 g, 10.7 mmol) and cyanoacetamide (1.07 g, 12.8 mmol) in EtOH (25 mL) was added piperidine (1.08 g, 12.8 mmol) at 75° C. After addition, the mixture was stirred with warming to reflux. After 1 h, the mixture was cooled to room temperature during which time precipitation occurred. The contents were filtered, and the filtered solid suspended in water and stirred for 1 h. The heterogenous mixture was filtered and dried to give a mixture of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (1.14 g, 57%). ¹H NMR (400 MHz, DMSO-d₆ in D₂O) δ 12.15-12.30 (br s, 2H), 6.39 (s, 1H), 6.34 (s, 1H), 2.40-2.28 (m, 7H), 2.23-2.25 (m, 3H), 2.18-2.21 (m, 4H), 1.99-2.11 (m, 2H), 1.84-1.90 (m, 2H).

13d) 3-(Aminomethyl)-6-cyclobutyl-4-methyl-2(1H)-pyridinone and 3-(aminomethyl)-4-cyclobutyl-6-methyl-2(1H)-pyridinone

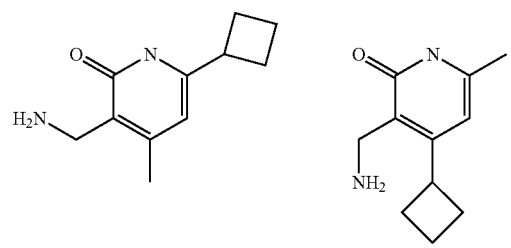

To an ice bath cooled THF (100 mL) solution of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (6 g, 32 mmol) was added NaBH₄ (2.73 g, 71.8 mmol), and I₂ (8.3 g, 32 mmol), and the mixture was stirred for 30 min. The reaction mixture was then heated at reflux for 3 h. After cooling to 0° C., the reaction mixture was adjusted to pH 5 with 6N HCl. The contents were dried, filtered, and concentrated in vacuo. The crude product was purified by HPLC to give a mixture of 3-(aminomethyl)-6-cyclobutyl-4-methyl-2(1H)-pyridinone and 3-(aminomethyl)-4-cyclobutyl-6-methyl-2(1H)-pyridinone (5.6 g, 91%). ¹H NMR (400 MHz, DMSO-d₆) δ 11.60-11.70 (br s, 2H), 7.85 (br s, 4H), 6.15 (s, 1H), 6.03 (s, 1H), 3.72-3.79 (m, 2H), 3.29-3.33 (m, 2H), 2.16 (s, 6H), 2.05-2.10 (m, 6H), 1.88-1.93 (m, 4H), 1.69-1.79 (m, 4H).

13e) 1,1-Dimethylethyl [(6-cyclobutyl-4-methyl-2-oxo-1,2-dihydro-3-pyridinyl)methyl]carbamate and 1,1-dimethylethyl [(4-cyclobutyl-6-methyl-2-oxo-1,2-dihydro-3-pyridinyl)methyl]carbamate

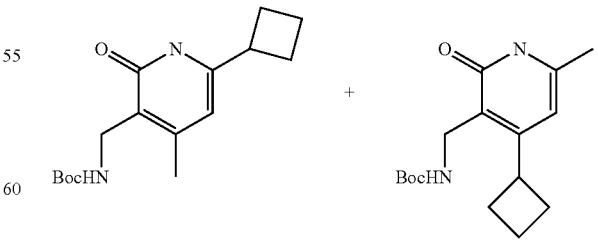

To an ice bath cooled solution of 3-(aminomethyl)-6-cyclobutyl-4-methyl-2(1H)-pyridinone and 3-(aminomethyl)-4-cyclobutyl-6-methyl-2(1H)-pyridinone (3.5 g, 18 mmol) in THF (10 mL) and DMF (10 mL) were added Boc₂O (4.68 g, 21.8 mmol) and triethylamine (5.4 g, 54 mmol). The contents were then stirred for 30 min. at 30° C. The reaction was quenched by addition of ice water, during which time precipitation occurred. The reaction mixture was filtered and dried to give a mixture of the crude products. The crude products were separated by HPLC to give 1,1-dimethylethyl [(6-cyclobutyl-4-methyl-2-oxo-1,2-dihydro-3-pyridinyl)methyl]carbamate (2.1 g, 20%) and 1,1-dimethylethyl [(4-cyclobutyl-6-methyl-2-oxo-1,2-dihydro-3-pyridinyl)methyl]carbamate (1 g, 9.5%). Data for 1,1-dimethylethyl [(6-cyclobutyl-4-methyl-2-oxo-1,2-dihydro-3-pyridinyl)methyl]carbamate: $^1$H NMR (400 MHz, DMSO-$d_6$) δ 11.28 (br s, 1H), 6.49 (br s, 1H), 5.86 (br s, 1H), 3.85 (br s, 2H), 1.97-2.14 (m, 7H), 1.87-1.94 (m, 1H), 1.72-1.77 (m, 1H), 1.28 (s, 9H).

13f) 3-(Aminomethyl)-6-cyclobutyl-4-methyl-2(1H)-pyridinone hydrochloride

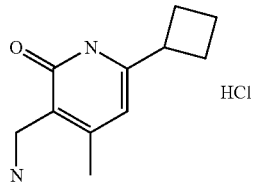

A solution of 1,1-dimethylethyl [(6-cyclobutyl-4-methyl-2-oxo-1,2-dihydro-3pyridinyl)methyl]carbamate (2.1 g, 7.2 mmol) in 4N HCl (in 15 mL 1,4 dioxane) was heated to 60° C. for 1 h. The mixture was cooled to room temperature. The mixture was filtered and dried to give 3-(aminomethyl)-6-cyclobutyl-4-methyl-2(1H)-pyridinone as an HCl salt (1.95 g, 90%). LCMS MH+=193.1 $^1$H NMR (400 MHz, DMSO-$d_6$) δ 11.70 (br s, 1H), 8.01 (s, 3H), 6.04 (s, 1H), 3.74 (d, 2H), 3.32-3.39 (m, 1H), 2.22 (s, 3H), 2.17-2.20 (m, 2H), 2.06-2.11 (m, 2H), 1.85-1.95 (m, 1H), 1.71-1.79 (m, 1H).

Intermediate 14

3-(Aminomethyl)-6-methyl-4-[(methyloxy)methyl]-2(1H)-pyridinone

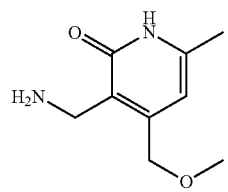

14a) 1-(Methyloxy)-2,4-pentanedione

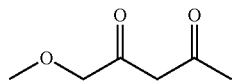

To a solution of sodium (5.83 g, 243.3 mmol) in dry toluene (62.5 mL) was added ethyl(methyloxy)acetate (24 g, 203.4 mmol) at −5° C. After stirring for 3 h, acetone (14 g, 231.4 mmol) was slowly added, upon which the mixture became brown and viscous. Next added 72 mL of tert-butyl methyl ether, and the reaction mixture was stirred at room temperature for 12 h, after which time the sodium salt precipitated. After collection and washing with additional tert-butyl methyl ether, the sodium salt was dissolved in 46 mL of 20% $H_2SO_4$. The contents were extracted with tert-butyl methyl ether and the organic layers concentrated to afford 1-(methyloxy)-2,4-pentanedione (9.76 g, 36.9%). $^1$H NMR (400 MHz, CDCl$_3$-$d_3$) δ 5.76 (s, 1H), 3.96 (s, 2H), 3.38 (s, 3H), 2.07 (s, 3H).

14b) 6-Methyl-4-[(methyloxy)methyl]-2-oxo-1,2-dihydro-3-pyridinecarbonitrile

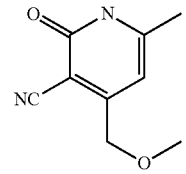

1-(Methyloxy)-2,4-pentanedione (9.51 g, 73.12 mmol) and cyanoacetamide (6.17 g, 73.12 mmol) were dissolved in EtOH (76 mL) and heated until homogenous (ca. 75° C.). Piperidine (6.25 g, 73.12 mmol) was added and the reaction mixture heated at reflux for 20 mins, followed by cooling to room temperature. The contents were filtered to give a solid which was suspended in 140 mL water and stirred vigorously for 20 min. The heterogenous mixture was filtered to afford 6-methyl-4-[(methyloxy)methyl]-2-oxo-1,2-dihydro-3-pyridinecarbonitrile (7.8 g, 65.6%). LCMS MH+=179.0 $^1$H NMR (400 MHz, DMSO-$d_6$) δ 12.47 (br s, 1H), 6.26 (s, 1H), 4.40 (s, 2H), 3.29 (s, 3H), 2.25 (s, 3H).

14c) 3-(Aminomethyl)-6-methyl-4-[(methyloxy)methyl]-2(1H)-pyridinone

6-Methyl-4-[(methyloxy)methyl]-2-oxo-1,2-dihydro-3-pyridinecarbonitrile (1.000 g, 5.61 mmol) was suspended in acetic acid (150 ml) and the solution passed through an H-cube instrument equipped with Raney-Ni cartridge at a rate of 1 mL/min at 50 psi and 60° C. After 18 h. the acetic acid was removed under reduced pressure and the remaining residue was dissolved in MeOH. The methanolic solution was passed through a 0.2 μm teflon syringe filter. The methanolic filtrate was purified by reverse phase HPLC (Gemini 50×100 5 μm column. Run 1: 3 min, 90-10%. Run 2, 5 min 0-10%. Run 3, 10 min, 0-20%. The product fractions were concentrated to dryness on a Genevac HT-4 instrument to afford 3-(aminomethyl)-6-methyl-4-[(methyloxy)methyl]-2(1H)-pyridinone as a pale grey waxy solid (900 mg, 70.2% yield) LCMS MH+=183.0 $^1$H NMR (400 MHz, DMSO-$d_6$) δ 8.40 (br. s., 1H), 6.10 (s, 1H), 4.39 (s, 2H), 3.66 (br. s., 2H), 3.32 (s, 3H), 2.19 (s, 3H).

Intermediate 15

3-(Aminomethyl)-6-methyl-4-(phenylmethyl)-2(1H)-pyridinone and 3-(aminomethyl)-4-methyl-6-(phenylmethyl)-2(1H)-pyridinone

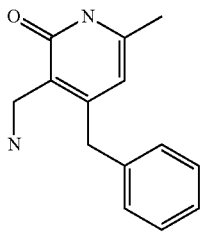

15a) 1-Phenyl-2,4-pentanedione

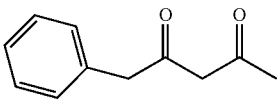

To a solution of NaNH$_2$ (19.02 g, 480 mmol) in anhydrous ether (400 mL) under N$_2$ at −5° C. was added dropwise ethyl phenylacetate (19.2 g, 150 mmol) and then acetone (21.23 g, 370 mmol) with vigorous stirring. After addition, the reaction mixture was stirred at room temperature overnight. The mixture was then acidified to pH 4.0-5.0 with 1N HCl. The organic layer was separated and concentrated in vacuo. The crude product was purified by silica gel chromatography to give 1-phenyl-2,4-pentanedione (18.32 g, 44%). $^1$H NMR (400 MHz, CDCl$_3$-d$_3$) δ 15.49 (br s, 1H), 7.33-7.45 (m, 5H), 5.53 (s, 1H), 3.66 (s, 2H), 2.10 (s, 3H).

15b) 6-Methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile

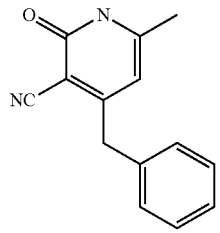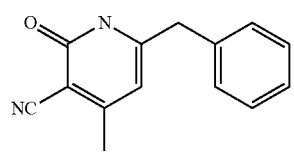

1-Phenyl-2,4-pentanedione (18.32 g, 104 mmol) and cyanoacetamide (8.74 g, 104 mmol) were dissolved in EtOH (104 mL) and heated until homogenous (ca. 75° C.). Piperidine (8.86 g, 104 mmol) was added and the reaction mixture heated at reflux for 15-30 min. followed by cooling to room temperature, during which time precipitation occurred. The heterogenous contents were filtered to give a solid which was suspended in 200 mL water and stirred vigorously for 20 min. The heterogenous mixture was filtered to afford 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (12.06 g, 52%). LCMS MH+=225.1 $^1$H NMR (400 MHz, DMSO-d$_6$) (mixture of compounds) δ 7.21-7.31 (m, 10H), 6.06 (s, 2H), 3.89 (s, 2H), 3.79 (s, 2H), 2.24 (s, 3H), 2.15 (s, 3H).

15c) 3-(Aminomethyl)-6-methyl-4-(phenylmethyl)-2(1H)-pyridinone and 3-(aminomethyl)-4-methyl-6-(phenylmethyl)-2(1H)-pyridinone

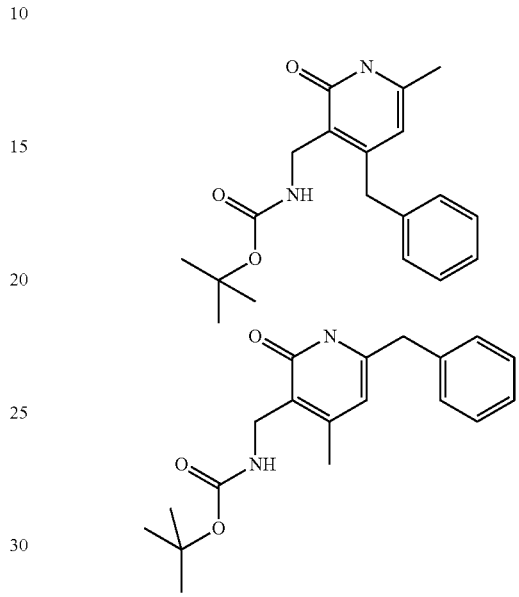

Sodium acetate (6.14 g, 74.8 mmol), Pd/C (0.65 g, 1 mmol), and platinum (II) oxide (45 mg, 1 mmol) were placed in a dried Parr bottle equipped with nitrogen inlet. A small amount of acetic acid was added to wet the catalysts. A solution of 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (6 g, 26.7 mmol) in acetic acid (300 mL) was added to the vessel. The contents were sealed and hydrogenated on Parr shaker at 45 psi for 12 h. The reaction mixture was filtered and washed with acetic acid. The filtrate was removed under reduced pressure. The residue was washed with methanol and filtered to afford a crude mixture of 3-(aminomethyl)-6-methyl-4-(phenylmethyl)-2(1H)-pyridinone and 3-(aminomethyl)-4-methyl-6-(phenylmethyl)-2(1H)-pyridinone. The reaction was run in duplicate to afford a total crude recovery of 14.5 g. To a solution of the above crude product mixture (4.0 g, 17.5 mmol) in THF (10 mL) and DMF (10 mL) was added di-tert-butoxycarbonyl anhydride (5.0 g, 23.4 mmoL) and triethylamine (5.2 g, 52.5 mmol) at 0° C. The reaction mixture was stirred with warming to room temperature and then stirred for an additional 4 h. The contents were diluted with ice water and then filtered. The collected solid was dried and the products separated by HPLC to furnish 1.2 g of 1,1-dimethylethyl {[4-methyl-2-oxo-6-(phenylmethyl)-1,2-dihydro-3-pyridinyl]methyl}carbamate ($^1$H NMR (400 MHz, DMSO-d$_6$) δ 11.55-1.60 (br s, 1H), 7.20-7.29 (m, 5H), 5.85 (s, 1H), 3.92 (s, 2H), 3.90 (s, 2H), 2.10 (s, 3H), 1.32 (s, 9H) and 1.0 g of 1,1-dimethylethyl {[6-methyl-2-oxo-4-(phenylmethyl)-1,2-dihydro-3-pyridinyl]methyl}carbamate ($^1$H NMR (400

MHz, DMSO-$d_6$) δ 11.50-11.55 (br s, 1H), 7.18-7.25 (m, 5H), 5.75 (s, 1H), 4.02 (s, 2H), 3.85 (s, 2H), 2.05 (s, 3H), 1.32 (s, 9H).

15d) 3-(Aminomethyl)-4-methyl-6-(phenylmethyl)-2 (1H)-pyridinone hydrochloride

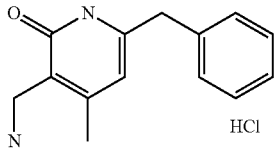 [SMILES: Cc1cc(Cc2ccccc2)[nH]c(=O)c1CN ; Cl]

A solution of 1,1-dimethylethyl {[4-methyl-2-oxo-6-(phenylmethyl)-1,2-dihydro-3-pyridinyl]methyl}carbamate (1.2 g, 3.66 mmol) in 4N HCl (in 15 mL 1,4 dioxane) was heated to 60° C. for 1 h. The mixture was cooled to room temperature. The mixture was filtered and dried to give 3-(aminomethyl)-4-methyl-6-(phenylmethyl)-2(1H)-pyridinone as an HCl salt (0.725 g, 87%). LCMS MH+=229.1 $^1$H NMR (400 MHz, DMSO-$d_6$) δ 11.9-12.0 (br s, 1H), 7.99 (br s, 3H), 7.20 (s, 5H), 5.97 (s, 1H), 3.72-3.75 (m, 4H), 2.17 (s, 3H).

15e) 3-(Aminomethyl)-6-methyl-4-(phenylmethyl)-2 (1H)-pyridinone hydrochloride

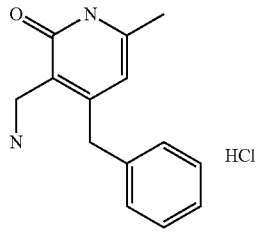 [SMILES: Cc1cc(Cc2ccccc2)c(CN)c(=O)[nH]1 ; Cl]

A solution of 1,1-dimethylethyl {[6-methyl-2-oxo-4-(phenylmethyl)-1,2-dihydro-3-pyridinyl]methyl}carbamate (1.0 g, 3.0 mmol) in 4N HCl (in 15 mL 1,4 dioxane) was heated to 60° C. for 1 h. The mixture was cooled to room temperature. The mixture was filtered and dried to give 3-(aminomethyl)-6-methyl-4-(phenylmethyl)-2(1H)-pyridinone as an HCl salt (0.600 g, 86%). LCMS MH+=229.1 $^1$H NMR (400 MHz, DMSO-$d_6$) δ 11.9-12.0 (br s, 1H), 8.03 (br s, 3H), 7.16-7.30 (m, 5H), 5.84 (s, 1H), 3.91 (s, 2H), 3.81 (s, 2H), 2.10 (s, 3H).

Intermediate 16

3-(Aminomethyl)-6-methyl-4-(4-morpholinylmethyl)-2(1H)-pyridinone

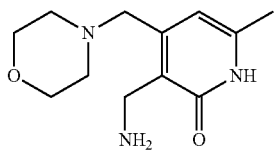

a) 5-(4-Morpholinyl)-3-pentyn-2-one

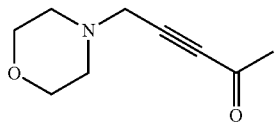

To a cooled (−40° C., $CH_3CN/CO_2$) solution of 4-(2-propyn-1-yl)morpholine (2.2 g, 17.58 mmol) in THF (5 mL) was added dropwise via. syringe under $N_2$ a solution of 2M isopropylmagnesium chloride in THF (10 mL, 20.00 mmol). The reaction was stirred for 1 hr then a solution of N-methoxy-N-methylacetamide (2.2 mL, 20.69 mmol) in THF (5 mL) was added in one portion. The reaction was stirred for 2 hr (allowed to slowly warm to RT), quenched with aq. $NH_4Cl$, extracted with EtOAc, washed with brine, dried ($Na_2SO_4$), filtered and evaporated to dryness under vacuum. The remaining was purified by silica gel chromatography (Analogix, SF25-60g, 0 to 80% EtOAc in hexanes). The pure fractions were combined and evaporated to dryness to give the product 5-(4-morpholinyl)-3-pentyn-2-one (2.09 g, 12.50 mmol, 71.1% yield) as a yellow oil. $^1$H NMR (400 MHz, DMSO-$d_6$) δ 3.62-3.57 (m, 4H), 3.56 (s, 2H), 2.49-2.43 (m, 4H), 2.34 (s, 3H). MS(ES)+ m/e 168.0 [M+H]$^+$.

b) 6-Methyl-4-(4-morpholinylmethyl)-2-oxo-1,2-dihydro-3-pyridinecarbonitrile

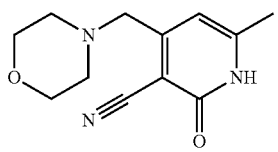 [SMILES: Cc1cc(CN2CCOCC2)c(C#N)c(=O)[nH]1]

To a stirred solution of 21 wt % sodium ethoxide in EtOH (4.2 g, 12.96 mmol) in EtOH (30 mL) was added 2-cyanoacetamide (1.1 g, 13.08 mmol). The reaction was stirred for 15 min. then a solution of 5-(4-morpholinyl)-3-pentyn-2-one (2.0 g, 11.96 mmol) in EtOH was added to the reaction in one portion. (The reaction quickly turned dark red.) The reaction was stirred overnight at RT, neutralized with 6N HCl (2.17 mL, 13.02 mmol) and evaporated to dryness under vacuum. Dried under vacuum overnight. The remaining dark solid was triturated with a solution of (9:1) $CH_2Cl_2$, MeOH (50 mL), filtered from insoluble material, washed with (9:1) $CH_2Cl_2$, MeOH, and the filtrate evaporated to dryness under vacuum. The dark solid was triturated with a solution of (1:1) EtOAc in hexanes, filtered, washed with (1:1) EtOAc in hexanes, and dried under vacuum to give a brown solid (removed a lot of fast running non-polar impurities). The crude product was purified by silica gel chromatography (Analogix, SF25-60g, 0 to 15% $CH_2Cl_2$/20% (5% $NH_4OH$ in MeOH) in $CH_2Cl_2$). The pure fractions were combined, evaporated to dryness, triturated with hexanes and dried under vacuum to give the product 6-methyl-4-(4-morpholinylmethyl)-2-oxo-1,2-dihydro-3-pyridinecarbonitrile (0.90 g, 3.86 mmol, 32.3% yield) as a light tan solid.

$^1$H NMR (400 MHz, DMSO-$d_6$) δ 12.44 (br. s., 1H), 6.34 (s, 1H), 3.63-3.56 (m, 4H), 3.48 (s, 2H), 2.45-2.36 (m, 4H), 2.27 (s, 3H)

MS(ES)+ m/e 234.1 [M+H]$^+$.

c) 3-(Aminomethyl)-6-methyl-4-(4-morpholinylmethyl)-2(1H)-pyridinone

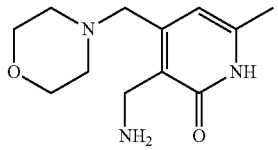 [SMILES: Cc1cc(CN2CCOCC2)c(CN)c(=O)[nH]1]

A clear solution of 6-methyl-4-(4-morpholinylmethyl)-2-oxo-1,2-dihydro-3-pyridinecarbonitrile (0.60 g, 2.57 mmol) in HOAc (20 mL) was treated on an H-Cube apparatus (50 psi, 60° C., 1 mL/min., Raney Nickel cartridge) for 18 hr overnight. LCMS showed that the reaction was complete. The reaction was evaporated to dryness, taken up in a small volume of MeOH and treated with 4N HCl in dioxane (5 mL, 20.00 mmol). The mixture was evaporated to dryness under vacuum (began to ppt. out during evaporation), triturated with $Et_2O$, filtered and dried under vacuum to give the product 3-(aminomethyl)-6-methyl-4-(4-morpholinylmethyl)-2(1H)-pyridinone (0.76 g, 2.450 mmol, 95% yield) as a light grey solid. $^1$H NMR (400 MHz, DMSO-$d_6$) δ 6.39 (s, 1H), 4.28 (s, 2H), 3.99 (s, 2H), 3.87 (br. s., 4H), 3.27 (br. s., 4H), 2.22 (s, 3H). MS(ES)+ m/e 238.0 [M+H]+ (weak), 221.3 [M+H]+ —NH$_3$ (strong).

Intermediate 17 tert-Butyl (5-(aminomethyl)-6-methoxy-4-methylpyridin-2-yl)carbamate

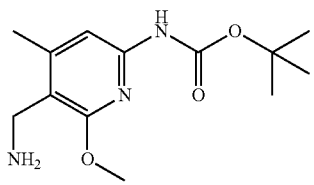 [SMILES: COc1nc(NC(=O)OC(C)(C)C)cc(C)c1CN]

a) Ethyl 4-ethoxy-2-oxopent-3-enoate

To a stirred solution of ethyl 2,4-dioxopentanoate (36.5 g, 231 mmol) and triethyl orthoformate (41 mL, 246 mmol) in ethanol (60 mL) was added ammonium chloride (3.7 g, 69 mmol). The suspension was stirred at RT overnight. LCMS showed that the reaction was mostly complete. (Hydrolyzes on LCMS to some degree?) The reaction was concentrated under vacuum. The remaining oil was taken up in $Et_2O$ (300 mL), filtered to remove insolubles, rinsed with $Et_2O$, and concentrated under vacuum. The product was obtained by short path distillation under vacuum (bp 70 to 77° C. at 0.09 mmHg) to give the product ethyl 4-ethoxy-2-oxopent-3-enoate (36.5 g, 47.3 mmol, 79% yield) as a light yellow oil.

$^1$H NMR (400 MHz, CHLOROFORM-d) δ 6.24 (s, 1H), 4.32 (q, J=7.2 Hz, 2H), 4.02 (q, J=6.9 Hz, 2H), 2.41 (s, 3H), 1.41 (t, J=7.1 Hz, 3H), 1.39 (t, J=7.2 Hz, 3H). MS(ES)+ m/e 186.8 [M+H]+, 208.8 M+Na+.

b) Ethyl 5-cyano-4-methyl-6-oxo-1,6-dihydropyridine-2-carboxylate

To a stirred solution of ethyl 4-ethoxy-2-oxopent-3-enoate (22.5 g, 121 mmol) and 2-cyanoacetamide (9.0 g, 107 mmol) in acetone (250 mL) was added potassium carbonate (15.8 g, 114 mmol). The reaction was refluxed (85° C. oil bath) for 10 hr (the reaction formed a thick ppt. in a deep red solution). The slurry was added to cold 1N HCl (230 mL) in ice. After stirring for 30 min. the suspension was filtered, washed with water and dried under vacuum to give the product ethyl 5-cyano-4-methyl-6-oxo-1,6-dihydropyridine-2-carboxylate (14.51 g, 70.4 mmol, 65.7% yield) as a light pink solid. $^1$H NMR (400 MHz, DMSO-$d_6$) δ 12.60 (br. s., 1H), 7.05 (br. s., 1H), 4.34 (q, J=7.1 Hz, 2H), 2.45 (s, 3H), 1.32 (t, J=7.1 Hz, 3H). MS(ES)+ m/e 206.8 [M+H]+.

c) Ethyl 5-cyano-6-methoxy-4-methylpicolinate

To a stirred suspension of ethyl 5-cyano-4-methyl-6-oxo-1,6-dihydropyridine-2-carboxylate (2.0 g, 9.70 mmol) in $CH_2Cl_2$ (25 mL) was added trimethyloxonium tetrafluoroborate (2.0 g, 13.52 mmol). The reaction was rinsed down with $CH_2Cl_2$ and stirred at RT for 24 hr. (The reaction eventually cleared up.) To the reaction was added 1N NaOH (75 mL). After stirring for 10 minutes the mixture was poured into a separatory funnel. The $CH_2Cl_2$ phase was removed, dried ($Na_2SO_4$), filtered and concentrated under vacuum. Purification by silica gel chromatography (Analogix SF25-40g, 50 to 100% $CH_2Cl_2$ in hexanes) gave the product ethyl 5-cyano-6-methoxy-4-methylpicolinate (1.13 g, 5.13 mmol, 52.9% yield) as a white solid. $^1$H NMR (400 MHz, DMSO-$d_6$) δ 7.75 (s, 1H), 4.37 (q, J=7.1 Hz, 2H), 4.03 (s, 3H), 2.55 (s, 3H), 1.33 (t, J=7.2 Hz, 3H). MS(ES)+ m/e 221.2 [M+H]+.

d) 5-Cyano-6-methoxy-4-methylpicolinic acid

To a stirred solution of ethyl 5-cyano-6-methoxy-4-methylpicolinate (1.0 g, 4.54 mmol) in MeOH (30 mL) and THF (10 mL) was added 6N NaOH (2 mL, 12.00 mmol). The suspension was heated to 60° C. and stirred for 2 hr. (The reaction cleared up right away.) LCMS indicated that the reaction was complete. The reaction was cooled to RT and concentrated to near dryness. The slurry was neutralized with 6N HCl (2 mL) diluted with water, filtered, washed with water and dried under vacuum to give the product 5-cyano-6-methoxy-4-methylpicolinic acid (0.76 g, 3.95 mmol, 87% yield) as a white solid. $^1$H NMR (400 MHz, DMSO-$d_6$) δ 13.65 (br. s., 1H), 7.73 (s, 1H), 4.03 (s, 3H), 2.54 (s, 3H). MS(ES)+ m/e 192.9 [M+H]+.

e) tert-Butyl (5-cyano-6-methoxy-4-methylpyridin-2-yl)carbamate

To a stirred solution of 5-cyano-6-methoxy-4-methylpicolinic acid (0.75 g, 3.90 mmol) in tert-butanol (25 mL) was added triethylamine (0.7 mL, 5.02 mmol). After the reaction became clear DPPA (1 mL, 4.64 mmol) was added dropwise over 5 minutes. The reaction was slowly heated to 100° C. and stirred for 4 hr. The reaction was cooled to RT and evaporated to dryness under vacuum. Purified by silica gel chromatography (Analogix, SF25-60g, 0 to 20% EtOAc in hexanes) to give, after trituration and filtration from hexanes, the product tert-butyl (5-cyano-6-methoxy-4-methylpyridin-2-yl)carbamate (0.61 g, 2.317 mmol, 59.4% yield) as a white solid. $^1$H NMR (400 MHz, DMSO-$d_6$) δ10.20 (s, 1H), 7.44 (s, 1H), 3.91 (s, 3H), 2.40 (s, 3H), 1.48 (s, 9H). MS(ES)+ m/e 264.0 [M+H]+.

f) tert-Butyl (5-(aminomethyl)-6-methoxy-4-methylpyridin-2-yl)carbamate

A clear solution of tert-butyl (5-cyano-6-methoxy-4-methylpyridin-2-yl)carbamate (0.60 g, 2.279 mmol) in HOAc (5 mL) and ethanol (20 mL) was treated on an H-Cube apparatus (50 psi, 40° C., 1 mL/min., Raney Nickel cartridge) for 18 hr. LCMS showed that the reaction was complete (86% pure). The reaction was evaporated to dryness under vacuum. Purified by silica gel chromatography (Analogix, SF25-60g, 0 to 12% (5% $NH_4OH$/MeOH) in $CH_2Cl_2$). The pure fractions were combined and evaporated to dryness under vacuum to give the product tert-butyl (5-(aminomethyl)-6-methoxy-4-methylpyridin-2-yl)carbamate (0.42 g, 1.571 mmol, 68.9% yield) as a white solid. $^1$H NMR (400 MHz, DMSO-$d_6$) δ 9.33 (s, 1H), 7.16 (s, 1H), 3.80 (s, 3H), 3.57 (s, 2H), 2.28 (s, 3H), 1.46 (s, 9H). MS(ES)+ m/e 268.1 [M+H]+.

Intermediate 18

[5-(Aminomethyl)-4-methyl-6-(methyloxy)-2-pyridinyl]methanol

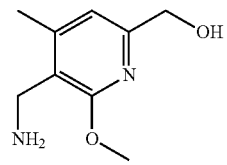

a) 6-(Hydroxymethyl)-2-methoxy-4-methylnicotinonitrile

To a stirred suspension of ethyl 5-cyano-6-methoxy-4-methylpicolinate (5.0 g, 22.70 mmol) and calcium chloride (10 g, 90 mmol) in tetrahydrofuran (50 mL) and ethanol (50.0 mL) at 0° C. in an ice bath was added sodium borohydride (2.5 g, 66.1 mmol). The reaction was slowly allowed to warm to RT and stirred for 18 hr. A large amount of ppt. formed and LCMS showed that the reaction was complete. An equal volume of EtOAc was added and the reaction stirred for 1 hr. The suspension was filtered through a pad of Celite and washed with EtOAc. The filtrate was transferred to a separatory funnel, washed with aq. $NH_4Cl$, brine, dried ($Na_2SO_4$), filtered and concentrated under vacuum. Purification by silica gel chromatography (Analogix, SF40-120g, 0 to 30% EtOAc in $CH_2Cl_2$) gave the product 6-(hydroxymethyl)-2-methoxy-4-methylnicotinonitrile (3.75 g, 21.05 mmol, 93% yield) as a white solid. $^1$H NMR (400 MHz, DMSO-$d_6$) δ 7.16 (s, 1H), 5.61 (t, J=5.8 Hz, 1H), 4.51 (d, J=5.8 Hz, 2H), 3.94 (s, 3H), 2.47 (s, 3H). MS(ES)+ m/e 179.1 [M+H]+.

b) (5-(Aminomethyl)-6-methoxy-4-methylpyridin-2-yl)methanol

A clear solution of 6-(hydroxymethyl)-2-methoxy-4-methylnicotinonitrile (0.50 g, 2.81 mmol) in HOAc (5 mL) and Ethanol (20 mL) was treated on an H-Cube apparatus (50 psi, 40° C., 1 mL/min., Raney Nickel cartridge) for 18 hr overnight. LCMS showed that the reaction was complete (crude contained 57% product and 43% dimeric side product). The reaction was evaporated to dryness under vacuum. Purified by silica gel chromatography (Analogix, SF25-40g, 0 to 12% (5% $NH_4OH$ in MeOH) in $CH_2Cl_2$) (step gradient to 8% to elute off the dimeric side product then to 12% to elute off the product). The pure fractions were combined and evaporated to dryness under vacuum to give the product (5-(aminomethyl)-6-methoxy-4-methylpyridin-2-yl)methanol (0.30 g, 1.646 mmol, 58.7% yield) as a white solid. MS(ES)+ m/e 183.1 [M+H]+, 166.1 [M+H]+—$NH_3$.

Intermediate 19 tert-Butyl ((5-(aminomethyl)-6-methoxy-4-methylpyridin-2-yl)methyl)carbamate

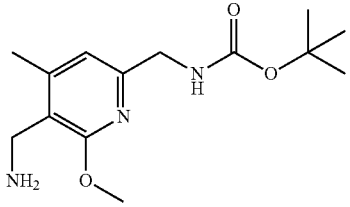 [SMILES: COc1nc(CNC(=O)OC(C)(C)C)cc(C)c1CN]

a) 6-((1,3-Dioxoisoindolin-2-yl)methyl)-2-methoxy-4-methylnicotinonitrile

To a stirred solution of 6-(hydroxymethyl)-2-methoxy-4-methylnicotinonitrile (1.50 g, 8.42 mmol), phthalimide (1.3 g, 8.84 mmol) and triphenylphosphine (2.3 g, 8.77 mmol) in Tetrahydrofuran (THF) (50 mL) at 0° C. in an ice bath was added dropwise DIAD (1.8 mL, 9.26 mmol). Within minutes a white suspension formed. Additional THF (~50 mL) was added to allow stirring. The reaction was allowed to warm to RT and stirred for 3 h. LCMS showed that the reaction was complete. The reaction was evaporated to dryness under vacuum. The remaining solid was triturated with a small volume of EtOAc, filtered, washed with a small volume of EtOAc, then dried under vacuum to give the product 6-((1,3-dioxoisoindolin-2-yl)methyl)-2-methoxy-4-methylnicotinonitrile (2.12 g, 6.90 mmol, 82% yield) as a white solid. $^1$H NMR (400 MHz, DMSO-$d_6$) δ 8.00-7.92 (m, 2H), 7.92-7.87 (m, 2H), 7.15 (s, 1H), 4.86 (s, 2H), 3.74 (s, 3H), 2.43 (s, 3H). MS(ES)+ m/e 308.2 [M+H]+.

b) tert-Butyl ((5-cyano-6-methoxy-4-methylpyridin-2-yl)methyl)carbamate

To a stirred fine suspension of 6-((1,3-dioxoisoindolin-2-yl)methyl)-2-methoxy-4-methylnicotinonitrile (2.1 g, 6.83 mmol) in Ethanol (100 mL) was added hydrazine monohydrate (1.4 ml, 28.9 mmol). The reaction was stirred at RT for 18 hr. LCMS showed that the reaction was done. The thick white suspension was filtered, pressed dry, washed with EtOH, and the filtrate evaporated to dryness under vacuum. The remaining solid was taken up in Dichloromethane (50 ml), filtered to remove additional insoluble material, and washed with $CH_2Cl_2$. To the clear filtrate with stirring was added $Boc_2O$ (1.809 ml, 7.79 mmol). After stirring at RT for 1 hr LCMS showed that the reaction was complete. The reaction was concentrated under vacuum and purified by silica gel chromatography (Analogix, SF25-60, 0 to 10% EtOAc in hexanes). The pure fractions were combined and evaporated to dryness to give the product tert-butyl ((5-cyano-6-methoxy-4-methylpyridin-2-yl)methyl)carbamate (1.42 g, 5.12 mmol, 74.9% yield) as a white solid. $^1$H NMR (400 MHz, DMSO-d$_6$) δ 7.48 (t, J=6.1 Hz, 1H), 6.91 (s, 1H), 4.16 (d, J=6.1 Hz, 2H), 3.96 (s, 3H), 2.45 (s, 3H), 1.41 (s, 9H). MS(ES)+ m/e 278.2 [M+H]$^+$.

c) tert-Butyl ((5-(aminomethyl)-6-methoxy-4-methylpyridin-2-yl)methyl)carbamate

A clear solution of tert-butyl ((5-cyano-6-methoxy-4-methylpyridin-2-yl)methyl)carbamate (0.65 g, 2.344 mmol) in HOAc (5 mL) and Ethanol (20 mL) was treated on an H-Cube apparatus (50 psi, 40° C., 1 mL/min., Raney Nickel cartridge) for 18 hr overnight. LCMS showed that the reaction was complete. The reaction was evaporated to dryness under vacuum. Purified by silica gel chromatography (Analogix, SF25-60g, 0 to 10% (5% NH$_4$OH/MeOH) in CH$_2$Cl$_2$). The pure fractions were combined and evaporated to dryness under vacuum to give the product tert-butyl ((5-(aminomethyl)-6-methoxy-4-methylpyridin-2-yl)methyl)carbamate (0.58 g, 2.061 mmol, 88% yield) as a clear thick oil. $^1$H NMR (400 MHz, DMSO-d$_6$) δ 7.31 (t, J=6.1 Hz, 1H), 6.63 (s, 1H), 4.06 (d, J=6.3 Hz, 2H), 3.84 (s, 3H), 3.61 (s, 2H), 2.29 (s, 3H), 1.53 (br. s., 2H), 1.41 (s, 9H). MS(ES)+ m/e 282.2 [M+H]$^+$.

Intermediate 20

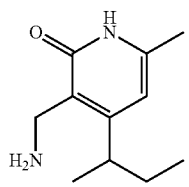

The title compound was prepared in the same manner as described for 3-(aminomethyl)-4-ethyl-6-methyl-2(1H)-pyridinone (Intermediate 10c). LCMS (ES+) m/z=195.22 (M+H). $^1$H NMR (DMSO-d$_6$, 400 MHz): δ 0.809-0.774 (t, 3H, J=6.8 Hz), 1.113-1.097 (d, 3H, J=6.4 Hz), 1.504-1.468 (t, 2H, J=7.2 Hz), 2.184 (s, 3H), 2.839-2.822 (d, 1H, J=6.8 Hz), 3.822 (s, 2H), 6.059 (s, 1H), 8.315 (bs, 2H).

Scheme 8

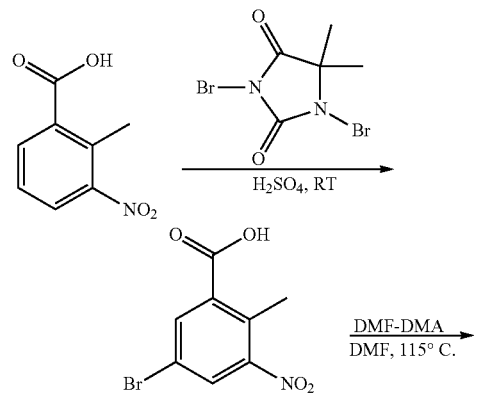

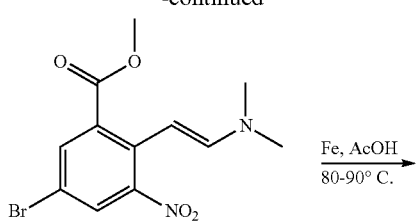

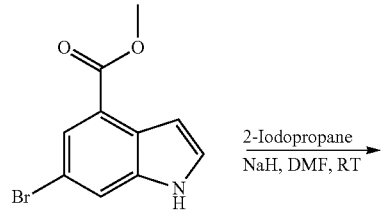

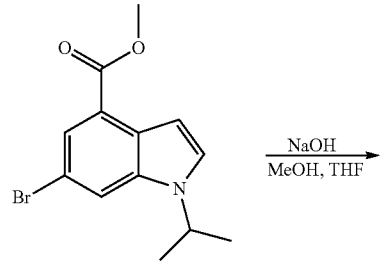

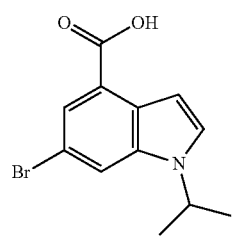

Intermediate 21

Methyl 6-bromo-1-isopropyl-1H-indole-4-carboxylate a) 5-Bromo-2-methyl-3-nitro-benzoic add

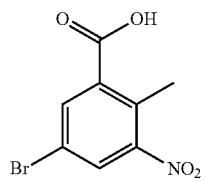

To a stirred solution of 2-methyl-3-nitro benzoic acid (300 g, 1647 mmol) in conc. H$_2$SO$_4$ (1.5 L) was added 1,3-dibromo-5,5 dimethyl-2,4-imadazolidinedione (258 g, 906 mmol) and the mixture was stirred at room temperature for 5 h. The reaction mixture was slowly added to ice water (4 L), and solid was precipitated out. The solid was filtered off and washed with water (1.2 L), pet ether (1 l) and dried to afford the title compound as a white solid (411 g, 96%), which was used without further purification. $^1$H NMR (DMSO, 400 MHz): δ2.446 (s, 3H), 8.136 (s, 1H), 8.294 (s, 1H). LCMS (ES−) m/z=257.93 (M−H)$^−$ b) Methyl 6-bromo-1H-indole-4-carboxylate

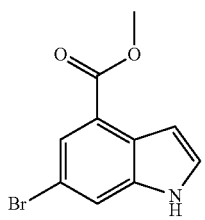

To a stirred solution of 5-bromo-2-methyl-3-nitro-benzoic acid (140 g, 538.4 mmol) in DMF (550 ml) was added DMF-DMA (599 mL, 4846 mmol) at room temperature. The reaction mixture was stirred at 115° C. for 18 h. The reaction mixture was then concentrated in vacuo. The residual contents (176 g, 536.5 mmol) were dissolved in acetic acid (696 mL) and added to a suspension of iron (329.2 g, 5902 mmol) in acetic acid (1.4 L) at 50° C. After completion of addition, the reaction mixture was stirred at 80-90° C. for 4 h. The reaction mixture was then filtered through a Celite pad. The filtrate was poured onto ice water (1 L) and extracted with diethyl ether (3×700 ml). The combined organic layers were washed with sat NaHCO$_3$, brine, and dried over anhydrous Na$_2$SO$_4$, filtered, and evaporated under vacuum. The crude product was purified by silica gel chromatography (eluent: 10% ethyl acetate in pet ether) and afforded the title compound as a solid (80 g, 59%). $^1$H NMR (DMSO-d$_6$, 400 MHz) δ: 3.980 (s, 3H), 7.168 (d, J=3.2 Hz, 1H), 7.334 (d, J=3.2 Hz, 1H), 7.734 (s, 1H), 8.017 (s, 1H), 8.384 (brs, 1H); LCMS (ES−) m/z=251.9 (M−H).

c) Methyl 6-bromo-1-isopropyl-1H-indole-4-carboxylate

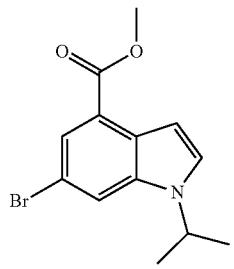 [SMILES: COC(=O)c1cc(Br)cc2c1ccn2C(C)C]

To a stirred solution of methyl 6-bromo-1H-indole-4-carboxylate (100 g, 393.7 mmol) in DMF (800 mL) was added 2-iodopropane (160 g, 944.8 mmol) followed by portionwise addition of sodium hydride (20.4 g, 511.8 mmol) at 0° C. The reaction mixture was stirred at room temperature for 18 h. Diluted the reaction mixture with cold water and extracted with ethylacetate (200 mL×4), finally organic layer was washed with cold water, brine solution dried over anhydrous Na$_2$SO$_4$ and concentrated under reduced pressure to afford crude, which was purified by column chromatography using silica gel (60-120 mesh) with 5% EtOAC: pet ether as an eluent to afford methyl 6-bromo-1-isopropyl-1H-indole-4-carboxylate (65 g, 55.7%) as a solid. $^1$H NMR (CDCl$_3$, 400 MHz) δ 1.53 (d, 6H, J=6.4 Hz), 3.973 (s, 3H), 4.598-4.664 (m, 1H), 7.111 (d, 1H, J=2.4 Hz), 7.338 (d, 1H, J=2.8 Hz), 7.711 (s, 1H), 7.987 (s, 1H).

d) 6-Bromo-1-(1-methylethyl)-1H-indole-4-carboxylic acid

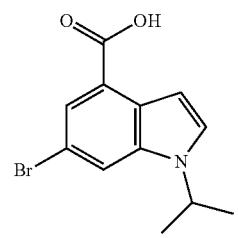 [SMILES: CC(C)n1ccc2c(C(=O)O)cc(Br)cc21]

To a solution of methyl 6-bromo-1-(1-methylethyl)-1H-indole-4-carboxylate (0.52 g, 1.756 mmol) in methanol (15 mL) and tetrahydrofuran (3 mL) was added 3M NaOH (1.756 mL, 5.27 mmol) via syringe drop wise (over 2 min). The solution was maintained at RT for 2 h, at which time LCMS showed only 12% conversion to product. Then 1.5 mL 3M NaOH was added and the solution was maintained at RT overnight. LCMS showed complete conversion to product. Removed volatiles in vacuo and dissolved the residue in water and slowly acidified with 1M HCl (solids precipitated). Extracted with EtOAc (2×), combined organics and dried over MgSO$_4$. Filtered and concentrated in vacuo to give 6-bromo-1-(1-methylethyl)-1H-indole-4-carboxylic acid (0.50 g, 1.737 mmol, 99% yield) as a white solid.

Alternatively, the alkylation of the indole nitrogen could be performed as follows: To a cooled (0° C.) suspension of methyl 6-bromo-1H-indole-4-carboxylate (10 g, 39.4 mmol) and (cyanomethyl)(trimethyl)phosphonium chloride (14.91 g, 98 mmol) in THF (400 mL) was added 2-propanol (6.06 mL, 79 mmol), followed by sodium hydride (3.46 g, 87 mmol). The mixture was stirred at ambient temperature for 2 h, at which time LCMS showed no product formation. Heated at 50° C. for 18 h. LC/MS showed reaction complete. Filtered reaction mixture and concentrated in vacuo. The residue was diluted with methylene chloride and passed through a pad of silica (washed with methylene chloride). Purification by flash chromatography (Analogix SF65-200g; 5-10% EtOAc/hexanes) gave methyl 6-bromo-1-(1-methylethyl)-1H-indole-4-carboxylate (9.7 g, 31.4 mmol, 80% yield). MS(ES) [M+H]$^+$ 296.2, 298.4.

Examples 22-23 were prepared by the methods described above for Intermediate 16 or routine variations thereof, starting from the requisite 2-methyl-3-nitrobenzoic acid:

| Ex | Structure | Name | 1H NMR | MS(ES) [M + H]+ |
|---|---|---|---|---|
| 22 | (structure) | 6-fluoro-1-(1-methylethyl)-1H-indole-4-carboxylic acid | 1.44 (d, 6 H), 4.63-4.96 (m, 1 H), 6.97 (d, J = 3.03 Hz, 1 H), 7.46 (dd, J = 10.36, 2.27 Hz, 1 H), 7.67 (d, J = 3.28 Hz, 1 H), 7.75 (dd, J = 10.11, 2.02 Hz, 1 H), 12.97 (s, 1 H) | 222.1 |
| 23 | (structure) | 6-chloro-1-(1-methylethyl)-1H-indole-4-carboxylic acid | (CHLOROFORM-d) 1.57 (d, 6 H), 4.67 (spt, J = 6.69 Hz, 1 H), 7.19 (d, J = 3.03 Hz, 1 H), 7.41 (d, J = 3.28 Hz, 1 H), 7.63 (d, J = 1.01 Hz, 1 H), 7.97 (d, J = 1.77 Hz, 1 H) | 237.9 |

Scheme 9

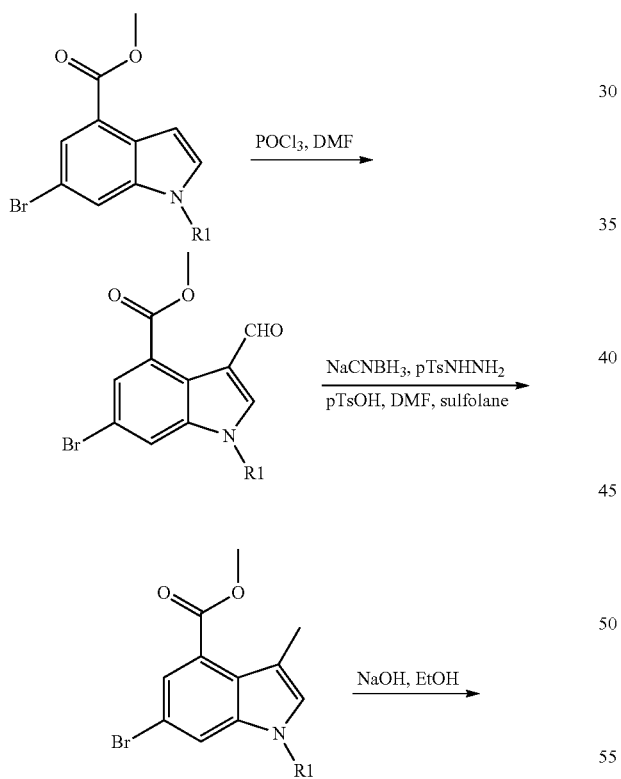

Intermediate 24

Meth 6-bromo-1-isopropyl-1H-indole-4-carboxylate

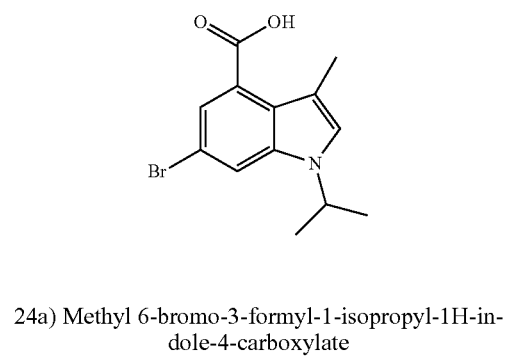

24a) Methyl 6-bromo-3-formyl-1-isopropyl-1H-indole-4-carboxylate

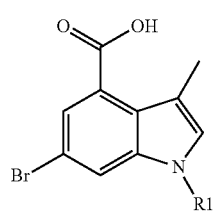

To a stirred solution of DMF (1.04 lit) POCl$_3$ (40.3 g, 263 mmol) was added at 0° C. and stirred for 20 min. Then methyl 6-bromo-1-isopropyl-1H-indole-4-carboxylate (65 g, 219.5 mmol) in DMF (260 mL) was added to the reaction mixture at 0° C. The reaction mixture was stirred at room temperature for 3 h. Diluted the reaction mixture with cold water and adjusted PH~8 using with 2N NaOH solution, extracted with ethylacetate (4×1 lit). The organic layer washed with cold water, brine solution, dried over anhydrous Na$_2$SO$_4$ and concentrated under reduced pressure to afford desired product methyl 6-bromo-3-formyl-1-isopropyl-1H-indole-4-carboxylate (65 g, 91.3%). ¹H NMR (CDCl₃, 400 MHz): δ 1.588 (d, 6H, J=6.8 Hz), 3.994 (s, 3H), 4.634-4.701 (m, 1H), 7.760 (d, 1H, J=1.6 Hz), 7.958 (d, 1H, J=1.6 Hz), 8.122 (s, 1H), 10.446 (s, 1H). LC-MS (ES+) m/z=324.02 (M+H)

24b) Methyl 6-bromo-1-isopropyl-3-methyl-1H-indole-4-carboxylate

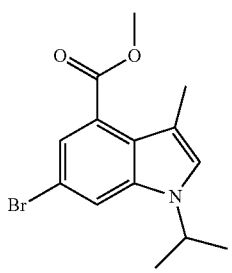

To a stirred solution of methyl 6-bromo-3-formyl-1-isopropyl-1H-indole-4-carboxylate (60 g, 185 mmol) in DMF (220 mL) was added p-toluenesulfonic acid mono hydride (4.57 g, 24 mmol), p-toluenesulfonyl hydrazide (44.8 g, 240 mmol) followed by sulfolane (220 mL). The mixture was stirred at 100° C. for 1 h. The contents were cooled to room temperature and then sodium cyanoborohydride (46.5 g, 740 mmol) was added portion wise over a period of 25 min. Then the mixture was stirred at 100° C. for 2 h. Then the reaction mixture was stirred for 16 h at room temperature. The reaction mixture was diluted with water and extracted with 20% EtOAc: Pet ether, finally organic layer was washed with cold water, brine solution dried over anhydrous Na₂SO₄ and concentrated. Crude compound was purified by column chromatography using silica gel (100-200 mesh) and 20% DCM:Pet ether as an eluent to afford desired product methyl 6-bromo-1-isopropyl-3-methyl-1H-indole-4-carboxylate (24 g, 89.2% purity), (16 g, and 62.2% purity). ¹H NMR (CDCl₃, 400 MHz) δ 1.486 (d, J=6.4 Hz, 6H), 2.361 (s, 3H), 3.947 (s, 3H), 4.535-4.602 (m, 1H), 7.080 (s, 1H), 7.619 (s, 1H), 7.684 (s, 1H). LCMS (ES+) m/z=310.07 (M+H)

24c) 6-Bromo-1-isopropyl-3-methyl-1H-indole-4-carboxylic acid

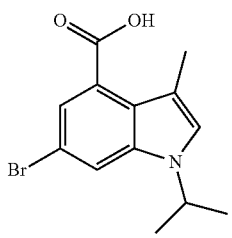

To a stirred solution of methyl 6-bromo-1-isopropyl-3-methyl-1H-indole-4-carboxylate (24 g, 77.4 mmol) in ethanol (400 mL) was added sodium hydroxide (4.02 g, 100.6 mmol), water (11 mL) and the mixture was stirred at reflux condition for 6 h. Ethanol was distilled off and residue was diluted with water, extracted with ethylacetate (40 mL) adjusted aqueous layer to PH~3 with 1N HCl and extracted with ethyl acetate (3×250 mL), finally organic layer was washed with brine solution, dried over anhydrous Na₂SO₄ and concentrated. The crude was washed with pet ether, filtered the solid and dried to afford desired product 6-bromo-1-isopropyl-3-methyl-1H-indole-4-carboxylic acid (20.6 g, 89.8%). ¹H NMR (DMSO-d₆, 400 MHz): δ 1.407 (d, J=6.4 Hz, 6H), 2.296 (s, 3H), 4.754-4.819 (m, 1H), 7.455 (s, 1H), 7.472 (s, 1H), 7.938 (s, 1H), 12.950 (brs, 1H). LCMS (ES+) m/z=296.15 (M+H).

Intermediate 25

6-Bromo-1-(sec-butyl)-3-methyl-1H-indole-4-carboxylic acid

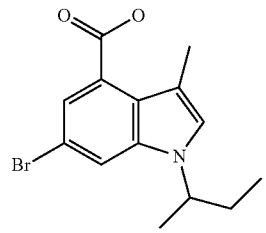 [SMILES: CCC(C)n1cc(C)c2c(C(=O)O)cc(Br)cc21]

a) Methyl 6-bromo-1-sec-butyl-1H-indole-4-carboxylate

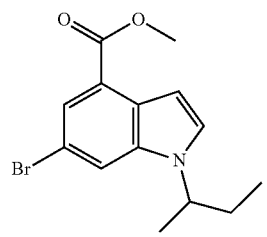 [SMILES: CCC(C)n1ccc2c(C(=O)OC)cc(Br)cc21]

To a stirred suspension of sodium hydride (5.66 g, 141.7 mmol) in DMF (100 mL) was added a solution of methyl 6-bromo-1H-indole-4-carboxylate (4) (30 g, 118.1 mmol) in DMF (50 mL) at 0° C. and stirred for 20 min. Then 2-Bromo butane (29.1 g, 212.5 mmol) was added at 0° C. and the reaction mixture was stirred at room temperature for 16 h. The reaction mixture was diluted with cold water and extracted with ethyl acetate (4×150 mL). The combined organic layer was washed with cold water (150 mL), brine (100 mL) and dried over anhydrous Na₂SO₄ and concentrated under reduced pressure to afford crude, which was purified by column chromatography over silica gel (60-120 mesh) using 5% EtOAc: Pet ether as eluent to afford the title compound methyl 6-bromo-1-sec-butyl-1H-indole-4-carboxylate, 5 (14 g, 40.1%) as pale yellow solid. ¹H NMR (CDCl₃, 400 MHz) δ 0.843-0.870 (m, 3H), 1.512 (d, J=6.4 Hz, 3H), 1.844-1.926

(m, 2H), 3.976 (s, 3H), 4.333-4.385 (m, 1H), 7.132 (d, J=3.2 Hz, 1H), 7.302 (d, J=3.6 Hz, 1H), 7.707 (s, 1H), 7.984 (d, J=1.6 Hz, 1H).

b) Methyl 6-bromo-1-sec-butyl-3-formyl-1H-indole-4-carboxylate

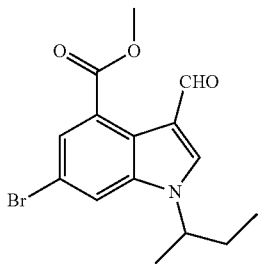 [SMILES: CCC(C)n1cc(C=O)c2c(C(=O)OC)cc(Br)cc21]

POCl$_3$ (8.3 g, 54.3 mmol) was added at 0° C. to anhydrous DMF (230 mL) in a round bottom flask and stirred for 30 min. Then a solution of methyl 6-bromo-1-sec-butyl-1H-indole-4-carboxylate, 5 (14 g, 45.3 mmol) in DMF (60 mL) was added to the reaction mixture at 0° C. and stirred at room temperature for 2.5 h. The reaction mixture was diluted with cold water, adjusted pH~8 using with 2N NaOH solution and extracted with ethyl acetate (4×200 mL). The combined organic layer was washed with cold water (2×100 mL), brine (100 mL), dried over anhydrous Na$_2$SO$_4$ and concentrated under reduced pressure to afford desired product methyl 6-bromo-1-sec-butyl-3-formyl-1H-indole-4-carboxylate, 6 (15.2 g, 99%) as pale yellow solid. This was used as such in the next step without purification. $^1$H NMR (CDCl$_3$, 400 MHz) δ (0.831-0.859 (m, 3H), 1.515-1.574 (d, J=6.8 Hz, 3H), 1.729-1.972 (m, 2H) 3.997 (s, 3H), 4.394-4.445 (m, 1H), 7.756 (d, J=1.2 Hz, 1H), 7.958 (d, J=2 Hz, 1H), 8.079 (s, 1H), 10.452 (s, 1H).

c) Methyl 6-bromo-1-sec-butyl-3-methyl-1H-indole-4-carboxylate

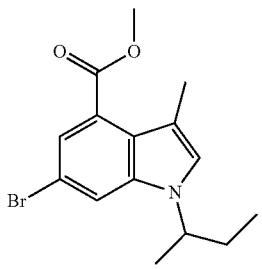 [SMILES: CCC(C)n1cc(C)c2c(C(=O)OC)cc(Br)cc21]

To a stirred solution of methyl 6-bromo-1-sec-butyl-3-formyl-1H-indole-4-carboxylate (15 g, 44.6 mmol) in DMF (115 mL) was added p-toluenesulfonic acid mono hydrate (1.1 g, 5.8 mmol), p-toluenesulfonyl hydrazide (10.8 g, 58 mmol) followed by sulfolane (115 mL) at RT and the reaction mixture was stirred at 100° C. for 1 h. The reaction mixture was cooled to room temperature, treated with sodium cyanoborohydride (11.9 g, 178.5 mmol) portion wise over a period of 5 min and stirred at 100° C. for 2 h. The reaction mixture was cooled to room temperature and stirred at the same temperature for 16 h. The reaction mixture was diluted with water and extracted with 30% EtOAc: Pet ether. The organic layer was washed with cold water (100 mL), brine (100 mL) and dried over anhydrous Na$_2$SO$_4$ and concentrated under reduced pressure to afford crude, which was purified by column chromatography over silica gel (100-200 mesh) using 5% EtOAc: Pet ether as eluent to afford title compound methyl 6-bromo-1-sec-butyl-3-methyl-1H-indole-4-carboxylate (7.88 g, 54.6%) as pale yellow gum. $^1$H NMR (CDCl$_3$, 400 MHz): δ 0.804-0.841 (t, J=7.4 Hz, 3H), 1.454-1.470 (d, J=6.4 Hz, 3H), 1.865-1.884 (m, 2H), 2.363 (s, 3H), 3.950 (s, 3H), 4.265-4.316 (m, 1H), 7.038 (s, 1H), 7.609 (d, J=1.2 Hz, 1H), 7.671 (d, J=2 Hz, 1H). MS (ES+): 324.19 [M+H] ion present.

d) 6-Bromo-1-(sec-butyl)-3-methyl-1H-indole-4-carboxylic acid

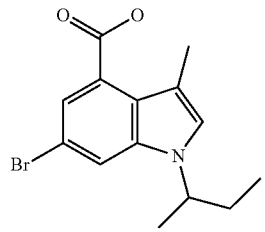 [SMILES: CCC(C)n1cc(C)c2c(C(=O)O)cc(Br)cc21]

Methyl 6-bromo-1-(sec-butyl)-3-methyl-1H-indole-4-carboxylate (3.24 g, 9.99 mmol) was dissolved in methanol (30 mL) and tetrahydrofuran (THF) (7 mL). The contents were stirred for 5 min., and then aq. 3N NaOH (19.99 mL, 60.0 mmol) was added via addition funnel over 3 min. The contents rapidly became a yellow suspension and were stirred at room temperature for 65 h. The volatiles were removed in vacuo and the residue dissolved in water (60 mL). The contents were washed with ether (1×50 mL). The aq layer was cooled in an ice bath and adjusted to pH 3-4 with 1M HCl, from which an oily residue precipitated. The contents were extracted with EtOAc (2×60 mL). The combined organic layers were dried over magnesium sulfate, filtered through celite, and concentrated in vacuo. The residue obtained was treated with TBME, concentrated in vacuo, and then dried under hi vacuum to afford a yellow foam as 3.08 g (93%). $^1$H NMR (400 MHz, DMSO-d$_6$) δ ppm 0.70 (t, J=7.33 Hz, 3H), 1.39 (d, J=6.82 Hz, 3H), 1.71-1.86 (m, 2H), 2.30 (s, 3H), 4.48-4.62 (m, 1H), 7.40-7.49 (m, 2H), 7.96 (d, J=1.77 Hz, 1H), 12.99 (s, 1H); LCMS=310.0/312.0 (MH+).

Examples 26-27 were prepared by the methods described above for Intermediate 16 or routine variations thereof, starting from the requisite 6-substituted indole:

| Ex | Structure | Name | 1H NMR | MS(ES) [M + H]+ |
|---|---|---|---|---|
| 26 | 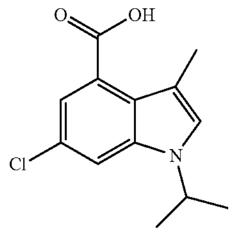 [SMILES: Cc1cn(C(C)C)c2cc(Cl)cc(C(=O)O)c12] | 6-chloro-3-methyl-1-(1-methylethyl)-1H-indole-4-carboxylic acid | 12.99 (br. s., 1 H), 7.82 (d, J = 2.0 Hz, 1 H), 7.47 (d, J = 1.0 Hz, 1 H), 7.36 (d, J = 2.0 Hz, 1 H), 4.78 (quin, J = 6.6 Hz, 1 H), 2.30 (d, J = 1.0 Hz, 3 H), 1.41 (d, J = 6.6 Hz, 6 H) | 252.4 |
| 27 | 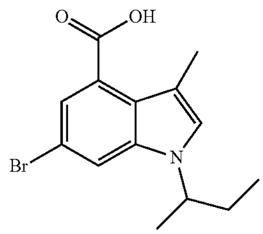 [SMILES: CCC(C)n1cc(C)c2c(C(=O)O)cc(Br)cc21] | 6-bromo-1-(sec-butyl)-3-methyl-1H-indole-4-carboxylic acid | 0.70 (t, J = 7.33 Hz, 3 H) 1.39 (d, J = 6.82 Hz, 3 H) 1.71-1.86 (m, 2 H) 2.30 (s, 3 H) 4.48-4.62 (m, 1 H) 7.40-7.49 (m, 2 H) 7.96 (d, J = 1.77 Hz, 1 H) 12.99 (s, 1 H) | 310.0 |

Intermediate 28

6-Bromo-1-cyclopropyl-1H-indole-4-carboxylic acid

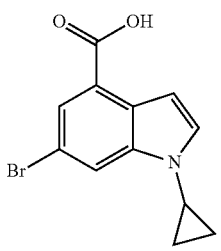 [SMILES: O=C(O)c1cc(Br)cc2c1ccn2C1CC1]

a) Methyl 6-bromo-1-cyclopropyl-1H-indole-4-carboxylate

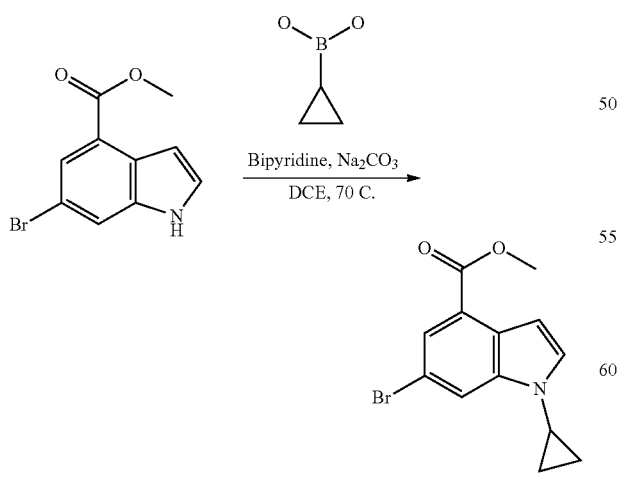

In a oven dried 100 ml RBF equipped, stir bar, septum and Nitrogen inlet was added methyl 6-bromo-1H-indole-4-carboxylate (0.508 g, 2.0 mmol) and 1,2-dichloroethane (7 mL). The solution was stirred for 15 min, then cyclopropylboronic acid (0.344 g, 4.00 mmol) and sodium carbonate (0.424 g, 4.00 mmol) were added. Diluted copper(II) acetate (0.363 g, 2.000 mmol) and 2,2'-bipyridine (0.312 g, 2.000 mmol) in 1,2-dichloroethane (12 mL), heated the mixture, and added the hot suspension to the reaction. The reaction was heated at 70° C. and monitored by LCMS. Stopped heating after 6 h and allowed to sit for 3 days at RT. Added to reaction saturated NH$_4$Cl and water. Extracted with DCM (2×). The combined organics were washed with brine, dried over magnesium sulfate, filtered and concentrated in vacuo. Purification of the residue by column chromatography (24 g Isco silica column; gradient B: 3-25%. A: hexane. B: ethyl acetate) to give methyl 6-bromo-1-cyclopropyl-1H-indole-4-carboxylate (0.43 g, 1.433 mmol, 71.6% yield) as a yellow residue. $^1$H NMR (400 MHz, DMSO-d$_6$) δppm 0.96-1.01 (m, 2H) 1.06-1.12 (m, 2H) 3.52 (dt, J=7.20, 3.47 Hz, 1H) 3.90 (s, 3H) 6.85-6.91 (m, 1H) 7.57 (d, J=3.03 Hz, 1H) 7.82 (d, J=1.77 Hz, 1H) 8.04 (d, J=1.01 Hz, 1H).

MS(ES) [M+H]$^+$ 294.1.

b) 6-Bromo-1-cyclopropyl-1H-indole-4-carboxylic acid

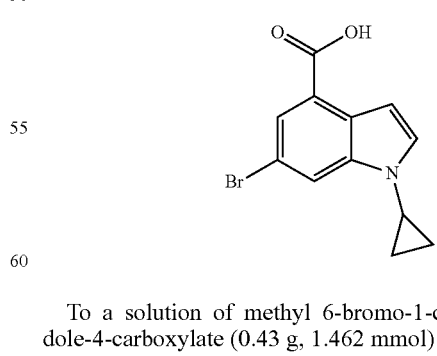

To a solution of methyl 6-bromo-1-cyclopropyl-1H-indole-4-carboxylate (0.43 g, 1.462 mmol) in MeOH (12 mL) and THF (3 mL) was added 3M NaOH (1.949 mL, 5.85 mmol). The reaction was stirred for 18 h at RT, at which time the volatiles were removed in vacuo. The residue was diluted with water and slowly acidified with 1N HCl to pH 4-5, then extracted with EtOAc (2×). The combine organics were wash with brine, dried over magnesium sulfate, filtered, and concentrated to give 6-bromo-1-cyclopropyl-1H-indole-4-carboxylic acid (0.376 g, 1.315 mmol, 90% yield) as a pale yellow solid. $^1$H NMR (400 MHz, DMSO-d$_6$) δ ppm 0.92-1.01 (m, 2H) 1.05-1.12 (m, 2H) 3.51 (tt, J=7.07, 3.66 Hz, 1H) 6.89 (d, J=2.53 Hz, 1H) 7.52 (d, J=3.03 Hz, 1H) 7.80 (d, J=1.77 Hz, 1H) 7.99 (d, J=1.01 Hz, 1H) 13.05 (br. s., 1H). MS(ES) [M+H]$^+$ 280.1.

Intermediate 29

6-Bromo-1-cyclobutyl-1H-indole-4-carboxylic acid

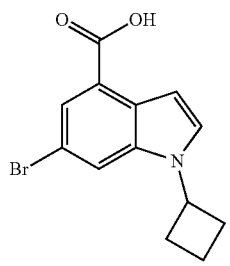 [SMILES: O=C(O)c1cc(Br)cc2c1ccn2C1CCC1]

a) Methyl 6-bromo-1-cyclobutyl-1H-indole-4-carboxylate

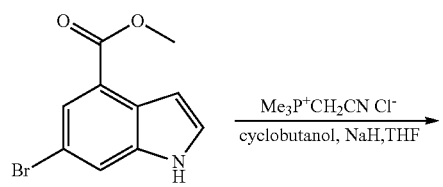

In an oven dried 100 ml RBF, equipped with a stir bar, septum, nitrogen inlet was added methyl 6-bromo-1H-indole-4-carboxylate (1.0 g, 3.94 mmol) and (cyanomethyl)(trimethyl)phosphonium chloride (1.491 g, 9.84 mmol). Added in THF (40 mL) and stirred suspension for 5 min. The reaction was cooled with an ice bath for 10 min, then was added cyclobutanol (0.616 mL, 7.87 mmol), followed by sodium hydride (0.346 g, 8.66 mmol) portionwise. The ice bath was removed and the reaction stirred at ambient temperature for 45 min, then heated at 50° C. for 18 h. LCMS showed mostly SM. Heated at 75° C. for 24 h. The reaction was allowed to cool to RT, then poured into water (200 ml) and extracted with EtOAc (2×). The combined organics were dried over magnesium sulfate, filtered, and concentrated. Purification of the residue by column chromatography (40 g Isco silica column; gradient B: 2-25%; A: hexane, B: EtOAc) gave methyl 6-bromo-1-cyclobutyl-1H-indole-4-carboxylate (0.3 g, 25% yield, ~45% pure by HPLC). MS(ES) [M+H]$^+$ 308.2.

b) 6-Bromo-1-cyclobutyl-1H-indole-4-carboxylic acid

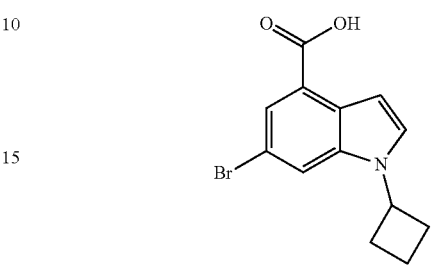

To a solution of ethyl 6-bromo-1-cyclobutyl-1H-indole-4-carboxylate (0.3 g, 0.973 mmol) (crude residue from above) in MeOH (8 mL) and THF (2 mL) was added 3M NaOH (1.298 mL, 3.89 mmol). The reaction was stirred at RT for 16 h, at which time the volatiles were removed in vacuo. The residue was diluted with water and slowly acidified with 1N HCl to pH 3-4. The solids were filtered and dried on hivac for 16 h to give 6-bromo-1-cyclobutyl-1H-indole-4-carboxylic acid (0.21 g, 0.535 mmol, 55.0% yield). $^1$H NMR (400 MHz, DMSO-d$_6$) δ ppm 1.79-1.89 (m, 2H) 2.34-2.46 (m, 2H) 3.84 (s, 1H) 5.08 (t, J=8.21 Hz, 1H) 6.99 (d, J=3.03 Hz, 1H) 7.75-7.79 (m, 1H) 7.81 (d, J=3.03 Hz, 1H) 8.01-8.05 (m, 1H) 13.03 (br. s., 1H). MS(ES) [M+H]$^+$ 294.1.

Intermediate 30

1-Isopropyl-3-methyl-6-(methylsulfonyl)-1H-indole-4-carboxylic acid

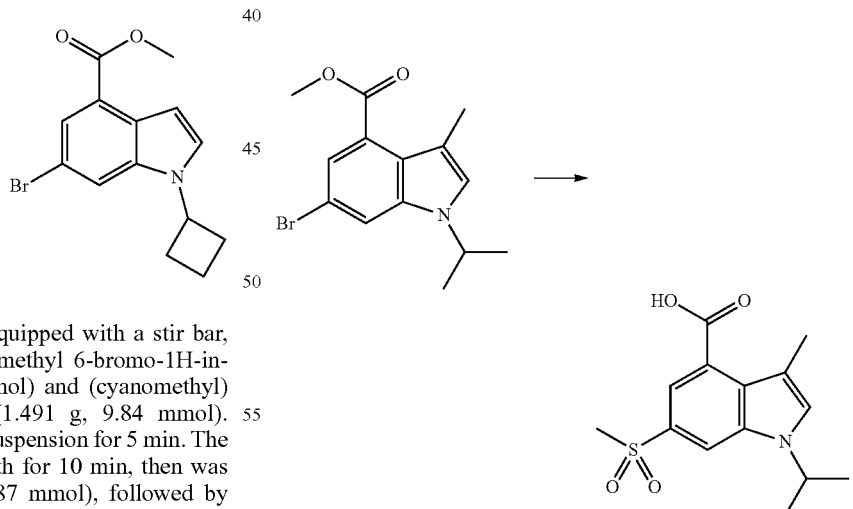

To a 30-mL microwave tube were added methyl 6-bromo-3-methyl-1-(1-methylethyl)-1H-indole-4-carboxylate (490 mg, 1.580 mmol), methanesulfinic acid (212 mg, 2.054 mmol), DMSO (7 mL), N,N'-dimethyl-1,2-ethanediamine (18.10 mg, 0.205 mmol), and the mixture was degassed for 5 min by bubbling N2. Copper(I) trifluoromethanesulfonate benzene complex (63.6 mg, 0.126 mmol) was added and the tube was sealed. The mixture was heated at 165° C. overnight with stirring. The mixture was allowed to cool, filtered and purified using reverse-phase HPLC (Gemini 5u C18(2) 100A, AXIA; 30×100 mm 5 micron; 30 mL/min, 30% ACN/H2O, 0.1% formic acid to 60% ACN/H2O, 0.1% formic acid) to give the title compound (118 mg, 25%) as a white solid. ¹H NMR (400 MHz, DMSO-d₆) ppm 1.47 (d, J=8.00 Hz, 6H), 2.30-2.41 (m, 3H), 4.94 (quin, J=6.63 Hz, 1H), 7.80 (s, 1H), 7.88 (d, J=1.77 Hz, 1H), 8.24 (d, J=1.52 Hz, 1H), 13.17 (br. s., 1H). MS: (M+H)⁺=296.3.

Intermediate 31

1-Isopropyl-6-(methylsulfonyl)-1H-indole-4-carboxylic acid

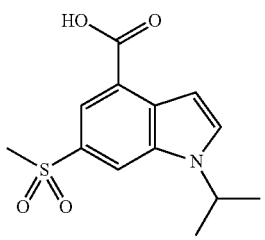 [SMILES: CC(C)n1ccc2c(C(=O)O)cc(S(C)(=O)=O)cc21]

To a 10-mL microwave tube were added methyl 6-bromo-1-(1-methylethyl)-1H-indole-4-carboxylate (160 mg, 0.540 mmol), sodium methanesulfinate (80 mg, 0.702 mmol), DMSO (2 mL), and N,N'-dimethyl-1,2-ethanediamine (6.19 mg, 0.070 mmol), and the mixture was degassed for 5 min by bubbling N₂. Copper(I) trifluoromethanesulfonate benzene complex (25.6 mg, 0.043 mmol) was added and the mixture was heated to 165° C. for 2 h with stirring. The mixture was filtered and the DMSO solution was purified using reverse-phase HPLC to give 14 mg of product as white solid. ¹H NMR (400 MHz, DMSO-d₆) ppm 1.51 (d, J=4.00 Hz, 6H), 4.90-5.11 (m, 1H), 7.13 (d, J=3.03 Hz, 1H), 7.98-8.08 (m, 1H), 8.15-8.23 (m, 1H), 8.32-8.46 (m, 1H), 13.19 (br. s., 1H). MS: (M+H)⁺=281.9.

Intermediate 32

6-(Cyclopropylsulfonyl)-1-(1-methylethyl)-1H-indole-4-carboxylic acid

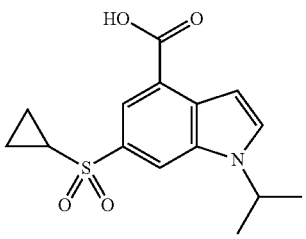 [SMILES: CC(C)n1ccc2c(C(=O)O)cc(S(=O)(=O)C3CC3)cc21]

¹H NMR (400 MHz, DMSO-d₆) δ ppm 1.03 (dd, J=7.71, 2.40 Hz, 2H), 1.17 (dd, J=7.20, 3.41 Hz, 2H), 1.50 (d, 6H), 2.83-2.97 (m, 1H), 5.02 (dt, J=13.14, 6.57 Hz, 1H), 7.17 (d, J=2.27 Hz, 1H), 7.99 (d, J=3.03 Hz, 1H), 8.13 (s, 1H), 8.28 (s, 1H). MS: (M+H)⁺=308.3.

Intermediate 33

6-Hydroxy-1-isopropyl-1H-indole-4-carboxylic acid methyl ester

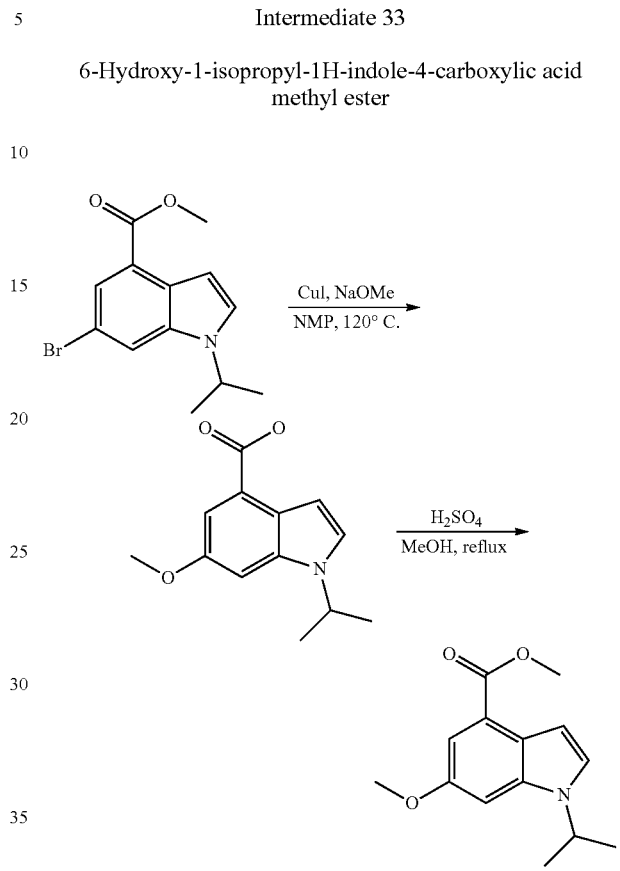

Freshly prepared sodium methoxide (500 mg in 5 mL methanol) was added to a stirred suspension of 6-bromo-1-isopropyl-1H-indole-4-carboxylic acid methyl ester (500 mg, 1.68 mmol) and CuI (480 mg, 2.53 mmol) in NMP (8 mL) and then heated at 120° C. for 2 h. The reaction mixture was cooled to room temperature, diluted with water (5 mL) and acidified with 1N HCl. The reaction mixture was filtered through Celite and washed with EtOAc (5 mL). Separated the EtOAc layer from filtrate, dried over anhydrous Na₂SO₄ and concentrated under reduced pressure to furnish the crude 1-isopropyl-6-methoxy-1H-indole-4-carboxylic acid (700 mg), which was used in the next stage without further purification. ¹H NMR (400 MHz, DMSO-d₆): δ 1.44 (d, J=6.4 Hz, 6H), 3.84 (s, 3H), 4.80-4.76 (m, 1H), 6.87 (d, 1H), 7.33 (t, J=3.2 Hz, 2H), 7.49 (d, J=3.2 Hz, 1H), 12.65 (bs, 1H). LCMS (ES+): m/z=234.11 [M+H].

To a stirred suspension of 1-isopropyl-6-methoxy-1H-indole-4-carboxylic acid (700 mg, 3.00 mmol) in MeOH was added H₂SO₄ (440 mg, 4.50 mmol) and then heated at reflux for 3 h. Methanol was distilled off completely under reduced pressure and the residue basified with saturated aqueous NaHCO₃ solution and extracted with ethyl acetate (2×5 mL). The combined organic layers were dried over anhydrous Na₂SO₄, filtered and concentrated. The residue was purified by column chromatography (SiO₂, 100-200) by eluting 5% ethyl acetate in petroleum ether to afford 1-isopropyl-6-methoxy-1H-indole-4-carboxylic acid methyl ester (240 mg, 32.4%) as white solid. ¹H NMR (400 MHz, DMSO-d₆): δ 1.45 (d, J=6.8 Hz, 6H), 3.84 (s, 3H), 3.88 (s, 3H), 4.81-4.78

(m, 1H), 6.86 (d, J=3.2 Hz, 1H), 7.34 (d, J=2.4 Hz, 1H), 7.39 (d, J=2 Hz, 1H), 7.54 (d, J=3.6 Hz, 1H). LCMS (ES+): m/z=248.16 [M+H].

Intermediate 34

1-Isopropyl-6-methoxy-1H-indole-4-carboxylic acid

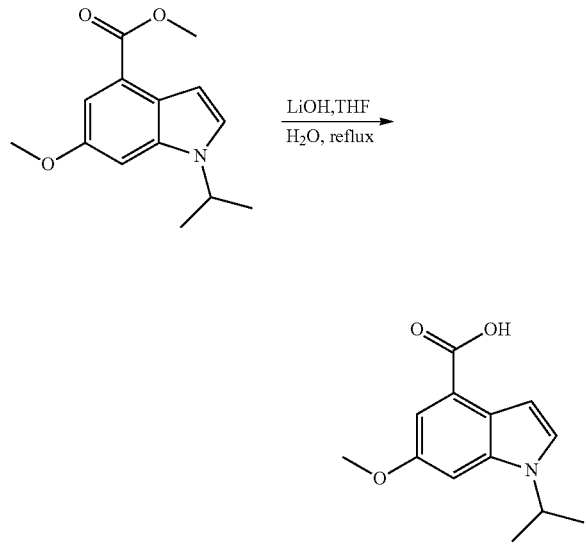

To a stirred solution of 1-isopropyl-6-methoxy-1H-indole-4-carboxylic acid methyl ester (320 mg, 1.29 mmol) in THF (2 mL) was added LiOH.H$_2$O (160 mg, 3.88 mmol) in water (2 mL) at room temperature and heated at reflux for 2 h. The THF was removed under reduced pressure and the resulting aqueous layer was acidified with 1N HCl (pH 6) and extracted with ethyl acetate (2×5 mL). The combined organic layer was dried over anhydrous Na$_2$SO$_4$ and concentrated to afford 1-isopropyl-6-methoxy-1H-indole-4-carboxylic acid (210 mg). $^1$H NMR (400 MHz, DMSO-d$_6$): δ 1.42 (d, 6H), 3.88 (s, 3H), 4.85 (m, 1H), 6.81 (d, J=2.8 Hz, 1H), 7.26 (s, 2H), 7.45 (s, 1H), 12.68 (s, 1H).

Intermediate 35

6-Hydroxy-1-isopropyl-1H-indole-4-carboxylic acid methyl ester

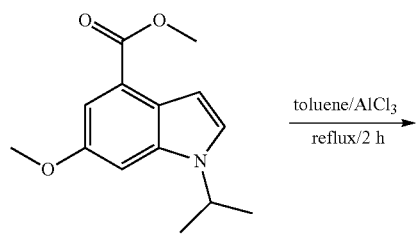

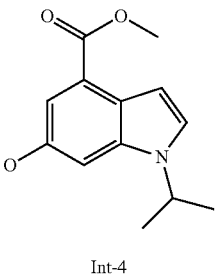

Int-4

To a stirred solution of 1-isopropyl-6-methoxy-1H-indole-4-carboxylic acid methyl ester (1.9 g, 7.69 mmol) in toluene (20 mL) was added anhydrous aluminum chloride (5.11 g, 38.4 mmol) at room temperature and then heated to reflux for 2 h. The reaction mixture was diluted with water and extracted with ethyl acetate (2×20 mL). The combined organic layer was dried over Na$_2$SO$_4$ and concentrated under reduced pressure. The residue was purified by column chromatography by eluting 3-15% Ethyl acetate in petroleum ether to afford the title compound 6-hydroxy-1-isopropyl-1H-indole-4-carboxylic acid methyl ester (1.5 g, 83%) as yellow colored gum. $^1$H NMR (400 MHz, DMSO-d$_6$): δ 1.43 (d, J=6.8 Hz, 6H), 3.86 (s, 3H), 4.65-4.61 (m, 1H), 6.81 (d, J=2.8 Hz, 1H), 7.11 (s, 1H), 7.29 (s, 1H), 7.44 (d, J=2.8 Hz, 1H), 9.32 (bs, 1H). LCMS (ES+): m/z=234.09 [M+H]

Intermediate 36

3-Methyl-1-(1-methylethyl)-6-(methyloxy)-1H-indole-4-carboxylic acid

To methyl 6-bromo-3-methyl-1-(1-methylethyl)-1H-indole-4-carboxylate (1.3 g, 4.19 mmol) and copper(I) iodide (1.0 g, 5.25 mmol) was added NMP (8 mL). To the mixture was added dropwise a solution of sodium methoxide 25 wt % in methanol (4.0 mL, 17.49 mmol) with stirring. The reaction was heated to 120° C. and stirred for 1.5 hr. The reaction was allowed to cool and when the temperature reached 80° C., water (200 uL) was added. The reaction was allowed to continue to cool to RT and stirred overnight. The reaction was acidified with 1N HCl (17 mL) and diluted with water and EtOAc. The mixture was filtered through Celite and washed with EtOAc. The filtrate was poured into a separatory funnel and the organic phase was separated, washed with brine, dried (MgSO$_4$), filtered, and concentrated under vacuum. Purification by silica gel chromatography (Analogix, SF25-60g, 20 to 50% EtOAc in hexanes) gave after concentration, trituration with hexanes, filtration and drying under vacuum 3-methyl-1-(1-methylethyl)-6-(methyloxy)-1H-indole-4-carboxylic acid (825 mg, 3.34 mmol, 80% yield) as an light yellow solid. MS(ES)+ m/e 248.3 [M+H]+.

Intermediate 37

6-Iodo-1-(1-methylethyl)-1H-indole-4-carboxylic acid

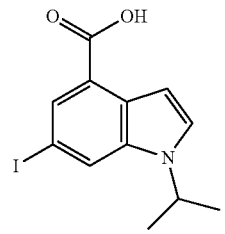 [SMILES: CC(C)n1ccc2c(C(=O)O)cc(I)cc21]

To a stirred solution of methyl 6-bromo-1-(1-methylethyl)-1H-indole-4-carboxylate (1.1 g, 3.71 mmol) in dioxane (50 mL) was added sodium iodide (1.2 g, 8.01 mmol), N,N'-dimethylethylenediamine (200 µL, 1.858 mmol) and copper (I) iodide (150 mg, 0.788 mmol). The reaction was purged with $N_2$ then refluxed (110° C. oil bath) overnight. LCMS indicated that the reaction was 90% complete with 6% remaining SM. Another 0.75 g sodium iodide and 75 mg copper(I) iodide was added and the reaction refluxed for another 24 hr. (LCMS showed less than 4% bromide SM.) The reaction was concentrated under vacuum, taken up in EtOAc, washed with water, brine, dried (MgSO_4), filtered and concentrated under vacuum. Purification by silica gel chromatography (Analogix, SF25-60g, 0 to 10% EtOAc in hexanes) gave the ester product as a light yellow oil. (1.27 g, 100%). MS(ES)+ m/e 344.0 [M+H]+.

The above ester was taken up in 40 mL (3:1) MeOH, THF and treated with 1N NaOH (15 mL). The reaction was refluxed overnight, cooled to RT and concentrated under vacuum. Neutralization with 1N HCl (15 mL) gave a white suspension that was filtered, washed with cold water and dried under vacuum to give the product 6-iodo-1-(1-methylethyl)-1H-indole-4-carboxylic acid (1.12 g, 3.40 mmol, 92% yield) as a light yellow solid. $^1$H NMR (400 MHz, DMSO-d_6) δ=12.94 (br. s., 1H), 8.20 (s, 1H), 7.94 (d, J=1.5 Hz, 1H), 7.66 (d, J=3.3 Hz, 1H), 6.97 (d, 1H), 4.86 (quin, J=6.6 Hz, 1H), 1.44 (d, J=6.6 Hz, 6H). MS(ES)+ m/e 330.0 [M+H]+.

Intermediate 38

6-Cyano-1-isopropyl-3-methyl-1H-indole-4-carboxylic acid

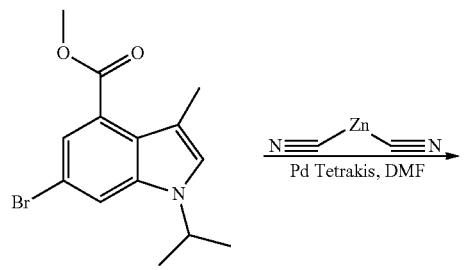

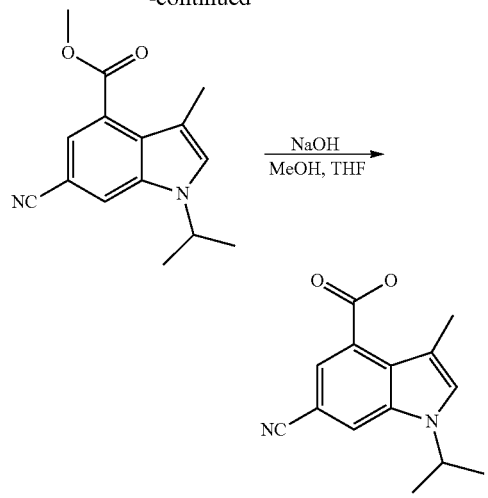

a) Methyl 6-cyano-3-methyl-1-(1-methylethyl)-1H-indole-4-carboxylate

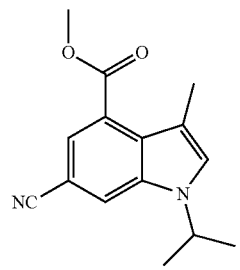 [SMILES: COC(=O)c1cc(C#N)cc2c1c(C)cn2C(C)C]

To a 10 ml microwave vial was added methyl 6-bromo-3-methyl-1-(1-methylethyl)-1H-indole-4-carboxylate (500 mg, 1.612 mmol), dicyanozinc (150 mg, 1.277 mmol) and DMF (5 mL). The mixture was degassed and stirred at rt under N2 for 15 min. To the mixture was added palladium tetrakis (118 mg, 0.102 mmol) and the reaction was stirred at 95° C. for 1 h. The reaction was allowed to cool and poured into saturated aqueous Na_2CO_3 (50 mL) and EtOAc (50 mL) and stirred for 20 min. The mixture was extracted with ether (100 ml) and EtOAc (100 ml) (1:1), followed by filtration and evaporation to yield a residue. The residue was purified by silica gel chromatography (Analogix IF280, 0-8% EtOAc/hexanes, SF25-40g, 30 minutes) to give methyl 6-cyano-3-methyl-1-(1-methylethyl)-1H-indole-4-carboxylate (130 mg, 0.497 mmol, 38.9% yield) as a white solid. $^1$H NMR (400 MHz, DMSO-d_6) δ ppm 8.38 (d, J=1.52 Hz, 1H) 7.82 (s, 1H) 7.71 (d, J=1.52 Hz, 1H) 4.85-4.97 (m, 1H) 3.90 (s, 3H) 2.29 (s, 3H) 1.45 (d, J=6.57 Hz, 6H). MS(ES) [M+H]+ 257.4.

b) 6-Cyano-1-isopropyl-3-methyl-1H-indole-4-carboxylic acid

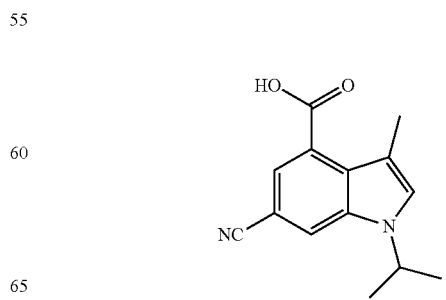

To a 50 ml round bottom was added methyl 6-cyano-3-methyl-1-(1-methylethyl)-1H-indole-4-carboxylate (230 mg, 0.897 mmol), followed by methanol (1 mL) and THF (1 mL). To the solution was added 3M NaOH (0.449 mL, 2.69 mmol). The reaction stirred at rt for 20 h. The reaction was evaporated and treated with acidic water to pH 5. A brown solid crashed out and was collected by filtration. The solid was an impurity. The pH of the liquid was adjusted to 3 and the liquid was evaporated leaving a residue. Trituration of the residue with water, followed by filtration yielded 6-cyano-3-methyl-1-(1-methylethyl)-1H-indole-4-carboxylic acid (155 mg, 0.576 mmol, 64.2% yield) as a yellow solid. $^1$H NMR (400 MHz, DMSO-d$_6$) δ ppm 13.16 (br. s., 1H) 8.33 (s, 1H) 7.78 (s, 1H) 7.66 (s, 1H) 4.81-4.98 (m, 1H) 2.33 (s, 4H) 1.45 (d, J=6.57 Hz, 6H). MS(ES) [M+H]$^+$ 243.3.

Intermediate 39

1-Isopropyl-3-methyl-6-(1H-tetrazol-5-yl)-1H-indole-4-carboxylic acid

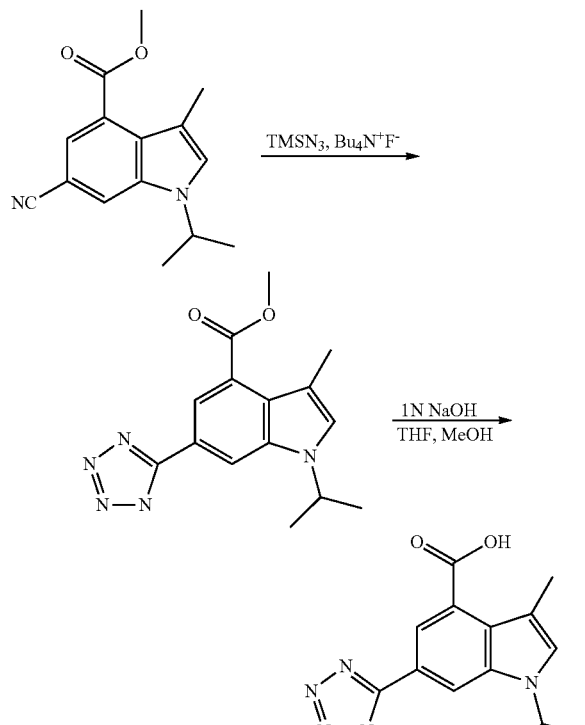

To a stirred suspension of methyl 6-cyano-1-isopropyl-3-methyl-1H-indole-4-carboxylate (0.50 g, 1.951 mmol) in azidotrimethylsilane (1.0 mL, 7.53 mmol) in a small vial was added tetrabutylammonium fluoride trihydrate (300 mg, 0.951 mmol). The reaction was heated to 85° C. and stirred for 18 hr (attached a small reflux condensor). (The reaction became a semi-solid mass.) The reaction was taken up in EtOAc (75 mL), washed with 1N HCl (75 mL) (stirred till dissolved). The organic phase was removed, dried (Na$_2$SO$_4$), filtered and concentrated under vacuum. Purification by silica gel chromatography (Analogix, SF40-80g, 0 to 3% MeOH/CH$_2$Cl$_2$ with 0.1% HOAc) gave the product methyl 1-isopropyl-3-methyl-6-(1H-tetrazol-5-yl)-1H-indole-4-carboxylate (0.28 g, 0.935 mmol, 48.0% yield) as a white solid. $^1$H NMR (400 MHz, DMSO-d$_6$) δ 8.40 (d, J=1.3 Hz, 1H), 8.15 (d, J=1.5 Hz, 1H), 7.69 (s, 1H), 4.86 (quin, J=6.6 Hz, 1H), 3.94 (s, 3H), 2.33 (s, 3H), 1.50 (d, J=6.6 Hz, 6H). MS(ES)+ m/e 300.3 [M+H]$^+$.

b) 1-isopropyl-3-methyl-6-(1H-tetrazol-5-yl)-1H-indole-4-carboxylic acid

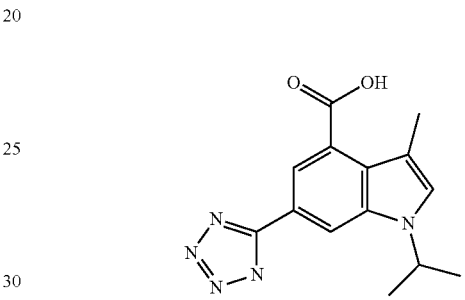

To a stirred solution of methyl 1-isopropyl-3-methyl-6-(1H-tetrazol-5-yl)-1H-indole-4-carboxylate (0.27 g, 0.902 mmol) in MeOH (15 mL) and tetrahydrofuran (5 mL) was added 1N NaOH (5 mL, 5.00 mmol). The reaction was heated to 60° C. and stirred for 48 hr. LCMS showed that the reaction was complete. The reaction was concentrated to near dryness under vacuum, acidified with 1N HCl (5 mL), triturated, filtered and washed with a small volume of water, and dried under vacuum to give the product 1-isopropyl-3-methyl-6-(1H-tetrazol-5-yl)-1H-indole-4-carboxylic acid (0.26 g, 0.911 mmol, 101% yield) as a light yellow solid. $^1$H NMR (400 MHz, DMSO-d$_6$) δ 13.04 (br. s., 1H), 8.36 (d, J=1.5 Hz, 1H), 8.13 (d, J=1.3 Hz, 1H), 7.65 (s, 1H), 4.85 (quin, J=6.6 Hz, 1H), 2.36 (s, 3H), 1.50 (d, J=6.6 Hz, 6H). MS(ES)+ m/e 286.1 [M+H]$^+$.

Intermediate 40

6-Bromo-3-chloro-1-isopropyl-1H-indole-4-carboxylic acid

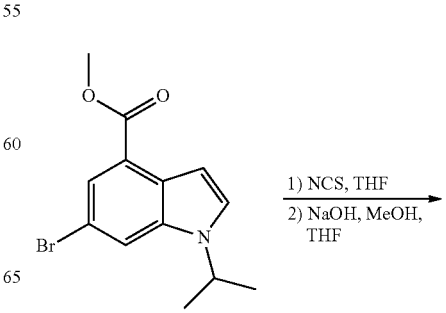

a) Methyl 1-isopropyl-3-methyl-6-(1H-tetrazol-5-yl)-1H-indole-4-carboxylate

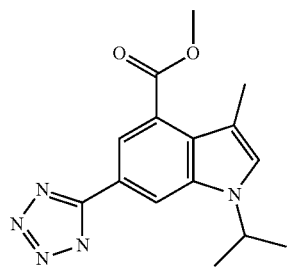 [SMILES: COC(=O)c1cc(-c2nnn[nH]2)cc2c1c(C)cn2C(C)C]

-continued

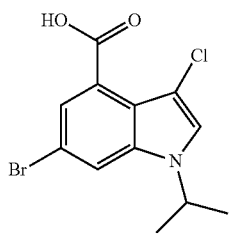

To a 100 ml round bottom flask was added methyl 6-bromo-1-(1-methylethyl)-1H-indole-4-carboxylate (1.100 g, 3.71 mmol) as a solution in THF and a magnetic stir bar. To the same was added 1-chloro-2,5-pyrrolidinedione (0.546 g, 4.09 mmol) and the system stirred at room temperature overnight. The solvent was removed under reduced pressure and the residue dissolved in EtOAc (60 ml) and washed with saturated NaHCO$_3$ (20 ml) and brine (8 ml). The organic layer was dried over Na$_2$SO$_4$, filtered and concentrated. Purification of the residue by column chromatography provided methyl 6-bromo-3-chloro-1-isopropyl-1H-indole-4-carboxylate (as a thick gold oil), which was used in the next step. $^1$H NMR (400 MHz, DMSO-d$_6$) δ 8.15 (d, J=1.52 Hz, 1H), 7.93 (s, 1H), 7.50 (d, J=1.77 Hz, 1H), 4.90 (quin, J=6.63 Hz, 1H), 3.89 (s, 3H), 1.43 (d, J=6.57 Hz, 6H). MS(ES) [M+H]$^+$ 332.2.

To a solution of methyl 6-bromo-3-chloro-1-(1-methylethyl)-1H-indole-4-carboxylate (1.2 g, 3.63 mmol) in THF (2.368 ml) and MeOH (14.21 ml) was added 3N NaOH (1.573 ml, 4.72 mmol). The resulting mixture was heated at 55° C. for 4 h. The reaction was removed from the heat and the solvent removed in-vacuo. The remaining residue was dissolved with water (12 ml) and made acidic dropwise with 1N HCl. The product precipitated and the slurry became too thick to stir and was diluted with water (10 ml). After the precipitation halted no more acid was added. The solid was collected by vacuum filtration, washed with water, and air dried under vacuum overnight to give 6-bromo-3-chloro-1-(1-methylethyl)-1H-indole-4-carboxylic acid (650 mg, 2.033 mmol, 56.0% yield over 2 steps) as a white solid. $^1$H NMR (400 MHz, DMSO-d$_6$) δ 13.22 (s, 1H), 8.09 (d, J=1.77 Hz, 1H), 7.89 (s, 1H), 7.45 (d, J=1.77 Hz, 1H), 4.88 (quin, J=6.63 Hz, 1H), 1.43 (d, J=6.57 Hz, 6H). MS(ES) [M+H]$^+$ 316.0.

Intermediate 41

Methyl 2-bromo-6-chloro-1-isopropyl-3-methyl-1H-indole-4-carboxylate

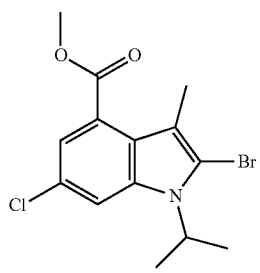 [SMILES: COC(=O)c1cc(Cl)cc2c1c(C)c(Br)n2C(C)C]

To a stirred solution of methyl 6-chloro-1-isopropyl-3-methyl-1H-indole-4-carboxylate (2.5 g, 9.41 mmol) in DMF (25 mL) was added NBS (1.7 g, 9.55 mmol). The reaction was stirred for 18 h then evaporated to dryness under vacuum. The reaction was purified by silica gel chromatography (Analogix, SF40-80g, 0 to 5% EtOAc in hexanes) then (Analogix, SF25-60g, 25% CH$_2$Cl$_2$ in hexanes) to give the product methyl 2-bromo-6-chloro-1-isopropyl-3-methyl-1H-indole-4-carboxylate (1.79 g, 5.19 mmol, 55.2% yield) as a clear oil. $^1$H NMR (400 MHz, DMSO-d$_6$) δ=7.98 (d, J=1.8 Hz, 1H), 7.41 (d, J=1.8 Hz, 1H), 5.05 (dt, J=6.7, 13.4 Hz, 1H), 3.89 (s, 3H), 2.22 (s, 3H), 1.57 (d, J=7.1 Hz, 6H). MS(ES)+ m/e 344.0 [M+H]$^+$.

Intermediate 42

1-Isopropyl-3-methyl-6-(pyridazin-4-yl)-1H-indole-4-carboxylic acid

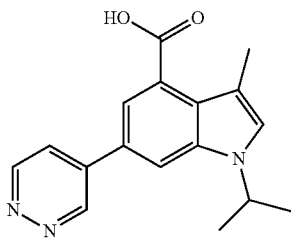 [SMILES: Cc1cn(C(C)C)c2cc(-c3ccnnc3)cc(C(=O)O)c12]

a) Methyl 1-isopropyl-3-methyl-6-(pyridazin-4-yl)-1H-indole-4-carboxylate

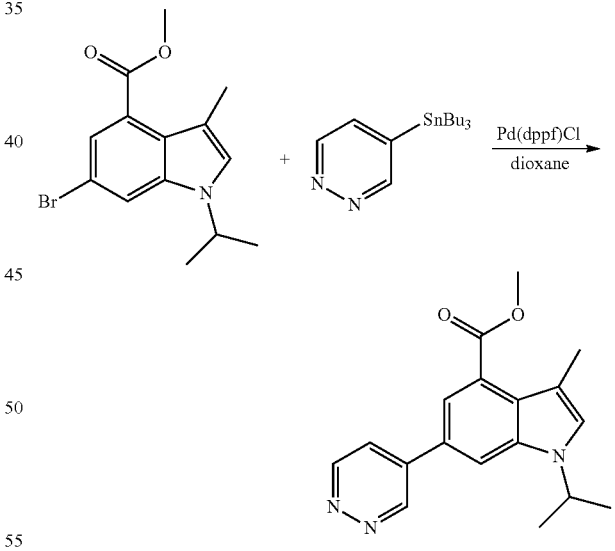

To a 50 ml round bottom flask was added; methyl 6-bromo-1-isopropyl-3-methyl-1H-indole-4-carboxylate (150 mg, 0.484 mmol), PdCl2(dppf)-CH2Cl2 adduct (39.5 mg, 0.048 mmol) and 1,4-Dioxane (4836 μl) followed with 4-(tributylstannyl)pyridazine (179 mg, 0.484 mmol) and a magnetic stir bar. The flask was equipped with a reflux condenser and an exhaust bubbler and heated to 105° C. The reaction solution changed to a dark brown at 30 minutes. LCMS (105 C-3 h) showed the reaction to be complete. The reaction solvent was removed in-vacuo and the remaining residue taken up with DMSO. (1.5 ml). The DMSO solution was purified by reverse phase HPLC using a Phenomenex Gemini 100×30 mm column, neutral acetonitrile and 0.1% formic acid in water, 40-70%, 10 min gradient. The desired fractions were dried in a Genovac EZ-2 evaporator and the solid residues combined. The product, methyl 1-isopropyl-3-methyl-6-(pyridazin-4-yl)-1H-indole-4-carboxylate, was obtained as a white solid. $^1$H NMR (400 MHz, METHANOL-$\delta_4$) δ 9.68 (δ, J=1.26 Hz, 1H), 9.19 (d, J=5.56 Hz, 1H), 8.20 (d, J=1.52 Hz, 1H), 8.13 (dd, J=2.53, 5.56 Hz, 1H), 7.98 (d, J=1.52 Hz, 1H), 7.48 (s, 1H), 4.96 (dt, J=6.60, 13.33 Hz, 1H), 4.00 (s, 3H), 2.39 (s, 3H), 1.56 (d, 6H). MS(ES) [M+H]$^+$ 310.2.

b) 1-Isopropyl-3-methyl-6-(pyridazin-4-yl)-1H-indole-4-carboxylic acid

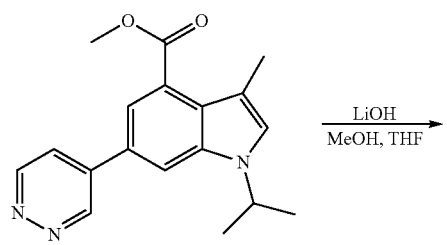

LiOH
MeOH, THF

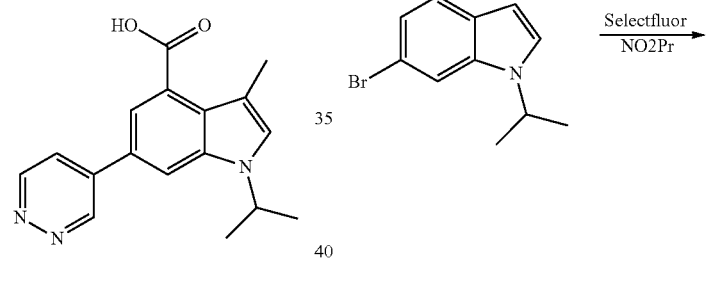

To a 100 ml round bottom flask was added methyl 1-isopropyl-3-methyl-6-(pyridazin-4-yl)-1H-indole-4-carboxylate (74.0 mg, 0.239 mmol), Methanol (1595 μl), Tetrahydrofuran (THF) (3189 μl) and a magnetic stir bar. To the same was added lithium hydroxide, H2O (30.1 mg, 0.718 mmol) and the mixture was stirred at 55° C. Reaction progress was monitored by LCMS. LCMS (weekend) showed 50% conversion. To the reaction mixture was added lithium hydroxide, H2O (20.08 mg, 0.478 mmol) The reaction was continued to stir and heated to 55° C. After complete conversion the reaction solvent was removed and the remaining residue dissolved with water (1.5 ml). The aqueous solution was made acidic drop wise with 1N HCl until precipitation was complete. The solid was collected by vacuum filtration and washed with water (5 ml). The solid was dried under vacuum open to the air overnight. The product, 1-isopropyl-3-methyl-6-(pyridazin-4-yl)-1H-indole-4-carboxylic acid (68 mg, 0.228 mmol, 95% yield), was obtained as a brown solid. $^1$H NMR (400 MHz, DMSO-$\delta_6$) δ 9.71-9.83 (m, 1H), 9.23 (dd, J=1.26, 5.56 Hz, 1H), 8.32 (s, 1H), 8.11 (dd, J=2.65, 5.43 Hz, 1H), 7.86 (s, 1H), 7.58 (s, 1H), 4.90-5.09 (m, 1H), 2.34 (s, 3H), 1.47 (d, J=6.82 Hz, 6H). MS(ES) [M+H]$^+$ 296.2.

Intermediate 43

6-Bromo-3-fluoro-1-isopropyl-1H-indole-4-carboxylic acid

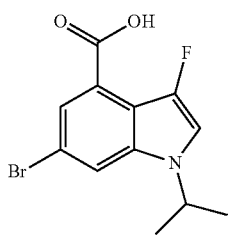 [SMILES: CC(C)n1cc(F)c2c(C(=O)O)cc(Br)cc21]

a) Methyl 6-bromo-3-fluoro-1-isopropyl-1H-indole-4-carboxylate

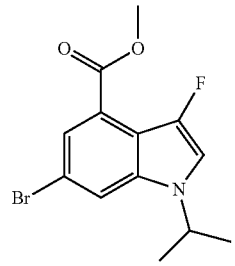

To a 20 ml vial was added methyl 6-bromo-1-isopropyl-1H-indole-4-carboxylate (50.0 mg, 0.169 mmol), (selectfluor) 1-(chloromethyl)-4-fluoro-1,4-diazoniabicyclo[2.2.2]octane ditetrafluoroborate (78 mg, 0.219 mmol) followed with a magnetic stir bar and nitroethane (2 ml). The vial was capped and the reaction stirred at room temperature. Reaction progress was monitored by LCMS. After reaction completion the reaction solvent was removed in-vacuo. The residue was dissolved with DCM (1.4 ml). The DCM solution was charged onto an analogix Si35 SF10-8 gram column. The compound was eluted with EtOAc/Hexanes, 5-15%, 20 min. The desired product and side MW629 co-eluted. The mixture was dissolved with DMSO (1 ml) and purified by reverse phase HPLC using a Gemini 5μ 30×100 mm column, neutral acetonitrile/0.1% formic acid in water, 50-80%, 7 min gradient. The desired product eluted at 6.8 minutes and the side product MW 629 at 9.5 minutes. The desired fractions were concentrated to a residue. LCMS and NMR support the desired structure and analytical HPLC showed 100% purity. The product, methyl 6-bromo-3-fluoro-1-isopropyl-1H-indole-4-carboxylate (11 mg, 0.035 mmol, 20.53% yield), was obtained as a white solid. ¹H NMR (400 MHz, METHANOL-d₄) δ 7.95 (t, J=1.77 Hz, 1H), 7.78 (d, J=1.77 Hz, 1H), 7.47 (d, J=2.53 Hz, 1H), 4.76-4.84 (m, J=1.64, 6.65, 6.65, 13.36 Hz, 1H), 3.96 (s, 3H), 1.50 (d, 6H).

MS(ES)[M+H]⁺ 315.1.

b) 6-Bromo-3-fluoro-1-isopropyl-1H-indole-4-carboxylic acid

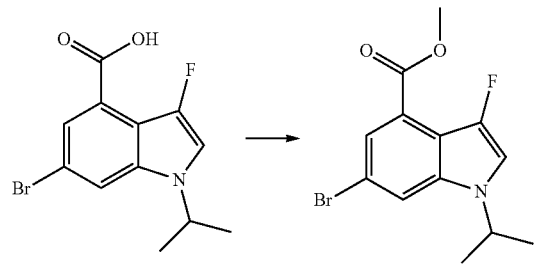 [SMILES: CC(C)n1cc(F)c2c(C(=O)O)cc(Br)cc21 ; COC(=O)c1cc(Br)cc2c1c(F)cn2C(C)C]

To a 100 ml round bottom flask was added methyl 6-bromo-3-fluoro-1-isopropyl-1H-indole-4-carboxylate (33.0 mg, 0.105 mmol), Methanol (700 µl), Tetrahydrofuran (THF) (1401 µl) and a magnetic stir bar. To the same was added lithium hydroxide, H2O (13.22 mg, 0.315 mmol) and the mixture was stirred at room temperature. Reaction progress was monitored by LCMS. LCMS (18 h) showed 60% conversion. The reaction was heated to 50° C. in an aluminum heating block with stirring. After complete conversion the solvent was removed in-vacuo and the remaining residue was dissolved with water (1 ml) and 1N HCl was added dropwise (9 drops) until precipitation stopped. The fine pale-yellow solid was collected by vacuum filtration. LCMS and HPLC showed 100% purity and NMR supports the desired structure. The product, 6-bromo-3-fluoro-1-isopropyl-1H-indole-4-carboxylic acid (24 mg, 0.080 mmol, 76% yield), was obtained as a yellow solid. ¹H NMR (400 MHz, DMSO-d₆) δ 13.07 (br. s., 1H), 8.12 (t, J=1.89 Hz, 1H), 7.77 (d, J=2.27 Hz, 1H), 7.66 (d, J=1.77 Hz, 1H), 4.88 (qd, J=5.31, 6.65 Hz, 1H), 1.40 (d, 6H). MS(ES) [M+H]⁺ 300.1.

Intermediate 44

N-[(4,6-dimethyl-2-oxo-1,2-dihydro-3-pyridinyl)methyl]-3-methyl-1-(1-methylethyl)-6-(4,4,5,5-tetramethyl-1,3,2-dioxaborolan-2-yl)-1H-indole-4-carboxamide

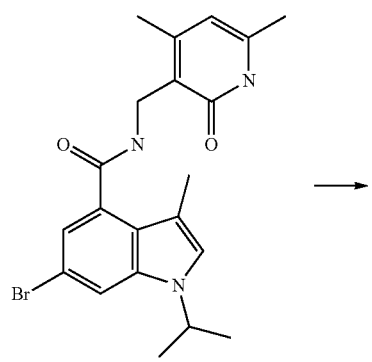

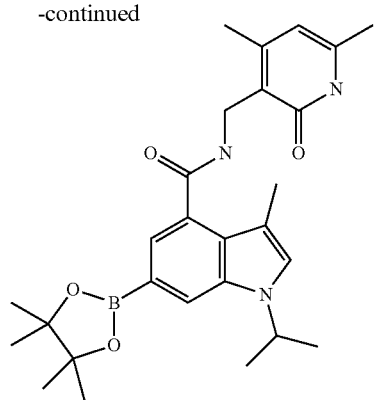

Trial run: A mixture of 6-bromo-N-((4,6-dimethyl-2-oxo-1,2-dihydropyridin-3-yl)methyl)-1-isopropyl-3-methyl-1H-indole-4-carboxamide (1.0 g, 2.32 mmol, 1 equiv), bis(pinacolato)diboron (0.71 g, 2.79 mmol, 1.2 equiv), KOAc (0.47 g, 4.76 mmol, 2 equiv) and PdCl₂(dppf)-CH₂Cl₂ adduct (104 mg, 00.13 mmol, 0.1 equiv) in 10 mL of dioxane in a 20 mL microwave vial was bubbled with nitrogen for 10 min, followed by capping and heating in an oil bath at 80° C. for 3 h. LCMS showed conversion complete. Only 4% debromo byproduct was detected.

Production run: A mixture of 6-bromo-N-((4,6-dimethyl-2-oxo-1,2-dihydropyridin-3-yl)methyl)-1-isopropyl-3-methyl-1H-indole-4-carboxamide (22.0 g, 51.1 mmol, 1 equiv), bis(pinacolato)diboron (15.58 g, 61.3 mmol, 1.2 equiv), KOAc (10.29 g, 105 mmol, 2 equiv) and PdCl₂ (dppf)-CH₂Cl₂ adduct (2.30 g, 2.81 mmol, 0.1 equiv) in 190 mL of dioxane was degassed and backflushed with nitrogen (repeated 4×). The mixture was heated in an oil bath at 90° C. for 2 h. The dark brownish mixture was combined with the crude mixture from the trial run above, and filtered through celite (rinsing with EtOAc). The filtrate was conc in vacuo. The residue was taken up in CHCl₃ and split into 9 equal portions. One portion was absorbed onto a celite-packed dryload cartridge. Purification was done on an SF40-80g silica gel cartridge using gradient elution of 25% EtOAc in hexane to 100% EtOAc (gradient: 0-5 min, 25% EtOAc, 5-20 min, linear gradient 25-100% EtOAc, 25-65 min, 100% EtOAc). The desired product eluted at 100% EtOAc (with a long tail). The DASI portion was clogged during the process, and needed to be removed to continue the chromatography, causing loss of material. Thus the use of FCC was abandoned and switched to gravity column.

The remaining 8 portions were recombined and dissolved in CHCl₃, followed by adding to a silica gel column (500 g of coarse grade silica gel packed in 25% EtOAc in hexane), and then elution with 1 L of 25% EtOAc in hexane, 1 L of 50% EtOAc, 1 L of 75% EtOAc in hexane, 2 L of 100% EtOAc, 1 L of EtOAc with 25 mL increments of MeOH. The desired product eluted at 100% EtOAc, 25 mL-100 mL of MeOH in EtOAc fractions.

The EtOAc fractions were combined with the FCC purified material. The mixture was conc in vacuo. The residue was taken up in MTBE (5 mL) and hexane (100 mL) as a suspension, which was filtered. The cake was washed with hexane (30 mL) and dried under vacuum at rt for 4 h to provide N-[(4,6-dimethyl-2-oxo-1,2-dihydro-3-pyridinyl)methyl]-3-methyl-1-(1-methylethyl)-6-(4,4,5,5-tetramethyl-1,3,2-dioxaborolan-2-yl)-1H-indole-4-carboxamide (14.01 g) as light beige solid. ¹H NMR (400 MHz, DMSO-d₆) δ ppm 1.31 (s, 12H), 1.41 (d, J=6.8 Hz, 6H), 2.11 (s, 3H), 2.16 (s, 3H), 2.22 (s, 3H), 4.33 (d, J=8 Hz, 2H), 4.79 (quin, J=6.6 Hz, 1H), 5.87 (s, 1H), 7.23 (s, 1H), 7.40 (d, J=1.0 Hz, 1H), 7.75 (s, 1H), 8.04 (t, J=5.1 Hz, 1H), 11.46 (s, 1H).

ASSAY PROTOCOL

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 mL of compound from the dilution plate into reaction plates (Grenier Bio-One, 384-well, Cat#784075).

Part B. Reagent Preparation
Prepare the following solutions:
1. 50 mM Tris-HCl, pH 8: Per 1 L of base buffer, combine 1M Tris-HCl, pH 8 (50 mL) and distilled water (950 mL).
2. 1×Assay Buffer: Per 10 mL of 1×Assay Buffer, combine 50 mM Tris-HCl, pH 8 (9958 uL), 1M $MgCl_2$ (20 uL), 2M DTT (20 uL), and 10% Tween-20 (2 uL) to provide a final concentration of 50 mM Tris-HCl, pH 8, 2 mM $MgCl_2$, 4 mM DTT, 0.002% Tween-20.
3. 2× Enzyme Solution: Per 10 mL of 2× Enzyme Solution, combine 1× Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and ddH2O (1 mL) to provide a final concentration of 40 mg/mL.
5. 2× Substrate Solution: Per 10 mL of 2× Substrate Solution, combine 1× Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine $ddH_2O$ (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-well Grenier Bio-One Plates
Compound Addition
1. Dispense 100 mL/well of 100× Compound to test wells (as noted above).
2. Dispense 100 mL/well of 100% DMSO to columns 6 & 18 for high and low controls, respectively.

Assay
1. Dispense 5 uL/well of 1× Assay Buffer to column 18 (low control reactions).
2. Dispense 5 uL/well of 2× Enzyme Solution to columns 1-17, 19-24.
3. Spin assay plates for ~1 minute at 500 rpm.
4. Stack the assay plates, covering the top plate.
5. Incubate the compound/DMSO with the enzyme for 30 minutes at room temperature.
6. Dispense 5 uL/well of 2× Substrate Solution to columns 1-24.
7. Spin assay plates for ~1 minute at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for ~1 minute at 500 rpm.
4. Equilibrate the plates for >20 min.

Read Plates
1. Read the assay plates on the Viewlux Plate Reader utilizing the 613 nm emission filter with a 300 s read time.

Reagent addition can be done manually or with automated liquid handler.
*The final DMSO concentration in this assay is 1%.
*The positive control is in column 6; negative control is in column 18.
*Final starting concentration of compounds is 100 μM.

Part D. Data Analysis
Percent inhibition was calculated relative to the DMSO control for each compound concentration and the resulting values were fit using standard $IC_{50}$ fitting parameters within the ABASE data fitting software package.

Exemplified compounds of the present invention were generally tested according to the above or an analogous assay and were found to be inhibitors of EZH2. The $IC_{50}$ values ranged from about 1 nM to about 10 μM; The $IC_{50}$ values of the more active compounds range from about 1 nM to about 500 nM; The most active compounds are under 50 nM. As tested in the foregoing assay or an analogous assay, compounds of the various Examples gave the $pIC_{50}$ data in the compound table above or the $IC_{50}$ data in the paragraph below. Repeating the assay run(s) may result in a somewhat different.

Ex 78, 1800; Ex 174, 18; Ex 211, 14; Ex 212, 9; Ex 234, 1000; Ex 244, 29; Ex 264, 13; Ex 265, 13; Ex 266, 25; Ex 267, 20; Ex 268, 40; Ex 269, 4; Ex 270, 4; Ex 271, 8; Ex 272, 13; Ex 273, 10; Ex 274, 32; Ex 275, 3; Ex 339, 13.

Preparation of Specific Compounds (Compound A, B and C) that were Tested in the T Cell Proliferation and Cytokine Production Studies N-((4,6-dimethyl-2-oxo-1,2-dihydropyridin-3-yl)methyl)-6-(4-(2-(dimethylamino)ethoxy)phenyl)-1-isopropyl-1H-indazole-4-carboxamide

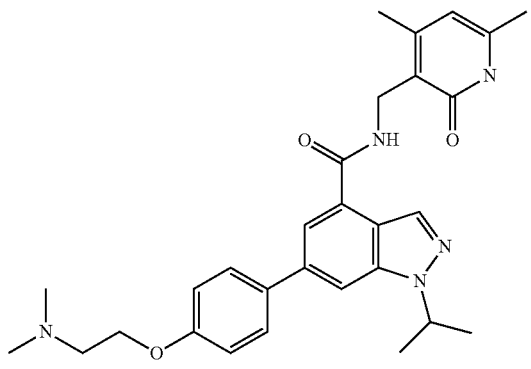

6-bromo-N-(4,6-dimethyl-2-oxo-1,2-dihydropyridin-3-yl)methyl)-1-isopropyl-1H-indazole-4-carboxamide (80 mg, 0.19 mmol), N,N-dimethyl-2-(4-(4,4,5,5-tetramethyl-1,3,2-dioxaborolan-2-yl)phenoxy)ethanamine (84 mg, 0.29 mmol) and PdCl$_2$(dppf)-CH$_2$Cl$_2$ adduct (7.8 mg, 0.009 mmol) in dioxane/water (3 ml:1 ml) were stirred for 10 min under nitrogen. Sodium bicarbonate (48.3 mg, 0.58 mmol) was added and the insoluble mixture was irradiated in a microwave at 100° C. for 20 min. The reaction mixture was evaporated, dissolved in DCM/MeOH (1:1), and preabsorbed on silica gel and purified using silica gel chromatography (eluent: DCM/MeOH/NH$_4$OH; gradient 0 to 80:20:2 in DCM). The isolated product was dissolved in hot DMSO/MeOH and purified using reversed-phase HPLC (25-80% gradient of MeCN in water with 0.1% TFA). Most of the solvent from the combined product fractions were evaporated and sat. sol. NaHCO$_3$ was added, solids that crashed out were filtered, air-dried for 15 min, and dried in vacuum-oven overnight. The product was collected as a white solid (56 mg, 56%). $^1$H NMR (400 MHz, DMSO-d$_6$)™ ppm 11.54 (br. s., 1H) 8.64 (t, J=4.80 Hz, 1H) 8.35 (s, 1H) 8.05 (s, 1H) 7.81-7.84 (m, 2H). LC-MS(ES) m/z=528.1 [M+H]$^+$ Compound A can be prepared according to a procedure analogous to the above example:

Compound A: 1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indazole-4-carboxamide

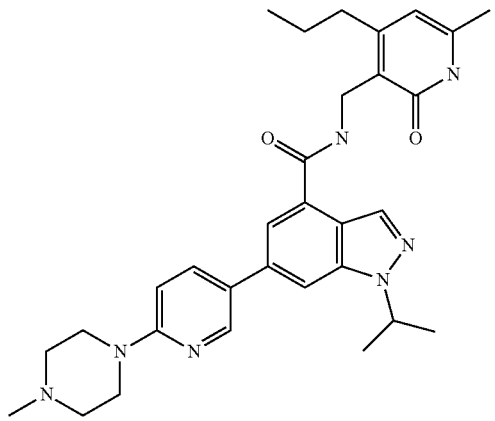

The title compound was prepared in a similar manner as described for the above example from 6-bromo-1-(1-methylethyl)-N-[(6-methyl-2-oxo-4-propyl-1,2-dihydro-3-pyridinyl)methyl]-1H-indazole-4-carboxamide (90 mg, 0.202 mmol) and 1-methyl [5-(4,4,5,5-tetramethyl-1,3,2-dioxaborolan-2-yl)-2-pyridinyl]piperazine (92 mg, 0.303 mmol). The final product was collected as a light brown solid (54 mg, 49%). $^1$H NMR (400 MHz, DMSO-d$_6$)™ ppm $^1$H NMR (400 MHz, DMSO-d6)™ ppm 11.54 (br. s., 1H) 8.65 (d, J=2.27 Hz, 1H) 8.61 (t, J=4.80 Hz, 1H) 8.36 (s, 1H) 8.04-8.08 (m, 2H) 7.83 (s, 1H) 6.96 (d, J=9.09 Hz, 1H) 5.92 (s, 1H) 5.14 (quin, J=6.57 Hz, 1H) 4.42 (d, J=4.80 Hz, 2H) 3.53-3.59 (m, 4H) 2.53-2.61 (m, 2H) 2.40-2.45 (m, 4H) 2.23 (s, 3H) 2.14 (s, 3H) 1.51-1.58 (m, 2H) 1.50 (s, 3H) 1.49 (s, 3H) 0.88 (t, J=7.33 Hz, 3H). LC-MS(ES) m/z=542.2 [M+H]$^+$ Compound B: N-[(4,6-dimethyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide

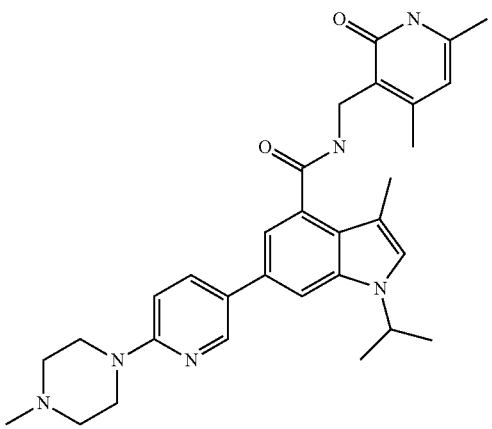

Compound B can be prepared according to the general procedure described in the above experimental section.

6-Cyclopropyl-1-(1-methylethyl)-N-[(4-methyl-2-oxo-6-propyl-1,2-dihydro-3-pyridinyl)methyl]-1H-pyrazolo[3,4-b]pyridine-4-carboxamide

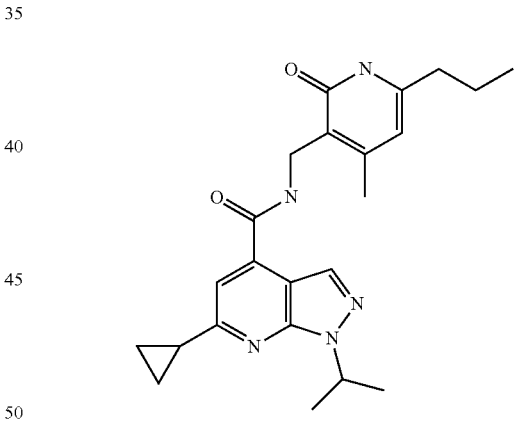

6-Cyclopropyl-1-(1-methylethyl)-1H-pyrazolo[3,4-b]pyridine-4-carboxylic acid (167 mg, 0.680 mmol), 3-(aminomethyl)-4-methyl-6-propyl-2(1H)-pyridinone trifluoroacetate (200 mg, 0.680 mmol), HOAT (139 mg, 1.019 mmol), EDC (195 mg, 1.019 mmol), and N-methylmorpholine (0.299 mL, 2.72 mmol) were dissolved in DMF (6 mL) and stirred at 40° C. for 24 h. The reaction mixture was poured into water (20 mL) and extracted with ethyl acetate (3×50 mL). The combined organic layers were dried over sodium sulfate and concentrated to an orange oil. The residue was dissolved in DMSO, and purified by reverse phase HPLC (mobile phase: 40-60% ACN in H$_2$O, 0.1% TFA). The isolated product was dried in a vacuum oven overnight and furnished the TFA salt of the title compound as a white solid, 0.113 g (32%). LCMS E-S (M+H)=408.1. $^1$H NMR (400 MHz, DMSO-d$_6$) δ ppm 0.80-0.98 (m, 3H), 1.06 (d, J=7.07 Hz, 4H), 1.46 (d, J=6.82

Hz, 6H), 1.52-1.67 (m, 2H), 2.17-2.31 (m, 4H), 2.37 (t, J=7.58 Hz, 2H), 4.36 (d, J=4.80 Hz, 2H), 5.02-5.27 (m, 1H), 5.91 (s, 1H), 7.43 (s, 1H), 8.21 (s, 1H), 8.62-8.87 (m, 1H), 11.54 (br. s., 1H).

Compound C can be prepared according to a procedure analogous to the above example:

6-cyclopropyl-1-(1-methylethyl)-N-[(6-methyl-2-oxo-1,2-dihydro-3-pyridinyl)methyl]-1H-pyrazolo[3,4-b]pyridine-4-carboxamide

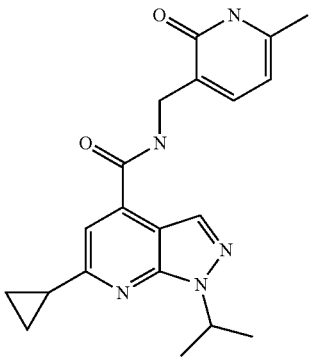 [SMILES: Cc1ccc(CNC(=O)c2cc(C3CC3)nc3c2cnn3C(C)C)c(=O)[nH]1]

Examples

Proliferation Studies

The EZH1/EZH2 inhibitors, Compound A and Compound B, concentration-dependently impaired T cell receptor-induced proliferation of CD4+ T cells with a pIC50 of 5.30±0.06 and 4.93±0.05 respectively (n=4; FIG. 1). In contrast, Compound C had no effect on T cell receptor-induced proliferation of CD4+ T cells (n=4).

Figure 2:
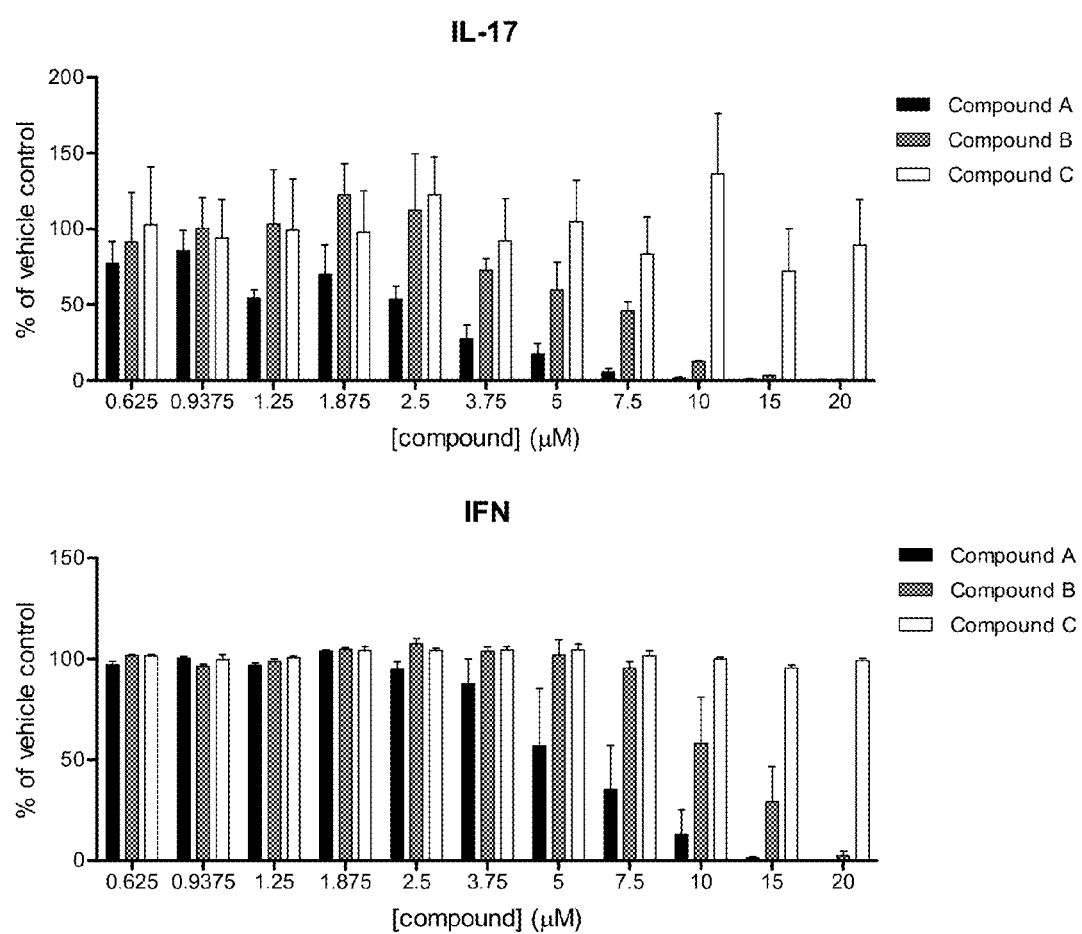
FIG. 2: $EZH_1/EZH_2$ inhibitors impair T cell receptor-induced effector cytokine production in CD4+ T cells. Cytokine production was measured 72 h post stimulation with 10 µg/mL αCD3+2 µg/mL αCD28. Data are presented as means±standard error of the mean, n=4.
Figure 2:
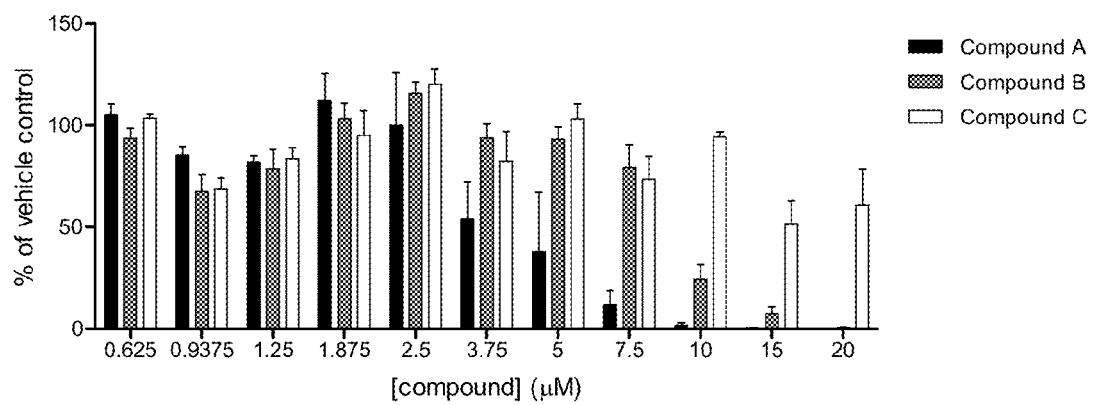
Figure 2:
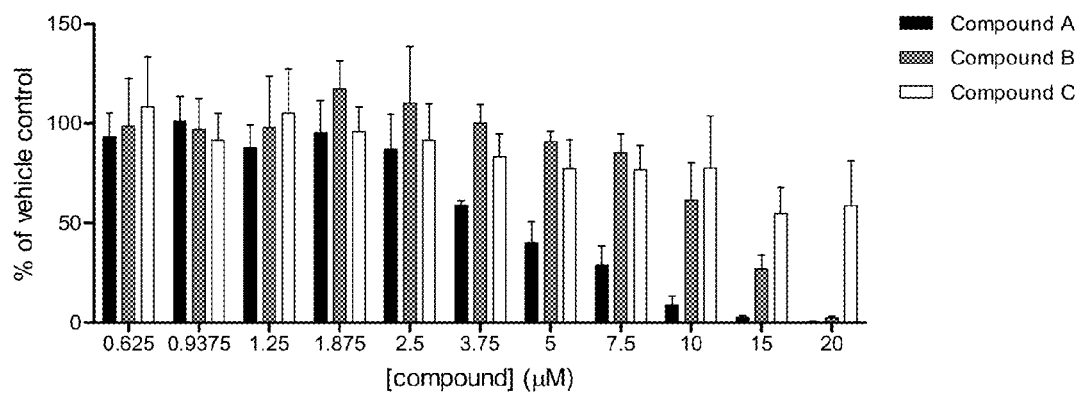
Figure 2:
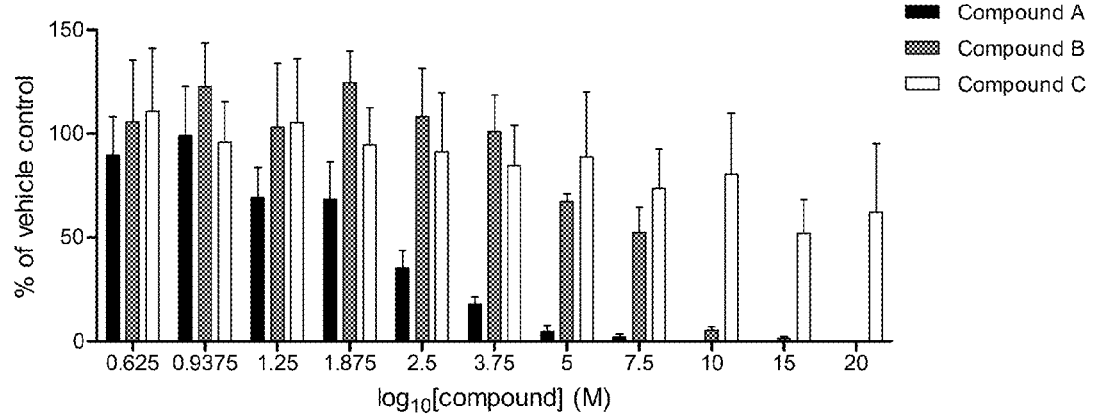

Cytokine Production Studies:

The EZH1/EZH2 inhibitors, Compound A and Compound B, concentration-dependently impaired T cell receptor-induced production of IL-10, IL-13, IL-17, IFN & TNF in CD4+ T cells with pIC50 values ranging between 5.65±0.06-5.23±0.03 and 5.21±0.09-4.94±0.03 respectively (n=4; FIG. 2 & FIG. 4). In contrast, Compound C had no effect on T cell receptor-induced production of IL-17 or IFN in CD4+ T cells (n=4). High concentrations of Compound C (i.e. >15 µM) reduced IL-10, IL-13 & TNF production (n=4).

Figure 3:
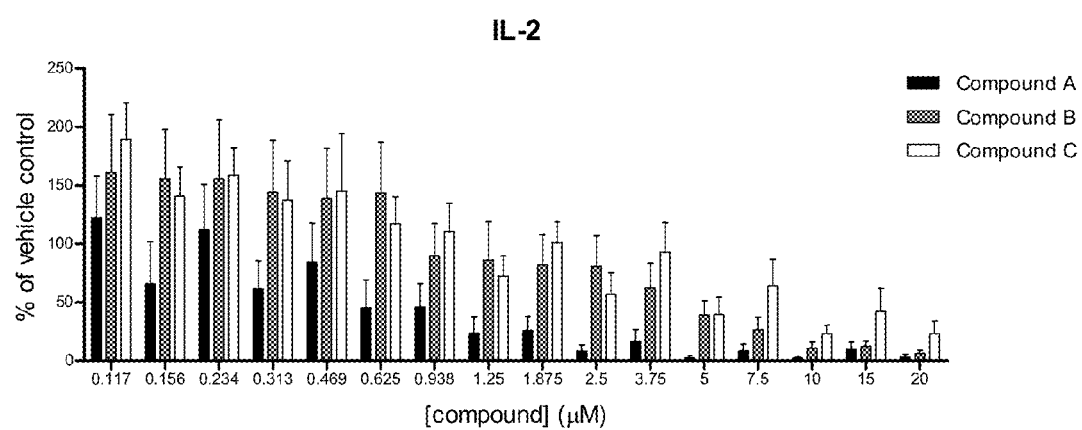
FIG. 3: $EZH_1/EZH_2$ inhibitors impair T cell receptor-induced IL-2 production in CD4+ T cells. IL-2 production was measured 18 h post stimulation with 10 µg/mL αCD3+2 µg/mL αCD28. Data are presented as means±standard error of the mean, n=4.

The EZH1/EZH2 inhibitors, Compound A and Compound B, concentration-dependently impaired T cell receptor-induced production of IL-2 in CD4+ T cells with pIC50 values of 6.24±0.24 and 5.76±0.25 respectively (n=4; FIG. 3). Compound C also impaired T cell receptor-induced production of IL-2 in CD4+ T cells, although a pIC50 could not be calculated (n=4; FIG. 3).

Methods:

CD4 T Cell Isolation from Human Blood:

15 mls ficoll was added to 8×50 mL accuspin tubes per donor and centrifuged at 2000 RPM for 1 min. Whole blood samples (200 mL+1% heparin) were collected from human donors. Approximately 25 ml blood was added to each ficoll pre-filled 50 ml falcon tubes with filter and centrifuged at 1500 RPM for 20 min with the brake off to avoid disturbing cell separation. 45 ml with PBS was added to the PBMC fraction of each tube and centrifuged at 1500 RPM for 10 min with brake. Supernatant were discarded and cell pellets resuspended in 2 ml PBS. Cell suspensions for each donor were recombined into a single falcon tube, made up to 45 ml with PBS and centrifuged at 1500 RPM for 10 min. CD4+ T cells were isolated by negative depletion using a CD4 T cell Isolation Kit from Miltenyi Biotech according to manufacturers protocol.

Proliferation Studies:

96-well flat-bottom plates were coated with 10 µg/mL anti-CD3+2 µg/mL anti-CD28 at 4° C. overnight. The following day, plates were washed with PBS. For proliferation studies, cells were stained with CFSE (Invitrogen) according to manufacturer's protocol. Cells were then added to anti-CD3+anti-CD28 pre-coated 96-well plates at $0.2 \times 10^6$ cells/well in the presence of EZH1/EZH2 inhibitors (Compound A & Compound B), an inactive control compound (Compound C) or vehicle (0.1% DMSO) and incubated for 6 days at 37° C./5% CO2. Cells were then transferred to 96-well round-bottom plates, washed and then analysed by flow cytometry.

Cytokine Production Studies:

96-well flat-bottom plates were coated with 10 µg/mL anti-CD3+2 µg/mL anti-CD28 at 4° C. overnight. The following day, plates were washed with PBS. For cytokine production studies, cells were added to anti-CD3+anti-CD28 pre-coated 96-well plates at $0.4 \times 10^6$ cells/well in the presence of EZH1/EZH2 inhibitors or vehicle and incubated at 37° C./5% CO2. Supernatants were taken 18 h (IL-2) or 72 h (IL-10, IL-13, IL-17, IFN, TNF) for determination of cytokine production by multiplex ELISA from Mesoscale discovery according to the manufacturers protocols.

Drugs and Materials

Anti-CD3 (HU CD3 NALE MAB UCHT1; Cat #555329) and anti-CD28 (HU CD28 NALE MAB CD28.2; Cat #: 555725), were obtained from BD Pharmingen and dissolved in Dulbecco's Phosphate Buffered Saline (with Ca2+/Mg2+; Gibco). Ficoll-paque (Cat #17-1440-03) was obtained from GE Healthcare. The CD4+ T cell isolation kit (Cat #130-091-155) was obtained from Miltenyi Biotec. Cells were cultured in RPMI 1640 containing 10% FCS+1% pen/strep+1% L-glutamine. The CellTrace CFSE cell proliferation kit (Cat #C34554) was obtained from Invitrogen. Compound A, Compound B and Compound C were all synthesised in house and dissolved in 100% DMSO.

Data Analysis

Proliferation Studies:

Flowjo Software was used to calculate a division index using fluorescence intensity. Data are expressed as mean±standard error of the mean; n values are the numbers of human donors used. pIC50 values were generated using GraphPad Prism software and non-linear sigmoid dose curve-fit.

Cytokine Production Studies:

Data were analysed using Excel and are expressed as mean±standard error of the mean; n values are the numbers of human donors used. pIC50 values were generated using GraphPad Prism software and non-linear sigmoid dose curve-fit.

The invention claimed is:
1. A method of treating a T cell mediated inflammatory immune disease, comprising administering to a human in need thereof an effective amount of a compound which is N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide, or a pharmaceutically acceptable salt thereof; wherein said T cell mediated inflammatory immune disease is selected from a group consisting of: acute disseminated alopecia universalise, Behcet's disease, Chagas' disease, chronic fatigue syndrome, dysautono- mia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, Reiter's syndrome, Sjogren's syndrome, temporal arteritis, Wegener's granulomatosis, warm autoimmune haemolytic anemia, interstitial cystitis, lyme disease, morphea, sarcoidosis, scleroderma, ulcerative colitis, and vitiligo.

2. The method according to claim 1 wherein the compound is administered as a free base.

3. A method of treating a T cell mediated hypersensitivity disease, comprising administering to a human in need thereof an effective amount of a compound which is N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide, or a pharmaceutically acceptable salt thereof; wherein said T cell mediated hypersensitivity disease is selected from the group consisting of: contact hypersensitivity, contact dermatitis, uticaria, skin allergies, respiratory allergies, and gluten-sensitive enteropathy.

4. The method according to claim 3 wherein the compound is administered as a free base.

\* \* \* \* \*